US009688978B2

(12) United States Patent
Buechler et al.

(10) Patent No.: US 9,688,978 B2
(45) Date of Patent: Jun. 27, 2017

(54) ASPARTYL-TRNA SYNTHETASE-FC CONJUGATES

(71) Applicant: aTyr Pharma, Inc., San Diego, CA (US)

(72) Inventors: Ying Ji Buechler, Carlsbad, CA (US); Chi-Fang Wu, San Diego, CA (US); Ryan Andrew Adams, San Diego, CA (US); Jeffrey D. Watkins, Encinitas, CA (US); John D. Mendlein, Encinitas, CA (US)

(73) Assignee: aTyr Pharma, Inc., San Diego, CA (US)

( * ) Notice: Subject to any disclaimer, the term of this patent is extended or adjusted under 35 U.S.C. 154(b) by 191 days.

(21) Appl. No.: 14/368,759

(22) PCT Filed: Dec. 27, 2012

(86) PCT No.: PCT/US2012/071762
§ 371 (c)(1),
(2) Date: Jun. 25, 2014

(87) PCT Pub. No.: WO2013/115926
PCT Pub. Date: Aug. 8, 2013

(65) Prior Publication Data
US 2014/0335087 A1 Nov. 13, 2014

Related U.S. Application Data

(60) Provisional application No. 61/581,550, filed on Dec. 29, 2011.

(51) Int. Cl.
| | |
|---|---|
| *C12N 9/96* | (2006.01) |
| *C07K 14/00* | (2006.01) |
| *G01N 33/68* | (2006.01) |
| *C12N 9/00* | (2006.01) |
| *C07K 16/00* | (2006.01) |
| *A61K 38/00* | (2006.01) |

(52) U.S. Cl.
CPC ............... *C12N 9/93* (2013.01); *C07K 16/00* (2013.01); *C12Y 601/01012* (2013.01); *A61K 38/00* (2013.01); *C07K 2319/02* (2013.01); *C07K 2319/21* (2013.01); *C07K 2319/30* (2013.01); *C07K 2319/50* (2013.01); *C12Y 601/01002* (2013.01)

(58) Field of Classification Search
CPC .. C12N 9/96; C07K 2319/00; C07K 2319/33; C07K 14/00; G01N 33/68; G01N 2500/00; G01N 33/5008; G01N 2500/04; G01N 2500/10; G01N 2333/52; A61K 38/00; A61K 48/00; C12Y 601/01012; C12Y 601/01023
See application file for complete search history.

(56) References Cited

U.S. PATENT DOCUMENTS

| | | |
|---|---|---|
| 5,370,995 A | 12/1994 | Hennecke et al. |
| 5,484,703 A | 1/1996 | Raben et al. |
| 5,663,066 A | 9/1997 | Raben et al. |
| 5,747,315 A | 5/1998 | Lowlor |
| 5,750,387 A | 5/1998 | Hodgson et al. |
| 5,753,480 A | 5/1998 | Lawlor |
| 5,756,327 A | 5/1998 | Sassanfar et al. |
| 5,759,833 A | 6/1998 | Shiba et al. |
| 5,776,749 A | 7/1998 | Hodgson et al. |
| 5,795,757 A | 8/1998 | Hodgson et al. |
| 5,798,240 A | 8/1998 | Martinis et al. |
| 5,801,013 A | 9/1998 | Tao et al. |
| 5,866,390 A | 2/1999 | Lawlor |
| 5,885,815 A | 3/1999 | Sassanfar et al. |
| 5,928,920 A | 7/1999 | Hodgson et al. |
| 5,939,298 A | 8/1999 | Brown et al. |
| 6,225,060 B1 | 5/2001 | Clark et al. |
| 6,255,090 B1 | 7/2001 | Famodu et al. |
| 6,265,188 B1 | 7/2001 | Brown et al. |
| 6,428,960 B1 | 8/2002 | Clark et al. |
| 6,548,060 B1 | 4/2003 | Kim |
| 6,696,619 B1 | 2/2004 | Famodu et al. |
| 6,852,512 B2 | 2/2005 | Choi et al. |
| 6,903,189 B2 | 6/2005 | Schimmel et al. |
| 7,037,505 B2 | 5/2006 | Kim et al. |
| 7,067,126 B2 | 6/2006 | Schimmel et al. |

(Continued)

FOREIGN PATENT DOCUMENTS

| | | |
|---|---|---|
| CA | 2531146 | 3/2005 |
| CN | 1341725 | 3/2002 |

(Continued)

OTHER PUBLICATIONS

International Preliminary Report on Patentability for International Application No. PCT/US2009/048915, dated Jan. 5, 2011.
International Search Report and Written Opinion for International Application No. PCT/US2009/048915, mailed Nov. 2, 2009.
Office Action for U.S. Appl. No. 12/482,151, mailed Oct. 11, 2011, 43 pages.
Office Action for U.S. Appl. No. 12/482,151, mailed Mar. 18, 2011, 11 pages.
International Preliminary Report on Patentability for International Application No. PCT/US2009/046910, dated Dec. 13, 2010.
International Search Report and Written Opinion for International Application No. PCT/US2009/046910, mailed Mar. 4, 2010.
Supplementary European Search Report for European Application No. 06838844.6, mailed Apr. 9, 2009, 10 pages.

(Continued)

*Primary Examiner* — Kagnew H Gebreyesus
(74) *Attorney, Agent, or Firm* — Cooley LLP

(57) ABSTRACT

The present invention provides aspartyl-tRNA synthetase and Fc region conjugate polypeptides (DRS-Fc conjugates), such as DRS-Fc fusion proteins, compositions comprising the same, and methods of using such conjugates and compositions for treating or diagnosing a variety of conditions. The DRS-Fc conjugates of the invention have improved controlled release properties, stability, half-life, and other pharmacokinetic and biological properties relative to corresponding, unmodified DRS polypeptides.

16 Claims, 10 Drawing Sheets

(56) References Cited

U.S. PATENT DOCUMENTS

| | | |
|---|---|---|
| 7,144,984 B2 | 12/2006 | Schimmel et al. |
| 7,196,068 B2 | 3/2007 | Kim et al. |
| 7,273,844 B2 | 9/2007 | Schimmel et al. |
| 7,282,208 B2 | 10/2007 | Kim |
| 7,413,885 B2 | 8/2008 | Schimmel et al. |
| 7,459,529 B2 | 12/2008 | Kim |
| 7,476,651 B2 | 1/2009 | Schimmel et al. |
| 7,521,215 B2 | 4/2009 | Schimmel et al. |
| 7,528,106 B2 | 5/2009 | Friedlander et al. |
| 7,572,452 B2 | 8/2009 | Kim |
| 7,745,391 B2 | 6/2010 | Mintz et al. |
| 7,842,467 B1 | 11/2010 | Heidbrink et al. |
| 7,901,917 B2 | 3/2011 | Schimmel et al. |
| 7,902,165 B2 | 3/2011 | Kim |
| 7,981,426 B2 | 7/2011 | Kim |
| 8,003,780 B2 | 8/2011 | Kim et al. |
| 8,017,593 B2 | 9/2011 | Schimmel et al. |
| 8,026,088 B2 | 9/2011 | Yang |
| 8,101,566 B2 | 1/2012 | Schimmel et al. |
| 8,148,125 B2 | 4/2012 | Schimmel et al. |
| 8,404,242 B2 | 3/2013 | Zhou et al. |
| 8,404,471 B2 | 3/2013 | Greene et al. |
| 8,481,296 B2 | 7/2013 | Yang |
| 8,747,840 B2 | 6/2014 | Greene et al. |
| 8,753,638 B2 | 6/2014 | Zhou et al. |
| 8,828,395 B2 | 9/2014 | Watkins et al. |
| 8,835,387 B2 | 9/2014 | Chiang et al. |
| 8,945,541 B2 | 2/2015 | Greene et al. |
| 8,946,157 B2 | 2/2015 | Greene et al. |
| 8,961,960 B2 | 2/2015 | Chiang et al. |
| 8,961,961 B2 | 2/2015 | Greene et al. |
| 8,962,560 B2 | 2/2015 | Greene et al. |
| 8,969,301 B2 | 3/2015 | Greene et al. |
| 8,980,253 B2 | 3/2015 | Greene et al. |
| 8,981,045 B2 | 3/2015 | Greene et al. |
| 8,986,680 B2 | 3/2015 | Greene et al. |
| 8,986,681 B2 | 3/2015 | Greene et al. |
| 8,993,723 B2 | 3/2015 | Greene et al. |
| 8,999,321 B2 | 4/2015 | Greene et al. |
| 9,029,506 B2 | 5/2015 | Greene et al. |
| 9,034,320 B2 | 5/2015 | Greene et al. |
| 9,034,321 B2 | 5/2015 | Greene et al. |
| 9,034,598 B2 | 5/2015 | Greene et al. |
| 9,062,301 B2 | 6/2015 | Greene et al. |
| 9,062,302 B2 | 6/2015 | Greene et al. |
| 9,068,177 B2 | 6/2015 | Greene et al. |
| 9,127,268 B2 | 9/2015 | Watkins et al. |
| 9,273,302 B2 | 3/2016 | Chiang et al. |
| 9,315,794 B2 | 4/2016 | Greene et al. |
| 2002/0182666 A1 | 12/2002 | Schimmel et al. |
| 2003/0004309 A1 | 1/2003 | Kim et al. |
| 2003/0017564 A1 | 1/2003 | Schimmel et al. |
| 2003/0018985 A1 | 1/2003 | Falco et al. |
| 2003/0082575 A1 | 5/2003 | Schultz et al. |
| 2003/0158400 A1 | 8/2003 | Tang et al. |
| 2003/0165921 A1 | 9/2003 | Tang et al. |
| 2003/0166241 A1 | 9/2003 | Famodu et al. |
| 2003/0215827 A1 | 11/2003 | Yue et al. |
| 2004/0009163 A1 | 1/2004 | Schimmel et al. |
| 2004/0018505 A1 | 1/2004 | Lee et al. |
| 2004/0048290 A1 | 3/2004 | Lee et al. |
| 2004/0101879 A1 | 5/2004 | Seidel-Dugan et al. |
| 2004/0152079 A1 | 8/2004 | Schimmel et al. |
| 2004/0203094 A1 | 10/2004 | Martinis et al. |
| 2004/0214216 A1 | 10/2004 | Famodu et al. |
| 2004/0224981 A1 | 11/2004 | Janjic et al. |
| 2005/0136513 A1 | 6/2005 | Zhang |
| 2005/0196754 A1 | 9/2005 | Drmanac et al. |
| 2005/0208536 A1 | 9/2005 | Schultz et al. |
| 2006/0024288 A1 | 2/2006 | Glidden |
| 2006/0035232 A1 | 2/2006 | McGregor et al. |
| 2006/0046250 A1 | 3/2006 | Kim |
| 2006/0078553 A1 | 4/2006 | Glidden |
| 2006/0160175 A1 | 7/2006 | Anderson et al. |
| 2006/0248617 A1 | 11/2006 | Imanaka et al. |
| 2007/0048322 A1 | 3/2007 | Schimmel et al. |
| 2007/0061916 A1 | 3/2007 | Kovalic et al. |
| 2007/0111238 A1 | 5/2007 | Jamieson et al. |
| 2007/0224201 A1 | 9/2007 | Wu et al. |
| 2008/0044854 A1 | 2/2008 | Wang et al. |
| 2008/0113914 A1 | 5/2008 | Hays et al. |
| 2008/0153745 A1 | 6/2008 | Tian |
| 2009/0123971 A1 | 5/2009 | Paulsel et al. |
| 2009/0221794 A1 | 9/2009 | Kim et al. |
| 2009/0226966 A1 | 9/2009 | Yokoyama et al. |
| 2009/0227002 A1 | 9/2009 | Schultz et al. |
| 2009/0227662 A1 | 9/2009 | Schimmel et al. |
| 2009/0285792 A1 | 11/2009 | Friedlander et al. |
| 2009/0305973 A1 | 12/2009 | Kim et al. |
| 2010/0003230 A1 | 1/2010 | Glidden |
| 2010/0028352 A1 | 2/2010 | Greene et al. |
| 2010/0048413 A1 | 2/2010 | Arcus et al. |
| 2010/0092434 A1 | 4/2010 | Belani et al. |
| 2010/0093082 A1 | 4/2010 | Tian et al. |
| 2010/0138941 A1 | 6/2010 | Kim et al. |
| 2010/0167997 A1 | 7/2010 | Kim |
| 2010/0297149 A1 | 11/2010 | Zhou et al. |
| 2010/0310576 A1 | 12/2010 | Adams et al. |
| 2011/0104139 A1 | 5/2011 | Faber |
| 2011/0110917 A1 | 5/2011 | Schimmel et al. |
| 2011/0117572 A1 | 5/2011 | Kim et al. |
| 2011/0124582 A1 | 5/2011 | Kim et al. |
| 2011/0136119 A1 | 6/2011 | Kim et al. |
| 2011/0150885 A1 | 6/2011 | Watkins et al. |
| 2011/0189195 A1 | 8/2011 | Kim et al. |
| 2011/0250701 A1 | 10/2011 | Kim et al. |
| 2011/0256119 A1 | 10/2011 | Kim et al. |
| 2012/0004185 A1 | 1/2012 | Greene |
| 2012/0010141 A1 | 1/2012 | Kim |
| 2012/0015383 A1 | 1/2012 | Park et al. |
| 2012/0058133 A1 | 3/2012 | Whitman et al. |
| 2012/0064082 A1 | 3/2012 | Watkins et al. |
| 2013/0052177 A1 | 2/2013 | Schimmel et al. |
| 2013/0108630 A1 | 5/2013 | Watkins et al. |
| 2013/0129703 A1 | 5/2013 | Chiang et al. |
| 2013/0129704 A1 | 5/2013 | Greene et al. |
| 2013/0129705 A1 | 5/2013 | Greene et al. |
| 2013/0142774 A1 | 6/2013 | Greene et al. |
| 2013/0195832 A1 | 8/2013 | Greene et al. |
| 2013/0202574 A1 | 8/2013 | Greene et al. |
| 2013/0202575 A1 | 8/2013 | Greene et al. |
| 2013/0202576 A1 | 8/2013 | Greene et al. |
| 2013/0209434 A1 | 8/2013 | Greene et al. |
| 2013/0209472 A1 | 8/2013 | Greene et al. |
| 2013/0224173 A1 | 8/2013 | Greene et al. |
| 2013/0224174 A1 | 8/2013 | Greene et al. |
| 2013/0230505 A1 | 9/2013 | Greene et al. |
| 2013/0230507 A1 | 9/2013 | Greene et al. |
| 2013/0230508 A1 | 9/2013 | Greene et al. |
| 2013/0236440 A1 | 9/2013 | Greene et al. |
| 2013/0236455 A1 | 9/2013 | Greene et al. |
| 2013/0243745 A1 | 9/2013 | Greene et al. |
| 2013/0243766 A1 | 9/2013 | Zhou et al. |
| 2013/0273045 A1 | 10/2013 | Watkins et al. |
| 2013/0280230 A1 | 10/2013 | Greene et al. |
| 2013/0287755 A1 | 10/2013 | Greene et al. |
| 2013/0315887 A1 | 11/2013 | Greene et al. |
| 2013/0330312 A1 | 12/2013 | Greene et al. |
| 2013/0344096 A1 | 12/2013 | Chiang et al. |
| 2014/0066321 A1 | 3/2014 | Xu et al. |
| 2014/0255375 A1 | 9/2014 | Belani et al. |
| 2014/0255378 A1 | 9/2014 | Watkins et al. |
| 2014/0302075 A1 | 10/2014 | Buechler et al. |
| 2014/0349369 A1 | 11/2014 | Buechler et al. |
| 2014/0363415 A1 | 12/2014 | Greene et al. |
| 2014/0371294 A1 | 12/2014 | Zhou et al. |
| 2015/0064188 A1 | 3/2015 | Greene |
| 2015/0093799 A1 | 4/2015 | Chiang et al. |
| 2015/0140072 A1 | 5/2015 | Watkins et al. |
| 2015/0159148 A1 | 6/2015 | Buechler et al. |
| 2015/0231214 A1 | 8/2015 | Greene et al. |
| 2015/0240227 A1 | 8/2015 | Greene et al. |
| 2015/0240228 A1 | 8/2015 | Greene et al. |
| 2015/0252347 A1 | 9/2015 | Greene et al. |

(56) References Cited

U.S. PATENT DOCUMENTS

| | | |
|---|---|---|
| 2015/0252348 A1 | 9/2015 | Greene et al. |
| 2015/0252349 A1 | 9/2015 | Greene et al. |
| 2015/0284704 A1 | 10/2015 | Greene et al. |
| 2015/0284705 A1 | 10/2015 | Greene et al. |
| 2015/0284706 A1 | 10/2015 | Greene et al. |
| 2015/0290304 A1 | 10/2015 | Greene et al. |
| 2015/0290305 A1 | 10/2015 | Greene et al. |
| 2015/0344866 A1 | 12/2015 | Greene et al. |
| 2015/0353914 A1 | 12/2015 | Greene et al. |
| 2015/0361411 A1 | 12/2015 | Greene et al. |
| 2015/0361412 A1 | 12/2015 | Greene et al. |
| 2015/0361413 A1 | 12/2015 | Greene et al. |
| 2016/0010075 A1 | 1/2016 | Greene et al. |
| 2016/0017311 A1 | 1/2016 | Greene |

FOREIGN PATENT DOCUMENTS

| | | |
|---|---|---|
| CN | 1341727 | 3/2002 |
| CN | 1352242 | 6/2002 |
| CN | 1352252 | 6/2002 |
| EP | 0785265 | 7/1997 |
| EP | 0893494 | 1/1999 |
| EP | 0893496 | 1/1999 |
| EP | 0897004 | 2/1999 |
| EP | 1275720 | 1/2003 |
| EP | 1300468 | 4/2003 |
| EP | 1377305 | 1/2009 |
| EP | 1776138 | 10/2009 |
| EP | 2177610 | 4/2010 |
| EP | 1274834 | 7/2010 |
| EP | 2084190 | 3/2011 |
| JP | 2002-511738 | 4/2002 |
| JP | 2008-508349 | 3/2008 |
| WO | WO 97/25426 | 7/1997 |
| WO | WO 97/26351 | 7/1997 |
| WO | WO 97/39017 | 10/1997 |
| WO | WO 98/14591 | 4/1998 |
| WO | WO 98/36072 | 8/1998 |
| WO | WO 98/50554 | 11/1998 |
| WO | WO 99/45130 | 9/1999 |
| WO | WO 01/07628 | 2/2001 |
| WO | WO 01/19999 | 3/2001 |
| WO | WO 01/64892 | 9/2001 |
| WO | WO 01/74841 | 10/2001 |
| WO | WO 01/75067 | 10/2001 |
| WO | WO 01/75078 | 10/2001 |
| WO | WO 01/88188 | 11/2001 |
| WO | WO 01/90330 | 11/2001 |
| WO | WO 01/94568 | 12/2001 |
| WO | WO 02/44349 | 6/2002 |
| WO | WO 02/055663 | 7/2002 |
| WO | WO 02/059323 | 8/2002 |
| WO | WO 02/067970 | 9/2002 |
| WO | WO 03/009813 | 2/2003 |
| WO | WO 03/080648 | 10/2003 |
| WO | WO 03/094862 | 11/2003 |
| WO | WO 2004/030615 | 4/2004 |
| WO | WO 2004/087875 | 10/2004 |
| WO | WO 2005/019258 | 3/2005 |
| WO | WO 2005/019415 | 3/2005 |
| WO | WO 2005/102395 | 11/2005 |
| WO | WO 2005/117954 | 12/2005 |
| WO | WO 2006/016217 | 2/2006 |
| WO | WO 2006/057500 | 6/2006 |
| WO | WO 2007/064941 | 6/2007 |
| WO | WO 2007/139397 | 12/2007 |
| WO | WO 2008/007818 | 1/2008 |
| WO | WO 2008/016356 | 2/2008 |
| WO | WO 2008/021290 | 2/2008 |
| WO | WO 2008/133359 | 11/2008 |
| WO | WO 2009/059056 | 5/2009 |
| WO | WO 2009/114623 | 9/2009 |
| WO | WO 2009/152247 | 12/2009 |
| WO | WO 2009/158649 | 12/2009 |
| WO | WO 2010/021415 | 2/2010 |
| WO | WO 2010/041892 | 4/2010 |
| WO | WO 2010/041913 | 4/2010 |
| WO | WO 2010/090471 | 8/2010 |
| WO | WO 2010/096170 | 8/2010 |
| WO | WO 2010/099477 | 9/2010 |
| WO | WO 2010/107825 | 9/2010 |
| WO | WO 2010/120509 | 10/2010 |
| WO | WO 2011/072265 | 6/2011 |
| WO | WO 2011/072266 | 6/2011 |
| WO | WO 2011/097031 | 8/2011 |
| WO | WO 2011/139714 | 11/2011 |
| WO | WO 2011/139799 | 11/2011 |
| WO | WO 2011/139801 | 11/2011 |
| WO | WO 2011/139853 | 11/2011 |
| WO | WO 2011/139854 | 11/2011 |
| WO | WO 2011/139907 | 11/2011 |
| WO | WO 2011/139986 | 11/2011 |
| WO | WO 2011/139988 | 11/2011 |
| WO | WO 2011/140132 | 11/2011 |
| WO | WO 2011/140135 | 11/2011 |
| WO | WO 2011/140266 | 11/2011 |
| WO | WO 2011/140267 | 11/2011 |
| WO | WO 2011/143482 | 11/2011 |
| WO | WO 2011/146410 | 11/2011 |
| WO | WO 2011/150279 | 12/2011 |
| WO | WO 2011/153277 | 12/2011 |
| WO | WO 2012/009289 | 1/2012 |
| WO | WO 2012/021247 | 2/2012 |
| WO | WO 2012/021249 | 2/2012 |
| WO | WO 2012/027611 | 3/2012 |
| WO | WO 2012/048125 | 4/2012 |
| WO | WO 2012/158945 | 11/2012 |
| WO | WO 2013/022982 | 2/2013 |
| WO | WO 2013/086216 | 6/2013 |
| WO | WO 2013/086228 | 6/2013 |
| WO | WO 2013/115926 | 8/2013 |
| WO | WO 2013/123432 | 8/2013 |

OTHER PUBLICATIONS

Office Action for European Patent Application No. 06838844.6, mailed Apr. 9, 2009.
Office Action for U.S. Appl. No. 12/085,884, mailed Jan. 20, 2011.
International Preliminary Report on Patentability for International Application No. PCT/US2006/046106, dated Jun. 4, 2008.
International Search Report and Written Opinion for International Application No. PCT/US2006/046106, mailed Aug. 9, 2007.
Supplementary European Search Report for European Application No. 10746935.5, mailed Oct. 26, 2012.
Office Action for U.S. Appl. No. 13/203,831, mailed Oct. 7, 2013, 20 pages.
International Preliminary Report on Patentability for International Application No. PCT/US2010/025642, dated Aug. 30, 2011.
International Search Report and Written Opinion for International Application No. PCT/US2010/025642, mailed Oct. 29, 2010.
Supplementary European Search Report for European Application No. 10764856.0, mailed Sep. 5, 2012.
Office Action for U.S. Appl. No. 12/751,358, mailed Dec. 2, 2014.
Office Action for U.S. Appl. No. 12/751,358, mailed Jun. 11, 2014.
Office Action for U.S. Appl. No. 12/751,358, mailed Oct. 3, 2011.
Office Action for U.S. Appl. No. 12/751,358, mailed Mar. 3, 2011.
International Preliminary Report on Patentability for International Application No. PCT/US2010/029377, dated Oct. 4, 2011.
International Search Report and Written Opinion for International Application No. PCT/US2010/029377, mailed Jan. 26, 2011.
Office Action for U.S. Appl. No. 12/725,272, mailed Jul. 13, 2012, 9 pages.
Restriction Requirement for U.S. Appl. No. 12/725,272, mailed Apr. 27, 2012.
International Preliminary Report on Patentability for International Application No. PCT/US2010/027525, dated Sep. 20, 2011.
International Search Report and Written Opinion for International Application No. PCT/US2010/027525, mailed Jan. 10, 2011.
International Search Report and Written Opinion for International Application No. PCT/US2010/059964, mailed Aug. 25, 2011.

(56) References Cited

OTHER PUBLICATIONS

International Preliminary Report on Patentability for International Application No. PCT/US2010/059964, dated Jun. 12, 2012.
International Preliminary Report on Patentability for International Application No. PCT/US2010/059963, dated Jun. 12, 2012, 18 pages.
International Search Report and Written Opinion for International Application No. PCT/US2010/059963, mailed May 12, 2011.
International Search Report and Written Opinion for International Application No. PCT/US2011/000210, mailed Aug. 12, 2011.
International Preliminary Report on Patentabiltity for International Application No. PCT/US2011/000210, dated Aug. 7, 2012.
Supplementary European Search Report for European Application No. 11778025.4, mailed Nov. 6, 2013.
International Search Report and Written Opinion for International Application No. PCT/US2011/034387, mailed on Mar. 23, 2012.
International Preliminary Report on Patentability for International Application No. PCT/US2011/034387, dated Oct. 30, 2012.
Supplementary European Search Report for European Application No. 11778026.2, mailed Oct. 22, 2013.
International Search Report and Written Opinion for International Application No. PCT/US2011/034388, mailed on Mar. 23, 2012.
International Preliminary Report on Patentability for International Application No. PCT/US2011/034388, dated Oct. 30, 2012.
Supplementary European Search Report for European Application No. 11807357.6, mailed Dec. 22, 2014.
Notice of Allowance for U.S. Appl. No. 13/809,750, mailed Oct. 17, 2014, 10 pages.
International Search Report and Written Opinion for International Application No. PCT/US2011/043596, mailed on Feb. 29, 2012.
International Preliminary Report on Patentability for International Application No. PCT/US2011/043596, dated Jan. 15, 2013.
Supplementary European Search Report for European Application No. 11778118.7, mailed Aug. 19, 2013.
International Search Report and Written Opinion for International Application No. PCT/US2011/034838, mailed Jan. 9, 2012.
International Preliminary Report on Patentability for International Application No. PCT/US2011/034838, dated Nov. 6, 2012.
International Search Report and Written Opinion for International Application No. PCT/US2011/033988, mailed on Feb. 9, 2012.
International Preliminary Report on Patentability for International Application No. PCT/US2011/033988, dated Oct. 30, 2012.
International Search Report and Written Opinion for International Application No. PCT/US2011/038240, mailed on Feb. 9, 2012.
International Preliminary Report on Patentability for International Application No. PCT/US2011/038240, dated Nov. 27, 2012.
Supplementary European Search Report for European Application No. 11778296.1, mailed Nov. 12, 2013.
International Search Report and Written Opinion for International Application No. PCT/US2011/035250, mailed on Jan. 19, 2012.
International Preliminary Report on Patentability for International Application No. PCT/2011/035250, dated Nov. 6, 2012.
International Search Report and Written Opinion for International Application No. PCT/US2011/043756, mailed on Mar. 2, 2012.
International Preliminary Report on Patentability for International Application No. PCT/US2011/043756, dated Jan. 15, 2013.
International Search Report and Written Opinion for International Application No. PCT/US2011/043758, mailed on Mar. 2, 2012.
International Preliminary Report on Patentability for International Application No. PCT/US2011/043758, dated Jan. 15, 2013.
International Search Report and Written Opinion for International Application No. PCT/US2011/034205, mailed on Feb. 8, 2012.
International Preliminary Report on Patentability for International Application No. PCT/US2011/034205, dated Oct. 30, 2012.
International Search Report and Written Opinion for International Application No. PCT/US2011/036684, mailed on Feb. 9, 2012.
International Preliminary Report on Patentability for International Application No. PCT/US2011/036684, dated Nov. 20, 2012.
International Search Report and Written Opinion for International Application No. PCT/US2011/038813, mailed on Mar. 28, 2012.
International Preliminary Report on Patentability for International Application No. PCT/US2011/038813, dated Dec. 4, 2012.
International Search Report and Written Opinion for International Application No. PCT/US2011/035056, mailed on Mar. 23, 2012.
International Preliminary Report on Patentability for International Application No. PCT/US2011/035056, dated Nov. 6, 2012.
International Search Report and Written Opinion for International Application No. PCT/US2011/035053, mailed Mar. 23, 2012.
International Preliminary Report on Patentability for International Application No. PCT/US2011/035053, dated Nov. 6, 2012.
Supplementary European Search Report for European Application No. 11778120.3, mailed Nov. 15, 2013.
International Search Report and Written Opinion for International Application No. PCT/US2011/034840, mailed on Feb. 10, 2012.
International Preliminary Report on Patentability for International Application No. PCT/US2011/034840, dated Nov. 6, 2012.
Supplementary European Search Report for European Application No. 11777984.3, mailed Oct. 18, 2013.
International Search Report and Written Opinion for International Application No. PCT/US2011/034207, mailed Feb. 8, 2012.
International Preliminary Report on Patentability for International Application No. PCT/US2011/034207, dated Oct. 30, 2012.
International Search Report and Written Opinion for International Application No. PCT/US2011/055130, mailed on May 14, 2012.
International Preliminary Report on Patentability for International Application No. PCT/US2011/055130, dated Apr. 9, 2013.
International Search Report and Written Opinion for International Application No. PCT/US2011/049223, mailed Mar. 27, 2012.
International Preliminary Report on Patentability for International Application No. PCT/US2011/049223, dated Feb. 26, 2013.
International Search Report and Written Opinion for International Application No. PCT/US2011/034626, mailed on Jan. 19, 2012.
International Preliminary Report on Patentability for International Application No. PCT/US2011/034626, dated Oct. 30, 2012.
Supplementary European Search Report for European Application No. 11781304.8, mailed Oct. 23, 2013.
International Search Report and Written Opinion for International Application No. PCT/US2011/036326, mailed on Feb. 9, 2012.
International Preliminary Report on Patentability for International Application No. PCT/US2011/036326, dated Nov. 20, 2012.
International Search Report and Written Opinion for International Application No. PCT/US2011/035251, mailed on Feb. 8, 2012.
International Preliminary Report on Patentability for International Application No. PCT/US2011/035251, dated Nov. 6, 2012.
International Search Report and Written Opinion for International Application No. PCT/US2012/068282, mailed on Apr. 1, 2013.
International Search Report and Written Opinion for International Application No. PCT/US2012/068296, mailed on Apr. 19, 2013.
Supplementary Partial European Search Report for European Application No. 12867497.5, mailed Apr. 29, 2015.
International Preliminary Report on Patentability for International Application No. PCT/US2012/071762, dated Jul. 1, 2014.
Adams, M. D. et al., "The genome sequence of *Drosophila melanogaster*," Science, 287(5961):2185-2195 (2000).
Aderem, A. et al., "Toll-like receptors in the induction of the innate immune response," Nature, 406:782-787 (2000).
Amaar, Y. G. et al., "Cloning and characterization of the C.elegans histidyl-tRNA synthetase gene," Nucleic Acids Research, 21(18):4344-4347 (1993).
Antonellis, A. et al., "The Role of Aminoacyl-tRNA Synthetases in Genetic Diseases," Annual Review of Genomics and Human Genetics, 9(1):87-107 (2008).
Ascherman, D. P. et al., "Critical Requirement for Professional APCs in Eliciting T Cell Responses to Novel Fragments of Histidyl-tRNA Synthetase (Jo-1) in Jo-1 Antibody-Positive Polymyositis," J. Immunol., 169:7127-7134 (2002).
Ascherman, D. P., "The Role of Jo-1 in the Immunopathogenesis of Polymyositis: Current Hypotheses," Current Rheumatology Reports, 5:425-430 (2003).
Barbasso, S. et al., "Sera From Anti-Jo-1-Positive Patients with Polymyositis and Interstitial Lung Disease Induce Expression of Intercellular Adhesion Molecule 1 in Human Lung Endothelial Cells," Arthritis & Rheumatism, 60(8):2524-2530 (2009).

(56) References Cited

OTHER PUBLICATIONS

Bernstein, R. M. et al., "Anti-Jo-1 antibody: a marker for myositis with interstitial lung disease," British Medical Journal, 289:151-152 (1984).
Blechynden, L.M. et al., "Sequence and polymorphism analysis of the murine gene encoding histidyl-tRNA synthetase," Gene, 178:151-156 (1996).
Blechynden, L.M. et al., "Myositis Induced by Naked DNA Immunization with the Gene for Histidyl-tRNA Synthetase," Human Gene Therapy, 8:1469-1480 (Aug. 10, 1997).
Blum, D. et al., "Extracellular toxicity of 6-hydroxydopamine on PC12 cells," Neuroscience Letters, 283(3):193-196 (2000).
Branden et al., "Introduction to Protein Structure," Garland Publishing Inc., New York, p. 247 (1991).
Brightbill, H. D. et al., "Toll-like receptors: molecular mechanisms of the mammalian immune response," Immunology, 101:1-10 (2000).
Broun, P. et al., "Catalytic plasticity of fatty acid modification enzymes underlying chemical diversity of plant lipids," Science, 282:1315-1317 (1998).
Brown, M. V. et al., "Mammalian aminoacyl-tRNA synthetases: Cell signaling functions of the protein translation machinery," Vascular Pharmacology, 52(1-2):21-26 (2010).
Car, B. D. et al., "Interferon y Receptor Deficient Mice Are Resistant to Endotoxic Shock," J. Exp. Med., 179:1437-1444, 1994.
Casciola-Rosen, L. et al., "Cleavage by Granzyme B Is Strongly Predictive of Autoantigen Status: Implications for Initiation of Autoimmunity," J. Exp. Med., 190(6):815-825 (1999).
Casciola-Rosen, L., "Histidyl-Transfer RNA Synthetase: A Key Participant in Idiopathic Inflammatory Myopathies," Arthritis and Rheumatism, 63(2):331-333 (2011).
Cheong et al., "Structure of the N-terminal extension of human aspartyl-tRNA synthetase: implications for its biological function," The International Journal of Biochemistry & Cell Biology, 35:1548-1557, 2003.
Chica, R. A. et al., "Semi-rational approaches to engineering enzyme activity: combining the benefits of directed evolution and rational design," Curr. Opin. Biotechnol., 16:378-384 (2005).
Choi, W. S. et al., "Two Distinct Mechanisms Are Involved in 6-Hydroxydopamine-and MPP+-Induced Dopaminergic Neuronal Cell Death: Role of Caspases, ROS, and JNK," Journal of Neuroscience Research, 57(1):86-94 (1999).
Datson, N. A. et al., "Development of the first marmoset-specific DNA microarray (EUMAMA): a new genetic tool for large-scale expression profiling in a non-human primate," BMC Genomics, 8(190):1-9 (2007).
Deiters, A. et al., "Site-specific PEGylation of proteins containing unnatural amino acids," Bioorg Med Chem Lett, 14(23):5743-5745 (2004).
Delgado, C. et al., "The uses and properties of PEG-linked proteins," Critical Reviews in Therapeutic Drug Carrier Systems, 9(3,4):249-304 (1992).
Devos, D. et al., "Practical limits of function prediction," Proteins: Structure, Function, and Genetics, 41:98-107 (2000).
Dumont, J. A. et al., "Monomeric Fc Fusions: Impact on pharmacokinetic and biological activity of protein therapeutics," Biodrugs: Clinical Immunotherapeutics, Biopharmaceuticals and Gene Therapy, 20(3):151-160 (2006).
Eriani, G. et al., "Cytoplasmic aspartyl-tRNA synthetase from *Saccharomyces cerevisiae*. Study of its functional organisation by deletion anaylsis," European Journal of Biochemistry, 200(2):337-343 (1991).
Escalante, C., et al., "Expression of human aspartyl-tRNA synthetase in COS cells," Molecular and Cellular Biochemistry, 140(1):55-63 (1994).
Escalante, C. et al., "Expression of Human Aspartyl-tRNA Synthetase in *Escherichia coli*: Functional Analysis of the N-Terminal Putative Amphiphilic Helix," The Journal of Biological Chemistry, 268(8):6014-6023 (1993).

Ewalt, K. L. et al., "Activation of Angiogenic Signaling Pathways by Two Human tRNA Synthetases," Biochemistry, 41(45):13344-13349 (2002).
Fontanesi, L. et al., "Identification and association analysis of several hundred single nucleotide polymorphisms within candidate genes for back fat thickness in Italian large white pigs using a selective genotyping approach," J Anim Sci, 90(8):2450-2464 (2012).
Frommhold, D. et al., "Sialyltransferase ST3Gal-IV controls CXCR2-mediated firm leukocyte arrest during inflammation," Journal of Experimental Medicine, 205(6):1435-1446 (2008).
GenBank Accession No. AA131122, Nov. 27, 1996.
GenBank Accession No. AA281081, Apr. 2, 1997.
GenBank Accession No. AA355758, Apr. 21, 1997.
GenBank Accession No. AA984229, published May 27, 1998.
GenBank Accession No. AAP36306.1, published May 13, 2003.
GenBank Accession No. BT007638.1, published May 13, 2003.
GenBank Accession No. AI985978, Aug. 31, 1999.
GenBank Accession No. AK055917, published Jan. 19, 2008.
GenBank Accession No. AK124831, published Jul. 3, 2008.
GenBank Accession No. AK225776, published Jul. 22, 2006.
GenBank Accession No. AK293154, published Jul. 24, 2008.
GenBank Accession No. AK295219, published Jul. 24, 2008.
GenBank Accession No. AK302295, published Jul. 24, 2008.
GenBank Accession No. AK303778, published Jul. 24, 2008.
GenBank Accession No. AU129836, published Feb. 18, 2011.
GenBank Accession No. AV685924, Sep. 25, 2000.
GenBank Accession No. AW070887, Oct. 13, 1999.
GenBank Accession No. BE561651, Aug. 10, 2000.
GenBank Accession No. BE695954, Sep. 11, 2000.
GenBank Accession No. BE872272, published Jan. 13, 2011.
GenBank Accession No. BF437672, Nov. 29, 2000.
GenBank Accession No. BF526055, Dec. 4, 2000.
GenBank Accession No. BF791754, published Jan. 13, 2011.
GenBank Accession No. BG108830, published Jun. 1, 2001.
GenBank Accession No. BG700836, May 7, 2001.
GenBank Accession No. BI559642, Sep. 4, 2001.
GenBank Accession No. BI599431, Sep. 5, 2001.
GenBank Accession No. BM827507, Mar. 6, 2002.
GenBank Accession No. BP268250, published Feb. 10, 2011.
GenBank Accession No. BQ002750, Mar. 26, 2002.
GenBank Accession No. BU599828, Sep. 19, 2002.
GenBank Accession No. CA865450, Dec. 20, 2002.
GenBank Accession No. CA865692, Dec. 20, 2002.
GenBank Accession No. CD694017, Jun. 25, 2003.
GenBank Accession No. CR749809, Oct. 7, 2008.
GenBank Accession No. DA083923, published Feb. 17, 2011.
GenBank Accession No. DB146646, published Feb. 16, 2011.
GenBank Accession No. J05032, published Apr. 27, 1993.
GenBank Accession No. Q7QD89, Anopheles gambiae Sequence Committee, submitted Apr. 2002, [Retrieved from the Internet Apr. 24, 2007], <URL: http://www.ncbi.nlm.nih.gov/entrez/viewer.fcgi?db=protein&val=74803944>.
GenBank Accession No. Q9VV60, published May 1, 2000.
GenBank Accession No. Z11518, published Oct. 7, 2008.
Goldgur, Y. et al., "The crystal structure of phenylalanyl-tRNA synthetase from Thermus thermophilus complexed with cognate tRNA," Structure, 5(1):59-68 (1997).
Greenberg, Y. et al., "The novel fragment of tyrosyl tRNA synthetase, mini-TyrRS, is secreted to induce an angiogenic response in endothelial cells," FASEB Journal, 22(5):1597-1605 (2008).
Guijarro, J. I. et al., "Structure and Dynamics of the Anticodon Arm Binding Domain of Bacillus stearothermophilus Tyrosyl-tRNA Synthetase," Structure, 10(3):311-317 (2002).
Guo, R-T. et al., "Crystal structures and biochemical analyses suggest a unique mechanism and role for human glycyl-tRNA synthetase in Ap4A homeostasis," Journal of Biological Chemistry, 284(42):28968-28976 (2009).
Guo, M. et al., "Functional expansion of human tRNA synthetases achieved by structural inventions," FEBS Letters, 584(2):434-442 (2010).

(56) References Cited

OTHER PUBLICATIONS

Guo, M. et al., "New functions of aminoacyl-tRNA synthetases beyond translation," Nature Reviews Molecular Cell Biology, 11:668-674 (2010).

Hanrott, K. et al., "6-Hydroxydopamine-induced Apoptosis Is Mediated via Extracellular Auto-oxidation and Caspase 3-dependent Activation of Protein Kinase C8," The Journal of Biological Chemistry, 281(9):5373-5382 (2006).

Hausmann, C. D. et al., "Aminoacyl-tRNA synthetase complexes: molecular multitasking revealed," FEMS Microbiol. Rev., 32(4):705-721 (2008).

Hengstman, G. J. D. et al., "Anti-Jo-1 positive inclusion body myositis with a marked and sustained clinical improvement after oral prednisone," J. Neurol. Neurosurg. Psychiatry, 70(5):706 (2001).

Hou, Y-M. et al., "Sequence determination and modeling of structural motifs for the smallest monomeric aminoacyl-tRNA synthetase," Proc. Nat. Acad. Sci., 88(3):976-980 (1991).

Howard, O. M. Z. et al., "Histidyl-tRNA Synthetase and Asparaginyl-tRNA Synthetase, Autoantigens in Myositis, Activate Chemokine Receptors on T Lymphocytes and Immature Dendritic Cells," The Journal of Experimental Medicine, 196(6):781-791 (2002).

Howard, O. M. Z. et al., "Autoantigens signal through cheokine receptors: uveitis antigens induce CXCR3- and CRCR5-expressing lymphocytes and immature dendritic cells to migrate", Blood, 105(11) 4207-4214 (2005).

Ivakhno, S. S. et al., "Cytokine-Like Activities of Some Aminoacyl-tRNA Synthetases and Auxiliary p43 Cofactor of Aminoacylation Reactin and Their Role in Oncogenesis," Exp. Oncol., 26(4):250-255 (2004).

Ivanov, K. A. et al., "Non-canonical Functions of Aminoacyl-tRNA Synthetases," Biochemistry (Moscow), 65(8):888-897 (2000).

Izumi, Y. et al., "p-Quinone Mediates 6-Hydroxydopamine-Induced Dopaminergic Neuronal Death and Ferrous Iron Accelerates the conversion of p-Quinone Into Melanin Extracellularly," Journal of Neuroscience Research, 79(6):849-860 (2005).

Jacobo-Molina, A. et al., "cDNA Sequence, Predicted Primary Structure, and Evolving Amphiphilic Helix of Human Aspartyl-tRNA Synthetase," Journal of Biological Chemistry, 264(28):16608-16612 (1989).

Jura, M. et al., "Comprehensive Insight into human aminoacyl-tRNA synthetases as autoantigens in idiopathic inflammatory myopathies," Critical Reviews in Immunology, 27(6):559-572 (2007).

Kapoor, M. et al., "Mutational separation of aminoacylation and cytokine activities of human tyrosyl-tRNA synthetase," Chemistry & Biology, 16(5):531-539 (2009).

Katsumata, Y. et al., "Species-specific immune responses generated by histidyl-tRNA synthetase immunization are associated with muscle and lung inflammation," Journal of Autoimmunity, 29(2-3):174-186 (2007).

Katsumata, Y. et al., "Animal models in myositis," Current Opinion in Rheumatology, 20:681-685 (2008).

Kimchi-Sarfaty, C. et al., "A 'Silent' polymorphism in the MDR1 gene changes substrate specificty," Science, 315:525-528 (2007).

Kise, Y. et al., "A short peptide insertion crucial for angiostatic activity of human tryptophanyl-tRNA synthetase," Nature Structural & Molecular Biology, 11(2):149-156 (2004).

Kochendoerfer, G. G., "Site-specific polymer modification of therapeutic proteins," Current Opinion in Chemical Biology, 9:555-560 (2005).

Kovaleski, B. J. et al.,"In vitro characterization of the interaction between HIV-1 Gag and human lysyl-tRNA synthetase," J. Bio. Chem., 281(28):19449-19456 (2006).

Levine, S. M. et al., "Anti-aminoacyl tRNA synthetase immune responses: insights into the pathogenesis of the idiopathic inflammatory myopathies," Current Opinion in Rheumatology, 15(6):708-713 (2003).

Levine, S. M., et al., "Novel Conformation of Histidyl-Transfer RNA Synthetase in the Lung", Arthritis & Rheumatism, 56(8): 2729-2739 (2007).

Link, A. J. et al., "Discovery of aminoacyl-tRNA synthetase activity through cell-surface display of noncanonical amino acids," Proc. Nat. Acad. Sci., 103(27):10180-10185 (2006).

Lorber, B. et al., "Properties of N-terminal truncated yeast aspartyl-tRNA synthetase and structural characteristics of the cleaved domain," Eur. J. Biochem. 174, pp. 155-161 (1988).

Ma, P. T. S. et al., "Mevinolin, an inhibitor of cholesterol synthesis, induces mRNA for low density lipoprotein receptor in livers of hamsters and rabbits," Proc. Natl. Acad. Sci. USA, 83:8370-8374 (1986).

Martin, A. et al., "Epitope studies indicate that histidyl-tRNA synthetase is a stimulating antigen in idiopathic myositis," The FASEB Journal, 9:1226-1233 (1995).

Merritt, E. A. et al., "Crystal structure of the aspartyl-tRNA synthetase from Engamoeba histolytica," Mol. Biochem. Parasitol, 169(2):95-100 (2009).

Miller, F. W., et al., "Origin and Regulation of a Disease-specific Autoantibody Response, Antigenic Epitopes, Spectrotype Stability, and Isotype Restriction of Anti-Jo-1 Autoantibodies," J. Clin. Invest., 85:468-475 (1990).

Mirande, M. et al., "Engineering mammalian aspartyl-tRNA synthetase to probe structural features mediating its association with the multisynthetase complex," Eur. J. Biochem., 203(3):459-466 (1992).

Molecular Modeling Database (MMDB), "Solution Structures of the Whep-trs domain of human histidyl-trna synthetase," MMDB ID No. 35920, available for www.ncbi.nlm.nih.gov/Structure/mmdb, accessed Aug. 24, 2012.

Mukhopadhyay, R. et al., "The GAIT System: a gatekeeper of inflammatory gene expression," Trends in Biochemical Sciences, 34(7):324-331 (2009).

Nackley, A. G. et al., "Human Caechol-O-Methytransferase haplotypes modulate protein expression by altering mRNA secondary structure," Science, 314:1930-1933 (2006).

NCBI Accession No. NP001340, Feb. 27, 2011.

Ngo, J. T. et al., "Computational complexity, protein structure prediction, and the Levinthal paradox," In The Protein Folding Problem and Tertiary Structure Prediction, Merz et al. (ed.), Birkhauser, Boston, MA, pp. 433 and 492-495 (1994).

Nichols, R. C. et al., "Human isoleucyl-tRNA synthetase: sequence of the cDNA, alternative mRNA splicing, and the characteristics of an unusually long C-terminal extension," Gene, 155(2):299-304 (1995).

Nishikai, M. et al., "Heterogeneity of Precipitating Antibodies in Polymyositis and Dermatomyositis," Arthritis and Rheumatism, 23(8):881-888 (1980).

O'Hanlon, T. P. et al., "Genomic organization, transcriptional mapping, and evolutionary implications of the human bi-directional histidyl-tRNA synthetase locus (HARS/HARSL)," Biochemical and Biophysical Research Communications, 294:609-614 (2002).

Oppenheim, J. J. et al., "Autoantigens act as tissue-specific chemoattractants," Journal of Leukocyte Biology, 77:854-861 (2005).

Park, S. G., et al., "Aminoacyl tRNA synthetases and their connections to disease," PNAS, 105(32):11043-11049 (2008).

Park, S. G. et al., "Dose-dependent biphasic activity of tRNA synthetase-associating factor, p43, in angiogenesis," The Journal of Biological Chemistry, 277(47):45243-45248 (2002).

Park, S. G. et al., "Human lysyl-tRNA syntetase is secreted to trigger proinflammatory response," PNAS, 102(18):6356-6361 (2005).

Park, S. G. et al., "Is there an answer? Do aminoacyl-tRNA synthetases have biological functions other than in protein biosynthesis?" IUBMB Life, 58(9):556-558 (2006).

Parker, L. C. et al., "Toll-Like Receptor (TLR)2 and TLR4 Agonists Regulate CCR Expression in Human Monocytic Cells," The Journal of Immunology, 172:4977-4986 (2004).

(56) References Cited

OTHER PUBLICATIONS

Pierce, S. B. et al., "Mutations in mitochondrial histidyl tRNA synthetase HARS2 cause ovarian dysgenesis and sensorineural hearing loss of Perrault syndrome," PNAS, 108(16):6543-6548 (2011).
Quesniaux, V. F.J. et al., "Hematopoiesis, including lymphocyte developmet and maturation," Principles of Immunopharmacology, pp. 3-17 (2005).
Raben, N. et al., "A Motif in Human Histidyl-tRNA Synthetase Which Is Shared among Several Aminoacyl-tRNA Synthetases Is a Coiled-coil That is Essential for Enzymatic Activity and Contains the Major Autoantigenic Epitope," The Journal of Biological Chemistry, 269(39):24277-24283 (1994).
Reed, V. S. et al., "Characterization of a Novel N-terminal Peptide in Human Aspartyl-tRNA Synthetase," Journal of Biological Chemistry, 269(52):32937-32941 (1994).
Rho, S. B. et al., "Genetic dissection of protein-protein interactions in multi-tRNA synthetase complex," Proc. Natl. Acad. Sci. USA, 96:4488-4493 (1999).
Richardson, R. M. et al., "Role of the cytoplasmic tails of CXCR1 and CXCR2 in mediating leukocyte migration, activation, and regulation," Journal of Immunology, 170(6):2904-2911 (2003).
Rudinger-Thirion et al., "Misfolded human tRNA isodecoder binds and neutralizes a 3' UTR-embedded Alu element," Proc. Natl. Acad. Sci. USA, 108(40):E794-E802 (2011).
Sato et al., "Synergy and Cross-Tolerance Between Toll-Like Receptor (TLR) 2- and TLR4-Mediated Signaling Pathways," The Journal of Immunology, 165:7096-7101 (2000).
Sauna, Z. E. et al., "Silent polymorhisms speak: How they affect pharmacogenomics and the treatment of cancer," Cancer Res., 67(20):9609-9612 (2007).
Seburn, K. L. et al., "An active dominant mutation of glycyl-tRNA synthetase causes neuropathy in a Charcot-Marie-Tooth 2D mouse model," Neuron, 51(6):715-726 (2006).
Sen, S. et al., "Developments in directed evolution for improving enzyme functions," Appl. Biochem. Biotechnol., 143:212-223 (2007).
Smith, D. F. et al., "Leukocyte phosphoinositide-3 kinase γ is required for chemokine-induced, sustained adhesion under flow in vivo," Journal of Leukocyte Biology, 80(6):1491-1499 (2006).
Soejima, M. et al., "Role of Innate Immunity in a Murine Model of Histidyl-Transfer RNA Snythetase (Jo-1)-Mediated Myositis," Arthritis and Rheumatism, 63(2):479-487 (2011).
Sultan, S. M. et al., "Re-classifiyng myositis," Rheumatology, 49:831-833 (2010).
Tarabishy, A. B. et al., "Retinal Vasculitis Associated with the Anti-Synthetase Syndrome," Ocular Immunology & Inflamation, 18(1):16-18 (2010).
Targoff, I. N., "Update on myositis-specific and myositis-associated autoantibodies," Current Opinion in Rheumatology, 12:475-481 (2000).
Traves, S. L. et al., "Specific CXC but not CC chemokines cause elevated monocyte migration in COPD: a role for CXCR$_2$," Journal of Leukocyte Biology, 76(2):441-450 (2004).
Tsui, H. W. et al., "Transcriptional analyses of the gene region that encodes human histidyl-tRNA sysnthetase: identification of a novel bidirectional regulatory element," Gene, 131:201-208 (1993).
Tzioufas, A. G. et al., "Antisynthetase syndrome," Orphanet Encyclopedia, http:/www.orpha.net/data/patho/GB/uk-antisynthetase.pdf, pp. 1-5 Nov. 2001.
Veronese, F. M. et al., "Preface: Introduction and overview of peptide and protein pegylation," Advanced Drug Delivery Reviews, 54:453-456 (2002).
Wakasugi, K. et al., "Two distinct cytokines released from a human aminoacyl-tRNA synthetase," Science, 284:147-151 (1999).

Wakasugi, K. et al., "A human aminoacyl-tRNA synthetase as a regulator of angiogenesis," PNAS USA, 99(1):173-177 (2002).
Wakasugi, K. et al., "Induction of angiogenesis by a frament of human tyrosyl-tRNA synthetase," The Journal of Biological Chemistry, 277(23):20124-20126 (2002).
Wallace, E. A. et al., "Diagnosis and management of inflammatory muscle disease," The Journal of Musculoskeletal Medicine, 27(12):1-7 (2010).
Wan et al., "Epitope Map for a Growth Hormone Receptor Agonist Monoclonal Antibody, MAb 263," Molecular Endocrinology, 17(11):2240-2250 (2003).
Whisstock, J. C. et al., "Prediction of protein function from protein sequence," Q. Rev. Biophysics., 36(3):307-340 (2003).
Wishart, M. J. et al., "A single mutation converts a novel phosphotyrosine binding domain into a dual-specificity phosphatase," J. Biol. Chem., 270(45):26782-26785 (1995).
Witkowski, A. et al., "Conversion of β-ketoacyl synthase to a Malonyl Decarboxylase by replacement of the active cysteine with glutamine," Biochemistry, 38:11643-11650 (1999).
WPI Database Accession No. 2002-090149 (2013).
WPI Database Accession No. 2002-501208 (2013).
WPI Database Accession No. 2002-501210 (2013).
WPI Database Accession No. 2002-692409 (2013).
WPI Database Accession No. 2002-714440 (2013).
Xie, W. et al., "Long-range structural effects of a Charcot-Marie-Tooth disease-causing mutation in human glycyl-tRNA synthetase," PNAS, 104(24):9976-9981 (2007).
Yang, X-L et al., "Crystal structure of a human aminoacyl-tRNA synthetase cytokine," PNAS, 99(24):15369-15374 (2002).
Yang, X-L et al., "Relationship of two human tRNA synthetases used in cell signaling," Trends in Biochemical Sciences, 29(5):250-256 (2004).
Yang, X-L et al., "Gain-of-Function Mutational Activation of Human tRNA Synthetase Procytokine," Chemistry & Biology, 14(12):1323-1333 (2007).
Yokoyama, M. et al., "Effects of lipoprotein lipase and statins on cholesterol uptake into heart and skeletal muscle," J. Lipid Res., 48:646-655 (2007).
Yousem, S. A. et al., "The pulmonary histopathologic manifestations of the anti-Jo-1 tRNA synthetase syndrome," Modern Pathology, 23:874-880 (2010).
Yu, Y. et al., "Crystal structure of human tryptophanyl-tRNA synthetase catalytic fragment," The Journal of Biological Chemistry, 279(9):8378-8388 (2004).
Zalipsky, S. et al., "Use of functionalized poly(ethylene glycol)s for modification of polypeptides," Chapter 21 In: Poly(Ethylene Glycol) Chemistry: Biotechnical and Biomedical Applications, Harris, J. M. (ed.), pp. 347-370, Plenum Press, New York (1992).
Zhou, Q. et al., "Orthogonal use of a human tRNA synthetase active site to achieve multifunctionality," Nature Structural & Molecular Biology, 17(1):57-62 (2010).
Zwijnenburg, P. J. G. et al., B-1426, "Tyrosyl tRNA synthetase is a chemotactic factor in cerebrospinal fluid from patients with bacterial meningitis," Abstracts of the 42nd Interscience Conference on Antimicrobial Agents and Chemotherapy, San Diego, California, Sep. 27-30, 2002, Session 156(B), p. 55.
International Search Report and Written Opinion for International Application No. PCT/US2012/071762, mailed Aug. 20, 2013, 12 pages.
Chappel, M. S. et al., "Identification of the Fcγ Receptor Class I Binding Site in Human IgG Through the Use of Recombinant IgG1/IgG2 Hybrid and Point-Mutated Antibodies," PNAS USA, 88(20):9036-9040 (1991).
Guo, H. H., "Protein tolerance to random amino acid change," PNAS, 101(25):9205-9210 (Jun. 22, 2004).
Kern, D. et al., "The three cysteine residues of cytoplasmic aspartyl-tRNA synthetase from *Saccharomyces cerecisiae* are not essential for its activity," Eur. J. Biochem., 193(1):97-103 (1990).
Matthews, B. W., "Structural and genetic analysis of protein stability," Annu. Rev. Biochem., 62:139-160 (1993).

FIG. 6

SEQUENCE LISTING

<160> NUMBER OF SEQ ID NOS: 278

<210> SEQ ID NO 1
<211> LENGTH: 501
<212> TYPE: PRT
<213> ORGANISM: Homo sapiens

<400> SEQUENCE: 1

Met Pro Ser Ala Ser Ala Ser Arg Lys Ser Gln Glu Lys Pro Arg Glu
1               5                   10                  15

Ile Met Asp Ala Ala Glu Asp Tyr Ala Lys Glu Arg Tyr Gly Ile Ser
            20                  25                  30

Ser Met Ile Gln Ser Gln Glu Lys Pro Asp Arg Val Leu Val Arg Val
        35                  40                  45

Arg Asp Leu Thr Ile Gln Lys Ala Asp Glu Val Val Trp Val Arg Ala
    50                  55                  60

Arg Val His Thr Ser Arg Ala Lys Gly Lys Gln Cys Phe Leu Val Leu
65                  70                  75                  80

Arg Gln Gln Gln Phe Asn Val Gln Ala Leu Val Ala Val Gly Asp His

```
                      85                  90                  95
Ala Ser Lys Gln Met Val Lys Phe Ala Ala Asn Ile Asn Lys Glu Ser
                100                 105                 110

Ile Val Asp Val Glu Gly Val Val Arg Lys Val Asn Gln Lys Ile Gly
                115                 120                 125

Ser Cys Thr Gln Gln Asp Val Glu Leu His Val Gln Lys Ile Tyr Val
130                 135                 140

Ile Ser Leu Ala Glu Pro Arg Leu Pro Leu Gln Leu Asp Asp Ala Val
145                 150                 155                 160

Arg Pro Glu Ala Glu Gly Glu Gly Arg Ala Thr Val Asn Gln
                165                 170                 175

Asp Thr Arg Leu Asp Asn Arg Val Ile Asp Leu Arg Thr Ser Thr Ser
                180                 185                 190

Gln Ala Val Phe Arg Leu Gln Ser Gly Ile Cys His Leu Phe Arg Glu
                195                 200                 205

Thr Leu Ile Asn Lys Gly Phe Val Glu Ile Gln Thr Pro Lys Ile Ile
                210                 215                 220

Ser Ala Ala Ser Glu Gly Gly Ala Asn Val Phe Thr Val Ser Tyr Phe
225                 230                 235                 240

Lys Asn Asn Ala Tyr Leu Ala Gln Ser Pro Gln Leu Tyr Lys Gln Met
                245                 250                 255

Cys Ile Cys Ala Asp Phe Glu Lys Val Phe Ser Ile Gly Pro Val Phe
                260                 265                 270

Arg Ala Glu Asp Ser Asn Thr His Arg His Leu Thr Glu Phe Val Gly
                275                 280                 285

Leu Asp Ile Glu Met Ala Phe Asn Tyr His Tyr His Glu Val Met Glu
                290                 295                 300

Glu Ile Ala Asp Thr Met Val Gln Ile Phe Lys Gly Leu Gln Glu Arg
305                 310                 315                 320

Phe Gln Thr Glu Ile Gln Thr Val Asn Lys Gln Phe Pro Cys Glu Pro
                325                 330                 335

Phe Lys Phe Leu Glu Pro Thr Leu Arg Leu Glu Tyr Cys Glu Ala Leu
                340                 345                 350

Ala Met Leu Arg Glu Ala Gly Val Glu Met Gly Asp Glu Asp Leu
                355                 360                 365

Ser Thr Pro Asn Glu Lys Leu Leu Gly His Leu Val Lys Glu Lys Tyr
                370                 375                 380

Asp Thr Asp Phe Tyr Ile Leu Asp Lys Tyr Pro Leu Ala Val Arg Pro
385                 390                 395                 400

Phe Tyr Thr Met Pro Asp Pro Arg Asn Pro Lys Gln Ser Asn Ser Tyr
                405                 410                 415

Asp Met Phe Met Arg Gly Glu Glu Ile Leu Ser Gly Ala Gln Arg Ile
                420                 425                 430

His Asp Pro Gln Leu Leu Thr Glu Arg Ala Leu His His Gly Ile Asp
                435                 440                 445

Leu Glu Lys Ile Lys Ala Tyr Ile Asp Ser Phe Arg Phe Gly Ala Pro
                450                 455                 460

Pro His Ala Gly Gly Gly Ile Gly Leu Glu Arg Val Thr Met Leu Phe
465                 470                 475                 480

Leu Gly Leu His Asn Val Arg Gln Thr Ser Met Phe Pro Arg Asp Pro
                485                 490                 495

Lys Arg Leu Thr Pro
                500
```

<210> SEQ ID NO 2
<211> LENGTH: 1506
<212> TYPE: DNA
<213> ORGANISM: Homo sapiens

<400> SEQUENCE: 2

```
atgcccagcg ccagcgccag ccgcaagagt caggagaagc cgcgggagat catggacgcg      60
gcggaagatt atgctaaaga gagatatgga atatcttcaa tgatacaatc acaagaaaaa     120
ccagatcgag ttttggttcg ggttagagac ttgacaatac aaaaagctga tgaagttgtt     180
tgggtacgtg caagagttca tacaagcaga gctaaaggga acagtgctt cttagtccta      240
cgtcagcagc agtttaatgt ccaggctctt gtggcggtgg agaccatgc aagcaagcag      300
atggttaaat ttgctgccaa catcaacaaa gagagcattg tggatgtaga aggtgttgtg     360
agaaaagtga atcagaaaat tggaagctgt acacagcaag acgttgagtt acatgttcag     420
aagatttatg tgatcagttt ggctgaaccc cgtctgcccc tgcagctgga tgatgctgtt     480
cggcctgagg cagaaggaga gaggaagga agagctactg ttaaccagga tacaagatta      540
gacaacagag tcattgatct taggacatca actagtcagg cagtcttccg tctccagtct     600
ggcatctgcc atctcttccg agaaacttta attaacaaag gttttgtgga atccaaact      660
cctaaaatta tttcagctgc cagtgaagga ggagccaatg ttttactgt gtcatatttt      720
aaaaataatg catacctggc tcagtcccca cagctatata agcaaatgtg catttgtgct     780
gattttgaga aggtttttctc tattggacca gtattcagag cggaagactc taatacccat     840
agacatctaa ctgagtttgt tggtttggac attgaaatgg cttttaatta ccattaccac     900
gaagttatgg aagaaattgc tgacaccatg gtacaaatat caaaggact tcaagaaagg     960
tttcagactg aaattcaaac agtgaataaa cagttcccat gtgagccatt caaattttg    1020
gagccaactc taagactaga atattgtgaa gcattggcta tgcttaggga agctggagtc    1080
gaaatgggag atgaagacga tctgagcaca ccaaatgaaa agctgttggg tcatttggta    1140
aaggaaaagt atgatacaga ttttatatt cttgataaat atccattggc tgtaagacct    1200
ttctatacca tgcctgaccc aagaaatccc aaacagtcca actcttacga tatgttcatg    1260
agaggagaag aaatattgtc aggagctcaa agaatacatg atcctcaact gctaacagag    1320
agagctttac atcatggaat tgatttggag aaaattaagg cttacattga ttccttccgc    1380
tttggagccc tcctcatgc tggtggaggc attggattgg aacgagttac tatgctgttt    1440
ctgggattgc ataatgttcg tcagacctcc atgttccctc gtgatcccaa acgactcact    1500
ccttag                                                                1506
```

<210> SEQ ID NO 3
<211> LENGTH: 154
<212> TYPE: PRT
<213> ORGANISM: Homo sapiens

<400> SEQUENCE: 3

```
Met Pro Ser Ala Ser Ala Ser Arg Lys Ser Gln Glu Lys Pro Arg Glu
1               5                   10                  15

Ile Met Asp Ala Ala Glu Asp Tyr Ala Lys Glu Arg Tyr Gly Ile Ser
            20                  25                  30

Ser Met Ile Gln Ser Gln Glu Lys Pro Asp Arg Val Leu Val Arg Val
        35                  40                  45

Arg Asp Leu Thr Ile Gln Lys Ala Asp Glu Val Val Trp Val Arg Ala
```

```
                    50                  55                  60
Arg Val His Thr Ser Arg Ala Lys Gly Lys Gln Cys Phe Leu Val Leu
 65                  70                  75                  80

Arg Gln Gln Gln Phe Asn Val Gln Ala Leu Val Ala Val Gly Asp His
                 85                  90                  95

Ala Ser Lys Gln Met Val Lys Phe Ala Ala Asn Ile Asn Lys Glu Ser
                100                 105                 110

Ile Val Asp Val Glu Gly Val Val Arg Lys Val Asn Gln Lys Ile Gly
            115                 120                 125

Ser Cys Thr Gln Gln Asp Val Glu Leu His Val Gln Lys Ile Tyr Val
130                 135                 140

Ile Ser Leu Ala Glu Pro Arg Leu Pro Leu
145                 150
```

```
<210> SEQ ID NO 4
<211> LENGTH: 171
<212> TYPE: PRT
<213> ORGANISM: Homo sapiens

<400> SEQUENCE: 4

Met Pro Ser Ala Ser Ala Ser Arg Lys Ser Gln Glu Lys Pro Arg Glu
 1               5                  10                  15

Ile Met Asp Ala Ala Glu Asp Tyr Ala Lys Glu Arg Tyr Gly Ile Ser
                20                  25                  30

Ser Met Ile Gln Ser Gln Glu Lys Pro Asp Arg Val Leu Val Arg Val
            35                  40                  45

Arg Asp Leu Thr Ile Gln Lys Ala Asp Glu Val Val Trp Val Arg Ala
 50                  55                  60

Arg Val His Thr Ser Arg Ala Lys Gly Lys Gln Cys Phe Leu Val Leu
 65                  70                  75                  80

Arg Gln Gln Gln Phe Asn Val Gln Ala Leu Val Ala Val Gly Asp His
                 85                  90                  95

Ala Ser Lys Gln Met Val Lys Phe Ala Ala Asn Ile Asn Lys Glu Ser
                100                 105                 110

Ile Val Asp Val Glu Gly Val Val Arg Lys Val Asn Gln Lys Ile Gly
            115                 120                 125

Ser Cys Thr Gln Gln Asp Val Glu Leu His Val Gln Lys Ile Tyr Val
130                 135                 140

Ile Ser Leu Ala Glu Pro Arg Leu Pro Leu Gln Leu Asp Asp Ala Val
145                 150                 155                 160

Arg Pro Glu Ala Glu Gly Glu Glu Glu Gly Arg
                165                 170
```

```
<210> SEQ ID NO 5
<211> LENGTH: 174
<212> TYPE: PRT
<213> ORGANISM: Homo sapiens

<400> SEQUENCE: 5

Met Pro Ser Ala Ser Ala Ser Arg Lys Ser Gln Glu Lys Pro Arg Glu
 1               5                  10                  15

Ile Met Asp Ala Ala Glu Asp Tyr Ala Lys Glu Arg Tyr Gly Ile Ser
                20                  25                  30

Ser Met Ile Gln Ser Gln Glu Lys Pro Asp Arg Val Leu Val Arg Val
            35                  40                  45

Arg Asp Leu Thr Ile Gln Lys Ala Asp Glu Val Val Trp Val Arg Ala
```

```
                50                  55                  60
Arg Val His Thr Ser Arg Ala Lys Gly Lys Gln Cys Phe Leu Val Leu
 65                  70                  75                  80

Arg Gln Gln Gln Phe Asn Val Gln Ala Leu Val Ala Val Gly Asp His
                 85                  90                  95

Ala Ser Lys Gln Met Val Lys Phe Ala Ala Asn Ile Asn Lys Glu Ser
                100                 105                 110

Ile Val Asp Val Glu Gly Val Val Arg Lys Val Asn Gln Lys Ile Gly
                115                 120                 125

Ser Cys Thr Gln Gln Asp Val Glu Leu His Val Gln Lys Ile Tyr Val
                130                 135                 140

Ile Ser Leu Ala Glu Pro Arg Leu Pro Leu Gln Leu Asp Asp Ala Val
145                 150                 155                 160

Arg Pro Glu Ala Glu Gly Glu Glu Glu Gly Arg Ala Thr Val
                165                 170

<210> SEQ ID NO 6
<211> LENGTH: 182
<212> TYPE: PRT
<213> ORGANISM: Homo sapiens

<400> SEQUENCE: 6

Met Pro Ser Ala Ser Ala Ser Arg Lys Ser Gln Glu Lys Pro Arg Glu
  1               5                  10                  15

Ile Met Asp Ala Ala Glu Asp Tyr Ala Lys Glu Arg Tyr Gly Ile Ser
                 20                  25                  30

Ser Met Ile Gln Ser Gln Glu Lys Pro Asp Arg Val Leu Val Arg Val
                 35                  40                  45

Arg Asp Leu Thr Ile Gln Lys Ala Asp Glu Val Val Trp Val Arg Ala
                 50                  55                  60

Arg Val His Thr Ser Arg Ala Lys Gly Lys Gln Cys Phe Leu Val Leu
 65                  70                  75                  80

Arg Gln Gln Gln Phe Asn Val Gln Ala Leu Val Ala Val Gly Asp His
                 85                  90                  95

Ala Ser Lys Gln Met Val Lys Phe Ala Ala Asn Ile Asn Lys Glu Ser
                100                 105                 110

Ile Val Asp Val Glu Gly Val Val Arg Lys Val Asn Gln Lys Ile Gly
                115                 120                 125

Ser Cys Thr Gln Gln Asp Val Glu Leu His Val Gln Lys Ile Tyr Val
                130                 135                 140

Ile Ser Leu Ala Glu Pro Arg Leu Pro Leu Gln Leu Asp Asp Ala Val
145                 150                 155                 160

Arg Pro Glu Ala Glu Gly Glu Glu Glu Gly Arg Ala Thr Val Asn Gln
                165                 170                 175

Asp Thr Arg Leu Asp Asn
                180

<210> SEQ ID NO 7
<211> LENGTH: 184
<212> TYPE: PRT
<213> ORGANISM: Homo sapiens

<400> SEQUENCE: 7

Met Pro Ser Ala Ser Ala Ser Arg Lys Ser Gln Glu Lys Pro Arg Glu
  1               5                  10                  15

Ile Met Asp Ala Ala Glu Asp Tyr Ala Lys Glu Arg Tyr Gly Ile Ser
```

```
                    20                  25                  30
Ser Met Ile Gln Ser Gln Glu Lys Pro Asp Arg Val Leu Val Arg Val
            35                  40                  45

Arg Asp Leu Thr Ile Gln Lys Ala Asp Glu Val Val Trp Val Arg Ala
    50                  55                  60

Arg Val His Thr Ser Arg Ala Lys Gly Lys Gln Cys Phe Leu Val Leu
65                  70                  75                  80

Arg Gln Gln Gln Phe Asn Val Gln Ala Leu Val Ala Val Gly Asp His
                85                  90                  95

Ala Ser Lys Gln Met Val Lys Phe Ala Ala Asn Ile Asn Lys Glu Ser
            100                 105                 110

Ile Val Asp Val Glu Gly Val Val Arg Lys Val Asn Gln Lys Ile Gly
        115                 120                 125

Ser Cys Thr Gln Gln Asp Val Glu Leu His Val Gln Lys Ile Tyr Val
    130                 135                 140

Ile Ser Leu Ala Glu Pro Arg Leu Pro Leu Gln Leu Asp Asp Ala Val
145                 150                 155                 160

Arg Pro Glu Ala Glu Gly Glu Glu Gly Arg Ala Thr Val Asn Gln
                165                 170                 175

Asp Thr Arg Leu Asp Asn Arg Val
            180
```

```
<210> SEQ ID NO 8
<211> LENGTH: 274
<212> TYPE: PRT
<213> ORGANISM: Homo sapiens

<400> SEQUENCE: 8

Met Pro Ser Ala Ser Ala Ser Arg Lys Ser Gln Glu Lys Pro Arg Glu
1               5                   10                  15

Ile Met Asp Ala Ala Glu Asp Tyr Ala Lys Glu Arg Tyr Gly Ile Ser
            20                  25                  30

Ser Met Ile Gln Ser Gln Glu Lys Pro Asp Arg Val Leu Val Arg Val
        35                  40                  45

Arg Asp Leu Thr Ile Gln Lys Ala Asp Glu Val Val Trp Val Arg Ala
    50                  55                  60

Arg Val His Thr Ser Arg Ala Lys Gly Lys Gln Cys Phe Leu Val Leu
65                  70                  75                  80

Arg Gln Gln Gln Phe Asn Val Gln Ala Leu Val Ala Val Gly Asp His
                85                  90                  95

Ala Ser Lys Gln Met Val Lys Phe Ala Ala Asn Ile Asn Lys Glu Ser
            100                 105                 110

Ile Val Asp Val Glu Gly Val Val Arg Lys Val Asn Gln Lys Ile Gly
        115                 120                 125

Ser Cys Thr Gln Gln Asp Val Glu Leu His Val Gln Lys Ile Tyr Val
    130                 135                 140

Ile Ser Leu Ala Glu Pro Arg Leu Pro Leu Gln Leu Asp Asp Ala Val
145                 150                 155                 160

Arg Pro Glu Ala Glu Gly Glu Glu Gly Arg Ala Thr Val Asn Gln
                165                 170                 175

Asp Thr Arg Leu Asp Asn Arg Val Ile Asp Leu Arg Thr Ser Thr Ser
            180                 185                 190

Gln Ala Val Phe Arg Leu Gln Ser Gly Ile Cys His Leu Phe Arg Glu
        195                 200                 205
```

```
Thr Leu Ile Asn Lys Gly Phe Val Glu Ile Gln Thr Pro Lys Ile Ile
    210                 215                 220

Ser Ala Ala Ser Glu Gly Gly Ala Asn Val Phe Thr Val Ser Tyr Phe
225                 230                 235                 240

Lys Asn Asn Ala Tyr Leu Ala Gln Ser Pro Gln Leu Tyr Lys Gln Met
                245                 250                 255

Cys Ile Cys Ala Asp Phe Glu Lys Val Phe Ser Ile Gly Pro Val Phe
                260                 265                 270

Arg Ala
```

<210> SEQ ID NO 9
<211> LENGTH: 224
<212> TYPE: PRT
<213> ORGANISM: Homo sapiens

<400> SEQUENCE: 9

```
Met Pro Ser Ala Ser Ala Ser Arg Lys Ser Gln Glu Lys Pro Arg Glu
1               5                   10                  15

Ile Met Asp Ala Ala Glu Asp Tyr Ala Lys Glu Arg Tyr Gly Ile Ser
                20                  25                  30

Ser Met Ile Gln Ser Gln Glu Lys Pro Asp Arg Val Leu Val Arg Val
            35                  40                  45

Arg Asp Leu Thr Ile Gln Lys Ala Asp Glu Val Val Trp Val Arg Ala
    50                  55                  60

Arg Val His Thr Ser Arg Ala Lys Gly Lys Gln Cys Phe Leu Val Leu
65                  70                  75                  80

Arg Gln Gln Gln Phe Asn Val Gln Ala Leu Val Ala Val Gly Asp His
                85                  90                  95

Ala Ser Lys Gln Met Val Lys Phe Ala Ala Asn Ile Asn Lys Glu Ser
                100                 105                 110

Ile Val Asp Val Glu Gly Val Val Arg Lys Val Asn Gln Lys Ile Gly
            115                 120                 125

Ser Cys Thr Gln Gln Asp Val Glu Leu His Val Gln Lys Ile Tyr Val
    130                 135                 140

Ile Ser Leu Ala Glu Pro Arg Leu Pro Leu Gln Leu Asp Asp Ala Val
145                 150                 155                 160

Arg Pro Glu Ala Glu Gly Glu Glu Gly Arg Ala Thr Val Asn Gln
                165                 170                 175

Asp Thr Arg Leu Asp Asn Arg Val Ile Asp Leu Arg Thr Ser Thr Ser
                180                 185                 190

Gln Ala Val Phe Arg Leu Gln Ser Gly Ile Cys His Leu Phe Arg Glu
            195                 200                 205

Thr Leu Ile Asn Lys Gly Phe Val Glu Ile Gln Thr Pro Lys Ile Ile
    210                 215                 220
```

<210> SEQ ID NO 10
<211> LENGTH: 255
<212> TYPE: PRT
<213> ORGANISM: Homo sapiens

<400> SEQUENCE: 10

```
Gln Glu Lys Pro Asp Arg Val Leu Val Arg Val Arg Asp Leu Thr Ile
1               5                   10                  15

Gln Lys Ala Asp Glu Val Val Trp Val Arg Ala Arg Val His Thr Ser
                20                  25                  30

Arg Ala Lys Gly Lys Gln Cys Phe Leu Val Leu Arg Gln Gln Gln Phe
```

```
                35                  40                  45
Asn Val Gln Ala Leu Val Ala Val Gly Asp His Ala Ser Lys Gln Met
 50                  55                  60
Val Lys Phe Ala Ala Asn Ile Asn Lys Glu Ser Ile Val Asp Val Glu
 65                  70                  75                  80
Gly Val Val Arg Lys Val Asn Gln Lys Ile Gly Ser Cys Thr Gln Gln
                 85                  90                  95
Asp Val Glu Leu His Val Gln Lys Ile Tyr Val Ile Ser Leu Ala Glu
                100                 105                 110
Pro Arg Leu Pro Leu Gln Leu Asp Asp Ala Val Arg Pro Glu Ala Glu
                115                 120                 125
Gly Glu Glu Glu Gly Arg Ala Thr Val Asn Gln Asp Thr Arg Leu Asp
130                 135                 140
Asn Arg Val Ile Asp Leu Arg Thr Ser Thr Ser Gln Ala Val Phe Arg
145                 150                 155                 160
Leu Gln Ser Gly Ile Cys His Leu Phe Arg Glu Thr Leu Ile Asn Lys
                165                 170                 175
Gly Phe Val Glu Ile Gln Thr Pro Lys Ile Ile Ser Ala Ala Ser Glu
                180                 185                 190
Gly Gly Ala Asn Val Phe Thr Val Ser Tyr Phe Lys Asn Asn Ala Tyr
                195                 200                 205
Leu Ala Gln Ser Pro Gln Leu Tyr Lys Gln Met Cys Ile Cys Ala Asp
210                 215                 220
Phe Glu Lys Val Phe Ser Ile Gly Pro Val Phe Arg Ala Glu Asp Ser
225                 230                 235                 240
Asn Thr His Arg His Leu Thr Glu Phe Val Gly Leu Asp Ile Glu
                245                 250                 255

<210> SEQ ID NO 11
<211> LENGTH: 132
<212> TYPE: PRT
<213> ORGANISM: Homo sapiens

<400> SEQUENCE: 11

Asp Tyr Ala Lys Glu Arg Tyr Gly Ile Ser Ser Met Ile Gln Ser Gln
  1               5                  10                  15
Glu Lys Pro Asp Arg Val Leu Val Arg Val Arg Asp Leu Thr Ile Gln
                 20                  25                  30
Lys Ala Asp Glu Val Val Trp Val Arg Ala Arg Val His Thr Ser Arg
                 35                  40                  45
Ala Lys Gly Lys Gln Cys Phe Leu Val Leu Arg Gln Gln Gln Phe Asn
 50                  55                  60
Val Gln Ala Leu Val Ala Val Gly Asp His Ala Ser Lys Gln Met Val
 65                  70                  75                  80
Lys Phe Ala Ala Asn Ile Asn Lys Glu Ser Ile Val Asp Val Glu Gly
                 85                  90                  95
Val Val Arg Lys Val Asn Gln Lys Ile Gly Ser Cys Thr Gln Gln Asp
                100                 105                 110
Val Glu Leu His Val Gln Lys Ile Tyr Val Ile Ser Leu Ala Glu Pro
                115                 120                 125
Arg Leu Pro Leu
130

<210> SEQ ID NO 12
<211> LENGTH: 122
```

<212> TYPE: PRT
<213> ORGANISM: Homo sapiens

<400> SEQUENCE: 12

Ser Met Ile Gln Ser Gln Glu Lys Pro Asp Arg Val Leu Val Arg Val
1               5                   10                  15

Arg Asp Leu Thr Ile Gln Lys Ala Asp Glu Val Val Trp Val Arg Ala
            20                  25                  30

Arg Val His Thr Ser Arg Ala Lys Gly Lys Gln Cys Phe Leu Val Leu
        35                  40                  45

Arg Gln Gln Gln Phe Asn Val Gln Ala Leu Val Ala Val Gly Asp His
50                  55                  60

Ala Ser Lys Gln Met Val Lys Phe Ala Ala Asn Ile Asn Lys Glu Ser
65                  70                  75                  80

Ile Val Asp Val Glu Gly Val Val Arg Lys Val Asn Gln Lys Ile Gly
                85                  90                  95

Ser Cys Thr Gln Gln Asp Val Glu Leu His Val Gln Lys Ile Tyr Val
            100                 105                 110

Ile Ser Leu Ala Glu Pro Arg Leu Pro Leu
        115                 120

<210> SEQ ID NO 13
<211> LENGTH: 205
<212> TYPE: PRT
<213> ORGANISM: Homo sapiens

<400> SEQUENCE: 13

Tyr His Tyr His Glu Val Met Glu Glu Ile Ala Asp Thr Met Val Gln
1               5                   10                  15

Ile Phe Lys Gly Leu Gln Glu Arg Phe Gln Thr Glu Ile Gln Thr Val
            20                  25                  30

Asn Lys Gln Phe Pro Cys Glu Pro Phe Lys Phe Leu Glu Pro Thr Leu
        35                  40                  45

Arg Leu Glu Tyr Cys Glu Ala Leu Ala Met Leu Arg Glu Ala Gly Val
50                  55                  60

Glu Met Gly Asp Glu Asp Leu Ser Thr Pro Asn Gly Lys Leu Leu
65                  70                  75                  80

Gly His Leu Val Lys Glu Lys Tyr Asp Thr Asp Phe Tyr Ile Leu Asp
                85                  90                  95

Lys Tyr Pro Leu Ala Val Arg Pro Phe Tyr Thr Met Pro Asp Pro Arg
            100                 105                 110

Asn Pro Lys Gln Ser Asn Ser Tyr Asp Met Phe Met Arg Gly Glu Glu
        115                 120                 125

Ile Leu Ser Gly Ala Gln Arg Ile His Asp Pro Gln Leu Leu Thr Glu
130                 135                 140

Arg Ala Leu His His Gly Ile Asp Leu Glu Lys Ile Lys Ala Tyr Ile
145                 150                 155                 160

Asp Ser Phe Arg Phe Gly Ala Pro Pro His Ala Gly Gly Ile Gly
                165                 170                 175

Leu Glu Arg Val Thr Met Leu Phe Leu Gly Leu His Asn Val Arg Gln
            180                 185                 190

Thr Ser Met Phe Pro Arg Asp Pro Lys Arg Leu Thr Pro
        195                 200                 205

<210> SEQ ID NO 14
<211> LENGTH: 401

<212> TYPE: PRT
<213> ORGANISM: Homo sapiens

<400> SEQUENCE: 14

Met Val Lys Phe Ala Ala Asn Ile Asn Lys Glu Ser Ile Val Asp Val
1               5                   10                  15

Glu Gly Val Val Arg Lys Val Asn Gln Lys Ile Gly Ser Cys Thr Gln
            20                  25                  30

Gln Asp Val Glu Leu His Val Gln Lys Ile Tyr Val Ile Ser Leu Ala
        35                  40                  45

Glu Pro Arg Leu Pro Leu Gln Leu Asp Asp Ala Val Arg Pro Glu Ala
    50                  55                  60

Glu Gly Glu Glu Glu Gly Arg Ala Thr Val Asn Gln Asp Thr Arg Leu
65                  70                  75                  80

Asp Asn Arg Val Ile Asp Leu Arg Thr Ser Thr Ser Gln Ala Val Phe
                85                  90                  95

Arg Leu Gln Ser Gly Ile Cys His Leu Phe Arg Glu Thr Leu Ile Asn
            100                 105                 110

Lys Gly Phe Val Glu Ile Gln Thr Pro Lys Ile Ile Ser Ala Ala Ser
        115                 120                 125

Glu Gly Gly Ala Asn Val Phe Thr Val Ser Tyr Phe Lys Asn Asn Ala
130                 135                 140

Tyr Leu Ala Gln Ser Pro Gln Leu Tyr Lys Gln Met Cys Ile Cys Ala
145                 150                 155                 160

Asp Phe Glu Lys Val Phe Ser Ile Gly Pro Val Phe Arg Ala Glu Asp
                165                 170                 175

Ser Asn Thr His Arg His Leu Thr Glu Phe Val Gly Leu Asp Ile Glu
            180                 185                 190

Met Ala Phe Asn Tyr His Tyr His Glu Val Met Glu Gly Ile Ala Asp
        195                 200                 205

Thr Met Val Gln Ile Phe Lys Gly Leu Gln Glu Arg Phe Gln Thr Glu
    210                 215                 220

Ile Gln Thr Val Asn Lys Gln Phe Pro Cys Glu Pro Phe Lys Phe Leu
225                 230                 235                 240

Glu Pro Thr Leu Arg Leu Glu Tyr Cys Glu Ala Leu Ala Met Leu Arg
                245                 250                 255

Glu Ala Gly Val Glu Met Gly Asp Glu Asp Asp Leu Ser Thr Pro Asn
            260                 265                 270

Glu Lys Leu Leu Gly His Leu Val Lys Glu Lys Tyr Asp Thr Asp Phe
        275                 280                 285

Tyr Ile Leu Asp Lys Tyr Pro Leu Ala Val Arg Pro Phe Tyr Thr Met
    290                 295                 300

Pro Asp Pro Arg Asn Pro Lys Gln Ser Asn Ser Tyr Asp Met Phe Met
305                 310                 315                 320

Arg Gly Glu Glu Ile Leu Ser Gly Ala Gln Arg Ile His Asp Pro Gln
                325                 330                 335

Leu Leu Thr Glu Arg Ala Leu His His Gly Ile Asp Leu Glu Lys Ile
            340                 345                 350

Lys Ala Tyr Ile Asp Ser Phe Arg Phe Gly Ala Pro Pro His Ala Gly
        355                 360                 365

Gly Gly Ile Gly Leu Glu Arg Val Thr Met Leu Phe Leu Gly Leu His
    370                 375                 380

Asn Val Arg Gln Thr Ser Met Phe Pro Arg Asp Pro Lys Arg Leu Thr
385                 390                 395                 400

Pro

<210> SEQ ID NO 15
<211> LENGTH: 470
<212> TYPE: PRT
<213> ORGANISM: Homo sapiens

<400> SEQUENCE: 15

Met Pro Ser Ala Ser Ala Ser Arg Lys Ser Gln Glu Lys Pro Arg Glu
1               5                   10                  15

Ile Met Asp Ala Ala Glu Asp Tyr Ala Lys Glu Arg Tyr Gly Ile Ser
            20                  25                  30

Ser Met Ile Gln Ser Gln Glu Lys Pro Gly Lys Gln Cys Phe Leu Val
        35                  40                  45

Leu Arg Gln Gln Gln Phe Asn Val Gln Ala Leu Val Ala Val Gly Asp
    50                  55                  60

His Ala Ser Lys Gln Met Val Lys Phe Ala Ala Asn Ile Asn Lys Glu
65                  70                  75                  80

Ser Ile Val Asp Val Glu Gly Val Val Arg Lys Val Asn Gln Lys Ile
                85                  90                  95

Gly Ser Cys Thr Gln Gln Asp Val Glu Leu His Val Gln Lys Ile Tyr
            100                 105                 110

Val Ile Ser Leu Ala Glu Pro Arg Leu Pro Leu Gln Leu Asp Asp Ala
        115                 120                 125

Val Arg Pro Glu Ala Gly Glu Glu Gly Arg Ala Thr Val Asn
    130                 135                 140

Gln Asp Thr Arg Leu Asp Asn Arg Val Ile Asp Leu Arg Thr Ser Thr
145                 150                 155                 160

Ser Gln Ala Val Phe Arg Leu Gln Ser Gly Ile Cys His Leu Phe Arg
                165                 170                 175

Glu Thr Leu Ile Asn Lys Gly Phe Val Glu Ile Gln Thr Pro Lys Ile
            180                 185                 190

Ile Ser Ala Ala Ser Glu Gly Gly Ala Asn Val Phe Thr Val Ser Tyr
        195                 200                 205

Phe Lys Asn Asn Ala Tyr Leu Ala Gln Ser Pro Gln Leu Tyr Lys Gln
    210                 215                 220

Met Cys Ile Cys Ala Asp Phe Glu Lys Val Phe Ser Ile Gly Pro Val
225                 230                 235                 240

Phe Arg Ala Glu Asp Ser Asn Thr His Arg His Leu Thr Glu Phe Val
                245                 250                 255

Gly Leu Asp Ile Glu Met Ala Phe Asn Tyr His Tyr His Glu Val Met
            260                 265                 270

Glu Glu Ile Ala Asp Thr Met Val Gln Ile Phe Lys Gly Leu Gln Glu
        275                 280                 285

Arg Phe Gln Thr Glu Ile Gln Thr Val Asn Lys Gln Phe Pro Cys Glu
    290                 295                 300

Pro Phe Lys Phe Leu Glu Pro Thr Leu Arg Leu Glu Tyr Cys Glu Ala
305                 310                 315                 320

Leu Ala Met Leu Arg Glu Ala Gly Val Glu Met Gly Asp Glu Asp
                325                 330                 335

Leu Ser Thr Pro Asn Glu Lys Leu Leu Gly His Leu Val Lys Glu Lys
            340                 345                 350

Tyr Asp Thr Asp Phe Tyr Ile Leu Asp Lys Tyr Pro Leu Ala Val Arg
        355                 360                 365

```
Pro Phe Tyr Thr Met Pro Asp Pro Arg Asn Pro Lys Gln Ser Asn Ser
        370                 375                 380

Tyr Asp Met Phe Met Arg Gly Glu Glu Ile Leu Ser Gly Ala Gln Arg
385                 390                 395                 400

Ile His Asp Pro Gln Leu Leu Thr Glu Arg Ala Leu His His Gly Ile
                405                 410                 415

Asp Leu Glu Lys Ile Lys Ala Tyr Ile Asp Ser Phe Arg Phe Gly Ala
                420                 425                 430

Pro Pro His Ala Gly Gly Ile Gly Leu Glu Arg Val Thr Met Leu
                435                 440                 445

Phe Leu Gly Leu His Asn Val Arg Gln Thr Ser Met Phe Pro Arg Asp
450                 455                 460

Pro Lys Arg Leu Thr Pro
465                 470

<210> SEQ ID NO 16
<211> LENGTH: 454
<212> TYPE: PRT
<213> ORGANISM: Homo sapiens

<400> SEQUENCE: 16

Met Pro Ser Ala Ser Ala Ser Arg Lys Ser Gln Glu Lys Pro Arg Glu
1               5                   10                  15

Ile Met Asp Ala Ala Glu Asp Tyr Ala Lys Glu Arg Tyr Gly Ile Ser
                20                  25                  30

Ser Met Ile Gln Ser Gln Glu Lys Pro Asp Arg Val Leu Val Arg Val
            35                  40                  45

Arg Asp Leu Thr Ile Gln Lys Ala Asp Glu Val Val Trp Val Arg Ala
        50                  55                  60

Arg Val His Thr Ser Arg Ala Lys Gly Lys Gln Cys Phe Leu Val Leu
65                  70                  75                  80

Arg Gln Gln Gln Phe Asn Val Gln Ala Leu Val Ala Val Gly Asp His
                    85                  90                  95

Ala Ser Lys Gln Met Val Lys Phe Ala Ala Asn Ile Asn Lys Glu Ser
                100                 105                 110

Ile Val Asp Val Glu Gly Val Val Arg Lys Val Asn Gln Lys Ile Gly
            115                 120                 125

Ser Cys Thr Gln Gln Asp Val Glu Leu His Val Gln Lys Thr Ser Thr
        130                 135                 140

Ser Gln Ala Val Phe Arg Leu Gln Ser Gly Ile Cys His Leu Phe Arg
145                 150                 155                 160

Glu Thr Leu Ile Asn Lys Gly Phe Val Glu Ile Gln Thr Pro Lys Ile
                165                 170                 175

Ile Ser Ala Ala Ser Glu Gly Gly Ala Asn Val Phe Thr Val Ser Tyr
                180                 185                 190

Phe Lys Asn Asn Ala Tyr Leu Ala Gln Ser Pro Gln Leu Tyr Lys Gln
            195                 200                 205

Met Cys Ile Cys Ala Asp Phe Glu Lys Val Phe Ser Ile Gly Pro Val
        210                 215                 220

Phe Arg Ala Glu Asp Ser Asn Thr His Arg His Leu Thr Glu Phe Val
225                 230                 235                 240

Gly Leu Asp Ile Glu Met Ala Phe Asn Tyr His Tyr His Glu Val Met
                245                 250                 255

Glu Glu Ile Ala Asp Thr Met Val Gln Ile Phe Lys Gly Leu Gln Glu
```

```
                260              265              270
Arg Phe Gln Thr Glu Ile Gln Thr Val Asn Lys Gln Phe Pro Cys Glu
            275              280              285

Pro Phe Lys Phe Leu Glu Pro Thr Leu Arg Leu Glu Tyr Cys Glu Ala
        290              295              300

Leu Ala Met Leu Arg Glu Ala Gly Val Glu Met Gly Asp Glu Asp Asp
305              310              315              320

Leu Ser Thr Pro Asn Glu Lys Leu Leu Gly His Leu Val Lys Glu Lys
                325              330              335

Tyr Asp Thr Asp Phe Tyr Ile Leu Asp Lys Tyr Pro Leu Ala Val Arg
            340              345              350

Pro Phe Tyr Thr Met Pro Asp Pro Arg Asn Pro Lys Gln Ser Asn Ser
        355              360              365

Tyr Asp Met Phe Met Arg Gly Glu Glu Ile Leu Ser Gly Ala Gln Arg
    370              375              380

Ile His Asp Pro Gln Leu Leu Thr Glu Arg Ala Leu His His Gly Ile
385              390              395              400

Asp Leu Glu Lys Ile Lys Ala Tyr Ile Asp Ser Phe Arg Phe Gly Ala
                405              410              415

Pro Pro His Ala Gly Gly Gly Ile Gly Leu Glu Arg Val Thr Met Leu
            420              425              430

Phe Leu Gly Leu His Asn Val Arg Gln Thr Ser Met Phe Pro Arg Asp
        435              440              445

Pro Lys Arg Leu Thr Pro
    450

<210> SEQ ID NO 17
<211> LENGTH: 452
<212> TYPE: PRT
<213> ORGANISM: Homo sapiens

<400> SEQUENCE: 17

Met Pro Ser Ala Ser Ala Ser Arg Lys Ser Gln Glu Lys Pro Arg Glu
1               5                   10                  15

Ile Met Asp Ala Ala Glu Asp Tyr Ala Lys Glu Arg Tyr Gly Ile Ser
            20                  25                  30

Ser Met Ile Gln Ser Gln Glu Lys Pro Asp Arg Val Leu Val Arg Val
        35                  40                  45

Arg Asp Leu Thr Ile Gln Lys Ala Asp Glu Val Val Trp Val Arg Ala
    50                  55                  60

Arg Val His Thr Ser Arg Ala Lys Gly Lys Gln Cys Phe Leu Val Leu
65                  70                  75                  80

Arg Gln Gln Gln Phe Asn Val Gln Ala Leu Val Ala Val Gly Asp His
                85                  90                  95

Ala Ser Lys Gln Met Val Lys Phe Ala Ala Asn Ile Asn Lys Glu Ser
            100                 105                 110

Ile Val Asp Val Glu Gly Val Val Arg Lys Val Asn Gln Lys Ile Gly
        115                 120                 125

Ser Cys Thr Gln Gln Asp Val Glu Leu His Val Gln Lys Ile Tyr Val
    130                 135                 140

Ile Ser Leu Ala Glu Pro Arg Leu Pro Leu Gln Leu Asp Asp Ala Val
145                 150                 155                 160

Arg Pro Glu Ala Glu Gly Glu Glu Gly Arg Ala Thr Val Asn Gln
                165                 170                 175
```

-continued

```
Asp Thr Arg Leu Asp Asn Arg Val Ile Asp Leu Arg Thr Ser Thr Ser
            180                 185                 190

Gln Ala Val Phe Arg Leu Gln Ser Gly Ile Cys His Leu Phe Arg Glu
        195                 200                 205

Thr Leu Ile Asn Lys Gly Phe Val Glu Ile Gln Thr Pro Lys Ile Ile
    210                 215                 220

Ser Ala Ala Ser Glu Gly Gly Ala Asn Val Phe Thr Val Ser Tyr Phe
225                 230                 235                 240

Lys Asn Asn Ala Tyr Leu Ala Gln Ser Pro Gln Leu Tyr Lys Gln Met
                245                 250                 255

Cys Ile Cys Ala Asp Phe Glu Lys Val Phe Ser Ile Gly Pro Val Phe
            260                 265                 270

Arg Ala Glu Asp Ser Asn Thr His Arg His Leu Thr Glu Phe Val Gly
        275                 280                 285

Leu Asp Ile Glu Met Ala Phe Asn Tyr His Tyr His Glu Val Met Glu
    290                 295                 300

Glu Ile Ala Asp Thr Met Val Gln Ile Phe Lys Gly Leu Gln Glu Ser
305                 310                 315                 320

Thr Pro Asn Glu Lys Leu Leu Gly His Leu Val Lys Glu Lys Tyr Asp
                325                 330                 335

Thr Asp Phe Tyr Ile Leu Asp Lys Tyr Pro Leu Ala Val Arg Pro Phe
            340                 345                 350

Tyr Thr Met Pro Asp Pro Arg Asn Pro Lys Gln Ser Asn Ser Tyr Asp
        355                 360                 365

Met Phe Met Arg Gly Glu Glu Ile Leu Ser Gly Ala Gln Arg Ile His
    370                 375                 380

Asp Pro Gln Leu Leu Thr Glu Arg Ala Leu His His Gly Ile Asp Leu
385                 390                 395                 400

Glu Lys Ile Lys Ala Tyr Ile Asp Ser Phe Arg Phe Gly Ala Pro Pro
                405                 410                 415

His Ala Gly Gly Gly Ile Gly Leu Glu Arg Val Thr Met Leu Phe Leu
            420                 425                 430

Gly Leu His Asn Val Arg Gln Thr Ser Met Phe Pro Arg Asp Pro Lys
        435                 440                 445

Arg Leu Thr Pro
450

<210> SEQ ID NO 18
<211> LENGTH: 85
<212> TYPE: PRT
<213> ORGANISM: Homo sapiens

<400> SEQUENCE: 18

Met Pro Ser Ala Ser Ala Ser Arg Lys Ser Gln Glu Lys Pro Arg Glu
1               5                   10                  15

Ile Met Asp Ala Ala Glu Asp Trp Asn Glu Leu Leu Cys Cys Phe Trp
            20                  25                  30

Asp Cys Ile Met Phe Val Arg Pro Pro Cys Ser Leu Val Ile Pro Asn
        35                  40                  45

Asp Ser Leu Leu Lys Phe Thr Leu Cys His Leu Thr Pro Val Trp Met
    50                  55                  60

Thr Glu Arg Asp Pro Ala Ser Lys Lys Lys Lys Lys Glu Ser His
65                  70                  75                  80

Thr Tyr Ser Phe Gln
                85
```

<210> SEQ ID NO 19
<211> LENGTH: 27
<212> TYPE: PRT
<213> ORGANISM: Homo sapiens

<400> SEQUENCE: 19

Met Pro Ser Ala Ser Ala Ser Arg Lys Ser Gln Glu Lys Pro Arg Glu
1               5                   10                  15

Ile Met Asp Ala Ala Glu Gly Asn Ser Ala Ser
            20                  25

<210> SEQ ID NO 20
<211> LENGTH: 401
<212> TYPE: PRT
<213> ORGANISM: Homo sapiens

<400> SEQUENCE: 20

Met Val Lys Phe Ala Ala Asn Ile Asn Lys Glu Ser Ile Val Asp Val
1               5                   10                  15

Glu Gly Val Val Arg Lys Val Asn Gln Lys Ile Gly Ser Cys Thr Gln
                20                  25                  30

Gln Asp Val Glu Leu His Val Gln Lys Ile Tyr Val Ile Ser Leu Ala
            35                  40                  45

Glu Pro Arg Leu Pro Leu Gln Leu Asp Asp Ala Val Arg Pro Glu Ala
        50                  55                  60

Glu Gly Glu Glu Glu Gly Arg Ala Thr Val Asn Gln Asp Thr Arg Leu
65                  70                  75                  80

Asp Asn Arg Val Ile Asp Leu Arg Thr Ser Thr Ser Gln Ala Val Phe
                85                  90                  95

Arg Leu Gln Ser Gly Ile Cys His Leu Phe Arg Glu Thr Leu Ile Asn
            100                 105                 110

Lys Gly Phe Val Glu Ile Gln Thr Pro Lys Ile Ile Ser Ala Ala Ser
        115                 120                 125

Glu Gly Gly Ala Asn Val Phe Thr Val Ser Tyr Phe Lys Asn Asn Ala
130                 135                 140

Tyr Leu Ala Gln Ser Pro Gln Leu Tyr Lys Gln Met Cys Ile Cys Ala
145                 150                 155                 160

Asp Phe Glu Lys Val Phe Ser Ile Gly Pro Val Phe Arg Ala Glu Asp
                165                 170                 175

Ser Asn Thr His Arg His Leu Thr Glu Phe Val Gly Leu Asp Ile Glu
            180                 185                 190

Met Ala Phe Asn Tyr His Tyr His Glu Val Met Glu Glu Ile Ala Asp
        195                 200                 205

Thr Met Val Gln Ile Phe Lys Gly Leu Gln Glu Arg Phe Gln Thr Glu
    210                 215                 220

Ile Gln Thr Val Asn Lys Gln Phe Pro Cys Glu Pro Phe Lys Phe Leu
225                 230                 235                 240

Glu Pro Thr Leu Arg Leu Glu Tyr Cys Glu Ala Leu Ala Met Leu Arg
                245                 250                 255

Glu Ala Gly Val Glu Met Gly Asp Glu Asp Leu Ser Thr Pro Asn
            260                 265                 270

Glu Lys Leu Leu Gly His Leu Val Lys Glu Lys Tyr Asp Thr Asp Phe
        275                 280                 285

Tyr Ile Leu Asp Lys Tyr Pro Leu Ala Val Arg Pro Phe Tyr Thr Met
    290                 295                 300

```
Pro Asp Pro Arg Asn Pro Lys Gln Ser Asn Ser Tyr Asp Met Phe Met
305                 310                 315                 320

Arg Gly Glu Glu Ile Leu Ser Gly Ala Gln Arg Ile His Asp Pro Gln
                325                 330                 335

Leu Leu Thr Glu Arg Ala Leu His His Gly Ile Asp Leu Glu Lys Ile
            340                 345                 350

Lys Ala Tyr Ile Asp Ser Phe Arg Phe Gly Ala Pro Pro His Ala Gly
        355                 360                 365

Gly Gly Ile Gly Leu Glu Arg Val Thr Met Leu Phe Leu Gly Leu His
    370                 375                 380

Asn Val Arg Gln Thr Ser Met Phe Pro Arg Asp Pro Lys Arg Leu Thr
385                 390                 395                 400

Pro

<210> SEQ ID NO 21
<211> LENGTH: 24
<212> TYPE: PRT
<213> ORGANISM: Homo sapiens

<400> SEQUENCE: 21

Met Leu Phe Leu Gly Leu His Asn Val Arg Gln Thr Ser Met Phe Pro
1               5                   10                  15

Arg Asp Pro Lys Arg Leu Thr Pro
            20

<210> SEQ ID NO 22
<211> LENGTH: 154
<212> TYPE: PRT
<213> ORGANISM: Artificial Sequence
<220> FEATURE:
<223> OTHER INFORMATION: Reduced cysteine content AspRS1

<400> SEQUENCE: 22

Met Pro Ser Ala Ser Ala Ser Arg Lys Ser Gln Glu Lys Pro Arg Glu
1               5                   10                  15

Ile Met Asp Ala Ala Glu Asp Tyr Ala Lys Glu Arg Tyr Gly Ile Ser
            20                  25                  30

Ser Met Ile Gln Ser Gln Glu Lys Pro Asp Arg Val Leu Val Arg Val
        35                  40                  45

Arg Asp Leu Thr Ile Gln Lys Ala Asp Glu Val Val Trp Val Arg Ala
    50                  55                  60

Arg Val His Thr Ser Arg Ala Lys Gly Lys Gln Ser Phe Leu Val Leu
65                  70                  75                  80

Arg Gln Gln Gln Phe Asn Val Gln Ala Leu Val Ala Val Gly Asp His
                85                  90                  95

Ala Ser Lys Gln Met Val Lys Phe Ala Ala Asn Ile Asn Lys Glu Ser
            100                 105                 110

Ile Val Asp Val Glu Gly Val Val Arg Lys Val Asn Gln Lys Ile Gly
        115                 120                 125

Ser Cys Thr Gln Gln Asp Val Glu Leu His Val Gln Lys Ile Tyr Val
    130                 135                 140

Ile Ser Leu Ala Glu Pro Arg Leu Pro Leu
145                 150

<210> SEQ ID NO 23
<211> LENGTH: 154
<212> TYPE: PRT
```

<213> ORGANISM: Artificial Sequence
<220> FEATURE:
<223> OTHER INFORMATION: Reduced cysteine content AspRS1

<400> SEQUENCE: 23

Met Pro Ser Ala Ser Ala Ser Arg Lys Ser Gln Glu Lys Pro Arg Glu
1               5                   10                  15

Ile Met Asp Ala Ala Glu Asp Tyr Ala Lys Glu Arg Tyr Gly Ile Ser
                20                  25                  30

Ser Met Ile Gln Ser Gln Glu Lys Pro Asp Arg Val Leu Val Arg Val
            35                  40                  45

Arg Asp Leu Thr Ile Gln Lys Ala Asp Glu Val Val Trp Val Arg Ala
        50                  55                  60

Arg Val His Thr Ser Arg Ala Lys Gly Lys Gln Cys Phe Leu Val Leu
65                  70                  75                  80

Arg Gln Gln Gln Phe Asn Val Gln Ala Leu Val Ala Val Gly Asp His
                85                  90                  95

Ala Ser Lys Gln Met Val Lys Phe Ala Ala Asn Ile Asn Lys Glu Ser
            100                 105                 110

Ile Val Asp Val Glu Gly Val Val Arg Lys Val Asn Gln Lys Ile Gly
        115                 120                 125

Ser Ser Thr Gln Gln Asp Val Glu Leu His Val Gln Lys Ile Tyr Val
    130                 135                 140

Ile Ser Leu Ala Glu Pro Arg Leu Pro Leu
145                 150

<210> SEQ ID NO 24
<211> LENGTH: 154
<212> TYPE: PRT
<213> ORGANISM: Artificial Sequence
<220> FEATURE:
<223> OTHER INFORMATION: Reduced content cysteine AspRS1

<400> SEQUENCE: 24

Met Pro Ser Ala Ser Ala Ser Arg Lys Ser Gln Glu Lys Pro Arg Glu
1               5                   10                  15

Ile Met Asp Ala Ala Glu Asp Tyr Ala Lys Glu Arg Tyr Gly Ile Ser
                20                  25                  30

Ser Met Ile Gln Ser Gln Glu Lys Pro Asp Arg Val Leu Val Arg Val
            35                  40                  45

Arg Asp Leu Thr Ile Gln Lys Ala Asp Glu Val Val Trp Val Arg Ala
        50                  55                  60

Arg Val His Thr Ser Arg Ala Lys Gly Lys Gln Ser Phe Leu Val Leu
65                  70                  75                  80

Arg Gln Gln Gln Phe Asn Val Gln Ala Leu Val Ala Val Gly Asp His
                85                  90                  95

Ala Ser Lys Gln Met Val Lys Phe Ala Ala Asn Ile Asn Lys Glu Ser
            100                 105                 110

Ile Val Asp Val Glu Gly Val Val Arg Lys Val Asn Gln Lys Ile Gly
        115                 120                 125

Ser Ser Thr Gln Gln Asp Val Glu Leu His Val Gln Lys Ile Tyr Val
    130                 135                 140

Ile Ser Leu Ala Glu Pro Arg Leu Pro Leu
145                 150

<210> SEQ ID NO 25
<211> LENGTH: 462

<212> TYPE: DNA
<213> ORGANISM: Artificial Sequence
<220> FEATURE:
<223> OTHER INFORMATION: Codon optimization of wild type DRS

<400> SEQUENCE: 25

```
atgccgagcg cgagcgccag ccgtaagagc caggaaaaac cacgtgagat tatggatgcc      60
gcagaggact atgcgaaaga cgttacggt atttccagca tgatccaatc tcaggagaaa     120
ccggaccgcg ttctggttcg tgttcgcgat ctgaccattc agaaggcgga cgaggtggtt     180
tgggtgcgtg cgcgcgtgca caccagccgt gcaaaaggca acagtgctt tctggtcctg     240
cgtcagcagc aattcaacgt ccaggcgctg gtggcagtgg gtgaccacgc agcaaacaa     300
atggtgaagt cgctgctaa catcaataaa gaatccattg ttgatgttga aggcgtcgtt     360
cgcaaggtca atcaaaagat cggctcgtgt acgcaacaag atgtcgagct gcatgtgcag     420
aagatttacg tcatcagcct ggcggagccg cgtttgccgc tg                       462
```

<210> SEQ ID NO 26
<211> LENGTH: 525
<212> TYPE: DNA
<213> ORGANISM: Artificial Sequence
<220> FEATURE:
<223> OTHER INFORMATION: Codon optimization of wild type DRS

<400> SEQUENCE: 26

```
atgccgagcg cgagcgccag ccgtaagagc caggaaaaac cacgtgagat tatggatgcc      60
gcagaggact atgcgaaaga cgttacggt atttccagca tgatccaatc tcaggagaaa     120
ccggaccgcg ttctggttcg tgttcgcgat ctgaccattc agaaggcgga cgaggtggtt     180
tgggtgcgtg cgcgcgtgca caccagccgt gcaaaaggca acagagctt tctggtcctg     240
cgtcagcagc aattcaacgt ccaggcgctg gtggcagtgg gtgaccacgc agcaaacaa     300
atggtgaagt cgctgctaa catcaataaa gaatccattg ttgatgttga aggcgtcgtt     360
cgcaaggtca atcaaaagat cggctcgtgt acgcaacaag atgtcgagct gcatgtgcag     420
aagatttacg tcatcagcct ggcggagccg cgtttgccgc tgggtaagcc gatccctaac     480
ccgctgttgg gtctggacag cacgcatcac catcaccacc actaa                    525
```

<210> SEQ ID NO 27
<211> LENGTH: 1503
<212> TYPE: DNA
<213> ORGANISM: Artificial Sequence
<220> FEATURE:
<223> OTHER INFORMATION: Codon optimization of wild type DRS

<400> SEQUENCE: 27

```
atgccatcag cctcagcatc tcgtaaaagc caggaaaaac cgcgcgaaat catggacgct      60
gccgaagatt atgccaaaga cgctatggt atcagttcga tgatccagtc acaagagaaa     120
ccagatcgtg tgctggtccg tgttcgtgac ctgaccatcc agaaagcgga tgaagttgtt     180
tgggtccgtg ctcgtgttca tacaagccgt gccaaaggca acagtgctt cctggttctg     240
cgtcaacagc agtttaacgt tcaggccctg gtagccgttg gtgatcacgc tcaaaacaa     300
atggtgaaat cgccgccaa catcaacaaa gagagcatcg tcgacgttga aggtgtcgtc     360
cgtaaagtga atcagaaaat cggctcctgt acacagcaag atgtggagct gcatgtccaa     420
aaaatctatg tcatctcact ggccgaacct cgtctgcctc tgcaactgga tgatgctgta     480
cgccctgaag ctgaaggcga agaagaaggt cgtgctacgg ttaatcagga tactcgcctg     540
```

| | |
|---|---|
| gacaaccgtg tcattgatct gcgcacctca acctctcaag cggtattccg cctgcaatcc | 600 |
| ggcatctgtc acctgttccg tgaaacgctg atcaacaaag ggtttgtgga gattcagacc | 660 |
| ccgaaaatca ttagtgccgc cagcgaaggt ggagcaaatg tgtttaccgt gtcctatttc | 720 |
| aaaaacaatg cctatctggc acagtctcct cagctgtata acaaatgtg tatctgtgct | 780 |
| gacttcgaga agtgttctc aatcgggccg gtattccgtg cagaggatag caacacacac | 840 |
| cgccatctga ccgaatttgt aggcctggac atcgaaatgg ccttcaacta tcattatcac | 900 |
| gaggtgatgg aagaaatcgc tgatacaatg gtacagatct ttaaagggct gcaagaacgc | 960 |
| tttcaaacag agattcaaac cgtcaataaa cagttcccgt gtgaaccgtt caaatttctg | 1020 |
| gaaccgaccc tgcgtctgga atattgtgaa gcactggcta tgctgcgcga agctggtgtc | 1080 |
| gaaatgggtg atgaggatga cctgtctacc cctaacgaaa aactgctggg ccacctggta | 1140 |
| aaagaaaaat atgacacaga cttctatatc ctggacaaat atccgctggc agttcgtccg | 1200 |
| ttttatacga tgcctgatcc tcgtaatccg aaacaaagca actcctatga catgttcatg | 1260 |
| cgtggtgaag agatcctgtc tggtgctcaa cgtatccatg atccacagct gctgacagaa | 1320 |
| cgtgcactgc atcacggtat tgatctggag aaaatcaaag cctatatcga ctcctttcgc | 1380 |
| tttggtgccc ctccacatgc cggtggtgga attgggctgg agcgtgtaac aatgctgttc | 1440 |
| ctgggactgc acaacgtccg tcaaacctca atgtttccac gtgaccctaa acgtctgaca | 1500 |
| cct | 1503 |

<210> SEQ ID NO 28
<211> LENGTH: 525
<212> TYPE: DNA
<213> ORGANISM: Artificial Sequence
<220> FEATURE:
<223> OTHER INFORMATION: E. coli codon optimized nucleic acid sequence
    DRS polypeptide AspRS1(N1)

<400> SEQUENCE: 28

| | |
|---|---|
| atgccgagcg cgagcgccag ccgtaagagc caggaaaaac cacgtgagat tatggatgcc | 60 |
| gcagaggact atgcgaaaga acgttacggt atttccagca tgatccaatc tcaggagaaa | 120 |
| ccggaccgcg ttctggttcg tgttcgcgat ctgaccattc agaaggcgga cgaggtggtt | 180 |
| tgggtgcgtg cgcgcgtgca caccagccgt gcaaaaggca aacagagctt tctggtcctg | 240 |
| cgtcagcagc aattcaacgt ccaggcgctg gtggcagtgg gtgaccacgc cagcaaacaa | 300 |
| atggtgaagt cgctgctaa catcaataaa gaatccattg ttgatgttga aggcgtcgtt | 360 |
| cgcaaggtca atcaaaagat cggctcgtgt acgaacaag atgtcgagct gcatgtgcag | 420 |
| aagatttacg tcatcagcct ggcggagccg cgtttgccgc tgggtaagcc gatccctaac | 480 |
| ccgctgttgg gtctggacag cacgcatcac catcaccacc actaa | 525 |

<210> SEQ ID NO 29
<211> LENGTH: 174
<212> TYPE: PRT
<213> ORGANISM: Artificial Sequence
<220> FEATURE:
<223> OTHER INFORMATION: AspRs1(N1) polypeptide with C-terminal 6 His
    tag.

<400> SEQUENCE: 29

```
Met Pro Ser Ala Ser Ala Ser Arg Lys Ser Gln Glu Lys Pro Arg Glu
1               5                   10                  15

Ile Met Asp Ala Ala Glu Asp Tyr Ala Lys Glu Arg Tyr Gly Ile Ser
            20                  25                  30
```

Ser Met Ile Gln Ser Gln Glu Lys Pro Asp Arg Val Leu Val Arg Val
        35                  40                  45

Arg Asp Leu Thr Ile Gln Lys Ala Asp Glu Val Val Trp Val Arg Ala
    50                  55                  60

Arg Val His Thr Ser Arg Ala Lys Gly Lys Gln Ser Phe Leu Val Leu
65                  70                  75                  80

Arg Gln Gln Gln Phe Asn Val Gln Ala Leu Val Ala Val Gly Asp His
                85                  90                  95

Ala Ser Lys Gln Met Val Lys Phe Ala Ala Asn Ile Asn Lys Glu Ser
            100                 105                 110

Ile Val Asp Val Glu Gly Val Val Arg Lys Val Asn Gln Lys Ile Gly
        115                 120                 125

Ser Cys Thr Gln Gln Asp Val Glu Leu His Val Gln Lys Ile Tyr Val
    130                 135                 140

Ile Ser Leu Ala Glu Pro Arg Leu Pro Leu Gly Lys Pro Ile Pro Asn
145                 150                 155                 160

Pro Leu Leu Gly Leu Asp Ser Thr His His His His His
                165                 170

<210> SEQ ID NO 30
<211> LENGTH: 525
<212> TYPE: DNA
<213> ORGANISM: Artificial Sequence
<220> FEATURE:
<223> OTHER INFORMATION: Human wild type DRS polynucleotide with His tag
      codons

<400> SEQUENCE: 30
atgcccagcg ccagcgccag ccgcaagagt caggagaagc cgcgggagat catggacgcg      60
gcggaagatt atgctaaaga gagatatgga atatcttcaa tgatacaatc acaagaaaaa     120
ccagatcgag ttttggttcg ggttagagac ttgacaatac aaaaagctga tgaagttgtt     180
tgggtacgtg caagagttca tacaagcaga gctaaaggga acagtgctt cttagtccta      240 cgtcagcagc agtttaatgt ccaggctctt gtggcggtgg agaccatgc aagcaagcag      300 atggttaaat ttgctgccaa catcaacaaa gagagcattt ggatgtaga aggtgttgtg      360 agaaaagtga atcagaaaat tggaagctgt acacagcaag acgttgagtt acatgttcag     420
aagatttatg tgatcagttt ggctgaaccc cgtctgcccc tgggtaagcc tatccctaac     480
cctctcctcg gtctcgattc tacgcaccac caccaccacc actga                     525

<210> SEQ ID NO 31
<211> LENGTH: 174
<212> TYPE: PRT
<213> ORGANISM: Artificial Sequence
<220> FEATURE:
<223> OTHER INFORMATION: AspRS1 wild type polypeptide with C-terminal
      6 His tag

<400> SEQUENCE: 31

Met Pro Ser Ala Ser Ala Ser Arg Lys Ser Gln Glu Lys Pro Arg Glu
1               5                   10                  15

Ile Met Asp Ala Ala Glu Asp Tyr Ala Lys Glu Arg Tyr Gly Ile Ser
            20                  25                  30

Ser Met Ile Gln Ser Gln Glu Lys Pro Asp Arg Val Leu Val Arg Val
        35                  40                  45

Arg Asp Leu Thr Ile Gln Lys Ala Asp Glu Val Val Trp Val Arg Ala
    50                  55                  60

```
Arg Val His Thr Ser Arg Ala Lys Gly Lys Gln Cys Phe Leu Val Leu
 65                  70                  75                  80

Arg Gln Gln Gln Phe Asn Val Gln Ala Leu Val Ala Val Gly Asp His
                 85                  90                  95

Ala Ser Lys Gln Met Val Lys Phe Ala Ala Asn Ile Asn Lys Glu Ser
            100                 105                 110

Ile Val Asp Val Glu Gly Val Val Arg Lys Val Asn Gln Lys Ile Gly
        115                 120                 125

Ser Cys Thr Gln Gln Asp Val Glu Leu His Val Gln Lys Ile Tyr Val
130                 135                 140

Ile Ser Leu Ala Glu Pro Arg Leu Pro Leu Gly Lys Pro Ile Pro Asn
145                 150                 155                 160

Pro Leu Leu Gly Leu Asp Ser Thr His His His His His
                165                 170
```

<210> SEQ ID NO 32
<211> LENGTH: 591
<212> TYPE: DNA
<213> ORGANISM: Artificial Sequence
<220> FEATURE:
<223> OTHER INFORMATION: Secretory AspRs1(N1) polynucleotide

<400> SEQUENCE: 32

```
atgtacagga tgcaactcct gtcttgcatt gcactaagtc ttgcacttgt cacgaattcg      60
atgcccagcg ccagcgccag ccgcaagagt caggagaagc gcgggagat catggacgcg     120
gcggaagatt atgctaaaga gagatatgga atatcttcaa tgatacaatc acaagaaaaa     180
ccagatcgag ttttggttcg ggttagagac ttgacaatac aaaaagctga tgaagttgtt     240
tgggtacgtg caagagttca tacaagcaga gctaaaggga acagtgctt cttagtccta     300
cgtcagcagc agtttaatgt ccaggctctt gtggcggtgg gagaccatgc aagcaagcag     360
atggttaaat tgctgccaa catcaacaaa gagagcattg tggatgtaga aggtgttgtg     420
agaaaagtga atcagaaaat tggaagctgt acacagcaag acgttgagtt acatgttcag     480
aagatttatg tgatcagttt ggctgaaccc cgtctgcccc tgggtaagcc tatccctaac     540
cctctcctcg gtctcgattc tacggactac aaagacgatg acgacaagtg a              591
```

<210> SEQ ID NO 33
<211> LENGTH: 531
<212> TYPE: DNA
<213> ORGANISM: Artificial Sequence
<220> FEATURE:
<223> OTHER INFORMATION: Intracellular AspRS1(n1) polynuleotide sequence

<400> SEQUENCE: 33

```
atgcccagcg ccagcgccag ccgcaagagt caggagaagc gcgggagat catggacgcg      60
gcggaagatt atgctaaaga gagatatgga atatcttcaa tgatacaatc acaagaaaaa     120
ccagatcgag ttttggttcg ggttagagac ttgacaatac aaaaagctga tgaagttgtt     180
tgggtacgtg caagagttca tacaagcaga gctaaaggga acagtgctt cttagtccta     240
cgtcagcagc agtttaatgt ccaggctctt gtggcggtgg gagaccatgc aagcaagcag     300
atggttaaat tgctgccaa catcaacaaa gagagcattg tggatgtaga aggtgttgtg     360
agaaaagtga atcagaaaat tggaagctgt acacagcaag acgttgagtt acatgttcag     420
aagatttatg tgatcagttt ggctgaaccc cgtctgcccc tgggtaagcc tatccctaac     480
cctctcctcg gtctcgattc tacggactac aaagacgatg acgacaagtg a              531
```

<210> SEQ ID NO 34
<211> LENGTH: 1146
<212> TYPE: DNA
<213> ORGANISM: Artificial Sequence
<220> FEATURE:
<223> OTHER INFORMATION: DRS and human Fc fusion construct

<400> SEQUENCE: 34

| | | |
|---|---|---|
| atgcccagcg ccagcgccag ccgcaagagt caggagaagc cgcgggagat catggacgcg | 60 |
| gcggaagatt atgctaaaga gagatatgga atatcttcaa tgatacaatc acaagaaaaa | 120 |
| ccagatcgag ttttggttcg ggttagagac ttgacaatac aaaaagctga tgaagttgtt | 180 |
| tgggtacgtg caagagttca tacaagcaga gctaaaggga acagtgctt cttagtccta | 240 |
| cgtcagcagc agtttaatgt ccaggctctt gtggcggtgg agaccatgc aagcaagcag | 300 |
| atggttaaat ttgctgccaa catcaacaaa gagagcattg tggatgtaga aggtgttgtg | 360 |
| agaaaagtga atcagaaaat tggaagctgt acacagcaag acgttgagtt acatgttcag | 420 |
| aagatttatg tgatcagttt ggctgaaccc cgtctgcccc tggacaaaac tcacacatgc | 480 |
| ccaccgtgcc cagcacctga actcctgggg ggaccgtcag tcttcctctt ccccccaaaa | 540 |
| cccaaggaca cnctcatgat ctcccggacc cctgaggtca catgcgtggt ggtggacgtg | 600 |
| agccacgaag accctgaggt caagttcaac tggtacgtgg acggcgtgga ggtgcataat | 660 |
| gccaagacaa agccgcggga ggagcagtac aacagcacgt accgtgtggt cagcgtcctc | 720 |
| accgtcctgc accaggactg gctgaatggc aaggagtaca agtgcaaggt ctccaacaaa | 780 |
| gccctcccag cccccatcga gaaaaccatc tccaaagcca agggcagcc cgagaaccca | 840 |
| caggtgtaca ccctgccccc atcccgggag gagatgacca gaaccaggt cagcctgacc | 900 |
| tgcctggtca aaggcttcta tcccagcgac atcgccgtgg agtgggagag caatgggcag | 960 |
| ccggagaaca actacaagac cacgcctccc gtgctggact ccgacggctc cttcttcctc | 1020 |
| tacagcaagc tcaccgtgga caagagcagg tggcagcagg ggaacgtctt ctcatgctcc | 1080 |
| gtgatgcacg aggctctgca caaccactac acgcagaaga gcctctccct gtctccgggt | 1140 |
| aaatga | 1146 |

<210> SEQ ID NO 35
<211> LENGTH: 1146
<212> TYPE: DNA
<213> ORGANISM: Artificial Sequence
<220> FEATURE:
<223> OTHER INFORMATION: human Fc and DRS fusion construct

<400> SEQUENCE: 35

| | | |
|---|---|---|
| atggacaaaa ctcacacatg cccaccgtgc ccagcacctg aactcctggg gggaccgtca | 60 |
| gtcttcctct tccccccaaa acccaaggac accctcatga tctcccggac ccctgaggtc | 120 |
| acatgcgtgg tggtggacgt gagccacgaa gaccctgagg tcaagttcaa ctggtacgtg | 180 |
| gacggcgtgg aggtgcataa tgccaagaca aagccgcggg aggagcagta caacagcacg | 240 |
| taccgtgtgg tcagcgtcct caccgtcctg caccaggact ggctgaatgg caaggagtac | 300 |
| aagtgcaagg tctccaacaa agccctccca gcccccatcg agaaaaccat ctccaaagcc | 360 |
| aagggcagcc ccgagaacca caggtgtaca ccctgccccc atcccgggga ggagatgacc | 420 |
| aagaaccagg tcagcctgac ctgcctggtc aaaggcttct atcccagcga catcgccgtg | 480 |
| gagtgggaga gcaatgggca gccggagaac aactacaaga ccacgcctcc cgtgctggac | 540 |

```
tccgacggct ccttcttcct ctacagcaag ctcaccgtgg acaagagcag gtggcagcag      600
gggaacgtct tctcatgctc cgtgatgcac gaggctctgc acaaccacta cacgcagaag      660
agcctctccc tgtctccggg taaacccagc gccagcgcca gccgcaagag tcaggagaag      720
ccgcgggaga tcatggacgc ggcggaagat tatgctaaag agagatatgg aatatcttca      780
atgatacaat cacaagaaaa accagatcga gttttggttc gggttagaga cttgacaata      840
caaaaagctg atgaagttgt ttgggtacgt gcaagagttc atacaagcag agctaaaggg      900
aaacagtgct tcttagtcct acgtcagcag cagtttaatg tccaggctct tgtggcggtg      960
ggagaccatg caagcaagca gatggttaaa tttgctgcca acatcaacaa agagagcatt     1020
gtggatgtag aaggtgttgt gagaaaagtg aatcagaaaa ttggaagctg tacacagcaa     1080
gacgttgagt tacatgttca gaagatttat gtgatcagtt tggctgaacc ccgtctgccc     1140
ctgtga                                                                1146
```

<210> SEQ ID NO 36
<211> LENGTH: 381
<212> TYPE: PRT
<213> ORGANISM: Artificial Sequence
<220> FEATURE:
<223> OTHER INFORMATION: DRS and human Fc protein fusion construct

<400> SEQUENCE: 36

```
Met Pro Ser Ala Ser Ala Ser Arg Lys Ser Gln Glu Lys Pro Arg Glu
1               5                   10                  15

Ile Met Asp Ala Ala Glu Asp Tyr Ala Lys Glu Arg Tyr Gly Ile Ser
            20                  25                  30

Ser Met Ile Gln Ser Gln Glu Lys Pro Asp Arg Val Leu Val Arg Val
        35                  40                  45

Arg Asp Leu Thr Ile Gln Lys Ala Asp Glu Val Val Trp Val Arg Ala
    50                  55                  60

Arg Val His Thr Ser Arg Ala Lys Gly Lys Gln Cys Phe Leu Val Leu
65                  70                  75                  80

Arg Gln Gln Gln Phe Asn Val Gln Ala Leu Val Ala Val Gly Asp His
                85                  90                  95

Ala Ser Lys Gln Met Val Lys Phe Ala Ala Asn Ile Asn Lys Glu Ser
            100                 105                 110

Ile Val Asp Val Glu Gly Val Val Arg Lys Val Asn Gln Lys Ile Gly
        115                 120                 125

Ser Cys Thr Gln Gln Asp Val Glu Leu His Val Gln Lys Ile Tyr Val
    130                 135                 140

Ile Ser Leu Ala Glu Pro Arg Leu Pro Leu Asp Lys Thr His Thr Cys
145                 150                 155                 160

Pro Pro Cys Pro Ala Pro Glu Leu Leu Gly Gly Pro Ser Val Phe Leu
                165                 170                 175

Phe Pro Pro Lys Pro Lys Asp Thr Leu Met Ile Ser Arg Thr Pro Glu
            180                 185                 190

Val Thr Cys Val Val Val Asp Val Ser His Glu Asp Pro Glu Val Lys
        195                 200                 205

Phe Asn Trp Tyr Val Asp Gly Val Glu Val His Asn Ala Lys Thr Lys
    210                 215                 220

Pro Arg Glu Glu Gln Tyr Asn Ser Thr Tyr Arg Val Val Ser Val Leu
225                 230                 235                 240

Thr Val Leu His Gln Asp Trp Leu Asn Gly Lys Glu Tyr Lys Cys Lys
                245                 250                 255
```

-continued

```
Val Ser Asn Lys Ala Leu Pro Ala Pro Ile Glu Lys Thr Ile Ser Lys
            260                 265                 270

Ala Lys Gly Gln Pro Arg Glu Pro Gln Val Tyr Thr Leu Pro Pro Ser
        275                 280                 285

Arg Glu Glu Met Thr Lys Asn Gln Val Ser Leu Thr Cys Leu Val Lys
290                 295                 300

Gly Phe Tyr Pro Ser Asp Ile Ala Val Glu Trp Glu Ser Asn Gly Gln
305                 310                 315                 320

Pro Glu Asn Asn Tyr Lys Thr Thr Pro Pro Val Leu Asp Ser Asp Gly
                325                 330                 335

Ser Phe Phe Leu Tyr Ser Lys Leu Thr Val Asp Lys Ser Arg Trp Gln
            340                 345                 350

Gln Gly Asn Val Phe Ser Cys Ser Val Met His Glu Ala Leu His Asn
        355                 360                 365

His Tyr Thr Gln Lys Ser Leu Ser Leu Ser Pro Gly Lys
            370                 375                 380

<210> SEQ ID NO 37
<211> LENGTH: 381
<212> TYPE: PRT
<213> ORGANISM: Artificial Sequence
<220> FEATURE:
<223> OTHER INFORMATION: human Fc and DRS protein fusion construct

<400> SEQUENCE: 37

Met Asp Lys Thr His Thr Cys Pro Pro Cys Pro Ala Pro Glu Leu Leu
1               5                   10                  15

Gly Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

His Glu Asp Pro Glu Val Lys Phe Asn Trp Tyr Val Asp Gly Val Glu
    50                  55                  60

Val His Asn Ala Lys Thr Lys Pro Arg Glu Glu Gln Tyr Asn Ser Thr
65                  70                  75                  80

Tyr Arg Val Val Ser Val Leu Thr Val Leu His Gln Asp Trp Leu Asn
                85                  90                  95

Gly Lys Glu Tyr Lys Cys Lys Val Ser Asn Lys Ala Leu Pro Ala Pro
            100                 105                 110

Ile Glu Lys Thr Ile Ser Lys Ala Lys Gly Gln Pro Arg Glu Pro Gln
        115                 120                 125

Val Tyr Thr Leu Pro Pro Ser Arg Glu Glu Met Thr Lys Asn Gln Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Lys Leu Thr
            180                 185                 190

Val Asp Lys Ser Arg Trp Gln Gln Gly Asn Val Phe Ser Cys Ser Val
        195                 200                 205

Met His Glu Ala Leu His Asn His Tyr Thr Gln Lys Ser Leu Ser Leu
    210                 215                 220

Ser Pro Gly Lys Pro Ser Ala Ser Ala Ser Arg Lys Ser Gln Glu Lys
225                 230                 235                 240
```

```
Pro Arg Glu Ile Met Asp Ala Ala Glu Asp Tyr Ala Lys Glu Arg Tyr
                245                 250                 255

Gly Ile Ser Ser Met Ile Gln Ser Gln Glu Lys Pro Asp Arg Val Leu
            260                 265                 270

Val Arg Val Arg Asp Leu Thr Ile Gln Lys Ala Asp Glu Val Val Trp
        275                 280                 285

Val Arg Ala Arg Val His Thr Ser Arg Ala Lys Gly Lys Gln Cys Phe
    290                 295                 300

Leu Val Leu Arg Gln Gln Gln Phe Asn Val Gln Ala Leu Val Ala Val
305                 310                 315                 320

Gly Asp His Ala Ser Lys Gln Met Val Lys Phe Ala Ala Asn Ile Asn
                325                 330                 335

Lys Glu Ser Ile Val Asp Val Glu Gly Val Val Arg Lys Val Asn Gln
            340                 345                 350

Lys Ile Gly Ser Cys Thr Gln Gln Asp Val Glu Leu His Val Gln Lys
        355                 360                 365

Ile Tyr Val Ile Ser Leu Ala Glu Pro Arg Leu Pro Leu
    370                 375                 380

<210> SEQ ID NO 38
<211> LENGTH: 19
<212> TYPE: PRT
<213> ORGANISM: Homo sapiens
<220> FEATURE:
<221> NAME/KEY: MISC_FEATURE
<222> LOCATION: (1)..(19)
<223> OTHER INFORMATION: Human IgA1 hinge region

<400> SEQUENCE: 38

Val Pro Ser Thr Pro Pro Thr Pro Ser Pro Ser Thr Pro Pro Thr Pro
1               5                   10                  15

Ser Pro Ser

<210> SEQ ID NO 39
<211> LENGTH: 101
<212> TYPE: PRT
<213> ORGANISM: Homo sapiens
<220> FEATURE:
<221> NAME/KEY: MISC_FEATURE
<222> LOCATION: (1)..(101)
<223> OTHER INFORMATION: Human IgA1 CH2 region

<400> SEQUENCE: 39

Cys Cys His Pro Arg Leu Ser Leu His Arg Pro Ala Leu Glu Asp Leu
1               5                   10                  15

Leu Leu Gly Ser Glu Ala Asn Leu Thr Cys Thr Leu Thr Gly Leu Arg
            20                  25                  30

Asp Ala Ser Gly Val Thr Phe Thr Trp Thr Pro Ser Ser Gly Lys Ser
        35                  40                  45

Ala Val Gln Gly Pro Pro Glu Arg Asp Leu Cys Gly Cys Tyr Ser Val
    50                  55                  60

Ser Ser Val Leu Pro Gly Cys Ala Glu Pro Trp Asn His Gly Lys Thr
65                  70                  75                  80

Phe Thr Cys Thr Ala Ala Tyr Pro Glu Ser Lys Thr Pro Leu Thr Ala
                85                  90                  95

Thr Leu Ser Lys Ser
            100
```

```
<210> SEQ ID NO 40
<211> LENGTH: 131
<212> TYPE: PRT
<213> ORGANISM: Homo sapiens
<220> FEATURE:
<221> NAME/KEY: MISC_FEATURE
<222> LOCATION: (1)..(131)
<223> OTHER INFORMATION: human IgA1 CH3 region

<400> SEQUENCE: 40

Gly Asn Thr Phe Arg Pro Glu Val His Leu Leu Pro Pro Ser Glu
1               5                   10                  15

Glu Leu Ala Leu Asn Glu Leu Val Thr Leu Thr Cys Leu Ala Arg Gly
            20                  25                  30

Phe Ser Pro Lys Asp Val Leu Val Arg Trp Leu Gln Gly Ser Gln Glu
        35                  40                  45

Leu Pro Arg Glu Lys Tyr Leu Thr Trp Ala Ser Arg Gln Glu Pro Ser
    50                  55                  60

Gln Gly Thr Thr Thr Phe Ala Val Thr Ser Ile Leu Arg Val Ala Ala
65                  70                  75                  80

Glu Asp Trp Lys Lys Gly Asp Thr Phe Ser Cys Met Val Gly His Glu
                85                  90                  95

Ala Leu Pro Leu Ala Phe Thr Gln Lys Thr Ile Asp Arg Leu Ala Gly
            100                 105                 110

Lys Pro Thr His Val Asn Val Ser Val Val Met Ala Glu Val Asp Gly
        115                 120                 125

Thr Cys Tyr
    130

<210> SEQ ID NO 41
<211> LENGTH: 6
<212> TYPE: PRT
<213> ORGANISM: Homo sapiens
<220> FEATURE:
<221> NAME/KEY: MISC_FEATURE
<222> LOCATION: (1)..(6)
<223> OTHER INFORMATION: human IgA2 hinge region

<400> SEQUENCE: 41

Val Pro Pro Pro Pro Pro
1               5

<210> SEQ ID NO 42
<211> LENGTH: 101
<212> TYPE: PRT
<213> ORGANISM: Homo sapiens
<220> FEATURE:
<221> NAME/KEY: MISC_FEATURE
<222> LOCATION: (1)..(101)
<223> OTHER INFORMATION: human IgA2 CH2

<400> SEQUENCE: 42

Cys Cys His Pro Arg Leu Ser Leu His Arg Pro Ala Leu Glu Asp Leu
1               5                   10                  15

Leu Leu Gly Ser Glu Ala Asn Leu Thr Cys Thr Leu Thr Gly Leu Arg
            20                  25                  30

Asp Ala Ser Gly Ala Thr Phe Thr Trp Thr Pro Ser Ser Gly Lys Ser
        35                  40                  45

Ala Val Gln Gly Pro Pro Glu Arg Asp Leu Cys Gly Cys Tyr Ser Val
    50                  55                  60

Ser Ser Val Leu Pro Gly Cys Ala Gln Pro Trp Asn His Gly Glu Thr
65                  70                  75                  80
```

Phe Thr Cys Thr Ala Ala His Pro Glu Leu Lys Thr Pro Leu Thr Ala
                85                  90                  95

Asn Ile Thr Lys Ser
            100

<210> SEQ ID NO 43
<211> LENGTH: 131
<212> TYPE: PRT
<213> ORGANISM: Homo sapiens
<220> FEATURE:
<221> NAME/KEY: MISC_FEATURE
<222> LOCATION: (1)..(131)
<223> OTHER INFORMATION: human IgA2 CH3 region

<400> SEQUENCE: 43

Gly Asn Thr Phe Arg Pro Glu Val His Leu Leu Pro Pro Ser Glu
1               5                   10                  15

Glu Leu Ala Leu Asn Glu Leu Val Thr Leu Thr Cys Leu Ala Arg Gly
                20                  25                  30

Phe Ser Pro Lys Asp Val Leu Val Arg Trp Leu Gln Gly Ser Gln Glu
            35                  40                  45

Leu Pro Arg Glu Lys Tyr Leu Thr Trp Ala Ser Arg Gln Glu Pro Ser
    50                  55                  60

Gln Gly Thr Thr Thr Phe Ala Val Thr Ser Ile Leu Arg Val Ala Ala
65                  70                  75                  80

Glu Asp Trp Lys Lys Gly Asp Thr Phe Ser Cys Met Val Gly His Glu
                85                  90                  95

Ala Leu Pro Leu Ala Phe Thr Gln Lys Thr Ile Asp Arg Leu Ala Gly
            100                 105                 110

Lys Pro Thr His Val Asn Val Ser Val Val Met Ala Glu Val Asp Gly
        115                 120                 125

Thr Cys Tyr
    130

<210> SEQ ID NO 44
<211> LENGTH: 58
<212> TYPE: PRT
<213> ORGANISM: Homo sapiens
<220> FEATURE:
<221> NAME/KEY: MISC_FEATURE
<222> LOCATION: (1)..(58)
<223> OTHER INFORMATION: human IgD hinge region

<400> SEQUENCE: 44

Glu Ser Pro Lys Ala Gln Ala Ser Ser Val Pro Thr Ala Gln Pro Gln
1               5                   10                  15

Ala Glu Gly Ser Leu Ala Lys Ala Thr Thr Ala Pro Ala Thr Thr Arg
                20                  25                  30

Asn Thr Gly Arg Gly Gly Glu Glu Lys Lys Lys Glu Lys Glu Lys Glu
            35                  40                  45

Glu Gln Glu Glu Arg Glu Thr Lys Thr Pro
    50                  55

<210> SEQ ID NO 45
<211> LENGTH: 108
<212> TYPE: PRT
<213> ORGANISM: Homo sapiens
<220> FEATURE:
<221> NAME/KEY: MISC_FEATURE
<222> LOCATION: (1)..(108)
<223> OTHER INFORMATION: human IgD CH2 region

```
<400> SEQUENCE: 45

Glu Cys Pro Ser His Thr Gln Pro Leu Gly Val Tyr Leu Leu Thr Pro
1               5                   10                  15

Ala Val Gln Asp Leu Trp Leu Arg Asp Lys Ala Thr Phe Thr Cys Phe
            20                  25                  30

Val Val Gly Ser Asp Leu Lys Asp Ala His Leu Thr Trp Glu Val Ala
        35                  40                  45

Gly Lys Val Pro Thr Gly Gly Val Glu Glu Gly Leu Leu Glu Arg His
    50                  55                  60

Ser Asn Gly Ser Gln Ser Gln His Ser Arg Leu Thr Leu Pro Arg Ser
65              70                  75                  80

Leu Trp Asn Ala Gly Thr Ser Val Thr Cys Thr Leu Asn His Pro Ser
            85                  90                  95

Leu Pro Pro Gln Arg Leu Met Ala Leu Arg Glu Pro
            100                 105

<210> SEQ ID NO 46
<211> LENGTH: 117
<212> TYPE: PRT
<213> ORGANISM: Homo sapiens
<220> FEATURE:
<221> NAME/KEY: MISC_FEATURE
<222> LOCATION: (1)..(117)
<223> OTHER INFORMATION: human IgD CH3 region

<400> SEQUENCE: 46

Ala Ala Gln Ala Pro Val Lys Leu Ser Leu Asn Leu Leu Ala Ser Ser
1               5                   10                  15

Asp Pro Pro Glu Ala Ala Ser Trp Leu Leu Cys Glu Val Ser Gly Phe
            20                  25                  30

Ser Pro Pro Asn Ile Leu Leu Met Trp Leu Glu Asp Gln Arg Glu Val
        35                  40                  45

Asn Thr Ser Gly Phe Ala Pro Ala Arg Pro Pro Gln Pro Arg Ser
    50                  55                  60

Thr Thr Phe Trp Ala Trp Ser Val Leu Arg Val Pro Ala Pro Pro Ser
65              70                  75                  80

Pro Gln Pro Ala Thr Tyr Thr Cys Val Val Ser His Glu Asp Ser Arg
            85                  90                  95

Thr Leu Leu Asn Ala Ser Arg Ser Leu Glu Val Ser Tyr Val Thr Asp
            100                 105                 110

His Gly Pro Met Lys
        115

<210> SEQ ID NO 47
<211> LENGTH: 107
<212> TYPE: PRT
<213> ORGANISM: Homo sapiens
<220> FEATURE:
<221> NAME/KEY: MISC_FEATURE
<222> LOCATION: (1)..(107)
<223> OTHER INFORMATION: human IgE CH2 region

<400> SEQUENCE: 47

Val Cys Ser Arg Asp Phe Thr Pro Pro Thr Val Lys Ile Leu Gln Ser
1               5                   10                  15

Ser Cys Asp Gly Gly Gly His Phe Pro Pro Thr Ile Gln Leu Leu Cys
            20                  25                  30

Leu Val Ser Gly Tyr Thr Pro Gly Thr Ile Asn Ile Thr Trp Leu Glu
```

```
              35                  40                  45
Asp Gly Gln Val Met Asp Val Asp Leu Ser Thr Ala Ser Thr Thr Gln
 50                  55                  60

Glu Gly Glu Leu Ala Ser Thr Gln Ser Glu Leu Thr Leu Ser Gln Lys
 65                  70                  75                  80

His Trp Leu Ser Asp Arg Thr Tyr Thr Cys Gln Val Thr Tyr Gln Gly
                 85                  90                  95

His Thr Phe Glu Asp Ser Thr Lys Lys Cys Ala
            100                 105

<210> SEQ ID NO 48
<211> LENGTH: 108
<212> TYPE: PRT
<213> ORGANISM: Homo sapiens
<220> FEATURE:
<221> NAME/KEY: MISC_FEATURE
<222> LOCATION: (1)..(108)
<223> OTHER INFORMATION: human IgE CH3 region

<400> SEQUENCE: 48

Asp Ser Asn Pro Arg Gly Val Ser Ala Tyr Leu Ser Arg Pro Ser Pro
 1               5                  10                  15

Phe Asp Leu Phe Ile Arg Lys Ser Pro Thr Ile Thr Cys Leu Val Val
                20                  25                  30

Asp Leu Ala Pro Ser Lys Gly Thr Val Asn Leu Thr Trp Ser Arg Ala
             35                  40                  45

Ser Gly Lys Pro Val Asn His Ser Thr Arg Lys Glu Glu Lys Gln Arg
 50                  55                  60

Asn Gly Thr Leu Thr Val Thr Ser Thr Leu Pro Val Gly Thr Arg Asp
 65                  70                  75                  80

Trp Ile Glu Gly Glu Thr Tyr Gln Cys Arg Val Thr His Pro His Leu
                 85                  90                  95

Pro Arg Ala Leu Met Arg Ser Thr Thr Lys Thr Ser
            100                 105

<210> SEQ ID NO 49
<211> LENGTH: 110
<212> TYPE: PRT
<213> ORGANISM: Homo sapiens
<220> FEATURE:
<221> NAME/KEY: MISC_FEATURE
<222> LOCATION: (1)..(110)
<223> OTHER INFORMATION: human IgE CH4 region

<400> SEQUENCE: 49

Gly Pro Arg Ala Ala Pro Glu Val Tyr Ala Phe Ala Thr Pro Glu Trp
 1               5                  10                  15

Pro Gly Ser Arg Asp Lys Arg Thr Leu Ala Cys Leu Ile Gln Asn Phe
                20                  25                  30

Met Pro Glu Asp Ile Ser Val Gln Trp Leu His Asn Glu Val Gln Leu
             35                  40                  45

Pro Asp Ala Arg His Ser Thr Thr Gln Pro Arg Lys Thr Lys Gly Ser
 50                  55                  60

Gly Phe Phe Val Phe Ser Arg Leu Glu Val Thr Arg Ala Glu Trp Glu
 65                  70                  75                  80

Gln Lys Asp Glu Phe Ile Cys Arg Ala Val His Glu Ala Ala Ser Pro
                 85                  90                  95

Ser Gln Thr Val Gln Arg Ala Val Ser Val Asn Pro Gly Lys
            100                 105                 110
```

<210> SEQ ID NO 50
<211> LENGTH: 15
<212> TYPE: PRT
<213> ORGANISM: Homo sapiens
<220> FEATURE:
<221> NAME/KEY: MISC_FEATURE
<222> LOCATION: (1)..(15)
<223> OTHER INFORMATION: human IgG1 hinge region

<400> SEQUENCE: 50

Glu Pro Lys Ser Cys Asp Lys Thr His Thr Cys Pro Pro Cys Pro
1               5                   10                  15

<210> SEQ ID NO 51
<211> LENGTH: 110
<212> TYPE: PRT
<213> ORGANISM: Homo sapiens
<220> FEATURE:
<221> NAME/KEY: MISC_FEATURE
<222> LOCATION: (1)..(110)
<223> OTHER INFORMATION: human IgG1 CH2 region

<400> SEQUENCE: 51

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys
            100                 105                 110

<210> SEQ ID NO 52
<211> LENGTH: 107
<212> TYPE: PRT
<213> ORGANISM: Homo sapiens
<220> FEATURE:
<221> NAME/KEY: MISC_FEATURE
<222> LOCATION: (1)..(107)
<223> OTHER INFORMATION: human IgG1 CH3 region

<400> SEQUENCE: 52

Gly Gln Pro Arg Glu Pro Gln Val Tyr Thr Leu Pro Pro Ser Arg Asp
1               5                   10                  15

Glu Leu Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 53
<211> LENGTH: 12
<212> TYPE: PRT
<213> ORGANISM: Homo sapiens
<220> FEATURE:
<221> NAME/KEY: MISC_FEATURE
<222> LOCATION: (1)..(12)
<223> OTHER INFORMATION: human IgG2 hinge region

<400> SEQUENCE: 53

Glu Arg Lys Cys Cys Val Glu Cys Pro Pro Cys Pro
1               5                   10

<210> SEQ ID NO 54
<211> LENGTH: 109
<212> TYPE: PRT
<213> ORGANISM: Homo sapiens
<220> FEATURE:
<221> NAME/KEY: MISC_FEATURE
<222> LOCATION: (1)..(109)
<223> OTHER INFORMATION: human IgG2 CH2 region

<400> SEQUENCE: 54

Ala Pro Pro Val Ala Gly Pro Ser Val Phe Leu Phe Pro Pro Lys Pro
1               5                   10                  15

Lys Asp Thr Leu Met Ile Ser Arg Thr Pro Glu Val Thr Cys Val Val
            20                  25                  30

Val Asp Val Ser His Glu Asp Pro Glu Val Gln Phe Asn Trp Tyr Val
        35                  40                  45

Asp Gly Val Glu Val His Asn Ala Lys Thr Lys Pro Arg Glu Glu Gln
    50                  55                  60

Phe Asn Ser Thr Phe Arg Val Val Ser Val Leu Thr Val Val His Gln
65                  70                  75                  80

Asp Trp Leu Asn Gly Lys Glu Tyr Lys Cys Lys Val Ser Asn Lys Gly
                85                  90                  95

Leu Pro Ala Pro Ile Glu Lys Thr Ile Ser Lys Thr Lys
            100                 105

<210> SEQ ID NO 55
<211> LENGTH: 107
<212> TYPE: PRT
<213> ORGANISM: Homo sapiens
<220> FEATURE:
<221> NAME/KEY: MISC_FEATURE
<222> LOCATION: (1)..(107)
<223> OTHER INFORMATION: human IgG2 CH3 region

<400> SEQUENCE: 55

Gly Gln Pro Arg Glu Pro Gln Val Tyr Thr Leu Pro Pro Ser Arg Glu
1               5                   10                  15

Glu Met Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Met Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr

```
                        85                  90                  95

Thr Gln Lys Ser Leu Ser Leu Ser Pro Gly Lys
            100                 105

<210> SEQ ID NO 56
<211> LENGTH: 62
<212> TYPE: PRT
<213> ORGANISM: Homo sapiens
<220> FEATURE:
<221> NAME/KEY: MISC_FEATURE
<222> LOCATION: (1)..(62)
<223> OTHER INFORMATION: human IgG3 hinge region

<400> SEQUENCE: 56

Glu Leu Lys Thr Pro Leu Gly Asp Thr Thr His Thr Cys Pro Arg Cys
1               5                   10                  15

Pro Glu Pro Lys Ser Cys Asp Thr Pro Pro Cys Pro Arg Cys Pro
            20                  25                  30

Glu Pro Lys Ser Cys Asp Thr Pro Pro Cys Pro Arg Cys Pro Glu
        35                  40                  45

Pro Lys Ser Cys Asp Thr Pro Pro Cys Pro Arg Cys Pro
    50                  55                  60

<210> SEQ ID NO 57
<211> LENGTH: 110
<212> TYPE: PRT
<213> ORGANISM: Homo sapiens
<220> FEATURE:
<221> NAME/KEY: MISC_FEATURE
<222> LOCATION: (1)..(110)
<223> OTHER INFORMATION: human IgG3 CH2 region

<400> SEQUENCE: 57

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Gln Phe Lys Trp Tyr
        35                  40                  45

Val Asp Gly Val Glu Val His Asn Ala Lys Thr Lys Pro Arg Glu Glu
    50                  55                  60

Gln Tyr Asn Ser Thr Phe Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Thr Lys
            100                 105                 110

<210> SEQ ID NO 58
<211> LENGTH: 107
<212> TYPE: PRT
<213> ORGANISM: Homo sapiens
<220> FEATURE:
<221> NAME/KEY: MISC_FEATURE
<222> LOCATION: (1)..(107)
<223> OTHER INFORMATION: human IgG3 CH3 region

<400> SEQUENCE: 58

Gly Gln Pro Arg Glu Pro Gln Val Tyr Thr Leu Pro Pro Ser Arg Glu
1               5                   10                  15

Glu Met Thr Lys Asn Gln Val Ser Leu Thr Cys Leu Val Lys Gly Phe
            20                  25                  30
```

-continued

```
Tyr Pro Ser Asp Ile Ala Val Glu Trp Glu Ser Ser Gly Gln Pro Glu
            35                  40                  45

Asn Asn Tyr Asn Thr Thr Pro Pro Met Leu Asp Ser Asp Gly Ser Phe
 50                  55                  60

Phe Leu Tyr Ser Lys Leu Thr Val Asp Lys Ser Arg Trp Gln Gln Gly
 65                  70                  75                  80

Asn Ile Phe Ser Cys Ser Val Met His Glu Ala Leu His Asn Arg Phe
                 85                  90                  95

Thr Gln Lys Ser Leu Ser Leu Ser Pro Gly Lys
            100                 105
```

<210> SEQ ID NO 59
<211> LENGTH: 12
<212> TYPE: PRT
<213> ORGANISM: Homo sapiens
<220> FEATURE:
<221> NAME/KEY: MISC_FEATURE
<222> LOCATION: (1)..(12)
<223> OTHER INFORMATION: human IgG4 hinge region

<400> SEQUENCE: 59

```
Glu Ser Lys Tyr Gly Pro Pro Cys Pro Ser Cys Pro
 1               5                  10
```

<210> SEQ ID NO 60
<211> LENGTH: 110
<212> TYPE: PRT
<213> ORGANISM: Homo sapiens
<220> FEATURE:
<221> NAME/KEY: MISC_FEATURE
<222> LOCATION: (1)..(110)
<223> OTHER INFORMATION: human IgG4 CH2 region

<400> SEQUENCE: 60

```
Ala Pro Glu Phe Leu Gly Gly Pro Ser Val Phe Leu Phe Pro Pro Lys
 1               5                  10                  15

Pro Lys Asp Thr Leu Met Ile Ser Arg Thr Pro Glu Val Thr Cys Val
             20                  25                  30

Val Val Asp Val Ser Gln Glu Asp Pro Glu Val Gln Phe Asn Trp Tyr
             35                  40                  45

Val Asp Gly Val Glu Val His Asn Ala Lys Thr Lys Pro Arg Glu Glu
 50                  55                  60

Gln Phe Asn Ser Thr Tyr Arg Val Val Ser Val Leu Thr Val Leu His
 65                  70                  75                  80

Gln Asp Trp Leu Asn Gly Lys Glu Tyr Lys Cys Lys Val Ser Asn Lys
                 85                  90                  95

Gly Leu Pro Ser Ser Ile Glu Lys Thr Ile Ser Lys Ala Lys
            100                 105                 110
```

<210> SEQ ID NO 61
<211> LENGTH: 107
<212> TYPE: PRT
<213> ORGANISM: Homo sapiens
<220> FEATURE:
<221> NAME/KEY: MISC_FEATURE
<222> LOCATION: (1)..(107)
<223> OTHER INFORMATION: human IgG4 CH3 region

<400> SEQUENCE: 61

```
Gly Gln Pro Arg Glu Pro Gln Val Tyr Thr Leu Pro Pro Ser Gln Glu
 1               5                  10                  15
```

```
Glu Met Thr Lys Asn Gln Val Ser Leu Thr Cys Leu Val Lys Gly Phe
             20                  25                  30

Tyr Pro Ser Asp Ile Ala Val Glu Trp Glu Ser Asn Gly Gln Pro Glu
         35                  40                  45

Asn Asn Tyr Lys Thr Thr Pro Pro Val Leu Asp Ser Asp Gly Ser Phe
 50                  55                  60

Phe Leu Tyr Ser Arg Leu Thr Val Asp Lys Ser Arg Trp Gln Glu Gly
 65                  70                  75                  80

Asn Val Phe Ser Cys Ser Val Met His Glu Ala Leu His Asn His Tyr
                 85                  90                  95

Thr Gln Lys Ser Leu Ser Leu Ser Leu Gly Lys
            100                 105
```

<210> SEQ ID NO 62
<211> LENGTH: 112
<212> TYPE: PRT
<213> ORGANISM: Homo sapiens
<220> FEATURE:
<221> NAME/KEY: MISC_FEATURE
<222> LOCATION: (1)..(112)
<223> OTHER INFORMATION: human IgM CH2 region

<400> SEQUENCE: 62

```
Val Ile Ala Glu Leu Pro Pro Lys Val Ser Val Phe Val Pro Pro Arg
 1               5                  10                  15

Asp Gly Phe Phe Gly Asn Pro Arg Lys Ser Lys Leu Ile Cys Gln Ala
             20                  25                  30

Thr Gly Phe Ser Pro Arg Gln Ile Gln Val Ser Trp Leu Arg Glu Gly
         35                  40                  45

Lys Gln Val Gly Ser Gly Val Thr Thr Asp Gln Val Gln Ala Glu Ala
 50                  55                  60

Lys Glu Ser Gly Pro Thr Thr Tyr Lys Val Thr Ser Thr Leu Thr Ile
 65                  70                  75                  80

Lys Glu Ser Asp Trp Leu Gly Gln Ser Met Phe Thr Cys Arg Val Asp
                 85                  90                  95

His Arg Gly Leu Thr Phe Gln Gln Asn Ala Ser Ser Met Cys Val Pro
            100                 105                 110
```

<210> SEQ ID NO 63
<211> LENGTH: 106
<212> TYPE: PRT
<213> ORGANISM: Homo sapiens
<220> FEATURE:
<221> NAME/KEY: MISC_FEATURE
<222> LOCATION: (1)..(106)
<223> OTHER INFORMATION: human IgM CH3 region

<400> SEQUENCE: 63

```
Asp Gln Asp Thr Ala Ile Arg Val Phe Ala Ile Pro Pro Ser Phe Ala
 1               5                  10                  15

Ser Ile Phe Leu Thr Lys Ser Thr Lys Leu Thr Cys Leu Val Thr Asp
             20                  25                  30

Leu Thr Thr Tyr Asp Ser Val Thr Ile Ser Trp Thr Arg Gln Asn Gly
         35                  40                  45

Glu Ala Val Lys Thr His Thr Asn Ile Ser Glu Ser His Pro Asn Ala
 50                  55                  60

Thr Phe Ser Ala Val Gly Glu Ala Ser Ile Cys Glu Asp Asp Trp Asn
 65                  70                  75                  80

Ser Gly Glu Arg Phe Thr Cys Thr Val Thr His Thr Asp Leu Pro Ser
```

```
                    85                  90                  95
Pro Leu Lys Gln Thr Ile Ser Arg Pro Lys
            100                 105

<210> SEQ ID NO 64
<211> LENGTH: 131
<212> TYPE: PRT
<213> ORGANISM: Homo sapiens
<220> FEATURE:
<221> NAME/KEY: MISC_FEATURE
<222> LOCATION: (1)..(131)
<223> OTHER INFORMATION: human IgM CH4 region

<400> SEQUENCE: 64

Gly Val Ala Leu His Arg Pro Asp Val Tyr Leu Leu Pro Pro Ala Arg
1               5                   10                  15

Glu Gln Leu Asn Leu Arg Glu Ser Ala Thr Ile Thr Cys Leu Val Thr
            20                  25                  30

Gly Phe Ser Pro Ala Asp Val Phe Val Gln Trp Met Gln Arg Gly Gln
        35                  40                  45

Pro Leu Ser Pro Glu Lys Tyr Val Thr Ser Ala Pro Met Pro Glu Pro
    50                  55                  60

Gln Ala Pro Gly Arg Tyr Phe Ala His Ser Ile Leu Thr Val Ser Glu
65                  70                  75                  80

Glu Glu Trp Asn Thr Gly Glu Thr Tyr Thr Cys Val Val Ala His Glu
                85                  90                  95

Ala Leu Pro Asn Arg Val Thr Glu Arg Thr Val Asp Lys Ser Thr Gly
            100                 105                 110

Lys Pro Thr Leu Tyr Asn Val Ser Leu Val Met Ser Asp Thr Ala Gly
        115                 120                 125

Thr Cys Tyr
    130

<210> SEQ ID NO 65
<211> LENGTH: 230
<212> TYPE: PRT
<213> ORGANISM: Artificial Sequence
<220> FEATURE:
<223> OTHER INFORMATION: Fc variant
<220> FEATURE:
<221> NAME/KEY: VARIANT
<222> LOCATION: (1)..(1)
<223> OTHER INFORMATION: Xaa is Ala or absent
<220> FEATURE:
<221> NAME/KEY: VARIANT
<222> LOCATION: (16)..(16)
<223> OTHER INFORMATION: Xaa is Pro or Glu
<220> FEATURE:
<221> NAME/KEY: VARIANT
<222> LOCATION: (17)..(17)
<223> OTHER INFORMATION: Xaa is Phe, Val or Ala
<220> FEATURE:
<221> NAME/KEY: VARIANT
<222> LOCATION: (18)..(18)
<223> OTHER INFORMATION: Xaa is Leu, Glu or Ala
<220> FEATURE:
<221> NAME/KEY: VARIANT
<222> LOCATION: (80)..(80)
<223> OTHER INFORMATION: Xaa is Asn or Ala
<220> FEATURE:
<221> NAME/KEY: VARIANT
<222> LOCATION: (230)..(230)
<223> OTHER INFORMATION: Xaa is Lys or absent

<400> SEQUENCE: 65

Xaa Glu Ser Lys Tyr Gly Pro Pro Cys Pro Pro Cys Pro Ala Pro Xaa
```

```
            1               5                  10                 15
Xaa Xaa Gly Gly Pro Ser Val Phe Leu Phe Pro Pro Lys Pro Lys Asp
                20                  25                  30
Thr Leu Met Ile Ser Arg Thr Pro Glu Val Thr Cys Val Val Val Asp
                35                  40                  45
Val Ser Gln Glu Asp Pro Glu Val Gln Phe Asn Trp Tyr Val Asp Gly
                50                  55                  60
Val Glu Val His Asn Ala Lys Thr Lys Pro Arg Glu Glu Gln Phe Xaa
 65                 70                  75                  80
Ser Thr Tyr Arg Val Val Ser Val Leu Thr Val Leu His Gln Asp Trp
                85                  90                  95
Leu Asn Gly Lys Glu Tyr Lys Cys Lys Val Ser Asn Lys Gly Leu Pro
                100                 105                 110
Ser Ser Ile Glu Lys Thr Ile Ser Lys Ala Lys Gly Gln Pro Arg Glu
                115                 120                 125
Pro Gln Val Tyr Thr Leu Pro Pro Ser Gln Glu Glu Met Thr Lys Asn
                130                 135                 140
Gln Val Ser Leu Thr Cys Leu Val Lys Gly Phe Tyr Pro Ser Asp Ile
145                 150                 155                 160
Ala Val Glu Trp Glu Ser Asn Gly Gln Pro Glu Asn Asn Tyr Lys Thr
                165                 170                 175
Thr Pro Pro Val Leu Asp Ser Asp Gly Ser Phe Phe Leu Tyr Ser Arg
                180                 185                 190
Leu Thr Val Asp Lys Ser Arg Trp Gln Glu Gly Asn Val Phe Ser Cys
                195                 200                 205
Ser Val Met His Glu Ala Leu His Asn His Tyr Thr Gln Lys Ser Leu
                210                 215                 220
Ser Leu Ser Leu Gly Xaa
225                 230

<210> SEQ ID NO 66
<211> LENGTH: 209
<212> TYPE: PRT
<213> ORGANISM: Homo sapiens

<400> SEQUENCE: 66

Cys His Pro Arg Leu Ser Leu His Arg Pro Ala Leu Glu Asp Leu Leu
 1              5                   10                  15
Leu Gly Ser Glu Ala Asn Leu Thr Cys Thr Leu Thr Gly Leu Arg Asp
                20                  25                  30
Ala Ser Gly Val Thr Phe Thr Trp Thr Pro Ser Ser Gly Lys Ser Ala
                35                  40                  45
Val Gln Gly Pro Pro Glu Arg Asp Leu Cys Gly Cys Tyr Ser Val Ser
                50                  55                  60
Ser Val Leu Pro Gly Cys Ala Glu Pro Trp Asn His Gly Lys Thr Phe
 65                 70                  75                  80
Thr Cys Thr Ala Ala Tyr Pro Glu Ser Lys Thr Pro Leu Thr Ala Thr
                85                  90                  95
Leu Ser Lys Ser Gly Asn Thr Phe Arg Pro Glu Val His Leu Leu Pro
                100                 105                 110
Pro Pro Ser Glu Glu Leu Ala Leu Asn Glu Leu Val Thr Leu Thr Cys
                115                 120                 125
Leu Ala Arg Gly Phe Ser Pro Lys Asp Val Leu Val Arg Trp Leu Gln
                130                 135                 140
```

```
Gly Ser Gln Glu Leu Pro Arg Glu Lys Tyr Leu Thr Trp Ala Ser Arg
145                 150                 155                 160

Gln Glu Pro Ser Gln Gly Thr Thr Thr Phe Ala Val Thr Ser Ile Leu
            165                 170                 175

Arg Val Ala Ala Glu Asp Trp Lys Lys Gly Asp Thr Phe Ser Cys Met
        180                 185                 190

Val Gly His Glu Ala Leu Pro Leu Ala Phe Thr Gln Lys Thr Ile Asp
    195                 200                 205

Arg

<210> SEQ ID NO 67
<211> LENGTH: 209
<212> TYPE: PRT
<213> ORGANISM: Homo sapiens

<400> SEQUENCE: 67

Cys His Pro Arg Leu Ser Leu His Arg Pro Ala Leu Glu Asp Leu Leu
1               5                   10                  15

Leu Gly Ser Glu Ala Asn Leu Thr Cys Thr Leu Thr Gly Leu Arg Asp
            20                  25                  30

Ala Ser Gly Ala Thr Phe Thr Trp Thr Pro Ser Ser Gly Lys Ser Ala
        35                  40                  45

Val Gln Gly Pro Pro Glu Arg Asp Leu Cys Gly Cys Tyr Ser Val Ser
    50                  55                  60

Ser Val Leu Pro Gly Cys Ala Gln Pro Trp Asn His Gly Glu Thr Phe
65                  70                  75                  80

Thr Cys Thr Ala Ala His Pro Glu Leu Lys Thr Pro Leu Thr Ala Asn
                85                  90                  95

Ile Thr Lys Ser Gly Asn Thr Phe Arg Pro Glu Val His Leu Leu Pro
            100                 105                 110

Pro Pro Ser Glu Glu Leu Ala Leu Asn Glu Leu Val Thr Leu Thr Cys
        115                 120                 125

Leu Ala Arg Gly Phe Ser Pro Lys Asp Val Leu Val Arg Trp Leu Gln
    130                 135                 140

Gly Ser Gln Glu Leu Pro Arg Glu Lys Tyr Leu Thr Trp Ala Ser Arg
145                 150                 155                 160

Gln Glu Pro Ser Gln Gly Thr Thr Thr Phe Ala Val Thr Ser Ile Leu
            165                 170                 175

Arg Val Ala Ala Glu Asp Trp Lys Lys Gly Asp Thr Phe Ser Cys Met
        180                 185                 190

Val Gly His Glu Ala Leu Pro Leu Ala Phe Thr Gln Lys Thr Ile Asp
    195                 200                 205

Arg

<210> SEQ ID NO 68
<211> LENGTH: 212
<212> TYPE: PRT
<213> ORGANISM: Homo sapiens

<400> SEQUENCE: 68

Thr Ala Ile Arg Val Phe Ala Ile Pro Pro Ser Phe Ala Ser Ile Phe
1               5                   10                  15

Leu Thr Lys Ser Thr Lys Leu Thr Cys Leu Val Thr Asp Leu Thr Thr
            20                  25                  30

Tyr Asp Ser Val Thr Ile Ser Trp Thr Arg Gln Asn Gly Glu Ala Val
        35                  40                  45
```

Lys Thr His Thr Asn Ile Ser Glu Ser His Pro Asn Ala Thr Phe Ser
    50                  55                  60

Ala Val Gly Glu Ala Ser Ile Cys Glu Asp Asp Trp Asn Ser Gly Glu
65                  70                  75                  80

Arg Phe Thr Cys Thr Val Thr His Thr Asp Leu Pro Ser Pro Leu Lys
                    85                  90                  95

Gln Thr Ile Ser Arg Pro Lys Gly Val Ala Leu His Arg Pro Asp Val
            100                 105                 110

Tyr Leu Leu Pro Pro Ala Arg Glu Gln Leu Asn Leu Arg Glu Ser Ala
            115                 120                 125

Thr Ile Thr Cys Leu Val Thr Gly Phe Ser Pro Ala Asp Val Phe Val
    130                 135                 140

Gln Trp Met Gln Arg Gly Gln Pro Leu Ser Pro Glu Lys Tyr Val Thr
145                 150                 155                 160

Ser Ala Pro Met Pro Glu Pro Gln Ala Pro Gly Arg Tyr Phe Ala His
                165                 170                 175

Ser Ile Leu Thr Val Ser Glu Glu Trp Asn Thr Gly Glu Thr Tyr
            180                 185                 190

Thr Cys Val Val Ala His Glu Ala Leu Pro Asn Arg Val Thr Glu Arg
                195                 200                 205

Thr Val Asp Lys
        210

<210> SEQ ID NO 69
<211> LENGTH: 208
<212> TYPE: PRT
<213> ORGANISM: Homo sapiens

<400> SEQUENCE: 69

Ala Gly Pro Ser Val Phe Leu Phe Pro Pro Lys Pro Lys Asp Thr Leu
1               5                   10                  15

Met Ile Ser Arg Thr Pro Glu Val Thr Cys Val Val Val Asp Val Ser
            20                  25                  30

His Glu Asp Pro Glu Val Gln Phe Asn Trp Tyr Val Asp Gly Met Glu
        35                  40                  45

Val His Asn Ala Lys Thr Lys Pro Arg Glu Glu Gln Phe Asn Ser Thr
    50                  55                  60

Phe Arg Val Val Ser Val Leu Thr Val Val His Gln Asp Trp Leu Asn
65                  70                  75                  80

Gly Lys Glu Tyr Lys Cys Lys Val Ser Asn Lys Gly Leu Pro Ala Pro
                85                  90                  95

Ile Glu Lys Thr Ile Ser Lys Thr Lys Gly Gln Pro Arg Glu Pro Gln
            100                 105                 110

Val Tyr Thr Leu Pro Pro Ser Arg Glu Glu Met Thr Lys Asn Gln Val
        115                 120                 125

Ser Leu Thr Cys Leu Val Lys Gly Phe Tyr Pro Ser Asp Ile Ala Val
    130                 135                 140

Glu Trp Glu Ser Asn Gly Gln Pro Glu Asn Asn Tyr Lys Thr Thr Pro
145                 150                 155                 160

Pro Met Leu Asp Ser Asp Gly Ser Phe Phe Leu Tyr Ser Lys Leu Thr
                165                 170                 175

Val Asp Lys Ser Arg Trp Gln Gln Gly Asn Val Phe Ser Cys Ser Val
            180                 185                 190

Met His Glu Ala Leu His Asn His Tyr Thr Gln Lys Ser Leu Ser Leu

-continued

```
                    195                 200                 205

<210> SEQ ID NO 70
<211> LENGTH: 208
<212> TYPE: PRT
<213> ORGANISM: Homo sapiens

<400> SEQUENCE: 70

Gly Gly Pro Ser Val Phe Leu Phe Pro Pro Lys Pro Lys Asp Thr Leu
1               5                   10                  15

Met Ile Ser Arg Thr Pro Glu Val Thr Cys Val Val Val Asp Val Ser
            20                  25                  30

His Glu Asp Pro Glu Val Lys Phe Asn Trp Tyr Val Asp Gly Val Glu
        35                  40                  45

Val His Asn Ala Lys Thr Lys Pro Arg Glu Glu Gln Tyr Asn Ser Thr
    50                  55                  60

Tyr Arg Val Val Ser Val Leu Thr Val Leu His Gln Asp Trp Leu Asn
65                  70                  75                  80

Gly Lys Glu Tyr Lys Cys Lys Val Ser Asn Lys Ala Leu Pro Ala Pro
                85                  90                  95

Ile Glu Lys Thr Ile Ser Lys Ala Lys Gly Gln Pro Arg Glu Pro Gln
            100                 105                 110

Val Tyr Thr Leu Pro Pro Ser Arg Asp Glu Leu Thr Lys Asn Gln Val
        115                 120                 125

Ser Leu Thr Cys Leu Val Lys Gly Phe Tyr Pro Ser Asp Ile Ala Val
    130                 135                 140

Glu Trp Glu Ser Asn Gly Gln Pro Glu Asn Asn Tyr Lys Thr Thr Pro
145                 150                 155                 160

Pro Val Leu Asp Ser Asp Gly Ser Phe Phe Leu Tyr Ser Lys Leu Thr
                165                 170                 175

Val Asp Lys Ser Arg Trp Gln Gln Gly Asn Val Phe Ser Cys Ser Val
            180                 185                 190

Met His Glu Ala Leu His Asn His Tyr Thr Gln Lys Ser Leu Ser Leu
        195                 200                 205

<210> SEQ ID NO 71
<211> LENGTH: 208
<212> TYPE: PRT
<213> ORGANISM: Homo sapiens

<400> SEQUENCE: 71

Gly Gly Pro Ser Val Phe Leu Phe Pro Pro Lys Pro Lys Asp Thr Leu
1               5                   10                  15

Met Ile Ser Arg Thr Pro Glu Val Thr Cys Val Val Val Asp Val Ser
            20                  25                  30

His Glu Asp Pro Glu Val Lys Phe Asn Trp Tyr Val Asp Gly Val Glu
        35                  40                  45

Val His Asn Ala Lys Thr Lys Pro Arg Glu Glu Gln Tyr Asn Ser Thr
    50                  55                  60

Tyr Arg Val Val Ser Val Leu Thr Val Leu His Gln Asp Trp Leu Asn
65                  70                  75                  80

Gly Lys Glu Tyr Lys Cys Lys Val Ser Asn Lys Ala Leu Pro Ala Pro
                85                  90                  95

Ile Glu Lys Thr Ile Ser Lys Ala Lys Gly Gln Pro Arg Glu Pro Gln
            100                 105                 110

Val Tyr Thr Leu Pro Pro Ser Arg Glu Glu Met Thr Lys Asn Gln Val
```

```
            115                 120                 125
Ser Leu Thr Cys Leu Val Lys Gly Phe Tyr Pro Ser Asp Ile Ala Val
        130                 135                 140

Glu Trp Glu Ser Asn Gly Gln Pro Glu Asn Asn Tyr Lys Thr Thr Pro
145                 150                 155                 160

Pro Val Leu Asp Ser Asp Gly Ser Phe Phe Leu Tyr Ser Lys Leu Thr
                165                 170                 175

Val Asp Lys Ser Arg Trp Gln Gln Gly Asn Val Phe Ser Cys Ser Val
                180                 185                 190

Met His Glu Ala Leu His Asn His Tyr Thr Gln Lys Ser Leu Ser Leu
                195                 200                 205

<210> SEQ ID NO 72
<211> LENGTH: 208
<212> TYPE: PRT
<213> ORGANISM: Homo sapiens
<220> FEATURE:
<221> NAME/KEY: VARIANT
<222> LOCATION: (80)..(80)
<223> OTHER INFORMATION: Xaa = any amino acid
<220> FEATURE:
<221> NAME/KEY: VARIANT
<222> LOCATION: (90)..(90)
<223> OTHER INFORMATION: Xaa = any amino acid
<220> FEATURE:
<221> NAME/KEY: VARIANT
<222> LOCATION: (103)..(103)
<223> OTHER INFORMATION: Xaa = any amino acid
<220> FEATURE:
<221> NAME/KEY: VARIANT
<222> LOCATION: (105)..(105)
<223> OTHER INFORMATION: Xaa = any amino acid
<220> FEATURE:
<221> NAME/KEY: VARIANT
<222> LOCATION: (181)..(181)
<223> OTHER INFORMATION: Xaa = any amino acid

<400> SEQUENCE: 72

Gly Gly Pro Ser Val Phe Leu Phe Pro Pro Lys Pro Lys Asp Thr Leu
1               5                   10                  15

Met Ile Ser Arg Thr Pro Glu Val Thr Cys Val Val Val Asp Val Ser
                20                  25                  30

Gln Glu Asp Pro Glu Val Gln Phe Asn Trp Tyr Val Asp Gly Val Glu
            35                  40                  45

Val His Asn Ala Lys Thr Lys Pro Arg Glu Glu Gln Phe Asn Ser Thr
    50                  55                  60

Tyr Arg Val Val Ser Val Leu Thr Val Leu His Gln Asp Trp Leu Xaa
65                  70                  75                  80

Gly Lys Glu Tyr Lys Cys Lys Val Ser Xaa Lys Gly Leu Pro Ser Ser
                85                  90                  95

Ile Glu Lys Thr Ile Ser Xaa Ala Xaa Gly Gln Pro Arg Glu Pro Gln
                100                 105                 110

Val Tyr Thr Leu Pro Pro Ser Gln Glu Glu Met Thr Lys Asn Gln Val
            115                 120                 125

Ser Leu Thr Cys Leu Val Lys Gly Phe Tyr Pro Ser Asp Ile Ala Val
        130                 135                 140

Glu Trp Glu Ser Asn Gly Gln Pro Glu Asn Asn Tyr Lys Thr Thr Pro
145                 150                 155                 160

Pro Val Leu Asp Ser Asp Gly Ser Phe Phe Leu Tyr Ser Arg Leu Thr
                165                 170                 175

Val Asp Lys Ser Xaa Trp Gln Glu Gly Asn Val Phe Ser Cys Ser Val
```

```
                    180                 185                 190
Met His Glu Ala Leu His Asn His Tyr Thr Gln Lys Ser Leu Ser Leu
            195                 200                 205

<210> SEQ ID NO 73
<211> LENGTH: 210
<212> TYPE: PRT
<213> ORGANISM: Homo sapiens

<400> SEQUENCE: 73

Arg Gly Val Ser Ala Tyr Leu Ser Arg Pro Ser Pro Phe Asp Leu Phe
1               5                   10                  15

Ile Arg Lys Ser Pro Thr Ile Thr Cys Leu Val Val Asp Leu Ala Pro
            20                  25                  30

Ser Lys Gly Thr Val Gln Leu Thr Trp Ser Arg Ala Ser Gly Lys Pro
        35                  40                  45

Val Asn His Ser Thr Arg Lys Glu Glu Lys Gln Arg Asn Gly Thr Leu
    50                  55                  60

Thr Val Thr Ser Thr Leu Pro Val Gly Thr Arg Asp Trp Ile Glu Gly
65                  70                  75                  80

Glu Thr Tyr Gln Cys Arg Val Thr His Pro His Leu Pro Arg Ala Leu
                85                  90                  95

Met Arg Ser Thr Thr Lys Thr Ser Gly Pro Arg Ala Ala Pro Glu Val
            100                 105                 110

Tyr Ala Phe Ala Thr Pro Glu Trp Pro Gly Ser Arg Asp Lys Arg Thr
        115                 120                 125

Leu Ala Cys Leu Ile Gln Asn Phe Met Pro Glu Asp Ile Ser Val Gln
130                 135                 140

Trp Leu His Asn Glu Val Gln Leu Pro Asp Ala Arg His Ser Thr Thr
145                 150                 155                 160

Gln Pro Arg Lys Thr Lys Gly Ser Gly Phe Phe Val Phe Ser Arg Leu
                165                 170                 175

Glu Val Thr Arg Ala Glu Trp Glu Gln Lys Asp Glu Phe Ile Cys Arg
            180                 185                 190

Ala Val His Glu Ala Ala Ser Pro Ser Gln Thr Val Gln Arg Ala Val
        195                 200                 205

Ser Val
    210

<210> SEQ ID NO 74
<211> LENGTH: 14
<212> TYPE: PRT
<213> ORGANISM: Artificial Sequence
<220> FEATURE:
<223> OTHER INFORMATION: V5 tag sequence

<400> SEQUENCE: 74

Gly Lys Pro Ile Pro Asn Pro Leu Leu Gly Leu Asp Ser Thr
1               5                   10

<210> SEQ ID NO 75
<211> LENGTH: 8
<212> TYPE: PRT
<213> ORGANISM: Artificial Sequence
<220> FEATURE:
<223> OTHER INFORMATION: Flag tag sequence

<400> SEQUENCE: 75

Asp Tyr Lys Asp Asp Asp Asp Lys
1               5
```

```
<210> SEQ ID NO 76
<211> LENGTH: 25
<212> TYPE: DNA
<213> ORGANISM: Homo sapiens

<400> SEQUENCE: 76
aaaaaaaaaa aaaaaaaaaa tccaa                                          25

<210> SEQ ID NO 77
<211> LENGTH: 18
<212> TYPE: DNA
<213> ORGANISM: Homo sapiens

<400> SEQUENCE: 77 acttttttgat ggggttgt                                                 18

<210> SEQ ID NO 78
<211> LENGTH: 39
<212> TYPE: DNA
<213> ORGANISM: Homo sapiens

<400> SEQUENCE: 78 ccttttcat gggcttgttt ttttcttgta aatttgttt                            39

<210> SEQ ID NO 79
<211> LENGTH: 10
<212> TYPE: DNA
<213> ORGANISM: Artificial Sequence
<220> FEATURE:
<223> OTHER INFORMATION: Kozak consensus sequence

<400> SEQUENCE: 79 rccrccatgg                                                           10

<210> SEQ ID NO 80
<211> LENGTH: 4
<212> TYPE: PRT
<213> ORGANISM: Artificial Sequence
<220> FEATURE:
<223> OTHER INFORMATION: Exemplary peptide linker sequence

<400> SEQUENCE: 80

Gly Ser Gly Ser
1

<210> SEQ ID NO 81
<211> LENGTH: 4
<212> TYPE: PRT
<213> ORGANISM: Artificial Sequence
<220> FEATURE:
<223> OTHER INFORMATION: Exemplary peptide linker sequence

<400> SEQUENCE: 81

Gly Gly Ser Gly
1

<210> SEQ ID NO 82
<211> LENGTH: 4
<212> TYPE: PRT
<213> ORGANISM: Artificial Sequence
<220> FEATURE:
<223> OTHER INFORMATION: Exemplary peptide linker sequence

<400> SEQUENCE: 82
```

```
Gly Gly Gly Ser
1

<210> SEQ ID NO 83
<211> LENGTH: 5
<212> TYPE: PRT
<213> ORGANISM: Artificial Sequence
<220> FEATURE:
<223> OTHER INFORMATION: Exemplary peptide linker sequence

<400> SEQUENCE: 83

Gly Gly Gly Gly Ser
1               5

<210> SEQ ID NO 84
<211> LENGTH: 4
<212> TYPE: PRT
<213> ORGANISM: Artificial Sequence
<220> FEATURE:
<223> OTHER INFORMATION: Exemplary peptide linker sequence

<400> SEQUENCE: 84

Gly Asn Gly Asn
1

<210> SEQ ID NO 85
<211> LENGTH: 4
<212> TYPE: PRT
<213> ORGANISM: Artificial Sequence
<220> FEATURE:
<223> OTHER INFORMATION: Exemplary peptide linker sequence

<400> SEQUENCE: 85

Gly Gly Asn Gly
1

<210> SEQ ID NO 86
<211> LENGTH: 4
<212> TYPE: PRT
<213> ORGANISM: Artificial Sequence
<220> FEATURE:
<223> OTHER INFORMATION: Exemplary peptide linker sequence

<400> SEQUENCE: 86

Gly Gly Gly Asn
1

<210> SEQ ID NO 87
<211> LENGTH: 5
<212> TYPE: PRT
<213> ORGANISM: Artificial Sequence
<220> FEATURE:
<223> OTHER INFORMATION: Exemplary peptide linker sequence

<400> SEQUENCE: 87

Gly Gly Gly Gly Asn
1               5

<210> SEQ ID NO 88
<211> LENGTH: 15
<212> TYPE: PRT
<213> ORGANISM: Artificial Sequence
<220> FEATURE:
<223> OTHER INFORMATION: Exemplary peptide linker sequence

<400> SEQUENCE: 88
```

Gly Gly Gly Gly Ser Gly Gly Gly Ser Gly Gly Gly Ser
1               5                   10                  15

<210> SEQ ID NO 89
<211> LENGTH: 22
<212> TYPE: PRT
<213> ORGANISM: Artificial Sequence
<220> FEATURE:
<223> OTHER INFORMATION: Exemplary peptide linker sequence

<400> SEQUENCE: 89

Gly Ser Gly Gly Gly Gly Ser Gly Gly Gly Gly Ser Gly Gly Gly Gly
1               5                   10                  15

Ser Gly Gly Gly Gly Ser
            20

<210> SEQ ID NO 90
<211> LENGTH: 30
<212> TYPE: PRT
<213> ORGANISM: Artificial Sequence
<220> FEATURE:
<223> OTHER INFORMATION: Exemplary peptide linker sequence

<400> SEQUENCE: 90

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser
            20                  25                  30

<210> SEQ ID NO 91
<211> LENGTH: 25
<212> TYPE: PRT
<213> ORGANISM: Artificial Sequence
<220> FEATURE:
<223> OTHER INFORMATION: Exemplary peptide linker sequence

<400> SEQUENCE: 91

Asp Ala Ala Ala Lys Glu Ala Ala Ala Lys Asp Ala Ala Ala Arg Glu
1               5                   10                  15

Ala Ala Ala Arg Asp Ala Ala Ala Lys
            20                  25

<210> SEQ ID NO 92
<211> LENGTH: 14
<212> TYPE: PRT
<213> ORGANISM: Artificial Sequence
<220> FEATURE:
<223> OTHER INFORMATION: Exemplary peptide linker sequence

<400> SEQUENCE: 92

Asn Val Asp His Lys Pro Ser Asn Thr Lys Val Asp Lys Arg
1               5                   10

<210> SEQ ID NO 93
<211> LENGTH: 5
<212> TYPE: PRT
<213> ORGANISM: Artificial Sequence
<220> FEATURE:
<223> OTHER INFORMATION: Peptide linker sequence

<400> SEQUENCE: 93

Asp Gly Gly Gly Ser
1               5

<210> SEQ ID NO 94

<211> LENGTH: 5
<212> TYPE: PRT
<213> ORGANISM: Artificial Sequence
<220> FEATURE:
<223> OTHER INFORMATION: Peptide linker sequence

<400> SEQUENCE: 94

Thr Gly Glu Lys Pro
1               5

<210> SEQ ID NO 95
<211> LENGTH: 4
<212> TYPE: PRT
<213> ORGANISM: Artificial Sequence
<220> FEATURE:
<223> OTHER INFORMATION: Peptide linker sequence

<400> SEQUENCE: 95

Gly Gly Arg Arg
1

<210> SEQ ID NO 96
<211> LENGTH: 14
<212> TYPE: PRT
<213> ORGANISM: Artificial Sequence
<220> FEATURE:
<223> OTHER INFORMATION: Peptide linker sequence

<400> SEQUENCE: 96

Glu Gly Lys Ser Ser Gly Ser Gly Ser Glu Ser Lys Val Asp
1               5                   10

<210> SEQ ID NO 97
<211> LENGTH: 18
<212> TYPE: PRT
<213> ORGANISM: Artificial Sequence
<220> FEATURE:
<223> OTHER INFORMATION: Peptide linker sequence

<400> SEQUENCE: 97

Lys Glu Ser Gly Ser Val Ser Ser Glu Gln Leu Ala Gln Phe Arg Ser
1               5                   10                  15

Leu Asp

<210> SEQ ID NO 98
<211> LENGTH: 8
<212> TYPE: PRT
<213> ORGANISM: Artificial Sequence
<220> FEATURE:
<223> OTHER INFORMATION: Peptide linker sequence

<400> SEQUENCE: 98

Gly Gly Arg Arg Gly Gly Gly Ser
1               5

<210> SEQ ID NO 99
<211> LENGTH: 9
<212> TYPE: PRT
<213> ORGANISM: Artificial Sequence
<220> FEATURE:
<223> OTHER INFORMATION: Peptide linker sequence

<400> SEQUENCE: 99

Leu Arg Gln Arg Asp Gly Glu Arg Pro
1               5

```
<210> SEQ ID NO 100
<211> LENGTH: 12
<212> TYPE: PRT
<213> ORGANISM: Artificial Sequence
<220> FEATURE:
<223> OTHER INFORMATION: Peptide linker sequence

<400> SEQUENCE: 100

Leu Arg Gln Lys Asp Gly Gly Gly Ser Glu Arg Pro
1               5                   10

<210> SEQ ID NO 101
<211> LENGTH: 16
<212> TYPE: PRT
<213> ORGANISM: Artificial Sequence
<220> FEATURE:
<223> OTHER INFORMATION: Peptide linker sequence

<400> SEQUENCE: 101

Leu Arg Gln Lys Asp Gly Gly Gly Ser Gly Gly Gly Ser Glu Arg Pro
1               5                   10                  15

<210> SEQ ID NO 102
<211> LENGTH: 19
<212> TYPE: PRT
<213> ORGANISM: Unknown
<220> FEATURE:
<223> OTHER INFORMATION: Naturally occurring 2A or 2A-like self
      cleaving peptide

<400> SEQUENCE: 102

Leu Leu Asn Phe Asp Leu Leu Lys Leu Ala Gly Asp Val Glu Ser Asn
1               5                   10                  15

Pro Gly Pro

<210> SEQ ID NO 103
<211> LENGTH: 19
<212> TYPE: PRT
<213> ORGANISM: Unknown
<220> FEATURE:
<223> OTHER INFORMATION: Naturally occurring 2A or 2A-like self
      cleaving peptide

<400> SEQUENCE: 103

Thr Leu Asn Phe Asp Leu Leu Lys Leu Ala Gly Asp Val Glu Ser Asn
1               5                   10                  15

Pro Gly Pro

<210> SEQ ID NO 104
<211> LENGTH: 14
<212> TYPE: PRT
<213> ORGANISM: Unknown
<220> FEATURE:
<223> OTHER INFORMATION: Naturally occurring 2A or 2A-like self cleaving
      peptide

<400> SEQUENCE: 104

Leu Leu Lys Leu Ala Gly Asp Val Glu Ser Asn Pro Gly Pro
1               5                   10

<210> SEQ ID NO 105
<211> LENGTH: 17
<212> TYPE: PRT
<213> ORGANISM: Unknown
<220> FEATURE:
<223> OTHER INFORMATION: Naturally occurring 2A or 2A-like self cleaving
      peptide
```

<400> SEQUENCE: 105

Asn Phe Asp Leu Leu Lys Leu Ala Gly Asp Val Glu Ser Asn Pro Gly
1               5                   10                  15

Pro

<210> SEQ ID NO 106
<211> LENGTH: 20
<212> TYPE: PRT
<213> ORGANISM: Unknown
<220> FEATURE:
<223> OTHER INFORMATION: Naturally occurring 2A or 2A-like self cleaving
      peptide

<400> SEQUENCE: 106

Gln Leu Leu Asn Phe Asp Leu Leu Lys Leu Ala Gly Asp Val Glu Ser
1               5                   10                  15

Asn Pro Gly Pro
            20

<210> SEQ ID NO 107
<211> LENGTH: 24
<212> TYPE: PRT
<213> ORGANISM: Unknown
<220> FEATURE:
<223> OTHER INFORMATION: Naturally occurring 2A or 2A-like self cleaving
      peptide

<400> SEQUENCE: 107

Ala Pro Val Lys Gln Thr Leu Asn Phe Asp Leu Leu Lys Leu Ala Gly
1               5                   10                  15

Asp Val Glu Ser Asn Pro Gly Pro
            20

<210> SEQ ID NO 108
<211> LENGTH: 40
<212> TYPE: PRT
<213> ORGANISM: Unknown
<220> FEATURE:
<223> OTHER INFORMATION: Naturally occurring 2A or 2A-like self cleaving
      peptide

<400> SEQUENCE: 108

Val Thr Glu Leu Leu Tyr Arg Met Lys Arg Ala Glu Thr Tyr Cys Pro
1               5                   10                  15

Arg Pro Leu Leu Ala Ile His Pro Thr Glu Ala Arg His Lys Gln Lys
            20                  25                  30

Ile Val Ala Pro Val Lys Gln Thr
        35                  40

<210> SEQ ID NO 109
<211> LENGTH: 18
<212> TYPE: PRT
<213> ORGANISM: Unknown
<220> FEATURE:
<223> OTHER INFORMATION: Naturally occurring 2A or 2A-like self cleaving
      peptide

<400> SEQUENCE: 109

Leu Asn Phe Asp Leu Leu Lys Leu Ala Gly Asp Val Glu Ser Asn Pro
1               5                   10                  15

Gly Pro

```
<210> SEQ ID NO 110
<211> LENGTH: 40
<212> TYPE: PRT
<213> ORGANISM: Unknown
<220> FEATURE:
<223> OTHER INFORMATION: Naturally occurring 2A or 2A-like self cleaving
      peptide

<400> SEQUENCE: 110

Leu Leu Ala Ile His Pro Thr Glu Ala Arg His Lys Gln Lys Ile Val
1               5                   10                  15

Ala Pro Val Lys Gln Thr Leu Asn Phe Asp Leu Leu Lys Leu Ala Gly
            20                  25                  30

Asp Val Glu Ser Asn Pro Gly Pro
        35                  40

<210> SEQ ID NO 111
<211> LENGTH: 0
<212> TYPE: PRT
<213> ORGANISM: Unknown
<220> FEATURE:
<223> OTHER INFORMATION: Naturally occurring 2A or 2A-like self cleaving
      peptide

<400> SEQUENCE: 111

000

<210> SEQ ID NO 112
<211> LENGTH: 7
<212> TYPE: PRT
<213> ORGANISM: Tobacco etch virus
<220> FEATURE:
<221> NAME/KEY: VARIANT
<222> LOCATION: (2)..(2)
<223> OTHER INFORMATION: Xaa = any amino acid
<220> FEATURE:
<221> NAME/KEY: VARIANT
<222> LOCATION: (3)..(3)
<223> OTHER INFORMATION: Xaa = any amino acid
<220> FEATURE:
<221> NAME/KEY: VARIANT
<222> LOCATION: (5)..(5)
<223> OTHER INFORMATION: Xaa = any amino acid
<220> FEATURE:
<221> NAME/KEY: VARIANT
<222> LOCATION: (7)..(7)
<223> OTHER INFORMATION: Xaa is either Gly or Ser

<400> SEQUENCE: 112

Glu Xaa Xaa Tyr Xaa Gln Xaa
1               5

<210> SEQ ID NO 113
<211> LENGTH: 7
<212> TYPE: PRT
<213> ORGANISM: Tobacco etch virus

<400> SEQUENCE: 113

Glu Asn Leu Tyr Phe Gln Gly
1               5

<210> SEQ ID NO 114
<211> LENGTH: 7
<212> TYPE: PRT
<213> ORGANISM: Tabacco etch virus

<400> SEQUENCE: 114

Glu Asn Leu Tyr Phe Gln Ser
```

```
1               5

<210> SEQ ID NO 115
<211> LENGTH: 4
<212> TYPE: PRT
<213> ORGANISM: Artificial Sequence
<220> FEATURE:
<223> OTHER INFORMATION: Thrombin cleavable linker

<400> SEQUENCE: 115

Gly Arg Gly Asp
1

<210> SEQ ID NO 116
<211> LENGTH: 6
<212> TYPE: PRT
<213> ORGANISM: Artificial Sequence
<220> FEATURE:
<223> OTHER INFORMATION: Thrombin cleavable linker

<400> SEQUENCE: 116

Gly Arg Gly Asp Asn Pro
1               5

<210> SEQ ID NO 117
<211> LENGTH: 5
<212> TYPE: PRT
<213> ORGANISM: Artificial Sequence
<220> FEATURE:
<223> OTHER INFORMATION: Thrombin cleavable linker

<400> SEQUENCE: 117

Gly Arg Gly Asp Ser
1               5

<210> SEQ ID NO 118
<211> LENGTH: 7
<212> TYPE: PRT
<213> ORGANISM: Artificial Sequence
<220> FEATURE:
<223> OTHER INFORMATION: Thrombin cleavable linker

<400> SEQUENCE: 118

Gly Arg Gly Asp Ser Pro Lys
1               5

<210> SEQ ID NO 119
<211> LENGTH: 4
<212> TYPE: PRT
<213> ORGANISM: Artificial Sequence
<220> FEATURE:
<223> OTHER INFORMATION: Elastase cleavable linker

<400> SEQUENCE: 119

Ala Ala Pro Val
1

<210> SEQ ID NO 120
<211> LENGTH: 4
<212> TYPE: PRT
<213> ORGANISM: Artificial Sequence
<220> FEATURE:
<223> OTHER INFORMATION: Elastase cleavable linker

<400> SEQUENCE: 120

Ala Ala Pro Leu
1
```

<210> SEQ ID NO 121
<211> LENGTH: 4
<212> TYPE: PRT
<213> ORGANISM: Artificial Sequence
<220> FEATURE:
<223> OTHER INFORMATION: Elastase cleavable linker

<400> SEQUENCE: 121

Ala Ala Pro Phe
1

<210> SEQ ID NO 122
<211> LENGTH: 4
<212> TYPE: PRT
<213> ORGANISM: Artificial Sequence
<220> FEATURE:
<223> OTHER INFORMATION: Elastase cleavable linker

<400> SEQUENCE: 122

Ala Tyr Leu Val
1

<210> SEQ ID NO 123
<211> LENGTH: 6
<212> TYPE: PRT
<213> ORGANISM: Artificial Sequence
<220> FEATURE:
<223> OTHER INFORMATION: Matrix metalloproteinase cleavable linker
<220> FEATURE:
<221> NAME/KEY: VARIANT
<222> LOCATION: (3)..(3)
<223> OTHER INFORMATION: Xaa = Any amino acid
<220> FEATURE:
<221> NAME/KEY: VARIANT
<222> LOCATION: (6)..(6)
<223> OTHER INFORMATION: Xaa = Any amino acid

<400> SEQUENCE: 123

Gly Pro Xaa Gly Pro Xaa
1               5

<210> SEQ ID NO 124
<211> LENGTH: 4
<212> TYPE: PRT
<213> ORGANISM: Artificial Sequence
<220> FEATURE:
<223> OTHER INFORMATION: Matrix metalloproteinase cleavable linker
<220> FEATURE:
<221> NAME/KEY: VARIANT
<222> LOCATION: (4)..(4)
<223> OTHER INFORMATION: Xaa = Any amino acid

<400> SEQUENCE: 124

Leu Gly Pro Xaa
1

<210> SEQ ID NO 125
<211> LENGTH: 6
<212> TYPE: PRT
<213> ORGANISM: Artificial Sequence
<220> FEATURE:
<223> OTHER INFORMATION: Matrix metalloproteinase cleavable linker
<220> FEATURE:
<221> NAME/KEY: VARIANT
<222> LOCATION: (6)..(6)
<223> OTHER INFORMATION: Xaa = Any amino acid

<400> SEQUENCE: 125

```
Gly Pro Ile Gly Pro Xaa
1               5

<210> SEQ ID NO 126
<211> LENGTH: 5
<212> TYPE: PRT
<213> ORGANISM: Artificial Sequence
<220> FEATURE:
<223> OTHER INFORMATION: Matrix metalloproteinase cleavable linker
<220> FEATURE:
<221> NAME/KEY: VARIANT
<222> LOCATION: (5)..(5)
<223> OTHER INFORMATION: Xaa = Any amino acid

<400> SEQUENCE: 126

Ala Pro Gly Leu Xaa
1               5

<210> SEQ ID NO 127
<211> LENGTH: 7
<212> TYPE: PRT
<213> ORGANISM: Artificial Sequence
<220> FEATURE:
<223> OTHER INFORMATION: Collagenase cleavable linker
<220> FEATURE:
<221> NAME/KEY: VARIANT
<222> LOCATION: (7)..(7)
<223> OTHER INFORMATION: Xaa = Any amino acid

<400> SEQUENCE: 127

Pro Leu Gly Pro Asp Arg Xaa
1               5

<210> SEQ ID NO 128
<211> LENGTH: 7
<212> TYPE: PRT
<213> ORGANISM: Artificial Sequence
<220> FEATURE:
<223> OTHER INFORMATION: Collagenase cleavable linker
<220> FEATURE:
<221> NAME/KEY: VARIANT
<222> LOCATION: (7)..(7)
<223> OTHER INFORMATION: Xaa = Any amino acid

<400> SEQUENCE: 128

Pro Leu Gly Leu Leu Gly Xaa
1               5

<210> SEQ ID NO 129
<211> LENGTH: 7
<212> TYPE: PRT
<213> ORGANISM: Artificial Sequence
<220> FEATURE:
<223> OTHER INFORMATION: Collagenase cleavable linker

<400> SEQUENCE: 129

Pro Gln Gly Ile Ala Gly Trp
1               5

<210> SEQ ID NO 130
<211> LENGTH: 5
<212> TYPE: PRT
<213> ORGANISM: Artificial Sequence
<220> FEATURE:
<223> OTHER INFORMATION: Collagenase cleavable linker

<400> SEQUENCE: 130

Pro Leu Gly Cys His
1               5
```

```
<210> SEQ ID NO 131
<211> LENGTH: 6
<212> TYPE: PRT
<213> ORGANISM: Artificial Sequence
<220> FEATURE:
<223> OTHER INFORMATION: Collagenase cleavable linker

<400> SEQUENCE: 131

Pro Leu Gly Leu Tyr Ala
1               5

<210> SEQ ID NO 132
<211> LENGTH: 7
<212> TYPE: PRT
<213> ORGANISM: Artificial Sequence
<220> FEATURE:
<223> OTHER INFORMATION: Collagenase cleavable linker

<400> SEQUENCE: 132

Pro Leu Ala Leu Trp Ala Arg
1               5

<210> SEQ ID NO 133
<211> LENGTH: 7
<212> TYPE: PRT
<213> ORGANISM: Artificial Sequence
<220> FEATURE:
<223> OTHER INFORMATION: Collagenase cleavable linker

<400> SEQUENCE: 133

Pro Leu Ala Tyr Trp Ala Arg
1               5

<210> SEQ ID NO 134
<211> LENGTH: 7
<212> TYPE: PRT
<213> ORGANISM: Artificial Sequence
<220> FEATURE:
<223> OTHER INFORMATION: Stromelysin cleavable linker

<400> SEQUENCE: 134

Pro Tyr Ala Tyr Tyr Met Arg
1               5

<210> SEQ ID NO 135
<211> LENGTH: 7
<212> TYPE: PRT
<213> ORGANISM: Artificial Sequence
<220> FEATURE:
<223> OTHER INFORMATION: Gelatinase cleavable linker

<400> SEQUENCE: 135

Pro Leu Gly Met Tyr Ser Arg
1               5

<210> SEQ ID NO 136
<211> LENGTH: 4
<212> TYPE: PRT
<213> ORGANISM: Artificial Sequence
<220> FEATURE:
<223> OTHER INFORMATION: Angiotensin converting enzyme cleavable linker

<400> SEQUENCE: 136

Gly Asp Lys Pro
1
```

```
<210> SEQ ID NO 137
<211> LENGTH: 5
<212> TYPE: PRT
<213> ORGANISM: Artificial Sequence
<220> FEATURE:
<223> OTHER INFORMATION: Angiotensin converting enzyme cleavable linker

<400> SEQUENCE: 137

Gly Ser Asp Lys Pro
1               5

<210> SEQ ID NO 138
<211> LENGTH: 4
<212> TYPE: PRT
<213> ORGANISM: Artificial Sequence
<220> FEATURE:
<223> OTHER INFORMATION: Cathepsin B cleavable linker

<400> SEQUENCE: 138

Ala Leu Ala Leu
1

<210> SEQ ID NO 139
<211> LENGTH: 4
<212> TYPE: PRT
<213> ORGANISM: Artificial Sequence
<220> FEATURE:
<223> OTHER INFORMATION: Cathepsin B cleavable linker

<400> SEQUENCE: 139

Gly Phe Leu Gly
1

<210> SEQ ID NO 140
<211> LENGTH: 45
<212> TYPE: DNA
<213> ORGANISM: Homo sapiens

<400> SEQUENCE: 140
agtcttgcac ttgtcacgaa ttcgatgccc agcgccagcg ccagc          45

<210> SEQ ID NO 141
<211> LENGTH: 75
<212> TYPE: DNA
<213> ORGANISM: Homo sapiens

<400> SEQUENCE: 141
cggtgggcat gtgtgagttt tgtctcactt gtcgtcatcg tctttgtagt ccgtagaatc    60
gagaccgagg agagg                                                    75

<210> SEQ ID NO 142
<211> LENGTH: 45
<212> TYPE: DNA
<213> ORGANISM: Homo sapiens

<400> SEQUENCE: 142
gatcaccggc gaaggagggc caccatgccc agcgccagcg ccagc          45

<210> SEQ ID NO 143
<211> LENGTH: 75
<212> TYPE: DNA
<213> ORGANISM: Homo sapiens

<400> SEQUENCE: 143
```

```
cggtgggcat gtgtgagttt tgtctcactt gtcgtcatcg tctttgtagt ccgtagaatc    60
gagaccgagg agagg                                                     75
```

<210> SEQ ID NO 144
<211> LENGTH: 37
<212> TYPE: DNA
<213> ORGANISM: Homo sapiens
<220> FEATURE:
<221> NAME/KEY: misc_feature
<222> LOCATION: (1)..(37)
<223> OTHER INFORMATION: Human C76X Primer

<400> SEQUENCE: 144

```
gctaaaggga aacagagctt cttagtccta cgtcagc                             37
```

<210> SEQ ID NO 145
<211> LENGTH: 37
<212> TYPE: DNA
<213> ORGANISM: Homo sapiens
<220> FEATURE:
<221> NAME/KEY: misc_feature
<222> LOCATION: (1)..(37)
<223> OTHER INFORMATION: Human C130X Primer

<400> SEQUENCE: 145

```
gtgaatcaga aaattggaag cagcacacag caagacg                             37
```

<210> SEQ ID NO 146
<211> LENGTH: 40
<212> TYPE: DNA
<213> ORGANISM: Artificial Sequence
<220> FEATURE:
<223> OTHER INFORMATION: E.coli codon optimized C76X Primer

<400> SEQUENCE: 146

```
cgtgcaaaag gcaaacagag ctttctggtc ctgcgtcagc                           40
```

<210> SEQ ID NO 147
<211> LENGTH: 41
<212> TYPE: DNA
<213> ORGANISM: Artificial Sequence
<220> FEATURE:
<223> OTHER INFORMATION: E.coli codon optimized C130X Primer

<400> SEQUENCE: 147

```
caatcaaaag atcggctcga gcacgcaaca agatgtcgag c                         41
```

<210> SEQ ID NO 148
<211> LENGTH: 44
<212> TYPE: DNA
<213> ORGANISM: Homo sapiens

<400> SEQUENCE: 148

```
ctgaaccccg tctgcccctg gacaaaactc acacatgccc accg                      44
```

<210> SEQ ID NO 149
<211> LENGTH: 47
<212> TYPE: DNA
<213> ORGANISM: Homo sapiens

<400> SEQUENCE: 149

```
gctttgttag cagccggatc tcatttaccc ggagacaggg agaggct                   47
```

<210> SEQ ID NO 150
<211> LENGTH: 57

<210> SEQ ID NO 150
<211> LENGTH: 57
<212> TYPE: DNA
<213> ORGANISM: Homo sapiens

<400> SEQUENCE: 150
ttttgtttaa ctttaagaag gagatatacc atggacaaaa ctcacacatg cccaccg      57

<210> SEQ ID NO 151
<211> LENGTH: 41
<212> TYPE: DNA
<213> ORGANISM: Homo sapiens

<400> SEQUENCE: 151
ctggcgctgg cgctgggttt acccggagac agggagaggc t      41

<210> SEQ ID NO 152
<211> LENGTH: 4
<212> TYPE: PRT
<213> ORGANISM: Homo sapiens

<400> SEQUENCE: 152

His Ile Gly His
1

<210> SEQ ID NO 153
<211> LENGTH: 5
<212> TYPE: PRT
<213> ORGANISM: Homo sapiens

<400> SEQUENCE: 153

Lys Met Ser Lys Ser
1               5

<210> SEQ ID NO 154
<211> LENGTH: 182
<212> TYPE: PRT
<213> ORGANISM: Homo sapiens

<400> SEQUENCE: 154

Met Pro Ser Ala Ser Ala Ser Arg Lys Ser Gln Glu Lys Pro Arg Glu
1               5                   10                  15

Ile Met Asp Ala Ala Glu Asp Tyr Ala Lys Glu Arg Tyr Gly Ile Ser
                20                  25                  30

Ser Met Ile Gln Ser Gln Glu Lys Pro Asp Arg Val Leu Val Arg Val
            35                  40                  45

Arg Asp Leu Thr Ile Gln Lys Ala Asp Glu Val Val Trp Val Arg Ala
        50                  55                  60

Arg Val His Thr Ser Arg Ala Lys Gly Lys Gln Cys Phe Leu Val Leu
65                  70                  75                  80

Arg Gln Gln Gln Phe Asn Val Gln Ala Leu Val Ala Val Gly Asp His
                85                  90                  95

Ala Ser Lys Gln Met Val Lys Phe Ala Ala Asn Ile Asn Lys Glu Ser
                100                 105                 110

Ile Val Asp Val Glu Gly Val Val Arg Lys Val Asn Gln Lys Ile Gly
            115                 120                 125

Ser Cys Thr Gln Gln Asp Val Glu Leu His Val Gln Lys Ile Tyr Val
        130                 135                 140

Ile Ser Leu Ala Glu Pro Arg Leu Pro Leu Gln Leu Asp Asp Ala Val
145                 150                 155                 160

Arg Pro Glu Ala Glu Gly Glu Glu Glu Gly Arg Ala Thr Val Asn Gln
                165                 170                 175

Asp Thr Arg Leu Asp Asn
            180

<210> SEQ ID NO 155
<211> LENGTH: 180
<212> TYPE: PRT
<213> ORGANISM: Homo sapiens

<400> SEQUENCE: 155

Met Pro Ser Ala Ser Ala Ser Arg Lys Ser Gln Glu Lys Pro Arg Glu
1               5                   10                  15

Ile Met Asp Ala Ala Glu Asp Tyr Ala Lys Glu Arg Tyr Gly Ile Ser
            20                  25                  30

Ser Met Ile Gln Ser Gln Glu Lys Pro Asp Arg Val Leu Val Arg Val
        35                  40                  45

Arg Asp Leu Thr Ile Gln Lys Ala Asp Glu Val Val Trp Val Arg Ala
    50                  55                  60

Arg Val His Thr Ser Arg Ala Lys Gly Lys Gln Cys Phe Leu Val Leu
65                  70                  75                  80

Arg Gln Gln Gln Phe Asn Val Gln Ala Leu Val Ala Val Gly Asp His
                85                  90                  95

Ala Ser Lys Gln Met Val Lys Phe Ala Ala Asn Ile Asn Lys Glu Ser
            100                 105                 110

Ile Val Asp Val Glu Gly Val Val Arg Lys Val Asn Gln Lys Ile Gly
        115                 120                 125

Ser Cys Thr Gln Gln Asp Val Glu Leu His Val Gln Lys Ile Tyr Val
    130                 135                 140

Ile Ser Leu Ala Glu Pro Arg Leu Pro Leu Gln Leu Asp Asp Ala Val
145                 150                 155                 160

Arg Pro Glu Ala Glu Gly Glu Glu Gly Arg Ala Thr Val Asn Gln
                165                 170                 175

Asp Thr Arg Leu
            180

<210> SEQ ID NO 156
<211> LENGTH: 178
<212> TYPE: PRT
<213> ORGANISM: Homo sapiens

<400> SEQUENCE: 156

Met Pro Ser Ala Ser Ala Ser Arg Lys Ser Gln Glu Lys Pro Arg Glu
1               5                   10                  15

Ile Met Asp Ala Ala Glu Asp Tyr Ala Lys Glu Arg Tyr Gly Ile Ser
            20                  25                  30

Ser Met Ile Gln Ser Gln Glu Lys Pro Asp Arg Val Leu Val Arg Val
        35                  40                  45

Arg Asp Leu Thr Ile Gln Lys Ala Asp Glu Val Val Trp Val Arg Ala
    50                  55                  60

Arg Val His Thr Ser Arg Ala Lys Gly Lys Gln Cys Phe Leu Val Leu
65                  70                  75                  80

Arg Gln Gln Gln Phe Asn Val Gln Ala Leu Val Ala Val Gly Asp His
                85                  90                  95

Ala Ser Lys Gln Met Val Lys Phe Ala Ala Asn Ile Asn Lys Glu Ser
            100                 105                 110

Ile Val Asp Val Glu Gly Val Val Arg Lys Val Asn Gln Lys Ile Gly
        115                 120                 125

```
Ser Cys Thr Gln Gln Asp Val Glu Leu His Val Gln Lys Ile Tyr Val
        130                 135                 140

Ile Ser Leu Ala Glu Pro Arg Leu Pro Leu Gln Leu Asp Asp Ala Val
145                 150                 155                 160

Arg Pro Glu Ala Glu Gly Glu Glu Gly Arg Ala Thr Val Asn Gln
                165                 170                 175

Asp Thr

<210> SEQ ID NO 157
<211> LENGTH: 176
<212> TYPE: PRT
<213> ORGANISM: Homo sapiens

<400> SEQUENCE: 157

Met Pro Ser Ala Ser Ala Ser Arg Lys Ser Gln Glu Lys Pro Arg Glu
1               5                   10                  15

Ile Met Asp Ala Ala Glu Asp Tyr Ala Lys Glu Arg Tyr Gly Ile Ser
                20                  25                  30

Ser Met Ile Gln Ser Gln Glu Lys Pro Asp Arg Val Leu Val Arg Val
            35                  40                  45

Arg Asp Leu Thr Ile Gln Lys Ala Asp Glu Val Val Trp Val Arg Ala
        50                  55                  60

Arg Val His Thr Ser Arg Ala Lys Gly Lys Gln Cys Phe Leu Val Leu
65                  70                  75                  80

Arg Gln Gln Gln Phe Asn Val Gln Ala Leu Val Ala Val Gly Asp His
                85                  90                  95

Ala Ser Lys Gln Met Val Lys Phe Ala Ala Asn Ile Asn Lys Glu Ser
                100                 105                 110

Ile Val Asp Val Glu Gly Val Val Arg Lys Val Asn Gln Lys Ile Gly
            115                 120                 125

Ser Cys Thr Gln Gln Asp Val Glu Leu His Val Gln Lys Ile Tyr Val
        130                 135                 140

Ile Ser Leu Ala Glu Pro Arg Leu Pro Leu Gln Leu Asp Asp Ala Val
145                 150                 155                 160

Arg Pro Glu Ala Glu Gly Glu Glu Gly Arg Ala Thr Val Asn Gln
                165                 170                 175

<210> SEQ ID NO 158
<211> LENGTH: 174
<212> TYPE: PRT
<213> ORGANISM: Homo sapiens

<400> SEQUENCE: 158

Met Pro Ser Ala Ser Ala Ser Arg Lys Ser Gln Glu Lys Pro Arg Glu
1               5                   10                  15

Ile Met Asp Ala Ala Glu Asp Tyr Ala Lys Glu Arg Tyr Gly Ile Ser
                20                  25                  30

Ser Met Ile Gln Ser Gln Glu Lys Pro Asp Arg Val Leu Val Arg Val
            35                  40                  45

Arg Asp Leu Thr Ile Gln Lys Ala Asp Glu Val Val Trp Val Arg Ala
        50                  55                  60

Arg Val His Thr Ser Arg Ala Lys Gly Lys Gln Cys Phe Leu Val Leu
65                  70                  75                  80

Arg Gln Gln Gln Phe Asn Val Gln Ala Leu Val Ala Val Gly Asp His
                85                  90                  95
```

```
Ala Ser Lys Gln Met Val Lys Phe Ala Ala Asn Ile Asn Lys Glu Ser
            100                 105                 110

Ile Val Asp Val Glu Gly Val Val Arg Lys Val Asn Gln Lys Ile Gly
        115                 120                 125

Ser Cys Thr Gln Gln Asp Val Glu Leu His Val Gln Lys Ile Tyr Val
    130                 135                 140

Ile Ser Leu Ala Glu Pro Arg Leu Pro Leu Gln Leu Asp Asp Ala Val
145                 150                 155                 160

Arg Pro Glu Ala Glu Gly Glu Glu Glu Gly Arg Ala Thr Val
                165                 170

<210> SEQ ID NO 159
<211> LENGTH: 172
<212> TYPE: PRT
<213> ORGANISM: Homo sapiens

<400> SEQUENCE: 159

Met Pro Ser Ala Ser Ala Ser Arg Lys Ser Gln Glu Lys Pro Arg Glu
1               5                   10                  15

Ile Met Asp Ala Ala Glu Asp Tyr Ala Lys Glu Arg Tyr Gly Ile Ser
            20                  25                  30

Ser Met Ile Gln Ser Gln Glu Lys Pro Asp Arg Val Leu Val Arg Val
        35                  40                  45

Arg Asp Leu Thr Ile Gln Lys Ala Asp Glu Val Val Trp Val Arg Ala
    50                  55                  60

Arg Val His Thr Ser Arg Ala Lys Gly Lys Gln Cys Phe Leu Val Leu
65                  70                  75                  80

Arg Gln Gln Gln Phe Asn Val Gln Ala Leu Val Ala Val Gly Asp His
                85                  90                  95

Ala Ser Lys Gln Met Val Lys Phe Ala Ala Asn Ile Asn Lys Glu Ser
            100                 105                 110

Ile Val Asp Val Glu Gly Val Val Arg Lys Val Asn Gln Lys Ile Gly
        115                 120                 125

Ser Cys Thr Gln Gln Asp Val Glu Leu His Val Gln Lys Ile Tyr Val
    130                 135                 140

Ile Ser Leu Ala Glu Pro Arg Leu Pro Leu Gln Leu Asp Asp Ala Val
145                 150                 155                 160

Arg Pro Glu Ala Glu Gly Glu Glu Glu Gly Arg Ala
                165                 170

<210> SEQ ID NO 160
<211> LENGTH: 170
<212> TYPE: PRT
<213> ORGANISM: Homo sapiens

<400> SEQUENCE: 160

Met Pro Ser Ala Ser Ala Ser Arg Lys Ser Gln Glu Lys Pro Arg Glu
1               5                   10                  15

Ile Met Asp Ala Ala Glu Asp Tyr Ala Lys Glu Arg Tyr Gly Ile Ser
            20                  25                  30

Ser Met Ile Gln Ser Gln Glu Lys Pro Asp Arg Val Leu Val Arg Val
        35                  40                  45

Arg Asp Leu Thr Ile Gln Lys Ala Asp Glu Val Val Trp Val Arg Ala
    50                  55                  60

Arg Val His Thr Ser Arg Ala Lys Gly Lys Gln Cys Phe Leu Val Leu
65                  70                  75                  80
```

```
Arg Gln Gln Gln Phe Asn Val Gln Ala Leu Val Ala Val Gly Asp His
                85                  90                  95

Ala Ser Lys Gln Met Val Lys Phe Ala Ala Asn Ile Asn Lys Glu Ser
            100                 105                 110

Ile Val Asp Val Glu Gly Val Val Arg Lys Val Asn Gln Lys Ile Gly
        115                 120                 125

Ser Cys Thr Gln Gln Asp Val Glu Leu His Val Gln Lys Ile Tyr Val
    130                 135                 140

Ile Ser Leu Ala Glu Pro Arg Leu Pro Leu Gln Leu Asp Asp Ala Val
145                 150                 155                 160

Arg Pro Glu Ala Glu Gly Glu Glu Gly
                165                 170

<210> SEQ ID NO 161
<211> LENGTH: 168
<212> TYPE: PRT
<213> ORGANISM: Homo sapiens

<400> SEQUENCE: 161

Met Pro Ser Ala Ser Ala Ser Arg Lys Ser Gln Glu Lys Pro Arg Glu
1               5                   10                  15

Ile Met Asp Ala Ala Glu Asp Tyr Ala Lys Glu Arg Tyr Gly Ile Ser
            20                  25                  30

Ser Met Ile Gln Ser Gln Glu Lys Pro Asp Arg Val Leu Val Arg Val
        35                  40                  45

Arg Asp Leu Thr Ile Gln Lys Ala Asp Glu Val Val Trp Val Arg Ala
    50                  55                  60

Arg Val His Thr Ser Arg Ala Lys Gly Lys Gln Cys Phe Leu Val Leu
65                  70                  75                  80

Arg Gln Gln Gln Phe Asn Val Gln Ala Leu Val Ala Val Gly Asp His
                85                  90                  95

Ala Ser Lys Gln Met Val Lys Phe Ala Ala Asn Ile Asn Lys Glu Ser
            100                 105                 110

Ile Val Asp Val Glu Gly Val Val Arg Lys Val Asn Gln Lys Ile Gly
        115                 120                 125

Ser Cys Thr Gln Gln Asp Val Glu Leu His Val Gln Lys Ile Tyr Val
    130                 135                 140

Ile Ser Leu Ala Glu Pro Arg Leu Pro Leu Gln Leu Asp Asp Ala Val
145                 150                 155                 160

Arg Pro Glu Ala Glu Gly Glu Glu
                165

<210> SEQ ID NO 162
<211> LENGTH: 166
<212> TYPE: PRT
<213> ORGANISM: Homo sapiens

<400> SEQUENCE: 162

Met Pro Ser Ala Ser Ala Ser Arg Lys Ser Gln Glu Lys Pro Arg Glu
1               5                   10                  15

Ile Met Asp Ala Ala Glu Asp Tyr Ala Lys Glu Arg Tyr Gly Ile Ser
            20                  25                  30

Ser Met Ile Gln Ser Gln Glu Lys Pro Asp Arg Val Leu Val Arg Val
        35                  40                  45

Arg Asp Leu Thr Ile Gln Lys Ala Asp Glu Val Val Trp Val Arg Ala
    50                  55                  60
```

```
Arg Val His Thr Ser Arg Ala Lys Gly Lys Gln Cys Phe Leu Val Leu
 65                  70                  75                  80

Arg Gln Gln Gln Phe Asn Val Gln Ala Leu Val Ala Val Gly Asp His
                 85                  90                  95

Ala Ser Lys Gln Met Val Lys Phe Ala Ala Asn Ile Asn Lys Glu Ser
            100                 105                 110

Ile Val Asp Val Glu Gly Val Val Arg Lys Val Asn Gln Lys Ile Gly
        115                 120                 125

Ser Cys Thr Gln Gln Asp Val Glu Leu His Val Gln Lys Ile Tyr Val
    130                 135                 140

Ile Ser Leu Ala Glu Pro Arg Leu Pro Leu Gln Leu Asp Asp Ala Val
145                 150                 155                 160

Arg Pro Glu Ala Glu Gly
                165

<210> SEQ ID NO 163
<211> LENGTH: 164
<212> TYPE: PRT
<213> ORGANISM: Homo sapiens

<400> SEQUENCE: 163

Met Pro Ser Ala Ser Ala Ser Arg Lys Ser Gln Glu Lys Pro Arg Glu
1               5                   10                  15

Ile Met Asp Ala Ala Glu Asp Tyr Ala Lys Glu Arg Tyr Gly Ile Ser
            20                  25                  30

Ser Met Ile Gln Ser Gln Glu Lys Pro Asp Arg Val Leu Val Arg Val
        35                  40                  45

Arg Asp Leu Thr Ile Gln Lys Ala Asp Glu Val Val Trp Val Arg Ala
 50                  55                  60

Arg Val His Thr Ser Arg Ala Lys Gly Lys Gln Cys Phe Leu Val Leu
 65                  70                  75                  80

Arg Gln Gln Gln Phe Asn Val Gln Ala Leu Val Ala Val Gly Asp His
                 85                  90                  95

Ala Ser Lys Gln Met Val Lys Phe Ala Ala Asn Ile Asn Lys Glu Ser
            100                 105                 110

Ile Val Asp Val Glu Gly Val Val Arg Lys Val Asn Gln Lys Ile Gly
        115                 120                 125

Ser Cys Thr Gln Gln Asp Val Glu Leu His Val Gln Lys Ile Tyr Val
    130                 135                 140

Ile Ser Leu Ala Glu Pro Arg Leu Pro Leu Gln Leu Asp Asp Ala Val
145                 150                 155                 160

Arg Pro Glu Ala

<210> SEQ ID NO 164
<211> LENGTH: 162
<212> TYPE: PRT
<213> ORGANISM: Homo sapiens

<400> SEQUENCE: 164

Met Pro Ser Ala Ser Ala Ser Arg Lys Ser Gln Glu Lys Pro Arg Glu
1               5                   10                  15

Ile Met Asp Ala Ala Glu Asp Tyr Ala Lys Glu Arg Tyr Gly Ile Ser
            20                  25                  30

Ser Met Ile Gln Ser Gln Glu Lys Pro Asp Arg Val Leu Val Arg Val
        35                  40                  45

Arg Asp Leu Thr Ile Gln Lys Ala Asp Glu Val Val Trp Val Arg Ala
```

```
                   50                 55                 60
Arg Val His Thr Ser Arg Ala Lys Gly Lys Gln Cys Phe Leu Val Leu
 65                 70                 75                 80

Arg Gln Gln Gln Phe Asn Val Gln Ala Leu Val Ala Val Gly Asp His
                 85                 90                 95

Ala Ser Lys Gln Met Val Lys Phe Ala Ala Asn Ile Asn Lys Glu Ser
                100                105                110

Ile Val Asp Val Glu Gly Val Val Arg Lys Val Asn Gln Lys Ile Gly
                115                120                125

Ser Cys Thr Gln Gln Asp Val Glu Leu His Val Gln Lys Ile Tyr Val
                130                135                140

Ile Ser Leu Ala Glu Pro Arg Leu Pro Leu Gln Leu Asp Asp Ala Val
145                150                155                160

Arg Pro

<210> SEQ ID NO 165
<211> LENGTH: 160
<212> TYPE: PRT
<213> ORGANISM: Homo sapiens

<400> SEQUENCE: 165

Met Pro Ser Ala Ser Ala Ser Arg Lys Ser Gln Glu Lys Pro Arg Glu
  1               5                 10                 15

Ile Met Asp Ala Ala Glu Asp Tyr Ala Lys Glu Arg Tyr Gly Ile Ser
                 20                 25                 30

Ser Met Ile Gln Ser Gln Glu Lys Pro Asp Arg Val Leu Val Arg Val
                 35                 40                 45

Arg Asp Leu Thr Ile Gln Lys Ala Asp Glu Val Val Trp Val Arg Ala
 50                 55                 60

Arg Val His Thr Ser Arg Ala Lys Gly Lys Gln Cys Phe Leu Val Leu
 65                 70                 75                 80

Arg Gln Gln Gln Phe Asn Val Gln Ala Leu Val Ala Val Gly Asp His
                 85                 90                 95

Ala Ser Lys Gln Met Val Lys Phe Ala Ala Asn Ile Asn Lys Glu Ser
                100                105                110

Ile Val Asp Val Glu Gly Val Val Arg Lys Val Asn Gln Lys Ile Gly
                115                120                125

Ser Cys Thr Gln Gln Asp Val Glu Leu His Val Gln Lys Ile Tyr Val
                130                135                140

Ile Ser Leu Ala Glu Pro Arg Leu Pro Leu Gln Leu Asp Asp Ala Val
145                150                155                160

<210> SEQ ID NO 166
<211> LENGTH: 158
<212> TYPE: PRT
<213> ORGANISM: Homo sapiens

<400> SEQUENCE: 166

Met Pro Ser Ala Ser Ala Ser Arg Lys Ser Gln Glu Lys Pro Arg Glu
  1               5                 10                 15

Ile Met Asp Ala Ala Glu Asp Tyr Ala Lys Glu Arg Tyr Gly Ile Ser
                 20                 25                 30

Ser Met Ile Gln Ser Gln Glu Lys Pro Asp Arg Val Leu Val Arg Val
                 35                 40                 45

Arg Asp Leu Thr Ile Gln Lys Ala Asp Glu Val Val Trp Val Arg Ala
 50                 55                 60
```

Arg Val His Thr Ser Arg Ala Lys Gly Lys Gln Cys Phe Leu Val Leu
65                  70                  75                  80

Arg Gln Gln Gln Phe Asn Val Gln Ala Leu Val Ala Val Gly Asp His
                85                  90                  95

Ala Ser Lys Gln Met Val Lys Phe Ala Ala Asn Ile Asn Lys Glu Ser
            100                 105                 110

Ile Val Asp Val Glu Gly Val Val Arg Lys Val Asn Gln Lys Ile Gly
        115                 120                 125

Ser Cys Thr Gln Gln Asp Val Glu Leu His Val Gln Lys Ile Tyr Val
    130                 135                 140

Ile Ser Leu Ala Glu Pro Arg Leu Pro Leu Gln Leu Asp Asp
145                 150                 155

<210> SEQ ID NO 167
<211> LENGTH: 156
<212> TYPE: PRT
<213> ORGANISM: Homo sapiens

<400> SEQUENCE: 167

Met Pro Ser Ala Ser Ala Ser Arg Lys Ser Gln Glu Lys Pro Arg Glu
1               5                   10                  15

Ile Met Asp Ala Ala Glu Asp Tyr Ala Lys Glu Arg Tyr Gly Ile Ser
            20                  25                  30

Ser Met Ile Gln Ser Gln Glu Lys Pro Asp Arg Val Leu Val Arg Val
        35                  40                  45

Arg Asp Leu Thr Ile Gln Lys Ala Asp Glu Val Val Trp Val Arg Ala
    50                  55                  60

Arg Val His Thr Ser Arg Ala Lys Gly Lys Gln Cys Phe Leu Val Leu
65                  70                  75                  80

Arg Gln Gln Gln Phe Asn Val Gln Ala Leu Val Ala Val Gly Asp His
                85                  90                  95

Ala Ser Lys Gln Met Val Lys Phe Ala Ala Asn Ile Asn Lys Glu Ser
            100                 105                 110

Ile Val Asp Val Glu Gly Val Val Arg Lys Val Asn Gln Lys Ile Gly
        115                 120                 125

Ser Cys Thr Gln Gln Asp Val Glu Leu His Val Gln Lys Ile Tyr Val
    130                 135                 140

Ile Ser Leu Ala Glu Pro Arg Leu Pro Leu Gln Leu
145                 150                 155

<210> SEQ ID NO 168
<211> LENGTH: 154
<212> TYPE: PRT
<213> ORGANISM: Homo sapiens

<400> SEQUENCE: 168

Met Pro Ser Ala Ser Ala Ser Arg Lys Ser Gln Glu Lys Pro Arg Glu
1               5                   10                  15

Ile Met Asp Ala Ala Glu Asp Tyr Ala Lys Glu Arg Tyr Gly Ile Ser
            20                  25                  30

Ser Met Ile Gln Ser Gln Glu Lys Pro Asp Arg Val Leu Val Arg Val
        35                  40                  45

Arg Asp Leu Thr Ile Gln Lys Ala Asp Glu Val Val Trp Val Arg Ala
    50                  55                  60

Arg Val His Thr Ser Arg Ala Lys Gly Lys Gln Cys Phe Leu Val Leu
65                  70                  75                  80

```
Arg Gln Gln Gln Phe Asn Val Gln Ala Leu Val Ala Val Gly Asp His
                85                  90                  95

Ala Ser Lys Gln Met Val Lys Phe Ala Ala Asn Ile Asn Lys Glu Ser
            100                 105                 110

Ile Val Asp Val Glu Gly Val Val Arg Lys Val Asn Gln Lys Ile Gly
        115                 120                 125

Ser Cys Thr Gln Gln Asp Val Glu Leu His Val Gln Lys Ile Tyr Val
    130                 135                 140

Ile Ser Leu Ala Glu Pro Arg Leu Pro Leu
145                 150

<210> SEQ ID NO 169
<211> LENGTH: 152
<212> TYPE: PRT
<213> ORGANISM: Homo sapiens

<400> SEQUENCE: 169

Met Pro Ser Ala Ser Ala Ser Arg Lys Ser Gln Glu Lys Pro Arg Glu
1               5                   10                  15

Ile Met Asp Ala Ala Glu Asp Tyr Ala Lys Glu Arg Tyr Gly Ile Ser
            20                  25                  30

Ser Met Ile Gln Ser Gln Glu Lys Pro Asp Arg Val Leu Val Arg Val
        35                  40                  45

Arg Asp Leu Thr Ile Gln Lys Ala Asp Glu Val Val Trp Val Arg Ala
    50                  55                  60

Arg Val His Thr Ser Arg Ala Lys Gly Lys Gln Cys Phe Leu Val Leu
65                  70                  75                  80

Arg Gln Gln Gln Phe Asn Val Gln Ala Leu Val Ala Val Gly Asp His
                85                  90                  95

Ala Ser Lys Gln Met Val Lys Phe Ala Ala Asn Ile Asn Lys Glu Ser
            100                 105                 110

Ile Val Asp Val Glu Gly Val Val Arg Lys Val Asn Gln Lys Ile Gly
        115                 120                 125

Ser Cys Thr Gln Gln Asp Val Glu Leu His Val Gln Lys Ile Tyr Val
    130                 135                 140

Ile Ser Leu Ala Glu Pro Arg Leu
145                 150

<210> SEQ ID NO 170
<211> LENGTH: 150
<212> TYPE: PRT
<213> ORGANISM: Homo sapiens

<400> SEQUENCE: 170

Met Pro Ser Ala Ser Ala Ser Arg Lys Ser Gln Glu Lys Pro Arg Glu
1               5                   10                  15

Ile Met Asp Ala Ala Glu Asp Tyr Ala Lys Glu Arg Tyr Gly Ile Ser
            20                  25                  30

Ser Met Ile Gln Ser Gln Glu Lys Pro Asp Arg Val Leu Val Arg Val
        35                  40                  45

Arg Asp Leu Thr Ile Gln Lys Ala Asp Glu Val Val Trp Val Arg Ala
    50                  55                  60

Arg Val His Thr Ser Arg Ala Lys Gly Lys Gln Cys Phe Leu Val Leu
65                  70                  75                  80

Arg Gln Gln Gln Phe Asn Val Gln Ala Leu Val Ala Val Gly Asp His
                85                  90                  95
```

Ala Ser Lys Gln Met Val Lys Phe Ala Ala Asn Ile Asn Lys Glu Ser
            100                 105                 110

Ile Val Asp Val Glu Gly Val Arg Lys Val Asn Gln Lys Ile Gly
            115                 120                 125

Ser Cys Thr Gln Gln Asp Val Glu Leu His Val Gln Lys Ile Tyr Val
        130                 135                 140

Ile Ser Leu Ala Glu Pro
145             150

<210> SEQ ID NO 171
<211> LENGTH: 148
<212> TYPE: PRT
<213> ORGANISM: Homo sapiens

<400> SEQUENCE: 171

Met Pro Ser Ala Ser Ala Ser Arg Lys Ser Gln Glu Lys Pro Arg Glu
1               5                   10                  15

Ile Met Asp Ala Ala Glu Asp Tyr Ala Lys Glu Arg Tyr Gly Ile Ser
            20                  25                  30

Ser Met Ile Gln Ser Gln Glu Lys Pro Asp Arg Val Leu Val Arg Val
        35                  40                  45

Arg Asp Leu Thr Ile Gln Lys Ala Asp Glu Val Val Trp Val Arg Ala
    50                  55                  60

Arg Val His Thr Ser Arg Ala Lys Gly Lys Gln Cys Phe Leu Val Leu
65                  70                  75                  80

Arg Gln Gln Gln Phe Asn Val Gln Ala Leu Val Ala Val Gly Asp His
                85                  90                  95

Ala Ser Lys Gln Met Val Lys Phe Ala Ala Asn Ile Asn Lys Glu Ser
            100                 105                 110

Ile Val Asp Val Glu Gly Val Arg Lys Val Asn Gln Lys Ile Gly
            115                 120                 125

Ser Cys Thr Gln Gln Asp Val Glu Leu His Val Gln Lys Ile Tyr Val
        130                 135                 140

Ile Ser Leu Ala
145

<210> SEQ ID NO 172
<211> LENGTH: 146
<212> TYPE: PRT
<213> ORGANISM: Homo sapiens

<400> SEQUENCE: 172

Met Pro Ser Ala Ser Ala Ser Arg Lys Ser Gln Glu Lys Pro Arg Glu
1               5                   10                  15

Ile Met Asp Ala Ala Glu Asp Tyr Ala Lys Glu Arg Tyr Gly Ile Ser
            20                  25                  30

Ser Met Ile Gln Ser Gln Glu Lys Pro Asp Arg Val Leu Val Arg Val
        35                  40                  45

Arg Asp Leu Thr Ile Gln Lys Ala Asp Glu Val Val Trp Val Arg Ala
    50                  55                  60

Arg Val His Thr Ser Arg Ala Lys Gly Lys Gln Cys Phe Leu Val Leu
65                  70                  75                  80

Arg Gln Gln Gln Phe Asn Val Gln Ala Leu Val Ala Val Gly Asp His
                85                  90                  95

Ala Ser Lys Gln Met Val Lys Phe Ala Ala Asn Ile Asn Lys Glu Ser
            100                 105                 110

```
Ile Val Asp Val Glu Gly Val Val Arg Lys Val Asn Gln Lys Ile Gly
        115                 120                 125

Ser Cys Thr Gln Gln Asp Val Glu Leu His Val Gln Lys Ile Tyr Val
130                 135                 140

Ile Ser
145

<210> SEQ ID NO 173
<211> LENGTH: 151
<212> TYPE: PRT
<213> ORGANISM: Homo sapiens

<400> SEQUENCE: 173

Ala Ser Ala Ser Arg Lys Ser Gln Glu Lys Pro Arg Glu Ile Met Asp
1               5                   10                  15

Ala Ala Glu Asp Tyr Ala Lys Glu Arg Tyr Gly Ile Ser Ser Met Ile
            20                  25                  30

Gln Ser Gln Glu Lys Pro Asp Arg Val Leu Val Arg Val Arg Asp Leu
        35                  40                  45

Thr Ile Gln Lys Ala Asp Glu Val Val Trp Val Arg Ala Arg Val His
    50                  55                  60

Thr Ser Arg Ala Lys Gly Lys Gln Cys Phe Leu Val Leu Arg Gln Gln
65                  70                  75                  80

Gln Phe Asn Val Gln Ala Leu Val Ala Val Gly Asp His Ala Ser Lys
                85                  90                  95

Gln Met Val Lys Phe Ala Ala Asn Ile Asn Lys Glu Ser Ile Val Asp
            100                 105                 110

Val Glu Gly Val Val Arg Lys Val Asn Gln Lys Ile Gly Ser Cys Thr
        115                 120                 125

Gln Gln Asp Val Glu Leu His Val Gln Lys Ile Tyr Val Ile Ser Leu
    130                 135                 140

Ala Glu Pro Arg Leu Pro Leu
145                 150

<210> SEQ ID NO 174
<211> LENGTH: 149
<212> TYPE: PRT
<213> ORGANISM: Homo sapiens

<400> SEQUENCE: 174

Ala Ser Arg Lys Ser Gln Glu Lys Pro Arg Glu Ile Met Asp Ala Ala
1               5                   10                  15

Glu Asp Tyr Ala Lys Glu Arg Tyr Gly Ile Ser Ser Met Ile Gln Ser
            20                  25                  30

Gln Glu Lys Pro Asp Arg Val Leu Val Arg Val Arg Asp Leu Thr Ile
        35                  40                  45

Gln Lys Ala Asp Glu Val Val Trp Val Arg Ala Arg Val His Thr Ser
    50                  55                  60

Arg Ala Lys Gly Lys Gln Cys Phe Leu Val Leu Arg Gln Gln Gln Phe
65                  70                  75                  80

Asn Val Gln Ala Leu Val Ala Val Gly Asp His Ala Ser Lys Gln Met
                85                  90                  95

Val Lys Phe Ala Ala Asn Ile Asn Lys Glu Ser Ile Val Asp Val Glu
            100                 105                 110

Gly Val Val Arg Lys Val Asn Gln Lys Ile Gly Ser Cys Thr Gln Gln
        115                 120                 125
```

Asp Val Glu Leu His Val Gln Lys Ile Tyr Val Ile Ser Leu Ala Glu
            130                 135                 140

Pro Arg Leu Pro Leu
145

<210> SEQ ID NO 175
<211> LENGTH: 147
<212> TYPE: PRT
<213> ORGANISM: Homo sapiens

<400> SEQUENCE: 175

Arg Lys Ser Gln Glu Lys Pro Arg Glu Ile Met Asp Ala Ala Glu Asp
1               5                   10                  15

Tyr Ala Lys Glu Arg Tyr Gly Ile Ser Ser Met Ile Gln Ser Gln Glu
            20                  25                  30

Lys Pro Asp Arg Val Leu Val Arg Val Arg Asp Leu Thr Ile Gln Lys
        35                  40                  45

Ala Asp Glu Val Val Trp Val Arg Ala Arg Val His Thr Ser Arg Ala
    50                  55                  60

Lys Gly Lys Gln Cys Phe Leu Val Leu Arg Gln Gln Gln Phe Asn Val
65                  70                  75                  80

Gln Ala Leu Val Ala Val Gly Asp His Ala Ser Lys Gln Met Val Lys
                85                  90                  95

Phe Ala Ala Asn Ile Asn Lys Glu Ser Ile Val Asp Val Glu Gly Val
            100                 105                 110

Val Arg Lys Val Asn Gln Lys Ile Gly Ser Cys Thr Gln Gln Asp Val
        115                 120                 125

Glu Leu His Val Gln Lys Ile Tyr Val Ile Ser Leu Ala Glu Pro Arg
    130                 135                 140

Leu Pro Leu
145

<210> SEQ ID NO 176
<211> LENGTH: 145
<212> TYPE: PRT
<213> ORGANISM: Homo sapiens

<400> SEQUENCE: 176

Ser Gln Glu Lys Pro Arg Glu Ile Met Asp Ala Ala Glu Asp Tyr Ala
1               5                   10                  15

Lys Glu Arg Tyr Gly Ile Ser Ser Met Ile Gln Ser Gln Glu Lys Pro
            20                  25                  30

Asp Arg Val Leu Val Arg Val Arg Asp Leu Thr Ile Gln Lys Ala Asp
        35                  40                  45

Glu Val Val Trp Val Arg Ala Arg Val His Thr Ser Arg Ala Lys Gly
    50                  55                  60

Lys Gln Cys Phe Leu Val Leu Arg Gln Gln Gln Phe Asn Val Gln Ala
65                  70                  75                  80

Leu Val Ala Val Gly Asp His Ala Ser Lys Gln Met Val Lys Phe Ala
                85                  90                  95

Ala Asn Ile Asn Lys Glu Ser Ile Val Asp Val Glu Gly Val Val Arg
            100                 105                 110

Lys Val Asn Gln Lys Ile Gly Ser Cys Thr Gln Gln Asp Val Glu Leu
        115                 120                 125

His Val Gln Lys Ile Tyr Val Ile Ser Leu Ala Glu Pro Arg Leu Pro
    130                 135                 140

Leu
145

<210> SEQ ID NO 177
<211> LENGTH: 143
<212> TYPE: PRT
<213> ORGANISM: Homo sapiens

<400> SEQUENCE: 177

Glu Lys Pro Arg Glu Ile Met Asp Ala Ala Glu Asp Tyr Ala Lys Glu
1               5                   10                  15

Arg Tyr Gly Ile Ser Ser Met Ile Gln Ser Gln Glu Lys Pro Asp Arg
            20                  25                  30

Val Leu Val Arg Val Arg Asp Leu Thr Ile Gln Lys Ala Asp Glu Val
        35                  40                  45

Val Trp Val Arg Ala Arg Val His Thr Ser Arg Ala Lys Gly Lys Gln
    50                  55                  60

Cys Phe Leu Val Leu Arg Gln Gln Gln Phe Asn Val Gln Ala Leu Val
65                  70                  75                  80

Ala Val Gly Asp His Ala Ser Lys Gln Met Val Lys Phe Ala Ala Asn
                85                  90                  95

Ile Asn Lys Glu Ser Ile Val Asp Val Glu Gly Val Val Arg Lys Val
            100                 105                 110

Asn Gln Lys Ile Gly Ser Cys Thr Gln Gln Asp Val Glu Leu His Val
        115                 120                 125

Gln Lys Ile Tyr Val Ile Ser Leu Ala Glu Pro Arg Leu Pro Leu
    130                 135                 140

<210> SEQ ID NO 178
<211> LENGTH: 141
<212> TYPE: PRT
<213> ORGANISM: Homo sapiens

<400> SEQUENCE: 178

Pro Arg Glu Ile Met Asp Ala Ala Glu Asp Tyr Ala Lys Glu Arg Tyr
1               5                   10                  15

Gly Ile Ser Ser Met Ile Gln Ser Gln Glu Lys Pro Asp Arg Val Leu
            20                  25                  30

Val Arg Val Arg Asp Leu Thr Ile Gln Lys Ala Asp Glu Val Val Trp
        35                  40                  45

Val Arg Ala Arg Val His Thr Ser Arg Ala Lys Gly Lys Gln Cys Phe
    50                  55                  60

Leu Val Leu Arg Gln Gln Gln Phe Asn Val Gln Ala Leu Val Ala Val
65                  70                  75                  80

Gly Asp His Ala Ser Lys Gln Met Val Lys Phe Ala Ala Asn Ile Asn
                85                  90                  95

Lys Glu Ser Ile Val Asp Val Glu Gly Val Val Arg Lys Val Asn Gln
            100                 105                 110

Lys Ile Gly Ser Cys Thr Gln Gln Asp Val Glu Leu His Val Gln Lys
        115                 120                 125

Ile Tyr Val Ile Ser Leu Ala Glu Pro Arg Leu Pro Leu
    130                 135                 140

<210> SEQ ID NO 179
<211> LENGTH: 139
<212> TYPE: PRT
<213> ORGANISM: Homo sapiens

<400> SEQUENCE: 179

Glu Ile Met Asp Ala Ala Glu Asp Tyr Ala Lys Glu Arg Tyr Gly Ile
1               5                   10                  15

Ser Ser Met Ile Gln Ser Gln Glu Lys Pro Asp Arg Val Leu Val Arg
            20                  25                  30

Val Arg Asp Leu Thr Ile Gln Lys Ala Asp Glu Val Val Trp Val Arg
        35                  40                  45

Ala Arg Val His Thr Ser Arg Ala Lys Gly Lys Gln Cys Phe Leu Val
    50                  55                  60

Leu Arg Gln Gln Gln Phe Asn Val Gln Ala Leu Val Ala Val Gly Asp
65                  70                  75                  80

His Ala Ser Lys Gln Met Val Lys Phe Ala Ala Asn Ile Asn Lys Glu
                85                  90                  95

Ser Ile Val Asp Val Glu Gly Val Val Arg Lys Val Asn Gln Lys Ile
            100                 105                 110

Gly Ser Cys Thr Gln Gln Asp Val Glu Leu His Val Gln Lys Ile Tyr
        115                 120                 125

Val Ile Ser Leu Ala Glu Pro Arg Leu Pro Leu
    130                 135

<210> SEQ ID NO 180
<211> LENGTH: 137
<212> TYPE: PRT
<213> ORGANISM: Homo sapiens

<400> SEQUENCE: 180

Met Asp Ala Ala Glu Asp Tyr Ala Lys Glu Arg Tyr Gly Ile Ser Ser
1               5                   10                  15

Met Ile Gln Ser Gln Glu Lys Pro Asp Arg Val Leu Val Arg Val Arg
            20                  25                  30

Asp Leu Thr Ile Gln Lys Ala Asp Glu Val Val Trp Val Arg Ala Arg
        35                  40                  45

Val His Thr Ser Arg Ala Lys Gly Lys Gln Cys Phe Leu Val Leu Arg
    50                  55                  60

Gln Gln Gln Phe Asn Val Gln Ala Leu Val Ala Val Gly Asp His Ala
65                  70                  75                  80

Ser Lys Gln Met Val Lys Phe Ala Ala Asn Ile Asn Lys Glu Ser Ile
                85                  90                  95

Val Asp Val Glu Gly Val Val Arg Lys Val Asn Gln Lys Ile Gly Ser
            100                 105                 110

Cys Thr Gln Gln Asp Val Glu Leu His Val Gln Lys Ile Tyr Val Ile
        115                 120                 125

Ser Leu Ala Glu Pro Arg Leu Pro Leu
    130                 135

<210> SEQ ID NO 181
<211> LENGTH: 135
<212> TYPE: PRT
<213> ORGANISM: Homo sapiens

<400> SEQUENCE: 181

Met Asp Ala Ala Glu Asp Tyr Ala Lys Glu Arg Tyr Gly Ile Ser Ser
1               5                   10                  15

Met Ile Gln Ser Gln Glu Lys Pro Asp Arg Val Leu Val Arg Val Arg
            20                  25                  30

```
Asp Leu Thr Ile Gln Lys Ala Asp Glu Val Val Trp Val Arg Ala Arg
            35                  40                  45

Val His Thr Ser Arg Ala Lys Gly Lys Gln Cys Phe Leu Val Leu Arg
 50                  55                  60

Gln Gln Gln Phe Asn Val Gln Ala Leu Val Ala Val Gly Asp His Ala
 65                  70                  75                  80

Ser Lys Gln Met Val Lys Phe Ala Ala Asn Ile Asn Lys Glu Ser Ile
                85                  90                  95

Val Asp Val Glu Gly Val Val Arg Lys Val Asn Gln Lys Ile Gly Ser
                100                 105                 110

Cys Thr Gln Gln Asp Val Glu Leu His Val Gln Lys Ile Tyr Val Ile
            115                 120                 125

Ser Leu Ala Glu Pro Arg Leu
            130                 135

<210> SEQ ID NO 182
<211> LENGTH: 135
<212> TYPE: PRT
<213> ORGANISM: Homo sapiens

<400> SEQUENCE: 182

Met Asp Ala Ala Glu Asp Tyr Ala Lys Glu Arg Tyr Gly Ile Ser Ser
 1               5                  10                  15

Met Ile Gln Ser Gln Glu Lys Pro Asp Arg Val Leu Val Arg Val Arg
                20                  25                  30

Asp Leu Thr Ile Gln Lys Ala Asp Glu Val Val Trp Val Arg Ala Arg
            35                  40                  45

Val His Thr Ser Arg Ala Lys Gly Lys Gln Cys Phe Leu Val Leu Arg
 50                  55                  60

Gln Gln Gln Phe Asn Val Gln Ala Leu Val Ala Val Gly Asp His Ala
 65                  70                  75                  80

Ser Lys Gln Met Val Lys Phe Ala Ala Asn Ile Asn Lys Glu Ser Ile
                85                  90                  95

Val Asp Val Glu Gly Val Val Arg Lys Val Asn Gln Lys Ile Gly Ser
                100                 105                 110

Cys Thr Gln Gln Asp Val Glu Leu His Val Gln Lys Ile Tyr Val Ile
            115                 120                 125

Ser Leu Ala Glu Pro Arg Leu
            130                 135

<210> SEQ ID NO 183
<211> LENGTH: 133
<212> TYPE: PRT
<213> ORGANISM: Homo sapiens

<400> SEQUENCE: 183

Ala Ala Glu Asp Tyr Ala Lys Glu Arg Tyr Gly Ile Ser Ser Met Ile
 1               5                  10                  15

Gln Ser Gln Glu Lys Pro Asp Arg Val Leu Val Arg Val Arg Asp Leu
                20                  25                  30

Thr Ile Gln Lys Ala Asp Glu Val Val Trp Val Arg Ala Arg Val His
            35                  40                  45

Thr Ser Arg Ala Lys Gly Lys Gln Cys Phe Leu Val Leu Arg Gln Gln
 50                  55                  60

Gln Phe Asn Val Gln Ala Leu Val Ala Val Gly Asp His Ala Ser Lys
 65                  70                  75                  80
```

Gln Met Val Lys Phe Ala Ala Asn Ile Asn Lys Glu Ser Ile Val Asp
            85                  90                  95

Val Glu Gly Val Val Arg Lys Val Asn Gln Lys Ile Gly Ser Cys Thr
            100                 105                 110

Gln Gln Asp Val Glu Leu His Val Gln Lys Ile Tyr Val Ile Ser Leu
            115                 120                 125

Ala Glu Pro Arg Leu
            130

<210> SEQ ID NO 184
<211> LENGTH: 137
<212> TYPE: PRT
<213> ORGANISM: Homo sapiens

<400> SEQUENCE: 184

Met Gln Glu Lys Pro Arg Glu Ile Met Asp Ala Ala Glu Asp Tyr Ala
1               5                   10                  15

Lys Glu Arg Tyr Gly Ile Ser Ser Met Ile Gln Ser Gln Glu Lys Pro
            20                  25                  30

Asp Arg Val Leu Val Arg Val Arg Asp Leu Thr Ile Gln Lys Ala Asp
            35                  40                  45

Glu Val Val Trp Val Arg Ala Arg Val His Thr Ser Arg Ala Lys Gly
        50                  55                  60

Lys Gln Cys Phe Leu Val Leu Arg Gln Gln Gln Phe Asn Val Gln Ala
65                  70                  75                  80

Leu Val Ala Val Gly Asp His Ala Ser Lys Gln Met Val Lys Phe Ala
            85                  90                  95

Cys Asn Ile Asn Lys Glu Ser Ile Val Asp Val Glu Gly Val Val Arg
            100                 105                 110

Lys Val Asn Gln Lys Ile Gly Ser Cys Thr Gln Gln Asp Val Glu Leu
            115                 120                 125

His Val Gln Lys Ile Tyr Val Ile Ser
            130                 135

<210> SEQ ID NO 185
<211> LENGTH: 135
<212> TYPE: PRT
<213> ORGANISM: Homo sapiens

<400> SEQUENCE: 185

Met Lys Pro Arg Glu Ile Met Asp Ala Ala Glu Asp Tyr Ala Lys Glu
1               5                   10                  15

Arg Tyr Gly Ile Ser Ser Met Ile Gln Ser Gln Glu Lys Pro Asp Arg
            20                  25                  30

Val Leu Val Arg Val Arg Asp Leu Thr Ile Gln Lys Ala Asp Glu Val
            35                  40                  45

Val Trp Val Arg Ala Arg Val His Thr Ser Arg Ala Lys Gly Lys Gln
        50                  55                  60

Cys Phe Leu Val Leu Arg Gln Gln Gln Phe Asn Val Gln Ala Leu Val
65                  70                  75                  80

Ala Val Gly Asp His Ala Ser Lys Gln Met Val Lys Phe Ala Cys Asn
            85                  90                  95

Ile Asn Lys Glu Ser Ile Val Asp Val Glu Gly Val Val Arg Lys Val
            100                 105                 110

Asn Gln Lys Ile Gly Ser Cys Thr Gln Gln Asp Val Glu Leu His Val
            115                 120                 125

```
Gln Lys Ile Tyr Val Ile Ser
    130                 135

<210> SEQ ID NO 186
<211> LENGTH: 135
<212> TYPE: PRT
<213> ORGANISM: Homo sapiens

<400> SEQUENCE: 186

Met Lys Pro Arg Glu Ile Met Asp Ala Ala Glu Asp Tyr Ala Lys Glu
1               5                   10                  15

Arg Tyr Gly Ile Ser Ser Met Ile Gln Ser Gln Glu Lys Pro Asp Arg
            20                  25                  30

Val Leu Val Arg Val Arg Asp Leu Thr Ile Gln Lys Ala Asp Glu Val
        35                  40                  45

Val Trp Val Arg Ala Arg Val His Thr Ser Arg Ala Lys Gly Lys Gln
    50                  55                  60

Cys Phe Leu Val Leu Arg Gln Gln Gln Phe Asn Val Gln Ala Leu Val
65                  70                  75                  80

Ala Val Gly Asp His Ala Ser Lys Gln Met Val Lys Phe Ala Cys Asn
                85                  90                  95

Ile Asn Lys Glu Ser Ile Val Asp Val Glu Gly Val Val Arg Lys Val
            100                 105                 110

Asn Gln Lys Ile Gly Ser Cys Thr Gln Gln Asp Val Glu Leu His Val
        115                 120                 125

Gln Lys Ile Tyr Val Ile Ser
    130                 135

<210> SEQ ID NO 187
<211> LENGTH: 131
<212> TYPE: PRT
<213> ORGANISM: Homo sapiens

<400> SEQUENCE: 187

Met Ile Met Asp Ala Ala Glu Asp Tyr Ala Lys Glu Arg Tyr Gly Ile
1               5                   10                  15

Ser Ser Met Ile Gln Ser Gln Glu Lys Pro Asp Arg Val Leu Val Arg
            20                  25                  30

Val Arg Asp Leu Thr Ile Gln Lys Ala Asp Glu Val Val Trp Val Arg
        35                  40                  45

Ala Arg Val His Thr Ser Arg Ala Lys Gly Lys Gln Cys Phe Leu Val
    50                  55                  60

Leu Arg Gln Gln Gln Phe Asn Val Gln Ala Leu Val Ala Val Gly Asp
65                  70                  75                  80

His Ala Ser Lys Gln Met Val Lys Phe Ala Cys Asn Ile Asn Lys Glu
                85                  90                  95

Ser Ile Val Asp Val Glu Gly Val Val Arg Lys Val Asn Gln Lys Ile
            100                 105                 110

Gly Ser Cys Thr Gln Gln Asp Val Glu Leu His Val Gln Lys Ile Tyr
        115                 120                 125

Val Ile Ser
    130

<210> SEQ ID NO 188
<211> LENGTH: 127
<212> TYPE: PRT
<213> ORGANISM: Homo sapiens
```

<400> SEQUENCE: 188

Met Ala Glu Asp Tyr Ala Lys Glu Arg Tyr Gly Ile Ser Ser Met Ile
1               5                   10                  15

Gln Ser Gln Glu Lys Pro Asp Arg Val Leu Val Arg Val Arg Asp Leu
            20                  25                  30

Thr Ile Gln Lys Ala Asp Glu Val Trp Val Arg Ala Arg Val His
        35                  40                  45

Thr Ser Arg Ala Lys Gly Lys Gln Cys Phe Leu Val Leu Arg Gln Gln
    50                  55                  60

Gln Phe Asn Val Gln Ala Leu Val Ala Val Gly Asp His Ala Ser Lys
65                  70                  75                  80

Gln Met Val Lys Phe Ala Cys Asn Ile Asn Lys Glu Ser Ile Val Asp
                85                  90                  95

Val Glu Gly Val Val Arg Lys Val Asn Gln Lys Ile Gly Ser Cys Thr
            100                 105                 110

Gln Gln Asp Val Glu Leu His Val Gln Lys Ile Tyr Val Ile Ser
        115                 120                 125

<210> SEQ ID NO 189
<211> LENGTH: 501
<212> TYPE: PRT
<213> ORGANISM: Artificial Sequence
<220> FEATURE:
<223> OTHER INFORMATION: DRS polypeptide variant with reduced cysteine
      content

<400> SEQUENCE: 189

Met Pro Ser Ala Ser Ala Ser Arg Lys Ser Gln Glu Lys Pro Arg Glu
1               5                   10                  15

Ile Met Asp Ala Ala Glu Asp Tyr Ala Lys Glu Arg Tyr Gly Ile Ser
            20                  25                  30

Ser Met Ile Gln Ser Gln Glu Lys Pro Asp Arg Val Leu Val Arg Val
        35                  40                  45

Arg Asp Leu Thr Ile Gln Lys Ala Asp Glu Val Val Trp Val Arg Ala
    50                  55                  60

Arg Val His Thr Ser Arg Ala Lys Gly Lys Gln Cys Phe Leu Val Leu
65                  70                  75                  80

Arg Gln Gln Gln Phe Asn Val Gln Ala Leu Val Ala Val Gly Asp His
                85                  90                  95

Ala Ser Lys Gln Met Val Lys Phe Ala Ala Asn Ile Asn Lys Glu Ser
            100                 105                 110

Ile Val Asp Val Glu Gly Val Val Arg Lys Val Asn Gln Lys Ile Gly
        115                 120                 125

Ser Cys Thr Gln Gln Asp Val Glu Leu His Val Gln Lys Ile Tyr Val
    130                 135                 140

Ile Ser Leu Ala Glu Pro Arg Leu Pro Leu Gln Leu Asp Asp Ala Val
145                 150                 155                 160

Arg Pro Glu Ala Glu Gly Glu Glu Glu Gly Arg Ala Thr Val Asn Gln
                165                 170                 175

Asp Thr Arg Leu Asp Asn Arg Val Ile Asp Leu Arg Thr Ser Thr Ser
            180                 185                 190

Gln Ala Val Phe Arg Leu Gln Ser Gly Ile Cys His Leu Phe Arg Glu
        195                 200                 205

Thr Leu Ile Asn Lys Gly Phe Val Glu Ile Gln Thr Pro Lys Ile Ile
    210                 215                 220

-continued

```
Ser Ala Ala Ser Glu Gly Gly Ala Asn Val Phe Thr Val Ser Tyr Phe
225                 230                 235                 240

Lys Asn Asn Ala Tyr Leu Ala Gln Ser Pro Gln Leu Tyr Lys Gln Met
            245                 250                 255

Cys Ile Cys Ala Asp Phe Glu Lys Val Phe Ser Ile Gly Pro Val Phe
        260                 265                 270

Arg Ala Glu Asp Ser Asn Thr His Arg His Leu Thr Glu Phe Val Gly
    275                 280                 285

Leu Asp Ile Glu Met Ala Phe Asn Tyr His Tyr His Glu Val Met Glu
290                 295                 300

Glu Ile Ala Asp Thr Met Val Gln Ile Phe Lys Gly Leu Gln Glu Arg
305                 310                 315                 320

Phe Gln Thr Glu Ile Gln Thr Val Asn Lys Gln Phe Pro Ser Glu Pro
            325                 330                 335

Phe Lys Phe Leu Glu Pro Thr Leu Arg Leu Glu Tyr Cys Glu Ala Leu
        340                 345                 350

Ala Met Leu Arg Glu Ala Gly Val Glu Met Gly Asp Glu Asp Asp Leu
    355                 360                 365

Ser Thr Pro Asn Glu Lys Leu Leu Gly His Leu Val Lys Glu Lys Tyr
370                 375                 380

Asp Thr Asp Phe Tyr Ile Leu Asp Lys Tyr Pro Leu Ala Val Arg Pro
385                 390                 395                 400

Phe Tyr Thr Met Pro Asp Pro Arg Asn Pro Lys Gln Ser Asn Ser Tyr
            405                 410                 415

Asp Met Phe Met Arg Gly Glu Glu Ile Leu Ser Gly Ala Gln Arg Ile
        420                 425                 430

His Asp Pro Gln Leu Leu Thr Glu Arg Ala Leu His His Gly Ile Asp
    435                 440                 445

Leu Glu Lys Ile Lys Ala Tyr Ile Asp Ser Phe Arg Phe Gly Ala Pro
450                 455                 460

Pro His Ala Gly Gly Gly Ile Gly Leu Glu Arg Val Thr Met Leu Phe
465                 470                 475                 480

Leu Gly Leu His Asn Val Arg Gln Thr Ser Met Phe Pro Arg Asp Pro
            485                 490                 495

Lys Arg Leu Thr Pro
            500

<210> SEQ ID NO 190
<211> LENGTH: 501
<212> TYPE: PRT
<213> ORGANISM: Artificial Sequence
<220> FEATURE:
<223> OTHER INFORMATION: DRS polypeptide variant with reduced cysteine
      content

<400> SEQUENCE: 190

Met Pro Ser Ala Ser Ala Ser Arg Lys Ser Gln Glu Lys Pro Arg Glu
1               5                   10                  15

Ile Met Asp Ala Ala Glu Asp Tyr Ala Lys Glu Arg Tyr Gly Ile Ser
            20                  25                  30

Ser Met Ile Gln Ser Gln Glu Lys Pro Asp Arg Val Leu Val Arg Val
        35                  40                  45

Arg Asp Leu Thr Ile Gln Lys Ala Asp Glu Val Val Trp Val Arg Ala
    50                  55                  60

Arg Val His Thr Ser Arg Ala Lys Gly Lys Gln Cys Phe Leu Val Leu
65                  70                  75                  80
```

```
Arg Gln Gln Gln Phe Asn Val Gln Ala Leu Val Ala Val Gly Asp His
                85                  90                  95
Ala Ser Lys Gln Met Val Lys Phe Ala Ala Asn Ile Asn Lys Glu Ser
            100                 105                 110
Ile Val Asp Val Glu Gly Val Val Arg Lys Val Asn Gln Lys Ile Gly
            115                 120                 125
Ser Cys Thr Gln Gln Asp Val Glu Leu His Val Gln Lys Ile Tyr Val
        130                 135                 140
Ile Ser Leu Ala Glu Pro Arg Leu Pro Leu Gln Leu Asp Asp Ala Val
145                 150                 155                 160
Arg Pro Glu Ala Glu Gly Glu Glu Gly Arg Ala Thr Val Asn Gln
                165                 170                 175
Asp Thr Arg Leu Asp Asn Arg Val Ile Asp Leu Arg Thr Ser Thr Ser
            180                 185                 190
Gln Ala Val Phe Arg Leu Gln Ser Gly Ile Cys His Leu Phe Arg Glu
        195                 200                 205
Thr Leu Ile Asn Lys Gly Phe Val Glu Ile Gln Thr Pro Lys Ile Ile
        210                 215                 220
Ser Ala Ala Ser Glu Gly Gly Ala Asn Val Phe Thr Val Ser Tyr Phe
225                 230                 235                 240
Lys Asn Asn Ala Tyr Leu Ala Gln Ser Pro Gln Leu Tyr Lys Gln Met
                245                 250                 255
Cys Ile Cys Ala Asp Phe Glu Lys Val Phe Ser Ile Gly Pro Val Phe
                260                 265                 270
Arg Ala Glu Asp Ser Asn Thr His Arg His Leu Thr Glu Phe Val Gly
            275                 280                 285
Leu Asp Ile Glu Met Ala Phe Asn Tyr His Tyr His Glu Val Met Glu
        290                 295                 300
Glu Ile Ala Asp Thr Met Val Gln Ile Phe Lys Gly Leu Gln Glu Arg
305                 310                 315                 320
Phe Gln Thr Glu Ile Gln Thr Val Asn Lys Gln Phe Pro Cys Glu Pro
                325                 330                 335
Phe Lys Phe Leu Glu Pro Thr Leu Arg Leu Glu Tyr Ser Glu Ala Leu
                340                 345                 350
Ala Met Leu Arg Glu Ala Gly Val Glu Met Gly Asp Glu Asp Asp Leu
            355                 360                 365
Ser Thr Pro Asn Glu Lys Leu Leu Gly His Leu Val Lys Glu Lys Tyr
        370                 375                 380
Asp Thr Asp Phe Tyr Ile Leu Asp Lys Tyr Pro Leu Ala Val Arg Pro
385                 390                 395                 400
Phe Tyr Thr Met Pro Asp Pro Arg Asn Pro Lys Gln Ser Asn Ser Tyr
                405                 410                 415
Asp Met Phe Met Arg Gly Glu Glu Ile Leu Ser Gly Ala Gln Arg Ile
            420                 425                 430
His Asp Pro Gln Leu Leu Thr Glu Arg Ala Leu His His Gly Ile Asp
        435                 440                 445
Leu Glu Lys Ile Lys Ala Tyr Ile Asp Ser Phe Arg Phe Gly Ala Pro
        450                 455                 460
Pro His Ala Gly Gly Gly Ile Gly Leu Glu Arg Val Thr Met Leu Phe
465                 470                 475                 480
Leu Gly Leu His Asn Val Arg Gln Thr Ser Met Phe Pro Arg Asp Pro
                485                 490                 495
```

```
Lys Arg Leu Thr Pro
            500

<210> SEQ ID NO 191
<211> LENGTH: 501
<212> TYPE: PRT
<213> ORGANISM: Artificial Sequence
<220> FEATURE:
<223> OTHER INFORMATION: DRS polypeptide variant with reduced cysteine
      content

<400> SEQUENCE: 191

Met Pro Ser Ala Ser Ala Ser Arg Lys Ser Gln Glu Lys Pro Arg Glu
1               5                   10                  15

Ile Met Asp Ala Ala Glu Asp Tyr Ala Lys Glu Arg Tyr Gly Ile Ser
            20                  25                  30

Ser Met Ile Gln Ser Gln Glu Lys Pro Asp Arg Val Leu Val Arg Val
        35                  40                  45

Arg Asp Leu Thr Ile Gln Lys Ala Asp Glu Val Val Trp Val Arg Ala
    50                  55                  60

Arg Val His Thr Ser Arg Ala Lys Gly Lys Gln Cys Phe Leu Val Leu
65                  70                  75                  80

Arg Gln Gln Gln Phe Asn Val Gln Ala Leu Val Ala Val Gly Asp His
                85                  90                  95

Ala Ser Lys Gln Met Val Lys Phe Ala Ala Asn Ile Asn Lys Glu Ser
            100                 105                 110

Ile Val Asp Val Glu Gly Val Val Arg Lys Val Asn Gln Lys Ile Gly
        115                 120                 125

Ser Cys Thr Gln Gln Asp Val Glu Leu His Val Gln Lys Ile Tyr Val
130                 135                 140

Ile Ser Leu Ala Glu Pro Arg Leu Pro Leu Gln Leu Asp Asp Ala Val
145                 150                 155                 160

Arg Pro Glu Ala Glu Gly Glu Glu Gly Arg Ala Thr Val Asn Gln
                165                 170                 175

Asp Thr Arg Leu Asp Asn Arg Val Ile Asp Leu Arg Thr Ser Thr Ser
            180                 185                 190

Gln Ala Val Phe Arg Leu Gln Ser Gly Ile Cys His Leu Phe Arg Glu
        195                 200                 205

Thr Leu Ile Asn Lys Gly Phe Val Glu Ile Gln Thr Pro Lys Ile Ile
    210                 215                 220

Ser Ala Ala Ser Glu Gly Gly Ala Asn Val Phe Thr Val Ser Tyr Phe
225                 230                 235                 240

Lys Asn Asn Ala Tyr Leu Ala Gln Ser Pro Gln Leu Tyr Lys Gln Met
                245                 250                 255

Cys Ile Cys Ala Asp Phe Glu Lys Val Phe Ser Ile Gly Pro Val Phe
            260                 265                 270

Arg Ala Glu Asp Ser Asn Thr His Arg His Leu Thr Glu Phe Val Gly
        275                 280                 285

Leu Asp Ile Glu Met Ala Phe Asn Tyr His Tyr His Glu Val Met Glu
    290                 295                 300

Glu Ile Ala Asp Thr Met Val Gln Ile Phe Lys Gly Leu Gln Glu Arg
305                 310                 315                 320

Phe Gln Thr Glu Ile Gln Thr Val Asn Lys Gln Phe Pro Ser Glu Pro
                325                 330                 335

Phe Lys Phe Leu Glu Pro Thr Leu Arg Leu Glu Tyr Ser Glu Ala Leu
            340                 345                 350
```

```
Ala Met Leu Arg Glu Ala Gly Val Glu Met Gly Asp Glu Asp Leu
        355                 360                 365

Ser Thr Pro Asn Glu Lys Leu Leu Gly His Leu Val Lys Glu Lys Tyr
    370                 375                 380

Asp Thr Asp Phe Tyr Ile Leu Asp Lys Tyr Pro Leu Ala Val Arg Pro
385                 390                 395                 400

Phe Tyr Thr Met Pro Asp Pro Arg Asn Pro Lys Gln Ser Asn Ser Tyr
                405                 410                 415

Asp Met Phe Met Arg Gly Glu Glu Ile Leu Ser Gly Ala Gln Arg Ile
                420                 425                 430

His Asp Pro Gln Leu Leu Thr Glu Arg Ala Leu His His Gly Ile Asp
                435                 440                 445

Leu Glu Lys Ile Lys Ala Tyr Ile Asp Ser Phe Arg Phe Gly Ala Pro
    450                 455                 460

Pro His Ala Gly Gly Gly Ile Gly Leu Glu Arg Val Thr Met Leu Phe
465                 470                 475                 480

Leu Gly Leu His Asn Val Arg Gln Thr Ser Met Phe Pro Arg Asp Pro
                485                 490                 495

Lys Arg Leu Thr Pro
                500

<210> SEQ ID NO 192
<211> LENGTH: 501
<212> TYPE: PRT
<213> ORGANISM: Artificial Sequence
<220> FEATURE:
<223> OTHER INFORMATION: DRS polypeptide variant with reduced cysteine
      content

<400> SEQUENCE: 192

Met Pro Ser Ala Ser Ala Ser Arg Lys Ser Gln Glu Lys Pro Arg Glu
1               5                   10                  15

Ile Met Asp Ala Ala Glu Asp Tyr Ala Lys Glu Arg Tyr Gly Ile Ser
                20                  25                  30

Ser Met Ile Gln Ser Gln Glu Lys Pro Asp Arg Val Leu Val Arg Val
            35                  40                  45

Arg Asp Leu Thr Ile Gln Lys Ala Asp Glu Val Val Trp Val Arg Ala
    50                  55                  60

Arg Val His Thr Ser Arg Ala Lys Gly Lys Gln Cys Phe Leu Val Leu
65                  70                  75                  80

Arg Gln Gln Gln Phe Asn Val Gln Ala Leu Val Ala Val Gly Asp His
                85                  90                  95

Ala Ser Lys Gln Met Val Lys Phe Ala Ala Asn Ile Asn Lys Glu Ser
            100                 105                 110

Ile Val Asp Val Glu Gly Val Val Arg Lys Val Asn Gln Lys Ile Gly
        115                 120                 125

Ser Cys Thr Gln Gln Asp Val Glu Leu His Val Gln Lys Ile Tyr Val
    130                 135                 140

Ile Ser Leu Ala Glu Pro Arg Leu Pro Leu Gln Leu Asp Asp Ala Val
145                 150                 155                 160

Arg Pro Glu Ala Glu Gly Glu Glu Gly Arg Ala Thr Val Asn Gln
                165                 170                 175

Asp Thr Arg Leu Asp Asn Arg Val Ile Asp Leu Arg Thr Ser Thr Ser
                180                 185                 190

Gln Ala Val Phe Arg Leu Gln Ser Gly Ile Ala His Leu Phe Arg Glu
```

-continued

```
                195                 200                 205
Thr Leu Ile Asn Lys Gly Phe Val Glu Ile Gln Thr Pro Lys Ile Ile
    210                 215                 220

Ser Ala Ala Ser Glu Gly Gly Ala Asn Val Phe Thr Val Ser Tyr Phe
225                 230                 235                 240

Lys Asn Asn Ala Tyr Leu Ala Gln Ser Pro Gln Leu Tyr Lys Gln Met
                245                 250                 255

Cys Ile Cys Ala Asp Phe Glu Lys Val Phe Ser Ile Gly Pro Val Phe
            260                 265                 270

Arg Ala Glu Asp Ser Asn Thr His Arg His Leu Thr Glu Phe Val Gly
                275                 280                 285

Leu Asp Ile Glu Met Ala Phe Asn Tyr His Tyr His Glu Val Met Glu
        290                 295                 300

Glu Ile Ala Asp Thr Met Val Gln Ile Phe Lys Gly Leu Gln Glu Arg
305                 310                 315                 320

Phe Gln Thr Glu Ile Gln Thr Val Asn Lys Gln Phe Pro Cys Glu Pro
                325                 330                 335

Phe Lys Phe Leu Glu Pro Thr Leu Arg Leu Glu Tyr Cys Glu Ala Leu
            340                 345                 350

Ala Met Leu Arg Glu Ala Gly Val Glu Met Gly Asp Glu Asp Asp Leu
                355                 360                 365

Ser Thr Pro Asn Glu Lys Leu Leu Gly His Leu Val Lys Glu Lys Tyr
        370                 375                 380

Asp Thr Asp Phe Tyr Ile Leu Asp Lys Tyr Pro Leu Ala Val Arg Pro
385                 390                 395                 400

Phe Tyr Thr Met Pro Asp Pro Arg Asn Pro Lys Gln Ser Asn Ser Tyr
                405                 410                 415

Asp Met Phe Met Arg Gly Glu Glu Ile Leu Ser Gly Ala Gln Arg Ile
            420                 425                 430

His Asp Pro Gln Leu Leu Thr Glu Arg Ala Leu His His Gly Ile Asp
                435                 440                 445

Leu Glu Lys Ile Lys Ala Tyr Ile Asp Ser Phe Arg Phe Gly Ala Pro
        450                 455                 460

Pro His Ala Gly Gly Gly Ile Gly Leu Glu Arg Val Thr Met Leu Phe
465                 470                 475                 480

Leu Gly Leu His Asn Val Arg Gln Thr Ser Met Phe Pro Arg Asp Pro
                485                 490                 495

Lys Arg Leu Thr Pro
            500
```

<210> SEQ ID NO 193
<211> LENGTH: 501
<212> TYPE: PRT
<213> ORGANISM: Artificial Sequence
<220> FEATURE:
<223> OTHER INFORMATION: DRS polypeptide variant with reduced cysteine content

<400> SEQUENCE: 193

```
Met Pro Ser Ala Ser Ala Ser Arg Lys Ser Gln Glu Lys Pro Arg Glu
1               5                   10                  15

Ile Met Asp Ala Ala Glu Asp Tyr Ala Lys Glu Arg Tyr Gly Ile Ser
                20                  25                  30

Ser Met Ile Gln Ser Gln Glu Lys Pro Asp Arg Val Leu Val Arg Val
            35                  40                  45
```

```
Arg Asp Leu Thr Ile Gln Lys Ala Asp Glu Val Val Trp Val Arg Ala
 50                  55                  60
Arg Val His Thr Ser Arg Ala Lys Gly Lys Gln Cys Phe Leu Val Leu
 65                  70                  75                  80
Arg Gln Gln Gln Phe Asn Val Gln Ala Leu Val Ala Val Gly Asp His
                 85                  90                  95
Ala Ser Lys Gln Met Val Lys Phe Ala Ala Asn Ile Asn Lys Glu Ser
                100                 105                 110
Ile Val Asp Val Glu Gly Val Val Arg Lys Val Asn Gln Lys Ile Gly
                115                 120                 125
Ser Cys Thr Gln Gln Asp Val Glu Leu His Val Gln Lys Ile Tyr Val
            130                 135                 140
Ile Ser Leu Ala Glu Pro Arg Leu Pro Leu Gln Leu Asp Asp Ala Val
145                 150                 155                 160
Arg Pro Glu Ala Glu Gly Glu Glu Gly Arg Ala Thr Val Asn Gln
                165                 170                 175
Asp Thr Arg Leu Asp Asn Arg Val Ile Asp Leu Arg Thr Ser Thr Ser
            180                 185                 190
Gln Ala Val Phe Arg Leu Gln Ser Gly Ile Val His Leu Phe Arg Glu
            195                 200                 205
Thr Leu Ile Asn Lys Gly Phe Val Glu Ile Gln Thr Pro Lys Ile Ile
            210                 215                 220
Ser Ala Ala Ser Glu Gly Gly Ala Asn Val Phe Thr Val Ser Tyr Phe
225                 230                 235                 240
Lys Asn Asn Ala Tyr Leu Ala Gln Ser Pro Gln Leu Tyr Lys Gln Met
                245                 250                 255
Cys Ile Cys Ala Asp Phe Glu Lys Val Phe Ser Ile Gly Pro Val Phe
                260                 265                 270
Arg Ala Glu Asp Ser Asn Thr His Arg His Leu Thr Glu Phe Val Gly
            275                 280                 285
Leu Asp Ile Glu Met Ala Phe Asn Tyr His Tyr His Glu Val Met Glu
            290                 295                 300
Glu Ile Ala Asp Thr Met Val Gln Ile Phe Lys Gly Leu Gln Glu Arg
305                 310                 315                 320
Phe Gln Thr Glu Ile Gln Thr Val Asn Lys Gln Phe Pro Cys Glu Pro
                325                 330                 335
Phe Lys Phe Leu Glu Pro Thr Leu Arg Leu Glu Tyr Cys Glu Ala Leu
                340                 345                 350
Ala Met Leu Arg Glu Ala Gly Val Glu Met Gly Asp Glu Asp Leu
                355                 360                 365
Ser Thr Pro Asn Glu Lys Leu Leu Gly His Leu Val Lys Glu Lys Tyr
            370                 375                 380
Asp Thr Asp Phe Tyr Ile Leu Asp Lys Tyr Pro Leu Ala Val Arg Pro
385                 390                 395                 400
Phe Tyr Thr Met Pro Asp Pro Arg Asn Pro Lys Gln Ser Asn Ser Tyr
                405                 410                 415
Asp Met Phe Met Arg Gly Glu Glu Ile Leu Ser Gly Ala Gln Arg Ile
                420                 425                 430
His Asp Pro Gln Leu Leu Thr Glu Arg Ala Leu His His Gly Ile Asp
            435                 440                 445
Leu Glu Lys Ile Lys Ala Tyr Ile Asp Ser Phe Arg Phe Gly Ala Pro
450                 455                 460
Pro His Ala Gly Gly Gly Ile Gly Leu Glu Arg Val Thr Met Leu Phe
```

Leu Gly Leu His Asn Val Arg Gln Thr Ser Met Phe Pro Arg Asp Pro
465                 470                 475                 480

Lys Arg Leu Thr Pro
            485                 490                 495

Lys Arg Leu Thr Pro
            500

<210> SEQ ID NO 194
<211> LENGTH: 501
<212> TYPE: PRT
<213> ORGANISM: Artificial Sequence
<220> FEATURE:
<223> OTHER INFORMATION: DRS polypeptide variant with reduced cysteine
      content

<400> SEQUENCE: 194

Met Pro Ser Ala Ser Ala Ser Arg Lys Ser Gln Glu Lys Pro Arg Glu
1               5                   10                  15

Ile Met Asp Ala Ala Glu Asp Tyr Ala Lys Glu Arg Tyr Gly Ile Ser
                20                  25                  30

Ser Met Ile Gln Ser Gln Glu Lys Pro Asp Arg Val Leu Val Arg Val
            35                  40                  45

Arg Asp Leu Thr Ile Gln Lys Ala Asp Glu Val Val Trp Val Arg Ala
50                  55                  60

Arg Val His Thr Ser Arg Ala Lys Gly Lys Gln Cys Phe Leu Val Leu
65                  70                  75                  80

Arg Gln Gln Gln Phe Asn Val Gln Ala Leu Val Ala Val Gly Asp His
                85                  90                  95

Ala Ser Lys Gln Met Val Lys Phe Ala Ala Asn Ile Asn Lys Glu Ser
            100                 105                 110

Ile Val Asp Val Glu Gly Val Val Arg Lys Val Asn Gln Lys Ile Gly
            115                 120                 125

Ser Cys Thr Gln Gln Asp Val Glu Leu His Val Gln Lys Ile Tyr Val
130                 135                 140

Ile Ser Leu Ala Glu Pro Arg Leu Pro Leu Gln Leu Asp Asp Ala Val
145                 150                 155                 160

Arg Pro Glu Ala Glu Gly Glu Glu Gly Arg Ala Thr Val Asn Gln
                165                 170                 175

Asp Thr Arg Leu Asp Asn Arg Val Ile Asp Leu Arg Thr Ser Thr Ser
            180                 185                 190

Gln Ala Val Phe Arg Leu Gln Ser Gly Ile Ala His Leu Phe Arg Glu
                195                 200                 205

Thr Leu Ile Asn Lys Gly Phe Val Glu Ile Gln Thr Pro Lys Ile Ile
            210                 215                 220

Ser Ala Ala Ser Glu Gly Gly Ala Asn Val Phe Thr Val Ser Tyr Phe
225                 230                 235                 240

Lys Asn Asn Ala Tyr Leu Ala Gln Ser Pro Gln Leu Tyr Lys Gln Met
                245                 250                 255

Cys Ile Cys Ala Asp Phe Glu Lys Val Phe Ser Ile Gly Pro Val Phe
            260                 265                 270

Arg Ala Glu Asp Ser Asn Thr His Arg His Leu Thr Glu Phe Val Gly
            275                 280                 285

Leu Asp Ile Glu Met Ala Phe Asn Tyr His Tyr His Glu Val Met Glu
            290                 295                 300

Glu Ile Ala Asp Thr Met Val Gln Ile Phe Lys Gly Leu Gln Glu Arg
305                 310                 315                 320

```
Phe Gln Thr Glu Ile Gln Thr Val Asn Lys Gln Phe Pro Ser Glu Pro
                325                 330                 335

Phe Lys Phe Leu Glu Pro Thr Leu Arg Leu Glu Tyr Ser Glu Ala Leu
            340                 345                 350

Ala Met Leu Arg Glu Ala Gly Val Glu Met Gly Asp Glu Asp Asp Leu
                355                 360                 365

Ser Thr Pro Asn Glu Lys Leu Leu Gly His Leu Val Lys Glu Lys Tyr
370                 375                 380

Asp Thr Asp Phe Tyr Ile Leu Asp Lys Tyr Pro Leu Ala Val Arg Pro
385                 390                 395                 400

Phe Tyr Thr Met Pro Asp Pro Arg Asn Pro Lys Gln Ser Asn Ser Tyr
                405                 410                 415

Asp Met Phe Met Arg Gly Glu Glu Ile Leu Ser Gly Ala Gln Arg Ile
                420                 425                 430

His Asp Pro Gln Leu Leu Thr Glu Arg Ala Leu His His Gly Ile Asp
                435                 440                 445

Leu Glu Lys Ile Lys Ala Tyr Ile Asp Ser Phe Arg Phe Gly Ala Pro
450                 455                 460

Pro His Ala Gly Gly Gly Ile Gly Leu Glu Arg Val Thr Met Leu Phe
465                 470                 475                 480

Leu Gly Leu His Asn Val Arg Gln Thr Ser Met Phe Pro Arg Asp Pro
                485                 490                 495

Lys Arg Leu Thr Pro
                500

<210> SEQ ID NO 195
<211> LENGTH: 501
<212> TYPE: PRT
<213> ORGANISM: Artificial Sequence
<220> FEATURE:
<223> OTHER INFORMATION: DRS polypeptide variant with reduced cysteine
      content

<400> SEQUENCE: 195

Met Pro Ser Ala Ser Ala Ser Arg Lys Ser Gln Glu Lys Pro Arg Glu
1               5                   10                  15

Ile Met Asp Ala Ala Glu Asp Tyr Ala Lys Glu Arg Tyr Gly Ile Ser
                20                  25                  30

Ser Met Ile Gln Ser Gln Glu Lys Pro Asp Arg Val Leu Val Arg Val
            35                  40                  45

Arg Asp Leu Thr Ile Gln Lys Ala Asp Glu Val Val Trp Val Arg Ala
50                  55                  60

Arg Val His Thr Ser Arg Ala Lys Gly Lys Gln Cys Phe Leu Val Leu
65                  70                  75                  80

Arg Gln Gln Gln Phe Asn Val Gln Ala Leu Val Ala Val Gly Asp His
                85                  90                  95

Ala Ser Lys Gln Met Val Lys Phe Ala Ala Asn Ile Asn Lys Glu Ser
                100                 105                 110

Ile Val Asp Val Glu Gly Val Val Arg Lys Val Asn Gln Lys Ile Gly
        115                 120                 125

Ser Cys Thr Gln Gln Asp Val Glu Leu His Val Gln Lys Ile Tyr Val
    130                 135                 140

Ile Ser Leu Ala Glu Pro Arg Leu Pro Leu Gln Leu Asp Asp Ala Val
145                 150                 155                 160

Arg Pro Glu Ala Glu Gly Glu Glu Glu Gly Arg Ala Thr Val Asn Gln
                165                 170                 175
```

```
Asp Thr Arg Leu Asp Asn Arg Val Ile Asp Leu Arg Thr Ser Thr Ser
            180                 185                 190

Gln Ala Val Phe Arg Leu Gln Ser Gly Ile Val His Leu Phe Arg Glu
        195                 200                 205

Thr Leu Ile Asn Lys Gly Phe Val Glu Ile Gln Thr Pro Lys Ile Ile
    210                 215                 220

Ser Ala Ala Ser Glu Gly Gly Ala Asn Val Phe Thr Val Ser Tyr Phe
225                 230                 235                 240

Lys Asn Asn Ala Tyr Leu Ala Gln Ser Pro Gln Leu Tyr Lys Gln Met
                245                 250                 255

Cys Ile Ala Ala Asp Phe Glu Lys Val Phe Ser Ile Gly Pro Val Phe
            260                 265                 270

Arg Ala Glu Asp Ser Asn Thr His Arg His Leu Thr Glu Phe Val Gly
        275                 280                 285

Leu Asp Ile Glu Met Ala Phe Asn Tyr His Tyr His Glu Val Met Glu
    290                 295                 300

Glu Ile Ala Asp Thr Met Val Gln Ile Phe Lys Gly Leu Gln Glu Arg
305                 310                 315                 320

Phe Gln Thr Glu Ile Gln Thr Val Asn Lys Gln Phe Pro Ser Glu Pro
                325                 330                 335

Phe Lys Phe Leu Glu Pro Thr Leu Arg Leu Glu Tyr Ser Glu Ala Leu
            340                 345                 350

Ala Met Leu Arg Glu Ala Gly Val Glu Met Gly Asp Glu Asp Asp Leu
        355                 360                 365

Ser Thr Pro Asn Glu Lys Leu Leu Gly His Leu Val Lys Glu Lys Tyr
    370                 375                 380

Asp Thr Asp Phe Tyr Ile Leu Asp Lys Tyr Pro Leu Ala Val Arg Pro
385                 390                 395                 400

Phe Tyr Thr Met Pro Asp Pro Arg Asn Pro Lys Gln Ser Asn Ser Tyr
                405                 410                 415

Asp Met Phe Met Arg Gly Glu Glu Ile Leu Ser Gly Ala Gln Arg Ile
            420                 425                 430

His Asp Pro Gln Leu Leu Thr Glu Arg Ala Leu His His Gly Ile Asp
        435                 440                 445

Leu Glu Lys Ile Lys Ala Tyr Ile Asp Ser Phe Arg Phe Gly Ala Pro
    450                 455                 460

Pro His Ala Gly Gly Gly Ile Gly Leu Glu Arg Val Thr Met Leu Phe
465                 470                 475                 480

Leu Gly Leu His Asn Val Arg Gln Thr Ser Met Phe Pro Arg Asp Pro
                485                 490                 495

Lys Arg Leu Thr Pro
            500

<210> SEQ ID NO 196
<211> LENGTH: 501
<212> TYPE: PRT
<213> ORGANISM: Artificial Sequence
<220> FEATURE:
<223> OTHER INFORMATION: DRS polypeptide variant with reduced cysteine
      content

<400> SEQUENCE: 196

Met Pro Ser Ala Ser Ala Ser Arg Lys Ser Gln Glu Lys Pro Arg Glu
1               5                   10                  15

Ile Met Asp Ala Ala Glu Asp Tyr Ala Lys Glu Arg Tyr Gly Ile Ser
```

-continued

```
             20                  25                  30
Ser Met Ile Gln Ser Gln Glu Lys Pro Asp Arg Val Leu Val Arg Val
             35                  40                  45
Arg Asp Leu Thr Ile Gln Lys Ala Asp Glu Val Val Trp Val Arg Ala
 50                  55                  60
Arg Val His Thr Ser Arg Ala Lys Gly Lys Gln Cys Phe Leu Val Leu
 65                  70                  75                  80
Arg Gln Gln Gln Phe Asn Val Gln Ala Leu Val Ala Val Gly Asp His
                     85                  90                  95
Ala Ser Lys Gln Met Val Lys Phe Ala Ala Asn Ile Asn Lys Glu Ser
                     100                 105                 110
Ile Val Asp Val Glu Gly Val Arg Lys Val Asn Gln Lys Ile Gly
                     115                 120                 125
Ser Cys Thr Gln Gln Asp Val Glu Leu His Val Gln Lys Ile Tyr Val
             130                 135                 140
Ile Ser Leu Ala Glu Pro Arg Leu Pro Leu Gln Leu Asp Asp Ala Val
145                 150                 155                 160
Arg Pro Glu Ala Glu Gly Glu Glu Gly Arg Ala Thr Val Asn Gln
                     165                 170                 175
Asp Thr Arg Leu Asp Asn Arg Val Ile Asp Leu Arg Thr Ser Thr Ser
             180                 185                 190
Gln Ala Val Phe Arg Leu Gln Ser Gly Ile Ala His Leu Phe Arg Glu
             195                 200                 205
Thr Leu Ile Asn Lys Gly Phe Val Glu Ile Gln Thr Pro Lys Ile Ile
             210                 215                 220
Ser Ala Ala Ser Glu Gly Gly Ala Asn Val Phe Thr Val Ser Tyr Phe
225                 230                 235                 240
Lys Asn Asn Ala Tyr Leu Ala Gln Ser Pro Gln Leu Tyr Lys Gln Met
                     245                 250                 255
Cys Ile Ala Ala Asp Phe Glu Lys Val Phe Ser Ile Gly Pro Val Phe
                     260                 265                 270
Arg Ala Glu Asp Ser Asn Thr His Arg His Leu Thr Glu Phe Val Gly
             275                 280                 285
Leu Asp Ile Glu Met Ala Phe Asn Tyr His Tyr His Glu Val Met Glu
             290                 295                 300
Glu Ile Ala Asp Thr Met Val Gln Ile Phe Lys Gly Leu Gln Glu Arg
305                 310                 315                 320
Phe Gln Thr Glu Ile Gln Thr Val Asn Lys Gln Phe Pro Ser Glu Pro
                     325                 330                 335
Phe Lys Phe Leu Glu Pro Thr Leu Arg Leu Glu Tyr Ser Glu Ala Leu
                     340                 345                 350
Ala Met Leu Arg Glu Ala Gly Val Glu Met Gly Asp Glu Asp Leu
             355                 360                 365
Ser Thr Pro Asn Glu Lys Leu Leu Gly His Leu Val Lys Glu Lys Tyr
             370                 375                 380
Asp Thr Asp Phe Tyr Ile Leu Asp Lys Tyr Pro Leu Ala Val Arg Pro
385                 390                 395                 400
Phe Tyr Thr Met Pro Asp Pro Arg Asn Pro Lys Gln Ser Asn Ser Tyr
                     405                 410                 415
Asp Met Phe Met Arg Gly Glu Glu Ile Leu Ser Gly Ala Gln Arg Ile
                     420                 425                 430
His Asp Pro Gln Leu Leu Thr Glu Arg Ala Leu His His Gly Ile Asp
             435                 440                 445
```

```
Leu Glu Lys Ile Lys Ala Tyr Ile Asp Ser Phe Arg Phe Gly Ala Pro
    450                 455                 460

Pro His Ala Gly Gly Ile Gly Leu Glu Arg Val Thr Met Leu Phe
465             470                 475                 480

Leu Gly Leu His Asn Val Arg Gln Thr Ser Met Phe Pro Arg Asp Pro
                485                 490                 495

Lys Arg Leu Thr Pro
            500

<210> SEQ ID NO 197
<211> LENGTH: 501
<212> TYPE: PRT
<213> ORGANISM: Artificial Sequence
<220> FEATURE:
<223> OTHER INFORMATION: RS polypeptide variant with reduced cysteine
      content

<400> SEQUENCE: 197

Met Pro Ser Ala Ser Ala Ser Arg Lys Ser Gln Glu Lys Pro Arg Glu
1               5                   10                  15

Ile Met Asp Ala Ala Glu Asp Tyr Ala Lys Glu Arg Tyr Gly Ile Ser
            20                  25                  30

Ser Met Ile Gln Ser Gln Glu Lys Pro Asp Arg Val Leu Val Arg Val
        35                  40                  45

Arg Asp Leu Thr Ile Gln Lys Ala Asp Glu Val Val Trp Val Arg Ala
    50                  55                  60

Arg Val His Thr Ser Arg Ala Lys Gly Lys Gln Cys Phe Leu Val Leu
65                  70                  75                  80

Arg Gln Gln Gln Phe Asn Val Gln Ala Leu Val Ala Val Gly Asp His
                85                  90                  95

Ala Ser Lys Gln Met Val Lys Phe Ala Ala Asn Ile Asn Lys Glu Ser
            100                 105                 110

Ile Val Asp Val Glu Gly Val Val Arg Lys Val Asn Gln Lys Ile Gly
        115                 120                 125

Ser Cys Thr Gln Gln Asp Val Glu Leu His Val Gln Lys Ile Tyr Val
    130                 135                 140

Ile Ser Leu Ala Glu Pro Arg Leu Pro Leu Gln Leu Asp Asp Ala Val
145                 150                 155                 160

Arg Pro Glu Ala Glu Gly Glu Glu Gly Arg Ala Thr Val Asn Gln
                165                 170                 175

Asp Thr Arg Leu Asp Asn Arg Val Ile Asp Leu Arg Thr Ser Thr Ser
            180                 185                 190

Gln Ala Val Phe Arg Leu Gln Ser Gly Ile Val His Leu Phe Arg Glu
        195                 200                 205

Thr Leu Ile Asn Lys Gly Phe Val Glu Ile Gln Thr Pro Lys Ile Ile
    210                 215                 220

Ser Ala Ala Ser Glu Gly Gly Ala Asn Val Phe Thr Val Ser Tyr Phe
225                 230                 235                 240

Lys Asn Asn Ala Tyr Leu Ala Gln Ser Pro Gln Leu Tyr Lys Gln Met
                245                 250                 255

Cys Ile Ala Ala Asp Phe Glu Lys Val Phe Ser Ile Gly Pro Val Phe
            260                 265                 270

Arg Ala Glu Asp Ser Asn Thr His Arg His Leu Thr Glu Phe Val Gly
        275                 280                 285

Leu Asp Ile Glu Met Ala Phe Asn Tyr His Tyr His Glu Val Met Glu
```

Glu Ile Ala Asp Thr Met Val Gln Ile Phe Lys Gly Leu Gln Glu Arg
305                 310                 315                 320

Phe Gln Thr Glu Ile Gln Thr Val Asn Lys Gln Phe Pro Ser Glu Pro
            325                 330                 335

Phe Lys Phe Leu Glu Pro Thr Leu Arg Leu Glu Tyr Ser Glu Ala Leu
            340                 345                 350

Ala Met Leu Arg Glu Ala Gly Val Glu Met Gly Asp Glu Asp Asp Leu
            355                 360                 365

Ser Thr Pro Asn Glu Lys Leu Leu Gly His Leu Val Lys Glu Lys Tyr
        370                 375                 380

Asp Thr Asp Phe Tyr Ile Leu Asp Lys Tyr Pro Leu Ala Val Arg Pro
385                 390                 395                 400

Phe Tyr Thr Met Pro Asp Pro Arg Asn Pro Lys Gln Ser Asn Ser Tyr
            405                 410                 415

Asp Met Phe Met Arg Gly Glu Glu Ile Leu Ser Gly Ala Gln Arg Ile
            420                 425                 430

His Asp Pro Gln Leu Leu Thr Glu Arg Ala Leu His His Gly Ile Asp
        435                 440                 445

Leu Glu Lys Ile Lys Ala Tyr Ile Asp Ser Phe Arg Phe Gly Ala Pro
    450                 455                 460

Pro His Ala Gly Gly Gly Ile Gly Leu Glu Arg Val Thr Met Leu Phe
465                 470                 475                 480

Leu Gly Leu His Asn Val Arg Gln Thr Ser Met Phe Pro Arg Asp Pro
            485                 490                 495

Lys Arg Leu Thr Pro
            500

<210> SEQ ID NO 198
<211> LENGTH: 1503
<212> TYPE: DNA
<213> ORGANISM: Artificial Sequence
<220> FEATURE:
<223> OTHER INFORMATION: DRS polynucleotide encoding polypetide variant
      with reduced cysteine content

<400> SEQUENCE: 198
atgcccagcg ccagcgccag ccgcaagagt caggagaagc cgcgggagat catggacgcg      60
gcggaagatt atgctaaaga gagatatgga atatcttcaa tgatacaatc acaagaaaaa     120
ccagatcgag ttttggttcg ggttagagac ttgacaatac aaaaagctga tgaagttgtt     180
tgggtacgtg caagagttca tacaagcaga gctaaaggaa acagtgctt cttagtccta      240 cgtcagcagc agtttaatgt ccaggctctt gtggcggtgg agaccatgc aagcaagcag      300 atggttaaat ttgctgccaa catcaacaaa gagagcattg tggatgtaga aggtgttgtg     360
agaaaagtga atcagaaaat tggaagctgt cacacagcaag acgttgagtt acatgttcag    420
aagatttatg tgatcagttt ggctgaaccc cgtctgcccc tgcagctgga tgatgctgtt     480
cggcctgagg cagaaggaga agaggaagga agagctactg ttaaccagga tacaagatta    540
gacaacagag tcattgatct taggacatca actagtcagg cagtcttccg tctccagtct    600
ggcatctgcc atctcttccg agaaacttta attaacaaag gttttgtgga aatccaaact    660
cctaaaatta tttcagctgc cagtgaagga ggagccaatg ttttactgt gtcatatttt     720 aaaaataatg catacctggc tcagtcccca cagctatata agcaaatgtg catttgtgct    780
gattttgaga aggttttctc tattggacca gtattcagag cggaagactc taatacccat    840

```
agacatctaa ctgagtttgt tggtttggac attgaaatgg cttttaatta ccattaccac    900
gaagttatgg aagaaattgc tgacaccatg gtacaaatat tcaaaggact tcaagaaagg    960
tttcagactg aaattcaaac agtgaataaa cagttcccat ctgagccatt caaattttg    1020 gagccaactc taagactaga atattgtgaa gcattggcta tgcttaggga agctggagtc   1080
gaaatgggag atgaagacga tctgagcaca ccaaatgaaa agctgttggg tcatttggta   1140
aaggaaaagt atgatacaga tttttatatt cttgataaat atccattggc tgtaagacct   1200
ttctatacca tgcctgaccc aagaaatccc aaacagtcca actcttacga tatgttcatg   1260
agaggagaag aaatattgtc aggagctcaa agaatacatg atcctcaact gctaacagag   1320
agagctttac atcatggaat tgatttggag aaaattaagg cttacattga ttccttccgc   1380
tttggagccc ctcctcatgc tggtggaggc attggattgg aacgagttac tatgctgttt   1440
ctgggattgc ataatgttcg tcagacctcc atgttccctc gtgatcccaa acgactcact   1500
cct                                                                 1503
```

<210> SEQ ID NO 199
<211> LENGTH: 1503
<212> TYPE: DNA
<213> ORGANISM: Artificial Sequence
<220> FEATURE:
<223> OTHER INFORMATION: DRS polynucleotide encoding polypetide variant
      with reduced cysteine content

<400> SEQUENCE: 199

```
atgcccagcg ccagcgccag ccgcaagagt caggagaagc cgcgggagat catggacgcg    60
gcggaagatt atgctaaaga gagatatgga atatcttcaa tgatacaatc acaagaaaaa   120
ccagatcgag ttttggttcg ggttagagac ttgacaatac aaaaagctga tgaagttgtt   180
tgggtacgtg caagagttca tacaagcaga gctaaaggga acagtgctt cttagtccta    240 cgtcagcagc agtttaatgt ccaggctctt gtggcggtgg agaccatgc aagcaagcag    300 atggttaaat ttgctgccaa catcaacaaa gagagcattg tggatgtaga aggtgttgtg   360
agaaaagtga atcagaaaat tggaagctgt acacagcaag acgttgagtt acatgttcag   420
aagatttatg tgatcagttt ggctgaaccc cgtctgcccc tgcagctgga tgatgctgtt   480
cggcctgagg cagaaggaga agaggaagga agagctactg ttaaccagga tacaagatta   540
gacaacagag tcattgatct taggacatca actagtcagg cagtcttccg tctccagtct   600
ggcatctgcc atctcttccg agaaacttta attaacaaag gttttgtgga atccaaact    660 cctaaaatta tttcagctgc cagtgaagga ggagccaatg ttttttactgt gtcatatttt   720 aaaaataatg catacctggc tcagtcccca cagctatata gcaaatgtg catttgtgct    780 gattttgaga aggttttctc tattggacca gtattcagag cggaagactc taatacccat   840
agacatctaa ctgagtttgt tggtttggac attgaaatgg cttttaatta ccattaccac    900
gaagttatgg aagaaattgc tgacaccatg gtacaaatat tcaaaggact tcaagaaagg    960
tttcagactg aaattcaaac agtgaataaa cagttcccat gtgagccatt caaattttg    1020 gagccaactc taagactaga atattctgaa gcattggcta tgcttaggga agctggagtc   1080
gaaatgggag atgaagacga tctgagcaca ccaaatgaaa agctgttggg tcatttggta   1140
aaggaaaagt atgatacaga tttttatatt cttgataaat atccattggc tgtaagacct   1200
ttctatacca tgcctgaccc aagaaatccc aaacagtcca actcttacga tatgttcatg   1260
agaggagaag aaatattgtc aggagctcaa agaatacatg atcctcaact gctaacagag   1320
```

<210> SEQ ID NO 200
<211> LENGTH: 1503
<212> TYPE: DNA
<213> ORGANISM: Artificial Sequence
<220> FEATURE:
<223> OTHER INFORMATION: DRS polynucleotide encoding polypetide variant
    with reduced cysteine content

<400> SEQUENCE: 200

```
atgcccagcg ccagcgccag ccgcaagagt caggagaagc cgcgggagat catggacgcg      60
gcggaagatt atgctaaaga gagatatgga atatcttcaa tgatacaatc acaagaaaaa     120
ccagatcgag ttttggttcg ggttagagac ttgacaatac aaaaagctga tgaagttgtt     180
tgggtacgtg caagagttca tacaagcaga gctaaaggga acagtgctt cttagtccta      240
cgtcagcagc agtttaatgt ccaggctctt gtggcggtgg agaccatgc aagcaagcag      300
atggttaaat tgctgccaa catcaacaaa gagagcattg tggatgtaga aggtgttgtg     360
agaaaagtga atcagaaaat ggaagctgt acacagcaag acgttgagtt acatgttcag     420
aagatttatg tgatcagttt ggctgaaccc cgtctgcccc tgcagctgga tgatgctgtt     480
cggcctgagg cagaaggaga gaggaagga agagctactg ttaaccagga tacaagatta      540
gacaacagag tcattgatct taggacatca actagtcagg cagtcttccg tctccagtct      600
ggcatctgcc atctcttccg agaaacttta attaacaaag gttttgtgga atccaaact      660
cctaaaatta tttcagctgc cagtgaagga ggagccaatg ttttactgt gtcatatttt      720
aaaaataatg catacctggc tcagtcccca cagctatata agcaaatgtg catttgtgct      780
gattttgaga aggttttctc tattggacca gtattcagag cggaagactc taatacccat      840
agacatctaa ctgagtttgt tggttttggac attgaaatgg cttttaatta ccattaccac      900
gaagttatgg aagaaattgc tgacaccatg gtacaaatat caaaggact tcaagaaagg      960
tttcagactg aaattcaaac agtgaataaa cagttcccat ctgagccatt caaatttttg     1020
gagccaactc taagactaga atattctgaa gcattggcta tgcttaggga agctggagtc     1080
gaaatgggag atgaagacga tctgagcaca ccaaatgaaa agctgtttggg tcatttggta     1140
aaggaaaagt atgatacaga ttttttatt cttgataaat atccattggc tgtaagacct     1200
ttctatacca tgcctgaccc aagaaatccc aacagtcca actcttacga tatgttcatg     1260
agaggagaag aaatattgtc aggagctcaa agaatacatg atcctcaact gctaacagag     1320
agagctttac atcatggaat tgatttggag aaaattaagg cttacattga ttccttccgc     1380
tttggagccc ctcctcatgc tggtggaggc attggattgg aacgagttac tatgctgttt     1440
ctgggattgc ataatgttcg tcagacctcc atgttccctc gtgatcccaa acgactcact     1500
cct                                                                  1503
```

<210> SEQ ID NO 201
<211> LENGTH: 1503
<212> TYPE: DNA
<213> ORGANISM: Artificial Sequence
<220> FEATURE:
<223> OTHER INFORMATION: DRS polynucleotide encoding polypetide variant with reduced cysteine content

<400> SEQUENCE: 201

```
atgcccagcg ccagcgccag ccgcaagagt caggagaagc cgcgggagat catggacgcg    60
gcggaagatt atgctaaaga gagatatgga atatcttcaa tgatacaatc acaagaaaaa   120
ccagatcgag ttttggttcg ggttagagac ttgacaatac aaaaagctga tgaagttgtt   180
tgggtacgtg caagagttca tacaagcaga gctaaaggga acagtgctt cttagtccta    240
cgtcagcagc agtttaatgt ccaggctctt gtggcggtgg gagaccatgc aagcaagcag   300
atggttaaat ttgctgccaa catcaacaaa gagagcattg tggatgtaga aggtgttgtg   360
agaaaagtga atcagaaaat tggaagctgt acacagcaag acgttgagtt acatgttcag   420
aagatttatg tgatcagttt ggctgaaccc cgtctgcccc tgcagctgga tgatgctgtt   480
cggcctgagg cagaaggaga agaggaagga agagctactg ttaaccagga tacaagatta   540
gacaacagag tcattgatct taggacatca actagtcagg cagtcttccg tctccagtct   600
ggcatcgccc atctcttccg agaaactttta attaacaaag gttttgtgga aatccaaact   660
cctaaaatta tttcagctgc cagtgaagga ggagccaatg ttttttactgt gtcatatttt   720
aaaaataatg catacctggc tcagtcccca cagctatata gcaaatgtg catttgtgct    780
gattttgaga aggttttctc tattggacca gtattcagag cggaagactc taatacccat   840
agacatctaa ctgagtttgt tggtttggac attgaaatgg cttttaatta ccattaccac   900
gaagttatgg aagaaattgc tgacaccatg gtacaaatat caaaggact tcaagaaagg    960
tttcagactg aaattcaaac agtgaataaa cagttcccat gtgagccatt caaattttg   1020
gagccaactc taagactaga atattgtgaa gcattggcta tgcttaggga agctggagtc   1080
gaaatgggag atgaagacga tctgagcaca ccaaatgaaa agctgttggg tcatttggta   1140
aaggaaaagt atgatacaga tttttatatt cttgataaat atccattggc tgtaagacct   1200
ttctatacca tgcctgaccc aagaaatccc aaacagtcca actcttacga tatgttcatg   1260
agaggagaag aaatattgtc aggagctcaa agaatacatg atcctcaact gctaacagag   1320
agagctttac atcatggaat tgatttggag aaaattaagg cttacattga ttccttccgc   1380
tttggagccc ctcctcatgc tggtggaggc attggattgg aacgagttac tatgctgttt   1440
ctgggattgc ataatgttcg tcagacctcc atgttccctc gtgatcccaa acgactcact   1500
cct                                                                 1503
```

<210> SEQ ID NO 202
<211> LENGTH: 1503
<212> TYPE: DNA
<213> ORGANISM: Artificial Sequence
<220> FEATURE:
<223> OTHER INFORMATION: DRS polynucleotide encoding polypetide variant
      with reduced cysteine content

<400> SEQUENCE: 202

```
atgcccagcg ccagcgccag ccgcaagagt caggagaagc cgcgggagat catggacgcg    60
gcggaagatt atgctaaaga gagatatgga atatcttcaa tgatacaatc acaagaaaaa   120
ccagatcgag ttttggttcg ggttagagac ttgacaatac aaaaagctga tgaagttgtt   180
tgggtacgtg caagagttca tacaagcaga gctaaaggga acagtgctt cttagtccta    240
cgtcagcagc agtttaatgt ccaggctctt gtggcggtgg gagaccatgc aagcaagcag   300
atggttaaat ttgctgccaa catcaacaaa gagagcattg tggatgtaga aggtgttgtg   360
```

-continued

| | |
|---|---|
| agaaaagtga atcagaaaat tggaagctgt acacagcaag acgttgagtt acatgttcag | 420 |
| aagatttatg tgatcagttt ggctgaaccc cgtctgcccc tgcagctgga tgatgctgtt | 480 |
| cggcctgagg cagaaggaga agaggaagga agagctactg ttaaccagga tacaagatta | 540 |
| gacaacagag tcattgatct taggacatca actagtcagg cagtcttccg tctccagtct | 600 |
| ggcatcgtcc atctcttccg agaaacttta attaacaaag gttttgtgga aatccaaact | 660 |
| cctaaaatta tttcagctgc cagtgaagga ggagccaatg ttttttactgt gtcatatttt | 720 |
| aaaaataatg catacctggc tcagtcccca cagctatata agcaaatgtg catttgtgct | 780 |
| gattttgaga aggttttctc tattggacca gtattcagag cggaagactc taatacccat | 840 |
| agacatctaa ctgagtttgt tggtttggac attgaaatgg cttttaatta ccattaccac | 900 |
| gaagttatgg aagaaattgc tgacaccatg gtacaaatat caaaggact tcaagaaagg | 960 |
| tttcagactg aaattcaaac agtgaataaa cagttcccat gtgagccatt caaattttg | 1020 |
| gagccaactc taagactaga atattgtgaa gcattggcta tgcttaggga agctggagtc | 1080 |
| gaaatgggag atgaagacga tctgagcaca ccaaatgaaa agctgttggg tcatttggta | 1140 |
| aaggaaaagt atgatacaga tttttatatt cttgataaat atccattggc tgtaagacct | 1200 |
| ttctatacca tgcctgaccc aagaaatccc aaacagtcca actcttacga tatgttcatg | 1260 |
| agaggagaag aaatattgtc aggagctcaa agaatacatg atcctcaact gctaacagag | 1320 |
| agagctttac atcatggaat tgatttggag aaaattaagg cttacattga ttccttccgc | 1380 |
| tttggagccc ctcctcatgc tggtggaggc attggattgg aacgagttac tatgctgttt | 1440 |
| ctgggattgc ataatgttcg tcagacctcc atgttccctc gtgatcccaa acgactcact | 1500 |
| cct | 1503 |

<210> SEQ ID NO 203
<211> LENGTH: 1503
<212> TYPE: DNA
<213> ORGANISM: Artificial Sequence
<220> FEATURE:
<223> OTHER INFORMATION: DRS polynucleotide encoding polypetide variant
with reduced cysteine content

<400> SEQUENCE: 203

| | |
|---|---|
| atgcccagcg ccagcgccag ccgcaagagt caggagaagc cgcgggagat catggacgcg | 60 |
| gcggaagatt atgctaaaga gagatatgga atatcttcaa tgatacaatc acaagaaaaa | 120 |
| ccagatcgag ttttggttcg ggttagagac ttgacaatac aaaaagctga tgaagttgtt | 180 |
| tgggtacgtg caagagttca tacaagcaga gctaaaggaa acagtgctt cttagtccta | 240 |
| cgtcagcagc agtttaatgt ccaggctctt gtggcggtgg agaccatgc aagcaagcag | 300 |
| atggttaaat tgctgccaa catcaacaaa gagagcattg tggatgtaga aggtgttgtg | 360 |
| agaaaagtga atcagaaaat tggaagctgt acacagcaag acgttgagtt acatgttcag | 420 |
| aagatttatg tgatcagttt ggctgaaccc cgtctgcccc tgcagctgga tgatgctgtt | 480 |
| cggcctgagg cagaaggaga agaggaagga agagctactg ttaaccagga tacaagatta | 540 |
| gacaacagag tcattgatct taggacatca actagtcagg cagtcttccg tctccagtct | 600 |
| ggcatcgccc atctcttccg agaaacttta attaacaaag gttttgtgga aatccaaact | 660 |
| cctaaaatta tttcagctgc cagtgaagga ggagccaatg ttttttactgt gtcatatttt | 720 |
| aaaaataatg catacctggc tcagtcccca cagctatata agcaaatgtg catttgtgct | 780 |
| gattttgaga aggttttctc tattggacca gtattcagag cggaagactc taatacccat | 840 |

| agacatctaa ctgagtttgt tggtttggac attgaaatgg cttttaatta ccattaccac | 900 |
| gaagttatgg aagaaattgc tgacaccatg gtacaaatat tcaaaggact tcaagaaagg | 960 |
| tttcagactg aaattcaaac agtgaataaa cagttcccat ctgagccatt caaattttg | 1020 |
| gagccaactc taagactaga atattctgaa gcattggcta tgcttaggga agctggagtc | 1080 |
| gaaatgggag atgaagacga tctgagcaca ccaaatgaaa agctgttggg tcatttggta | 1140 |
| aaggaaaagt atgatacaga ttttatat cttgataaat atccattggc tgtaagacct | 1200 |
| ttctatacca tgcctgaccc aagaaatccc aaacagtcca actcttacga tatgttcatg | 1260 |
| agaggagaag aaatattgtc aggagctcaa agaatacatg atcctcaact gctaacagag | 1320 |
| agagctttac atcatggaat tgatttggag aaaattaagg cttacattga ttccttccgc | 1380 |
| tttggagccc ctcctcatgc tggtggaggc attggattgg aacgagttac tatgctgttt | 1440 |
| ctgggattgc ataatgttcg tcagacctcc atgttccctc gtgatcccaa acgactcact | 1500 |
| cct | 1503 |

<210> SEQ ID NO 204
<211> LENGTH: 1503
<212> TYPE: DNA
<213> ORGANISM: Artificial Sequence
<220> FEATURE:
<223> OTHER INFORMATION: DRS polynucleotide encoding polypetide variant with reduced cysteine content

<400> SEQUENCE: 204

| atgcccagcg ccagcgccag ccgcaagagt caggagaagc cgcgggagat catggacgcg | 60 |
| gcggaagatt atgctaaaga gagatatgga atatcttcaa tgatacaatc acaagaaaaa | 120 |
| ccagatcgag ttttggttcg ggttagagac ttgacaatac aaaaagctga tgaagttgtt | 180 |
| tgggtacgtg caagagttca tacaagcaga gctaaaggga acagtgcttc ttagtccta | 240 |
| cgtcagcagc agtttaatgt ccaggctctt gtggcggtgg agaccatgc aagcaagcag | 300 |
| atggttaaat ttgctgccaa catcaacaaa gagagcattg tggatgtaga aggtgttgtg | 360 |
| agaaaagtga atcagaaaat tggaagctgt acacagcaag acgttgagtt acatgttcag | 420 |
| aagatttatg tgatcagttt ggctgaaccc cgtctgcccc tgcagctgga tgatgctgtt | 480 |
| cggcctgagg cagaaggaga agaggaagga agagctactg ttaaccagga tacaagatta | 540 |
| gacaacagag tcattgatct taggacatca actagtcagg cagtcttccg tctccagtct | 600 |
| ggcatcgtcc atctcttccg agaaacttta attaacaaag gttttgtgga aatccaaact | 660 |
| cctaaaatta tttcagctgc cagtgaagga ggagccaatg tttttactgt gtcatatttt | 720 |
| aaaaataatg catacctggc tcagtcccca cagctatata agcaaatgtg catttgtgct | 780 |
| gattttgaga aggttttctc tattggacca gtattcagag cggaagactc taatacccat | 840 |
| agacatctaa ctgagtttgt tggtttggac attgaaatgg cttttaatta ccattaccac | 900 |
| gaagttatgg aagaaattgc tgacaccatg gtacaaatat tcaaaggact tcaagaaagg | 960 |
| tttcagactg aaattcaaac agtgaataaa cagttcccat ctgagccatt caaattttg | 1020 |
| gagccaactc taagactaga atattctgaa gcattggcta tgcttaggga agctggagtc | 1080 |
| gaaatgggag atgaagacga tctgagcaca ccaaatgaaa agctgttggg tcatttggta | 1140 |
| aaggaaaagt atgatacaga ttttatat cttgataaat atccattggc tgtaagacct | 1200 |
| ttctatacca tgcctgaccc aagaaatccc aaacagtcca actcttacga tatgttcatg | 1260 |
| agaggagaag aaatattgtc aggagctcaa agaatacatg atcctcaact gctaacagag | 1320 |

```
agagctttac atcatggaat tgatttggag aaaattaagg cttacattga ttccttccgc    1380
tttggagccc ctcctcatgc tggtggaggc attggattgg aacgagttac tatgctgttt    1440
ctgggattgc ataatgttcg tcagacctcc atgttccctc gtgatcccaa acgactcact    1500
cct                                                                  1503
```

<210> SEQ ID NO 205
<211> LENGTH: 1503
<212> TYPE: DNA
<213> ORGANISM: Artificial Sequence
<220> FEATURE:
<223> OTHER INFORMATION: DRS polynucleotide encoding polypetide variant
      with reduced cysteine content

<400> SEQUENCE: 205

```
atgcccagcg ccagcgccag ccgcaagagt caggagaagc cgcgggagat catggacgcg      60
gcggaagatt atgctaaaga gagatatgga atatcttcaa tgatacaatc acaagaaaaa     120
ccagatcgag ttttggttcg ggttagagac ttgacaatac aaaaagctga tgaagttgtt     180
tgggtacgtg caagagttca tacaagcaga gctaaaggga acagtgctt cttagtccta      240 cgtcagcagc agtttaatgt ccaggctctt gtggcggtgg agaccatgc aagcaagcag      300 atggttaaat ttgctgccaa catcaacaaa gagagcattg tggatgtaga aggtgttgtg     360
agaaaagtga atcagaaaat tggaagctgt acacagcaag acgttgagtt acatgttcag     420
aagatttatg tgatcagttt ggctgaaccc cgtctgcccc tgcagctgga tgatgctgtt     480
cggcctgagg cagaaggaga agaggaagga agagctactg ttaaccagga tacaagatta     540
gacaacagag tcattgatct taggacatca actagtcagg cagtcttccg tctccagtct     600
ggcatcgccc atctcttccg agaaacttta attaacaaag gttttgtgga aatccaaact     660
cctaaaatta tttcagctgc cagtgaagga ggagccaatg tttttactgt gtcatatttt     720
aaaaataatg catacctggc tcagtcccca cagctatata agcaaatgtg cattgcggct     780
gattttgaga aggtttttctc tattggacca gtattcagag cggaagactc taatacccat     840
agacatctaa ctgagtttgt tggttttggac attgaaatgg ctttaaatta ccattaccac     900
gaagttatgg aagaaattgc tgacaccatg gtacaaatat caaaggact tcaagaaagg     960 tttcagactg aaattcaaac agtgaataaa cagttcccat ctgagccatt caaatttttg    1020
gagccaactc taagactaga atattctgaa gcattggcta tgcttaggga agctggagtc    1080
gaaatgggag atgaagacga tctgagcaca ccaaatgaaa agctgttggg tcatttggta    1140
aaggaaaagt atgatacaga tttttatatt cttgataaat atccattggc tgtaagacct    1200
ttctatacca tgcctgaccc aagaaatccc aaacagtcca actcttacga tatgttcatg    1260
agaggagaag aaatattgtc aggagctcaa agaatacatg atcctcaact gctaacagag    1320
agagctttac atcatggaat tgatttggag aaaattaagg cttacattga ttccttccgc    1380
tttggagccc ctcctcatgc tggtggaggc attggattgg aacgagttac tatgctgttt    1440
ctgggattgc ataatgttcg tcagacctcc atgttccctc gtgatcccaa acgactcact    1500
cct                                                                  1503
```

<210> SEQ ID NO 206
<211> LENGTH: 1503
<212> TYPE: DNA
<213> ORGANISM: Artificial Sequence
<220> FEATURE:
<223> OTHER INFORMATION: DRS polynucleotide encoding polypetide variant
      with reduced cysteine content

<400> SEQUENCE: 206

```
atgcccagcg ccagcgccag ccgcaagagt caggagaagc cgcgggagat catggacgcg      60
gcggaagatt atgctaaaga gagatatgga atatcttcaa tgatacaatc acaagaaaaa     120
ccagatcgag ttttggttcg ggttagagac ttgacaatac aaaaagctga tgaagttgtt     180
tgggtacgtg caagagttca tacaagcaga gctaaaggga acagtgctt cttagtccta      240
cgtcagcagc agtttaatgt ccaggctctt gtggcggtgg agaccatgc aagcaagcag      300
atggttaaat tgctgccaa catcaacaaa gagagcattg tggatgtaga aggtgttgtg      360
agaaaagtga atcagaaaat ggaagctgt cacagcaag acgttgagtt acatgttcag       420
aagatttatg tgatcagttt ggctgaaccc cgtctgcccc tgcagctgga tgatgctgtt     480
cggcctgagg cagaaggaga gaggaagga gagctactg ttaaccagga tacaagatta       540
gacaacagag tcattgatct taggacatca actagtcagg cagtcttccg tctccagtct     600
ggcatcgtcc atctcttccg agaaacttta attaacaaag gttttgtgga aatccaaact     660
cctaaaatta tttcagctgc cagtgaagga ggagccaatg ttttttactgt gtcatatttt    720
aaaaataatg cataccctgg ctcagtcccca cagctatata agcaaatgtg cattgcggct    780
gattttgaga aggttttctc tattggacca gtattcagag cggaagactc taatacccat    840
agacatctaa ctgagtttgt tggttttggac attgaaatgg cttttaatta ccattaccac    900
gaagttatgg aagaaattgc tgacaccatg gtacaaatat tcaaaggact tcaagaaagg    960
tttcagactg aaattcaaac agtgaataaa cagttcccat ctgagccatt caaattttg    1020
gagccaactc taagactaga atattctgaa gcattggcta tgcttaggga agctggagtc   1080
gaaatgggag atgaagacga tctgagcaca ccaaatgaaa agctgttggg tcatttggta   1140
aaggaaaagt atgatacaga tttttatatt cttgataaat atccattggc tgtaagacct   1200
ttctatacca tgcctgaccc aagaaatccc aacagtcca actcttacga tatgttcatg    1260
agaggagaag aaatattgtc aggagctcaa agaatacatg atcctcaact gctaacagag   1320
agagctttac atcatggaat tgatttggag aaaattaagg cttacattga ttccttccgc   1380
tttggagccc ctcctcatgc tggtggaggc attggattgg aacagttac tatgctgttt    1440
ctgggattgc ataatgttcg tcagacctcc atgttccctc gtgatcccaa acgactcact   1500
cct                                                                  1503
```

<210> SEQ ID NO 207
<211> LENGTH: 546
<212> TYPE: DNA
<213> ORGANISM: Homo sapiens

<400> SEQUENCE: 207

```
atgcccagcg ccagcgccag ccgcaagagt caggagaagc cgcgggagat catggacgcg      60
gcggaagatt atgctaaaga gagatatgga atatcttcaa tgatacaatc acaagaaaaa     120
ccagatcgag ttttggttcg ggttagagac ttgacaatac aaaaagctga tgaagttgtt     180
tgggtacgtg caagagttca tacaagcaga gctaaaggga acagtgctt cttagtccta      240
cgtcagcagc agtttaatgt ccaggctctt gtggcggtgg agaccatgc aagcaagcag      300
atggttaaat tgctgccaa catcaacaaa gagagcattg tggatgtaga aggtgttgtg      360
agaaaagtga atcagaaaat ggaagctgt cacagcaag acgttgagtt acatgttcag       420
aagatttatg tgatcagttt ggctgaaccc cgtctgcccc tgcagctgga tgatgctgtt     480
```

```
cggcctgagg cagaaggaga agaggaagga agagctactg ttaaccagga tacaagatta    540
gacaac                                                                546
```

<210> SEQ ID NO 208
<211> LENGTH: 540
<212> TYPE: DNA
<213> ORGANISM: Homo sapiens

<400> SEQUENCE: 208

```
atgcccagcg ccagcgccag ccgcaagagt caggagaagc cgcgggagat catggacgcg     60
gcggaagatt atgctaaaga gagatatgga atatcttcaa tgatacaatc acaagaaaaa    120
ccagatcgag ttttggttcg ggttagagac ttgacaatac aaaaagctga tgaagttgtt    180
tgggtacgtg caagagttca tacaagcaga gctaaaggga acagtgctt cttagtccta     240 cgtcagcagc agtttaatgt ccaggctctt gtggcggtgg gagaccatgc aagcaagcag    300
atggttaaat ttgctgccaa catcaacaaa gagagcattg tggatgtaga aggtgttgtg    360
agaaaagtga atcagaaaat tggaagctgt acacagcaag acgttgagtt acatgttcag    420
aagatttatg tgatcagttt ggctgaaccc cgtctgcccc tgcagctgga tgatgctgtt    480
cggcctgagg cagaaggaga agaggaagga agagctactg ttaaccagga tacaagatta    540
```

<210> SEQ ID NO 209
<211> LENGTH: 534
<212> TYPE: DNA
<213> ORGANISM: Homo sapiens

<400> SEQUENCE: 209

```
atgcccagcg ccagcgccag ccgcaagagt caggagaagc cgcgggagat catggacgcg     60
gcggaagatt atgctaaaga gagatatgga atatcttcaa tgatacaatc acaagaaaaa    120
ccagatcgag ttttggttcg ggttagagac ttgacaatac aaaaagctga tgaagttgtt    180
tgggtacgtg caagagttca tacaagcaga gctaaaggga acagtgctt cttagtccta     240 cgtcagcagc agtttaatgt ccaggctctt gtggcggtgg gagaccatgc aagcaagcag    300
atggttaaat ttgctgccaa catcaacaaa gagagcattg tggatgtaga aggtgttgtg    360
agaaaagtga atcagaaaat tggaagctgt acacagcaag acgttgagtt acatgttcag    420
aagatttatg tgatcagttt ggctgaaccc cgtctgcccc tgcagctgga tgatgctgtt    480
cggcctgagg cagaaggaga agaggaagga agagctactg ttaaccagga taca          534
```

<210> SEQ ID NO 210
<211> LENGTH: 528
<212> TYPE: DNA
<213> ORGANISM: Homo sapiens

<400> SEQUENCE: 210

```
atgcccagcg ccagcgccag ccgcaagagt caggagaagc cgcgggagat catggacgcg     60
gcggaagatt atgctaaaga gagatatgga atatcttcaa tgatacaatc acaagaaaaa    120
ccagatcgag ttttggttcg ggttagagac ttgacaatac aaaaagctga tgaagttgtt    180
tgggtacgtg caagagttca tacaagcaga gctaaaggga acagtgctt cttagtccta     240 cgtcagcagc agtttaatgt ccaggctctt gtggcggtgg gagaccatgc aagcaagcag    300
atggttaaat ttgctgccaa catcaacaaa gagagcattg tggatgtaga aggtgttgtg    360
agaaaagtga atcagaaaat tggaagctgt acacagcaag acgttgagtt acatgttcag    420
aagatttatg tgatcagttt ggctgaaccc cgtctgcccc tgcagctgga tgatgctgtt    480
```
cggcctgagg cagaaggaga agaggaagga agagctactg ttaaccag          528

<210> SEQ ID NO 211
<211> LENGTH: 522
<212> TYPE: DNA
<213> ORGANISM: Homo sapiens

<400> SEQUENCE: 211
atgcccagcg ccagcgccag ccgcaagagt caggagaagc cgcgggagat catggacgcg     60
gcggaagatt atgctaaaga gagatatgga atatcttcaa tgatacaatc acaagaaaaa    120
ccagatcgag ttttggttcg ggttagagac ttgacaatac aaaaagctga tgaagttgtt    180
tgggtacgtg caagagttca tacaagcaga gctaaaggga acagtgctt cttagtccta     240 cgtcagcagc agtttaatgt ccaggctctt gtggcggtgg gagaccatgc aagcaagcag    300
atggttaaat ttgctgccaa catcaacaaa gagagcattg tggatgtaga aggtgttgtg    360
agaaaagtga atcagaaaat tggaagctgt acacagcaag acgttgagtt acatgttcag    420
aagatttatg tgatcagttt ggctgaaccc cgtctgcccc tgcagctgga tgatgctgtt    480
cggcctgagg cagaaggaga agaggaagga agagctactg tt                      522

<210> SEQ ID NO 212
<211> LENGTH: 516
<212> TYPE: DNA
<213> ORGANISM: Homo sapiens

<400> SEQUENCE: 212
atgcccagcg ccagcgccag ccgcaagagt caggagaagc cgcgggagat catggacgcg     60
gcggaagatt atgctaaaga gagatatgga atatcttcaa tgatacaatc acaagaaaaa    120
ccagatcgag ttttggttcg ggttagagac ttgacaatac aaaaagctga tgaagttgtt    180
tgggtacgtg caagagttca tacaagcaga gctaaaggga acagtgctt cttagtccta     240 cgtcagcagc agtttaatgt ccaggctctt gtggcggtgg gagaccatgc aagcaagcag    300
atggttaaat ttgctgccaa catcaacaaa gagagcattg tggatgtaga aggtgttgtg    360
agaaaagtga atcagaaaat tggaagctgt acacagcaag acgttgagtt acatgttcag    420
aagatttatg tgatcagttt ggctgaaccc cgtctgcccc tgcagctgga tgatgctgtt    480
cggcctgagg cagaaggaga agaggaagga agagct                             516

<210> SEQ ID NO 213
<211> LENGTH: 510
<212> TYPE: DNA
<213> ORGANISM: Homo sapiens

<400> SEQUENCE: 213
atgcccagcg ccagcgccag ccgcaagagt caggagaagc cgcgggagat catggacgcg     60
gcggaagatt atgctaaaga gagatatgga atatcttcaa tgatacaatc acaagaaaaa    120
ccagatcgag ttttggttcg ggttagagac ttgacaatac aaaaagctga tgaagttgtt    180
tgggtacgtg caagagttca tacaagcaga gctaaaggga acagtgctt cttagtccta     240 cgtcagcagc agtttaatgt ccaggctctt gtggcggtgg gagaccatgc aagcaagcag    300
atggttaaat ttgctgccaa catcaacaaa gagagcattg tggatgtaga aggtgttgtg    360
agaaaagtga atcagaaaat tggaagctgt acacagcaag acgttgagtt acatgttcag    420
aagatttatg tgatcagttt ggctgaaccc cgtctgcccc tgcagctgga tgatgctgtt    480

```
cggcctgagg cagaaggaga agaggaagga                                     510
```

<210> SEQ ID NO 214
<211> LENGTH: 504
<212> TYPE: DNA
<213> ORGANISM: Homo sapiens

<400> SEQUENCE: 214

```
atgcccagcg ccagcgccag ccgcaagagt caggagaagc cgcgggagat catggacgcg   60
gcggaagatt atgctaaaga gagatatgga atatcttcaa tgatacaatc acaagaaaaa  120
ccagatcgag ttttggttcg ggttagagac ttgacaatac aaaaagctga tgaagttgtt  180
tgggtacgtg caagagttca tacaagcaga gctaaaggga acagtgctt cttagtccta   240
cgtcagcagc agtttaatgt ccaggctctt gtggcggtgg agaccatgc aagcaagcag   300
atggttaaat ttgctgccaa catcaacaaa gagagcattg tggatgtaga aggtgttgtg  360
agaaaagtga atcagaaaat tggaagctgt acacagcaag acgttgagtt acatgttcag  420
aagatttatg tgatcagttt ggctgaaccc cgtctgcccc tgcagctgga tgatgctgtt  480
cggcctgagg cagaaggaga agag                                          504
```

<210> SEQ ID NO 215
<211> LENGTH: 498
<212> TYPE: DNA
<213> ORGANISM: Homo sapiens

<400> SEQUENCE: 215

```
atgcccagcg ccagcgccag ccgcaagagt caggagaagc cgcgggagat catggacgcg   60
gcggaagatt atgctaaaga gagatatgga atatcttcaa tgatacaatc acaagaaaaa  120
ccagatcgag ttttggttcg ggttagagac ttgacaatac aaaaagctga tgaagttgtt  180
tgggtacgtg caagagttca tacaagcaga gctaaaggga acagtgctt cttagtccta   240
cgtcagcagc agtttaatgt ccaggctctt gtggcggtgg agaccatgc aagcaagcag   300
atggttaaat ttgctgccaa catcaacaaa gagagcattg tggatgtaga aggtgttgtg  360
agaaaagtga atcagaaaat tggaagctgt acacagcaag acgttgagtt acatgttcag  420
aagatttatg tgatcagttt ggctgaaccc cgtctgcccc tgcagctgga tgatgctgtt  480
cggcctgagg cagaagga                                                 498
```

<210> SEQ ID NO 216
<211> LENGTH: 492
<212> TYPE: DNA
<213> ORGANISM: Homo sapiens

<400> SEQUENCE: 216

```
atgcccagcg ccagcgccag ccgcaagagt caggagaagc cgcgggagat catggacgcg   60
gcggaagatt atgctaaaga gagatatgga atatcttcaa tgatacaatc acaagaaaaa  120
ccagatcgag ttttggttcg ggttagagac ttgacaatac aaaaagctga tgaagttgtt  180
tgggtacgtg caagagttca tacaagcaga gctaaaggga acagtgctt cttagtccta   240
cgtcagcagc agtttaatgt ccaggctctt gtggcggtgg agaccatgc aagcaagcag   300
atggttaaat ttgctgccaa catcaacaaa gagagcattg tggatgtaga aggtgttgtg  360
agaaaagtga atcagaaaat tggaagctgt acacagcaag acgttgagtt acatgttcag  420
aagatttatg tgatcagttt ggctgaaccc cgtctgcccc tgcagctgga tgatgctgtt  480
cggcctgagg ca                                                       492
```

<210> SEQ ID NO 217
<211> LENGTH: 486
<212> TYPE: DNA
<213> ORGANISM: Homo sapiens

<400> SEQUENCE: 217

| | | | | | |
|---|---|---|---|---|---|
| atgcccagcg | ccagcgccag | ccgcaagagt | caggagaagc | cgcgggagat | catggacgcg | 60 |
| gcggaagatt | atgctaaaga | gagatatgga | atatcttcaa | tgatacaatc | acaagaaaaa | 120 |
| ccagatcgag | ttttggttcg | ggttagagac | ttgacaatac | aaaaagctga | tgaagttgtt | 180 |
| tgggtacgtg | caagagttca | tacaagcaga | gctaaaggga | aacagtgctt | cttagtccta | 240 |
| cgtcagcagc | agtttaatgt | ccaggctctt | gtggcggtgg | gagaccatgc | aagcaagcag | 300 |
| atggttaaat | ttgctgccaa | catcaacaaa | gagagcattg | tggatgtaga | aggtgttgtg | 360 |
| agaaaagtga | atcagaaaat | tggaagctgt | acacagcaag | acgttgagtt | acatgttcag | 420 |
| aagatttatg | tgatcagttt | ggctgaaccc | cgtctgcccc | tgcagctgga | tgatgctgtt | 480 |
| cggcct | | | | | | 486 |

<210> SEQ ID NO 218
<211> LENGTH: 480
<212> TYPE: DNA
<213> ORGANISM: Homo sapiens

<400> SEQUENCE: 218

| | | | | | |
|---|---|---|---|---|---|
| atgcccagcg | ccagcgccag | ccgcaagagt | caggagaagc | cgcgggagat | catggacgcg | 60 |
| gcggaagatt | atgctaaaga | gagatatgga | atatcttcaa | tgatacaatc | acaagaaaaa | 120 |
| ccagatcgag | ttttggttcg | ggttagagac | ttgacaatac | aaaaagctga | tgaagttgtt | 180 |
| tgggtacgtg | caagagttca | tacaagcaga | gctaaaggga | aacagtgctt | cttagtccta | 240 |
| cgtcagcagc | agtttaatgt | ccaggctctt | gtggcggtgg | gagaccatgc | aagcaagcag | 300 |
| atggttaaat | ttgctgccaa | catcaacaaa | gagagcattg | tggatgtaga | aggtgttgtg | 360 |
| agaaaagtga | atcagaaaat | tggaagctgt | acacagcaag | acgttgagtt | acatgttcag | 420 |
| aagatttatg | tgatcagttt | ggctgaaccc | cgtctgcccc | tgcagctgga | tgatgctgtt | 480 |

<210> SEQ ID NO 219
<211> LENGTH: 474
<212> TYPE: DNA
<213> ORGANISM: Homo sapiens

<400> SEQUENCE: 219

| | | | | | |
|---|---|---|---|---|---|
| atgcccagcg | ccagcgccag | ccgcaagagt | caggagaagc | cgcgggagat | catggacgcg | 60 |
| gcggaagatt | atgctaaaga | gagatatgga | atatcttcaa | tgatacaatc | acaagaaaaa | 120 |
| ccagatcgag | ttttggttcg | ggttagagac | ttgacaatac | aaaaagctga | tgaagttgtt | 180 |
| tgggtacgtg | caagagttca | tacaagcaga | gctaaaggga | aacagtgctt | cttagtccta | 240 |
| cgtcagcagc | agtttaatgt | ccaggctctt | gtggcggtgg | gagaccatgc | aagcaagcag | 300 |
| atggttaaat | ttgctgccaa | catcaacaaa | gagagcattg | tggatgtaga | aggtgttgtg | 360 |
| agaaaagtga | atcagaaaat | tggaagctgt | acacagcaag | acgttgagtt | acatgttcag | 420 |
| aagatttatg | tgatcagttt | ggctgaaccc | cgtctgcccc | tgcagctgga | tgat | 474 |

<210> SEQ ID NO 220
<211> LENGTH: 468
<212> TYPE: DNA

<213> ORGANISM: Homo sapiens

<400> SEQUENCE: 220

| | |
|---|---|
| atgcccagcg ccagcgccag ccgcaagagt caggagaagc cgcgggagat catggacgcg | 60 |
| gcggaagatt atgctaaaga gagatatgga atatcttcaa tgatacaatc acaagaaaaa | 120 |
| ccagatcgag ttttggttcg ggttagagac ttgacaatac aaaaagctga tgaagttgtt | 180 |
| tgggtacgtg caagagttca tacaagcaga gctaaaggga acagtgctt cttagtccta | 240 |
| cgtcagcagc agtttaatgt ccaggctctt gtggcggtgg gagaccatgc aagcaagcag | 300 |
| atggttaaat ttgctgccaa catcaacaaa gagagcattg tggatgtaga aggtgttgtg | 360 |
| agaaaagtga atcagaaaat tggaagctgt acacagcaag acgttgagtt acatgttcag | 420 |
| aagatttatg tgatcagttt ggctgaaccc cgtctgcccc tgcagctg | 468 |

<210> SEQ ID NO 221
<211> LENGTH: 462
<212> TYPE: DNA
<213> ORGANISM: Homo sapiens

<400> SEQUENCE: 221

| | |
|---|---|
| atgcccagcg ccagcgccag ccgcaagagt caggagaagc cgcgggagat catggacgcg | 60 |
| gcggaagatt atgctaaaga gagatatgga atatcttcaa tgatacaatc acaagaaaaa | 120 |
| ccagatcgag ttttggttcg ggttagagac ttgacaatac aaaaagctga tgaagttgtt | 180 |
| tgggtacgtg caagagttca tacaagcaga gctaaaggga acagtgctt cttagtccta | 240 |
| cgtcagcagc agtttaatgt ccaggctctt gtggcggtgg gagaccatgc aagcaagcag | 300 |
| atggttaaat ttgctgccaa catcaacaaa gagagcattg tggatgtaga aggtgttgtg | 360 |
| agaaaagtga atcagaaaat tggaagctgt acacagcaag acgttgagtt acatgttcag | 420 |
| aagatttatg tgatcagttt ggctgaaccc cgtctgcccc tg | 462 |

<210> SEQ ID NO 222
<211> LENGTH: 456
<212> TYPE: DNA
<213> ORGANISM: Homo sapiens

<400> SEQUENCE: 222

| | |
|---|---|
| atgcccagcg ccagcgccag ccgcaagagt caggagaagc cgcgggagat catggacgcg | 60 |
| gcggaagatt atgctaaaga gagatatgga atatcttcaa tgatacaatc acaagaaaaa | 120 |
| ccagatcgag ttttggttcg ggttagagac ttgacaatac aaaaagctga tgaagttgtt | 180 |
| tgggtacgtg caagagttca tacaagcaga gctaaaggga acagtgctt cttagtccta | 240 |
| cgtcagcagc agtttaatgt ccaggctctt gtggcggtgg gagaccatgc aagcaagcag | 300 |
| atggttaaat ttgctgccaa catcaacaaa gagagcattg tggatgtaga aggtgttgtg | 360 |
| agaaaagtga atcagaaaat tggaagctgt acacagcaag acgttgagtt acatgttcag | 420 |
| aagatttatg tgatcagttt ggctgaaccc cgtctg | 456 |

<210> SEQ ID NO 223
<211> LENGTH: 450
<212> TYPE: DNA
<213> ORGANISM: Homo sapiens

<400> SEQUENCE: 223

| | |
|---|---|
| atgcccagcg ccagcgccag ccgcaagagt caggagaagc cgcgggagat catggacgcg | 60 |
| gcggaagatt atgctaaaga gagatatgga atatcttcaa tgatacaatc acaagaaaaa | 120 |

```
ccagatcgag ttttggttcg ggttagagac ttgacaatac aaaaagctga tgaagttgtt      180
tgggtacgtg caagagttca tacaagcaga gctaaaggga aacagtgctt cttagtccta      240
cgtcagcagc agtttaatgt ccaggctctt gtggcggtgg gagaccatgc aagcaagcag      300
atggttaaat ttgctgccaa catcaacaaa gagagcattg tggatgtaga aggtgttgtg      360
agaaaagtga atcagaaaat tggaagctgt acacagcaag acgttgagtt acatgttcag      420
aagatttatg tgatcagttt ggctgaaccc                                       450
```

<210> SEQ ID NO 224
<211> LENGTH: 444
<212> TYPE: DNA
<213> ORGANISM: Homo sapiens

<400> SEQUENCE: 224

```
atgcccagcg ccagcgccag ccgcaagagt caggagaagc cgcgggagat catggacgcg      60
gcggaagatt atgctaaaga gagatatgga atatcttcaa tgatacaatc acaagaaaaa      120
ccagatcgag ttttggttcg ggttagagac ttgacaatac aaaaagctga tgaagttgtt      180
tgggtacgtg caagagttca tacaagcaga gctaaaggga aacagtgctt cttagtccta      240
cgtcagcagc agtttaatgt ccaggctctt gtggcggtgg gagaccatgc aagcaagcag      300
atggttaaat ttgctgccaa catcaacaaa gagagcattg tggatgtaga aggtgttgtg      360
agaaaagtga atcagaaaat tggaagctgt acacagcaag acgttgagtt acatgttcag      420
aagatttatg tgatcagttt ggct                                             444
```

<210> SEQ ID NO 225
<211> LENGTH: 438
<212> TYPE: DNA
<213> ORGANISM: Homo sapiens

<400> SEQUENCE: 225

```
atgcccagcg ccagcgccag ccgcaagagt caggagaagc cgcgggagat catggacgcg      60
gcggaagatt atgctaaaga gagatatgga atatcttcaa tgatacaatc acaagaaaaa      120
ccagatcgag ttttggttcg ggttagagac ttgacaatac aaaaagctga tgaagttgtt      180
tgggtacgtg caagagttca tacaagcaga gctaaaggga aacagtgctt cttagtccta      240
cgtcagcagc agtttaatgt ccaggctctt gtggcggtgg gagaccatgc aagcaagcag      300
atggttaaat ttgctgccaa catcaacaaa gagagcattg tggatgtaga aggtgttgtg      360
agaaaagtga atcagaaaat tggaagctgt acacagcaag acgttgagtt acatgttcag      420
aagatttatg tgatcagt                                                    438
```

<210> SEQ ID NO 226
<211> LENGTH: 453
<212> TYPE: DNA
<213> ORGANISM: Homo sapiens

<400> SEQUENCE: 226

```
gccagcgcca gccgcaagag tcaggagaag ccgcgggaga tcatggacgc ggcggaagat      60
tatgctaaag agagatatgg aatatcttca atgatacaat cacaagaaaa accagatcga      120
gttttggttc gggttagaga cttgacaata caaaaagctg atgaagttgt tgggtacgt      180 gcaagagttc atacaagcag agctaaaggg aaacagtgct tcttagtcct acgtcagcag      240
cagtttaatg tccaggctct gtggcggtg ggagaccatg caagcaagca gatggttaaa      300
```

```
tttgctgcca acatcaacaa agagagcatt gtggatgtag aaggtgttgt gagaaaagtg      360
aatcagaaaa ttggaagctg tacacagcaa gacgttgagt tacatgttca gaagatttat      420
gtgatcagtt tggctgaacc ccgtctgccc ctg                                   453

<210> SEQ ID NO 227
<211> LENGTH: 447
<212> TYPE: DNA
<213> ORGANISM: Homo sapiens

<400> SEQUENCE: 227
gccagccgca agagtcagga gaagccgcgg gagatcatgg acgcggcgga agattatgct       60
aaagagagat atggaatatc ttcaatgata caatcacaag aaaaaccaga tcgagttttg      120
gttcgggtta gagacttgac aatacaaaaa gctgatgaag ttgtttgggt acgtgcaaga      180
gttcatacaa gcagagctaa agggaaacag tgcttcttag tcctacgtca gcagcagttt      240
aatgtccagg ctcttgtggc ggtgggagac catgcaagca agcagatggt taaatttgct      300
gccaacatca caaagagag cattgtggat gtagaaggtg ttgtgagaaa agtgaatcag      360
aaaattggaa gctgtacaca gcaagacgtt gagttacatg ttcagaagat ttatgtgatc      420
agtttggctg aaccccgtct gccctg                                          447

<210> SEQ ID NO 228
<211> LENGTH: 441
<212> TYPE: DNA
<213> ORGANISM: Homo sapiens

<400> SEQUENCE: 228
cgcaagagtc aggagaagcc gcgggagatc atggacgcgg cggaagatta tgctaaagag       60
agatatggaa tatcttcaat gatacaatca agaaaaac cagatcgagt tttggttcgg      120
gttagagact tgacaataca aaaagctgat gaagttgttt gggtacgtgc aagagttcat      180
acaagcagag ctaaagggaa acagtgcttc ttagtcctac gtcagcagca gtttaatgtc      240
caggctcttg tggcggtggg agaccatgca agcaagcaga tggttaaatt tgctgccaac      300
atcaacaaag agagcattgt ggatgtagaa ggtgttgtga gaaaagtgaa tcagaaaatt      360
ggaagctgta cacagcaaga cgttgagtta catgttcaga gatttatgt gatcagtttg      420 gctgaacccc gtctgcccct g                                               441

<210> SEQ ID NO 229
<211> LENGTH: 435
<212> TYPE: DNA
<213> ORGANISM: Homo sapiens

<400> SEQUENCE: 229
agtcaggaga agccgcggga gatcatggac gcggcggaag attatgctaa agagagatat       60
ggaatatctt caatgataca atcacaagaa aaaccagatc gagttttggt tcgggttaga      120
gacttgacaa tacaaaaagc tgatgaagtt gtttgggtac gtgcaagagt tcatacaagc      180
agagctaaag ggaaacagtg cttcttagtc ctacgtcagc agcagtttaa tgtccaggct      240
cttgtggcgg tgggagacca tgcaagcaag cagatggtta aatttgctgc caacatcaac      300
aaagagagca ttgtggatgt agaaggtgtt gtgagaaaag tgaatcagaa aattggaagc      360
tgtacacagc aagacgttga gttacatgtt cagaagattt atgtgatcag tttggctgaa      420
ccccgtctgc ccctg                                                      435
```

```
<210> SEQ ID NO 230
<211> LENGTH: 429
<212> TYPE: DNA
<213> ORGANISM: Homo sapiens

<400> SEQUENCE: 230
gagaagccgc gggagatcat ggacgcggcg gaagattatg ctaaagagag atatggaata      60
tcttcaatga tacaatcaca agaaaaacca gatcgagttt tggttcgggt tagagacttg     120
acaatacaaa aagctgatga agttgtttgg gtacgtgcaa gagttcatac aagcagagct     180
aaagggaaac agtgcttctt agtcctacgt cagcagcagt ttaatgtcca ggctcttgtg     240
gcggtgggag accatgcaag caagcagatg gttaaatttg ctgccaacat caacaaagag     300
agcattgtgg atgtagaagg tgttgtgaga aaagtgaatc agaaaattgg aagctgtaca     360
cagcaagacg ttgagttaca tgttcagaag atttatgtga tcagtttggc tgaacccgt     420
ctgccctg                                                              429

<210> SEQ ID NO 231
<211> LENGTH: 423
<212> TYPE: DNA
<213> ORGANISM: Homo sapiens

<400> SEQUENCE: 231
ccgcgggaga tcatggacgc ggcggaagat tatgctaaag agagatatgg aatatcttca      60
atgatacaat cacaagaaaa accagatcga gttttggttc gggttagaga cttgacaata     120
caaaaagctg atgaagttgt ttgggtacgt gcaagagttc atacaagcag agctaaaggg     180
aaacagtgct tcttagtcct acgtcagcag cagtttaatg tccaggctct tgtggcggtg     240
ggagaccatg caagcaagca gatggttaaa tttgctgcca acatcaacaa agagagcatt     300
gtggatgtag aaggtgttgt gagaaaagtg aatcagaaaa ttggaagctg tacacagcaa     360
gacgttgagt tacatgttca gaagatttat gtgatcagtt tggctgaacc ccgtctgccc     420
ctg                                                                   423

<210> SEQ ID NO 232
<211> LENGTH: 417
<212> TYPE: DNA
<213> ORGANISM: Homo sapiens

<400> SEQUENCE: 232
gagatcatgg acgcggcgga agattatgct aaagagagat atggaatatc ttcaatgata      60
caatcacaag aaaaaccaga tcgagttttg gttcgggtta gagacttgac aatacaaaaa     120
gctgatgaag ttgtttgggt acgtgcaaga gttcatacaa gcagagctaa agggaaacag     180
tgcttcttag tcctacgtca gcagcagttt aatgtccagg ctcttgtggc ggtgggagac     240
catgcaagca agcagatggt taaatttgct gccaacatca acaaagagag cattgtggat     300
gtagaaggtg ttgtgagaaa agtgaatcag aaaattggaa gctgtacaca gcaagacgtt     360
gagttacatg ttcagaagat ttatgtgatc agtttggctg aacccgtct gccctg         417

<210> SEQ ID NO 233
<211> LENGTH: 411
<212> TYPE: DNA
<213> ORGANISM: Homo sapiens

<400> SEQUENCE: 233
atggacgcgg cggaagatta tgctaaagag agatatggaa tatcttcaat gatacaatca      60
```

```
caagaaaaac cagatcgagt tttggttcgg gttagagact tgacaataca aaaagctgat      120
gaagttgttt gggtacgtgc aagagttcat acaagcagag ctaaagggaa acagtgcttc      180
ttagtcctac gtcagcagca gtttaatgtc caggctcttg tggcggtggg agaccatgca      240
agcaagcaga tggttaaatt tgctgccaac atcaacaaag agagcattgt ggatgtagaa      300
ggtgttgtga gaaaagtgaa tcagaaaatt ggaagctgta cacagcaaga cgttgagtta      360
catgttcaga gatttatgt gatcagtttg gctgaacccc gtctgcccct g                411

<210> SEQ ID NO 234
<211> LENGTH: 405
<212> TYPE: DNA
<213> ORGANISM: Homo sapiens

<400> SEQUENCE: 234
gcggcggaag attatgctaa agagagatat ggaatatctt caatgataca atcacaagaa      60
aaaccagatc gagttttggt tcgggttaga gacttgacaa tacaaaaagc tgatgaagtt     120
gtttgggtac gtgcaagagt tcatacaagc agagctaaag ggaaacagtg cttcttagtc     180
ctacgtcagc agcagtttaa tgtccaggct cttgtggcgg tgggagacca tgcaagcaag     240
cagatggtta aatttgctgc caacatcaac aaagagagca ttgtggatgt agaaggtgtt     300
gtgagaaaag tgaatcagaa aattggaagc tgtacacagc aagacgttga gttacatgtt     360
cagaagattt atgtgatcag tttggctgaa ccccgtctgc ccctg                      405

<210> SEQ ID NO 235
<211> LENGTH: 399
<212> TYPE: DNA
<213> ORGANISM: Homo sapiens

<400> SEQUENCE: 235
gcggcggaag attatgctaa agagagatat ggaatatctt caatgataca atcacaagaa      60
aaaccagatc gagttttggt tcgggttaga gacttgacaa tacaaaaagc tgatgaagtt     120
gtttgggtac gtgcaagagt tcatacaagc agagctaaag ggaaacagtg cttcttagtc     180
ctacgtcagc agcagtttaa tgtccaggct cttgtggcgg tgggagacca tgcaagcaag     240
cagatggtta aatttgctgc caacatcaac aaagagagca ttgtggatgt agaaggtgtt     300
gtgagaaaag tgaatcagaa aattggaagc tgtacacagc aagacgttga gttacatgtt     360
cagaagattt atgtgatcag tttggctgaa ccccgtctg                             399

<210> SEQ ID NO 236
<211> LENGTH: 393
<212> TYPE: DNA
<213> ORGANISM: Homo sapiens

<400> SEQUENCE: 236
gcggcggaag attatgctaa agagagatat ggaatatctt caatgataca atcacaagaa      60
aaaccagatc gagttttggt tcgggttaga gacttgacaa tacaaaaagc tgatgaagtt     120
gtttgggtac gtgcaagagt tcatacaagc agagctaaag ggaaacagtg cttcttagtc     180
ctacgtcagc agcagtttaa tgtccaggct cttgtggcgg tgggagacca tgcaagcaag     240
cagatggtta aatttgctgc caacatcaac aaagagagca ttgtggatgt agaaggtgtt     300
gtgagaaaag tgaatcagaa aattggaagc tgtacacagc aagacgttga gttacatgtt     360
cagaagattt atgtgatcag tttggctgaa ccc                                    393
```

```
<210> SEQ ID NO 237
<211> LENGTH: 411
<212> TYPE: DNA
<213> ORGANISM: Homo sapiens

<400> SEQUENCE: 237
atgcaggaga agccgcggga gatcatggac gcggcggaag attatgctaa agagagatat      60
ggaatatctt caatgataca atcacaagaa aaaccagatc gagttttggt tcgggttaga     120
gacttgacaa tacaaaaagc tgatgaagtt gtttgggtac gtgcaagagt tcatacaagc     180
agagctaaag ggaaacagtg cttcttagtc ctacgtcagc agcagtttaa tgtccaggct     240
cttgtggcgg tgggagacca tgcaagcaag cagatggtta aatttgcttg caacatcaac     300
aaagagagca ttgtggatgt agaaggtgtt gtgagaaaag tgaatcagaa aattggaagc     360
tgtacacagc aagacgttga gttacatgtt cagaagattt atgtgatcag t             411

<210> SEQ ID NO 238
<211> LENGTH: 405
<212> TYPE: DNA
<213> ORGANISM: Homo sapiens

<400> SEQUENCE: 238
atgaagccgc gggagatcat ggacgcggcg gaagattatg ctaaagagag atatggaata      60
tcttcaatga tacaatcaca agaaaaacca gatcgagttt tggttcgggt tagagacttg     120
acaatacaaa aagctgatga agttgtttgg gtacgtgcaa gagttcatac aagcagagct     180
aaagggaaac agtgcttctt agtcctacgt cagcagcagt ttaatgtcca ggctcttgtg     240
gcggtgggag accatgcaag caagcagatg gttaaatttg cttgcaacat caacaaagag     300
agcattgtgg atgtagaagg tgttgtgaga aaagtgaatc agaaaattgg aagctgtaca     360
cagcaagacg ttgagttaca tgttcagaag atttatgtga tcagt                     405

<210> SEQ ID NO 239
<211> LENGTH: 405
<212> TYPE: DNA
<213> ORGANISM: Homo sapiens

<400> SEQUENCE: 239
atgaagccgc gggagatcat ggacgcggcg gaagattatg ctaaagagag atatggaata      60
tcttcaatga tacaatcaca agaaaaacca gatcgagttt tggttcgggt tagagacttg     120
acaatacaaa aagctgatga agttgtttgg gtacgtgcaa gagttcatac aagcagagct     180
aaagggaaac agtgcttctt agtcctacgt cagcagcagt ttaatgtcca ggctcttgtg     240
gcggtgggag accatgcaag caagcagatg gttaaatttg cttgcaacat caacaaagag     300
agcattgtgg atgtagaagg tgttgtgaga aaagtgaatc agaaaattgg aagctgtaca     360
cagcaagacg ttgagttaca tgttcagaag atttatgtga tcagt                     405

<210> SEQ ID NO 240
<211> LENGTH: 393
<212> TYPE: DNA
<213> ORGANISM: Homo sapiens

<400> SEQUENCE: 240
atgatcatgg acgcggcgga agattatgct aaagagagat atggaatatc ttcaatgata      60
caatcacaag aaaaaccaga tcgagttttg gttcgggtta gagacttgac aatacaaaaa     120
gctgatgaag ttgtttgggt acgtgcaaga gttcatacaa gcagagctaa agggaaacag     180
```

```
tgcttcttag tcctacgtca gcagcagttt aatgtccagg ctcttgtggc ggtgggagac    240
catgcaagca agcagatggt taaatttgct tgcaacatca acaaagagag cattgtggat    300
gtagaaggtg ttgtgagaaa agtgaatcag aaaattggaa gctgtacaca gcaagacgtt    360
gagttacatg ttcagaagat ttatgtgatc agt                                 393
```

<210> SEQ ID NO 241
<211> LENGTH: 381
<212> TYPE: DNA
<213> ORGANISM: Homo sapiens

<400> SEQUENCE: 241

```
atggcggaag attatgctaa agagagatat ggaatatctt caatgataca atcacaagaa     60
aaaccagatc gagttttggt tcgggttaga gacttgacaa tacaaaaagc tgatgaagtt    120
gtttgggtac gtgcaagagt tcatacaagc agagctaaag ggaaacagtg cttcttagtc    180
ctacgtcagc agcagtttaa tgtccaggct cttgtggcgg tgggagacca tgcaagcaag    240
cagatggtta aatttgcttg caacatcaac aaagagagca ttgtggatgt agaaggtgtt    300
gtgagaaaag tgaatcagaa aattggaagc tgtacacagc aagacgttga gttacatgtt    360
cagaagattt atgtgatcag t                                              381
```

<210> SEQ ID NO 242
<211> LENGTH: 21
<212> TYPE: DNA
<213> ORGANISM: Artificial Sequence
<220> FEATURE:
<223> OTHER INFORMATION: Primer

<400> SEQUENCE: 242

```
cagttcccat ctgagccatt c                                               21
```

<210> SEQ ID NO 243
<211> LENGTH: 25
<212> TYPE: DNA
<213> ORGANISM: Artificial Sequence
<220> FEATURE:
<223> OTHER INFORMATION: Primer

<400> SEQUENCE: 243

```
gactagaata ttctgaagca ttggc                                           25
```

<210> SEQ ID NO 244
<211> LENGTH: 26
<212> TYPE: DNA
<213> ORGANISM: Artificial Sequence
<220> FEATURE:
<223> OTHER INFORMATION: Primer

<400> SEQUENCE: 244

```
ccagtctggc atcgcccatc tcttcc                                          26
```

<210> SEQ ID NO 245
<211> LENGTH: 26
<212> TYPE: DNA
<213> ORGANISM: Artificial Sequence
<220> FEATURE:
<223> OTHER INFORMATION: Primer

<400> SEQUENCE: 245

```
ccagtctggc atcgtccatc tcttcc                                          26
```

```
<210> SEQ ID NO 246
<211> LENGTH: 42
<212> TYPE: DNA
<213> ORGANISM: Artificial Sequence
<220> FEATURE:
<223> OTHER INFORMATION: Primer

<400> SEQUENCE: 246
ccacagctat ataagcaaat gtgcattgcg gctgattttg ag                42

<210> SEQ ID NO 247
<211> LENGTH: 42
<212> TYPE: DNA
<213> ORGANISM: Artificial Sequence
<220> FEATURE:
<223> OTHER INFORMATION: Primer

<400> SEQUENCE: 247
gggttaggga taggcttacc agccaaactg atcacataaa tc                42

<210> SEQ ID NO 248
<211> LENGTH: 41
<212> TYPE: DNA
<213> ORGANISM: Artificial Sequence
<220> FEATURE:
<223> OTHER INFORMATION: Primer

<400> SEQUENCE: 248
gggttaggga taggcttacc gggttcagcc aaactgatca c                 41

<210> SEQ ID NO 249
<211> LENGTH: 40
<212> TYPE: DNA
<213> ORGANISM: Artificial Sequence
<220> FEATURE:
<223> OTHER INFORMATION: Primer

<400> SEQUENCE: 249
gggttaggga taggcttacc cagacggggt tcagccaaac                   40

<210> SEQ ID NO 250
<211> LENGTH: 41
<212> TYPE: DNA
<213> ORGANISM: Artificial Sequence
<220> FEATURE:
<223> OTHER INFORMATION: Primer

<400> SEQUENCE: 250
gggttaggga taggcttacc cagctgcagg ggcagacggg g                 41

<210> SEQ ID NO 251
<211> LENGTH: 41
<212> TYPE: DNA
<213> ORGANISM: Artificial Sequence
<220> FEATURE:
<223> OTHER INFORMATION: Primer

<400> SEQUENCE: 251
gggttaggga taggcttacc atcatccagc tgcagggca g                  41

<210> SEQ ID NO 252
<211> LENGTH: 42
<212> TYPE: DNA
<213> ORGANISM: Artificial Sequence
<220> FEATURE:
<223> OTHER INFORMATION: Primer
```

```
<400> SEQUENCE: 252
gggttaggga taggcttacc aacagcatca tccagctgca gg                              42

<210> SEQ ID NO 253
<211> LENGTH: 41
<212> TYPE: DNA
<213> ORGANISM: Artificial Sequence
<220> FEATURE:
<223> OTHER INFORMATION: Primer

<400> SEQUENCE: 253
gggttaggga taggcttacc aggccgaaca gcatcatcca g                               41

<210> SEQ ID NO 254
<211> LENGTH: 41
<212> TYPE: DNA
<213> ORGANISM: Artificial Sequence
<220> FEATURE:
<223> OTHER INFORMATION: Primer

<400> SEQUENCE: 254
gggttaggga taggcttacc tgcctcaggc cgaacagcat c                               41

<210> SEQ ID NO 255
<211> LENGTH: 41
<212> TYPE: DNA
<213> ORGANISM: Artificial Sequence
<220> FEATURE:
<223> OTHER INFORMATION: Primer

<400> SEQUENCE: 255
gggttaggga taggcttacc tccttctgcc tcaggccgaa c                               41

<210> SEQ ID NO 256
<211> LENGTH: 41
<212> TYPE: DNA
<213> ORGANISM: Artificial Sequence
<220> FEATURE:
<223> OTHER INFORMATION: Primer

<400> SEQUENCE: 256
gggttaggga taggcttacc ctcttctcct tctgcctcag g                               41

<210> SEQ ID NO 257
<211> LENGTH: 41
<212> TYPE: DNA
<213> ORGANISM: Artificial Sequence
<220> FEATURE:
<223> OTHER INFORMATION: Primer

<400> SEQUENCE: 257
gggttaggga taggcttacc tccttcctct tctccttctg c                               41

<210> SEQ ID NO 258
<211> LENGTH: 41
<212> TYPE: DNA
<213> ORGANISM: Artificial Sequence
<220> FEATURE:
<223> OTHER INFORMATION: Primer

<400> SEQUENCE: 258
gggttaggga taggcttacc agctcttcct tcctcttctc c                               41

<210> SEQ ID NO 259
<211> LENGTH: 41
```

```
<212> TYPE: DNA
<213> ORGANISM: Artificial Sequence
<220> FEATURE:
<223> OTHER INFORMATION: Primer

<400> SEQUENCE: 259
gggttaggga taggcttacc ctggttaaca gtagctcttc c          41

<210> SEQ ID NO 260
<211> LENGTH: 41
<212> TYPE: DNA
<213> ORGANISM: Artificial Sequence
<220> FEATURE:
<223> OTHER INFORMATION: Primer

<400> SEQUENCE: 260
gggttaggga taggcttacc tgtatcctgg ttaacagtag c          41

<210> SEQ ID NO 261
<211> LENGTH: 41
<212> TYPE: DNA
<213> ORGANISM: Artificial Sequence
<220> FEATURE:
<223> OTHER INFORMATION: Primer

<400> SEQUENCE: 261
gggttaggga taggcttacc taatcttgta tcctggttaa c          41

<210> SEQ ID NO 262
<211> LENGTH: 42
<212> TYPE: DNA
<213> ORGANISM: Artificial Sequence
<220> FEATURE:
<223> OTHER INFORMATION: Primer

<400> SEQUENCE: 262
gggttaggga taggcttacc gttgtctaat cttgtatcct gg         42

<210> SEQ ID NO 263
<211> LENGTH: 34
<212> TYPE: DNA
<213> ORGANISM: Artificial Sequence
<220> FEATURE:
<223> OTHER INFORMATION: Primer

<400> SEQUENCE: 263
gaaggagata taccatgagc gccagcgcca gccg                  34

<210> SEQ ID NO 264
<211> LENGTH: 34
<212> TYPE: DNA
<213> ORGANISM: Artificial Sequence
<220> FEATURE:
<223> OTHER INFORMATION: Primer

<400> SEQUENCE: 264
gaaggagata taccatgagc gccagccgca agag                  34

<210> SEQ ID NO 265
<211> LENGTH: 35
<212> TYPE: DNA
<213> ORGANISM: Artificial Sequence
<220> FEATURE:
<223> OTHER INFORMATION: Primer

<400> SEQUENCE: 265
```

-continued

```
gaaggagata taccatgagc cgcaagagtc aggag                          35

<210> SEQ ID NO 266
<211> LENGTH: 34
<212> TYPE: DNA
<213> ORGANISM: Artificial Sequence
<220> FEATURE:
<223> OTHER INFORMATION: Primer

<400> SEQUENCE: 266
gaaggagata taccatgaag agtcaggaga agcc                           34

<210> SEQ ID NO 267
<211> LENGTH: 35
<212> TYPE: DNA
<213> ORGANISM: Artificial Sequence
<220> FEATURE:
<223> OTHER INFORMATION: Primer

<400> SEQUENCE: 267
gaaggagata tcatatgcag gagaagccgc gggag                          35

<210> SEQ ID NO 268
<211> LENGTH: 35
<212> TYPE: DNA
<213> ORGANISM: Artificial Sequence
<220> FEATURE:
<223> OTHER INFORMATION: Primer

<400> SEQUENCE: 268
gaaggagata tcatatgaag ccgcgggaga tcatg                          35

<210> SEQ ID NO 269
<211> LENGTH: 36
<212> TYPE: DNA
<213> ORGANISM: Artificial Sequence
<220> FEATURE:
<223> OTHER INFORMATION: Primer

<400> SEQUENCE: 269
gaaggagata tcatatgcgg gagatcatgg acgcgg                         36

<210> SEQ ID NO 270
<211> LENGTH: 33
<212> TYPE: DNA
<213> ORGANISM: Artificial Sequence
<220> FEATURE:
<223> OTHER INFORMATION: Primer

<400> SEQUENCE: 270
gaaggagata tcatatgatc atggacgcgg cgg                            33

<210> SEQ ID NO 271
<211> LENGTH: 36
<212> TYPE: DNA
<213> ORGANISM: Artificial Sequence
<220> FEATURE:
<223> OTHER INFORMATION: Primer

<400> SEQUENCE: 271
gaaggagata tcatatggcg gaagattatg ctaaag                         36

<210> SEQ ID NO 272
<211> LENGTH: 30
<212> TYPE: DNA
<213> ORGANISM: Artificial Sequence
```

```
<220> FEATURE:
<223> OTHER INFORMATION: Primer

<400> SEQUENCE: 272
gaaggagata tcatatggat tatgctaaag                                         30

<210> SEQ ID NO 273
<211> LENGTH: 40
<212> TYPE: DNA
<213> ORGANISM: Artificial Sequence
<220> FEATURE:
<223> OTHER INFORMATION: Primer

<400> SEQUENCE: 273
accgatcaca tatgcaggag aagccgcggg agatcatgga                              40

<210> SEQ ID NO 274
<211> LENGTH: 39
<212> TYPE: DNA
<213> ORGANISM: Artificial Sequence
<220> FEATURE:
<223> OTHER INFORMATION: Primer

<400> SEQUENCE: 274
aagcttacgc atatgaagcc gcgggagatc atggacgcg                               39

<210> SEQ ID NO 275
<211> LENGTH: 40
<212> TYPE: DNA
<213> ORGANISM: Artificial Sequence
<220> FEATURE:
<223> OTHER INFORMATION: Primer

<400> SEQUENCE: 275
aactgttacc atatgatcat ggacgcggcg gaagattatg                              40

<210> SEQ ID NO 276
<211> LENGTH: 42
<212> TYPE: DNA
<213> ORGANISM: Artificial Sequence
<220> FEATURE:
<223> OTHER INFORMATION: Primer

<400> SEQUENCE: 276
aactgtcatc atatggcgga agattatgct aaagagagat at                           42

<210> SEQ ID NO 277
<211> LENGTH: 33
<212> TYPE: DNA
<213> ORGANISM: Artificial Sequence
<220> FEATURE:
<223> OTHER INFORMATION: Primer

<400> SEQUENCE: 277
tgacggctcg agactgatca cataaatctt ctg                                     33

<210> SEQ ID NO 278
<211> LENGTH: 47
<212> TYPE: DNA
<213> ORGANISM: Artificial Sequence
<220> FEATURE:
<223> OTHER INFORMATION: Primer

<400> SEQUENCE: 278
gcagatggtt aaatttgctt gcaacatcaa caaagagagc attgtgg                      47
```

ASPARTYL-TRNA SYNTHETASE-FC CONJUGATES

CROSS REFERENCE TO RELATED APPLICATIONS

This applications claims benefit under 35 U.S.C. §119(e) of U.S. Provisional Application No. 61/581,550, filed Dec. 29, 2011, which is incorporated by reference in its entirety.

STATEMENT REGARDING SEQUENCE LISTING

The Sequence Listing associated with this application is provided in text format in lieu of a paper copy, and is hereby incorporated by reference into the specification. The name of the text file containing the Sequence Listing is ATYR_109_01WO.ST25.txt. The text file is about 263 KB, was created on Dec. 20, 2012, and is being submitted electronically via EFS-Web.

BACKGROUND

Technical Field

The present invention relates generally to conjugates, such as fusion proteins, of one or more aspartyl-tRNA synthetase (DRS) polypeptide(s) and immunoglobulin Fc region(s), compositions comprising the same, and methods of using such polypeptides and compositions for treating or diagnosing a variety of conditions.

Description of the Related Art

Aspartyl-tRNA synthetases (DRS), and fragments and variants thereof, (collectively DRS or AspRS polypeptides) have recently been shown to possess a variety of non-canonical activities of therapeutic and diagnostic relevance. In particular it has been established that certain aspartyl-tRNA synthetase fragments are highly potent, endogenously produced, Toll-like receptor modulators. Without being bound to any one specific theory of operation, it is believed that such DRS polypeptides are released from macrophage cells upon proteolytic cleavage, or through alternative splicing of the full length DRS tRNA synthetase and are capable of binding to and modulating the activity of immunomodulatory, and other cell types. Such DRS polypeptides when administered, provide for a novel mechanism of selectively modulating inflammatory responses, without the side effect profiles typically associated with traditional anti-inflammatory agents such as steroids.

Toll-like receptors (TLRs) are a family of pattern recognition receptors that play a key role in initiating the rapid innate immune response in an organism. TLRs recognize certain pathogen or host derived cellular components which can be generally characterized as being either pathogen associated molecular patterns, (PAMPs), or damage-associated molecular pattern molecules, (DAMPS) respectively. PAMPS are typically unique to a given class of pathogen, and include for example bacterial components such as the lipopolysaccharide of Gram negative bacteria, and viral specific nucleic acid motifs or viral specific modifications of RNA or DNA. By contrast DAMPS are typically endogenous molecules released from dying host cells upon cellular stress or tissue damage.

TLRs are implicated in several chronic inflammatory and immune mediated disorders by various potential mechanisms, including those in which infectious agents have been proposed to initiate disease progression. For example in scenarios in which endogenous damage signals or self-antigens cause chronic inflammation in a TLR dependent manner, or where TLRs may be involved in the breakdown of immune tolerance. TLRs have been implicated in the pathogenesis of chronic inflammatory diseases such as inflammatory bowel disease, rheumatoid arthritis, psoriasis, and multiple sclerosis.

It is now increasingly recognized that the successful treatment of some autoimmune and inflammatory conditions of tissues requires effective control of the inflammatory reaction in order to preserve tissue integrity and function, without immune-compromising the patient. Recent experimental evidence has shown that specific modulation of TLR pathways induces an improvement in several inflammatory conditions, without comprising tissue function, or enhancing bacterial or viral infections, suggesting the potential for new therapeutic anti-inflammatory strategies with significantly improved side effect profiles. Moreover TLR agonists have already proved useful in clinical trials in allergic, infectious and autoimmune diseases and are under development for a broad range of other diseases including cancer, arthritis, multiple sclerosis, inflammatory bowel disease, see generally Zhu and Mohan (2010) Mediators of Inflammation doi:10.1155/2010/781235; Hennessy et al., *Nat. Rev.* 9:293-307, 2010). Therefore TLRs are becoming increasingly recognized as novel potential therapeutic targets for the modulation of a broad variety of diseases and disorders.

To best exploit these and other activities in therapeutic or diagnostic settings, there is a need in the art for DRS polypeptides having improved pharmacokinetic properties. These improved therapeutic forms of the DRS polypeptides enable the development of more effective therapeutic regimens for the treatment of various diseases and disorders, and require significantly less frequent administration than the unmodified proteins.

BRIEF DESCRIPTION OF THE DRAWINGS

FIG. 6 illustrates the structural make-up of an exemplary immunoglobulin, and provides an overview of antibody classes and subclasses.

BRIEF SUMMARY OF THE INVENTION

Figure 1:
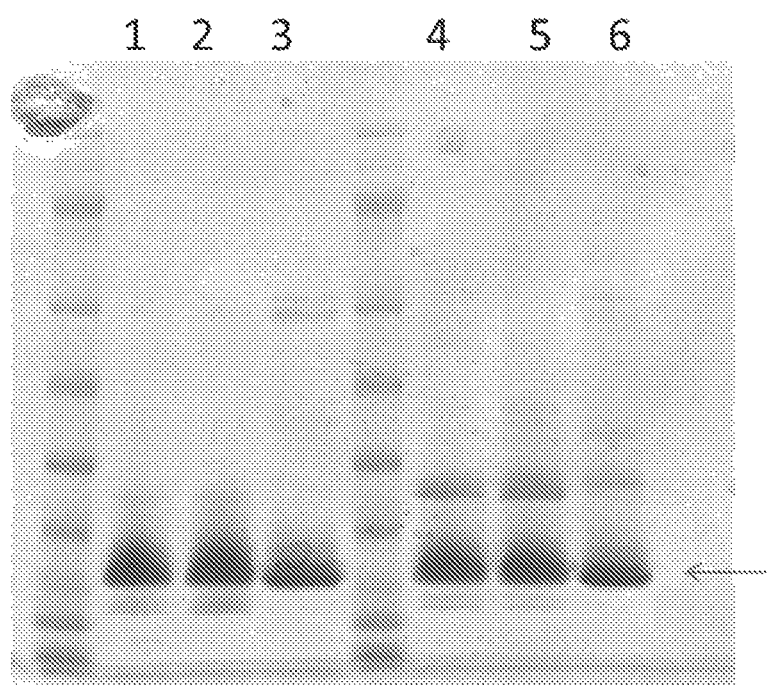
FIG. 1 shows an SDS-PAGE analysis of the purified proteins AspRS1$^{N1}$ (C76S) (DRS(1-154)(C76S) (SEQ ID NO:29), and the corresponding non mutated protein AspRS1$^{N1}$(DRS(1-154)) (SEQ ID NO:31). Lanes 1-3 were run under reduced conditions, and lanes 4-6 were run under non-reduced conditions. Lanes 1 and 4: AspRS1$^{N1}$ DRS(1-154) lot #D-N-1-V5H-046, lanes 2 and 5 AspRS1$^{N1}$(DRS(1-154))lot #D-N-1-V5H-047, lanes 3 and 6: AspRS1$^{N1}$ (C76S) (SEQ ID NO:29) lot #D-N1:1-V5H-048.

Embodiments of the present invention relate generally to aspartyl-tRNA synthetase (DRS) polypeptide conjugates having one or more immunoglobulin Fc regions covalently attached thereto, pharmaceutical compositions comprising such molecules, methods of manufacture, and methods for their therapeutic use. Among other advantages, the DRS-Fc conjugates of the present invention can possess improved pharmacokinetic properties and/or improved therapeutically relevant biological activities, relative to corresponding, unmodified DRS polypeptides.

Certain embodiments therefore include DRS fusion polypeptides, comprising a DRS amino acid sequence at least 80% identical to any one of SEQ ID NOS:1, 3-24, 29, 31, or 154-197, and at least one Fc region fused to the C-terminus, the N-terminus, or both of the DRS polypeptide. In some embodiments, the DRS polypeptide comprises an amino acid sequence at least 90% identical to any of SEQ ID NOS: 1, 3-24, 29, 31, or 154-197. In particular embodiments, the DRS polypeptide comprises an amino acid sequence of any one of SEQ ID NOS: 1, 3-24, 29, 31, or 154-197.

In certain embodiments, the DRS polypeptide is about 130-300 amino acids in length and comprises amino acid residues 1-154, 11-146, 13-146, 23-154, 1-171, or 1-174, 1-182, 1-184, 1-224, or 1-274 of SEQ ID NO:1, or an amino acid sequence at least 90% identical to residues 1-154, 11-146, 13-146, 23-154, 1-171, or 1-174, 1-182, 1-184, 1-224, or 1-274 of SEQ ID NO:1. In some embodiments, the DRS polypeptide is about 130-200 amino acids in length and comprises amino acid residues 1-154, 11-146, 13-146, 23-154, 1-171, 1-174, 1-182, or 1-184 of SEQ ID NO:1, or an amino acid sequence at least 90% identical to residues 1-154, 11-146, 13-146, 23-154, 1-171, 1-174, 1-182, or 1-184 of SEQ ID NO:1. In certain embodiments, the DRS polypeptide is about 130-175 amino acids in length and comprises amino acid residues 1-154, 23-154, 1-171, or 1-174 of SEQ ID NO:1, or an amino acid sequence at least 90% identical to residues 1-154, 23-154, 1-171, or 1-174 of SEQ ID NO:1. In certain embodiments, the DRS polypeptide comprises amino acid residues 1-154, 11-146, 13-146, 23-154, 1-171, or 1-174 of SEQ ID NO:1. In specific embodiments, the DRS polypeptide consists essentially of amino acid residues 1-154 of SEQ ID NO:1. In some embodiments, the DRS polypeptide consists essentially of amino acid residues 13-146 of SEQ ID NO:1. In particular embodiments, the DRS polypeptide comprises an OB fold domain, an N-terminal amphiphilic helix, or both.

In some embodiments, the Fc region and the DRS polypeptide are separated by a peptide linker. In certain embodiments, the peptide linker is about 1-200 amino acids, about 1-150 amino acids, about 1-100 amino acids, about 1-90 amino acids, about 1-80 amino acids, about 1-70 amino acids, about 1-60 amino acids, about 1-50 amino acids, about 1-40 amino acids, about 1-30 amino acids, about 1-20 amino acids, about 1-10 amino acids, or about 1-5 amino acids in length. In particular embodiments, peptide linker is about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, or 100 amino acids in length. In certain embodiments, the peptide linker consists or consists essentially of Gly and/or Ser residues. In some embodiments, the peptide linker is a physiologically stable linker. In other embodiments, the peptide linker is a releasable linker, optionally an enzymatically-cleavable linker. In specific embodiments, the peptide linker comprises a sequence of any one of SEQ ID NOS:80-139.

In some embodiments, the Fc region is fused to the C-terminus of the DRS polypeptide. In certain embodiments, the Fc region is fused to the N-terminus of the DRS polypeptide.

In certain embodiments, the Fc region comprises one or more of a hinge, $CH_2$, $CH_3$, and/or $CH_4$ domain from a mammalian IgA1, IgA2, IgD, IgE, IgG1, IgG2, IgG3, IgG4, and/or IgM. In particular embodiments, the DRS fusion polypeptide does not comprise the $CH_1$, $C_L$, $V_L$, and $V_H$ regions of an immunoglobulin. In specific embodiments, the Fc region comprises any one of SEQ ID NOS:38-64, or a variant, or a fragment, or a combination thereof.

In certain instances, the DRS fusion polypeptide has altered pharmacokinetics relative to a corresponding DRS polypeptide. Examples of said altered pharmacokinetics include increased serum half-life, increased bioavailability, and/or decreased clearance. In some instances, the DRS fusion polypeptide has altered immune effector activity relative to a corresponding DRS polypeptide. Examples of such immune effector activities include one or more of complement activation, complement-dependent cytotoxicity (CDC), antibody-dependent cell-mediated cytotoxicity (ADCC), or antibody-dependent cell-mediated phagocytosis (ADCP).

In certain embodiments, the Fc region comprises a variant Fc region, relative to a wild-type Fc region. In some embodiments, the variant Fc region comprises a sequence that is at least 90% identical to any one of SEQ ID NOS:38-64, or a combination of said sequences. In certain embodiments, the variant Fc region comprises a hybrid of one or more Fc regions from different species, different Ig classes, or different Ig subclasses. In particular embodiments, the variant Fc region comprises a hybrid of one or more hinge, $CH_2$, $CH_3$, and/or $CH_4$ domains of Fc regions from different species, different Ig classes, and/or different Ig subclasses.

In certain embodiments, the variant Fc region is a modified glycoform, relative to a corresponding, wild-type Fc region. In particular embodiments, the variant Fc region has altered pharmacokinetics relative to a corresponding, wild-type Fc region. Examples of such altered pharmacokinetics include serum half-life, bioavailability, and/or clearance. In some embodiments, the variant Fc region has altered effector activity relative to a corresponding, wild-type Fc region. Examples of such effector activities include one or more of complement activation, complement-dependent cytotoxicity (CDC), antibody-dependent cell-mediated cytotoxicity (ADCC), or antibody-dependent cell-mediated phagocytosis (ADCP).

In certain embodiments, the variant Fc region has altered binding to one or more Fcγ receptors, relative to a corresponding, wild-type Fc region. Exemplary Fcγ receptors are described herein and known in the art.

In some embodiments, the variant Fc region has altered (e.g., increased) solubility, relative to a corresponding, wild-type Fc region, and the DRS-Fc fusion protein has altered solubility, relative to a corresponding, unmodified DRS polypeptide.

In specific embodiments, the DRS-Fc fusion polypeptide is substantially in dimeric form in a physiological solution, or under other physiological conditions, such as in vivo conditions. In specific embodiments, the DRS-Fc fusion polypeptide has substantially the same secondary structure a corresponding unmodified or differently modified DRS polypeptide, as determined via UV circular dichroism analysis.

In some embodiments, the DRS-Fc fusion polypeptide has a plasma or sera pharmacokinetic AUC profile at least 5-fold greater than a corresponding, unmodified DRS polypeptide when administered to a mammal.

In certain embodiments, the DRS-Fc fusion polypeptide has substantially the same activity of a corresponding unmodified or differently modified DRS polypeptide in a TLR 2 or TLR 4 based assay.

In certain embodiments, the DRS-Fc fusion polypeptide has greater than 2 fold the activity of a corresponding unmodified or differently modified DRS polypeptide in a TLR 2 or TLR 4 based assay.

In certain embodiments, the DRS-Fc fusion polypeptide has a stability which is at least 30% greater than a corresponding unmodified or differently modified DRS polypeptide when compared under similar conditions at room temperature, for 7 days in PBS at pH 7.4.

Specific examples of DRS-Fc fusion polypeptides comprise SEQ ID NO:36 or 37, or an amino acid sequence at least 80%, 90%, 95%, 98% identical to SEQ ID NO:36 or 37.

In one embodiment the invention includes a dosing regimen which maintains an average steady-state concentration of DRS polypeptide in the subjects' plasma of between about 0.3 µg/ml and about 3 µg/ml when using a dosing interval of 3 days or longer, comprising administering to the patient a therapeutic dose of any of the DRS-Fc fusion polypeptides described herein.

In one embodiment the invention includes a method for maintaining DRS polypeptide levels above the minimum effective therapeutic level in a subject in need thereof, comprising administering to the subject a therapeutic dose of any of the DRS-Fc fusion polypeptides described herein.

In another aspect, the invention includes a method for treating an inflammatory response in a subject, comprising administering any of the previously disclosed DRS-Fc fusion polypeptides described herein to a subject in need thereof.

In another aspect, the invention includes a method for treating a TLR associated disease in a subject in need thereof, comprising administering to the subject a therapeutic dose of any of the DRS-Fc fusion polypeptides described herein.

In another aspect, the invention includes a method for method for modulating TLR activity in a subject, comprising administering to the subject a therapeutic dose of any of the DRS-Fc fusion polypeptides described herein.

In another aspect, the invention includes a method for method for killing cancer cells, comprising administering a vaccine or immunogenic composition comprising any of the DRS-Fc fusion polypeptides described herein to a subject in need thereof.

In another aspect, the invention includes a method for treating a subject with cancer, or preventing the development of cancer in a subject, comprising administering a vaccine or immunogenic composition comprising any of the DRS-Fc fusion polypeptides described herein to a subject in need thereof.

In another aspect, the invention includes a method for overcoming tolerance to an antigen in a subject, comprising administering a vaccine or immunogenic composition comprising any of the DRS-Fc fusion polypeptides described herein to a subject in need thereof.

Also included are isolated polynucleotides, comprising a nucleotide sequence that encodes a DRS-Fc fusion polypeptide described herein, including vectors that comprise such polynucleotides, and host cells that comprise said polynucleotides and/or vectors.

Some embodiments include methods for manufacturing a DRS-Fc fusion polypeptide described herein, comprising a) culturing a host cell to express a DRS-Fc fusion polypeptide, wherein the host cell comprises a polynucleotide that encodes a DRS-Fc fusion polypeptide described herein, which is operably linked to a regulatory element; and b) isolating the DRS-Fc fusion polypeptide from the host cell.

DETAILED DESCRIPTION OF THE INVENTION

The practice of the present invention will employ, unless indicated specifically to the contrary, conventional methods of molecular biology and recombinant DNA techniques within the skill of the art, many of which are described below for the purpose of illustration. Such techniques are explained fully in the literature. See, e.g., Sambrook, et al., *Molecular Cloning: A Laboratory Manual* ($3^{rd}$ Edition, 2000); *DNA Cloning: A Practical Approach*, vol. I & II (D. Glover, ed.); *Oligonucleotide Synthesis* (N. Gait, ed., 1984); *Oligonucleotide Synthesis: Methods and Applications* (P. Herdewijn, ed., 2004); *Nucleic Acid Hybridization* (B. Hames & S. Higgins, eds., 1985); *Nucleic Acid Hybridization: Modern Applications* (Buzdin and Lukyanov, eds., 2009); *Transcription and Translation* (B. Hames & S. Higgins, eds., 1984); *Animal Cell Culture* (R. Freshney, ed., 1986); Freshney, R. I. (2005) *Culture of Animal Cells, a Manual of Basic Technique*, $5^{th}$ Ed. Hoboken N.J., John Wiley & Sons; B. Perbal, *A Practical Guide to Molecular Cloning* ($3^{rd}$ Edition 2010); Farrell, R., *RNA Methodologies: A Laboratory Guide for Isolation and Characterization* ($3^{rd}$ Edition 2005). *Poly(ethylene glycol), Chemistry and Biological Applications*, ACS, Washington, 1997; Veronese, F., and J. M. Harris, Eds., *Peptide and protein PEGylation, Advanced Drug Delivery Reviews*, 54(4) 453-609 (2002); Zalipsky, S., et al., "*Use of functionalized Poly(Ethylene Glycols) for modification of polypeptides*" in Polyethylene Glycol Chemistry: Biotechnical and Biomedical Applications.

All publications, patents and patent applications cited herein are hereby incorporated by reference in their entirety.

DEFINITIONS

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred methods and materials are described. For the purposes of the present invention, the following terms are defined below.

The articles "a" and "an" are used herein to refer to one or to more than one (i.e., to at least one) of the grammatical object of the article. By way of example, "an element" means one element or more than one element.

By "about" is meant a quantity, level, value, number, frequency, percentage, dimension, size, amount, weight or length that varies by as much as 30, 25, 20, 15, 10, 9, 8, 7, 6, 5, 4, 3, 2 or 1% to a reference quantity, level, value, number, frequency, percentage, dimension, size, amount, weight or length.

As used herein, the term "amino acid" is intended to mean both naturally occurring and non-naturally occurring amino acids as well as amino acid analogs and mimetics. Naturally occurring amino acids include the 20 (L)-amino acids utilized during protein biosynthesis as well as others such as 4-hydroxyproline, hydroxylysine, desmosine, isodesmosine, homocysteine, citrulline and ornithine, for example. Non-naturally occurring amino acids include, for example, (D)-amino acids, norleucine, norvaline, p-fluorophenylalanine, ethionine and the like, which are known to a person skilled in the art. Amino acid analogs include modified forms of naturally and non-naturally occurring amino acids. Such modifications can include, for example, substitution or replacement of chemical groups and moieties on the amino acid or by derivitization of the amino acid Amino acid mimetics include, for example, organic structures which exhibit functionally similar properties such as charge and charge spacing characteristic of the reference amino acid. For example, an organic structure which mimics Arginine (Arg or R) would have a positive charge moiety located in similar molecular space and having the same degree of mobility as the e-amino group of the side chain of the naturally occurring Arg amino acid. Mimetics also include constrained structures so as to maintain optimal spacing and charge interactions of the amino acid or of the amino acid functional groups. Those skilled in the art know or can determine what structures constitute functionally equivalent amino acid analogs and amino acid mimetics.

Throughout this specification, unless the context requires otherwise, the words "comprise," "comprises," and "comprising" will be understood to imply the inclusion of a stated step or element or group of steps or elements but not the exclusion of any other step or element or group of steps or elements. By "consisting of" is meant including, and limited to, whatever follows the phrase "consisting of." Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they materially affect the activity or action of the listed elements.

The term "conjugate" is intended to refer to the entity formed as a result of covalent attachment of a molecule, e.g., a biologically active molecule, to an immunoglobulin Fc region. One example of a conjugate polypeptide is a "fusion protein" or "fusion polypeptide," that is, a polypeptide that is created through the joining of two or more coding sequences, which originally coded for separate polypeptides; translation of the joined coding sequences results in a single, fusion polypeptide, typically with functional properties derived from each of the separate polypeptides.

The recitation "endotoxin free" or "substantially endotoxin free" relates generally to compositions, solvents, and/or vessels that contain at most trace amounts (e.g., amounts having no clinically adverse physiological effects to a subject) of endotoxin, and preferably undetectable amounts of endotoxin. Endotoxins are toxins associated with certain bacteria, typically gram-negative bacteria, although endotoxins may be found in gram-positive bacteria, such as *Listeria monocytogenes*. The most prevalent endotoxins are lipopolysaccharides (LPS) or lipo-oligo-saccharides (LOS) found in the outer membrane of various Gram-negative bacteria, and which represent a central pathogenic feature in the ability of these bacteria to cause disease. Small amounts of endotoxin in humans may produce fever, a lowering of the blood pressure, and activation of inflammation and coagulation, among other adverse physiological effects.

Therefore, in pharmaceutical production, it is often desirable to remove most or all traces of endotoxin from drug products and/or drug containers, because even small amounts may cause adverse effects in humans. A depyrogenation oven may be used for this purpose, as temperatures in excess of 300° C. are typically required to break down most endotoxins. For instance, based on primary packaging material such as syringes or vials, the combination of a glass temperature of 250° C. and a holding time of 30 minutes is often sufficient to achieve a 3 log reduction in endotoxin levels. Other methods of removing endotoxins are contemplated, including, for example, chromatography and filtration methods, as described herein and known in the art. Also included are methods of producing DRS polypeptides in and isolating them from eukaryotic cells such as mammalian cells to reduce, if not eliminate, the risk of endotoxins being present in a composition of the invention. Preferred are methods of producing DRS polypeptides in and isolating them from serum free cells.

Endotoxins can be detected using routine techniques known in the art. For example, the Limulus Amoebocyte Lysate assay, which utilizes blood from the horseshoe crab, is a very sensitive assay for detecting presence of endotoxin. In this test, very low levels of LPS can cause detectable coagulation of the limulus lysate due a powerful enzymatic cascade that amplifies this reaction. Endotoxins can also be quantitated by enzyme-linked immunosorbent assay (ELISA). To be substantially endotoxin free, endotoxin levels may be less than about 0.001, 0.005, 0.01, 0.02, 0.03, 0.04, 0.05, 0.06, 0.08, 0.09, 0.1, 0.5, 1.0, 1.5, 2, 2.5, 3, 4, 5, 6, 7, 8, 9, or 10 EU/ml. Typically, 1 ng lipopolysaccharide (LPS) corresponds to about 1-10 EU.

As used herein, the terms "function" and "functional" and the like refer to a biological, enzymatic, or therapeutic function.

"Homology" refers to the percentage number of amino acids that are identical or constitute conservative substitutions. Homology may be determined using sequence comparison programs such as GAP (Deveraux et al., *Nucleic Acids Research.* 12, 387-395, 1984), which is incorporated herein by reference. In this way sequences of a similar or substantially different length to those cited herein could be compared by insertion of gaps into the alignment, such gaps being determined, for example, by the comparison algorithm used by GAP.

A "physiologically stable" linker refers to a linker that is substantially stable in water or under physiological conditions (e.g., in vivo, in vitro culture conditions, for example, in the presence of one or more proteases), that is to say, it does not undergo a degradation reaction (e.g., enzymatically degradable reaction) under physiological conditions to any appreciable extent over an extended period of time. Generally, a physiologically stable linker is one that exhibits a rate of degradation of less than about 0.5%, about 1%, about 2%, about 3%, about 4%, or about 5% per day under physiological conditions.

By "isolated" is meant material that is substantially or essentially free from components that normally accompany it in its native state. For example, an "isolated peptide" or an "isolated polypeptide" and the like, as used herein, includes the in vitro isolation and/or purification of a peptide or polypeptide molecule from its natural cellular environment, and from association with other components of the cell; i.e., it is not significantly associated with in vivo substances.

The term "half maximal effective concentration" or "$EC_{50}$" refers to the concentration of a DRS-Fc conjugate described herein at which it induces a response halfway between the baseline and maximum after some specified exposure time; the $EC_{50}$ of a graded dose response curve therefore represents the concentration of a compound at which 50% of its maximal effect is observed. In certain embodiments, the $EC_{50}$ of an agent provided herein is indicated in relation to a "non-canonical" activity, as noted above. $EC_{50}$ also represents the plasma concentration required for obtaining 50% of a maximum effect in vivo. Similarly, the "$EC_{90}$" refers to the concentration of an agent or composition at which 90% of its maximal effect is observed. The "$EC_{90}$" can be calculated from the "$EC_{50}$" and the Hill slope, or it can be determined from the data directly, using routine knowledge in the art. In some embodiments, the $EC_{50}$ of a DRS-Fc conjugate is less than about 0.01, 0.05, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 25, 30, 40, 50, 60, 70, 80, 90, or 100 nM. Preferably, biotherapeutic composition will have an $EC_{50}$ value of about 1 nM or less.

The "half-life" of a DRS-Fc conjugate can refer to the time it takes for the conjugate to lose half of its pharmacologic, physiologic, or other activity, relative to such activity at the time of administration into the serum or tissue of an organism, or relative to any other defined time-point. "Half-life" can also refer to the time it takes for the amount or concentration of a DRS-Fc conjugate to be reduced by half of a starting amount administered into the serum or tissue of an organism, relative to such amount or concentration at the time of administration into the serum or tissue of an organism, or relative to any other defined time-point. The half-life can be measured in serum and/or any one or more selected tissues.

The term "linkage," "linker," "linker moiety," or "L" is used herein to refer to a linker that can be used to separate a DRS polypeptides from another DRS polypeptide and/or from one or more Fc regions. The linker may be physiologically stable or may include a releasable linker such as an enzymatically degradable linker (e.g., proteolytically cleavable linkers). In certain aspects, the linker may be a peptide linker, for instance, as part of a DRS-Fc fusion protein. In some aspects, the linker may be a non-peptide linker.

The terms "modulating" and "altering" include "increasing," "enhancing" or "stimulating," as well as "decreasing" or "reducing," typically in a statistically significant or a physiologically significant amount or degree relative to a control. An "increased," "stimulated" or "enhanced" amount is typically a "statistically significant" amount, and may include an increase that is 1.1, 1.2, 2, 3, 4, 5, 6, 7, 8, 9, 10, 15, 20, 30 or more times (e.g., 500, 1000 times) (including all integers and decimal points in between and above 1, e.g., 1.5, 1.6, 1.7. 1.8, etc.) the amount produced by no composition (e.g., in the absence of any of the DRS-Fc conjugates of the invention) or a control composition, sample or test subject. A "decreased" or "reduced" amount is typically a "statistically significant" amount, and may include a 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100% decrease in the amount produced by no composition (the absence of an agent or compound) or a control composition, including all integers in between. As one non-limiting example, a control in comparing canonical and non-canonical activities could include the DRS-Fc conjugate of interest compared to a corresponding (sequence-wise), unmodified or differently modified DRS polypeptide. Other examples of comparisons and "statistically significant" amounts are described herein.

"Non-canonical" activity as used herein, refers generally to either i) a new activity possessed by DRS polypeptide of the invention that is not possessed to any significant degree by the intact native full length parental protein, or ii) an activity that was possessed by the by the intact native full length parental protein, where the DRS polypeptide either exhibits a significantly higher (i.e., at least 20% greater) specific activity with respect to the non-canonical activity compared to the intact native full length parental protein, or exhibits the activity in a new context; for example by isolating the activity from other activities possessed by the intact native full length parental protein. In the case of DRS polypeptides, non-limiting examples of non-canonical activities include extracellular signaling including the modulation of TLRs, modulation of cell proliferation, modulation of cell migration, modulation of cell differentiation (e.g., hematopoiesis, neurogenesis, myogenesis, osteogenesis, and adipogenesis), modulation of gene transcription, modulation of apoptosis or other forms of cell death, modulation of cell signaling, modulation of cellular uptake, or secretion, modulation of angiogenesis, modulation of cell binding, modulation of cellular metabolism, modulation of cytokine production or activity, modulation of cytokine receptor activity, modulation of inflammation, immunogenicity, and the like.

In certain embodiments, the "purity" of any given agent (e.g., DRS-Fc conjugate such as a fusion protein) in a composition may be specifically defined. For instance, certain compositions may comprise an agent that is at least 80, 85, 90, 91, 92, 93, 94, 95, 96, 97, 98, 99, or 100% pure, including all decimals in between, as measured, for example and by no means limiting, by high pressure liquid chromatography (HPLC), a well-known form of column chromatography used frequently in biochemistry and analytical chemistry to separate, identify, and quantify compounds.

Without wishing to be bound to any particular theory, an "enzymatically degradable linker" means a linker, e.g., amino acid sequence, which is subject to degradation by one or more enzymes, e.g., peptidases or proteases.

The terms "polypeptide" and "protein" are used interchangeably herein to refer to a polymer of amino acid residues and to variants and synthetic analogues of the same. Thus, these terms apply to amino acid polymers in which one or more amino acid residues are synthetic non-naturally occurring amino acids, such as a chemical analogue of a corresponding naturally occurring amino acid, as well as to naturally-occurring amino acid polymers.

A "releasable linker" includes, but is not limited to, a physiologically cleavable linker and an enzymatically degradable linker. Thus, a "releasable linker" is a linker that may undergo either spontaneous hydrolysis, or cleavage by some other mechanism (e.g., enzyme-catalyzed, acid-catalyzed, base-catalyzed, and so forth) under physiological conditions. For example, a "releasable linker" can involve an elimination reaction that has a base abstraction of a proton, (e.g., an ionizable hydrogen atom, Hα), as the driving force. For purposes herein, a "releasable linker" is synonymous with a "degradable linker." In particular embodiments, a releasable linker has a half life at pH 7.4, 25° C., e.g., a physiological pH, human body temperature (e.g., in vivo), of about 30 minutes, about 1 hour, about 2 hour, about 3 hours, about 4 hours, about 5 hours, about 6 hours, about 12 hours, about 18 hours, about 24 hours, about 36 hours, about 48 hours, about 72 hours, or about 96 hours or more.

By "statistically significant," it is meant that the result was unlikely to have occurred by chance. Statistical significance can be determined by any method known in the art. Commonly used measures of significance include the p-value, which is the frequency or probability with which the observed event would occur, if the null hypothesis were true. If the obtained p-value is smaller than the significance level, then the null hypothesis is rejected. In simple cases, the significance level is defined at a p-value of 0.05 or less.

The term "solubility" refers to the property of a DRS-Fc conjugate polypeptide provided herein to dissolve in a liquid solvent and form a homogeneous solution. Solubility is typically expressed as a concentration, either by mass of solute per unit volume of solvent (g of solute per kg of solvent, g per dL (100 mL), mg/ml, etc.), molarity, molality, mole fraction or other similar descriptions of concentration. The maximum equilibrium amount of solute that can dissolve per amount of solvent is the solubility of that solute in that solvent under the specified conditions, including temperature, pressure, pH, and the nature of the solvent. In certain embodiments, solubility is measured at physiological pH, or other pH, for example, at pH 5.0, pH 6.0, pH 7.0, or pH 7.4. In certain embodiments, solubility is measured in water or a physiological buffer such as PBS or NaCl (with or without NaP). In specific embodiments, solubility is measured at relatively lower pH (e.g., pH 6.0) and relatively higher salt (e.g., 500 mM NaCl and 10 mM NaP). In certain embodiments, solubility is measured in a biological fluid (solvent) such as blood or serum. In certain embodiments, the temperature can be about room temperature (e.g., about 20, 21, 22, 23, 24, 25° C.) or about body temperature (37° C.). In certain embodiments, a DRS-Fc conjugate polypeptide has a solubility of at least about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 25, or 30 mg/ml at room temperature or at 37° C.

A "subject," as used herein, includes any animal that exhibits a symptom, or is at risk for exhibiting a symptom, which can be treated or diagnosed with a DRS-Fc conjugate polypeptide of the invention. Suitable subjects (patients) include laboratory animals (such as mouse, rat, rabbit, or guinea pig), farm animals, and domestic animals or pets (such as a cat or dog). Non-human primates and, preferably, human patients, are included.

"Substantially" or "essentially" means nearly totally or completely, for instance, 95%, 96%, 97%, 98%, 99% or greater of some given quantity.

The term "therapeutically effective amount" as used herein, refers to the level or amount of agent such, as a DRS-Fc conjugate polypeptide or derivative thereof, needed to treat or improve a condition, or reduce injury or damage without causing significant negative or adverse side effects.

"Treatment" or "treating," as used herein, includes any desirable effect on the symptoms or pathology of a disease or condition, and may include even minimal changes or improvements in one or more measurable markers of the disease or condition being treated. "Treatment" or "treating" does not necessarily indicate complete eradication or cure of the disease or condition, or associated symptoms thereof. The subject receiving this treatment is any subject in need thereof. Exemplary markers of clinical improvement will be apparent to persons skilled in the art.

Aspartyl-tRNA Synthetase Derived Polypeptides

Embodiments of the present invention relate to the use of aspartyl-tRNA synthetase polypeptides (DRS or AspRS polypeptides), including wild-type sequences, naturally-occurring sequences, and non-naturally occurring sequences, and also include variants and fragments thereof. Specific examples of aspartyl-tRNA synthetase derived polypeptides include those with altered cysteine content.

Aspartyl-tRNA synthetases belong to the class I tRNA synthetase family, which has two highly conserved sequence motifs at the active site, HIGH (SEQ ID NO:152) and KMSKS (SEQ ID NO:153). Class I tRNA synthetases are widely recognized as being responsible the specific attachment of an amino acid to its cognate tRNA in a 2-step reaction: the amino acid (AA) is first activated by ATP to form AA-AMP and then transferred to the acceptor end of the tRNA. The full length Aspartyl-tRNA synthetases typically exists as a homodimer; and also forms part of a multisubunit complex that typically includes the proteins AIMP1, AIMP2, EEF1A1 and the tRNA synthetases for Arg, Asp, Glu, Gln, Ile, Leu, Lys, Met and Pro.

More recently it has been established that some biological fragments, or alternatively spliced isoforms of eukaryotic aspartyl-tRNA synthetases, or in some contexts the intact synthetase, can dissociate from the multisubunit complex, and activate certain cell-signaling pathways, or act within the nucleus to modulate transcription. These activities, which are distinct from the classical role of tRNA synthetases in protein synthesis, are collectively referred to herein as "non canonical activities." These DRS polypeptides may be produced naturally by either alternative splicing or proteolysis, and can act in a cell autonomous (i.e., within the host cell), or non-cell autonomous fashion (i.e., outside the host cell) to regulate a variety of homeostatic mechanisms. For example, as provided in the present invention, the N-terminal fragment of aspartyl-tRNA synthetase, DRS (1-154), is capable of modulating the activity of certain TLRs in vivo. In addition, certain mutations or deletions relative to the full-length DRS polypeptide sequence confer increased TLR binding or other non-canonical activities. The sequences of various exemplary DRS polypeptides are provided in Tables D1 to D5 and D7.

| Name | Residues | Amino acid and nucleic acid sequences | SEQ ID NO: |
|---|---|---|---|
| Table D1-A Exemplary DRS Polypeptides ||||
| Full length AspRS sequence | Protein/ Human/ 1-501 | MPSASASRKSQEKPREIMDAAEDYAKERYGISSMIQSQEKPDRVL VRVRDLTIQKADEVVWVRARVHTSRAKGKQCFLVLRQQQFNVQ ALVAVGDHASKQMVKFAANINKESIVDVEGVVRKVNQKIGSCT QQDVELHVQKIYVISLAEPRLPLQLDDAVRPEAEGEEEGRATVNQ DTRLDNRVIDLRTSTSQAVFRLQSGICHLFRETLINKGFVEIQTPKII SAASEGGANVFTVSYFKNNAYLAQSPQLYKQMCICADFEKVFSI GPVFRAEDSNTHRHLTEFVGLDIEMAFNYHYEVMEEIADTMVQ IFKGLQERFQTEIQTVNKQFPCEPFKFLEPTLRLEYCEALAMLREA GVEMGDEDDLSTPNEKLLGHLVKEKYDTDFYILDKYPLAVRPFY TMPDPRNPKQSNSYDMFMRGEEILSGAQRIHDPQLLTERALHHGI DLEKIKAYIDSFRFGAPPHAGGGIGLERVTMLFLGLHNVRQTSMF PRDPKRLTP | 1 |
| Table D1-B Exemplary AspRS nucleic Acids ||||
| Full length AspRS sequence Human codon usage | DNA/ Human/ 1-1506 | ATGCCCAGCGCCAGCGCCAGCCGCAAGAGTCAGGAGAAGCCG CGGGAGATCATGGACGCGGCGGAAGATTATGCTAAAGAGAGA TATGGAATATCTTCAATGATACAATCACAAGAAAAACCAGATC GAGTTTTGGTTCGGGTTAGAGACTTGACAATACAAAAAGCTGA TGAAGTTGTTTGGGTACGTGCAAGAGTTCATACAAGCAGAGCT AAAGGGAAACAGTGCTTCTTAGTCCTACGTCAGCAGCAGTTTA ATGTCCAGGCTCTTGTGGCGGTGGGAGACCATGCAAGCAAGC AGATGGTTAAATTTGCTGCCAACATCAACAAAGAGAGCATTGT GGATGTAGAAGGTGTTGTGAGAAAAGTGAATCAGAAAATTGG AAGCTGTACACAGCAAGACGTTGAGTTACATGTTCAGAAGATT TATGTGATCAGTTTGGCTGAACCCCGTCTGCCCCTGCAGCTGG ATGATGCTGTTCGGCCTGAGGCAGAAGGAGAAGAGGAAGGAA GAGCTACTGTTAACCAGGATACAAGATTAGACAACAGAGTCA TTGATCTTAGGACATCAACTAGTCAGGCAGTCTTCCGTCTCCA GTCTGGCATCTGCCATCTCTTCCGAGAAACTTTAATTAACAAA GGTTTTGTGGAAATCCAAACTCCTAAAATTATTTCAGCTGCCA GTGAAGGAGGAGCCAATGTTTTTACTGTGTCATATTTTAAAAA TAATGCATACCTGGCTCAGTCCCCACAGCTATATAAGCAAATG TGCATTTGTGCTGATTTTGAGAAGGTTTTCTCTATTGGACCAGT ATTCAGAGCGGAAGACTCTAATACCCATAGACATCTAACTGAG TTTGTTGGTTTGGACATTGAAATGGCTTTTAATTACCATTACCA CGAAGTTATGGAAGAAATTGCTGACACCATGGTACAAATATTC AAAGGACTTCAAGAAAGGTTTCAGACTGAAATTCAAACAGTG AATAAACAGTTCCCATGTGAGCCATTCAAATTTTTGGAGCCAA CTCTAAGACTAGAATATTGTGAAGCATTGGCTATGCTTAGGGA AGCTGGAGTCGAAATGGGAGATGAAGACGATCTGAGCACACC AAATGAAAAGCTGTTGGGTCATTTGGTAAAGGAAAAGTATGA TACAGATTTTTATATTCTTGATAAATATCCATTGGCTGTAAGAC CTTTCTATACCATGCCTGACCCAAGAAATCCCAAACAGTCCAA CTCTTACGATATGTTCATGAGAGGAGAAGAAATATTGTCAGGA GCTCAAAGAATACATGATCCTCAACTGCTAACAGAGAGAGCTT TACATCATGGAATTGATTTGGAGAAAATTAAGGCTTACATTGA TTCCTTCCGCTTTGGAGCCCCTCCTCATGCTGGTGGAGGCATTG GATTGGAACGAGTTACTATGCTGTTTCTGGGATTGCATAATGT TCGTCAGACCTCCATGTTCCCTCGTGATCCCAAACGACTCACT CCTTAG | 2 |

TABLE D2

Exemplary N-terminal DRS polypeptide Fragments

| Name | Amino Acid Residue Range of SEQ ID NO: 1 | Amino acid sequence | SEQ ID NO: |
|---|---|---|---|
| AspRS1[N1] | Protein/ Human/1-154 | MPSASASRKSQEKPREIMDAAEDYAKERYGISSMIQSQEKPDRVL VRVRDLTIQKADEVVWVRARVHTSRAKGKQCFLVLRQQQFNVQ ALVAVGDHASKQMVKFAANINKESIVDVEGVVRKVNQKIGSCT QQDVELHVQKIYVISLAEPRLPL | 3 |
| AspRS1[N11] | Protein/ Human/1- | MPSASASRKSQEKPREIMDAAEDYAKERYGISSMIQSQEKPDRVL VRVRDLTIQKADEVVWVRARVHTSRAKGKQCFLVLRQQQFNVQ | 4 |

TABLE D2-continued

Exemplary N-terminal DRS polypeptide Fragments

| Name | Amino Acid Residue Range of SEQ ID NO: 1 | Amino acid sequence | SEQ ID NO: |
|---|---|---|---|
| | 171 | ALVAVGDHASKQMVKFAANINKESIVDVEGVVRKVNQKIGSCT<br>QQDVELHVQKIYVISLAEPRLPLQLDDAVRPEAEGEEEGR | |
| AspRS1^N12 | Protein/<br>Human/1-<br>174 | MPSASASRKSQEKPREIMDAAEDYAKERYGISSMIQSQEKPDRVL<br>VRVRDLTIQKADEVVWVRARVHTSRAKGKQCFLVLRQQQFNVQ<br>ALVAVGDHASKQMVKFAANINKESIVDVEGVVRKVNQKIGSCT<br>QQDVELHVQKIYVISLAEPRLPLQLDDAVRPEAEGEEEGRATV | 5 |
| AspRS1^N13 | Protein/<br>Human/1-<br>182 | MPSASASRKSQEKPREIMDAAEDYAKERYGISSMIQSQEKPDRVL<br>VRVRDLTIQKADEVVWVRARVHTSRAKGKQCFLVLRQQQFNVQ<br>ALVAVGDHASKQMVKFAANINKESIVDVEGVVRKVNQKIGSCT<br>QQDVELHVQKIYVISLAEPRLPLQLDDAVRPEAEGEEEGRATVNQ<br>DTRLDN | 6 |
| AspRS1^N4 | Protein/<br>Human/1-<br>184 | MPSASASRKSQEKPREIMDAAEDYAKERYGISSMIQSQEKPDRVL<br>VRVRDLTIQKADEVVWVRARVHTSRAKGKQCFLVLRQQQFNVQ<br>ALVAVGDHASKQMVKFAANINKESIVDVEGVVRKVNQKIGSCT<br>QQDVELHVQKIYVISLAEPRLPLQLDDAVRPEAEGEEEGRATVNQ<br>DTRLDNRV | 7 |
| AspRS1^N2 | Protein/<br>Human/1-<br>274 | MPSASASRKSQEKPREIMDAAEDYAKERYGISSMIQSQEKPDRVL<br>VRVRDLTIQKADEVVWVRARVHTSRAKGKQCFLVLRQQQFNVQ<br>ALVAVGDHASKQMVKFAANINKESIVDVEGVVRKVNQKIGSCT<br>QQDVELHVQKIYVISLAEPRLPLQLDDAVRPEAEGEEEGRATVNQ<br>DTRLDNRVIDLRTSTSQAVFRLQSGICHLFRETLINKGFVEIQTPKII<br>SAASEGGANVFTVSYFKNNAYLAQSPQLYKQMCICADFEKVFSI<br>GPVFRA | 8 |
| AspRS1^N3 | Protein/<br>Human/1-<br>224 | MPSASASRKSQEKPREIMDAAEDYAKERYGISSMIQSQEKPDRVL<br>VRVRDLTIQKADEVVWVRARVHTSRAKGKQCFLVLRQQQFNVQ<br>ALVAVGDHASKQMVKFAANINKESIVDVEGVVRKVNQKIGSCT<br>QQDVELHVQKIYVISLAEPRLPLQLDDAVRPEAEGEEEGRATVNQ<br>DTRLDNRVIDLRTSTSQAVFRLQSGICHLFRETLINKGFVEIQTPKII | 9 |
| DRS 1-182 | 1-182 | MPSASASRKSQEKPREIMDAAEDYAKERYGISSMIQSQEKPDRVL<br>VRVRDLTIQKADEVVWVRARVHTSRAKGKQCFLVLRQQQFNVQ<br>ALVAVGDHASKQMVKFAANINKESIVDVEGVVRKVNQKIGSCT<br>QQDVELHVQKIYVISLAEPRLPLQLDDAVRPEAEGEEEGRATVNQ<br>DTRLDN | 154 |
| DRS 1-180 | 1-180 | MPSASASRKSQEKPREIMDAAEDYAKERYGISSMIQSQEKPDRVL<br>VRVRDLTIQKADEVVWVRARVHTSRAKGKQCFLVLRQQQFNVQ<br>ALVAVGDHASKQMVKFAANINKESIVDVEGVVRKVNQKIGSCT<br>QQDVELHVQKIYVISLAEPRLPLQLDDAVRPEAEGEEEGRATVNQ<br>DTRL | 155 |
| DRS 1-178 | 1-178 | MPSASASRKSQEKPREIMDAAEDYAKERYGISSMIQSQEKPDRVL<br>VRVRDLTIQKADEVVWVRARVHTSRAKGKQCFLVLRQQQFNVQ<br>ALVAVGDHASKQMVKFAANINKESIVDVEGVVRKVNQKIGSCT<br>QQDVELHVQKIYVISLAEPRLPLQLDDAVRPEAEGEEEGRATVNQ<br>DT | 156 |
| DRS 1-176 | 1-176 | MPSASASRKSQEKPREIMDAAEDYAKERYGISSMIQSQEKPDRVL<br>VRVRDLTIQKADEVVWVRARVHTSRAKGKQCFLVLRQQQFNVQ<br>ALVAVGDHASKQMVKFAANINKESIVDVEGVVRKVNQKIGSCT<br>QQDVELHVQKIYVISLAEPRLPLQLDDAVRPEAEGEEEGRATVNQ | 157 |
| DRS 1-174 | 1-174 | MPSASASRKSQEKPREIMDAAEDYAKERYGISSMIQSQEKPDRVL<br>VRVRDLTIQKADEVVWVRARVHTSRAKGKQCFEVLRQQQFNVQ<br>ALVAVGDHASKQMVKFAANINKESIVDVEGVVRKVNQKIGSCT<br>QQDVELHVQKIYVISLAEPRLPLQLDDAVRPEAEGEEEGRATV | 158 |
| DRS 1-172 | 1-172 | MPSASASRKSQEKPREIMDAAEDYAKERYGISSMIQSQEKPDRVL<br>VRVRDLTIQKADEVVWVRARVHTSRAKGKQCFLVLRQQQFNVQ<br>ALVAVGDHASKQMVKFAANINKESIVDVEGVVRKVNQKIGSCT<br>QQDVELHVQKIYVISLAEPRLPLQLDDAVRPEAEGEEEGRA | 159 |
| DRS 1-170 | 1-170 | MPSASASRKSQEKPREIMDAAEDYAKERYGISSMIQSQEKPDRVL<br>VRVRDLTIQKADEVVWVRARVHTSRAKGKQCFLVLRQQQFNVQ<br>ALVAVGDHASKQMVKFAANINKESIVDVEGVVRKVNQKIGSCT<br>QQDVELHVQKIYVISLAEPRLPLQLDDAVRPEAEGEEEG | 160 |

TABLE D2-continued

Exemplary N-terminal DRS polypeptide Fragments

| Name | Amino Acid Residue Range of SEQ ID NO: 1 | Amino acid sequence | SEQ ID NO: |
|---|---|---|---|
| DRS 1-168 | 1-168 | MPSASASRKSQEKPREIMDAAEDYAKERYGISSMIQSQEKPDRVL VRVRDLTIQKADEVVWVRARVHTSRAKGKQCFLVLRQQQFNVQ ALVAVGDHASKQMVKFAANINKESIVDVEGVVRKVNQKIGSCT QQDVELHVQKIYVISLAEPRLPLQLDDAVRPEAEGEE | 161 |
| DRS 1-166 | 1-166 | MPSASASRKSQEKPREIMDAAEDYAKERYGISSMIQSQEKPDRVL VRVRDKTIQKADEVVWVRARVHTSRAKGKQCFKVKRQQQFNVQ ALVAVGDHASKQMVKFAANINKESIVDVEGVVRKVNQKIGSCT QQDVELHVQKIYVISLAEPRLPLQLDDAVRPEAEG | 162 |
| DRS 1-164 | 1-164 | MPSASASRKSQEKPREIMDAAEDYAKERYGISSMIQSQEKPDRVL VRVRDLTIQKADEVVWVRARVHTSRAKGKQCFLVLRQQQFNVQ ALVAVGDHASKQMVKFAANINKESIVDVEGVVRKVNQKIGSCT QQDVELHVQKIYVISLAEPRLPLQLDDAVRPEA | 163 |
| DRS 1-162 | 1-162 | MPSASASRKSQEKPREIMDAAEDYAKERYGISSMIQSQEKPDRVL VRVRDLTIQKADEVVWVRARVHTSRAKGKQCFLVLRQQQFNVQ ALVAVGDHASKQMVKFAANINKESIVDVEGVVRKVNQKIGSCT QQDVELHVQKIYVISLAEPRLPLQLDDAVRP | 164 |
| DRS 1-160 | 1-160 | MPSASASRKSQEKPREIMDAAEDYAKERYGISSMIQSQEKPDRVL VRVRDLTIQKADEVVWVRARVHTSRAKGKQCFLVLRQQQFNVQ ALVAVGDHASKQMVKFAANINKESIVDVEGVVRKVNQKIGSCT QQDVELHVQKIYVISLAEPRLPLQLDDAV | 165 |
| DRS 1-158 | 1-158 | MPSASASRKSQEKPREIMDAAEDYAKERYGISSMIQSQEKPDRVL VRVRDLTIQKADEVVWVRARVHTSRAKGKQCFLVLRQQQFNVQ ALVAVGDHASKQMVKFAANINKESIVDVEGVVRKVNQKIGSCT QQDVELHVQKIYVISLAEPRLPLQLDD | 166 |
| DRS 1-156 | 1-156 | MPSASASRKSQEKPREIMDAAEDYAKERYGISSMIQSQEKPDRVL VRVRDLTIQKADEVVWVRARVHTSRAKGKQCFLVLRQQQFNVQ ALVAVGDHASKQMVKFAANINKESIVDVEGVVRKVNQKIGSCT QQDVELHVQKIYVISLAEPRLPLQL | 167 |
| DRS 1-154 | 1-154 | MPSASASRKSQEKPREIMDAAEDYAKERYGISSMIQSQEKPDRVL VRVRDLTIQKADEVVWVRARVHTSRAKGKQCFLVLRQQQFNVQ ALVAVGDHASKQMVKFAANINKESIVDVEGVVRKVNQKIGSCT QQDVELHVQKIYVISLAEPRLPL | 168 |
| DRS 1-152 | 1-152 | MPSASASRKSQEKPREIMDAAEDYAKERYGISSMIQSQEKPDRVL VRVRDLTIQKADEVVWVRARVHTSRAKGKQCFLVLRQQQFNVQ ALVAVGDHASKQMVKFAANINKESIVDVEGVVRKVNQKIGSCT QQDVELHVQKIYVISLAEPRL | 169 |
| DRS 1-150 | 1-150 | MPSASASRKSQEKPREIMDAAEDYAKERYGISSMIQSQEKPDRVL VRVRDLTIQKADEVVWVRARVHTSRAKGKQCFLVLRQQQFNVQ ALVAVGDHASKQMVKFAANINKESIVDVEGVVRKVNQKIGSCT QQDVELHVQKIYVISLAEP | 170 |
| DRS 1-148 | 148 | MPSASASRKSQEKPREIMDAAEDYAKERYGISSMIQSQEKPDRVL VRVRDLTIQKADEVVWVRARVHTSRAKGKQCFLVLRQQQFNVQ ALVAVGDHASKQMVKFAANINKESIVDVEGVVRKVNQKIGSCT QQDVELHVQKIYVISLA | 171 |
| DRS 1-146 | 1-146 | MPSASASRKSQEKPREIMDAAEDYAKERYGISSMIQSQEKPDRVL VRVRDLTIQKADEVVWVRARVHTSRAKGKQCFLVLRQQQFNVQ ALVAVGDHASKQMVKFAANINKESIVDVEGVVRKVNQKIGSCT QQDVELHVQKIYVIS | 172 |
| DRS 3-154 | 3-154 | ASASRKSQEKPREIMDAAEDYAKERYGISSMIQSQEKPDRVLVRV RDLTIQKADEVVWVRARVHTSRAKGKQCFLVLRQQQFNVQALV AVGDHASKQMVKFAANINKESIVDVEGVVRKVNQKIGSCTQQD VELHVQKIYVISLAEPRLPL | 173 |
| DRS 5-154 | 5-154 | ASRKSQEKPREIMDAAEDYAKERYGISSMIQSQEKPDRVLVRVRD LTIQKADEVVWVRARVHTSRAKGKQCFLVLRQQQFNVQALVAV GDHASKQMVKFAANINKESIVDVEGVVRKVNQKIGSCTQQDVEL HVQKIYVISLAEPRLPL | 174 |
| DRS 7-154 | 7-154 | RKSQEKPREIMDAAEDYAKERYGISSMIQSQEKPDRVLVRVRDLT IQKADEVVWVRARVHTSRAKGKQCFLVLRQQQFNVQALVAVG | 175 |

TABLE D2-continued

Exemplary N-terminal DRS polypeptide Fragments

| Name | Amino Acid Residue Range of SEQ ID NO: 1 | Amino acid sequence | SEQ ID NO: |
|---|---|---|---|
| | | DHASKQMVKFAANINKESIVDVEGVVRKVNQKIGSCTQQDVELH VQKIYVISLAEPRLPL | |
| DRS 9-154 | 9-154 | SQEKPREIMDAAEDYAKERYGISSMIQSQEKPDRVLVRVRDLTIQ KADEVVWVRARVHTSRAKGKQCFLVLRQQQFNVQALVAVGDH ASKQMVKFAANINKESIVDVEGVVRKVNQKIGSCTQQDVELHVQ KIYVISLAEPRLPL | 176 |
| DRS 11-154 | 11-154 | EKPREIMDAAEDYAKERYGISSMIQSQEKPDRVLVRVRDLTIQKA DEVVWVRARVHTSRAKGKQCFLVLRQQQFNVQALVAVGDHAS KQMVKFAANINKESIVDVEGVVRKVNQKIGSCTQQDVELHVQKI YVISLAEPRLPL | 177 |
| DRS 13-154 | 13-154 | PREIMDAAEDYAKERYGISSMIQSQEKPDRVLVRVRDLTIQKADE VVWVRARVHTSRAKGKQCFLVLRQQQFNVQALVAVGDHASKQ MVKFAANINKESIVDVEGVVRKVNQKIGSCTQQDVELHVQKIYV ISLAEPRLPL | 178 |
| DRS15 -154 | 15-154 | EIMDAAEDYAKERYGISSMIQSQEKPDRVLVRVRDLTIQKADEVV WVRARVHTSRAKGKQCFLVLRQQQFNVQALVAVGDHASKQMV KFAANINKESIVDVEGVVRKVNQKIGSCTQQDVELHVQKIYVISL AEPRLPL | 179 |
| DRS 17-154 | 17-154 | MDAAEDYAKERYGISSMIQSQEKPDRVLVRVRDLTIQKADEVVW VRARVHTSRAKGKQCFLVLRQQQFNVQALVAVGDHASKQMVK FAANINKESIVDVEGVVRKVNQKIGSCTQQDVELHVQKIYVISLA EPRLPL | 180 |
| DRS 19-154 | 19-154 | MDAAEDYAKERYGISSMIQSQEKPDRVLVRVRDLTIQKADEVVW VRARVHTSRAKGKQCFLVLRQQQFNVQALVAVGDHASKQMVK FAANINKESIVDVEGVVRKVNQKIGSCTQQDVELHVQKIYVISLA EPRL | 181 |
| DRS 21-154 | 21-154 | MDAAEDYAKERYGISSMIQSQEKPDRVLVRVRDLTIQKADEVVW VRARVHTSRAKGKQCFLVLRQQQFNVQALVAVGDHASKQMVK FAANINKESIVDVEGVVRKVNQKIGSCTQQDVELHVQKIYVISLA EPRL | 182 |
| DRS 23-154 | 23-154 | AAEDYAKERYGISSMIQSQEKPDRVLVRVRDLTIQKADEVVWVR ARVHTSRAKGKQCFLVLRQQQFNVQALVAVGDHASKQMVKFA ANINKESIVDVEGVVRKVNQKIGSCTQQDVELHVQKIYVISLAEP RL | 183 |
| DRS 11-146 | 11-146 | MQEKPREIMDAAEDYAKERYGISSMIQSQEKPDRVLVRVRDLTIQ KADEVVWVRARVHTSRAKGKQCFLVLRQQQFNVQALVAVGDH ASKQMVKFACNINKESIVDVEGVVRKVNQKIGSCTQQDVELHVQ KIYVIS | 184 |
| DRS 13-146 | 13-146 | MKPREIMDAAEDYAKERYGISSMIQSQEKPDRVLVRVRDLTIQK ADEVVWVRARVHTSRAKGKQCFLVLRQQQFNVQALVAVGDHA SKQMVKFACNINKESIVDVEGVVRKVNQKIGSCTQQDVELHVQK IYVIS | 185 |
| DRS 13-146/A106C | 13 -146 | MKPREIMDAAEDYAKERYGISSMIQSQEKPDRVLVRVRDLTIQK ADEVVWVRARVHTSRAKGKQCFLVLRQQQFNVQALVAVGDHA SKQMVKFACNINKESIVDVEGVVRKVNQKIGSCTQQDVELHVQK IYVIS | 186 |
| DRS 17-146 | 17-146 | MIMDAAEDYAKERYGISSMIQSQEKPDRVLVRVRDLTIQKADEV VWVRARVHTSRAKGKQCFLVLRQQQFNVQALVAVGDHASKQM VKFACNINKESIVDVEGVVRKVNQKIGSCTQQDVELHVQKIYVIS | 187 |
| DRS 21-146 | 21-146 | MAEDYAKERYGISSMIQSQEKPDRVLVRVRDLTIQKADEVVWVR ARVHTSRAKGKQCFLVLRQQQFNVQALVAVGDHASKQMVKFA CNINKESIVDVEGVVRKVNQKIGSCTQQDVELHVQKIYVIS | 188 |

TABLE D3

Exemplary Internal DRS polypeptide Fragments

| Name | Amino Acid Residue Range of SEQ ID NO: 1 | Amino acid sequence | SEQ ID NO: |
|---|---|---|---|
| AspRS1[I1] | Protein/ Human/ 38-292 | QEKPDRVLVRVRDLTIQKADEVVWVRARVHTSRAKGKQCFLVL RQQQFNVQALVAVGDHASKQMVKFAANINKESIVDVEGVVRKV NQKIGSCTQQDVELHVQKIYVISLAEPRLPLQLDDAVRPEAEGEE EGRATVNQDTRLDNRVIDLRTSTSQAVFRLQSGICHLFRETLINKG FVEIQTPKIISAASEGGANVFTVSYFKNNAYLAQSPQLYKQMCIC ADFEKVFSIGPVFRAEDSNTHRHLTEFVGLDIE | 10 |
| AspRS1[I2] | Protein/ Human/ 23-154 | DYAKERYGISSMIQSQEKPDRVLVRVRDLTIQKADEVVWVRARV HTSRAKGKQCFLVLRQQQFNVQALVAVGDHASKQMVKFAANIN KESIVDVEGVVRKVNQKIGSCTQQDVELHVQKIYVISLAEPRLPL | 11 |
| AspRS1[I3] | Protein/ Human/ 33-154 | SMIQSQEKPDRVLVRVRDLTIQKADEVVWVRARVHTSRAKGKQ CFLVLRQQQFNVQALVAVGDHASKQMVKFAANINKESIVDVEG VVRKVNQKIGSCTQQDVELHVQKIYVISLAEPRLPL | 12 |

TABLE D4

Exemplary C-Terminal DRS polypeptide Fragments

| Name | Amino Acid Residue Range of SEQ ID NO: 1 | Amino acid sequence | SEQ ID NO: |
|---|---|---|---|
| AspRS1[C1] | Protein/ Human/ 297-501 | YHYHEVMEEIADTMVQIFKGLQERFQTEIQTVNKQFPCEPFKFLE PTLRLEYCEALAMLREAGVEMGDEDDLSTPNEKLLGHLVKEKY DTDFYILDKYPLAVRPFYTMPDPRNPKQSNSYDMFMRGEEILSGA QRIHDPQLLTERALHHGIDLEKIKAYIDSFRFGAPPHAGGGIGLER VTMLFLGLHNVRQTSMFPRDPKRLTP | 13 |
| AspRS1[C2] | Protein/ Human/ 101-501 | MVKFAANINKESIVDVEGVVRKVNQKIGSCTQQDVELHVQKIYV ISLAEPRLPLQLDDAVRPEAEGEEEGRATVNQDTRLDNRVIDLRT STSQAVFRLQSGICHLFRETLINKGFVEIQTPKIISAASEGGANVFT VSYFKNNAYLAQSPQLYKQMCICADFEKVFSIGPVFRAEDSNTHR HLTEFVGLDIEMAFNYHYHEVMEEIADTMVQIFKGLQERFQTEIQ TVNKQFPCEPFKFLEPTLRLEYCEALAMLREAGVEMGDEDDLSTP NEKLLGHLVKEKYDTDFYILDKYPLAVRPFYTMPDPRNPKQSNS YDMFMRGEEILSGAQRIHDPQLLTERALHHGIDLEKIKAYIDSFRF GAPPHAGGGIGLERVTMLFLGLHNVRQTSMFPRDPKRLTP | 14 |

TABLE D5

Exemplary Alternatively Spliced DRS polypeptide Variants

| Name | Amino Acid Residue Range of SEQ ID NO: 1 | Amino acid sequence | SEQ ID NO: |
|---|---|---|---|
| AspRS1[N6] | Protein/ Human/1-41 + 73-501 | MPSASASRKSQEKPREIMDAAEDYAKERYGISSMIQSQEKPGKQC FLVLRQQQFNVQALVAVGDHASKQMVKFAANINKESIVDVEGV VRKVNQKIGSCTQQDVELHVQKIYVISLAEPRLPLQLDDAVRPEA EGEEEGRATVNQDTRLDNRVIDLRTSTSQAVFRLQSGICHLFRET LINKGFVEIQTPKIISAASEGGANVFTVSYFKNNAYLAQSPQLYKQ MCICADFEKVFSIGPVFRAEDSNTHRHLTEFVGLDIEMAFNYHYH EVMEEIADTMVQIFKGLQERFQTEIQTVNKQFPCEPFKFLEPTLRL EYCEALAMLREAGVEMGDEDDLSTPNEKLLGHLVKEKYDTDFYI LDKYPLAVRPFYTMPDPRNPKQSNSYDMFMRGEEILSGAQRIHDP QLLTERALHHGIDLEKIKAYIDSFRFGAPPHAGGGIGLERVTMLFL GLHNVRQTSMFPRDPKRLTP | 15 |
| AspRS1[N7] | Protein/ Human/1- | MPSASASRKSQEKPREIMDAAEDYAKERYGISSMIQSQEKPDRVL VRVRDLTIQKADEVVWVRARVHTSRAKGKQCFLVLRQQQFNVQ | 16 |

TABLE D5-continued

Exemplary Alternatively Spliced DRS polypeptide Variants

| Name | Amino Acid Residue Range of SEQ ID NO: 1 | Amino acid sequence | SEQ ID NO: |
|---|---|---|---|
| | 141 + 189-501 | ALVAVGDHASKQMVKFAANINKESIVDVEGVVRKVNQKIGSCT QQDVELHVQKTSTSQAVFRLQSGICHLFRETLINKGFVEIQTPKIIS AASEGGANVFTVSYFKNNAYLAQSPQLYKQMCICADFEKVFSIG PVFRAEDSNTHRHLTEFVGLDIEMAFNYHYHEVMEEIADTMVQIF KGLQERFQTEIQTVNKQFPCEPFKFLEPTLRLEYCEALAMLREAG VEMGDEDDLSTPNEKLLGHLVKEKYDTDFYILDKYPLAVRPFYT MPDPRNPKQSNSYDMFMRGEEILSGAQRIHDPQLLTERALHHGID LEKIKAYIDSFRFGAPPHAGGGIGLERVTMLFLGLHNVRQTSMFP RDPKRLTP | |
| AspRS1[N8] | Protein/ Human/ 1-319 + 369-501 | MPSASASRKSQEKPREIMDAAEDYAKERYGISSMIQSQEKPDRVL VRVRDLTIQKADEVVWVRARVHTSRAKGKQCFLVLRQQQFNVQ ALVAVGDHASKQMVKFAANINKESIVDVEGVVRKVNQKIGSCT QQDVELHVQKIYVISLAEPRLPLQLDDAVRPEAEGEEEGRATVNQ DTRLDNRVIDLRTSTSQAVFRLQSGICHLFRETLINKGFVEIQTPKII SAASEGGANVFTVSYFKNNAYLAQSPQLYKQMCICADFEKVFSI GPVFRAEDSNTHRHLTEFVGLDIEMAFNYHYHEVMEEIADTMVQ IFKGLQESTPNEKLLGHLVKEKYDTDFYILDKYPLAVRPFYTMPD PRNPKQSNSYDMFMRGEEILSGAQRIHDPQLLTERALHHGIDLEKI KAYIDSFRFGAPPHAGGGIGLERVTMLFLGLHNVRQTSMFPRDPK RLTP | 17 |
| AspRS1[N9] DRS (1-22 + 63 aa) | Protein/ Human/ 1-22 + 63 aa | MPSASASRKSQEKPREIMDAAEDWNELLCCFWDCIMFVRPPCSL VIPNDSLLKFTLCHLTPVWMTERDPASKKKKKKESHTYSFQ | 18 |
| AspRS1[N10] DRS (1-22 + 5 aa) | Protein/ Human/ 1-22 + 5 aa | MPSASASRKSQEKPREIMDAAEGNSAS | 19 |
| AspRS1[C2] | Protein/ Human/ 101-501 | MVKFAANINKESIVDVEGVVRKVNQKIGSCTQQDVELHVQKIYV ISLAEPRLPLQLDDAVRPEAEGEEEGRATVNQDTRLDNRVIDLRT STSQAVFRLQSGICHLFRETLINKGFVEIQTPKIISAASEGGANVFT VSYFKNNAYLAQSPQLYKQMCICADFEKVFSIGPVFRAEDSNTHR HLTEFVGLDIEMAFNYHYHEVMEEIADTMVQIFKGLQERFQTEIQ TVNKQFPCEPFKFLEPTLRLEYCEALAMLREAGVEMGDEDDLSTP NEKLLGHLVKEKYDTDFYILDKYPLAVRPFYTMPDPRNPKQSNS YDMFMRGEEILSGAQRIHDPQLLTERALHHGIDLEKIKAYIDSFRF GAPPHAGGGIGLERVTMLFLGLHNVRQTSMFPRDPKRLTP | 20 |
| AspRS1[C3] DRS (478-501) | Protein/ Human/ 478-501 | MLFLGLHNVRQTSMFPRDPKRLTP | 21 |

A number of naturally occurring aspartyl-tRNA synthetase single nucleotide polymorphisms (SNPs) and naturally occurring variants of the human gene have been sequenced, and are known in the art to be at least partially functionally interchangeable. Additionally homologs and orthologs of the human gene exist in other species, and it would thus be a routine matter to select a naturally occurring variant such as a DRS polypeptide encoded by a SNP, or other naturally occurring variant in place of any of the DRS polypeptide sequences listed in Tables D1-D5 or D7. Several such variants of aspartyl-tRNA synthetase (i.e., representative aspartyl-tRNA synthetase SNPs) are shown in Table D6.

TABLE D6

Human Aspartyl-tRNA synthetase SNPs

| Gene Bank Accession Number | Nucleotide Change | Gene Bank Accession Number | Nucleotide Change |
|---|---|---|---|
| rs118100102 | C/T | rs2164332 | C/G |
| rs117859527 | C/G | rs2164331 | C/T |
| rs117847055 | A/G | rs1867632 | A/G |
| rs117843158 | A/C | rs1803167 | C/T |

TABLE D6-continued

Human Aspartyl-tRNA synthetase SNPs

| Gene Bank Accession Number | Nucleotide Change | Gene Bank Accession Number | Nucleotide Change |
|---|---|---|---|
| rs117754321 | A/C | rs1803166 | C/T |
| rs117605910 | C/G | rs1803165 | G/T |
| rs117587018 | A/G | rs1347442 | C/T |
| rs117448010 | A/C | rs895285 | A/G |
| rs117438984 | A/G | rs834734 | C/T |
| rs117395206 | G/T | rs689002 | A/G |
| rs117045416 | C/T | rs687670 | C/T |
| rs116899241 | C/T | rs661562 | A/C |
| rs116807764 | C/T | rs660002 | C/T |
| rs116756668 | C/T | rs640727 | A/T |
| rs116755289 | C/T | rs567363 | C/T |
| rs116723553 | A/G | rs561980 | A/G |
| rs116719241 | C/T | rs522086 | C/T |
| rs116626412 | C/T | rs309172 | C/T |
| rs116599033 | A/G | rs309171 | C/G |
| rs116528963 | C/T | rs309170 | C/T |
| rs116504104 | A/G | rs309169 | C/T |
| rs116503734 | A/T | rs309168 | C/T |
| rs116471228 | G/T | rs309167 | C/T |
| rs116460118 | A/T | rs309166 | C/T |
| rs116376572 | A/G | rs309165 | C/T |
| rs116373537 | G/T | rs309164 | A/G |
| rs116190965 | C/T | rs309163 | C/T |
| rs116114585 | A/T | rs309162 | A/T |
| rs116069651 | C/T | rs309161 | C/T |
| rs116013288 | C/T | rs309160 | A/G |
| rs115947325 | C/T | rs309159 | A/G |
| rs115876148 | C/T | rs309158 | C/T |
| rs115771261 | C/T | rs309157 | A/G |
| rs115749352 | A/G | rs309156 | C/G |
| rs115704588 | C/T | rs309155 | A/G |
| rs115691888 | A/C | rs309154 | C/T |
| rs115651129 | C/G | rs309153 | A/G |
| rs115572299 | C/T | rs309150 | A/T |
| rs115553816 | A/G | rs309149 | C/T |
| rs115530645 | C/T | rs7587285 | C/T |
| rs115475999 | C/T | rs7585928 | C/G |

TABLE D6-continued

Human Aspartyl-tRNA synthetase SNPs

| Gene Bank Accession Number | Nucleotide Change | Gene Bank Accession Number | Nucleotide Change |
|---|---|---|---|
| rs115469964 | A/C | rs7573555 | C/T |
| rs115332530 | A/G | rs6760465 | A/T |
| rs115330084 | C/G | rs6757965 | A/G |
| rs115316382 | A/G | rs6754311 | C/T |
| rs115306423 | C/T | rs6752967 | A/G |
| rs115253602 | A/G | rs6750549 | A/G |
| rs115249754 | C/T | rs6743537 | A/G |
| rs115248017 | C/G | rs6742701 | C/T |
| rs114986027 | C/T | rs6740254 | C/G |
| rs114977327 | C/T | rs6738266 | C/T |
| rs114851922 | C/T | rs6733398 | A/G |
| rs114841878 | A/G | rs6724595 | A/G |
| rs114832662 | A/G | rs6711493 | A/G |
| rs114830940 | A/G | rs6430594 | A/G |
| rs114489290 | C/T | rs5834455 | -/T |
| rs114428384 | C/T | rs5834454 | -/AA |
| rs114422751 | C/T | rs5834453 | -/AAAAT |
| rs114414669 | A/C | rs4954551 | A/G |
| rs114412783 | C/T | rs4597591 | A/T |
| rs114399267 | C/T | rs4538260 | A/G |
| rs114398361 | A/G | rs4278979 | C/T |
| rs114345514 | C/T | rs3820789 | C/G |
| rs114337780 | A/C | rs3768999 | C/G |
| rs114164361 | C/G | rs3768998 | A/C |
| rs114162105 | A/T | rs3768997 | A/G |
| rs114126158 | A/G | rs3768996 | C/G |
| rs114110228 | A/C | rs3112496 | C/T |
| rs114058841 | G/T | rs3098104 | A/T |
| rs113998842 | G/T | rs2839741 | A/T |
| rs113995718 | A/C | rs2556175 | C/T |
| rs113884130 | C/T | rs2322725 | C/T |
| rs113882668 | A/C | rs2307720 | -/TTAG |
| rs113853485 | G/T | rs2305101 | G/T |
| rs113759327 | C/G | rs2278683 | A/C |
| rs113676252 | C/T | rs2278682 | C/G |
| rs113641203 | G/T | rs2278681 | C/T |
| rs113342018 | G/T | rs2164333 | A/T |

TABLE D6-continued

Human Aspartyl-tRNA synthetase SNPs

| Gene Bank Accession Number | Nucleotide Change | Gene Bank Accession Number | Nucleotide Change |
|---|---|---|---|
| rs113328159 | -/C | rs13397074 | A/C |
| rs113316632 | A/T | rs13392680 | A/T |
| rs113200654 | A/T | rs13388887 | C/T |
| rs113155677 | A/G | rs13034773 | A/C |
| rs113148022 | AAAAAAAAAAAAA AAAAAATCCAA (SEQ ID NO: 76) | rs13025460 | A/T |
| rs113012086 | A/G | rs13007697 | G/T |
| rs112923773 | A/G | rs13004546 | C/T |
| rs112910626 | C/T | rs12999871 | A/C |
| rs112868187 | C/T | rs12990346 | G/T |
| rs112849402 | A/G | rs12990316 | C/T |
| rs112848056 | C/T | rs12624144 | C/T |
| rs112835147 | C/T | rs12623506 | A/G |
| rs112767522 | C/T | rs12617586 | C/T |
| rs112396243 | C/T | rs12615624 | A/G |
| rs112369881 | A/T | rs12613540 | C/T |
| rs112319042 | C/T | rs12613074 | G/T |
| rs112300736 | G/T | rs12477103 | A/C |
| rs112205661 | C/T | rs12474975 | A/T |
| rs112205423 | G/T | rs12471430 | A/T |
| rs112138368 | C/T | rs11895669 | G/T |
| rs112136466 | C/T | rs11895436 | A/G |
| rs111956746 | A/G | rs11892136 | G/T |
| rs111909933 | C/T | rs11889473 | A/C |
| rs111766943 | A/G | rs11548872 | C/G |
| rs111731189 | C/T | rs11548870 | A/G |
| rs111716305 | C/T | rs11375996 | -/A |
| rs111670530 | C/T | rs11345750 | -/A |
| rs111613855 | A/G | rs11340194 | -/A |
| rs111608134 | C/T | rs11319623 | -/A |
| rs111600480 | A/G | rs11297201 | -/T |
| rs111578911 | A/C | rs10610928 | -/CTCT |
| rs111533002 | -/T | rs10606646 | -/AAAA |
| rs111432741 | C/T | rs10598545 | -/AAAA |
| rs111346414 | C/T | rs10566195 | -/TGA |
| rs111261866 | C/T | rs10546948 | -/TT |

TABLE D6-continued

Human Aspartyl-tRNA synthetase SNPs

| Gene Bank Accession Number | Nucleotide Change | Gene Bank Accession Number | Nucleotide Change |
|---|---|---|---|
| rs80342688 | A/C | rs10205844 | C/G |
| rs80296238 | A/C | rs35332762 | -/C |
| rs80290607 | G/T | rs35323281 | -/A |
| rs80201497 | A/C | rs35250856 | -/C |
| rs80160510 | C/T | rs35207721 | -/C |
| rs80095420 | C/T | rs35180509 | -/A |
| rs79933222 | A/C | rs35066766 | -/T |
| rs79908186 | G/T | rs34855029 | -/A |
| rs79826902 | A/G | rs34818704 | -/G |
| rs79811988 | G/T | rs34764820 | -/T |
| rs79778906 | C/T | rs34762161 | -/T |
| rs79745746 | C/T | rs34744196 | -/A |
| rs79719188 | C/T | rs34739918 | -/T |
| rs79715594 | C/T | rs34719779 | -/T |
| rs79685879 | -/TT | rs34713850 | -/A |
| rs79613305 | A/C | rs34698626 | -/AA |
| rs79513920 | C/T | rs34675243 | -/A |
| rs79507949 | A/G | rs34613097 | -/A |
| rs79494100 | A/T | rs34442772 | -/C |
| rs79478181 | A/T | rs34398897 | -/G |
| rs79327246 | C/G | rs34215176 | -/G |
| rs79301888 | C/T | rs34180776 | -/G |
| rs79274257 | A/G | rs34142242 | -/T |
| rs79268627 | A/T | rs34050823 | -/T |
| rs79238496 | A/G | rs17718194 | C/T |
| rs79231002 | C/T | rs16832417 | C/T |
| rs79227800 | C/T | rs16832413 | A/C |
| rs79173488 | A/G | rs16832394 | A/C |
| rs79161420 | -/A | rs16832326 | A/G |
| rs79139071 | A/G | rs16832275 | C/G |
| rs79137850 | C/T | rs16832274 | C/T |
| rs79121686 | C/T | rs16832248 | C/G |
| rs79078468 | G/T | rs16832243 | C/T |
| rs79018926 | C/T | rs16832221 | C/T |
| rs78993580 | A/G | rs16832205 | A/G |
| rs78943662 | -/A | rs16832200 | C/T |
| rs78919277 | G/T | rs16832172 | C/T |

TABLE D6-continued

Human Aspartyl-tRNA synthetase SNPs

| Gene Bank Accession Number | Nucleotide Change | Gene Bank Accession Number | Nucleotide Change |
|---|---|---|---|
| rs78915112 | A/C | rs16832162 | A/T |
| rs78898735 | A/T | rs13404551 | C/T |
| rs78793088 | A/G | rs13399128 | A/G |
| rs78784878 | G/T | rs71417582 | C/T |
| rs78770570 | C/T | rs71417581 | C/G |
| rs78700806 | C/G | rs71400535 | -/A |
| rs78638278 | C/T | rs67636722 | -/A |
| rs78629157 | A/G | rs67591467 | -/A |
| rs78628013 | C/T | rs66527494 | -/A |
| rs78577601 | A/T | rs66508408 | -/AA |
| rs78537103 | C/T | rs62159056 | A/C |
| rs78518056 | A/C | rs62159055 | A/T |
| rs78512447 | A/T | rs61569739 | -/AA |
| rs78497838 | -/TTT | rs61297566 | -/AAATA |
| rs78383997 | A/T | rs61222539 | C/T |
| rs78283445 | C/G | rs61133344 | C/T |
| rs78275586 | G/T | rs60878223 | -/T |
| rs78274583 | C/T | rs60538468 | A/C |
| rs78258066 | A/G | rs60485095 | -/TT |
| rs78168253 | C/T | rs60318326 | C/T |
| rs78143716 | A/G | rs59584448 | -/A |
| rs78130363 | A/G | rs59505882 | -/A |
| rs78083497 | A/C | rs59464486 | G/T |
| rs78081965 | G/T | rs59199326 | -/TT |
| rs78076875 | C/T | rs58805013 | A/C |
| rs78026280 | A/G | rs58799551 | -/G |
| rs78015725 | G/T | rs58666594 | G/T |
| rs77987440 | C/T | rs57046249 | -/A |
| rs77972711 | A/G | rs56721192 | -/AA |
| rs77930020 | A/C | rs56100046 | A/T |
| rs77902883 | C/T | rs55951873 | A/G |
| rs77883526 | A/T | rs55815289 | -/A |
| rs77862927 | -/TT | rs55759471 | G/T |
| rs77837755 | A/C | rs55641281 | A/G |
| rs77793053 | C/T | rs41269823 | A/G |
| rs77774340 | A/C | rs41269821 | A/G |
| rs77753457 | C/T | rs36023868 | -/T |

TABLE D6-continued

Human Aspartyl-tRNA synthetase SNPs

| Gene Bank Accession Number | Nucleotide Change | Gene Bank Accession Number | Nucleotide Change |
| --- | --- | --- | --- |
| rs77752694 | A/T | rs35921927 | A/G |
| rs77743403 | G/T | rs35814998 | -/C |
| rs77707512 | C/T | rs35760856 | -/C |
| rs77697045 | C/T | rs35460584 | -/C |
| rs77694994 | A/G | rs35363362 | C/G |
| rs77654242 | G/T | rs74661004 | C/T |
| rs77546304 | C/T | rs74527665 | C/T |
| rs77516029 | C/T | rs74479926 | C/T |
| rs77511888 | A/C | rs74462337 | G/T |
| rs77507602 | A/T | rs74399174 | A/C |
| rs77390314 | A/G | rs74398392 | C/T |
| rs77341293 | A/C | rs74266318 | G/T |
| rs77340433 | C/T | rs73957079 | C/T |
| rs77244692 | A/G | rs73957078 | C/T |
| rs77241600 | C/T | rs73957074 | A/C |
| rs77194466 | A/T | rs73957073 | A/G |
| rs77182879 | A/G | rs73957072 | A/G |
| rs77177301 | G/T | rs73957071 | A/G |
| rs77147958 | A/G | rs73957070 | A/G |
| rs77144439 | A/T | rs73957069 | C/G |
| rs77113180 | A/G | rs73957068 | C/T |
| rs77092452 | A/G | rs72974121 | A/G |
| rs77052188 | G/T | rs72974120 | C/G |
| rs77051588 | C/T | rs72974119 | A/G |
| rs76986930 | A/C | rs72974109 | A/G |
| rs76946722 | -/AA | rs72423998 | -/A |
| rs76862952 | A/C | rs72366475 | -/T |
| rs76856516 | G/T | rs72355283 | -/A |
| rs76798249 | A/C | rs72313616 | -/TT |
| rs76793136 | A/G | rs72270342 | -/A |
| rs76792531 | A/G | rs72268157 | -/A |
| rs76732000 | G/T | rs72097458 | -/A |
| rs76729798 | C/T | rs71937749 | -/AA |
| rs76677887 | C/T | rs71930676 | -/A |
| rs76672039 | C/T | rs71746189 | -/A |
| rs76496496 | A/G | rs71701797 | -/AAAA |
| rs76460134 | A/C | rs71697066 | -/A |

TABLE D6-continued

Human Aspartyl-tRNA synthetase SNPs

| Gene Bank Accession Number | Nucleotide Change | Gene Bank Accession Number | Nucleotide Change |
| --- | --- | --- | --- |
| rs76456107 | A/G | rs71535212 | A/T |
| rs76448970 | A/G | rs71535211 | C/T |
| rs76433055 | C/T | rs71417587 | A/C |
| rs76392392 | A/G | rs71417586 | A/C |
| rs76357426 | C/T | rs71417585 | C/G |
| rs76350348 | A/G | rs71417584 | C/G |
| rs76337990 | C/T | rs71417583 | A/C |
| rs76306255 | G/T | rs309148 | C/T |
| rs76302219 | C/T | rs309147 | C/T |
| rs76296777 | A/G | rs309146 | A/G |
| rs76285313 | A/T | rs309145 | A/G |
| rs76189476 | A/G | rs309144 | C/T |
| rs76089705 | G/T | rs309143 | A/G |
| rs76047098 | C/T | rs309142 | C/T |
| rs75999734 | C/T | rs309141 | A/C |
| rs75990169 | A/G | rs309140 | A/C |
| rs75935955 | C/T | rs309120 | C/G |
| rs75874749 | C/T | rs309119 | A/G |
| rs75843843 | C/G | rs309115 | C/T |
| rs75843510 | C/T | rs309114 | A/T |
| rs75842188 | A/G | rs309113 | A/C |
| rs75800473 | G/T | rs309112 | G/T |
| rs75794936 | A/C | rs192822 | A/T |
| rs75753154 | C/T | rs177917 | C/T |
| rs75732042 | C/G | rs167442 | G/T |
| rs75683158 | G/T | rs71518151 | ACTTTTTGATGGGGTT GT (SEQ ID NO: 77)/ CCTTTTTCATG GGCTTGTTTTTTCTT GTAAATTTGTTT (SEQ ID NO: 78) |
| rs75667274 | C/T | rs75123144 | -/AG |
| rs75657010 | A/T | rs75071131 | A/T |
| rs75647121 | C/T | rs74959174 | C/T |
| rs75572938 | A/T | rs74833182 | A/T |
| rs75560320 | A/G | rs74777619 | C/T |
| rs75524146 | C/T | rs74771413 | C/G |
| rs75437018 | C/G | rs74674565 | C/T |
| rs75402079 | A/C | rs75346069 | C/T |

TABLE D6-continued

Human Aspartyl-tRNA synthetase SNPs

| Gene Bank Accession Number | Nucleotide Change | Gene Bank Accession Number | Nucleotide Change |
|---|---|---|---|
| rs75394224 | C/G | rs75298650 | A/G |
| rs75365510 | A/G | rs75214175 | A/G |

Accordingly, the terms "DRS polypeptide" "DRS protein" or "DRS protein fragment" as used herein includes all naturally-occurring and synthetic forms of the aspartyl-tRNA synthetase that optionally retain at least one non canonical activity. Such DRS polypeptides include the full length human protein, the DRS peptides derived from the full length protein listed in Tables D1-D5, naturally occurring variants, for example as disclosed in Table D6, the exemplary cysteine mutants listed in Table D7, and synthetic codon optimized forms and other coding sequences as exemplified by the nucleic acid sequences in Table D9, among others. In specific embodiments, the term DRS polypeptide refers to a polypeptide sequence derived from human aspartyl-tRNA synthetase (SEQ ID NO:1 in Table D1) comprising at least one mutation at either Cys76 or Cys130.

DRS Variants

Thus all such homologues, orthologs, and naturally-occurring, or synthetic isoforms of aspartyl-tRNA synthetases (e.g., any of the proteins or nucleic acids listed in or derivable from Tables D1 to D9) are included in any of the conjugates, methods, kits and pharmaceutical compositions described herein. These DRS variants optionally retain at least one non-canonical activity such as an anti-inflammatory activity.

The DRS polypeptides may be in their native form, i.e., as different variants as they appear in nature in different species which may be viewed as functionally equivalent variants of human aspartyl-tRNA synthetase, or they may be functionally equivalent natural derivatives thereof, which may differ in their amino acid sequence, for example, by truncation (e.g., from the N- or C-terminus or both) or other amino acid deletions, additions, insertions, substitutions, or post-translational modifications. Naturally-occurring chemical derivatives, including post-translational modifications and degradation products of any DRS polypeptide, are also specifically included in any of the methods and pharmaceutical compositions of the invention including, e.g., pyroglutamyl, iso-aspartyl, proteolytic, phosphorylated, glycosylated, oxidatized, isomerized, and deaminated variants of a DRS polypeptide.

It is known in the art to synthetically modify the sequences of proteins or peptides, while retaining their useful activity, and this may be achieved using techniques which are standard in the art and widely described in the literature, e.g., random or site-directed mutagenesis, cleavage, and ligation of nucleic acids, or via the chemical synthesis or modification of amino acids or polypeptide chains. Similarly it is within the skill in the art to address and/or mitigate immunogenicity concerns if they arise using a DRS polypeptide or variant thereof, e.g., by the use of automated computer recognition programs to identify potential T cell epitopes, and directed evolution approaches to identify less immunogenic forms.

As noted above, embodiments of the present invention include all homologues, orthologs, and naturally-occurring isoforms of aspartyl-tRNA synthetase (e.g., any of the proteins, or their corresponding nucleic acids listed in or derivable from Tables D1 to D9, which optionally retain at least one detectable non canonical activity). Also included are "variants" of these DRS reference polypeptides. The recitation polypeptide "variant" refers to polypeptides that are distinguished from a reference DRS polypeptide by the addition, deletion, and/or substitution of at least one amino acid residue, and which typically retain (e.g., mimic) or modulate (e.g., antagonize) one or more non-canonical activities of a reference DRS polypeptide. The structure of human aspartyl-tRNA synthetase has been determined to a resolution of 1.7A. (See WO2010/120509) providing a detailed physical description of the protein, which in conjunction with the primary amino acid sequence provides precise insights into the roles played by specific amino acids within the protein. Accordingly it is within the skill of those in the art to identify amino acids suitable for substitution and to design variants with substantially unaltered, improved, or decreased activity with no more than routine experimentation.

In certain embodiments, a polypeptide variant is distinguished from a reference polypeptide by one or more substitutions, which may be conservative or non-conservative, as described herein and known in the art. In certain embodiments, the polypeptide variant comprises conservative substitutions and, in this regard, it is well understood in the art that some amino acids may be changed to others with broadly similar properties without changing the nature of the activity of the polypeptide.

Specific examples of DRS polypeptide variants useful in any of the methods and compositions of the invention include full-length DRS polypeptides, or truncations or splice variants thereof (e.g., any of the proteins or nucleic acids listed in or derivable from Tables D1 to D9 which i) optionally retain detectable non canonical activity and ii) have one or more additional amino acid substitutions, insertions, or deletions). In certain embodiments, a variant polypeptide includes an amino acid sequence having at least about 50%, 55%, 60%, 65%, 70%, 75%, 80%, 85%, 90%, 91%, 92%, 93%, 94%, 95%, 96%, 97%, 98% or more sequence identity or similarity to a corresponding sequence of a DRS reference polypeptide, as described herein (e.g., any of the proteins or nucleic acids listed in or derivable from Tables D1 to D9 and substantially retains the non-canonical activity of that reference polypeptide). Also included are sequences differing from the reference DRS sequences by the addition, deletion, or substitution of 1, 2, 3, 4, 5, 6, 7, 8, 9, 10, 11, 12, 13, 14, 15, 16, 17, 18, 19, 20, 30, 40, 50, 60, 70, 80, 90, 100, 110, 120, 130, 140, 150 or more amino acids but which retain the properties of the reference DRS polypeptide. In certain embodiments, the amino acid additions or deletions occur at the C-terminal end and/or the N-terminal end of the DRS reference polypeptide. In certain embodiments, the amino acid additions include 1, 2, 3, 4, 5, 6, 7, 8, 9, 10, 11, 12, 13, 14, 15, 16, 17, 18, 19, 20, 30, 40, 50 or more wild-type residues (e.g., from the corresponding full-length DRS polypeptide or a polypeptide listed in or derivable from Tables D1 to D9) that are proximal to the C-terminal end and/or the N-terminal end of the DRS reference polypeptide.

Certain illustrative embodiments comprise a DRS polypeptide fragment that ranges in size from about 20-50, 20-100, 20-150, 20-200, 20-250, 20-300, 20-400, or 20-500 amino acids in length. In other embodiments, the DRS polypeptide fragment ranges in size from about 50-100, 50-150, 50-200, 50-250, 50-300, 50-400, or 50-500 amino acids in length. In other embodiments, the DRS polypeptide fragment ranges in size from about 100-120, 100-130, 100-140, 100-150, 100-200, 100-250, 100-300, 100-400, or 100-500 amino acids in length, or from about 130-150, 150-175, 150-200, 150-250, 150-300, 150-400, or 150-500 amino acids in length. In still other illustrative embodiments, the DRS polypeptide fragment ranges in size from about 200-300, 200-250, 200-400, or 200-500 amino acids in length. In some embodiments, the DRS polypeptide or fragment will comprise or consists essentially of the amino acids 1-224, 1-184, 1-174, 1-171, 1-154, 11-146, 13-146, or 23-154 of the DRS polypeptide sequence set forth in SEQ ID NO:1, optionally comprising at least one mutation at either Cys76 or Cys130 (using the numbering of SEQ ID NO:1), and variants thereof. Certain embodiments comprise a polypeptide fragment of the full-length aspartyl-tRNA synthetase of up to about 50, 60, 70, 80, 90, 100, 110, 120, 130, 140, 150, 160, 170, 180, 190, 200, 210, 220, 230, 240, 250 or more amino acids, which comprises, or consists essentially of the amino acids 1-224, 1-184, 1-174, 1-171, 1-154, 11-146, 13-146, or 23-154 of the DRS polypeptide sequence set forth in SEQ ID NO:1, optionally comprising at least one mutation at either Cys76 or Cys130 (using the numbering of SEQ ID NO:1), and variants thereof.

In certain embodiments, a DRS polypeptide of the invention comprises the minimal active fragment of a full-length DRS polypeptide capable of modulating TLR activity etc., in vivo or having other desirable non-canonical aspartyl-tRNA synthetase activities. In one aspect, such a minimal active fragment consists essentially of the anticodon binding domain (e.g., about amino acids 23-154 or 13-146 of SEQ ID NO:1). In certain embodiments, the DRS polypeptide comprises an amphiphilic helix, such as the N-terminal amphiphilic helix of about residues 1-22 of SEQ ID NO:1, and/or an OB fold domain. In some aspects, the minimal active fragment consists essentially of the anticodon binding domain anticodon binding domain, and N-terminal amphiphilic helix (e.g., about amino acids 1-154 of SEQ ID NO:1). In some aspects, of either of these embodiments, the minimal active fragment consists essentially of the anticodon binding domain anticodon binding domain, and N-terminal amphiphilic helix and a variable amount of the flexible 29 amino acid linker (e.g., amino acids 154 to 182 of SEQ ID NO:1). In different embodiments, such minimal active fragments may comprise 1, 2, 3, 4, 5, 6, 7, 8, 9, 10, 11, 12, 13, 14, 15, 16, 17, 18, 19, 20, 21, 22, 23, 24, 25, 26, 27, 28, or all 29 amino acids of the flexible linker.

Without wishing to be bound by any one theory, the unique orientation, or conformation, of the anticodon-recognition domain in certain DRS polypeptides may contribute to the enhanced non canonical activities observed in these proteins. In certain embodiments, non-canonical activity may be modulated by the selective deletion, in whole or part of the Amphiphilic helix domain, anticodon-recognition domain, or the aminoacylation domain. Specific examples of splice variants that accomplish such embodiments include for example AspRS1$^{N6}$ and AspRS1$^{C2}$ (partial deletion of the anticodon binding domain), AspRS1$^{N7}$ (partial deletion of both the anticodon binding domain and aminoacylation domain), AspRS1$^{N7}$ (partial deletion of the aminoacylation domain). In some embodiments of the present invention, all such DRS polypeptides comprise at least one mutation at Cys76, Cys130, Cys 203, Cys259, Cys334, or Cys349 (using the numbering of SEQ ID NO:1).

The recitations "sequence identity" or, for example, comprising a "sequence 50% identical to," as used herein, refer to the extent that sequences are identical on a nucleotide-by-nucleotide basis or an amino acid-by-amino acid basis over a window of comparison. Thus, a "percentage of sequence identity" may be calculated by comparing two optimally aligned sequences over the window of comparison, determining the number of positions at which the identical nucleic acid base (e.g., A, T, C, G, I) or the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity.

Terms used to describe sequence relationships between two or more polypeptides include "reference sequence," "comparison window," "sequence identity," "percentage of sequence identity" and "substantial identity." A "reference sequence" is at least 12 but frequently 15 to 18 and often at least 25 monomer units, inclusive of nucleotides and amino acid residues, in length. Because two polypeptides may each comprise (1) a sequence (i.e., only a portion of the complete polypeptides sequence) that is similar between the two polypeptides, and (2) a sequence that is divergent between the two polypeptides, sequence comparisons between two (or more) polypeptides are typically performed by comparing sequences of the two polypeptides over a "comparison window" to identify and compare local regions of sequence similarity. A "comparison window" refers to a conceptual segment of at least 6 contiguous positions, usually about 50 to about 100, more usually about 100 to about 150 in which a sequence is compared to a reference sequence of the same number of contiguous positions after the two sequences are optimally aligned. The comparison window may comprise additions or deletions (i.e., gaps) of about 20% or less as compared to the reference sequence (which does not comprise additions or deletions) for optimal alignment of the two sequences. Optimal alignment of sequences for aligning a comparison window may be conducted by computerized implementations of algorithms (GAP, BESTFIT, FASTA, and TFASTA in the Wisconsin Genetics Software Package Release 7.0, Genetics Computer Group, 575 Science Drive Madison, Wis., USA) or by inspection and the best alignment (i.e., resulting in the highest percentage homology over the comparison window) generated by any of the various methods selected. Reference also may be made to the BLAST family of programs as for example disclosed by Altschul et al., *Nucl. Acids Res.* 25:3389, 1997. A detailed discussion of sequence analysis can be found in Unit 19.3 of Ausubel et al., "Current Protocols in Molecular Biology," John Wiley & Sons Inc, 1994-1998, Chapter 15.

Calculations of sequence similarity or sequence identity between sequences (the terms are used interchangeably herein) can be performed as follows. To determine the percent identity of two amino acid sequences, or of two nucleic acid sequences, the sequences can be aligned for optimal comparison purposes (e.g., gaps can be introduced in one or both of a first and a second amino acid or nucleic acid sequence for optimal alignment and non-homologous sequences can be disregarded for comparison purposes). In certain embodiments, the length of a reference sequence aligned for comparison purposes is at least 30%, preferably at least 40%, more preferably at least 50%, 60%, and even more preferably at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position.

The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch, (1970, *J. Mol. Biol.* 48: 444-453) algorithm which has been incorporated into the GAP program in the GCG software package, using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package, using a NWSgapdna.CMP matrix and a gap weight of 40, 50, 60, 70, or 80 and a length weight of 1, 2, 3, 4, 5, or 6. A particularly preferred set of parameters (and the one that should be used unless otherwise specified) are a Blossum 62 scoring matrix with a gap penalty of 12, a gap extend penalty of 4, and a frameshift gap penalty of 5. The percent identity between two amino acid or nucleotide sequences can also be determined using the algorithm of E. Meyers and W. Miller (1989, *Cabios*, 4: 11-17) which has been incorporated into the ALIGN program (version 2.0), using a PAM120 weight residue table, a gap length penalty of 12 and a gap penalty of 4.

The nucleic acid and protein sequences described herein can be used as a "query sequence" to perform a search against public databases to, for example, identify other family members or related sequences. Such searches can be performed using the NBLAST and XBLAST programs (version 2.0) of Altschul, et al., (*J. Mol. Biol*, 215: 403-10, 1990). BLAST nucleotide searches can be performed with the NBLAST program, score=100, wordlength=12 to obtain nucleotide sequences homologous to nucleic acid molecules of the invention. BLAST protein searches can be performed with the XBLAST program, score=50, wordlength=3 to obtain amino acid sequences homologous to protein molecules of the invention. To obtain gapped alignments for comparison purposes, Gapped BLAST can be utilized as described in Altschul et al., (*Nucleic Acids Res*, 25: 3389-3402, 1997). When utilizing BLAST and Gapped BLAST programs, the default parameters of the respective programs (e.g., XBLAST and NBLAST) can be used.

In certain embodiments, variant polypeptides differ from the corresponding DRS reference sequences by at least 1% but less than 20%, 15%, 10% or 5% of the residues. (If this comparison requires alignment, the sequences should be aligned for maximum similarity. "Looped" out sequences from deletions or insertions, or mismatches, are considered differences.) The differences are, suitably, differences or changes at a non-essential residue or a conservative substitution. In certain embodiments, the molecular weight of a variant DRS polypeptide differs from that of the DRS reference polypeptide by about 1%, 2%, 3%, 4%, 5%, 6%, 7%, 8%, 9%, 10%, 11%, 12%, 13%, 14%, 15%, 16%, 17%, 18%, 19%, 20%, or more.

In one embodiment, as noted above, polynucleotides and/or polypeptides can be evaluated using a BLAST alignment tool. A local alignment consists simply of a pair of sequence segments, one from each of the sequences being compared. A modification of Smith-Waterman or Sellers algorithms will find all segment pairs whose scores cannot be improved by extension or trimming, called high-scoring segment pairs (HSPs). The results of the BLAST alignments include statistical measures to indicate the likelihood that the BLAST score can be expected from chance alone.

The raw score, S, is calculated from the number of gaps and substitutions associated with each aligned sequence wherein higher similarity scores indicate a more significant alignment. Substitution scores are given by a look-up table (see PAM, BLOSUM).

Gap scores are typically calculated as the sum of G, the gap opening penalty and L, the gap extension penalty. For a gap of length n, the gap cost would be G+Ln. The choice of gap costs, G and L is empirical, but it is customary to choose a high value for G (10-15), e.g., 11, and a low value for L (1-2) e.g., 1.

The bit score, S', is derived from the raw alignment score S in which the statistical properties of the scoring system used have been taken into account. Bit scores are normalized with respect to the scoring system, therefore they can be used to compare alignment scores from different searches. The terms "bit score" and "similarity score" are used interchangeably. The bit score gives an indication of how good the alignment is; the higher the score, the better the alignment.

The E-Value, or expected value, describes the likelihood that a sequence with a similar score will occur in the database by chance. It is a prediction of the number of different alignments with scores equivalent to or better than S that are expected to occur in a database search by chance. The smaller the E-Value, the more significant the alignment. For example, an alignment having an E value of $e^{-117}$ means that a sequence with a similar score is very unlikely to occur simply by chance. Additionally, the expected score for aligning a random pair of amino acids is required to be negative, otherwise long alignments would tend to have high score independently of whether the segments aligned were related. Additionally, the BLAST algorithm uses an appropriate substitution matrix, nucleotide or amino acid and for gapped alignments uses gap creation and extension penalties. For example, BLAST alignment and comparison of polypeptide sequences are typically done using the BLOSUM62 matrix, a gap existence penalty of 11 and a gap extension penalty of 1.

In one embodiment, sequence similarity scores are reported from BLAST analyses done using the BLOSUM62 matrix, a gap existence penalty of 11 and a gap extension penalty of 1.

In a particular embodiment, sequence identity/similarity scores provided herein refer to the value obtained using GAP Version 10 (GCG, Accelrys, San Diego, Calif.) using the following parameters: % identity and % similarity for a nucleotide sequence using GAP Weight of 50 and Length Weight of 3, and the nwsgapdna.cmp scoring matrix; % identity and % similarity for an amino acid sequence using GAP Weight of 8 and Length Weight of 2, and the BLOSUM62 scoring matrix (Henikoff and Henikoff, PNAS USA. 89:10915-10919, 1992). GAP uses the algorithm of Needleman and Wunsch (1970) J Mol Biol 48:443-453, to find the alignment of two complete sequences that maximizes the number of matches and minimizes the number of gaps.

In one particular embodiment, the DRS polypeptides comprise an amino acid sequence that can be optimally aligned with a DRS reference polypeptide sequence described herein (e.g., amino acid residues 1-224, 1-184, 1-174, 1-171, 1-154, 11-146, 13-146, or 23-154 of the DRS polypeptide sequence set forth in SEQ ID NO:1, optionally comprising at least one mutation at either Cys76 or Cys130 (using the numbering of SEQ ID NO:1); or any one of SEQ ID NOS:1, 3-24, 29, 31, or 154-197) to generate a BLAST bit scores or sequence similarity scores of at least about 50, 60, 70, 80, 90, 100, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, or more, including all integers and ranges in between, wherein the BLAST alignment used the BLOSUM62 matrix, a gap existence penalty of 11, and a gap extension penalty of 1.

Also included are biologically active "fragments" of the DRS reference polypeptides, i.e., biologically active fragments of the DRS protein fragments. Representative biologically active fragments generally participate in an interaction, e.g., an intramolecular or an inter-molecular interaction. An inter-molecular interaction can be a specific binding interaction or an enzymatic interaction. An inter-molecular interaction can be between a DRS polypeptide and a cellular binding partner, such as a cellular receptor or other host molecule that participates in the non-canonical activity of the DRS polypeptide.

A biologically active fragment of a DRS reference polypeptide can be a polypeptide fragment which is, for example, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100, 110, 120, 130, 140, 150, 160, 170, 180, 190, 200, 220, 240, 260, 280, 300, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 38, 359, 360, 361, 362, 363, 364, 365, 380, 400, 450, 500 or more contiguous or non-contiguous amino acids, including all integers (e.g., 101, 102, 103) and ranges (e.g., 50-100, 50-150, 50-200) in between, of the amino acid sequences set forth in any one of the DRS reference polypeptides described herein. In certain embodiments, a biologically active fragment comprises a non-canonical activity-related sequence, domain, or motif. In certain embodiments, the C-terminal or N-terminal region of any DRS reference polypeptide may be truncated by about 1, 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, 110, 120, 130, 140, 150, 160, 170, 180, 190, 200, 250, 300, 350, 400, 450, 500 or more amino acids, or by about 10-50, 20-50, 50-100, 100-150, 150-200, 200-250, 250-300, 300-350, 350-400, 400-450, 450-500 or more amino acids, including all integers and ranges in between (e.g., 101, 102, 103, 104, 105), so long as the truncated DRS polypeptide retains the non-canonical activity of the reference polypeptide. Typically, the biologically-active fragment has no less than about 1%, 10%, 25%, or 50% of an activity of the biologically-active (i.e., non-canonical activity) DRS reference polypeptide from which it is derived. Exemplary methods for measuring such non-canonical activities are described in the Examples.

In some embodiments, DRS proteins, variants, and biologically active fragments thereof, bind to one or more cellular binding partners with an affinity of at least about 0.01, 0.05, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 50, 100, or 150 nM. In some embodiments, the binding affinity of a DRS protein fragment for a selected cellular binding partner, particularly a binding partner that participates in a non-canonical activity, can be stronger than that of the corresponding full length DRS polypeptide or a specific alternatively spliced DRS polypeptide variant, by at least about 1.5×, 2×, 2.5×, 3×, 3.5×, 4×, 4.5×, 5×, 6×, 7×, 8×, 9×, 10×, 15×, 20×, 25×, 30×, 40×, 50×, 60×, 70×, 80×, 90×, 100×, 200×, 300×, 400×, 500×, 600×, 700×, 800×, 900×, 1000× or more (including all integers in between).

As noted above, a DRS polypeptide may be altered in various ways including amino acid substitutions, deletions, truncations, and insertions. Methods for such manipulations are generally known in the art. For example, amino acid sequence variants of a DRS reference polypeptide can be prepared by mutations in the DNA. Methods for mutagenesis and nucleotide sequence alterations are well known in the art. See, for example, Kunkel (Proc. Natl. Acad. Sci. USA. 82: 488-492, 1985), Kunkel et al., (Methods in Enzymol. 154: 367-382, 1987), U.S. Pat. No. 4,873,192, Watson, J. D. et al., ("Molecular Biology of the Gene," Fourth Edition, Benjamin/Cummings, Menlo Park, Calif., 1987) and the references cited therein. Guidance as to appropriate amino acid substitutions that do not affect biological activity of the protein of interest may be found in the model of Dayhoff et al., (1978) Atlas of Protein Sequence and Structure (Natl. Biomed. Res. Found., Washington, D.C.).

Biologically active truncated and/or variant DRS polypeptides may contain conservative amino acid substitutions at various locations along their sequence, as compared to a reference DRS amino acid residue, and such additional substitutions may further enhance the activity or stability of the DRS polypeptides with altered cysteine content. A "conservative amino acid substitution" is one in which the amino acid residue is replaced with an amino acid residue having a similar side chain. Families of amino acid residues having similar side chains have been defined in the art, which can be generally sub-classified as follows:

Acidic: The residue has a negative charge due to loss of H ion at physiological pH and the residue is attracted by aqueous solution so as to seek the surface positions in the conformation of a peptide in which it is contained when the peptide is in aqueous medium at physiological pH. Amino acids having an acidic side chain include glutamic acid and aspartic acid.

Basic: The residue has a positive charge due to association with H ion at physiological pH or within one or two pH units thereof (e.g., histidine) and the residue is attracted by aqueous solution so as to seek the surface positions in the conformation of a peptide in which it is contained when the peptide is in aqueous medium at physiological pH. Amino acids having a basic side chain include arginine, lysine and histidine.

Charged: The residues are charged at physiological pH and, therefore, include amino acids having acidic or basic side chains (i.e., glutamic acid, aspartic acid, arginine, lysine and histidine).

Hydrophobic: The residues are not charged at physiological pH and the residue is repelled by aqueous solution so as to seek the inner positions in the conformation of a peptide in which it is contained when the peptide is in aqueous medium Amino acids having a hydrophobic side chain include tyrosine, valine, isoleucine, leucine, methionine, phenylalanine and tryptophan.

Neutral/polar: The residues are not charged at physiological pH, but the residue is not sufficiently repelled by aqueous solutions so that it would seek inner positions in the conformation of a peptide in which it is contained when the peptide is in aqueous medium. Amino acids having a neutral/polar side chain include asparagine, glutamine, cysteine, histidine, serine and threonine.

This description also characterizes certain amino acids as "small" since their side chains are not sufficiently large, even if polar groups are lacking, to confer hydrophobicity. With the exception of proline, "small" amino acids are those with four carbons or less when at least one polar group is on the side chain and three carbons or less when not Amino acids having a small side chain include glycine, serine, alanine and threonine. The gene-encoded secondary amino acid proline is a special case due to its known effects on the secondary conformation of peptide chains. The structure of proline differs from all the other naturally-occurring amino acids in that its side chain is bonded to the nitrogen of the α-amino group, as well as the α-carbon. Several amino acid similarity matrices are known in the art (see e.g., PAM120 matrix and PAM250 matrix as disclosed for example by Dayhoff et al., 1978, A model of evolutionary change in proteins). Matrices for determining distance relationships In M. O. Dayhoff, (ed.), Atlas of protein sequence and structure, Vol. 5, pp. 345-358, National Biomedical Research Foundation, Washington D.C.; and by Gonnet et al., (Science. 256: 14430-1445, 1992), however, include proline in the same group as glycine, serine, alanine and threonine. Accordingly, for the purposes of the present invention, proline is classified as a "small" amino acid.

The degree of attraction or repulsion required for classification as polar or nonpolar is arbitrary and, therefore, amino acids specifically contemplated by the invention have been classified as one or the other. Most amino acids not specifically named can be classified on the basis of known behavior.

Amino acid residues can be further sub-classified as cyclic or non-cyclic, and aromatic or non-aromatic, self-explanatory classifications with respect to the side-chain substituent groups of the residues, and as small or large. The residue is considered small if it contains a total of four carbon atoms or less, inclusive of the carboxyl carbon, provided an additional polar substituent is present; three or less if not. Small residues are, of course, always non-aromatic. Dependent on their structural properties, amino acid residues may fall in two or more classes. For the naturally-occurring protein amino acids, sub-classification according to this scheme is presented in Table A.

TABLE A

Amino acid sub-classification

| Sub-classes | Amino acids |
|---|---|
| Acidic | Aspartic acid, Glutamic acid |
| Basic | Noncyclic: Arginine, Lysine; Cyclic: Histidine |
| Charged | Aspartic acid, Glutamic acid, Arginine, Lysine, Histidine |
| Small | Glycine, Serine, Alanine, Threonine, Proline |
| Polar/neutral | Asparagine, Histidine, Glutamine, Cysteine, Serine, Threonine |
| Polar/large | Asparagine, Glutamine |
| Hydrophobic | Tyrosine, Valine, Isoleucine, Leucine, Methionine, Phenylalanine, Tryptophan |
| Aromatic | Tryptophan, Tyrosine, Phenylalanine |
| Residues that influence chain orientation | Glycine and Proline |

Conservative amino acid substitution also includes groupings based on side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulphur-containing side chains is cysteine and methionine. For example, it is reasonable to expect that replacement of a leucine with an isoleucine or valine, an aspartate with a glutamate, a threonine with a serine, or a similar replacement of an amino acid with a structurally related amino acid will not have a major effect on the properties of the resulting variant polypeptide. Whether an amino acid change results in a functional truncated and/or variant DRS polypeptide can readily be determined by assaying its non-canonical activity, as described herein. Conservative substitutions are shown in Table B under the heading of exemplary substitutions. Amino acid substitutions falling within the scope of the invention, are, in general, accomplished by selecting substitutions that do not differ significantly in their effect on maintaining (a) the structure of the peptide backbone in the area of the substitution, (b) the charge or hydrophobicity of the molecule at the target site, (c) the bulk of the side chain, or (d) the biological function. After the substitutions are introduced, the variants are screened for biological activity.

TABLE B

Exemplary Amino Acid Substitutions

| Original Residue | Exemplary Substitutions | Preferred Substitutions |
|---|---|---|
| Ala | Val, Leu, Ile | Val |
| Arg | Lys, Gln, Asn | Lys |
| Asn | Gln, His, Lys, Arg | Gln |
| Asp | Glu | Glu |
| Cys | Ser, Ala, Val | Ser |
| Gln | Asn, His, Lys, | Asn |
| Glu | Asp, Lys | Asp |
| Gly | Pro | Pro |
| His | Asn, Gln, Lys, Arg | Arg |
| Ile | Leu, Val, Met, Ala, Phe, Norleu | Leu |
| Leu | Norleu, Ile, Val, Met, Ala, Phe | Ile |
| Lys | Arg, Gln, Asn | Arg |
| Met | Leu, Ile, Phe | Leu |
| Phe | Leu, Val, Ile, Ala | Leu |
| Pro | Gly | Gly |
| Ser | Thr | Thr |

TABLE B-continued

Exemplary Amino Acid Substitutions

| Original Residue | Exemplary Substitutions | Preferred Substitutions |
|---|---|---|
| Thr | Ser | Ser |
| Trp | Tyr | Tyr |
| Tyr | Trp, Phe, Thr, Ser | Phe |
| Val | Ile, Leu, Met, Phe, Ala, Norleu | Leu |

Alternatively, similar amino acids for making conservative substitutions can be grouped into three categories based on the identity of the side chains. The first group includes glutamic acid, aspartic acid, arginine, lysine, histidine, which all have charged side chains; the second group includes glycine, serine, threonine, cysteine, tyrosine, glutamine, asparagine; and the third group includes leucine, isoleucine, valine, alanine, proline, phenylalanine, tryptophan, methionine, as described in Zubay, G., *Biochemistry*, third edition, Wm.C. Brown Publishers (1993).

Thus, a predicted non-essential amino acid residue in a truncated and/or variant DRS polypeptide is typically replaced with another amino acid residue from the same side chain family. Alternatively, mutations can be introduced randomly along all or part of a DRS coding sequence, such as by saturation mutagenesis, and the resultant mutants can be screened for an activity of the parent polypeptide to identify mutants which retain that activity. Following mutagenesis of the coding sequences, the encoded peptide can be expressed recombinantly and the activity of the peptide can be determined A "non-essential" amino acid residue is a residue that can be altered from the reference sequence of an embodiment polypeptide without abolishing or substantially altering one or more of its non canonical activities. Suitably, the alteration does not substantially abolish one of these activities, for example, the activity is at least 20%, 40%, 60%, 70% or 80% 100%, 500%, 1000% or more of the reference DRS sequence. An "essential" amino acid residue is a residue that, when altered from the reference sequence of a DRS polypeptide, results in abolition of an activity of the parent molecule such that less than 20% of the reference activity is present. For example, such essential amino acid residues include those that are conserved in DRS polypeptides across different species, including those sequences that are conserved in the active binding site(s) or motif(s) of DRS polypeptides from various sources.

DRS polypeptides may have one or more cysteine substitutions, where one or more naturally-occurring (non-cysteine) residues are substituted with cysteine, for example, to facilitate thiol-based attachment of other molecules. In some embodiments, cysteine substitutions are near the N-terminus and/or C-terminus of the DRS polypeptide (e.g., SEQ ID NOS: 1, 3-24, 29, 31, or 154-197). Particular embodiments include where one or more of residues within 0, 1, 2, 3, 4, 5, 6, 7, 8, 9, 10, 11, 12, 13, 14, 15, 16, 17, 18, 19, 20, 21, 22, 23, 24, or 25 amino acids relative to the N-terminus and/or C-terminus of any one of SEQ ID NOS:1, 3-24, 29, 31, or 154-197 are substituted with a cysteine residue. In some embodiments, cysteine residues may be added to the DRS polypeptide through the creation of N-terminal, or C-terminal fusion proteins. Such fusion proteins may be of any length, but will typically be about 1-5, or about 5-10, about 10 to 20, or about 20 to 30 amino acids in length. In some embodiments, fusion to the C-terminus is preferred.

Specific embodiments of such DRS polypeptides with an N-terminal cysteine substitution, include for example, those with a cysteine substitution within the first 23 amino acids, including the DRS polypeptides of any of SEQ ID NOS: 1, 3-24, 29, 31, or 154-197. Specific embodiments of such DRS polypeptides with a C-terminal cysteine substitution include for example, those with a cysteine substitution with the last 20 amino acids, including the DRS polypeptides of any of SEQ ID NOs: 1, 3-24, 29, 31, or 154-197.

These and related DRS polypeptides may also have additional substitutions at C76 and/or C130, to remove naturally-occurring cysteine residues. Specific embodiments include any one of SEQ ID NOS:1, 3-24, 29, 31, or 154-197, or variants thereof, having at mutation at C76 and/or C130. Exemplary mutations at these positions include for example the mutation of cysteine to serine, alanine, leucine, or glycine. Various exemplary proteins with reduced cysteine content are listed in Table D7.

TABLE D7

| Exemplary Variants with reduced cysteine content | | | |
|---|---|---|---|
| Name | Amino Acid Residue Range of SEQ ID NO: 1 | Amino acid sequence | SEQ ID NO: |
| AspRS1$^{N1}$ (C76S) | 1-154 | MPSASASRKSQEKPREIMDAAEDYAKERYGISSMIQSQEKPDRV<br>LVRVRDLTIQKADEVVWVRARVHTSRAKGKQSFLVLRQQQFN<br>VQALVAVGDHASKQMVKFAANINKESIVDVEGVVRKVNQKIGS<br>CTQQDVELHVQKIYVISLAEPRLPL | 22 |
| AspRS1$^{N1}$ (C130S) | 1-154 | MPSASASRKSQEKPREIMDAAEDYAKERYGISSMIQSQEKPDRV<br>LVRVRDLTIQKADEVVWVRARVHTSRAKGKQCFLVLRQQQFN<br>VQALVAVGDHASKQMVKFAANINKESIVDVEGVVRKVNQKIGS<br>STQQDVELHVQKIYVISLAEPRLPL | 23 |
| AspRS1$^{N1}$ (C76S, C130S) | 1-154 | MPSASASRKSQEKPREIMDAAEDYAKERYGISSMIQSQEKPDRV<br>LVRVRDLTIQKADEVVWVRARVHTSRAKGKQSFLVLRQQQFN<br>VQALVAVGDHASKQMVKFAANINKESIVDVEGVVRKVNQKIGS<br>STQQDVELHVQKIYVISLAEPRLPL | 24 |
| DRS C334S | 1-501 | MPSASASRKSQEKPREIMDAAEDYAKERYGISSMIQSQEKPDRV<br>LVRVRDLTIQKADEVVWVRARVHTSRAKGKQCFLVLRQQQFN<br>VQALVAVGDHASKQMVKFAANINKESIVDVEGVVRKVNQKIGS<br>CTQQDVELHVQKIYVISLAEPRLPLQLDDAVRPEAEGEEEGRAT | 189 |

TABLE D7-continued Exemplary Variants with reduced cysteine content

| Name | Amino Acid Residue Range of SEQ ID NO: 1 | Amino acid sequence | SEQ ID NO: |
|---|---|---|---|
| | | VNQDTRLDNRVIDLRTSTSQAVFRLQSGICHLFRETLINKGFVEI QTPKIISAASEGGANVFTSYFKNNAYLAQSPQLYKQMCICADF EKVFSIGPVFRAEDSNTHRHLTEFVGLDIEMAFNYHYEVMEEI ADTMVQIFKGLQERFQTEIQTVNKQFPSEPPFKFLEPTLRLEYCEA LAMLREAGVEMGDEDDLSTPNEKLLGHLVKEKYDTDFYILDKY PLAVRPFYTMPDPRNPKQSNSYDMFMRGEEILSGAQRIHDPQLL TERALHHGIDLEKIKAYIDSFRFGAPPHAGGGIGLERVTMLFLGL HNVRQTSMFPRDPKRLTP | |
| DRS C349S | 1-501 | MPSASASRKSQEKPREIMDAAEDYAKERYGISSMIQSQEKPDRV LVRVRDLTIQKADEVVWVRARVHTSRAKGKQCFLVLRQQQFN VQALVAVGDHASKQMVKFAANINKESIVDVEGVVRKVNQKIGS CTQQDVELHVQKIYVISLAEPRLPLQLDDAVRPEAEGEEEGRAT VNQDTRLDNRVIDLRTSTSQAVFRLQSGICHLFRETLINKGFVEI QTPKIISAASEGGANVFTSYFKNNAYLAQSPQLYKQMCICADF EKVFSIGPVFRAEDSNTHRHLTEFVGEDIEMAFNYHYEVMEEI ADTMVQIFKGLQERFQTEIQTVNKQFPCEPPFKFLEPTLRLEYSEA LAMLREAGVEMGDEDDLSTPNEKLLGHLVKEKYDTDFYILDKY PLAVRPFYTMPDPRNPKQSNSYDMFMRGEEILSGAQRIHDPQLL TERALHHGIDEEKIKAYIDSFRFGAPPHAGGGIGLERVTMLFLGL HNVRQTSMFPRDPKRLTP | 190 |
| DRS C334S/C349S | 1-501 | MPSASASRKSQEKPREIMDAAEDYAKERYGISSMIQSQEKPDRV LVRVRDLTIQKADEVVWVRARVHTSRAKGKQCFLVLRQQQFN VQALVAVGDHASKQMVKFAANINKESIVDVEGVVRKVNQKIGS CTQQDVELHVQKIYVISLAEPRLPLQLDDAVRPEAEGEEEGRAT VNQDTRLDNRVIDLRTSTSQAVFRLQSGICHLFRETLINKGFVEI QTPKIISAASEGGANVFTSYFKNNAYLAQSPQLYKQMCICADF EKVFSIGPVFRAEDSNTHRHLTEFVGEDIEMAFNYHYEVMEEI ADTMVQIFKGLQERFQTEIQTVNKQFPSEPPFKFLEPTLRLEYSEA LAMLREAGVEMGDEDDLSTPNEKLLGHLVKEKYDTDFYILDKY PLAVRPFYTMPDPRNPKQSNSYDMFMRGEEILSGAQRIHDPQLL TERALHHGIDEEKIKAYIDSFRFGAPPHAGGGIGLERVTMLFLGL HNVRQTSMFPRDPKRLTP | 191 |
| DRS C203A | 1-501 | MPSASASRKSQEKPREIMDAAEDYAKERYGISSMIQSQEKPDRV LVRVRDLTIQKADEVVWVRARVHTSRAKGKQCFLVLRQQQFN VQALVAVGDHASKQMVKFAANINKESIVDVEGVVRKVNQKIGS CTQQDVELHVQKIYVISLAEPRLPLQLDDAVRPEAEGEEEGRAT VNQDTRLDNRVIDLRTSTSQAVFRLQSGIAHLFRETLINKGFVEI QTPKIISAASEGGANVFTSYFKNNAYEAQSPQLYKQMCICADF EKVFSIGPVFRAEDSNTHRHLTEFVGLDIEMAFNYHYEVMEEI ADTMVQIFKGLQERFQTEIQTVNKQFPCEPPFKFLEPTLRLEYCEA LAMLREAGVEMGDEDDLSTPNEKLLGHLVKEKYDTDFYILDKY PLAVRPFYTMPDPRNPKQSNSYDMFMRGEEILSGAQRIHDPQLL TERALHHGIDLEKIKAYIDSFRFGAPPHAGGGIGLERVTMLFLGL HNVRQTSMFPRDPKRLTP | 192 |
| DRS C203V | 1-501 | MPSASASRKSQEKPREIMDAAEDYAKERYGISSMIQSQEKPDRV LVRVRDLTIQKADEVVWVRARVHTSRAKGKQCFLVLRQQQFN VQALVAVGDHASKQMVKFAANINKESIVDVEGVVRKVNQKIGS CTQQDVELHVQKIYVISLAEPRLPLQLDDAVRPEAEGEEEGRAT VNQDTRLDNRVIDLRTSTSQAVFRLQSGIVHLFRETLINKGFVEI QTPKIISAASEGGANVFTSYFKNNAYLAQSPQLYKQMCICADF EKVFSIGPVFRAEDSNTHRHLTEFVGLDIEMAFNYHYEVMEEI ADTMVQIFKGLQERFQTEIQTVNKQFPCEPPFKFLEPTLRLEYCEA LAMLREAGVEMGDEDDLSTPNEKLLGHLVKEKYDTDFYILDKY PLAVRPFYTMPDPRNPKQSNSYDMFMRGEEILSGAQRIHDPQLL TERALHHGIDLEKIKAYIDSFRFGAPPHAGGGIGLERVTMLFLGL HNVRQTSMFPRDPKRLTP | 193 |
| DRS C334S/C349S/C203A | 1-501 | MPSASASRKSQEKPREIMDAAEDYAKERYGISSMIQSQEKPDRV LVRVRDLTIQKADEVVWVRARVHTSRAKGKQCFLVLRQQQFN VQALVAVGDHASKQMVKFAANINKESIVDVEGVVRKVNQKIGS CTQQDVELHVQKIYVISLAEPRLPLQLDDAVRPEAEGEEEGRAT VNQDTRLDNRVIDLRTSTSQAVFRLQSGIAHLFRETLINKGFVEI QTPKIISAASEGGANVFTSYFKNNAYLAQSPQLYKQMCICADF EKVFSIGPVFRAEDSNTHRHLTEFVGLDIEMAFNYHYEVMEEI ADTMVQIFKGLQERFQTEIQTVNKQFPSEPPFKFLEPTLRLEYSEA LAMLREAGVEMGDEDDLSTPNEKLLGHLVKEKYDTDFYILDKY PLAVRPFYTMPDPRNPKQSNSYDMFMRGEEILSGAQRIHDPQLL | 194 |

TABLE D7-continued

Exemplary Variants with reduced cysteine content

| Name | Amino Acid Residue Range of SEQ ID NO: 1 | Amino acid sequence | SEQ ID NO: |
|---|---|---|---|
| | | TERALHHGIDLEKIKAYIDSFRFGAPPHAGGGIGLERVTMLFLGL HNVRQTSMFPRDPKRLTP | |
| DRS C334S/C349S/C203V | 1-501 | MPSASASRKSQEKPREIMDAAEDYAKERYGISSMIQSQEKPDRV LVRVRDLTIQKADEVVWVRARVHTSRAKGKQCFLVLRQQQFN VQALVAVGDHASKQMVKFAANINKESIVDVEGVVRKVNQKIGS CTQQDVELHVQKIYVISLAEPRLPLQLDDAVRPEAEGEEEGRAT VNQDTRLDNRVIDLRTSTSQAVFRLQSGIVHLFRETLINKGFVEI QTPKIISAASEGGANVFTVSYFKNNAYLAQSPQLYKQMCIAADF EKVFSIGPVFRAEDSNTHRHLTEFVGLDIEMAFNYHYHEVMEEI ADTMVQIFKGLQERFQTEIQTVNKQFPSEPPFKFLEPTLRLEYSEA LAMLREAGVEMGDEDDLSTPNEKLLGHLVKEKYDTDFYILDKY PLAVRPFYTMPDPRNPKQSNSYDMFMRGEEILSGAQRIHDPQLL TERALHHGIDLEKIKAYIDSFRFGAPPHAGGGIGLERVTMLFLGL HNVRQTSMFPRDPKRLTP | 195 |
| DRS C334S/C349S/C259A/C203A | 1-501 | MPSASASRKSQEKPREIMDAAEDYAKERYGISSMIQSQEKPDRV LVRVRDLTIQKADEVVWVRARVHTSRAKGKQCFLVLRQQQFN VQALVAVGDHASKQMVKFAANINKESIVDVEGVVRKVNQKIGS CTQQDVELHVQKIYVISLAEPRLPLQLDDAVRPEAEGEEEGRAT VNQDTRLDNRVIDLRTSTSQAVFRLQSGIAHLFRETLINKGFVEI QTPKIISAASEGGANVFTVSYFKNNAYLAQSPQLYKQMCIAADF EKVFSIGPVFRAEDSNTHRHLTEFVGLDIEMAFNYHYHEVMEEI ADTMVQIFKGLQERFQTEIQTVNKQFPSEPPFKFLEPTLRLEYSEA LAMLREAGVEMGDEDDLSTPNEKLLGHLVKEKYDTDFYILDKY PLAVRPFYTMPDPRNPKQSNSYDMFMRGEEILSGAQRIHDPQLL TERALHHGIDLEKIKAYIDSFRFGAPPHAGGGIGLERVTMLFLGL HNVRQTSMFPRDPKRLTP | 196 |
| DRS C334S/C349S/C259A/C203V | 1-501 | MPSASASRKSQEKPREIMDAAEDYAKERYGISSMIQSQEKPDRV LVRVRDLTIQKADEVVWVRARVHTSRAKGKQCFLVLRQQQFN VQALVAVGDHASKQMVKFAANINKESIVDVEGVVRKVNQKIGS CTQQDVELHVQKIYVISLAEPRLPLQLDDAVRPEAEGEEEGRAT VNQDTRLDNRVIDLRTSTSQAVFRLQSGIVHLFRETLINKGFVEI QTPKIISAASEGGANVFTVSYFKNNAYLAQSPQLYKQMCIAADF EKVFSIGPVFRAEDSNTHRHLTEFVGLDIEMAFNYHYHEVMEEI ADTMVQIFKGLQERFQTEIQTVNKQFPSEPPFKFLLPTLRLEYSEA LAMLREAGVEMGDEDDLSTPNEKLLGHLVKEKYDTDFYILDKY PLAVRPFYTMPDPRNPKQSNSYDMFMRGEEILSGAQRIHDPQLL TERALHHGIDLEKIKAYIDSFRFGAPPHAGGGIGLERVTMLFLGL HNVRQTSMFPRDPKRLTP | 197 |

DRS polypeptides may have one or more glutamine substitutions, where one or more naturally-occurring (non-glutamine) residues are substituted with glutamine. In some embodiments, glutamine substitutions are introduced near the N-terminus and/or C-terminus of the DRS polypeptide (e.g., SEQ ID NOS:1, 3-24, 29, 31, or 154-197). Particular embodiments include where one or more of residues within 0, 1, 2, 3, 4, 5, 6, 7, 8, 9, 10, 11, 12, 13, 14, 15, 16, 17, 18, 19, 20, 21, 22, 23, 24 or 25 amino acids relative to the N-terminus and/or C-terminus of any one of SEQ ID NOS:1, 3-24, 29, 31, or 154-197 are substituted with a glutamine residue. These and related DRS polypeptides can also include substitutions (e.g., conservative substitutions) to remove any naturally-occurring glutamine residues.

DRS polypeptides may have one or more lysine substitutions, where one or more naturally-occurring (non-lysine) residues are substituted with lysine. In some embodiments, lysine substations are near the N-terminus and/or C-terminus of the DRS polypeptide (e.g., SEQ ID NOS:1, 3-24, 29, 31, or 154-197). Particular embodiments include where one or more of residues within 0, 1, 2, 3, 4, 5, 6, 7, 8, 9, 10, 11, 12, 13, 14, 15, 16, 17, 18, 19, 20, 21, 22, 23, 24 or 25 amino acids to the N-terminus and/or C-terminus of any one of SEQ ID NOS:1, 3-24, 29, 31, or 154-197 are substituted with a lysine residue. These and related DRS polypeptides can also include substitutions (e.g., conservative substitutions) to remove any naturally-occurring lysine residues, if desired.

DRS variants may also be created by substituting one or more solvent accessible surface amino acids of a DRS polypeptide, or alternatively, by avoiding substitution of solvent accessible surface amino acids. Suitable solvent accessible amino acids may be determined based on the predicted solvent accessibility using the SPPIDER server (http://sppider.cchmc.org/) using the published crystal structure of an exemplary DRS polypeptide (WO2010/120509). Based on this analysis several amino acids on the surface may potentially be used as mutation sites, for instance, by conservative substitution to minimize effects on surface interactions, or by non-conservative substitution to interfere with certain surface interactions. The following Table D8 lists the surface accessibility score of amino acids based on the crystal structure above. In this table, the higher scores represent better accessibility. Accordingly in some embodiments an amino acid position selected from Table D8 may used to introduce a cysteine, lysine, glutamine, or non-naturally occurring amino acid. In other embodiments, an amino acid position selected from Table D8 may be used to introduce a conservative or non-conservative substitution. In still other embodiments, a DRS variant may retain one or more or all of the amino acid residues from Table D8. In specific embodiments, a DRS variant my retain an amino acid residue from Table D8 having a score of greater than about 45, 46, 47, 48, 49, 50, 51, 52, 53, 54, 55, 56, 57, 58, 59, 60, 61, 62, or 63.

TABLE D8

Surface Exposed Amino Acids

| ID | Position | Amino Acid | Score |
|----|----------|------------|-------|
| 1  | 125      | N          | 63    |
| 2  | 55       | Q          | 60    |
| 3  | 51       | D          | 57    |
| 4  | 54       | I          | 57    |
| 5  | 126      | Q          | 57    |
| 6  | 58       | D          | 56    |
| 7  | 96       | D          | 55    |
| 8  | 43       | D          | 53    |
| 9  | 104      | K          | 53    |
| 10 | 108      | N          | 53    |
| 11 | 130      | C          | 53    |
| 12 | 132      | T          | 53    |
| 13 | 151      | P          | 53    |
| 14 | 152      | R          | 52    |
| 15 | 40       | E          | 52    |
| 16 | 97       | H          | 52    |
| 17 | 127      | K          | 52    |
| 18 | 129      | G          | 51    |
| 19 | 50       | R          | 50    |
| 20 | 107      | A          | 50    |
| 21 | 72       | A          | 49    |
| 22 | 39       | Q          | 46    |
| 23 | 100      | K          | 45    |
| 24 | 95       | G          | 45    |

In particular embodiments, a solvent accessible surface amino acid from Table D8 is selected from the group consisting of: alanine, glycine, and serine, and can be substituted with naturally occurring amino acids including, but not limited to, cysteine, glutamine, or lysine, or a non-naturally occurring amino acid. In certain embodiments, one or more solvent accessible surface amino acids of the DRS polypeptide are selected from the group consisting of: C130, G129, A107, A72 and G95 are, substituted with cysteine, glutamine, lysine, or a non-naturally occurring amino acid.

As noted above, certain DRS polypeptides may contain one or more non-naturally occurring amino acids. Examples of non-naturally occurring amino acids include, without limitation, any amino acid, modified amino acid, or amino acid analogue other than selenocysteine and the following twenty genetically encoded alpha-amino acids: alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine. The generic structure of an alpha-amino acid is illustrated by the following formula:

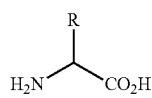

A non-natural amino acid is typically any structure having the foregoing formula wherein the R group is any substituent other than one used in the twenty natural amino acids. See, e.g., any biochemistry text such as Biochemistry by L. Stryer, 3rd ed. 1988, Freeman and Company, New York, for structures of the twenty natural amino acids. Note that the non-natural amino acids disclosed herein may be naturally occurring compounds other than the twenty alpha-amino acids above. Because the non-natural amino acids disclosed herein typically differ from the natural amino acids in side chain only, the non-natural amino acids form amide bonds with other amino acids, e.g., natural or non-natural, in the same manner in which they are formed in naturally occurring proteins. However, the non-natural amino acids have side chain groups that distinguish them from the natural amino acids. For example, R in foregoing formula optionally comprises an alkyl-, aryl-, aryl halide, vinyl halide, alkyl halide, acetyl, ketone, aziridine, nitrile, nitro, halide, acyl-, keto-, azido-, hydroxyl-, hydrazine, cyano-, halo-, hydrazide, alkenyl, alkynyl, ether, thio ether, epoxide, sulfone, boronic acid, boronate ester, borane, phenylboronic acid, thiol, seleno-, sulfonyl-, borate, boronate, phospho, phosphono, phosphine, heterocyclic-, pyridyl, naphthyl, benzophenone, a constrained ring such as a cyclooctyne, thio ester, enone, imine, aldehyde, ester, thioacid, hydroxylamine, amino, carboxylic acid, alpha-keto carboxylic acid, alpha or beta unsaturated acids and amides, glyoxylamide, or organosilane group, or the like or any combination thereof.

Specific examples of unnatural amino acids include, but are not limited to, p-acetyl-L-phenylalanine, O-methyl-L-tyrosine, an L-3-(2-naphthyl)alanine, a 3-methyl-phenylalanine, an O-4-allyl-L-tyrosine, a 4-propyl-L-tyrosine, a tri-O-acetyl-GlcNAcβ-serine, β-O-GlcNAc-L-serine, a tri-O-acetyl-GalNAc-α-threonine, an α-GalNAc-L-threonine, an L-Dopa, a fluorinated phenylalanine, an isopropyl-L-phenylalanine, a p-azido-L-phenylalanine, a p-acyl-L-phenylalanine, a p-benzoyl-L-phenylalanine, an L-phosphoserine, a phosphonoserine, a phosphonotyrosine, a p-iodo-phenylalanine, a p-bromophenylalanine, a p-amino-L-phenylalanine, an isopropyl-L-phenylalanine, those listed below, or elsewhere herein, and the like.

In certain aspects, the use of non-natural amino acids can be utilized to modify (e.g., increase) a selected non-canonical activity of a DRS polypeptide, or to alter the in vivo or in vitro half-life of the protein. Non-natural amino acids can also be used to facilitate (selective) chemical modifications (e.g., PEGylation) of a DRS protein. For instance, certain non-natural amino acids allow selective, protein-protein attachment of Fc regions to a DRS polypeptide, and thereby improve their pharmacokinetic properties.

Specific examples of amino acid analogs and mimetics can be found described in, for example, Roberts and Vellaccio, The Peptides: Analysis, Synthesis, Biology, Eds. Gross and Meinhofer, Vol. 5, p. 341, Academic Press, Inc., New York, N.Y. (1983), the entire volume of which is incorporated herein by reference. Other examples include peralkylated amino acids, particularly permethylated amino acids. See, for example, Combinatorial Chemistry, Eds. Wilson and Czarnik, Ch. 11, p. 235, John Wiley & Sons Inc., New York, N.Y. (1997), the entire book of which is incorporated herein by reference. Yet other examples include amino acids whose amide portion (and, therefore, the amide backbone of the resulting peptide) has been replaced, for example, by a sugar ring, steroid, benzodiazepine or carbo cycle. See, for instance, Burger's Medicinal Chemistry and Drug Discovery, Ed. Manfred E. Wolff, Ch. 15, pp. 619-620, John Wiley & Sons Inc., New York, N.Y. (1995), the entire book of which is incorporated herein by reference. Methods for synthesizing peptides, polypeptides, peptidomimetics and proteins are well known in the art (see, for example, U.S. Pat. No. 5,420,109; M. Bodanzsky, Principles of Peptide Synthesis (1st ed. & 2d rev. ed.), Springer-Verlag, New York, N.Y. (1984 & 1993), see Chapter 7; Stewart and Young, Solid Phase Peptide Synthesis, (2d ed.), Pierce Chemical Co., Rockford, Ill. (1984), each of which is incorporated herein by reference). Accordingly, the DRS polypeptides of the present invention may be composed of naturally occurring and non-naturally occurring amino acids as well as amino acid analogs and mimetics.

In one embodiment of any of these methods, compositions and kits, the DRS polypeptide is AspRS1$^{N1}$/DRS(1-154) comprising at least one mutation at Cys76 and/or Cys130.

In one embodiment of any of these methods, compositions and kits, the DRS polypeptide is DRS (11-146) comprising at least one mutation at Cys76 and/or Cys130.

In one embodiment of any of these methods, compositions and kits, the DRS polypeptide is DRS (13-146) comprising at least one mutation at Cys76 and/or Cys130.

In one embodiment of any of these methods, compositions and kits, the DRS polypeptide is full-length DRS (SEQ ID NO:1) comprising at least one mutation at Cys76, Cys130, Cys203, Cys259, Cys334, and/or Cys339.

In some embodiments, the DRS polypeptide may comprise at mutation at Cys76, Cys130, Cys203, Cys259, Cys334, and/or Cys339, wherein the substituted amino acid is independently selected from the group consisting of all 19 alternative naturally occurring amino acids except Cys, or a non-naturally occurring amino acid.

In some embodiments, the DRS polypeptide may comprise at mutation at Cys76, Cys130, Cys203, Cys259, Cys334, and/or Cys339, wherein the substituted amino acid is independently selected from the group consisting of Ser, Ala, Gly, Met, Leu, Val; Ile and Thr.

In some embodiments, the DRS polypeptide may comprise at mutation at Cys76, Cys130, Cys203, Cys259, Cys334, and/or Cys339, wherein the substituted amino acid is independently selected from the group consisting of Ser and Ala.

In some embodiments, the DRS polypeptide may comprise at mutation at Cys76, Cys130, Cys203, Cys259, Cys334, and/or Cys339, wherein the substituted amino acid is independently selected from the group consisting of Asp, Glu, Arg, Lys, Gln, and Asn.

In some embodiments, the DRS polypeptide may comprise at mutation at Cys76, Cys130, Cys203, Cys259, Cys334, and/or Cys339, wherein the substituted amino acid is independently selected from the group consisting of His, Pro, Tyr, Trp and Phe.

In some embodiments, the DRS polypeptide may comprise at mutation at Cys76, Cys130, Cys203, Cys259, Cys334, and/or Cys339, wherein the substitution is a independently selected from Ser, Ala, Gly, Met, Leu, Val; Ile and Thr, and a non-naturally occurring amino acid.

In any of these various embodiments, Cys76 and/or Cys203 may be selectively modified, while Cys130 remains unmodified. Conversely, in some embodiments, Cys130 and/or Cys203 may be selectively modified, while Cys76 remains unmodified. In some embodiments Cys76, Cys130, and/or Cys203 may be independently modified using any combination of the sub-groupings listed above.

In any of these various embodiments, Cys203, Cys259, Cys334, and Cys349 may be selectively modified, while Cys130 remains unmodified. In any of these various embodiments, Cys76, Cys203, Cys259, Cys334, and Cys349 may be selectively modified, while Cys130 remains unmodified. In some embodiments, Cys76 may be selectively modified, where the cysteine at position 130 is used to selectively chemically couple another molecule, such as an Fc region.

Polynucleotides

Certain embodiments relate to polynucleotides that encode a DRS polypeptide, such as a DRS-Fc fusion protein. Also included are polynucleotides that encode any one or more of the Fc regions described herein, alone or in combination with a DRS coding sequence. Among other uses, these embodiments may be utilized to recombinantly produce a desired DRS, Fc region, or DRS-Fc polypeptide or variant thereof, or to express the DRS, Fc region, or DRS-Fc polypeptide in a selected cell or subject. It will be appreciated by those of ordinary skill in the art that, as a result of the degeneracy of the genetic code, there are many nucleotide sequences that encode a DRS polypeptide as described herein. Some of these polynucleotides may bear minimal homology to the nucleotide sequence of any native gene. Nonetheless, polynucleotides that vary due to differences in codon usage are specifically contemplated by the present invention, for example polynucleotides that are optimized for human, yeast or bacterial codon selection.

Therefore, multiple polynucleotides can encode the DRS polypeptides, Fc regions, and fusion proteins of the invention. Moreover, the polynucleotide sequence can be manipulated for various reasons. Examples include but are not limited to the incorporation of preferred codons to enhance the expression of the polynucleotide in various organisms (see generally Nakamura et al., *Nuc. Acid. Res.* 28:292, 2000). In addition, silent mutations can be incorporated in order to introduce, or eliminate restriction sites, decrease the density of CpG dinucleotide motifs (see for example, Kameda et al., *Biochem. Biophys. Res. Commun.* 349:1269-1277, 2006) or reduce the ability of single stranded sequences to form stem-loop structures: (see, e.g., Zuker M., *Nucl. Acid Res.* 31:3406-3415, 2003). In addition, mammalian expression can be further optimized by including a Kozak consensus sequence (i.e., (a/g)cc(a/g)ccATGg) (SEQ ID NO:79) at the start codon. Kozak consensus sequences useful for this purpose are known in the art (Mantyh et al., *PNAS* 92: 2662-2666, 1995; Mantyh et al., *Prot. Exp. & Purif.* 6:124, 1995). Exemplary codon optimized versions of the wild type full length DRS polypeptide and AspRS1$^{N1}$ are provided in Table D9, below.

TABLE D9

| | DRS DNA Sequences | | |
|---|---|---|---|
| Name | Residue Range of SEQ ID NO: 2 | Nucleic acid sequence | SEQ NO ID: |
| AspRS1N1 DNA/ Synthetic/ | | ATGCCGAGCGCGAGCGCCAGCCGTAAGAGCCAGGAAAAACCA CGTGAGATTATGGATGCCGCAGAGGACTATGCGAAAGAACGT | 25 |

TABLE D9-continued

DRS DNA Sequences

| Name | Residue Range of SEQ ID NO: 2 | Nucleic acid sequence | SEQ NO ID: |
|---|---|---|---|
| | Codon optimized 1-462 | TACGGTATTTCCAGCATGATCCAATCTCAGGAGAAACCGGACC GCGTTCTGGTTCGTGTTCGCGATCTGACCATTCAGAAGGCGGA CGAGGTGGTTTGGGTGCGTGCGCGCGTGCACACCAGCCGTGCA AAAGGCAAACAGTGCTTTCTGGTCCTGCGTCAGCAGCAATTCA ACGTCCAGGCGCTGGTGGCAGTGGGTGACCACGCCAGCAAAC AAATGGTGAAGTTCGCTGCTAACATCAATAAAGAATCCATTGT TGATGTTGAAGGCGTCGTTCGCAAGGTCAATCAAAAGATCGGC TCGTGTACGCAACAAGATGTCGAGCTGCATGTGCAGAAGATTT ACGTCATCAGCCTGGCGGAGCCGCGTTTGCCGCTG | |
| AspRS1N1 (C76S) | DNA/ Synthetic/ Codon optimized 1-462 | ATGCCGAGCGCGAGCGCCAGCCGTAAGAGCCAGGAAAAACCA CGTGAGATTATGGATGCCGCAGAGGACTATGCGAAAGAACGT TACGGTATTTCCAGCATGATCCAATCTCAGGAGAAACCGGACC GCGTTCTGGTTCGTGTTCGCGATCTGACCATTCAGAAGGCGGA CGAGGTGGTTTGGGTGCGTGCGCGCGTGCACACCAGCCGTGCA AAAGGCAAACAGAGCTTTCTGGTCCTGCGTCAGCAGCAATTCA ACGTCCAGGCGCTGGTGGCAGTGGGTGACCACGCCAGCAAAC AAATGGTGAAGTTCGCTGCTAACATCAATAAAGAATCCATTGT TGATGTTGAAGGCGTCGTTCGCAAGGTCAATCAAAAGATCGGC TCGTGTACGCAACAAGATGTCGAGCTGCATGTGCAGAAGATTT ACGTCATCAGCCTGGCGGAGCCGCGTTTGCCGCTGGGTAAGCC GATCCCTAACCCGCTGTTGGGTCTGGACAGCACGCATCACCAT CACCACCACTAA | 26 |
| Full length AspRS sequence | DNA/ Synthetic/ Codon optimized 1-1503 | ATGCCATCAGCCTCAGCATCTCGTAAAAGCCAGGAAAAACCG CGCGAAATCATGGACGCTGCCGAAGATTATGCCAAAGAGCGC TATGGTATCAGTTCGATGATCCAGTCACAAGAGAAACCAGATC GTGTGCTGGTCCGTGTTCGTGACCTGACCATCCAGAAAGCGGA TGAAGTTGTTTGGGTCCGTGCTCGTGTTCATACAAGCCGTGCC AAAGGCAAACAGTGCTTCCTGGTTCTGCGTCAACAGCAGTTTA ACGTTCAGGCCCTGGTAGCCGTTGGTGATCACGCCTCAAAACA AATGGTGAAATTCGCCGCCAACATCAACAAAGAGAGCATCGT CGACGTTGAAGGTGTCGTCCGTAAAGTGAATCAGAAAATCGG CTCCTGTACACAGCAAGATGTGGAGCTGCATGTCCAAAAAATC TATGTCATCTCACTGGCCGAACCTCGTCTGCCTCTGCAACTGG ATGATGCTGTACGCCCTGAAGCTGAAGGCGAAGAAGAAGGTC GTGCTACGGTTAATCAGGATACTCGCCTGGACAACCGTGTCAT TGATCTGCGCACCTCAACCTCTCAAGCGGTATTCCGCCTGCAA TCCGGCATCTGTCACCTGTTCCGTGAAACGCTGATCAACAAAG GGTTTGTGGAGATTCAGACCCCGAAAATCATTAGTGCCGCCAG CGAAGGTGGAGCAAATGTGTTTACCGTGTCCTATTTCAAAAAC AATGCCTATCTGGCACAGTCCTCAGCTGTATAAACAAATGTGTATCTGTGCTGACTTCGAGAAAGTGTTCTCAATCGGGCCGGTATTCCGTGCAGAGGATAGCAACACACACCGCCATCTGACCGAATTTGTAGGCCTGGACATCGAAATGGCCTTCAACTATCATTATCACGAGGTGATGGAAGAAATCGCTGATACAATGGTACAGATCTTTAAAGGGCTGCAAGAACGCTTTCAAACAGAGATTCAAACCGTCAATAAACAGTTCCCGTGTGAACCGTTCAAATTTCTGGAACCGACCCTGCGTCTGGAATATTGTGAAGCACTGGCTATGCTGCGCGAAGCTGGTGTCGAAATGGGTGATGAGGATGACCTGTCTACCCCTAACGAAAAACTGCTGGGCCACCTGGTAAAAGAAAAATATGACACAGACTTCTATATCCTGGACAAATATCCGCTGGCAGTTCGTCCGTTTTATACGATGCCTGATCCTCGTAATCCGAAACAAGCAACTCCTATGACATGTTCATGCGTGGTGAAGAGATCCTGTCTGGTGCTCAACGTATCCATGATCCACAGCTGCTGACAGAACGTGCACTGCATCACGGTATTGATCTGGAGAAAATCAAAGCCTATATCGACTCCTTTCGCTTTGGTGCCCCTCCACATGCCGGTGGTGGAATTGGGCTGGAGCGTGTAACAATGCTGTTCCTGGGACTGCACAACGTCCGTCAAACCTCAATGTTTCCACGTGACCCTAAACGTCTGACACCT | 27 |
| DRS- C334S | 1-1503/ Reduced cysteine content | ATGCCCAGCGCCAGCGCCAGCCGCAAGAGTCAGGAGAAGCCG CGGGAGATCATGGACGCGGCGGAAGATTATGCTAAAGAGAGA TATGGAATATCTTCAATGATACAATCACAAGAAAAACCAGATC GAGTTTTGGTTCGGGTTAGAGACTTGACAATACAAAAAGCTGA TGAAGTTGTTTGGGTACGTGCAAGAGTTCATACAAGCAGAGCT AAAGGGAAACAGTGCTTCTTAGTCCTACGTCAGCAGCAGTTTA ATGTCCAGGCTCTTGTGGCGGTGGGAGACCATGCAAGCAAGC AGATGGTTAAATTTGCTGCCAACATCAACAAAGAGAGCATTGT GGATGTAGAAGGTGTTGTGAGAAAAGTGAATCAGAAAATTGG AAGCTGTACACAGCAAGACGTTGAGTTACATGTTCAGAAGATT TATGTGATCAGTTTGGCTGAACCCCGTCTGCCCCTGCAGCTGG | 198 |

TABLE D9-continued

DRS DNA Sequences

| Name | Residue Range of SEQ ID NO: 2 | Nucleic acid sequence | SEQ NO ID: |
|---|---|---|---|
| | | ATGATGCTGTTCGGCCTGAGGCAGAAGGAGAAGAGGAAGGAA<br>GAGCTACTGTTAACCAGGATACAAGATTAGACAACAGAGTCA<br>TTGATCTTAGGACATCAACTAGTCAGGCAGTCTTCCGTCTCCA<br>GTCTGGCATCTGCCATCTCTTCCGAGAAACTTTAATTAACAAA<br>GGTTTTGTGGAAATCCAAACTCCTAAAATTATTTCAGCTGCCA<br>GTGAAGGAGGAGCCAATGTTTTTACTGTGTCATATTTTAAAAA<br>TAATGCATACCTGGCTCAGTCCCCACAGCTATATAAGCAAATG<br>TGCATTTGTGCTGATTTTGAGAAGGTTTTCTCTATTGGACCAGT<br>ATTCAGAGCGGAAGACTCTAATACCCATAGACATCTAACTGAG<br>TTTGTTGGTTTGGACATTGAAATGGCTTTTAATTACCATTACCA<br>CGAAGTTATGGAAGAAATTGCTGACACCATGGTACAAATATTC<br>AAAGGACTTCAAGAAAGGTTTCAGACTGAAATTCAAACAGTG<br>AATAAACAGTTCCCATCTGAGCCATTCAAATTTTTGGAGCCAA<br>CTCTAAGACTAGAATATTGTGAAGCATTGGCTATGCTTAGGGA<br>AGCTGGAGTCGAAATGGGAGATGAAGACGATCTGAGCACACC<br>AAATGAAAAGCTGTTGGGTCATTTGGTAAAGGAAAAGTATGA<br>TACAGATTTTTATATTCTTGATAAATATCCATTGGCTGTAAGAC<br>CTTTCTATACCATGCCTGACCCAAGAAATCCCAAACAGTCCAA<br>CTCTTACGATATGTTCATGAGAGGAGAAGAAATATTGTCAGGA<br>GCTCAAAGAATACATGATCCTCAACTGCTAACAGAGAGAGCTT<br>TACATCATGGAATTGATTTGGAGAAAATTAAGGCTTACATTGA<br>TTCCTTCCGCTTTGGAGCCCCTCCTCATGCTGGTGGAGGCATTG<br>GATTGGAACGAGTTACTATGCTGTTTCTGGGATTGCATAATGT<br>TCGTCAGACCTCCATGTTCCCTCGTGATCCCAAACGACTCACT<br>CCT | |
| DRS-C349S | 1-1503/<br>Reduced<br>cysteine<br>content | ATGCCCAGCGCCAGCGCCAGCCGCAAGAGTCAGGAGAAGCCG<br>CGGGAGATCATGGACGCGGCGGAAGATTATGCTAAAGAGAGA<br>TATGGAATATCTTCAATGATACAATCACAAGAAAAACCAGATC<br>GAGTTTTGGTTCGGGTTAGAGACTTGACAATACAAAAAGCTGA<br>TGAAGTTGTTTGGGTACGTGCAAGAGTTCATCAAGCAGAGCT<br>AAAGGGAAACAGTGCTTCTTAGTCCTACGTCAGCAGCAGTTTA<br>ATGTCCAGGCTCTTGTGGCGGTGGGAGACCATGCAAGCAAGC<br>AGATGGTTAAATTTGCTGCCAACATCAACAAAGAGAGCATTGT<br>GGATGTAGAAGGTGTTGTGAGAAAAGTGAATCAGAAAATTGG<br>AAGCTGTACACAGCAAGACGTTGAGTTACATGTTCAGAAGATT<br>TATGTGATCAGTTTGGCTGAACCCCGTCTGCCCCTGCAGCTGG<br>ATGATGCTGTTCGGCCTGAGGCAGAAGGAGAAGAGGAAGGAA<br>GAGCTACTGTTAACCAGGATACAAGATTAGACAACAGAGTCA<br>TTGATCTTAGGACATCAACTAGTCAGGCAGTCTTCCGTCTCCA<br>GTCTGGCATCTGCCATCTCTTCCGAGAAACTTTAATTAACAAA<br>GGTTTTGTGGAAATCCAAACTCCTAAAATTATTTCAGCTGCCA<br>GTGAAGGAGGAGCCAATGTTTTTACTGTGTCATATTTTAAAAA<br>TAATGCATACCTGGCTCAGTCCCCACAGCTATATAAGCAAATG<br>TGCATTTGTGCTGATTTTGAGAAGGTTTTCTCTATTGGACCAGT<br>ATTCAGAGCGGAAGACTCTAATACCCATAGACATCTAACTGAG<br>TTTGTTGGTTTGGACATTGAAATGGCTTTTAATTACCATTACCA<br>CGAAGTTATGGAAGAAATTGCTGACACCATGGTACAAATATTC<br>AAAGGACTTCAAGAAAGGTTTCAGACTGAAATTCAAACAGTG<br>AATAAACAGTTCCCATGTGAGCCATTCAAATTTTTGGAGCCAA<br>CTCTAAGACTAGAATATTCTGAAGCATTGGCTATGCTTAGGGA<br>AGCTGGAGTCGAAATGGGAGATGAAGACGATCTGAGCACACC<br>AAATGAAAAGCTGTTGGGTCATTTGGTAAAGGAAAAGTATGA<br>TACAGATTTTTATATTCTTGATAAATATCCATTGGCTGTAAGAC<br>CTTTCTATACCATGCCTGACCCAAGAAATCCCAAACAGTCCAA<br>CTCTTACGATATGTTCATGAGAGGAGAAGAAATATTGTCAGGA<br>GCTCAAAGAATACATGATCCTCAACTGCTAACAGAGAGAGCTT<br>TACATCATGGAATTGATTTGGAGAAAATTAAGGCTTACATTGA<br>TTCCTTCCGCTTTGGAGCCCCTCCTCATGCTGGTGGAGGCATTG<br>GATTGGAACGAGTTACTATGCTGTTTCTGGGATTGCATAATGT<br>TCGTCAGACCTCCATGTTCCCTCGTGATCCCAAACGACTCACT<br>CCT | 199 |
| DRS C334S/C3 49S | 1-1503/<br>Reduced<br>cysteine<br>content | ATGCCCAGCGCCAGCGCCAGCCGCAAGAGTCAGGAGAAGCCG<br>CGGGAGATCATGGACGCGGCGGAAGATTATGCTAAAGAGAGA<br>TATGGAATATCTTCAATGATACAATCACAAGAAAAACCAGATC<br>GAGTTTTGGTTCGGGTTAGAGACTTGACAATACAAAAAGCTGA<br>TGAAGTTGTTTGGGTACGTGCAAGAGTTCATCAAGCAGAGCT<br>AAAGGGAAACAGTGCTTCTTAGTCCTACGTCAGCAGCAGTTTA<br>ATGTCCAGGCTCTTGTGGCGGTGGGAGACCATGCAAGCAAGC<br>AGATGGTTAAATTTGCTGCCAACATCAACAAAGAGAGCATTGT<br>GGATGTAGAAGGTGTTGTGAGAAAAGTGAATCAGAAAATTGG<br>AAGCTGTACACAGCAAGACGTTGAGTTACATGTTCAGAAGATT | 200 |

TABLE D9-continued

DRS DNA Sequences

| Name | Residue Range of SEQ ID NO: 2 | Nucleic acid sequence | SEQ NO ID: |
|---|---|---|---|
| | | TATGTGATCAGTTTGGCTGAACCCCGTCTGCCCCTGCAGCTGG ATGATGCTGTTCGGCCTGAGGCAGAAGGAGAAGAGGAAGGAA GAGCTACTGTTAACCAGGATACAAGATTAGACAACAGAGTCA TTGATCTTAGGACATCAACTAGTCAGGCAGTCTTCCGTCTCCA GTCTGGCATCTGCCATCTCTTCCGAGAAACTTTAATTAACAAA GGTTTTGTGGAAATCCAAACTCCTAAAATTATTTCAGCTGCCA GTGAAGGAGGAGCCAATGTTTTTACTGTGTCATATTTTAAAAA TAATGCATACCTGGCTCAGTCCCCACAGCTATATAAGCAAATG TGCATTTGTGCTGATTTTGAGAAGGTTTTCTCTATTGGACCAGT ATTCAGAGCGGAAGACTCTAATACCCATAGACATCTAACTGAG TTTGTTGGTTTGGACATTGAAATGGCTTTTAATTACCATTACCA CGAAGTTATGGAAGAAATTGCTGACACCATGGTACAAATATTC AAAGGACTTCAAGAAAGGTTTCAGACTGAAATTCAAACAGTG AATAAACAGTTCCCATCTGAGCCATTCAAATTTTTGGAGCCAA CTCTAAGACTAGAATATTCTGAAGCATTGGCTATGCTTAGGGA AGCTGGAGTCGAAATGGGAGATGAAGCGATCTGAGCACACC AAATGAAAAGCTGTTGGGTCATTTGGTAAAGGAAAAGTATGA TACAGATTTTTATATTCTTGATAAATATCCATTGGCTGTAAGAC CTTTCTATACCATGCCTGACCCAAGAAATCCCAAACAGTCCAA CTCTTACGATATGTTCATGAGAGGAGAAGAAATATTGTCAGGA GCTCAAAGAATACATGATCCTCAACTGCTAACAGAGAGCTT TACATCATGGAATTGATTTGGAGAAAATTAAGGCTTACATTGA TTCCTTCCGCTTTGGAGCCCCTCCTCATGCTGGTGGAGGCATTG GATTGGAACGAGTTACTATGCTGTTTCTGGGATTGCATAATGT TCGTCAGACCTCCATGTTCCCTCGTGATCCCAAACGACTCACT CCT | |
| DRS C203A | 1-1503/ Reduced cysteine content | ATGCCCAGCGCCAGCGCCAGCCGCAAGAGTCAGGAGAAGCCG CGGGAGATCATGGACGCGGCGGAAGATTATGCTAAAGAGAGA TATGGAATATCTTCAATGATACAATCACAAGAAAAACCAGATC GAGTTTTGGTTCGGGTTAGAGACTTGACAATACAAAAAGCTGA TGAAGTTGTTTGGGTACGTGCAAGAGTTCATACAAGCAGAGCT AAAGGGAAACAGTGCTTCTTAGTCCTACGTCAGCAGCAGTTTA ATGTCCAGGCTCTTGTGGCGGTGGGAGACCATGCAAGCAAGC AGATGGTTAAATTTGCTGCCAACATCAACAAAGAGAGCATTGT GGATGTAGAAGGTGTTGTGAGAAAAGTGAATCAGAAAATTGG AAGCTGTACACAGCAAGACGTTGAGTTACATGTTCAGAAGATT TATGTGATCAGTTTGGCTGAACCCCGTCTGCCCCTGCAGCTGG ATGATGCTGTTCGGCCTGAGGCAGAAGGAGAAGAGGAAGGAA GAGCTACTGTTAACCAGGATACAAGATTAGACAACAGAGTCA TTGATCTTAGGACATCAACTAGTCAGGCAGTCTTCCGTCTCCA GTCTGGCATCGCCCATCTCTTCCGAGAAACTTTAATTAACAAA GGTTTTGTGGAAATCCAAACTCCTAAAATTATTTCAGCTGCCA GTGAAGGAGGAGCCAATGTTTTTACTGTGTCATATTTTAAAAA TAATGCATACCTGGCTCAGTCCCCACAGCTATATAAGCAAATG TGCATTTGTGCTGATTTTGAGAAGGTTTTCTCTATTGGACCAGT ATTCAGAGCGGAAGACTCTAATACCCATAGACATCTAACTGAG TTTGTTGGTTTGGACATTGAAATGGCTTTTAATTACCATTACCA CGAAGTTATGGAAGAAATTGCTGACACCATGGTACAAATATTC AAAGGACTTCAAGAAAGGTTTCAGACTGAAATTCAAACAGTG AATAAACAGTTCCCATGTGAGCCATTCAAATTTTTGGAGCCAA CTCTAAGACTAGAATATTGTGAAGCATTGGCTATGCTTAGGGA AGCTGGAGTCGAAATGGGAGATGAAGCGATCTGAGCACACC AAATGAAAAGCTGTTGGGTCATTTGGTAAAGGAAAAGTATGA TACAGATTTTTATATTCTTGATAAATATCCATTGGCTGTAAGAC CTTTCTATACCATGCCTGACCCAAGAAATCCCAAACAGTCCAA CTCTTACGATATGTTCATGAGAGGAGAAGAAATATTGTCAGGA GCTCAAAGAATACATGATCCTCAACTGCTAACAGAGAGCTT TACATCATGGAATTGATTTGGAGAAAATTAAGGCTTACATTGA TTCCTTCCGCTTTGGAGCCCCTCCTCATGCTGGTGGAGGCATTG GATTGGAACGAGTTACTATGCTGTTTCTGGGATTGCATAATGT TCGTCAGACCTCCATGTTCCCTCGTGATCCCAAACGACTCACT CCT | 201 |
| DRS C203V | 1-1503/ Reduced cysteine content | ATGCCCAGCGCCAGCGCCAGCCGCAAGAGTCAGGAGAAGCCG CGGGAGATCATGGACGCGGCGGAAGATTATGCTAAAGAGAGA TATGGAATATCTTCAATGATACAATCACAAGAAAAACCAGATC GAGTTTTGGTTCGGGTTAGAGACTTGACAATACAAAAAGCTGA TGAAGTTGTTTGGGTACGTGCAAGAGTTCATACAAGCAGAGCT AAAGGGAAACAGTGCTTCTTAGTCCTACGTCAGCAGCAGTTTA ATGTCCAGGCTCTTGTGGCGGTGGGAGACCATGCAAGCAAGC AGATGGTTAAATTTGCTGCCAACATCAACAAAGAGAGCATTGT GGATGTAGAAGGTGTTGTGAGAAAAGTGAATCAGAAAATTGG | 202 |

TABLE D9-continued

DRS DNA Sequences

| Name | Residue Range of SEQ ID NO: 2 | Nucleic acid sequence | SEQ ID NO: |
|---|---|---|---|
| | | AAGCTGTACACAGCAAGACGTTGAGTTACATGTTCAGAAGATT TATGTGATCAGTTTGGCTGAACCCCGTCTGCCCCTGCAGCTGG ATGATGCTGTTCGGCCTGAGGCAGAAGGAGAAGAGGAAGGAA GAGCTACTGTTAACCAGGATACAAGATTAGACAACAGAGTCA TTGATCTTAGGACATCAACTAGTCAGGCAGTCTTCCGTCTCCA GTCTGGCATCGTCCATCTCTTCCGAGAAACTTTAATTAACAAA GGTTTTGTGGAAATCCAAACTCCTAAAATTATTTCAGCTGCCA GTGAAGGAGGAGCCAATGTTTTTACTGTGTCATATTTTAAAAA TAATGCATACCTGGCTCAGTCCCCACAGCTATATAAGCAAATG TGCATTTGTGCTGATTTTGAGAAGGTTTTCTCTATTGGACCAGT ATTCAGAGCGGAAGACTCTAATACCCATAGACATCTAACTGAG TTTGTTGGTTTGGACATTGAAATGGCTTTTAATTACCATTACCA CGAAGTTATGGAAGAAATTGCTGACACCATGGTACAAATATTC AAAGGACTTCAAGAAAGGTTTCAGACTGAAATTCAAACAGTG AATAAACAGTTCCCATGTGAGCCATTCAAATTTTTGGAGCCAA CTCTAAGACTAGAATATTGTGAAGCATTGGCTATGCTTAGGGA AGCTGGAGTCGAAATGGGAGATGAAGACGATCTGAGCACACC AAATGAAAAGCTGTTGGGTCATTTGGTAAAGGAAAAGTATGA TACAGATTTTTATATTCTTGATAAATATCCATTGGCTGTAAGAC CTTTCTATACCATGCCTGACCCAAGAAATCCCAAACAGTCCAA CTCTTACGATATGTTCATGAGAGGAGAAGAAATATTGTCAGGA GCTCAAAGAATACATGATCCTCAACTGCTAACAGAGAGCTT TACATCATGGAATTGATTTGGAGAAAATTAAGGCTTACATTGA TTCCTTCCGCTTTGGAGCCCCTCCTCATGCTGGTGGAGGCATTG GATTGGAACGAGTTACTATGCTGTTTCTGGGATTGCATAATGT TCGTCAGACCTCCATGTTCCCTCGTGATCCCAAACGACTCACT CCT | |
| DRS C334S/C349S/C203A | 1-1503/ Reduced cysteine content | ATGCCCAGCGCCAGCGCCAGCCGCAAGAGTCAGGAGAAGCCG CGGGAGATCATGGACGCGGCGGAAGATTATGCTAAAGAGAGA TATGGAATATCTTCAATGATACAATCACAAGAAAAACCAGATC GAGTTTTGGTTCGGGTTAGAGACTTGACAATACAAAAAGCTGA TGAAGTTGTTTGGGTACGTGCAAGAGTTCATCAAGCAGAGCT AAAGGGAAACAGTGCTTCTTAGTCCTACGTCAGCAGCAGTTTA ATGTCCAGGCTCTTGTGGCGGTGGGAGACCATGCAAGCAAGC AGATGGTTAAATTTGCTGCCAACATCAACAAAGAGAGCATTGT GGATGTAGAAGGTGTTGTGAGAAAAGTGAATCAGAAAATTGG AAGCTGTACACAGCAAGACGTTGAGTTACATGTTCAGAAGATT TATGTGATCAGTTTGGCTGAACCCCGTCTGCCCCTGCAGCTGG ATGATGCTGTTCGGCCTGAGGCAGAAGGAGAAGAGGAAGGAA GAGCTACTGTTAACCAGGATACAAGATTAGACAACAGAGTCA TTGATCTTAGGACATCAACTAGTCAGGCAGTCTTCCGTCTCCA GTCTGGCATCGCCCATCTCTTCCGAGAAACTTTAATTAACAAA GGTTTTGTGGAAATCCAAACTCCTAAAATTATTTCAGCTGCCA GTGAAGGAGGAGCCAATGTTTTTACTGTGTCATATTTTAAAAA TAATGCATACCTGGCTCAGTCCCCACAGCTATATAAGCAAATG TGCATTTGTGCTGATTTTGAGAAGGTTTTCTCTATTGGACCAGT ATTCAGAGCGGAAGACTCTAATACCCATAGACATCTAACTGAG TTTGTTGGTTTGGACATTGAAATGGCTTTTAATTACCATTACCA CGAAGTTATGGAAGAAATTGCTGACACCATGGTACAAATATTC AAAGGACTTCAAGAAAGGTTTCAGACTGAAATTCAAACAGTG AATAAACAGTTCCCATCTGAGCCATTCAAATTTTTGGAGCCAA CTCTAAGACTAGAATATTCTGAAGCATTGGCTATGCTTAGGGA AGCTGGAGTCGAAATGGGAGATGAAGACGATCTGAGCACACC AAATGAAAAGCTGTTGGGTCATTTGGTAAAGGAAAAGTATGA TACAGATTTTTATATTCTTGATAAATATCCATTGGCTGTAAGAC CTTTCTATACCATGCCTGACCCAAGAAATCCCAAACAGTCCAA CTCTTACGATATGTTCATGAGAGGAGAAGAAATATTGTCAGGA GCTCAAAGAATACATGATCCTCAACTGCTAACAGAGAGCTT TACATCATGGAATTGATTTGGAGAAAATTAAGGCTTACATTGA TTCCTTCCGCTTTGGAGCCCCTCCTCATGCTGGTGGAGGCATTG GATTGGAACGAGTTACTATGCTGTTTCTGGGATTGCATAATGT TCGTCAGACCTCCATGTTCCCTCGTGATCCCAAACGACTCACT CCT | 203 |
| DRS C34S/C349S/C203V | 1-1503/ Reduced cysteine content | ATGCCCAGCGCCAGCGCCAGCCGCAAGAGTCAGGAGAAGCCG CGGGAGATCATGGACGCGGCGGAAGATTATGCTAAAGAGAGA TATGGAATATCTTCAATGATACAATCACAAGAAAAACCAGATC GAGTTTTGGTTCGGGTTAGAGACTTGACAATACAAAAAGCTGA TGAAGTTGTTTGGGTACGTGCAAGAGTTCATCAAGCAGAGCT AAAGGGAAACAGTGCTTCTTAGTCCTACGTCAGCAGCAGTTTA ATGTCCAGGCTCTTGTGGCGGTGGGAGACCATGCAAGCAAGC AGATGGTTAAATTTGCTGCCAACATCAACAAAGAGAGCATTGT | 204 |

TABLE D9-continued

DRS DNA Sequences

| Name | Residue Range of SEQ ID NO: 2 | Nucleic acid sequence | SEQ NO ID: |
|---|---|---|---|
| | | GGATGTAGAAGGTGTTGTGAGAAAAGTGAATCAGAAAATTGG AAGCTGTACACAGCAAGACGTTGAGTTACATGTTCAGAAGATT TATGTGATCAGTTTGGCTGAACCCCGTCTGCCCCTGCAGCTGG ATGATGCTGTTCGGCCTGAGGCAGAAGGAGAAGAGGAAGGAA GAGCTACTGTTAACCAGGATACAAGATTAGACAACAGAGTCA TTGATCTTAGGACATCAACTAGTCAGGCAGTCTTCCGTCTCCA GTCTGGCATCGTCCATCTCTTCCGAGAAACTTTAATTAACAAA GGTTTTGTGGAAATCCAAACTCCTAAAATTATTTCAGCTGCCA GTGAAGGAGGAGCCAATGTTTTTACTGTGTCATATTTTAAAA TAATGCATACCTGGCTCAGTCCCCACAGCTATATAAGCAAATG TGCATTTGTGCTGATTTTGAGAAGGTTTTCTCTATTGGACCAGT ATTCAGAGCGGAAGACTCTAATACCCATAGACATCTAACTGAG TTTGTTGGTTTGGACATTGAAATGGCTTTTAATTACCATTACCA CGAAGTTATGGAAGAAATTGCTGACACCATGGTACAAATATTC AAAGGACTTCAAGAAAGGTTTCAGACTGAAATTCAAACAGTG AATAAACAGTTCCCATCTGAGCCATTCAAATTTTTGGAGCCAA CTCTAAGACTAGAATATTCTGAAGCATTGGCTATGCTTAGGGA AGCTGGAGTCGAAATGGGAGATGAAGACGATCTGAGCACACC AAATGAAAAGCTGTTGGGTCATTTGGTAAAGGAAAAGTATGA TACAGATTTTTATATTCTTGATAAATATCCATTGGCTGTAAGAC CTTTCTATACCATGCCTGACCCAAGAAATCCCAAACAGTCCAA CTCTTACGATATGTTCATGAGAGGAGAAGAAATATTGTCAGGA GCTCAAAGAATACATGATCCTCAACTGCTAACAGAGAGAGCTT TACATCATGGAATTGATTTGGAGAAAATTAAGGCTTACATTGA TTCCTTCCGCTTTGGAGCCCCTCCTCATGCTGGTGGAGGCATTG GATTGGAACGAGTTACTATGCTGTTTCTGGGATTGCATAATGT TCGTCAGACCTCCATGTTCCCTCGTGATCCCAAACGACTCACT CCT | |
| DRS C334S/C349S/C259A/C203A | 1-1503/ Reduced cysteine content | ATGCCCAGCGCCAGCGCCAGCCGCAAGAGTCAGGAGAAGCCG CGGGAGATCATGGACGCGGCGGAAGATTATGCTAAAGAGAGA TATGGAATATCTTCAATGATACAATCACAAGAAAAACCAGATC GAGTTTTGGTTCGGGTTAGAGACTTGACAATACAAAAAGCTGA TGAAGTTGTTGGGTACGTGCAAGAGTTCATACAAGCAGAGCT AAAGGGAAACAGTGCTTCTTAGTCCTACGTCAGCAGCAGTTTA ATGTCCAGGCTCTTGTGGCGGTGGGAGACCATGCAAGCAAGC AGATGGTTAAATTTGCTGCCAACATCAACAAAGAGAGCATTGT GGATGTAGAAGGTGTTGTGAGAAAAGTGAATCAGAAAATTGG AAGCTGTACACAGCAAGACGTTGAGTTACATGTTCAGAAGATT TATGTGATCAGTTTGGCTGAACCCCGTCTGCCCCTGCAGCTGG ATGATGCTGTTCGGCCTGAGGCAGAAGGAGAAGAGGAAGGAA GAGCTACTGTTAACCAGGATACAAGATTAGACAACAGAGTCA TTGATCTTAGGACATCAACTAGTCAGGCAGTCTTCCGTCTCCA GTCTGGCATCGCCCATCTCTTCCGAGAAACTTTAATTAACAAA GGTTTTGTGGAAATCCAAACTCCTAAAATTATTTCAGCTGCCA GTGAAGGAGGAGCCAATGTTTTTACTGTGTCATATTTTAAAA TAATGCATACCTGGCTCAGTCCCCACAGCTATATAAGCAAATG TGCATTGCGGCTGATTTTGAGAAGGTTTTCTCTATTGGACCAGT ATTCAGAGCGGAAGACTCTAATACCCATAGACATCTAACTGAG TTTGTTGGTTTGGACATTGAAATGGCTTTTAATTACCATTACCA CGAAGTTATGGAAGAAATTGCTGACACCATGGTACAAATATTC AAAGGACTTCAAGAAAGGTTTCAGACTGAAATTCAAACAGTG AATAAACAGTTCCCATCTGAGCCATTCAAATTTTTGGAGCCAA CTCTAAGACTAGAATATTCTGAAGCATTGGCTATGCTTAGGGA AGCTGGAGTCGAAATGGGAGATGAAGACGATCTGAGCACACC AAATGAAAAGCTGTTGGGTCATTTGGTAAAGGAAAAGTATGA TACAGATTTTTATATTCTTGATAAATATCCATTGGCTGTAAGAC CTTTCTATACCATGCCTGACCCAAGAAATCCCAAACAGTCCAA CTCTTACGATATGTTCATGAGAGGAGAAGAAATATTGTCAGGA GCTCAAAGAATACATGATCCTCAACTGCTAACAGAGAGAGCTT TACATCATGGAATTGATTTGGAGAAAATTAAGGCTTACATTGA TTCCTTCCGCTTTGGAGCCCCTCCTCATGCTGGTGGAGGCATTG GATTGGAACGAGTTACTATGCTGTTTCTGGGATTGCATAATGT TCGTCAGACCTCCATGTTCCCTCGTGATCCCAAACGACTCACT CCT | 205 |
| DRS C334S/C349S/C259A/C203V | 1-1503/ Reduced cysteine content | ATGCCCAGCGCCAGCGCCAGCCGCAAGAGTCAGGAGAAGCCG CGGGAGATCATGGACGCGGCGGAAGATTATGCTAAAGAGAGA TATGGAATATCTTCAATGATACAATCACAAGAAAAACCAGATC GAGTTTTGGTTCGGGTTAGAGACTTGACAATACAAAAAGCTGA TGAAGTTGTTGGGTACGTGCAAGAGTTCATACAAGCAGAGCT AAAGGGAAACAGTGCTTCTTAGTCCTACGTCAGCAGCAGTTTA ATGTCCAGGCTCTTGTGGCGGTGGGAGACCATGCAAGCAAGC | 206 |

TABLE D9-continued

DRS DNA Sequences

| Name | Residue Range of SEQ ID NO: 2 | Nucleic acid sequence | SEQ NO ID: |
|---|---|---|---|
| | | AGATGGTTAAATTTGCTGCCAACATCAACAAAGAGAGCATTGT<br>GGATGTAGAAGGTGTTGTGAGAAAAGTGAATCAGAAAATTGG<br>AAGCTGTACACAGCAAGACGTTGAGTTACATGTTCAGAAGATT<br>TATGTGATCAGTTTGGCTGAACCCCGTCTGCCCCTGCAGCTGG<br>ATGATGCTGTTCGGCCTGAGGCAGAAGGAGAAGAGGAAGGAA<br>GAGCTACTGTTAACCAGGATACAAGATTAGACAACAGAGTCA<br>TTGATCTTAGGACATCAACTAGTCAGGCAGTCTTCCGTCTCCA<br>GTCTGGCATCGTCCATCTCTTCCGAGAAACTTTAATTAACAAA<br>GGTTTTGTGGAAATCCAAACTCCTAAAATTATTTCAGCTGCCA<br>GTGAAGGAGGAGCCAATGTTTTTACTGTGTCATATTTTAAAAA<br>TAATGCATACCTGGCTCAGTCCCCACAGCTATATAAGCAAATG<br>TGCATTGCGGCTGATTTTGAGAAGGTTTTCTCTATTGGACCAGT<br>ATTCAGAGCGGAAGACTCTAATACCCATAGACATCTAACTGAG<br>TTTGTTGGTTTGGACATTGAAATGGCTTTTAATTACCATTACCA<br>CGAAGTTATGGAAGAAATTGCTGACACCATGGTACAAATATTC<br>AAAGGACTTCAAGAAAGGTTTCAGACTGAAATTCAAACAGTG<br>AATAAACAGTTCCCATCTGAGCCATTCAAATTTTTGGAGCCAA<br>CTCTAAGACTAGAATATTCTGAAGCATTGGCTATGCTTAGGGA<br>AGCTGGAGTCGAAATGGGAGATGAAGACGATCTGAGCACACC<br>AAATGAAAAGCTGTTGGGTCATTTGGTAAAGGAAAAGTATGA<br>TACAGATTTTTATATTCTTGATAAATATCCATTGGCTGTAAGAC<br>CTTTCTATACCATGCCTGACCCAAGAAATCCCAAACAGTCCAA<br>CTCTTACGATATGTTCATGAGAGGAGAAGAAATATTGTCAGGA<br>GCTCAAAGAATACATGATCCTCAACTGCTAACAGAGAGAGCTT<br>TACATCATGGAATTGATTTGGAGAAAATTAAGGCTTACATTGA<br>TTCCTTCCGCTTTGGAGCCCCTCCTCATGCTGGTGGAGGCATTG<br>GATTGGAACGAGTTACTATGCTGTTTCTGGGATTGCATAATGT<br>TCGTCAGACCTCCATGTTCCCTCGTGATCCCAAACGACTCACT<br>CCT | |
| DRS 1-<br>182 | | ATGCCCAGCGCCAGCGCCAGCCGCAAGAGTCAGGAGAAGCCG<br>CGGGAGATCATGGACGCGGCGGAAGATTATGCTAAAGAGAGA<br>TATGGAATATCTTCAATGATACAATCACAAGAAAAACCAGATC<br>GAGTTTTGGTTCGGGTTAGAGACTTGACAATACAAAAAGCTGA<br>TGAAGTTGTTTGGGTACGTGCAAGAGTTCATCAAGCAGAGCT<br>AAAGGGAAACAGTGCTTCTTAGTCCTACGTCAGCAGCAGTTTA<br>ATGTCCAGGCTCTTGTGGCGGTGGGAGACCATGCAAGCAAGC<br>AGATGGTTAAATTTGCTGCCAACATCAACAAAGAGAGCATTGT<br>GGATGTAGAAGGTGTTGTGAGAAAAGTGAATCAGAAAATTGG<br>AAGCTGTACACAGCAAGACGTTGAGTTACATGTTCAGAAGATT<br>TATGTGATCAGTTTGGCTGAACCCCGTCTGCCCCTGCAGCTGG<br>ATGATGCTGTTCGGCCTGAGGCAGAAGGAGAAGAGGAAGGAA<br>GAGCTACTGTTAACCAGGATACAAGATTAGACAAC | 207 |
| DRS 1-<br>180 | | ATGCCCAGCGCCAGCGCCAGCCGCAAGAGTCAGGAGAAGCCG<br>CGGGAGATCATGGACGCGGCGGAAGATTATGCTAAAGAGAGA<br>TATGGAATATCTTCAATGATACAATCACAAGAAAAACCAGATC<br>GAGTTTTGGTTCGGGTTAGAGACTTGACAATACAAAAAGCTGA<br>TGAAGTTGTTTGGGTACGTGCAAGAGTTCATCAAGCAGAGCT<br>AAAGGGAAACAGTGCTTCTTAGTCCTACGTCAGCAGCAGTTTA<br>ATGTCCAGGCTCTTGTGGCGGTGGGAGACCATGCAAGCAAGC<br>AGATGGTTAAATTTGCTGCCAACATCAACAAAGAGAGCATTGT<br>GGATGTAGAAGGTGTTGTGAGAAAAGTGAATCAGAAAATTGG<br>AAGCTGTACACAGCAAGACGTTGAGTTACATGTTCAGAAGATT<br>TATGTGATCAGTTTGGCTGAACCCCGTCTGCCCCTGCAGCTGG<br>ATGATGCTGTTCGGCCTGAGGCAGAAGGAGAAGAGGAAGGAA<br>GAGCTACTGTTAACCAGGATACAAGATTA | 208 |
| DRS 1-<br>178 | | ATGCCCAGCGCCAGCGCCAGCCGCAAGAGTCAGGAGAAGCCG<br>CGGGAGATCATGGACGCGGCGGAAGATTATGCTAAAGAGAGA<br>TATGGAATATCTTCAATGATACAATCACAAGAAAAACCAGATC<br>GAGTTTTGGTTCGGGTTAGAGACTTGACAATACAAAAAGCTGA<br>TGAAGTTGTTTGGGTACGTGCAAGAGTTCATCAAGCAGAGCT<br>AAAGGGAAACAGTGCTTCTTAGTCCTACGTCAGCAGCAGTTTA<br>ATGTCCAGGCTCTTGTGGCGGTGGGAGACCATGCAAGCAAGC<br>AGATGGTTAAATTTGCTGCCAACATCAACAAAGAGAGCATTGT<br>GGATGTAGAAGGTGTTGTGAGAAAAGTGAATCAGAAAATTGG<br>AAGCTGTACACAGCAAGACGTTGAGTTACATGTTCAGAAGATT<br>TATGTGATCAGTTTGGCTGAACCCCGTCTGCCCCTGCAGCTGG<br>ATGATGCTGTTCGGCCTGAGGCAGAAGGAGAAGAGGAAGGAA<br>GAGCTACTGTTAACCAGGATACA | 209 |

TABLE D9-continued

DRS DNA Sequences

| Name | Residue Range of SEQ ID NO: 2 | Nucleic acid sequence | SEQ NO ID: |
|---|---|---|---|
| DRS 1-176 | | ATGCCCAGCGCCAGCGCCAGCCGCAAGAGTCAGGAGAAGCCG CGGGAGATCATGGACGCGGCGGAAGATTATGCTAAAGAGAGA TATGGAATATCTTCAATGATACAATCACAAGAAAAACCAGATC GAGTTTTGGTTCGGGTTAGAGACTTGACAATACAAAAAGCTGA TGAAGTTGTTTGGGTACGTGCAAGAGTTCATACAAGCAGAGCT AAAGGGAAACAGTGCTTCTTAGTCCTACGTCAGCAGCAGTTTA ATGTCCAGGCTCTTGTGGCGGTGGGAGACCATGCAAGCAAGC AGATGGTTAAATTTGCTGCCAACATCAACAAAGAGAGCATTGT GGATGTAGAAGGTGTTGTGAGAAAAGTGAATCAGAAAATTGG AAGCTGTACACAGCAAGACGTTGAGTTACATGTTCAGAAGATT TATGTGATCAGTTTGGCTGAACCCCGTCTGCCCCTGCAGCTGG ATGATGCTGTTCGGCCTGAGGCAGAAGGAGAAGAGGAAGGAA GAGCTACTGTTAACCAG | 210 |
| DRS 1-174 | | ATGCCCAGCGCCAGCGCCAGCCGCAAGAGTCAGGAGAAGCCG CGGGAGATCATGGACGCGGCGGAAGATTATGCTAAAGAGAGA TATGGAATATCTTCAATGATACAATCACAAGAAAAACCAGATC GAGTTTTGGTTCGGGTTAGAGACTTGACAATACAAAAAGCTGA TGAAGTTGTTTGGGTACGTGCAAGAGTTCATACAAGCAGAGCT AAAGGGAAACAGTGCTTCTTAGTCCTACGTCAGCAGCAGTTTA ATGTCCAGGCTCTTGTGGCGGTGGGAGACCATGCAAGCAAGC AGATGGTTAAATTTGCTGCCAACATCAACAAAGAGAGCATTGT GGATGTAGAAGGTGTTGTGAGAAAAGTGAATCAGAAAATTGG AAGCTGTACACAGCAAGACGTTGAGTTACATGTTCAGAAGATT TATGTGATCAGTTTGGCTGAACCCCGTCTGCCCCTGCAGCTGG ATGATGCTGTTCGGCCTGAGGCAGAAGGAGAAGAGGAAGGAA GAGCTACTGTT | 211 |
| DRS 1-172 | | ATGCCCAGCGCCAGCGCCAGCCGCAAGAGTCAGGAGAAGCCG CGGGAGATCATGGACGCGGCGGAAGATTATGCTAAAGAGAGA TATGGAATATCTTCAATGATACAATCACAAGAAAAACCAGATC GAGTTTTGGTTCGGGTTAGAGACTTGACAATACAAAAAGCTGA TGAAGTTGTTTGGGTACGTGCAAGAGTTCATACAAGCAGAGCT AAAGGGAAACAGTGCTTCTTAGTCCTACGTCAGCAGCAGTTTA ATGTCCAGGCTCTTGTGGCGGTGGGAGACCATGCAAGCAAGC AGATGGTTAAATTTGCTGCCAACATCAACAAAGAGAGCATTGT GGATGTAGAAGGTGTTGTGAGAAAAGTGAATCAGAAAATTGG AAGCTGTACACAGCAAGACGTTGAGTTACATGTTCAGAAGATT TATGTGATCAGTTTGGCTGAACCCCGTCTGCCCCTGCAGCTGG ATGATGCTGTTCGGCCTGAGGCAGAAGGAGAAGAGGAAGGAA GAGCT | 212 |
| DRS 1-170 | | ATGCCCAGCGCCAGCGCCAGCCGCAAGAGTCAGGAGAAGCCG CGGGAGATCATGGACGCGGCGGAAGATTATGCTAAAGAGAGA TATGGAATATCTTCAATGATACAATCACAAGAAAAACCAGATC GAGTTTTGGTTCGGGTTAGAGACTTGACAATACAAAAAGCTGA TGAAGTTGTTTGGGTACGTGCAAGAGTTCATACAAGCAGAGCT AAAGGGAAACAGTGCTTCTTAGTCCTACGTCAGCAGCAGTTTA ATGTCCAGGCTCTTGTGGCGGTGGGAGACCATGCAAGCAAGC AGATGGTTAAATTTGCTGCCAACATCAACAAAGAGAGCATTGT GGATGTAGAAGGTGTTGTGAGAAAAGTGAATCAGAAAATTGG AAGCTGTACACAGCAAGACGTTGAGTTACATGTTCAGAAGATT TATGTGATCAGTTTGGCTGAACCCCGTCTGCCCCTGCAGCTGG ATGATGCTGTTCGGCCTGAGGCAGAAGGAGAAGAGGAAGGA | 213 |
| DRS 1-168 | | ATGCCCAGCGCCAGCGCCAGCCGCAAGAGTCAGGAGAAGCCG CGGGAGATCATGGACGCGGCGGAAGATTATGCTAAAGAGAGA TATGGAATATCTTCAATGATACAATCACAAGAAAAACCAGATC GAGTTTTGGTTCGGGTTAGAGACTTGACAATACAAAAAGCTGA TGAAGTTGTTTGGGTACGTGCAAGAGTTCATACAAGCAGAGCT AAAGGGAAACAGTGCTTCTTAGTCCTACGTCAGCAGCAGTTTA ATGTCCAGGCTCTTGTGGCGGTGGGAGACCATGCAAGCAAGC AGATGGTTAAATTTGCTGCCAACATCAACAAAGAGAGCATTGT GGATGTAGAAGGTGTTGTGAGAAAAGTGAATCAGAAAATTGG AAGCTGTACACAGCAAGACGTTGAGTTACATGTTCAGAAGATT TATGTGATCAGTTTGGCTGAACCCCGTCTGCCCCTGCAGCTGG ATGATGCTGTTCGGCCTGAGGCAGAAGGAGAAGAG | 214 |
| DRS 1-166 | | ATGCCCAGCGCCAGCGCCAGCCGCAAGAGTCAGGAGAAGCCG CGGGAGATCATGGACGCGGCGGAAGATTATGCTAAAGAGAGA TATGGAATATCTTCAATGATACAATCACAAGAAAAACCAGATC GAGTTTTGGTTCGGGTTAGAGACTTGACAATACAAAAAGCTGA | 215 |

TABLE D9-continued

DRS DNA Sequences

| Name | Residue Range of SEQ ID NO: 2 | Nucleic acid sequence | SEQ NO ID: |
|---|---|---|---|
| | | TGAAGTTGTTTGGGTACGTGCAAGAGTTCATACAAGCAGAGCT<br>AAAGGGAAACAGTGCTTCTTAGTCCTACGTCAGCAGCAGTTTA<br>ATGTCCAGGCTCTTGTGGCGGTGGGAGACCATGCAAGCAAGC<br>AGATGGTTAAATTTGCTGCCAACATCAACAAAGAGAGCATTGT<br>GGATGTAGAAGGTGTTGTGAGAAAAGTGAATCAGAAAATTGG<br>AAGCTGTACACAGCAAGACGTTGAGTTACATGTTCAGAAGATT<br>TATGTGATCAGTTTGGCTGAACCCCGTCTGCCCCTGCAGCTGG<br>ATGATGCTGTTCGGCCTGAGGCAGAAGGA | |
| DRS 1-164 | | ATGCCCAGCGCCAGCGCCAGCCGCAAGAGTCAGGAGAAGCCG<br>CGGGAGATCATGGACGCGGCGGAAGATTATGCTAAAGAGAGA<br>TATGGAATATCTTCAATGATACAATCACAAGAAAAACCAGATC<br>GAGTTTTGGTTCGGGTTAGAGACTTGACAATACAAAAAGCTGA<br>TGAAGTTGTTTGGGTACGTGCAAGAGTTCATACAAGCAGAGCT<br>AAAGGGAAACAGTGCTTCTTAGTCCTACGTCAGCAGCAGTTTA<br>ATGTCCAGGCTCTTGTGGCGGTGGGAGACCATGCAAGCAAGC<br>AGATGGTTAAATTTGCTGCCAACATCAACAAAGAGAGCATTGT<br>GGATGTAGAAGGTGTTGTGAGAAAAGTGAATCAGAAAATTGG<br>AAGCTGTACACAGCAAGACGTTGAGTTACATGTTCAGAAGATT<br>TATGTGATCAGTTTGGCTGAACCCCGTCTGCCCCTGCAGCTGG<br>ATGATGCTGTTCGGCCTGAGGCA | 216 |
| DRS 1-162 | | ATGCCCAGCGCCAGCGCCAGCCGCAAGAGTCAGGAGAAGCCG<br>CGGGAGATCATGGACGCGGCGGAAGATTATGCTAAAGAGAGA<br>TATGGAATATCTTCAATGATACAATCACAAGAAAAACCAGATC<br>GAGTTTTGGTTCGGGTTAGAGACTTGACAATACAAAAAGCTGA<br>TGAAGTTGTTTGGGTACGTGCAAGAGTTCATACAAGCAGAGCT<br>AAAGGGAAACAGTGCTTCTTAGTCCTACGTCAGCAGCAGTTTA<br>ATGTCCAGGCTCTTGTGGCGGTGGGAGACCATGCAAGCAAGC<br>AGATGGTTAAATTTGCTGCCAACATCAACAAAGAGAGCATTGT<br>GGATGTAGAAGGTGTTGTGAGAAAAGTGAATCAGAAAATTGG<br>AAGCTGTACACAGCAAGACGTTGAGTTACATGTTCAGAAGATT<br>TATGTGATCAGTTTGGCTGAACCCCGTCTGCCCCTGCAGCTGG<br>ATGATGCTGTTCGGCCT | 217 |
| DRS 1-160 | | ATGCCCAGCGCCAGCGCCAGCCGCAAGAGTCAGGAGAAGCCG<br>CGGGAGATCATGGACGCGGCGGAAGATTATGCTAAAGAGAGA<br>TATGGAATATCTTCAATGATACAATCACAAGAAAAACCAGATC<br>GAGTTTTGGTTCGGGTTAGAGACTTGACAATACAAAAAGCTGA<br>TGAAGTTGTTTGGGTACGTGCAAGAGTTCATACAAGCAGAGCT<br>AAAGGGAAACAGTGCTTCTTAGTCCTACGTCAGCAGCAGTTTA<br>ATGTCCAGGCTCTTGTGGCGGTGGGAGACCATGCAAGCAAGC<br>AGATGGTTAAATTTGCTGCCAACATCAACAAAGAGAGCATTGT<br>GGATGTAGAAGGTGTTGTGAGAAAAGTGAATCAGAAAATTGG<br>AAGCTGTACACAGCAAGACGTTGAGTTACATGTTCAGAAGATT<br>TATGTGATCAGTTTGGCTGAACCCCGTCTGCCCCTGCAGCTGG<br>ATGATGCTGTT | 218 |
| DRS 1-158 | | ATGCCCAGCGCCAGCGCCAGCCGCAAGAGTCAGGAGAAGCCG<br>CGGGAGATCATGGACGCGGCGGAAGATTATGCTAAAGAGAGA<br>TATGGAATATCTTCAATGATACAATCACAAGAAAAACCAGATC<br>GAGTTTTGGTTCGGGTTAGAGACTTGACAATACAAAAAGCTGA<br>TGAAGTTGTTTGGGTACGTGCAAGAGTTCATACAAGCAGAGCT<br>AAAGGGAAACAGTGCTTCTTAGTCCTACGTCAGCAGCAGTTTA<br>ATGTCCAGGCTCTTGTGGCGGTGGGAGACCATGCAAGCAAGC<br>AGATGGTTAAATTTGCTGCCAACATCAACAAAGAGAGCATTGT<br>GGATGTAGAAGGTGTTGTGAGAAAAGTGAATCAGAAAATTGG<br>AAGCTGTACACAGCAAGACGTTGAGTTACATGTTCAGAAGATT<br>TATGTGATCAGTTTGGCTGAACCCCGTCTGCCCCTGCAGCTGG<br>ATGAT | 219 |
| DRS 1-156 | | ATGCCCAGCGCCAGCGCCAGCCGCAAGAGTCAGGAGAAGCCG<br>CGGGAGATCATGGACGCGGCGGAAGATTATGCTAAAGAGAGA<br>TATGGAATATCTTCAATGATACAATCACAAGAAAAACCAGATC<br>GAGTTTTGGTTCGGGTTAGAGACTTGACAATACAAAAAGCTGA<br>TGAAGTTGTTTGGGTACGTGCAAGAGTTCATACAAGCAGAGCT<br>AAAGGGAAACAGTGCTTCTTAGTCCTACGTCAGCAGCAGTTTA<br>ATGTCCAGGCTCTTGTGGCGGTGGGAGACCATGCAAGCAAGC<br>AGATGGTTAAATTTGCTGCCAACATCAACAAAGAGAGCATTGT<br>GGATGTAGAAGGTGTTGTGAGAAAAGTGAATCAGAAAATTGG<br>AAGCTGTACACAGCAAGACGTTGAGTTACATGTTCAGAAGATT<br>TATGTGATCAGTTTGGCTGAACCCCGTCTGCCCCTGCAGCTG | 220 |

TABLE D9-continued

DRS DNA Sequences

| Name | Residue Range of SEQ ID NO: 2 | Nucleic acid sequence | SEQ ID NO: |
|---|---|---|---|
| DRS 1-154 | | ATGCCCAGCGCCAGCGCCAGCCGCAAGAGTCAGGAGAAGCCG CGGGAGATCATGGACGCGGCGGAAGATTATGCTAAAGAGAGA TATGGAATATCTTCAATGATACAATCACAAGAAAAACCAGATC GAGTTTTGGTTCGGGTTAGAGACTTGACAATACAAAAAGCTGA TGAAGTTGTTTGGGTACGTGCAAGAGTTCATACAAGCAGAGCT AAAGGGAAACAGTGCTTCTTAGTCCTACGTCAGCAGCAGTTTA ATGTCCAGGCTCTTGTGGCGGTGGGAGACCATGCAAGCAAGC AGATGGTTAAATTTGCTGCCAACATCAACAAAGAGAGCATTGT GGATGTAGAAGGTGTTGTGAGAAAAGTGAATCAGAAAATTGG AAGCTGTACACAGCAAGACGTTGAGTTACATGTTCAGAAGATT TATGTGATCAGTTTGGCTGAACCCCGTCTGCCCCTG | 221 |
| DRS 1-152 | | ATGCCCAGCGCCAGCGCCAGCCGCAAGAGTCAGGAGAAGCCG CGGGAGATCATGGACGCGGCGGAAGATTATGCTAAAGAGAGA TATGGAATATCTTCAATGATACAATCACAAGAAAAACCAGATC GAGTTTTGGTTCGGGTTAGAGACTTGACAATACAAAAAGCTGA TGAAGTTGTTTGGGTACGTGCAAGAGTTCATACAAGCAGAGCT AAAGGGAAACAGTGCTTCTTAGTCCTACGTCAGCAGCAGTTTA ATGTCCAGGCTCTTGTGGCGGTGGGAGACCATGCAAGCAAGC AGATGGTTAAATTTGCTGCCAACATCAACAAAGAGAGCATTGT GGATGTAGAAGGTGTTGTGAGAAAAGTGAATCAGAAAATTGG AAGCTGTACACAGCAAGACGTTGAGTTACATGTTCAGAAGATT TATGTGATCAGTTTGGCTGAACCCCGTCTG | 222 |
| DRS 1-150 | | ATGCCCAGCGCCAGCGCCAGCCGCAAGAGTCAGGAGAAGCCG CGGGAGATCATGGACGCGGCGGAAGATTATGCTAAAGAGAGA TATGGAATATCTTCAATGATACAATCACAAGAAAAACCAGATC GAGTTTTGGTTCGGGTTAGAGACTTGACAATACAAAAAGCTGA TGAAGTTGTTTGGGTACGTGCAAGAGTTCATACAAGCAGAGCT AAAGGGAAACAGTGCTTCTTAGTCCTACGTCAGCAGCAGTTTA ATGTCCAGGCTCTTGTGGCGGTGGGAGACCATGCAAGCAAGC AGATGGTTAAATTTGCTGCCAACATCAACAAAGAGAGCATTGT GGATGTAGAAGGTGTTGTGAGAAAAGTGAATCAGAAAATTGG AAGCTGTACACAGCAAGACGTTGAGTTACATGTTCAGAAGATT TATGTGATCAGTTTGGCTGAACCC | 223 |
| DRS 1-148 | | ATGCCCAGCGCCAGCGCCAGCCGCAAGAGTCAGGAGAAGCCG CGGGAGATCATGGACGCGGCGGAAGATTATGCTAAAGAGAGA TATGGAATATCTTCAATGATACAATCACAAGAAAAACCAGATC GAGTTTTGGTTCGGGTTAGAGACTTGACAATACAAAAAGCTGA TGAAGTTGTTTGGGTACGTGCAAGAGTTCATACAAGCAGAGCT AAAGGGAAACAGTGCTTCTTAGTCCTACGTCAGCAGCAGTTTA ATGTCCAGGCTCTTGTGGCGGTGGGAGACCATGCAAGCAAGC AGATGGTTAAATTTGCTGCCAACATCAACAAAGAGAGCATTGT GGATGTAGAAGGTGTTGTGAGAAAAGTGAATCAGAAAATTGG AAGCTGTACACAGCAAGACGTTGAGTTACATGTTCAGAAGATT TATGTGATCAGTTTGGCT | 224 |
| DRS 1-146 | | ATGCCCAGCGCCAGCGCCAGCCGCAAGAGTCAGGAGAAGCCG CGGGAGATCATGGACGCGGCGGAAGATTATGCTAAAGAGAGA TATGGAATATCTTCAATGATACAATCACAAGAAAAACCAGATC GAGTTTTGGTTCGGGTTAGAGACTTGACAATACAAAAAGCTGA TGAAGTTGTTTGGGTACGTGCAAGAGTTCATACAAGCAGAGCT AAAGGGAAACAGTGCTTCTTAGTCCTACGTCAGCAGCAGTTTA ATGTCCAGGCTCTTGTGGCGGTGGGAGACCATGCAAGCAAGC AGATGGTTAAATTTGCTGCCAACATCAACAAAGAGAGCATTGT GGATGTAGAAGGTGTTGTGAGAAAAGTGAATCAGAAAATTGG AAGCTGTACACAGCAAGACGTTGAGTTACATGTTCAGAAGATT TATGTGATCAGT | 225 |
| DRS 3-154 | | GCCAGCGCCAGCCGCAAGAGTCAGGAGAAGCCGCGGGAGATC ATGGACGCGGCGGAAGATTATGCTAAAGAGAGATATGGAATA TCTTCAATGATACAATCACAAGAAAAACCAGATCGAGTTTTGG TTCGGGTTAGAGACTTGACAATACAAAAAGCTGATGAAGTTGT TTGGGTACGTGCAAGAGTTCATACAAGCAGAGCTAAAGGGAA ACAGTGCTTCTTAGTCCTACGTCAGCAGCAGTTTAATGTCCAG GCTCTTGTGGCGGTGGGAGACCATGCAAGCAAGCAGATGGTT AAATTTGCTGCCAACATCAACAAAGAGAGCATTGTGGATGTA GAAGGTGTTGTGAGAAAAGTGAATCAGAAAATTGGAAGCTGT ACACAGCAAGACGTTGAGTTACATGTTCAGAAGATTTATGTGA TCAGTTTGGCTGAACCCCGTCTGCCCCTG | 226 |

TABLE D9-continued

DRS DNA Sequences

| Name | Residue Range of SEQ ID NO: 2 | Nucleic acid sequence | SEQ NO ID: |
|---|---|---|---|
| DRS 5-154 | | GCCAGCCGCAAGAGTCAGGAGAAGCCGCGGGAGATCATGGAC GCGGCGGAAGATTATGCTAAAGAGAGATATGGAATATCTTCA ATGATACAATCACAAGAAAAACCAGATCGAGTTTTGGTTCGG GTTAGAGACTTGACAATACAAAAAGCTGATGAAGTTGTTTGGG TACGTGCAAGAGTTCATACAAGCAGAGCTAAAGGGAAACAGT GCTTCTTAGTCCTACGTCAGCAGCAGTTTAATGTCCAGGCTCTT GTGGCGGTGGGAGACCATGCAAGCAAGCAGATGGTTAAATTT GCTGCCAACATCAACAAAGAGAGCATTGTGGATGTAGAAGGT GTTGTGAGAAAAGTGAATCAGAAAATTGGAAGCTGTACACAG CAAGACGTTGAGTTACATGTTCAGAAGATTTATGTGATCAGTT TGGCTGAACCCCGTCTGCCCCTG | 227 |
| DRS 7-154 | | CGCAAGAGTCAGGAGAAGCCGCGGGAGATCATGGACGCGGCG GAAGATTATGCTAAAGAGAGATATGGAATATCTTCAATGATAC AATCACAAGAAAAACCAGATCGAGTTTTGGTTCGGGTTAGAG ACTTGACAATACAAAAAGCTGATGAAGTTGTTTGGGTACGTGC AAGAGTTCATACAAGCAGAGCTAAAGGGAAACAGTGCTTCTT AGTCCTACGTCAGCAGCAGTTTAATGTCCAGGCTCTTGTGGCG GTGGGAGACCATGCAAGCAAGCAGATGGTTAAATTTGCTGCC AACATCAACAAAGAGAGCATTGTGGATGTAGAAGGTGTTGTG AGAAAAGTGAATCAGAAAATTGGAAGCTGTACACAGCAAGAC GTTGAGTTACATGTTCAGAAGATTTATGTGATCAGTTTGGCTG AACCCCGTCTGCCCCTG | 228 |
| DRS 9-154 | | AGTCAGGAGAAGCCGCGGGAGATCATGGACGCGGCGGAAGAT TATGCTAAAGAGAGATATGGAATATCTTCAATGATACAATCAC AAGAAAAACCAGATCGAGTTTTGGTTCGGGTTAGAGACTTGAC AATACAAAAAGCTGATGAAGTTGTTTGGGTACGTGCAAGAGTT CATACAAGCAGAGCTAAAGGGAAACAGTGCTTCTTAGTCCTAC GTCAGCAGCAGTTTAATGTCCAGGCTCTTGTGGCGGTGGGAGA CCATGCAAGCAAGCAGATGGTTAAATTTGCTGCCAACATCAAC AAAGAGAGCATTGTGGATGTAGAAGGTGTTGTGAGAAAAGTG AATCAGAAAATTGGAAGCTGTACACAGCAAGACGTTGAGTTA CATGTTCAGAAGATTTATGTGATCAGTTTGGCTGAACCCCGTC TGCCCCTG | 229 |
| DRS 11-154 | | GAGAAGCCGCGGGAGATCATGGACGCGGCGGAAGATTATGCT AAAGAGAGATATGGAATATCTTCAATGATACAATCACAAGAA AAACCAGATCGAGTTTTGGTTCGGGTTAGAGACTTGACAATAC AAAAAGCTGATGAAGTTGTTTGGGTACGTGCAAGAGTTCATAC AAGCAGAGCTAAAGGGAAACAGTGCTTCTTAGTCCTACGTCA GCAGCAGTTTAATGTCCAGGCTCTTGTGGCGGTGGGAGACCAT GCAAGCAAGCAGATGGTTAAATTTGCTGCCAACATCAACAAA GAGAGCATTGTGGATGTAGAAGGTGTTGTGAGAAAAGTGAAT CAGAAAATTGGAAGCTGTACACAGCAAGACGTTGAGTTACAT GTTCAGAAGATTTATGTGATCAGTTTGGCTGAACCCCGTCTGC CCCTG | 230 |
| DRS 13-154 | | CCGCGGGAGATCATGGACGCGGCGGAAGATTATGCTAAAGAG AGATATGGAATATCTTCAATGATACAATCACAAGAAAAACCA GATCGAGTTTTGGTTCGGGTTAGAGACTTGACAATACAAAAAG CTGATGAAGTTGTTTGGGTACGTGCAAGAGTTCATACAAGCAG AGCTAAAGGGAAACAGTGCTTCTTAGTCCTACGTCAGCAGCAG TTTAATGTCCAGGCTCTTGTGGCGGTGGGAGACCATGCAAGCA AGCAGATGGTTAAATTTGCTGCCAACATCAACAAAGAGAGCA TTGTGGATGTAGAAGGTGTTGTGAGAAAAGTGAATCAGAAAA TTGGAAGCTGTACACAGCAAGACGTTGAGTTACATGTTCAGAA GATTTATGTGATCAGTTTGGCTGAACCCCGTCTGCCCCTG | 231 |
| DRS15-154 | | GAGATCATGGACGCGGCGGAAGATTATGCTAAAGAGAGATAT GGAATATCTTCAATGATACAATCACAAGAAAAACCAGATCGA GTTTTGGTTCGGGTTAGAGACTTGACAATACAAAAAGCTGATG AAGTTGTTTGGGTACGTGCAAGAGTTCATACAAGCAGAGCTAA AGGGAAACAGTGCTTCTTAGTCCTACGTCAGCAGCAGTTTAAT GTCCAGGCTCTTGTGGCGGTGGGAGACCATGCAAGCAAGCAG ATGGTTAAATTTGCTGCCAACATCAACAAAGAGAGCATTGTGG ATGTAGAAGGTGTTGTGAGAAAAGTGAATCAGAAAATTGGAA GCTGTACACAGCAAGACGTTGAGTTACATGTTCAGAAGATTTA TGTGATCAGTTTGGCTGAACCCCGTCTGCCCCTG | 232 |
| DRS 17-154 | | ATGGACGCGGCGGAAGATTATGCTAAAGAGAGATATGGAATA TCTTCAATGATACAATCACAAGAAAAACCAGATCGAGTTTTGG | 233 |

TABLE D9-continued

DRS DNA Sequences

| Name | Residue Range of SEQ ID NO: 2 | Nucleic acid sequence | SEQ NO ID: |
|---|---|---|---|
| | | TTCGGGTTAGAGACTTGACAATACAAAAAGCTGATGAAGTTGT TTGGGTACGTGCAAGAGTTCATACAAGCAGAGCTAAAGGGAA ACAGTGCTTCTTAGTCCTACGTCAGCAGCAGTTTAATGTCCAG GCTCTTGTGGCGGTGGGAGACCATGCAAGCAAGCAGATGGTT AAATTTGCTGCCAACATCAACAAAGAGAGCATTGTGGATGTA GAAGGTGTTGTGAGAAAAGTGAATCAGAAAATTGGAAGCTGT ACACAGCAAGACGTTGAGTTACATGTTCAGAAGATTTATGTGA TCAGTTTGGCTGAACCCCGTCTGCCCCTG | |
| DRS 19-154 | | GCGGCGGAAGATTATGCTAAAGAGAGATATGGAATATCTTCA ATGATACAATCACAAGAAAAACCAGATCGAGTTTTGGTTCGG GTTAGAGACTTGACAATACAAAAAGCTGATGAAGTTGTTTGGG TACGTGCAAGAGTTCATACAAGCAGAGCTAAAGGGAAACAGT GCTTCTTAGTCCTACGTCAGCAGCAGTTTAATGTCCAGGCTCTT GTGGCGGTGGGAGACCATGCAAGCAAGCAGATGGTTAAATTT GCTGCCAACATCAACAAAGAGAGCATTGTGGATGTAGAAGGT GTTGTGAGAAAAGTGAATCAGAAAATTGGAAGCTGTACACAG CAAGACGTTGAGTTACATGTTCAGAAGATTTATGTGATCAGTT TGGCTGAACCCCGTCTGCCCCTG | 234 |
| DRS 21-154 | | GCGGCGGAAGATTATGCTAAAGAGAGATATGGAATATCTTCA ATGATACAATCACAAGAAAAACCAGATCGAGTTTTGGTTCGG GTTAGAGACTTGACAATACAAAAAGCTGATGAAGTTGTTTGGG TACGTGCAAGAGTTCATACAAGCAGAGCTAAAGGGAAACAGT GCTTCTTAGTCCTACGTCAGCAGCAGTTTAATGTCCAGGCTCTT GTGGCGGTGGGAGACCATGCAAGCAAGCAGATGGTTAAATTT GCTGCCAACATCAACAAAGAGAGCATTGTGGATGTAGAAGGT GTTGTGAGAAAAGTGAATCAGAAAATTGGAAGCTGTACACAG CAAGACGTTGAGTTACATGTTCAGAAGATTTATGTGATCAGTT TGGCTGAACCCCGTCTG | 235 |
| DRS 23-154 | | GCGGCGGAAGATTATGCTAAAGAGAGATATGGAATATCTTCA ATGATACAATCACAAGAAAAACCAGATCGAGTTTTGGTTCGG GTTAGAGACTTGACAATACAAAAAGCTGATGAAGTTGTTTGGG TACGTGCAAGAGTTCATACAAGCAGAGCTAAAGGGAAACAGT GCTTCTTAGTCCTACGTCAGCAGCAGTTTAATGTCCAGGCTCTT GTGGCGGTGGGAGACCATGCAAGCAAGCAGATGGTTAAATTT GCTGCCAACATCAACAAAGAGAGCATTGTGGATGTAGAAGGT GTTGTGAGAAAAGTGAATCAGAAAATTGGAAGCTGTACACAG CAAGACGTTGAGTTACATGTTCAGAAGATTTATGTGATCAGTT TGGCTGAACCC | 236 |
| DRS 11-146 | | ATGCAGGAGAAGCCGCGGGAGATCATGGACGCGGCGGAAGAT TATGCTAAAGAGAGATATGGAATATCTTCAATGATACAATCAC AAGAAAAACCAGATCGAGTTTTGGTTCGGGTTAGAGACTTGAC AATACAAAAAGCTGATGAAGTTGTTTGGGTACGTGCAAGAGTT CATACAAGCAGAGCTAAAGGGAAACAGTGCTTCTTAGTCCTAC GTCAGCAGCAGTTTAATGTCCAGGCTCTTGTGGCGGTGGGAGA CCATGCAAGCAAGCAGATGGTTAAATTTGCTTGCAACATCAAC AAAGAGAGCATTGTGGATGTAGAAGGTGTTGTGAGAAAAGTG AATCAGAAAATTGGAAGCTGTACACAGCAAGACGTTGAGTTA CATGTTCAGAAGATTTATGTGATCAGT | 237 |
| DRS 13-146 | | ATGAAGCCGCGGGAGATCATGGACGCGGCGGAAGATTATGCT AAAGAGAGATATGGAATATCTTCAATGATACAATCACAAGAA AAACCAGATCGAGTTTTGGTTCGGGTTAGAGACTTGACAATAC AAAAAGCTGATGAAGTTGTTTGGGTACGTGCAAGAGTTCATAC AAGCAGAGCTAAAGGGAAACAGTGCTTCTTAGTCCTACGTCA GCAGCAGTTTAATGTCCAGGCTCTTGTGGCGGTGGGAGACCAT GCAAGCAAGCAGATGGTTAAATTTGCTTGCAACATCAACAAA GAGAGCATTGTGGATGTAGAAGGTGTTGTGAGAAAAGTGAAT CAGAAAATTGGAAGCTGTACACAGCAAGACGTTGAGTTACAT GTTCAGAAGATTTATGTGATCAGT | 238 |
| DRS 13-146/A106C | | ATGAAGCCGCGGGAGATCATGGACGCGGCGGAAGATTATGCT AAAGAGAGATATGGAATATCTTCAATGATACAATCACAAGAA AAACCAGATCGAGTTTTGGTTCGGGTTAGAGACTTGACAATAC AAAAAGCTGATGAAGTTGTTTGGGTACGTGCAAGAGTTCATAC AAGCAGAGCTAAAGGGAAACAGTGCTTCTTAGTCCTACGTCA GCAGCAGTTTAATGTCCAGGCTCTTGTGGCGGTGGGAGACCAT GCAAGCAAGCAGATGGTTAAATTTGCTTGCAACATCAACAAA GAGAGCATTGTGGATGTAGAAGGTGTTGTGAGAAAAGTGAAT | 239 |

TABLE D9-continued

DRS DNA Sequences

| Name | Residue Range of SEQ ID NO: 2 | Nucleic acid sequence | SEQ NO ID: |
|---|---|---|---|
| | | CAGAAAATTGGAAGCTGTACACAGCAAGACGTTGAGTTACAT GTTCAGAAGATTTATGTGATCAGT | |
| DRS 17-146 | | ATGATCATGGACGCGGCGGAAGATTATGCTAAAGAGAGATAT GGAATATCTTCAATGATACAATCACAAGAAAAACCAGATCGA GTTTTGGTTCGGGTTAGAGACTTGACAATACAAAAAGCTGATG AAGTTGTTTGGGTACGTGCAAGAGTTCATACAAGCAGAGCTAA AGGGAAACAGTGCTTCTTAGTCCTACGTCAGCAGCAGTTTAAT GTCCAGGCTCTTGTGGCGGTGGGAGACCATGCAAGCAAGCAG ATGGTTAAATTTGCTTGCAACATCAACAAAGAGAGCATTGTGG ATGTAGAAGGTGTTGTGAGAAAAGTGAATCAGAAAATTGGAA GCTGTACACAGCAAGACGTTGAGTTACATGTTCAGAAGATTTA TGTGATCAGT | 240 |
| DRS 21-146 | | ATGGCGGAAGATTATGCTAAAGAGAGATATGGAATATCTTCA ATGATACAATCACAAGAAAAACCAGATCGAGTTTTGGTTCGG GTTAGAGACTTGACAATACAAAAAGCTGATGAAGTTGTTTGGG TACGTGCAAGAGTTCATACAAGCAGAGCTAAAGGGAAACAGT GCTTCTTAGTCCTACGTCAGCAGCAGTTTAATGTCCAGGCTCTT GTGGCGGTGGGAGACCATGCAAGCAAGCAGATGGTTAAATTT GCTTGCAACATCAACAAAGAGAGCATTGTGGATGTAGAAGGT GTTGTGAGAAAAGTGAATCAGAAAATTGGAAGCTGTACACAG CAAGACGTTGAGTTACATGTTCAGAAGATTTATGTGATCAGT | 241 |

Additional coding or non-coding sequences may, but need not, be present within a polynucleotide of the present invention, and a polynucleotide may, but need not, be linked to other molecules and/or support materials. Hence, the polynucleotides of the present invention, regardless of the length of the coding sequence itself, may be combined with other DNA sequences, such as promoters, polyadenylation signals, additional restriction enzyme sites, multiple cloning sites, other coding segments, and the like, such that their overall length may vary considerably.

It is therefore contemplated that a polynucleotide fragment of almost any length may be employed; with the total length preferably being limited by the ease of preparation and use in the intended recombinant DNA protocol. Included are polynucleotides of about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 41, 43, 44, 45, 46, 47, 48, 49, 50, 60, 70, 80, 90, 100, 110, 120, 130, 140, 150, 160, 170, 180, 190, 200, 220, 240, 260, 270, 280, 300, 350, 400, 450, 500, 550, 600, 650, 700, 750, 800, 850, 900, 950, 1000, 1100, 1200, 1300, 1400, 1500, 1600, 1700, 1800, 1900, 2000, 2100, 2200, 2300, 2400, 2500, 2600, 2700, 2800, 2900, 3000 or more (including all integers in between) bases in length, including any portion or fragment (e.g., greater than about 6, 7, 8, 9, or 10 nucleotides in length) of a DRS reference polynucleotide (e.g., base number X-Y, in which X is about 1-3000 or more and Y is about 10-3000 or more), or its complement.

Embodiments of the present invention also include "variants" of the DRS reference polynucleotide sequences. Polynucleotide "variants" may contain one or more substitutions, additions, deletions and/or insertions in relation to a reference polynucleotide. Generally, variants of a DRS reference polynucleotide sequence may have at least about 30%, 40% 50%, 55%, 60%, 65%, 70%, generally at least about 75%, 80%, 85%, desirably about 90% to 95% or more, and more suitably about 98% or more sequence identity to that particular nucleotide sequence (Such as for example, SEQ ID NOS:2, 25-28, 30, 32-35, or 198-241) as determined by sequence alignment programs described elsewhere herein using default parameters. In certain embodiments, variants may differ from a reference sequence by about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 41, 43, 44, 45, 46, 47, 48, 49, 50, 60, 70, 80, 90, 100 (including all integers in between) or more bases. In certain embodiments, such as when the polynucleotide variant encodes a DRS polypeptide having a non-canonical activity, the desired activity of the encoded DRS polypeptide is not substantially diminished relative to the unmodified polypeptide. The effect on the activity of the encoded polypeptide may generally be assessed as described herein.

Certain embodiments include polynucleotides that hybridize to a reference DRS polynucleotide sequence (such as for example, SEQ ID NOS: 2, 25-28, 30, 32-35, or 198-241) or to their complements, under stringency conditions described below. As used herein, the term "hybridizes under low stringency, medium stringency, high stringency, or very high stringency conditions" describes conditions for hybridization and washing. Guidance for performing hybridization reactions can be found in Ausubel et al., (1998, supra), Sections 6.3.1-6.3.6. Aqueous and non-aqueous methods are described in that reference and either can be used.

Reference herein to low stringency conditions include and encompass from at least about 1% v/v to at least about 15% v/v formamide and from at least about 1 M to at least about 2 M salt for hybridization at 42° C., and at least about 1 M to at least about 2 M salt for washing at 42° C. Low stringency conditions also may include 1% Bovine Serum Albumin (BSA), 1 mM EDTA, 0.5 M NaHPO$_4$ (pH 7.2), 7% SDS for hybridization at 65° C., and (i) 2×SSC, 0.1% SDS; or (ii) 0.5% BSA, 1 mM EDTA, 40 mM NaHPO$_4$ (pH 7.2), 5% SDS for washing at room temperature. One embodiment of low stringency conditions includes hybridization in 6× sodium chloride/sodium citrate (SSC) at about 45° C., followed by two washes in 0.2×SSC, 0.1% SDS at least at 50° C. (the temperature of the washes can be increased to 55° C. for low stringency conditions).

Medium stringency conditions include and encompass from at least about 16% v/v to at least about 30% v/v formamide and from at least about 0.5 M to at least about 0.9 M salt for hybridization at 42° C., and at least about 0.1 M to at least about 0.2 M salt for washing at 55° C. Medium stringency conditions also may include 1% Bovine Serum Albumin (BSA), 1 mM EDTA, 0.5 M NaHPO$_4$ (pH 7.2), 7% SDS for hybridization at 65° C., and (i) 2×SSC, 0.1% SDS; or (ii) 0.5% BSA, 1 mM EDTA, 40 mM NaHPO$_4$ (pH 7.2), 5% SDS for washing at 60-65° C. One embodiment of medium stringency conditions includes hybridizing in 6×SSC at about 45° C., followed by one or more washes in 0.2×SSC, 0.1% SDS at 60° C. High stringency conditions include and encompass from at least about 31% v/v to at least about 50% v/v formamide and from about 0.01 M to about 0.15 M salt for hybridization at 42° C., and about 0.01 M to about 0.02 M salt for washing at 55° C.

High stringency conditions also may include 1% BSA, 1 mM EDTA, 0.5 M NaHPO$_4$ (pH 7.2), 7% SDS for hybridization at 65° C., and (i) 0.2×SSC, 0.1% SDS; or (ii) 0.5% BSA, 1 mM EDTA, 40 mM NaHPO$_4$ (pH 7.2), 1% SDS for washing at a temperature in excess of 65° C. One embodiment of high stringency conditions includes hybridizing in 6×SSC at about 45° C., followed by one or more washes in 0.2×SSC, 0.1% SDS at 65° C. One embodiment of very high stringency conditions includes hybridizing in 0.5 M sodium phosphate, 7% SDS at 65° C., followed by one or more washes in 0.2×SSC, 1% SDS at 65° C.

Other stringency conditions are well known in the art and a skilled artisan will recognize that various factors can be manipulated to optimize the specificity of the hybridization. Optimization of the stringency of the final washes can serve to ensure a high degree of hybridization. For detailed examples, see Ausubel et al., supra at pages 2.10.1 to 2.10.16 and Sambrook et al. (1989, supra) at sections 1.101 to 1.104. While stringent washes are typically carried out at temperatures from about 42° C. to 68° C., one skilled in the art will appreciate that other temperatures may be suitable for stringent conditions. Maximum hybridization rate typically occurs at about 20° C. to 25° C. below the $T_m$ for formation of a DNA-DNA hybrid. It is well known in the art that the $T_m$ is the melting temperature, or temperature at which two complementary polynucleotide sequences dissociate. Methods for estimating $T_m$ are well known in the art (see Ausubel et al., supra at page 2.10.8).

In general, the $T_m$ of a perfectly matched duplex of DNA may be predicted as an approximation by the formula: $T_m = 81.5 + 16.6 \, (\log_{10} M) + 0.41 \, (\% \, G+C) - 0.63 \, (\% \, formamide) - (600/length)$ wherein: M is the concentration of Na$^+$, preferably in the range of 0.01 molar to 0.4 molar; % G+C is the sum of guanosine and cytosine bases as a percentage of the total number of bases, within the range between 30% and 75% G+C; % formamide is the percent formamide concentration by volume; length is the number of base pairs in the DNA duplex. The $T_m$ of a duplex DNA decreases by approximately 1° C. with every increase of 1% in the number of randomly mismatched base pairs. Washing is generally carried out at $T_m - 15°$ C. for high stringency, or $T_m - 30°$ C. for moderate stringency.

In one example of a hybridization procedure, a membrane (e.g., a nitrocellulose membrane or a nylon membrane) containing immobilized DNA is hybridized overnight at 42° C. in a hybridization buffer (50% deionized formamide, 5×SSC, 5×Denhardt's solution (0.1% ficoll, 0.1% polyvinylpyrollidone and 0.1% bovine serum albumin), 0.1% SDS and 200 mg/mL denatured salmon sperm DNA) containing a labeled probe. The membrane is then subjected to two sequential medium stringency washes (i.e., 2×SSC, 0.1% SDS for 15 min at 45° C., followed by 2×SSC, 0.1% SDS for 15 min at 50° C.), followed by two sequential higher stringency washes (i.e., 0.2×SSC, 0.1% SDS for 12 min at 55° C. followed by 0.2×SSC and 0.1% SDS solution for 12 min at 65-68° C.

Production of DRS Polypeptides and DRS-Fc Polypeptides

DRS-Fc conjugate polypeptides may be prepared by any suitable procedure known to those of skill in the art for example, by using standard solid-phase peptide synthesis (Merrifield, *J. Am. Chem. Soc.* 85:2149-2154 (1963)), or by recombinant technology using a genetically modified host. Protein synthesis may be performed using manual techniques or by automation. Automated synthesis may be achieved, for example, using Applied Biosystems 431A Peptide Synthesizer (Perkin Elmer). Alternatively, various fragments may be chemically synthesized separately and combined using chemical methods to produce the desired molecule.

DRS polypeptides can also be produced by expressing a DNA sequence encoding the DRS polypeptide in question in a suitable host cell by well-known techniques. The polynucleotide sequence coding for the DRS polypeptide may be prepared synthetically by established standard methods, e.g., the phosphoamidite method described by Beaucage et al., *Tetrahedron Letters* 22:1859-1869, 1981; or the method described by Matthes et al., *EMBO Journal* 3:801-805, 1984. According to the phosphoramidite method, oligonucleotides are synthesized, e.g., in an automatic DNA synthesizer, purified, duplexed and ligated to form the synthetic DNA construct. Alternatively the DNA construct can be constructed using standard recombinant molecular biological techniques including restriction enzyme mediated cloning and PCR based gene amplification.

The polynucleotide sequences may also be of mixed genomic, cDNA, and synthetic origin. For example, a genomic or cDNA sequence encoding a leader peptide may be joined to a genomic or cDNA sequence encoding the DRS polypeptide, after which the DNA sequence may be modified at a site by inserting synthetic oligonucleotides encoding the desired amino acid sequence for homologous recombination in accordance with well-known procedures or preferably generating the desired sequence by PCR using suitable oligonucleotides. In some embodiments a signal sequence can be included before the coding sequence. This sequence encodes a signal peptide N-terminal to the coding sequence which communicates to the host cell to direct the polypeptide to the cell surface or secrete the polypeptide into the media. Typically the signal peptide is clipped off by the host cell before the protein leaves the cell. Signal peptides can be found in variety of proteins in prokaryotes and eukaryotes.

A variety of expression vector/host systems are known and may be utilized to contain and express polynucleotide sequences. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems, including mammalian cell and more specifically human cell systems transformed with viral, plasmid, episomal or integrating expression vectors.

The "control elements" or "regulatory sequences" present in an expression vector are non-translated regions of the vector—enhancers, promoters, 5' and 3' untranslated regions—which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the PBLUESCRIPT phagemid (Stratagene, La Jolla, Calif.) or PSPORT1 plasmid (Gibco BRL, Gaithersburg, Md.) and the like may be used. In mammalian cell systems, promoters from mammalian genes or from mammalian viruses are generally preferred. If it is necessary to generate a cell line that contains multiple copies of the sequence encoding a polypeptide, vectors based on SV40 or EBV may be advantageously used with an appropriate selectable marker.

Certain embodiments may employ *E. coli*-based expression systems (see, e.g., Structural Genomics Consortium et al., *Nature Methods*. 5:135-146, 2008). These and related embodiments may rely partially or totally on ligation-independent cloning (LIC) to produce a suitable expression vector. In specific embodiments, protein expression may be controlled by a T7 RNA polymerase (e.g., pET vector series). These and related embodiments may utilize the expression host strain BL21(DE3), a λDE3 lysogen of BL21 that supports T7-mediated expression and is deficient in lon and ompT proteases for improved target protein stability. Also included are expression host strains carrying plasmids encoding tRNAs rarely used in *E. coli*, such as ROSETTA™ (DE3) and Rosetta 2 (DE3) strains. Cell lysis and sample handling may also be improved using reagents sold under the trademarks BENZONASE® nuclease and BUG-BUSTER® Protein Extraction Reagent. For cell culture, auto-inducing media can improve the efficiency of many expression systems, including high-throughput expression systems. Media of this type (e.g., OVERNIGHT EXPRESS™ Autoinduction System) gradually elicit protein expression through metabolic shift without the addition of artificial inducing agents such as IPTG.

Particular embodiments employ hexahistidine tags (such as those sold under the trademark HIS•TAG® fusions), followed by immobilized metal affinity chromatography (IMAC) purification, or related techniques. In certain aspects, however, clinical grade proteins can be isolated from *E. coli* inclusion bodies, without or without the use of affinity tags (see, e.g., Shimp et al., *Protein Expr Purif*. 50:58-67, 2006). As a further example, certain embodiments may employ a cold-shock induced *E. coli* high-yield production system, because over-expression of proteins in *Escherichia coli* at low temperature improves their solubility and stability (see, e.g., Qing et al., *Nature Biotechnology*. 22:877-882, 2004).

Also included are high-density bacterial fermentation systems. For example, high cell density cultivation of *Ralstonia eutropha* allows protein production at cell densities of over 150 g/L, and the expression of recombinant proteins at titers exceeding 10 g/L. In the yeast *Saccharomyces cerevisiae*, a number of vectors containing constitutive or inducible promoters such as alpha factor, alcohol oxidase, and PGH may be used. For reviews, see Ausubel et al. (supra) and Grant et al., *Methods Enzymol*. 153:516-544, 1987. Also included are *Pichia* pandoris expression systems (see, e.g., Li et al., *Nature Biotechnology*. 24, 210-215, 2006; and Hamilton et al., *Science*, 301:1244, 2003). Certain embodiments include yeast systems that are engineered to selectively glycosylate proteins, including yeast that have humanized N-glycosylation pathways, among others (see, e.g., Hamilton et al., *Science*. 313:1441-1443, 2006; Wildt et al., *Nature Reviews Microbiol*. 3:119-28, 2005; and Gerngross et al., *Nature-Biotechnology*. 22:1409-1414, 2004; U.S. Pat. Nos. 7,629,163; 7,326,681; and 7,029,872). Merely by way of example, recombinant yeast cultures can be grown in Fernbach Flasks or 15 L, 50 L, 100 L, and 200 L fermentors, among others.

In cases where plant expression vectors are used, the expression of sequences encoding polypeptides may be driven by any of a number of promoters. For example, viral promoters such as the 35S and 19S promoters of CaMV may be used alone or in combination with the omega leader sequence from TMV (Takamatsu, *EMBO J*. 6:307-311, 1987). Alternatively, plant promoters such as the small subunit of RUBISCO or heat shock promoters may be used (Coruzzi et al., *EMBO J*. 3:1671-1680, 1984; Broglie et al., *Science*. 224:838-843, 1984; and Winter et al., *Results Probl. Cell Differ*. 17:85-105, 1991). These constructs can be introduced into plant cells by direct DNA transformation or pathogen-mediated transfection. Such techniques are described in a number of generally available reviews (see, e.g., Hobbs in McGraw Hill, *Yearbook of Science and Technology*, pp. 191-196, 1992).

An insect system may also be used to express a polypeptide of interest. For example, in one such system, *Autographa californica* nuclear polyhedrosis virus (AcNPV) is used as a vector to express foreign genes in *Spodoptera frugiperda* cells or in *Trichoplusia* cells. The sequences encoding the polypeptide may be cloned into a non-essential region of the virus, such as the polyhedrin gene, and placed under control of the polyhedrin promoter. Successful insertion of the polypeptide-encoding sequence will render the polyhedrin gene inactive and produce recombinant virus lacking coat protein. The recombinant viruses may then be used to infect, for example, *S. frugiperda* cells or *Trichoplusia* cells in which the polypeptide of interest may be expressed (Engelhard et al., *PNAS USA*. 91:3224-3227, 1994). Also included are baculovirus expression systems, including those that utilize SF9, SF21, and *T. ni* cells (see, e.g., Murphy and Piwnica-Worms, *Curr Protoc Protein Sci*. Chapter 5:Unit5.4, 2001). Insect systems can provide post-translation modifications that are similar to mammalian systems.

In mammalian host cells, a number of expression systems are well known in the art and commercially available. Exemplary mammalian vector systems include for example, pCEP4, pREP4, and pREP7 from Invitrogen, the PerC6 system from Crucell, and Lentiviral based systems such as pLP1 from Invitrogen, and others. For example, in cases where an adenovirus is used as an expression vector, sequences encoding a polypeptide of interest may be ligated into an adenovirus transcription/translation complex consisting of the late promoter and tripartite leader sequence. Insertion in a non-essential E1 or E3 region of the viral genome may be used to obtain a viable virus which is capable of expressing the polypeptide in infected host cells (Logan & Shenk, *PNAS USA*. 81:3655-3659, 1984). In addition, transcription enhancers, such as the Rous sarcoma virus (RSV) enhancer, may be used to increase expression in mammalian host cells.

Examples of useful mammalian host cell lines include monkey kidney CV1 line transformed by SV40 (COS-7, ATCC CRL 1651); human embryonic kidney line (293 or 293 cells sub-cloned for growth in suspension culture, Graham et al., *J. Gen Vivol.* 36:59, 1977); baby hamster kidney cells (BHK, ATCC CCL 10); mouse sertoli cells (TM4, Mather, *Biol. Reprod.* 23:243-251, 1980); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TR1 cells (Mather et al., *Annals N.Y. Acad. Sci.* 383:44-68, 1982); MRC 5 cells; FS4 cells; and a human hepatoma line (Hep G2). Other useful mammalian host cell lines include Chinese hamster ovary (CHO) cells, including DHFR-CHO cells (Urlaub et al., *PNAS USA.* 77:4216, 1980); and myeloma cell lines such as NSO and Sp2/0. For a review of certain mammalian host cell lines suitable for antibody production, see, e.g., Yazaki and Wu, *Methods in Molecular Biology*, Vol. 248 (B. K. C Lo, ed., Humana Press, Totowa, N.J., 2003), pp. 255-268. Certain preferred mammalian cell expression systems include CHO and HEK293-cell based expression systems. Mammalian expression systems can utilize attached cell lines, for example, in T-flasks, roller bottles, or cell factories, or suspension cultures, for example, in 1 L and 5 L spinners, 5 L, 14 L, 40 L, 100 L and 200 L stir tank bioreactors, or 20/50 L and 100/200 L WAVE bioreactors, among others known in the art.

Also included is cell-free expression of proteins. These and related embodiments typically utilize purified RNA polymerase, ribosomes, tRNA and ribonucleotides; these reagents may be produced by extraction from cells or from a cell-based expression system.

In addition, a host cell strain may be chosen for its ability to modulate the expression of the inserted sequences or to process the expressed protein in the desired fashion. Such modifications of the polypeptide include, but are not limited to, post-translational modifications such as acetylation, carboxylation, glycosylation, phosphorylation, lipidation, and acylation, or the insertion of non-naturally occurring amino acids (see generally U.S. Pat. Nos. 7,939,496; 7,816,320; 7,947,473; 7,883,866; 7,838,265; 7,829,310; 7,820,766; 7,820,766; 7,7737,226, 7,736,872; 7,638,299; 7,632,924; and 7,230,068). In some embodiments, such non-naturally occurring amino acids may be inserted at position Cys130. Post-translational processing which cleaves a "prepro" form of the protein may also be used to facilitate correct insertion, folding and/or function. Different host cells such as yeast, CHO, HeLa, MDCK, HEK293, and W138, in addition to bacterial cells, which have or even lack specific cellular machinery and characteristic mechanisms for such post-translational activities, may be chosen to ensure the correct modification and processing of the foreign protein.

The DRS polypeptides produced by a recombinant cell can be purified and characterized according to a variety of techniques known in the art. Exemplary systems for performing protein purification and analyzing protein purity include fast protein liquid chromatography (FPLC) (e.g., AKTA and Bio-Rad FPLC systems), high-pressure liquid chromatography (HPLC) (e.g., Beckman and Waters HPLC). Exemplary chemistries for purification include ion exchange chromatography (e.g., Q, S), size exclusion chromatography, salt gradients, affinity purification (e.g., Ni, Co, FLAG, maltose, glutathione, protein A/G), gel filtration, reverse-phase, ceramic HYPERD® ion exchange chromatography, and hydrophobic interaction columns (HIC), among others known in the art. Several exemplary methods are also disclosed in the Examples sections.

DRS-Fc Polypeptides

As noted above, embodiments of the present invention relate to DRS-Fc conjugates, which comprise at least one Fc region that is covalently attached to one or more DRS polypeptide(s). Examples of DRS-Fc conjugates include fusion proteins and various forms of chemically cross-linked proteins. A wide variety of Fc region sequences may be employed in the DRS-Fc conjugates of the present invention, including wild-type sequences from any number of species, as well as variants, fragments, hybrids, and chemically modified forms thereof. The DRS-Fc polypeptides may also (optionally) comprise one or more linkers, which typically separate the Fc region(s) from the DRS polypeptide(s), including peptide linkers and chemical linkers, as described herein and known in the art.

DRS-Fc conjugate polypeptides can provide a variety of advantages relative to un-conjugated or unmodified DRS polypeptides, e.g., corresponding DRS polypeptides of the same or similar sequence having no Fc region(s) attached thereto. In such DRS-Fc conjugates the Fc region may be connected to the DRS polypeptide at any position. In certain embodiments, the Fc region is connected to the DRS polypeptide at the N terminus, C-terminus, or via a surface exposed amino acid with the DRS polypeptide. In certain embodiments the Fc region is connected at a cysteine residue within the DRS polypeptide. In some aspects the Cysteine residue is selected from Cys76, Cys130, Cys203, Cys259, Cys334, and Cys349 (using the numbering of SEQ ID NO:1). Merely by way of illustration, the covalent attachment of one or more Fc regions can alter (e.g., increase, decrease) the DRS polypeptide's solubility, half-life (e.g., in serum, in a selected tissue, in a test tube under storage conditions, for example, at room temperature or under refrigeration), dimerization or multimerization properties, biological activity or activities, for instance, by providing Fc-region-associated effector functions (e.g., activation of the classical complement cascade, interaction with immune effector cells via the Fc receptor (FcR), compartmentalization of immunoglobulins), cellular uptake, intracellular transport, tissue distribution, and/or bioavailability, relative to an unmodified DRS polypeptide having the same or similar sequence. In certain aspects, Fc regions can confer effector functions relating to complement-dependent cytotoxicity (CDC), antibody-dependent cell-mediated cytotoxicity (ADCC), and/or antibody-dependent cell-mediated phagocytosis (ADCP), which are believed to play a role in clearing specific target cells such as tumor cells and infected cells.

Certain embodiments employ DRS-Fc fusion proteins. "Fusion proteins" are defined elsewhere herein and well known in the art, as are methods of making fusion proteins (see, e.g., U.S. Pat. Nos. 5,116,964; 5,428,130; 5,455,165; 5,514,582; 6,406,697; 6,291,212; and 6,300,099 for general disclosure and methods related to Fc fusion proteins). In a DRS-Fc fusion protein, the Fc region can be fused to the N-terminus of the DRS polypeptide, the C-terminus, or both. In some embodiments, one or more Fc regions can be fused internally relative to DRS sequences, for instance, by placing an Fc region between a first DRS sequence (e.g., domain) and a second DRS sequence (e.g., domain), where the first DRS sequence is fused to the N-terminus of the Fc region and the second DRS sequence is fused to the C-terminus of the Fc region. In specific embodiments, the first and second DRS sequences are identical. In other embodiments, the first and second DRS sequences are different (e.g., they include different functional domains of the DRS polypeptide). Certain DRS-Fc fusion proteins can also include additional heterologous protein sequences, that is, non-Fc region and non-DRS polypeptide sequences.

The term "DRS-Fc" can indicate, but does not necessarily indicate, the N-terminal or C-terminal attachment of the Fc region to the DRS polypeptide. For instance, in certain instances the term "Fc-DRS" indicates fusion of the Fc region to the N-terminus of the DRS polypeptide, and the term "DRS-Fc" indicates fusion of the Fc region to the C-terminus of the DRS polypeptide. However, either term can be used more generally to refer to any fusion protein or conjugate of an Fc region and a DRS polypeptide.

Certain embodiments relate to DRS-Fc conjugates, where, for instance, one or more Fc regions are chemically conjugated or cross-linked to the DRS polypeptide(s). In these and related aspects, the Fc region can be conjugated to the DRS polypeptide at the N-terminal region (e.g., within the first 10, 20, 30, 40, 50, 60, 70, 80, 90, 100 or so amino acids), the internal region (between the N-terminal and C-terminal regions), and/or the C-terminal region (e.g., within the last 10, 20, 30, 40, 50, 60, 70, 80, 90, 100 or so amino acids). Polypeptides can be conjugated or cross-linked to other polypeptides according to a variety of routine techniques in the art. For instance, certain techniques employ the carboxyl-reactive carbodiimide crosslinker EDC (or EDAC), which covalently attaches via D, E, and C-terminal carboxyl groups. Other techniques employ activated EDC, which covalently attaches via K and N-terminal amino groups). Still other techniques employ m-maleimidobenzoyl-N-hydroxysuccinimide ester (MBS) or Sulfo-MBS, which covalently attach via the thiol group of a cysteine residue (see also U.S. Application No. 2007/0092940 for cysteine engineered Ig regions that can be used for thiol conjugation). Such cross-linked proteins can also comprise linkers, including cleavable or otherwise releasable linkers (e.g., enzymatically cleavable linkers, hydrolysable linkers), and non-cleavable linkers (i.e., physiologically-stable linkers). Certain embodiments may employ non-peptide polymers (e.g., PEG polymers; DRS-N-PEG-N-Fc conjugate) as a cross-linker between the Fc region(s) and the DRS polypeptide(s), as described, for example, in U.S. Application No. 2006/0269553. See also US Application No. 2007/0269369 for exemplary descriptions of Fc region conjugation sites.

In certain embodiments, discussed in greater detail below, variant or otherwise modified Fc regions can be employed, including those having altered properties or biological activities relative to wild-type Fc region(s). Examples of modified Fc regions include those having mutated sequences, for instance, by substitution, insertion, deletion, or truncation of one or more amino acids relative to a wild-type sequence, hybrid Fc polypeptides composed of domains from different immunoglobulin classes/subclasses, Fc polypeptides having altered glycosylationisialylation patterns, and Fc polypeptides that are modified or derivatized, for example, by biotinylation (see, e.g., US Application No. 2010/0209424), phosphorylation, sulfation, etc., or any combination of the foregoing. Such modifications can be employed to alter (e.g., increase, decrease) the binding properties of the Fc region to one or more particular FcRs (e.g., FcγRI, FcγRIIa, FcγRIIb, FcγRIIc, FcγRIIIa, FcγRIIIb), its pharmacokinetic properties (e.g., stability or half-life, bioavailability, tissue distribution, volume of distribution, concentration, elimination rate constant, elimination rate, area under the curve (AUC), clearance, $C_{max}$, $t_{max}$, $C_{min}$, fluctuation), its immunogenicity, its complement fixation or activation, and/or the CDC/ADCC/ADCP-related activities of the Fc region, among other properties described herein, relative to a corresponding wild-type Fc sequence.

Figure 6:
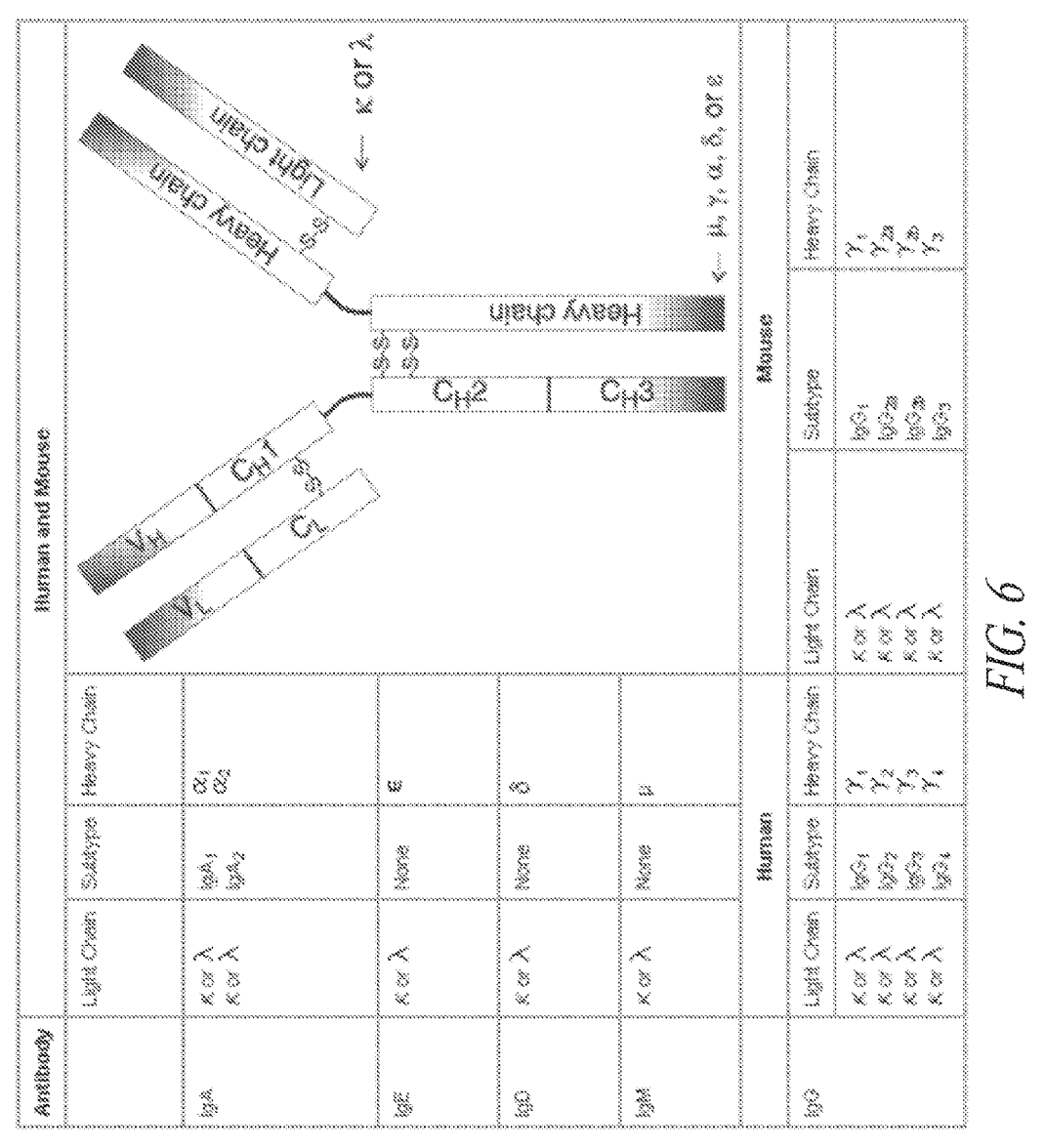

The "Fc region" of a DRS-Fc conjugate provided herein is usually derived from the heavy chain of an immunoglobulin (Ig) molecule. A typical Ig molecule is composed of two heavy chains and two light chains. The heavy chains can be divided into at least three functional regions: the Fd region, the Fc region (fragment crystallizable region), and the hinge region (see FIG. 6), the latter being found only in IgG, IgA, and IgD immunoglobulins. The Fd region comprises the variable ($V_H$) and constant ($CH_1$) domains of the heavy chains, and together with the variable ($V_L$) and constant ($C_L$) domains of the light chains forms the antigen-binding fragment or Fab region.

The Fc region of IgG, IgA, and IgD immunoglobulins comprises the heavy chain constant domains 2 and 3, designated respectively as $CH_2$ and $CH_3$ regions; and the Fc region of IgE and IgM immunoglobulins comprises the heavy chain constant domains 2, 3, and 4, designated respectively as $CH_2$, $CH_3$, and $CH_4$ regions. The Fc region is mainly responsible for the immunoglobulin effector functions, which include, for example, complement fixation and binding to cognate Fc receptors of effector cells.

The hinge region (found in IgG, IgA, and IgD) acts as a flexible spacer that allows the Fab portion to move freely in space relative to the Fc region. In contrast to the constant regions, the hinge regions are structurally diverse, varying in both sequence and length among immunoglobulin classes and subclasses. The hinge region may also contain one or more glycosylation site(s), which include a number of structurally distinct types of sites for carbohydrate attachment. For example, IgA1 contains five glycosylation sites within a 17 amino acid segment of the hinge region, conferring significant resistance of the hinge region polypeptide to intestinal proteases. Residues in the hinge proximal region of the $CH_2$ domain can also influence the specificity of the interaction between an immunoglobulin and its respective Fc receptor(s) (see, e.g., Shin et al., *Intern. Rev. Immunol.* 10:177-186, 1993).

The term "Fc region" or "Fc fragment" or "Fc" as used herein, thus refers to a protein that contains one or more of a $CH_2$ region, a $CH_3$ region, and/or a $CH_4$ region from one or more selected immunoglobulin(s), including fragments and variants and combinations thereof. An "Fc region" may also include one or more hinge region(s) of the heavy chain constant region of an immunoglobulin. In certain embodiments, the Fc region does not contain one or more of the $CH_1$, $C_L$, $V_L$, and/or $V_H$ regions of an immunoglobulin.

Figure 7:
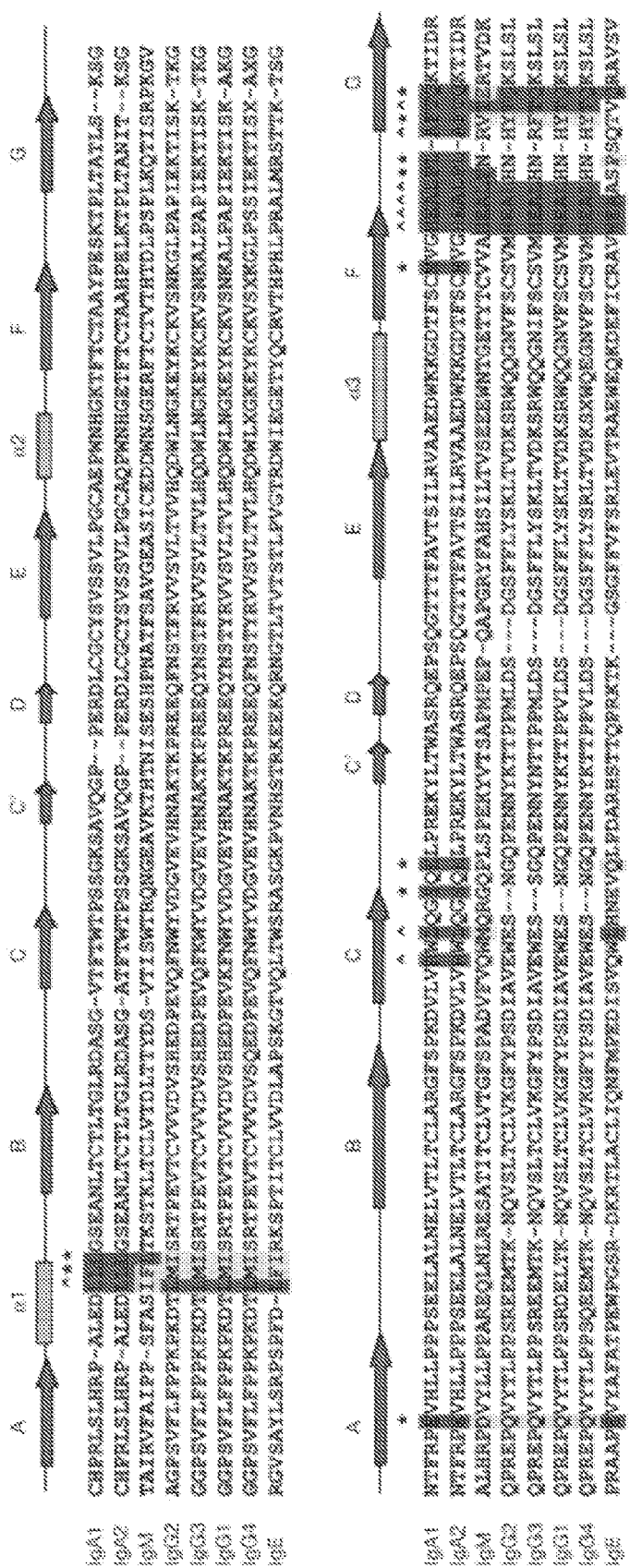
FIG. 7 shows an alignment of Fc regions from human IgA1 (SEQ ID NO:66), IgA2 (SEQ ID NO:67), IgM (SEQ ID NO:68), IgG1 (SEQ ID NO:69), IgG2 (SEQ ID NO:70), IgG3 (SEQ ID NO:71), IgG4 (SEQ ID NO:72), and IgE (SEQ ID NO:73). The secondary structure of Fcα is shown above the sequences. Carets (^) and asterisks (*) show residues that contribute respectively to 0-4% and 5-12% of the binding surface.

The Fc region can be derived from the $CH_2$ region, $CH_3$ region, $CH_4$ region, and/or hinge region(s) of any one or more immunoglobulin classes, including but not limited to IgA, IgD, IgE, IgG, IgM, including subclasses and combinations thereof. In some embodiments, the Fc region is derived from an IgA immunoglobulin, including subclasses IgA1 and/or IgA2. In certain embodiments, the Fc region is derived from an IgD immunoglobulin. In particular embodiments, the Fc region is derived from an IgE immunoglobulin. In some embodiments, the Fc region is derived from an IgG immunoglobulin, including subclasses IgG1, IgG2, IgG2, IgG3, and/or IgG4. In certain embodiments, the Fc region is derived from an IgM immunoglobulin. FIG. 7 shows an alignment of Fc regions from human IgA1 (SEQ ID NO:66), IgA2 (SEQ ID NO:67), IgM (SEQ ID NO:68), IgG1 (SEQ ID NO:69), IgG2 (SEQ ID NO:70), IgG3 (SEQ ID NO:71), IgG4 (SEQ ID NO:72), and IgE (SEQ ID NO:73).

Certain Fc regions demonstrate specific binding for one or more Fc-receptors (FcRs). Examples of classes of Fc receptors include Fcγ receptors (FcγR), Fcα receptors (FcαR), Fcε receptors (FcεR), and the neonatal Fc receptor (FcRn). For instance, certain Fc regions have increased binding to (or affinity for) one or more FcγRs, relative to FcαRs, FcεRs, and/or FcRn. In some embodiments, Fc regions have increased binding to FcαRs, relative to one or more FcγRs, FcεRs, and/or FcRn. In other embodiments, Fc regions have increased binding to FcεRs (e.g., FcαRI), relative to one or more FcγRs, FcαRs, and/or FcRn. In particular embodiments, Fc regions have increased binding to FcRn, relative to one or more FcγRs, FcαRs, and/or FcεRs. In certain embodiments, the binding (or affinity) of an Fc region to one or more selected FcR(s) is increased relative to its binding to (or affinity for) one or more different FcR(s), typically by about 1.5×, 2×, 2.5×, 3×, 3.5×, 4×, 4.5×, 5×, 6×, 7×, 8×, 9×, 10×, 15×, 20×, 25×, 30×, 40×, 50×, 60×, 70×, 80×, 90×, 100×, 200×, 300×, 400×, 500×, 600×, 700×, 800×, 900×, 1000× or more (including all integers in between).

Examples of FcγRs include FcγRI, FcγRIIa, FcγRIIb, FcγRIIc, FcγRIIIa, and FcγRIIIb. FcγRI (CD64) is expressed on macrophages and dendritic cells and plays a role in phagocytosis, respiratory burst, cytokine stimulation, and dendritic cell endocytic transport. Expression of FcγRI is upregulated by both GM-CSF and γ-interferon (γ-IFN) and downregulated by interleukin-4 (IL-4). FcγRIIa is expressed on polymorphonuclear leukocytes (PMN), macrophages, dendritic cells, and mast cells. FcγRIIa plays a role in phagocytosis, respiratory burst, and cytokine stimulation. Expression of FcγRIIa is upregulated by GM-CSF and γ-IFN, and decreased by IL-4. FcγIIb is expressed on B cells, PMN, macrophages, and mast cells. FcγIIb inhibits immunoreceptor tyrosine-based activation motif (ITAM) mediated responses, and is thus an inhibitory receptor. Expression of FcγRIIc is upregulated by intravenous immunoglobulin (IVIG) and IL-4 and decreased by γ-IFN. FcγRIIc is expressed on NK cells. FcγRIIIa is expressed on natural killer (NK) cells, macrophages, mast cells, and platelets. This receptor participates in phagocytosis, respiratory burst, cytokine stimulation, platelet aggregation and degranulation, and NK-mediated ADCC. Expression of FcγRIII is upregulated by C5a, TGF-β, and γ-IFN and downregulated by IL-4. FcγRIIIb is a GPI-linked receptor expressed on PMN.

Certain Fc regions have increased binding to FcγRI, relative to FcγRIIa, FcγRIIb, FcγRIIc, FcγRIIIa, and/or FcγRIIIb. Some embodiments have increased binding to FcγRIIa, relative to FcγRI, FcγRIIb, FcγRIIc, FcγRIIIa, and/or FcγRIIIb. Particular Fc regions have increased binding to FcγRIIb, relative to FcγRI, FcγRIIa, FcγRIIc, FcγRIIIa, and/or FcγRIIIb. Certain Fc regions have increased binding to FcγRIIc, relative to FcγRI, FcγRIIa, FcγRIIb, FcγRIIIa, and/or FcγRIIIb. Some Fc regions have increased binding to FcγRIIIa, relative to FcγRI, FcγRIIa, FcγRIIb, FcγRIIc, and/or FcγRIIIb. Specific Fc regions have increased binding to FcγRIIIb, relative to FcγRI, FcγRIIa, FcγRIIb, FcγRIIc, and/or FcγRIIIa.

FcαRs include FcαRI (CD89). FcαRI is found on the surface of neutrophils, eosinophils, monocytes, certain macrophages (e.g., Kupffer cells), and certain dendritic cells. FcαRI is composed of two extracellular Ig-like domains, is a member of both the immunoglobulin superfamily and the multi-chain immune recognition receptor (MIRR) family, and signals by associating with two FcRγ signaling chains.

FcεRs include FcεRI and FcεRII. The high-affinity receptor FcεRI is a member of the immunoglobulin superfamily, is expressed on epidermal Langerhans cells, eosinophils, mast cells and basophils, and plays a major role in controlling allergic responses. FcεRI is also expressed on antigen-presenting cells, and regulates the production pro-inflammatory cytokines. The low-affinity receptor FcεRII (CD23) is a C-type lectin that can function as a membrane-bound or soluble receptor. FcεRII regulates B cell growth and differentiation, and blocks IgE-binding of eosinophils, monocytes, and basophils. Certain Fc regions have increased binding to FcεRI, relative to FcεRII. Other Fc regions have increased binding to FcεRII, relative to FcεRI.

Table F1 below summarizes the characteristics of certain FcRs.

TABLE F1

Exemplary Fc-Receptors

| Receptor | Primary Antibody Ligand | Ligand Affinity | Cell Distribution | Exemplary Effects Following Binding to Fc Ligand |
|---|---|---|---|---|
| FcγRI (CD64) | IgG1 and IgG3 | High (Kd ~ $10^{-9}$M) | Macrophages Neutrophils Eosinophils Dendritic cells | Phagocytosis Cell activation Activation of respiratory burst Induction of microbe killing |
| FcγRIIa (CD32) | IgG | Low (Kd > $10^{-7}$M) | Macrophages Neutrophils Eosinophils Platelets Langerhans cells | Phagocytosis Degranulation (eosinophils) |
| FcγRIIb1 (CD32) | IgG | Low (Kd > $10^{-7}$M) | B Cells Mast cells | No phagocytosis Inhibition of cell activity |
| FcγRIIb2 (CD32) | IgG | Low (Kd > $10^{-7}$M) | Macrophages Neutrophils Eosinophils | Phagocytosis Inhibition of cell activity |
| FcγRIIIa (CD16a) | IgG | Low (Kd > $10^{-6}$M) | NK cells Macrophages (certain tissues) | Induction of antibody-dependent cell-mediated cytotoxicity (ADCC) Induction of cytokine release by macrophages |
| FcγRIIIb (CD16b) | IgG | Low (Kd > $10^{-6}$M) | Eosinophils Macrophages | Induction of microbe killing |

TABLE F1-continued

Exemplary Fc-Receptors

| Receptor | Primary Antibody Ligand | Ligand Affinity | Cell Distribution | Exemplary Effects Following Binding to Fc Ligand |
|---|---|---|---|---|
| | | | Neutrophils Mast cells Follicular dendritic cells | |
| FcεRI | IgE | High (Kd ~ $10^{-10}$M) | Mast cells Eosinophils Basophils Langerhans cells | Degranulation |
| FcεRII (CD23) | IgE | Low (Kd > $10^{-7}$M) | B cells Eosinophils Langerhans cells | Possible adhesion molecule |
| FcαRI (CD89) | IgA | Low (Kd > $10^{-6}$M) | Monocytes Macrophages Neutrophils Eosinophils | Phagocytosis Induction of microbe killing |
| Fcα/μR | IgA and IgM | High for IgM, Moderate for IgA | B cells Mesangial cells Macrophages | Endocytosis Induction of microbe killing |
| FcRn | IgG | | Monocytes Macrophages Dendrite cells Epithelial cells Endothelial cells Hepatocytes | Transfers IgG from a mother to fetus through the placenta Transfers IgG from a mother to infant in milk Protects IgG from degradation |

Fc regions can be derived from the immunoglobulin molecules of any animal, including vertebrates such as mammals such cows, goats, swine, dogs, mice, rabbits, hamsters, rats, guinea pigs, non-human primates, and humans. The amino acid sequences of $CH_2$, $CH_3$, $CH_4$, and hinge regions from exemplary, wild-type human IgA1, IgA2, IgD, IgE, IgG1, IgG2, IgG3, IgG4, and IgM immunoglobulins are shown below (SEQ ID NOS:38-64).

SEQ ID NO:38 is the amino acid sequence of a human IgA1 hinge region (VPSTPPTPSPSTPPTPSPS).

SEQ ID NO:39 is the amino acid sequence of a human IgA1 CH2 region (CCHPRLSLHRPALEDLLLGSEANLTCTLTGLRDASGVTFTWTPSSGKSAVQGPPERDLCGCYSV SSVLPGCAEPWNHGKTFTCTAAYPESKTPLTATLSKS).

SEQ ID NO:40 is the amino acid sequence of a human IgA1 CH3 region (GNTFRPEVHLLPPPSEELALNELVTLTCLARGFSPKDVLVRWLQGSQELPREKYLTWASRQEPS QGTTTFAVTSILRVAAEDWKKGDTFSCMVGHEALPLAFTQKTIDRLAGKPTHVNVSVVMAEVDGTCY).

SEQ ID NO:41 is the amino acid sequence of a human IgA2 hinge region (VPPPPP).

SEQ ID NO:42 is the amino acid sequence of a human IgA2 CH2 region (CCHPRLSLHRPALEDLLLGSEANLTCTLTGLRDASGATFTWTPSSGKSAVQGPPERDLCGCYSV SSVLPGCAQPWNHGETFTCTAAHPELKTPLTANITKS).

SEQ ID NO:43 is the amino acid sequence of a human IgA2 CH3 region (GNTFRPEVHLLPPPSEELALNELVTLTCLARGFSPKDVLVRWLQGSQELPREKYLTWASRQEPS QGTTTFAVTSILRVAAEDWKKGDTFSCMVGHEALPLAFTQKTIDRLAGKPTHVNVSVVMAEVDGTCY).

SEQ ID NO:44 is the amino acid sequence of a human IgD hinge region (ESPKAQASSVPTAQPQAEGSLAKATTAPATTRNTGRGGEEKKKEKEKEEQEERETKTP).

SEQ ID NO:45 is the amino acid sequence of a human IgD CH2 region (ECPSHTQPLGVYLLTPAVQDLWLRDKATFTCFVVGSDLKDAHLTWEVAGKVPTG-GVEEGLLER HSNGSQSQHSRLTLPRSLWNAGTSVTCTLNHPSLPPQRLMALREP).

SEQ ID NO:46 is the amino acid sequence of a human IgD CH3 region (AAQAPVKLSLNLLASSDPPEAASWLLCEVSGFSPPNILLMWLEDQREVNTSGFAPARPPPQPRST TFWAWSVLRVPAPPSPQPATYTCVVSHEDSRTLLNASRSLEVSYVTDHGPMK).

SEQ ID NO:47 is the amino acid sequence of a human IgE CH2 region (VCSRDFTPPTVKILQSSCDGGGHFPPTIQLLCLVSGYTPGTINITWLEDGQVMDVDLSTASTTQE GELASTQSELTLSQKHWLSDRTYTCQVTYQGHTFEDSTKKCA).

SEQ ID NO:48 is the amino acid sequence of a human IgE CH3 region (DSNPRGVSAYLSRPSPFDLFIRKSPTITCLVVDLAPSKGTVNLTWSRASGK-PVNHSTRKEEKQRN GTLTVTSTLPVGTRDWIEGETYQCRVTHPHLPRALMRSTTKTS).

SEQ ID NO:49 is the amino acid sequence of a human IgE CH4 region (GPRAAPEVYAFATPEWPGSRDKRTLACLIQNFMPEDISVQWLHNEVQLPDARHSTTQPRKTKGS GFFVFSRLEVTRAEWEQKDEFICRAVHEAASPSQTVQRAVSVNPGK).

SEQ ID NO:50 is the amino acid sequence of a human IgG1 hinge region (EPKSCDKTHTCPPCP).

SEQ ID NO:51 is the amino acid sequence of a human IgG1 CH2 region (APELLGGPSVFLFPPKPKDTLMISRTPEVTCVVVDVSHEDPEVKFNWYVDGVEVHNAKTKPREE QYNSTYRVVSVLTVLHQDWLNGKEYKCKVSNKALPAPIEKTISKAK).

SEQ ID NO:52 is the amino acid sequence of a human IgG1 CH3 region (GQPREPQVYTLPPSRDELTKNQVSLTCLVKGFYPSDIAVEWESNGQPENNYKTTPPVLDSDGSFF LYSKLTVDKSRWQQGNVFSCSVMHEALHNHYTQKSLSLSPGK).

SEQ ID NO:53 is the amino acid sequence of a human IgG2 hinge region (ERKCCVECPPCP).

SEQ ID NO:54 is the amino acid sequence of a human IgG2 CH2 region (APPVAGPSVFLFPPKPKDTLMISRTPEVTCVVVDVSHEDPEVQFNWYVDGVEVHNAKTKPREE QFNSTFRVVSVLTVVHQDWLNGKEYKCKVSNKGLPAPIEKTISKTK).

SEQ ID NO:55 is the amino acid sequence of a human IgG2 CH3 region (GQPREPQVYTLPPSREEMTKNQVSLTCLVKGFYPSDIAVEWESNGQPENNYKTTPPMLDSDGSF FLYSKLTVDKSRWQQGNVFSCSVMHEALHNHYTQKSLSLSPGK).

SEQ ID NO:56 is the amino acid sequence of a human IgG3 hinge region (ELKTPLGDTTHTCPRCPEPKSCDTPPPCPRCPEPKSCDTPPPCPRCPEPKSCDTPPPCPRCP).

SEQ ID NO:57 is the amino acid sequence of a human IgG3 CH2 region (APELLGGPSVFLFPPKPKDTLMISRTPEVTCVVVDVSHEDPEVQFKWYVDGVEVHNAKTKPREE QYNSTFRVVSVLTVLHQDWLNGKEYKCKVSNKALPAPIEKTISKTK).

SEQ ID NO:58 is the amino acid sequence of a human IgG3 CH3 region (GQPREPQVYTLPPSREEMTKNQVSLTCLVKGFYPSDIAVEWESSGQPENNYNTTPPMLDSDGSF FLYSKLTVDKSRWQQGNIFSCSVMHEALHNRFTQKSLSLSPGK).

SEQ ID NO:59 is the amino acid sequence of a human IgG4 hinge region (ESKYGPPCPSCP).

SEQ ID NO:60 is the amino acid sequence of a human IgG4 CH2 region (APEFLGGPSVFLFPPKPKDTLMISRTPEVTCVVVDVSQEDPEVQFNWYVDGVEVHNAKTKPREE QFNSTYRVVSVLTVLHQDWLNGKEYKCKVSNKGLPSSIEKTISKAK).

SEQ ID NO:61 is the amino acid sequence of a human IgG4 CH3 region (GQPREPQVYTLPPSQEEMTKNQVSLTCLVKGFYPSDIAVEWESNGQPENNYKTTPPVLDSDGSF FLYSRLTVDKSRWQEGNVFSCSVMHEALHNHYTQKSLSLSLGK).

SEQ ID NO:62 is the amino acid sequence of a human IgM CH2 region (VIAELPPKVSVFVPPRDGFFGNPRKSKLICQATGFSPRQIQVSWLREGKQVGSGVTTDQVQAEA KESGPTTYKVTSTLTIKESDWLGQSMFTCRVDHRGLTFQQNASSMCVP).

SEQ ID NO:63 is the amino acid sequence of a human IgM CH3 region (DQDTAIRVFAIPPSFASIFLTKSTKLTCLVTDLTTYDSVTISWTRQNGEAVKTHTNISESHPNATFS AVGEASICEDDWNSGERFTCTVTHTDLPSPLKQTISRPK).

SEQ ID NO:64 is the amino acid sequence of a human IgM CH4 region (GVALHRPDVYLLPPAREQLNLRESATITCLVTGFSPADVFVQWMQRGQPLSPEKYVTSAPMPEP QAPGRYFAHSILTVSEEEWNTGETYTCVVAHEALPNRVTERTVDKSTGKPTLYNVSLVMSDTAG TCY).

A DRS-Fc conjugate of the present invention can thus comprise, consist of, or consist essentially of one or more of the human Fc region amino acid sequences of SEQ ID NOS:38-73, including variants, fragments, homologs, orthologs, paralogs, and combinations thereof. Certain illustrative embodiments comprise an Fc region that ranges in size from about 20-50, 20-100, 20-150, 20-200, 20-250, 20-300, 20-400, 50-100, 50-150, 50-200, 50-250, 50-300, 50-400, 100-150, 100-200, 100-250, 100-300, 100-350, 100-400, 200-250, 200-300, 200-350, or 200-400 amino acids in length, and optionally comprises, consists of, or consists essentially of any one or more of SEQ ID NOS: 38-64. Certain embodiments comprise an Fc region of up to about 50, 60, 70, 80, 90, 100, 110, 120, 130, 140, 150, 160, 170, 180, 190, 200, 210, 220, 230, 240, 250, 300, 350, 400 or more amino acids, which optionally comprises, consists of, or consists essentially of any one or more of SEQ ID NOS: 38-64.

Certain Fc regions comprise, consist of, or consist essentially of human IgA1 sequences set forth in SEQ ID NOS: 38-40 or 66, in any order reading from N-terminus to C-terminus, including combinations thereof (e.g., SEQ ID NOS:38 and 39 and 40, SEQ ID NOS:38 and 39; SEQ ID NOS:38 and 40; SEQ ID NOS:39 and 40), and variants and fragments thereof. Certain Fc regions comprise, consist of, or consist essentially of human the IgA1 sequence set forth in SEQ ID NOS:39. Certain Fc regions comprise, consist of, or consist essentially of the human IgA1 sequence set forth in SEQ ID NOS:38. Certain Fc regions comprise, consist of, or consist essentially of the human IgA1 sequence set forth in SEQ ID NOS:40.

Some Fc regions comprise, consist of, or consist essentially of human IgA2 sequences set forth in SEQ ID NOS: 41-43 or 67, in any order reading from N-terminus to C-terminus, including combinations thereof (e.g., SEQ ID NOS:41 and 42 and 43, SEQ ID NOS:41 and 42; SEQ ID NOS:41 and 43; SEQ ID NOS:42 and 43), and variants and fragments thereof. Certain Fc regions comprise, consist of, or consist essentially of human the IgA2 sequence set forth in SEQ ID NOS:41. Certain Fc regions comprise, consist of, or consist essentially of the human IgA2 sequence set forth in SEQ ID NOS:42. Certain Fc regions comprise, consist of, or consist essentially of the human IgA2 sequence set forth in SEQ ID NOS:43.

Certain Fc regions comprise, consist of, or consist essentially of human IgD sequences set forth in SEQ ID NOS: 44-46, in any order reading from N-terminus to C-terminus, including combinations thereof (e.g., SEQ ID NOS:44 and 45 and 46, SEQ ID NOS:44 and 45; SEQ ID NOS:44 and 46; SEQ ID NOS:45 and 46), and variants and fragments of these sequences and combinations. Certain Fc regions comprise, consist of, or consist essentially of human the IgD sequence set forth in SEQ ID NOS:44. Certain Fc regions comprise, consist of, or consist essentially of the human IgD sequence set forth in SEQ ID NOS:45. Certain Fc regions comprise, consist of, or consist essentially of the human IgD sequence set forth in SEQ ID NOS:46.

Certain Fc regions comprise, consist of, or consist essentially of human IgE sequences set forth in SEQ ID NOS: 47-49 or 73, in any order reading from N-terminus to C-terminus, including combinations thereof (e.g., SEQ ID NOS:47 and 48 and 49, SEQ ID NOS:47 and 48; SEQ ID NOS:47 and 49; SEQ ID NOS:48 and 49), and variants and fragments of these sequences and combinations. Certain Fc regions comprise, consist of, or consist essentially of human the IgE sequence set forth in SEQ ID NOS:47. Certain Fc regions comprise, consist of, or consist essentially of the human IgE sequence set forth in SEQ ID NOS:48. Certain Fc regions comprise, consist of, or consist essentially of the human IgE sequence set forth in SEQ ID NOS:49.

Certain Fc regions comprise, consist of, or consist essentially of human IgG1 sequences set forth in SEQ ID NOS: 50-52 or 69, in any order reading from N-terminus to C-terminus, including combinations thereof (e.g., SEQ ID NOS:50 and 51 and 52, SEQ ID NOS:50 and 51; SEQ ID NOS:50 and 52; SEQ ID NOS:51 and 52), and variants and fragments of these sequences and combinations. Certain Fc regions comprise, consist of, or consist essentially of human the IgG1 sequence set forth in SEQ ID NOS:50. Certain Fc regions comprise, consist of, or consist essentially of the human IgG1 sequence set forth in SEQ ID NOS:51. Certain Fc regions comprise, consist of, or consist essentially of the human IgG1 sequence set forth in SEQ ID NOS:52.

Certain Fc regions comprise, consist of, or consist essentially of human IgG2 sequences set forth in SEQ ID NOS: 53-55 or 70, in any order reading from N-terminus to C-terminus, including combinations thereof (e.g., SEQ ID NOS:53 and 54 and 55, SEQ ID NOS:53 and 54; SEQ ID NOS:53 and 55; SEQ ID NOS:54 and 55), and variants and fragments of these sequences and combinations. Certain Fc regions comprise, consist of, or consist essentially of human the IgG2 sequence set forth in SEQ ID NOS:53. Certain Fc regions comprise, consist of, or consist essentially of the human IgG2 sequence set forth in SEQ ID NOS:54. Certain Fc regions comprise, consist of, or consist essentially of the human IgG2 sequence set forth in SEQ ID NOS:55.

Certain Fc regions comprise, consist of, or consist essentially of human IgG3 sequences set forth in SEQ ID NOS: 56-58 or 71, in any order reading from N-terminus to C-terminus, including combinations thereof (e.g., SEQ ID NOS:56 and 57 and 58, SEQ ID NOS:56 and 57; SEQ ID NOS:56 and 58; SEQ ID NOS:57 and 58), and variants and fragments of these sequences and combinations. Certain Fc regions comprise, consist of, or consist essentially of human the IgG3 sequence set forth in SEQ ID NOS:56. Certain Fc regions comprise, consist of, or consist essentially of the human IgG3 sequence set forth in SEQ ID NOS:57. Certain Fc regions comprise, consist of, or consist essentially of the human IgG3 sequence set forth in SEQ ID NOS:58.

Certain Fc regions comprise, consist of, or consist essentially of human IgG4 sequences set forth in SEQ ID NOS: 59-61 or 72, in any order reading from N-terminus to C-terminus, including combinations thereof (e.g., SEQ ID NOS:59 and 60 and 61, SEQ ID NOS:59 and 60; SEQ ID NOS:59 and 61; SEQ ID NOS:60 and 61), and variants and fragments of these sequences and combinations. Certain Fc regions comprise, consist of, or consist essentially of human the IgG4 sequence set forth in SEQ ID NOS:59. Certain Fc regions comprise, consist of, or consist essentially of the human IgG4 sequence set forth in SEQ ID NOS:60. Certain Fc regions comprise, consist of, or consist essentially of the human IgG4 sequence set forth in SEQ ID NOS:61.

Certain Fc regions comprise, consist of, or consist essentially of human IgM sequences set forth in SEQ ID NOS: 62-64 or 68, in any order reading from N-terminus to C-terminus, including combinations thereof (e.g., SEQ ID NOS:62 and 63 and 64, SEQ ID NOS:62 and 63; SEQ ID NOS:62 and 64; SEQ ID NOS:63 and 64), and variants and fragments of these sequences and combinations. Certain Fc regions comprise, consist of, or consist essentially of human the IgM sequence set forth in SEQ ID NOS:62. Certain Fc regions comprise, consist of, or consist essentially of the human IgM sequence set forth in SEQ ID NOS:63. Certain Fc regions comprise, consist of, or consist essentially of the human IgM sequence set forth in SEQ ID NOS:64.

As noted above, certain embodiments employ variants, fragments, hybrids, and/or otherwise modified forms an Fc region described herein and known in the art (e.g., the human Ig sequences of SEQ ID NOS:38-73).

Included are variants having one or more amino acid substitutions, insertions, deletions, and/or truncations relative to a reference sequence, such as any one or more of the reference sequences set forth in SEQ ID NOS:38-64. In certain embodiments, a variant Fc region includes an amino acid sequence having at least about 50%, 55%, 60%, 65%, 70%, 75%, 80%, 85%, 90%, 91%, 92%, 93%, 94%, 95%, 96%, 97%, 98% or more sequence identity or similarity or homology to any one or more of SEQ ID NOS:38-73. Also included are Fc regions differing from one or more of SEQ ID NOS:38-64 by the addition, deletion, insertion, or substitution of 1, 2, 3, 4, 5, 6, 7, 8, 9, 10, 11, 12, 13, 14, 15, 16, 17, 18, 19, 20, 30, 40, 50, 60, 70, 80, 90, 100, 110, 120, 130, 140, 150 or more amino acids. In certain embodiments, the amino acid additions or deletions occur at the C-terminal end and/or the N-terminal end of the Fc reference sequence.

In particular embodiments, a variant Fc region comprises an amino acid sequence that can be optimally aligned with any one or more of SEQ ID NOS:38-73 to generate a BLAST bit scores or sequence similarity scores of at least about 50, 60, 70, 80, 90, 100, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, or more, including all integers and ranges in between, wherein the BLAST alignment used the BLOSUM62 matrix, a gap existence penalty of 11, and a gap extension penalty of 1.

Also included are hybrid Fc regions, for example, Fc regions that comprise a combination of Fc domains (e.g., hinge, $CH_2$, $CH_3$, $CH_4$) from immunoglobulins of different species, different Ig classes, and/or different Ig subclasses. General examples include hybrid Fc regions that comprise, consist of, or consist essentially of the following combination of $CH_2/CH_3$ domains: IgA1/IgA1, IgA1/IgA2, IgA1/IgD, IgA1/IgE, IgA1/IgG1, IgA1/IgG2, IgA1/IgG3, IgA1/IgG4, IgA1/IgM, IgA2/IgA1, IgA2/IgA2, IgA2/IgD, IgA2/IgE, IgA2/IgG1, IgA2/IgG2, IgA2/IgG3, IgA2/IgG4, IgA2/IgM, IgD/IgA1, IgD/IgA2, IgD/IgD, IgD/IgE, IgD/IgG1, IgD/IgG2, IgD/IgG3, IgD/IgG4, IgD/IgM, IgE/IgA1, IgE/IgA2, IgE/IgD, IgE/IgE, IgE/IgG1, IgE/IgG2, IgE/IgG3, IgE/IgG4, IgE/IgM, IgG1/IgA1, IgG1/IgA2, IgG1/IgD, IgG1/IgE, IgG1/IgG1, IgG1/IgG2, IgG1/IgG3, IgG1/IgG4, IgG1/IgM, IgG2/IgA1, IgG2/IgA2, IgG2/IgD, IgG2/IgE, IgG2/IgG1, IgG2/IgG2, IgG2/IgG3, IgG2/IgG4, IgG2/IgM, IgG3/IgA1, IgG3/IgA2, IgG3/IgD, IgG3/IgE, IgG3/IgG1, IgG3/IgG2, IgG3/IgG3, IgG3/IgG4, IgG3/IgM, IgG4/IgA1, IgG4/IgA2, IgG4/IgD, IgG4/IgE, IgG4/IgG1, IgG4/IgG2, IgG4/IgG3, IgG4/IgG4, IgG4/IgM, IgM/IgA1, IgM/IgA2, IgM/IgD, IgM/IgE, IgM/IgG1, IgM/IgG2, IgM/IgG3, IgM/IgG4, IgM/IgM (or fragments or variants thereof), and optionally include a hinge from one or more of IgA1, IgA2, IgD, IgG1, IgG2, IgG3, or IgG4, and/or a $CH_4$ domain from IgE and/or IgM. In specific embodiments, the hinge, $CH_2$, $CH_3$, and $CH_4$ domains are from human Ig.

Additional examples include hybrid Fc regions that comprise, consist of, or consist essentially of the following combination of $CH_2/CH_4$ domains: IgA1/IgE, IgA2/IgE, IgD/IgE, IgE/IgE, IgG1/IgE, IgG2/IgE, IgG3/IgE, IgG4/IgE, IgM/IgE, IgA1/IgM, IgA2/IgM, IgD/IgM, IgE/IgM, IgG1/IgM, IgG2/IgM, IgG3/IgM, IgG4/IgM, IgM/IgM (or fragments or variants thereof), and optionally include a hinge from one or more of IgA1, IgA2, IgD, IgG1, IgG2, IgG3, IgG4, and/or a $CH_3$ domain from one or more of IgA1, IgA2, IgD, IgE, IgG1, IgG2, IgG3, IgG4, or IgM. In specific embodiments, the hinge, $CH_2$, $CH_3$, and $CH_4$ domains are from human Ig.

Certain examples include hybrid Fc regions that comprise, consist of, or consist essentially of the following combination of $CH_3/CH_4$ domains: IgA1/IgE, IgA2/IgE, IgD/IgE, IgE/IgE, IgG1/IgE, IgG2/IgE, IgG3/IgE, IgG4/IgE, IgM/IgE, IgA1/IgM, IgA2/IgM, IgD/IgM, IgE/IgM, IgG1/IgM, IgG2/IgM, IgG3/IgM, IgG4/IgM, IgM/IgM (or fragments or variants thereof), and optionally include a hinge from one or more of IgA1, IgA2, IgD, IgG1, IgG2, IgG3, IgG4, and/or a $CH_2$ domain from one or more of IgA1, IgA2, IgD, IgE, IgG1, IgG2, IgG3, IgG4, or IgM. In specific embodiments, the hinge, $CH_2$, $CH_3$, and $CH_4$ domains are from human Ig.

Particular examples include hybrid Fc regions that comprise, consist of, or consist essentially of the following combination of hinge/$CH_2$ domains: IgA1/IgA1, IgA1/IgA2, IgA1/IgD, IgA1/IgE, IgA1/IgG1, IgA1/IgG2, IgA1/IgG3, IgA1/IgG4, IgA1/IgM, IgA2/IgA1, IgA2/IgA2, IgA2/IgD, IgA2/IgE, IgA2/IgG1, IgA2/IgG2, IgA2/IgG3, IgA2/IgG4, IgA2/IgM, IgD/IgA1, IgD/IgA2, IgD/IgD, IgD/IgE, IgD/IgG1, IgD/IgG2, IgD/IgG3, IgD/IgG4, IgD/IgM, IgG1/IgA1, IgG1/IgA2, IgG1/IgD, IgG1/IgE, IgG1/IgG1, IgG1/IgG2, IgG1/IgG3, IgG1/IgG4, IgG1/IgM, IgG2/IgA1, IgG2/IgA2, IgG2/IgD, IgG2/IgE, IgG2/IgG1, IgG2/IgG2, IgG2/IgG3, IgG2/IgG4, IgG2/IgM, IgG3/IgA1, IgG3/IgA2, IgG3/IgD, IgG3/IgE, IgG3/IgG1, IgG3/IgG2, IgG3/IgG3, IgG3/IgG4, IgG3/IgM, IgG4/IgA1, IgG4/IgA2, IgG4/IgD, IgG4/IgE, IgG4/IgG1, IgG4/IgG2, IgG4/IgG3, IgG4/IgG4, IgG4/IgM (or fragments or variants thereof), and optionally include a $CH_3$ domain from one or more of IgA1, IgA2, IgD, IgE, IgG1, IgG2, IgG3, IgG4, or IgM, and/or a $CH_4$ domain from IgE and/or IgM. In specific embodiments, the hinge, $CH_2$, $CH_3$, and $CH_4$ domains are from human Ig.

Certain examples include hybrid Fc regions that comprise, consist of, or consist essentially of the following combination of hinge/$CH_3$ domains: IgA1/IgA1, IgA1/IgA2, IgA1/IgD, IgA1/IgE, IgA1/IgG1, IgA1/IgG2, IgA1/IgG3, IgA1/IgG4, IgA1/IgM, IgA2/IgA1, IgA2/IgA2, IgA2/IgD, IgA2/IgE, IgA2/IgG1, IgA2/IgG2, IgA2/IgG3, IgA2/IgG4, IgA2/IgM, IgD/IgA1, IgD/IgA2, IgD/IgD, IgD/IgE, IgD/IgG1, IgD/IgG2, IgD/IgG3, IgD/IgG4, IgD/IgM, IgG1/IgA1, IgG1/IgA2, IgG1/IgD, IgG1/IgE, IgG1/IgG1, IgG1/IgG2, IgG1/IgG3, IgG1/IgG4, IgG1/IgM, IgG2/IgA1, IgG2/IgA2, IgG2/IgD, IgG2/IgE, IgG2/IgG1, IgG2/IgG2, IgG2/IgG3, IgG2/IgG4, IgG2/IgM, IgG3/IgA1, IgG3/IgA2, IgG3/IgD, IgG3/IgE, IgG3/IgG1, IgG3/IgG2, IgG3/IgG3, IgG3/IgG4, IgG3/IgM, IgG4/IgA1, IgG4/IgA2, IgG4/IgD, IgG4/IgE, IgG4/IgG1, IgG4/IgG2, IgG4/IgG3, IgG4/IgG4, IgG4/IgM (or fragments or variants thereof), and optionally include a $CH_2$ domain from one or more of IgA1, IgA2, IgD, IgE, IgG1, IgG2, IgG3, IgG4, or IgM, and/or a $CH_4$ domain from IgE and/or IgM. In specific embodiments, the hinge, $CH_2$, $CH_3$, and $CH_4$ domains are from human Ig.

Some examples include hybrid Fc regions that comprise, consist of, or consist essentially of the following combination of hinge/$CH_4$ domains: IgA1/IgE, IgA1/IgM, IgA2/IgE, IgA2/IgM, IgD/IgE, IgD/IgM, IgG1/IgE, IgG1/IgM, IgG2/IgE, IgG2/IgM, IgG3/IgE, IgG3/IgM, IgG4/IgE, IgG4/IgM (or fragments or variants thereof), and optionally include a $CH_2$ domain from one or more of IgA1, IgA2, IgD, IgE, IgG1, IgG2, IgG3, IgG4, or IgM, and/or a $CH_3$ domain from one or more of IgA1, IgA2, IgD, IgE, IgG1, IgG2, IgG3, IgG4, or IgM.

Specific examples of hybrid Fc regions can be found, for example, in WO 2008/147143, which are derived from combinations of IgG subclasses or combinations of human IgD and IgG.

Also included are derivatized or otherwise modified Fc regions. In certain aspects, the Fc region may be modified by phosphorylation, sulfation, acrylation, glycosylation, methylation, farnesylation, acetylation, amidation, and the like, for instance, relative to a wild-type or naturally-occurring Fc region. In certain embodiments, the Fc region may comprise wild-type or native glycosylation patterns, or alternatively, it may comprise increased glycosylation relative to a native form, decreased glycosylation relative to a native form, or it may be entirely deglycosylated. As one example of a modified Fc glycoform, decreased glycosylation of an Fc region reduces binding to the C1q region of the first complement component C1, a decrease in ADCC-related activity, and/or a decrease in CDC-related activity. Certain embodiments thus employ a deglycosylated or aglycosylated Fc region. See, e.g., WO 2005/047337 for the production of exemplary aglycosylated Fc regions. Another example of an Fc region glycoform can be generated by substituting the Q295 position with a cysteine residue (see, e.g., U.S. Application No. 2010/0080794), according to the Kabat et al. numbering system. Certain embodiments may include Fc regions where about 80-100% of the glycoprotein in Fc region comprises a mature core carbohydrate structure that lacks fructose (see, e.g., U.S. Application No. 2010/0255013). Some embodiments may include Fc regions that are optimized by substitution or deletion to reduce the level of fucosylation, for instance, to increase affinity for FcγRI, FcγRIa, or FcγRIIIa, and/or to improve phagocytosis by FcγRIIa-expressing cells (see U.S. Application Nos. 2010/0249382 and 2007/0148170).

As another example of a modified Fc glycoform, an Fc region may comprise oligomannose-type N-glycans, and optionally have one or more of the following: increased ADCC activity, increased binding affinity for FcγRIIIA (and certain other FcRs), similar or increased binding specificity for the target of the DRS polypeptide, similar or higher binding affinity for the target of the DRS polypeptide, and/or similar or lower binding affinity for mannose receptor, relative to a corresponding Fc region or DRS-Fc conjugate that contains complex-type N-glycans (see, e.g., U.S. Application No. 2007/0092521 and U.S. Pat. No. 7,700,321). As another example, enhanced affinity of Fc regions for FcγRs has been achieved using engineered glycoforms generated by expression of antibodies in engineered or variant cell lines (see, e.g., Umana et al., Nat Biotechnol. 17:176-180, 1999; Davies et al., Biotechnol Bioeng. 74:288-294, 2001; Shields et al., J Biol Chem. 277:26733-26740, 2002; Shinkawa et al., 2003, J Biol Chem. 278:3466-3473, 2003; and U.S. Application No. 2007/0111281). Certain Fc region glycoforms comprise an increased proportion of N-glycoside bond type complex sugar chains, which do not have the 1-position of fucose bound to the 6-position of N-acetylglucosamine at the reducing end of the sugar chain (see, e.g., U.S. Application No. 2010/0092997). Particular embodiments may include IgG Fc region that is glycosylated with at least one galactose moiety connected to a respective terminal sialic acid moiety by an α-2,6 linkage, optionally where the Fc region has a higher anti-inflammatory activity relative to a corresponding, wild-type Fc region (see U.S. Application No. 2008/0206246). Certain of these and related altered glycosylation approaches have generated substantial enhancements of the capacity of Fc regions to selectively bind FcRs such as FcγRIII, to mediate ADCC, and to alter other properties of Fc regions, as described herein.

Certain variant, fragment, hybrid, or otherwise modified Fc regions may have altered binding to one or more FcRs, relative to a corresponding, wild-type Fc sequence (e.g., same species, same Ig class, same Ig subclass). For instance, such Fc regions may have increased binding to one or more of Fcγ receptors, Fcα receptors, Fcε receptors, and/or the neonatal Fc receptor, relative to a corresponding, wild-type Fc sequence. In other embodiments, variant, fragment, hybrid, or modified Fc regions may have decreased binding to one or more of Fcγ receptors, Fcα receptors, Fcε receptors, and/or the neonatal Fc receptor, relative to a corresponding, wild-type Fc sequence. Specific FcRs are described elsewhere herein.

Specific examples of Fc variants having altered (e.g., increased, decreased) FcR binding can be found, for example, in U.S. Pat. Nos. 5,624,821 and 7,425,619; U.S. Application Nos. 2009/0017023, 2009/0010921, and 2010/0203046; and WO 2000/42072 and WO 2004/016750. Certain examples include human Fc regions having a one or more substitutions at position 298, 333, and/or 334, for example, S298A, E333A, and/or K334A (based on the numbering of the EU index of Kabat et al.), which have been shown to increase binding to the activating receptor FcγRIIIa and reduce binding to the inhibitory receptor FcγRIIb. These mutations can be combined to obtain double and triple mutation variants that have further improvements in binding to FcRs. Certain embodiments include a S298A/E333A/K334A triple mutant, which has increased binding to FcγRIIIa, decreased binding to FcγRIIb, and increased ADCC (see, e.g., Shields et al., *J Biol Chem.* 276:6591-6604, 2001; and Presta et al., *Biochem Soc Trans.* 30:487-490, 2002). See also engineered Fc glycoforms that have increased binding to FcRs, as disclosed in Umana et al., supra; and U.S. Pat. No. 7,662,925. Some embodiments include Fc regions that comprise one or more substitutions selected from 434S, 252Y/428L, 252Y/434S, and 428L/434S (see U.S. Application Nos. 2009/0163699 and 20060173170), based on the EU index of Kabat et al.

Certain variant, fragment, hybrid, or modified Fc regions may have altered effector functions, relative to a corresponding, wild-type Fc sequence. For example, such Fc regions may have increased complement fixation or activation, increased C1q binding affinity, increased CDC-related activity, increased ADCC-related activity, and/or increased ADCP-related activity, relative to a corresponding, wild-type Fc sequence. In other embodiments, such Fc regions may have decreased complement fixation or activation, decreased C1q binding affinity, decreased CDC-related activity, decreased ADCC-related activity, and/or decreased ADCP-related activity, relative to a corresponding, wild-type Fc sequence. As merely one illustrative example, an Fc region may comprise a deletion or substitution in a complement-binding site, such as a C1q-binding site, and/or a deletion or substitution in an ADCC site. Examples of such deletions/substitutions are described, for example, in U.S. Pat. No. 7,030,226. Many Fc effector functions, such as ADCC, can be assayed according to routine techniques in the art. (see, e.g., Zuckerman et al., *CRC Crit Rev Microbiol.* 7:1-26, 1978). Useful effector cells for such assays includes, but are not limited to, natural killer (NK) cells, macrophages, and other peripheral blood mononuclear cells (PBMC). Alternatively, or additionally, certain Fc effector functions may be assessed in vivo, for example, by employing an animal model described in Clynes et al. *PNAS.* 95:652-656, 1998.

Certain variant hybrid, or modified Fc regions may have altered stability or half-life relative to a corresponding, wild-type Fc sequence. In certain embodiments, such Fc regions may have increased half-life relative to a corresponding, wild-type Fc sequence. In other embodiments, variant hybrid, or modified Fc regions may have decreased half-life relative to a corresponding, wild-type Fc sequence. Half-life can be measured in vitro (e.g., under physiological conditions) or in vivo, according to routine techniques in the art, such as radiolabeling, ELISA, or other methods. In vivo measurements of stability or half-life can be measured in one or more bodily fluids, including blood, serum, plasma, urine, or cerebrospinal fluid, or a given tissue, such as the liver, kidneys, muscle, central nervous system tissues, bone, etc. As one example, modifications to an Fc region that alter its ability to bind the FcRn can alter its half-life in vivo. Assays for measuring the in vivo pharmacokinetic properties (e.g., in vivo mean elimination half-life) and non-limiting examples of Fc modifications that alter its binding to the FcRn are described, for example, in U.S. Pat. Nos. 7,217,797 and 7,732,570; and U.S. Application Nos. US 2010/0143254 and 2010/0143254.

Additional non-limiting examples of modifications to alter stability or half-life include substitutions/deletions at one or more of amino acid residues selected from 251-256, 285-290, and 308-314 in the $CH_2$ domain, and 385-389 and 428-436 in the $CH_3$ domain, according to the numbering system of Kabat et al. See U.S. Application No. 2003/0190311. Specific examples include substitution with leucine at position 251, substitution with tyrosine, tryptophan or phenylalanine at position 252, substitution with threonine or serine at position 254, substitution with arginine at position 255, substitution with glutamine, arginine, serine, threonine, or glutamate at position 256, substitution with threonine at position 308, substitution with proline at position 309, substitution with serine at position 311, substitution with aspartate at position 312, substitution with leucine at position 314, substitution with arginine, aspartate or serine at position 385, substitution with threonine or proline at position 386, substitution with arginine or proline at position 387, substitution with proline, asparagine or serine at position 389, substitution with methionine or threonine at position 428, substitution with tyrosine or phenylalanine at position 434, substitution with histidine, arginine, lysine or serine at position 433, and/or substitution with histidine, tyrosine, arginine or threonine at position 436, including any combination thereof. Such modifications optionally increase affinity of the Fc region for the FcRn and thereby increase half-life, relative to a corresponding, wild-type Fc region.

Certain variant hybrid, or modified Fc regions may have altered solubility relative to a corresponding, wild-type Fc sequence. In certain embodiments, such Fc regions may have increased solubility relative to a corresponding, wild-type Fc sequence. In other embodiments, variant hybrid, or modified Fc regions may have decreased solubility relative to a corresponding, wild-type Fc sequence. Solubility can be measured, for example, in vitro (e.g., under physiological conditions) according to routine techniques in the art. Exemplary solubility measurements are described elsewhere herein.

Additional examples of variants include IgG Fc regions having conservative or non-conservative substitutions (as described elsewhere herein) at one or more of positions 250, 314, or 428 of the heavy chain, or in any combination thereof, such as at positions 250 and 428, or at positions 250 and 314, or at positions 314 and 428, or at positions 250, 314, and 428 (see, e.g., U.S. Application No. 2011/0183412). In specific embodiments, the residue at position 250 is substituted with glutamic acid or glutamine, and/or the residue at position 428 is substituted with leucine or phenylalanine. As another illustrative example of an IgG Fc variant, any one or more of the amino acid residues at positions 214 to 238, 297 to 299, 318 to 322, and/or 327 to 331 may be used as a suitable target for modification (e.g., conservative or non-conservative substitution, deletion). In particular embodiments, the IgG Fc variant $CH_2$ domain contains amino acid substitutions at positions 228, 234, 235, and/or 331 (e.g., human IgG4 with Ser228Pro and Leu235Ala mutations) to attenuate the effector functions of the Fc region (see U.S. Pat. No. 7,030,226). Here, the numbering of the residues in the heavy chain is that of the EU index (see Kabat et al., "Sequences of Proteins of Immunological Interest," 5th, Ed., National Institutes of Health, Bethesda, Md. (1991)). Certain of these and related embodiments have altered (e.g., increased, decreased) FcRn binding and/or serum half-life, optionally without reduced effector functions such as ADCC or CDC-related activities.

Additional examples include variant Fc regions that comprise one or more amino acid substitutions at positions 279, 341, 343 or 373 of a wild-type Fc region, or any combination thereof (see, e.g., U.S. Application No. 2007/0224188). The wild-type amino acid residues at these positions for human IgG are valine (279), glycine (341), proline (343) and tyrosine (373). The substation(s) can be conservative or non-conservative, or can include non-naturally occurring amino acids or mimetics, as described herein. Alone or in combination with these substitutions, certain embodiments may also employ a variant Fc region that comprises at least 1, 2, 3, 4, 5, 6, 7, 8, 9, 10 or more amino acid substitutions selected from the following: 235G, 235R, 236F, 236R, 236Y, 237K, 237N, 237R, 238E, 238G, 238H, 238I, 238L, 238V, 238W, 238Y, 244L, 245R, 247A, 247D, 247E, 247F, 247M, 247N, 247Q, 247R, 247S, 247T, 247W, 247Y, 248F, 248P, 248Q, 248W, 249L, 249M, 249N, 249P, 249Y, 251H, 251I, 251W, 254D, 254E, 254F, 254G, 254H, 254I, 254K, 254L, 254M, 254N, 254P, 254Q, 254R, 254V, 254W, 254Y, 255K, 255N, 256H, 256I, 256K, 256L, 256V, 256W, 256Y, 257A, 257I, 257M, 257N, 257S, 258D, 260S, 262L, 264S, 265K, 265S, 267H, 267I, 267K, 268K, 269N, 269Q, 271T, 272H, 272K, 272L, 272R, 279A, 279D, 279F, 279G, 279H, 279I, 279K, 279L, 279M, 279N, 279Q, 279R, 279S, 279T, 279W, 279Y, 280T, 283F, 283G, 283H, 283I, 283K, 283L, 283M, 283P, 283R, 283T, 283W, 283Y, 285N, 286F, 288N, 288P, 292E, 292F, 292G, 292I, 292L, 293S, 293V, 301W, 304E, 307E, 307M, 312P, 315F, 315K, 315L, 315P, 315R, 316F, 316K, 317P, 317T, 318N, 318P, 318T, 332F, 332G, 332L, 332M, 332S, 332V, 332W, 339D, 339E, 339F, 339G, 339H, 339I, 339K, 339L, 339M, 339N, 339Q, 339R, 339S, 339W, 339Y, 341D, 341E, 341F, 341H, 341I, 341K, 341L, 341M, 341N, 341P, 341Q, 341R, 341S, 341T, 341V, 341W, 341Y, 343A, 343D, 343E, 343F, 343G, 343H, 343I, 343K, 343L, 343M, 343N, 343Q, 343R, 343S, 343T, 343V, 343W, 343Y, 373D, 373E, 373F, 373G, 373H, 373I, 373K, 373L, 373M, 373N, 373Q, 373R, 373S, 373T, 373V, 373W, 375R, 376E, 376F, 376G, 376H, 376I, 376L, 376M, 376N, 376P, 376Q, 376R, 376S, 376T, 376V, 376W, 376Y, 377G, 377K, 377P, 378N, 379N, 379Q, 379S, 379T, 380D, 380N, 380S, 380T, 382D, 382F, 382H, 382I, 382K, 382L, 382M, 382N, 382P, 382Q, 382R, 382S, 382T, 382V, 382W, 382Y, 385E, 385P, 386K, 423N, 424H, 424M, 424V, 426D, 426L, 427N, 429A, 429F, 429M, 430A, 430D, 430F, 430G, 430H, 430I, 430K, 430L, 430M, 430N, 430P, 430Q, 430R, 430S, 430T, 430V, 430W, 430Y, 431H, 431K, 431P, 432R, 432S, 438G, 438K, 438L, 438T, 438W, 439E, 439H, 439Q, 440D, 440E, 440F, 440G, 440H, 440I, 440K, 440L, 440M, 440Q, 440T, 440V or 442K. As above, the numbering of the residues in the heavy chain is that of the EU index (see Kabat et al., supra). Such variant Fc regions typically confer an altered effector function or altered serum half-life upon DRS polypeptide to which the variant Fc region is operably attached. Preferably the altered effector function is an increase in ADCC, a decrease in ADCC, an increase in CDC, a decrease in CDC, an increase in C1q binding affinity, a decrease in C1q binding affinity, an increase in FcR (preferably FcRn) binding affinity or a decrease in FcR (preferably FcRn) binding affinity as compared to a corresponding Fc region that lacks such amino acid substitution(s).

Additional examples include variant Fc regions that comprise an amino acid substitution at one or more of position(s) 221, 222, 224, 227, 228, 230, 231, 223, 233, 234, 235, 236, 237, 238, 239, 240, 241, 243, 244, 245, 246, 247, 249, 250, 258, 262, 263, 264, 265, 266, 267, 268, 269, 270, 271, 272, 273, 274, 275, 276, 278, 280, 281, 283, 285, 286, 288, 290, 291, 293, 294, 295, 296, 297, 298, 299, 300, 302, 313, 317, 318, 320, 322, 323, 324, 325, 326, 327, 328, 329, 330, 331, 332, 333, 334, 335 336 and/or 428 (see, e.g., U.S. Pat. No. 7,662,925). In specific embodiments, the variant Fc region comprises at least one amino acid substitution selected from the group consisting of: P230A, E233D, L234E, L234Y, L234I, L235D, L235S, L235Y, L235I, S239D, S239E, S239N, S239Q, S239T, V240I, V240M, F243L, V264I, V264T, V264Y, V266I, E272Y, K274T, K274E, K274R, K274L, K274Y, F275W, N276L, Y278T, V302I, E318R, S324D, S324I, S324V, N325T, K326I, K326T, L328M, L328I, L328Q, L328D, L328V, L328T, A330Y, A330L, A330I, I332D, I332E, I332N, I332Q, T335D, T335R, and T335Y. In other specific embodiments, the variant Fc region comprises at least one amino acid substitution selected from the group consisting of: V264I, F243L/V264I, L328M, I332E, L328M/I332E, V264I/I332E, S298A/I332E, S239E/I332E, S239Q/I332E, S239E, A330Y, I332D, L328I/I332E, L328Q/I332E, V264T, V240I, V266I, S239D, S239D/I332D, S239D/I332E, S239D/I332N, S239D/I332Q, S239E/I332D, S239E/I332N, S239E/I332Q, S239N/I332D, S239N/I332E, S239Q/I332D, A330Y/I332E, V264I/A330Y/I332E, A330L/I332E, V264I/A330L/I332E, L234E, L234Y, L234I, L235D, L235S, L235Y, L235I, S239T, V240M, V264Y, A330I, N325T, L328D/I332E, L328V/I332E, L328T/I332E, L328I/I332E, S239E/V264I/I332E, S239Q/V264I/I332E, S239E/V264I/A330Y/I332E, S239D/A330Y/I332E, S239N/A330Y/I332E, S239D/A330L/I332E, S239N/A330L/I332E, V264I/S298A/I332E, S239D/S298A/I332E, S239N/S298A/I332E, S239D/V264I/I332E, S239D/V264I/S298A/I332E, S239D/V264I/A330L/I332E, S239D/I332E/A330I, P230A, P230A/E233D/I332E, E272Y, K274T, K274E, K274R, K274L, K274Y, F275W, N276L, Y278T, V302I, E318R, S324D, S324I, S324V, K326I, K326T, T335D, T335R, T335Y, V240I/V266I, S239D/A330Y/I332E/L234I, S239D/A330Y/I332E/L235D, S239D/A330Y/I332E/V240I, S239D/A330Y/I332E/V264T, S239D/A330Y/I332E/K326E, and S239D/A330Y/I332E/K326T, In more specific embodiments, the variant Fc region comprises a series of substitutions selected from the group consisting of: N297D/I332E, F241Y/F243Y/V262T/V264T/N297D/I332E, S239D/N297D/I332E, S239E/N297D/I332E, S239D/D265Y/N297D/I332E, S239D/D265H/N297D/I332E, V264E/N297D/I332E, Y296N/N297D/I332E, N297D/A330Y/I332E, S239D/D265V/N297D/I332E, S239D/D265I/N297D/I332E, and N297D/S298A/A330Y/I332E. In specific embodiments, the variant Fc region comprises an amino acid substitution at position 332 (using the numbering of the EU index, Kabat et al., supra). Examples of substitutions include 332A, 332D, 332E, 332F, 332G, 332H, 332K, 332L, 332M, 332N, 332P, 332Q, 332R, 332S, 332T, 332V, 332W and 332Y. The numbering of the residues in the Fc region is that of the EU index of Kabat et al. Among other properties described herein, such variant Fc regions may have increased affinity for an FcγR, increased stability, and/or increased solubility, relative to a corresponding, wild-type Fc region.

Further examples include variant Fc regions that comprise one or more of the following amino acid substitutions:

224N/Y, 225A, 228L, 230S, 239P, 240A, 241L, 243S/L/G/ H/I, 244L, 246E, 247L/A, 252T, 254T/P, 258K, 261Y, 265V, 266A, 267G/N, 268N, 269K/G, 273A, 276D, 278H, 279M, 280N, 283G, 285R, 289A, 290E, 291L, 292Q, 297D, 299A, 300H, 301C, 304G, 305A, 306I/F, 311R, 312N, 315D/K/S, 320R, 322E, 323A, 324T, 325S, 326E/R, 332T, 333D/G, 335I, 338R, 339T, 340Q, 341E, 342R, 344Q, 347R, 351S, 352A, 354A, 355W, 356G, 358T, 361D/Y, 362L, 364C, 365Q/P, 370R, 372L, 377V, 378T, 383N, 389S, 390D, 391C, 393A, 394A, 399G, 404S, 408G, 409R, 411I, 412A, 414M, 421S, 422I, 426F/P, 428T, 430K, 431S, 432P, 433P, 438L, 439E/R, 440G, 441F, 442T, 445R, 446A, 447E, optionally where the variant has altered recognition of an Fc ligand and/or altered effector function compared with a parent Fc polypeptide, and wherein the numbering of the residues is that of the EU index as in Kabat et al. Specific examples of these and related embodiments include variant Fc regions that comprise or consist of the following sets of substitutions: (1) N276D, R292Q, V305A, I377V, T394A, V412A and K439E; (2) P244L, K246E, D399G and K409R; (3) 5304G, K320R, S324T, K326E and M358T; (4) F243S, P247L, D265V, V266A, S383N and T411I; (5) H224N, F243L, T393A and H433P; (6) V240A, S267G, G341E and E356G; (7) M252T, P291L, P352A, R355W, N390D, S408G, S426F and A431S; (8) P228L, T289A, L365Q, N389S and S440G; (9) F241L, V273A, K340Q and L441F; (10) F241L, T299A, I332T and M428T; (11) E269K, Y300H, Q342R, V422I and G446A; (12) T225A, R301c, S304G, D312N, N315D, L351S and N421S; (13) S254T, L306I, K326R and Q362L; (14) H224Y, P230S, V323A, E333D, K338R and S364C; (15) T335I, K414M and P445R; (16) T335I and K414M; (17) P247A, E258K, D280N, K288R, N297D, T299A, K322E, Q342R, S354A and L365P; (18) H268N, V279M, A339T, N361D and S426P; (19) C261Y, K290E, L306F, Q311R, E333G and Q438L; (20) E283G, N315K, E333G, R344Q, L365P and S442T; (21) Q347R, N361Y and K439R; (22) S239P, S254P, S267N, H285R, N315S, F372L, A378T, N390D, Y391C, F404S, E430K, L432P and K447E; and (23) E269G, Y278H, N325S and K370R, wherein the numbering of the residues is that of the EU index as in Kabat et al. (see, e.g., U.S. Application No. 2010/0184959).

Another specific example of an Fc variant comprises the sequence of SEQ ID NO:65, wherein Xaa at position 1 is Ala or absent; Xaa at position 16 is Pro or Glu; Xaa at position 17 is Phe, Val, or Ala; Xaa at position 18 is Leu, Glu, or Ala; Xaa at position 80 is Asn or Ala; and/or Xaa at position 230 is Lys or is absent (see, e.g., U.S. Application No. 2007/0253966). Certain of these Fc regions, and related DRS-Fc conjugates, have increased half-life, reduced effector activity, and/or are significantly less immunogenic than wild-type Fc sequences.

Variant Fc regions can also have one or more mutated hinge regions, as described, for example, in U.S. Application No. 2003/0118592. For instance, one or more cysteines in a hinge region can be deleted or substituted with a different amino acid. The mutated hinge region can comprise no cysteine residues, or it can comprise 1, 2, or 3 fewer cysteine residues than a corresponding, wild-type hinge region. In some embodiments, an Fc region having a mutated hinge region of this type exhibits a reduced ability to dimerize, relative to a wild-type Ig hinge region.

As noted above, DRS-Fc conjugates such as DRS-Fc fusion proteins typically have altered (e.g., improved, increased, decreased) pharmacokinetic properties relative to corresponding DRS polypeptides. Examples of pharmacokinetic properties include stability or half-life, bioavailability (the fraction of a drug that is absorbed), tissue distribution, volume of distribution (apparent volume in which a drug is distributed immediately after it has been injected intravenously and equilibrated between plasma and the surrounding tissues), concentration (initial or steady-state concentration of drug in plasma), elimination rate constant (rate at which drugs are removed from the body), elimination rate (rate of infusion required to balance elimination), area under the curve (AUC; integral of the concentration-time curve, after a single dose or in steady state), clearance (volume of plasma cleared of the drug per unit time), $C_{max}$ (peak plasma concentration of a drug after oral administration), $t_{max}$ (time to reach $C_{max}$), $C_{min}$ (lowest concentration that a drug reaches before the next dose is administered), and fluctuation (peak trough fluctuation within one dosing interval at steady state). In some aspects, these improved properties are achieved without significantly altering the secondary structure and/or reducing the non-canonical biological activity of the DRS polypeptide. Indeed, some DRS-Fc conjugates have increased non-canonical biological activity.

Hence, in some embodiments, the DRS-Fc fusion polypeptide has a plasma or sera pharmacokinetic AUC profile at least 2, 3, 4, 5, 6, 7, 8, 9, 10, 11, 12, 13, 14, 15, 16, 17, 18, 19, or 20-fold greater than a corresponding unmodified or differently modified DRS polypeptide when administered to a mammal. In certain embodiments, the DRS-Fc fusion polypeptide has a stability (e.g., as measured by half-life) which is at least 10%, 20%, 30%, 40%, 50%, 60%, 70%, 80%, 90%, 100%, 200%, 300%, 400%, or 500% greater than a corresponding unmodified or differently modified DRS polypeptide when compared under similar conditions at room temperature, for example, in PBS at pH 7.4 for about 1, 2, 3, 4, 5, 6, 7, 8, 9, 10, 11, 12, 13, 14 days, or 1, 2, 3, 4 weeks or so. In particular embodiments, a DRS-Fc conjugate has a half life at pH 7.4, 25° C., e.g., a physiological pH, human body temperature (e.g., in vivo, in serum, in a given tissue), of about 30 minutes, about 1 hour, about 2 hour, about 3 hours, about 4 hours, about 5 hours, about 6 hours, about 12 hours, about 18 hours, about 24 hours, about 36 hours, about 48 hours, about 60 hours, about 72 hours, about 84 hours, about 96 hours, about 120 hours, or about 144 hours or more or any intervening half-life.

In certain embodiments, the DRS-Fc fusion polypeptide has substantially the same secondary structure as a corresponding unmodified or differently modified DRS polypeptide, as determined via UV circular dichroism analysis. In certain embodiments, the DRS-Fc fusion polypeptide has substantially the same activity of a corresponding unmodified or differently modified DRS polypeptide in a TLR 2 or TLR 4 based assay. In other embodiments, the DRS-Fc fusion polypeptide has greater than 2, 3, 4, 5, 6, 7, 8, 9, 10, 11, 12, 13, 14, 15, 16, 17, 18, 19, or 20-fold the activity of a corresponding unmodified or differently modified DRS polypeptide in a TLR 2 or TLR 4-based assay.

Peptide Linkers

In certain embodiments, a peptide linker sequence may be employed to separate the DRS polypeptide(s) and the Fc region(s) by a distance sufficient to ensure that each polypeptide folds into its desired secondary and tertiary structures. Such a peptide linker sequence can be incorporated into the fusion protein using standard techniques well known in the art.

Certain peptide linker sequences may be chosen based on the following exemplary factors: (1) their ability to adopt a flexible extended conformation; (2) their inability to adopt a secondary structure that could interact with functional epitopes on the first and second polypeptides; (3) their physiological stability; and (4) the lack of hydrophobic or charged residues that might react with the polypeptide functional epitopes, or other features. See, e.g., George and Heringa, *J Protein Eng.* 15:871-879, 2002.

The linker sequence may generally be from 1 to about 200 amino acids in length. Particular linkers can have an overall amino acid length of about 1-200 amino acids, 1-150 amino acids, 1-100 amino acids, 1-90 amino acids, 1-80 amino acids, 1-70 amino acids, 1-60 amino acids, 1-50 amino acids, 1-40 amino acids, 1-30 amino acids, 1-20 amino acids, 1-10 amino acids, 1-5 amino acids, 1-4 amino acids, 1-3 amino acids, or about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100 or more amino acids.

A peptide linker may employ any one or more naturally-occurring amino acids, non-naturally occurring amino acid(s), amino acid analogs, and/or amino acid mimetics as described elsewhere herein and known in the art. Certain amino acid sequences which may be usefully employed as linkers include those disclosed in Maratea et al., *Gene* 40:39-46, 1985; Murphy et al., *PNAS USA.* 83:8258-8262, 1986; U.S. Pat. No. 4,935,233 and U.S. Pat. No. 4,751,180. Particular peptide linker sequences contain Gly, Ser, and/or Asn residues. Other near neutral amino acids, such as Thr and Ala may also be employed in the peptide linker sequence, if desired.

Certain exemplary linkers include Gly, Ser and/or Asn-containing linkers, as follows: $[G]_x$, $[S]_x$, $[N]_x$, $[GS]_x$, $[GGS]_x$, $[GSS]_x$, $[GSGS]_x$ (SEQ ID NO:80), $[GGSG]_x$ (SEQ ID NO:81), $[GGGS]_x$ (SEQ ID NO:82), $[GGGGS]_x$ (SEQ ID NO:83), $[GN]_x$, $[GGN]_x$, $[GNN]_x$, $[GNGN]_x$ (SEQ ID NO:84), $[GGNG]_x$ (SEQ ID NO:85), $[GGGN]_x$ (SEQ ID NO:86), $[GGGGN]_x$ (SEQ ID NO:87) linkers, where $_x$ is 1, 2, 3, 4, 5, 6, 7, 8, 9, 10, 11, 12, 13, 14, 15, 16, 17, 18, 19, or 20 or more. Other combinations of these and related amino acids will be apparent to persons skilled in the art.

Additional examples of linker peptides include, but are not limited to the following amino acid sequences:

(SEQ ID NO:97) (Bird et al., *Science.* 242:423-426, 1988), GGRRGGGS (SEQ ID NO:98); LRQRDGERP (SEQ ID NO:99); LRQKDGGGSERP (SEQ ID NO:100); LRQKd (GGGS)$_2$ ERP (SEQ ID NO:101). In specific embodiments, the linker sequence comprises a Gly3 linker sequence, which includes three glycine residues. In particular embodiments, flexible linkers can be rationally designed using a computer program capable of modeling both DNA-binding sites and the peptides themselves (Desjarlais & Berg, *PNAS.* 90:2256-2260, 1993; and *PNAS.* 91:11099-11103, 1994) or by phage display methods.

The peptide linkers may be physiologically stable or may include a releasable linker such as a physiologically degradable or enzymatically cleavable linker (e.g., proteolytically cleavable linker). In certain embodiments, one or more releasable linkers can result in a shorter half-life and more rapid clearance of the conjugate. These and related embodiments can be used, for example, to enhance the solubility and blood circulation lifetime of DRS polypeptides in the bloodstream, while also delivering a DRS polypeptide into the bloodstream that, subsequent to linker degradation, is substantially free of the Fc region(s). These aspects are especially useful in those cases where DRS polypeptides, when permanently conjugated to an Fc region, demonstrate reduced activity. By using the linkers as provided herein, such DRS polypeptides can maintain their therapeutic activity when in conjugated form. As another example, a large and relatively inert DRS-Fc conjugate polypeptide may be administered, which is then degraded in vivo (via the degradable linker) to generate a bioactive DRS polypeptide possessing a portion of the Fc region or lacking the Fc region entirely. In these and other ways, the properties of the DRS-Fc conjugate polypeptide can be more effectively tailored to balance the bioactivity and circulating half-life of the DRS polypeptide over time.

In particular embodiments, the linker peptide comprises an autocatalytic or self-cleaving peptide cleavage site. In a particular embodiment, self-cleaving peptides include those

```
                                                          (SEQ ID NO: 88)
Gly-Gly-Gly-Gly-Ser-Gly-Gly-Gly-Gly-Ser-Gly-Gly-Gly-Gly-Ser-;

(SEQ ID NO: 89)
Gly-Ser-Gly-Gly-Gly-Gly-Ser-Gly-Gly-Gly-Gly-Ser-Gly-Gly-Gly-

Gly-Ser-Gly-Gly-Gly-Gly-Ser-;

(SEQ ID NO: 90)
Gly-Gly-Gly-Gly-Ser-Gly-Gly-Gly-Gly-Ser-Gly-Gly-Gly-Gly-Ser-

Gly-Gly-Gly-Gly-Ser-Gly-Gly-Gly-Gly-Ser-Gly-Gly-Gly-Gly-Ser-;

(SEQ ID NO: 91)
Asp-Ala-Ala-Ala-Lys-Glu-Ala-Ala-Ala-Lys-Asp-Ala-Ala-Ala-Arg-Glu-

Ala-Ala-Ala-Arg-Asp-Ala-Ala-Ala-Lys-;
and (SEQ ID NO: 92)
Asn-Val-Asp-His-Lys-Pro-Ser-Asn-Thr-Lys-Val-Asp-Lys-Arg-.
```

Further non-limiting examples of linker peptides include DGGGS (SEQ ID NO:93); TGEKP (SEQ ID NO:94) (see, e.g., Liu et al., *PNAS.* 94:5525-5530, 1997); GGRR (SEQ ID NO:95) (Pomerantz et al. 1995); (GGGGS)$_n$ (SEQ ID NO:83) (Kim et al., *PNAS.* 93:1156-1160, 1996); EGKSSGSGSESKVD (SEQ ID NO:96) (Chaudhary et al., *PNAS.* 87:1066-1070, 1990); KESGSVSSEQLAQFRSLD polypeptide sequences obtained from potyvirus and cardiovirus 2A peptides, FMDV (foot-and-mouth disease virus), equine rhinitis A virus, Thosea asigna virus and porcine teschovirus. In certain embodiments, the self-cleaving polypeptide site comprises a 2A or 2A-like site, sequence or domain (Donnelly et al., *J. Gen. Virol.* 82:1027-1041, 2001). Exemplary 2A sites include the following sequences:

LLNFDLLKLAGDVESNPGP; (SEQ ID NO: 102)

TLNFDLLKLAGDVESNPGP; (SEQ ID NO: 103)

LLKLAGDVESNPGP; (SEQ ID NO: 104)

NFDLLKLAGDVESNPGP; (SEQ ID NO: 105)

QLLNFDLLKLAGDVESNPGP; (SEQ ID NO: 106)

APVKQTLNFDLLKLAGDVESNPGP; (SEQ ID NO: 107)

VTELLYRMKRAETYCPRPLLAIHPTEARHKQKIVAPVKQT; (SEQ ID NO: 108)

LNFDLLKLAGDVESNPGP; (SEQ ID NO: 109)

LLAIHPTEARHKQKIVAPVKQTLNFDLLKLAGDVESNPGP; (SEQ ID NO: 110)
and

EARHKQKIVAPVKQTLNFDLLKLAGDVESNPGP. (SEQ ID NO: 111)

In one embodiment, the autocatalytic peptide cleavage site comprises a translational 2A signal sequence, such as, e.g., the 2A region of the aphthovirus foot-and-mouth disease virus (FMDV) polyprotein, which is an 18 amino acid sequence. Additional examples of 2A-like sequences that may be used include insect virus polyproteins, the NS34 protein of type C rotaviruses, and repeated sequences in *Trypanosoma* spp., as described, for example, in Donnelly et al., *Journal of General Virology*. 82:1027-1041, 2001.

Suitable protease cleavages sites and self-cleaving peptides are known to the skilled person (see, e.g., Ryan et al., *J. Gener. Virol.* 78:699-722, 1997; and Scymczak et al., *Nature Biotech.* 5:589-594, 2004). Exemplary protease cleavage sites include, but are not limited to the cleavage sites of potyvirus NIa proteases (e.g., tobacco etch virus protease), potyvirus HC proteases, potyvirus P1 (P35) proteases, byovirus NIa proteases, byovirus RNA-2-encoded proteases, aphthovirus L proteases, enterovirus 2A proteases, rhinovirus 2A proteases, picorna 3C proteases, comovirus 24K proteases, nepovirus 24K proteases, RTSV (rice tungro spherical virus) 3C-like protease, PYVF (parsnip yellow fleck virus) 3C-like protease, heparin, thrombin, factor Xa and enterokinase. Due to its high cleavage stringency, TEV (tobacco etch virus) protease cleavage sites are included in some embodiments, e.g., EXXYXQ(G/S) (SEQ ID NO:112), for example, ENLYFQG (SEQ ID NO:113) and ENLYFQS (SEQ ID NO:114), wherein X represents any amino acid (cleavage by TEV occurs between Q and G or Q and S).

Further examples of enzymatically degradable linkers suitable for use in particular embodiments of the present invention include, but are not limited to: an amino acid sequence cleaved by a serine protease such as thrombin, chymotrypsin, trypsin, elastase, kallikrein, or subtilisin. Illustrative examples of thrombin-cleavable amino acid sequences include, but are not limited to:

-Gly-Arg-Gly-Asp-, (SEQ ID NO: 115)

-Gly-Gly-Arg-, -Gly- Arg-Gly-Asp-Asn-Pro-, (SEQ ID NO: 116)

-Gly-Arg-Gly-Asp-Ser-, (SEQ ID NO: 117)

-Gly-Arg-Gly-Asp-Ser-Pro-Lys-, (SEQ ID NO: 118)

-Gly-Pro- Arg-, -Val-Pro-Arg-,
and

-Phe-Val-Arg-.

Illustrative examples of elastase-cleavable amino acid sequences include, but are not limited to: -Ala-Ala-Ala-, -Ala-Ala-Pro-Val-(SEQ ID NO:119), -Ala-Ala-Pro-Leu-(SEQ ID NO:120), -Ala-Ala-Pro-Phe-(SEQ ID NO:121), -Ala-Ala-Pro-Ala-(SEQ ID NO:119), and -Ala-Tyr-Leu-Val-(SEQ ID NO:122).

Enzymatically degradable linkers also include amino acid sequences that can be cleaved by a matrix metalloproteinase such as collagenase, stromelysin, and gelatinase. Illustrative examples of matrix metalloproteinase-cleavable amino acid sequences include, but are not limited to: -Gly-Pro-Y-Gly-Pro-Z-(SEQ ID NO:123), -Gly-Pro-, Leu-Gly-Pro-Z-(SEQ ID NO:124), -Gly-Pro-Ile-Gly-Pro-Z-(SEQ ID NO:125), and -Ala-Pro-Gly-Leu-Z-(SEQ ID NO:126), where Y and Z are amino acids. Illustrative examples of collagenase-cleavable amino acid sequences include, but are not limited to: -Pro-Leu-Gly-Pro-D-Arg-Z-(SEQ ID NO:127), -Pro-Leu-Gly-Leu-Leu-Gly-Z-(SEQ ID NO:128), -Pro-Gln-Gly-Ile-Ala-Gly-Trp-(SEQ ID NO:129), -Pro-Leu-Gly-Cys(Me)-His-(SEQ ID NO:130), -Pro-Leu-Gly-Leu-Tyr-Ala-(SEQ ID NO:131), -Pro-Leu-Ala-Leu-Trp-Ala-Arg-(SEQ ID NO:132), and -Pro-Leu-Ala-Tyr-Trp-Ala-Arg-(SEQ ID NO:133), where Z is an amino acid. An illustrative example of a stromelysin-cleavable amino acid sequence is -Pro-Tyr-Ala-Tyr-Tyr-Met-Arg-(SEQ ID NO:134); and an example of a gelatinase-cleavable amino acid sequence is -Pro-Leu-Gly-Met-Tyr-Ser-Arg-(SEQ ID NO:135).

Enzymatically degradable linkers suitable for use in particular embodiments of the present invention also include amino acid sequences that can be cleaved by an angiotensin converting enzyme, such as, for example, -Asp-Lys-Pro-, -Gly-Asp-Lys-Pro-(SEQ ID NO:136), and -Gly-Ser-Asp-Lys-Pro-(SEQ ID NO:137).

Enzymatically degradable linkers suitable for use in particular embodiments of the present invention also include amino acid sequences that can be degraded by cathepsin B, such as, for example, Val-Cit, Ala-Leu-Ala-Leu-(SEQ ID NO:138), Gly-Phe-Leu-Gly-(SEQ ID NO:139) and Phe-Lys.

In particular embodiments, a releasable linker has a half life at pH 7.4, 25° C., e.g., a physiological pH, human body temperature (e.g., in vivo, in serum, in a given tissue), of about 30 minutes, about 1 hour, about 2 hour, about 3 hours, about 4 hours, about 5 hours, about 6 hours, about 12 hours, about 18 hours, about 24 hours, about 36 hours, about 48 hours, about 72 hours, or about 96 hours or more or any intervening half-life. One having skill in the art would appreciate that the half life of a DRS-Fc conjugate polypeptide can be finely tailored by using a particular releasable linker.

In certain embodiments, however, any one or more of the peptide linkers are optional. For instance, linker sequences may not required when the first and second polypeptides have non-essential N-terminal and/or C-terminal amino acid regions that can be used to separate the functional domains and prevent steric interference.

Methods for Use

Embodiments of the present invention relate to the discovery that Fc region-aspartyl-tRNA synthetase (DRS-Fc) conjugate polypeptides, and fragments and variants thereof, offer improved methods of modulating Toll like receptors (TLRs) and other inflammatory-response pathways in a variety of useful ways, both in vitro and in vivo. The compositions of the invention may thus be useful as immunomodulators for treating anti- or pro-inflammatory indications by modulating the cells that mediate, either directly or indirectly, autoimmune and/or inflammatory disease, conditions and disorders. The utility of the compositions of the invention as immunomodulators can be monitored using any of a number of known and available techniques in the art including, for example, migration assays (e.g., using leukocytes or lymphocytes), cytokine production assays, or cell viability assays (e.g., using B-cells, T-cells, monocytes or NK cells).

"Inflammation" refers generally to the biological response of tissues to harmful stimuli, such as pathogens, damaged cells (e.g., wounds), and irritants. The term "inflammatory response" refers to the specific mechanisms by which inflammation is achieved and regulated, including, merely by way of illustration, immune cell activation or migration, cytokine production, vasodilation, including kinin release, fibrinolysis, and coagulation, among others described herein and known in the art. Ideally, inflammation is a protective attempt by the body to both remove the injurious stimuli and initiate the healing process for the affected tissue or tissues. In the absence of inflammation, wounds and infections would never heal, creating a situation in which progressive destruction of the tissue would threaten survival. On the other hand, excessive or chronic inflammation may associate with a variety of diseases, such as hay fever, atherosclerosis, and rheumatoid arthritis, among others described herein and known in the art.

Clinical signs of chronic inflammation are dependent upon duration of the illness, inflammatory lesions, cause and anatomical area affected, (see, e.g., Kumar et al., Robbins Basic Pathology-8 ft Ed., 2009 Elsevier, London; Miller, L M, Pathology Lecture Notes, Atlantic Veterinary College, Charlottetown, PEI, Canada). Chronic inflammation is associated with a variety of pathological conditions or diseases, including, for example, allergies, Alzheimer's disease, anemia, aortic valve stenosis, arthritis such as rheumatoid arthritis and osteoarthritis, cancer, congestive heart failure, fibromyalgia, fibrosis, heart attack, kidney failure, lupus, gout and gout flares, pancreatitis, hepatitis, stroke, surgical complications, acetaminophen-induced liver toxicity, inflammatory lung disease, inflammatory bowel diseases including Crohn's disease (CD), necrotizing enterocolitis, and ulcerative colitis (UC), atherosclerosis, neurological disorders, (neuro)inflammatory disorders, diabetes, metabolic disorders, obesity, graft versus host disease, myositis, emphysema/COPD and psoriasis, among others described herein and known in the art. Hence, DRS polypeptide compositions may be used to treat or manage chronic inflammation, modulate any of one or more of the individual chronic inflammatory responses, or treat any one or more diseases or conditions associated with chronic inflammation.

Certain specific inflammatory responses include cytokine production and activity, and related pathways. For instance, certain exemplary embodiments relate to modulating cell-signaling through nuclear factor-kB (NF-kB), such as by increasing the downstream activities of this transcription factor. In certain instances, increases in NF-kB activity can lead to increases in cytokine signaling or activity, such as pro-inflammatory cytokines (e.g., TNF-alpha or beta), and anti-inflammatory cytokines (e.g., IL-10).

Criteria for assessing the signs and symptoms of inflammatory and other conditions, including for purposes of making differential diagnosis and also for monitoring treatments such as determining whether a therapeutically effective dose has been administered in the course of treatment, e.g., by determining improvement according to accepted clinical criteria, will be apparent to those skilled in the art and are exemplified by the teachings of e.g., Berkow et al., eds., The Merck Manual, 16th edition, Merck and Co., Rahway, N.J., 1992; Goodman et al., eds., Goodman and Gilman's The Pharmacological Basis of Therapeutics, 10th edition, Pergamon Press, Inc., Elmsford, N.Y., (2001); Avery's Drug Treatment: Principles and Practice of Clinical Pharmacology and Therapeutics, 3rd edition, ADIS Press, Ltd., Williams and Wilkins, Baltimore, Md. (1987); Ebadi, Pharmacology, Little, Brown and Co., Boston, (1985); Osolci al., eds., Remington's Pharmaceutical Sciences, 18th edition, Mack Publishing Co., Easton, Pa. (1990); Katzung, Basic and Clinical Pharmacology, Appleton and Lange, Norwalk, Conn. (1992).

Also included are methods of modulating an immune response, such as an innate immune response. As used herein, the term "immune response" includes a measurable or observable reaction to an antigen, vaccine composition, or immunomodulatory molecule mediated by one or more cells of the immune system. An immune response typically begins with an antigen or immunomodulatory molecule binding to an immune system cell. A reaction to an antigen or immunomodulatory molecule may be mediated by many cell types, including a cell that initially binds to an antigen or immunomodulatory molecule and cells that participate in mediating an innate, humoral, cell-mediated immune response.

An "innate immune response," as used herein, may involve binding of pathogen-associated molecular patterns (PAMPs) or damage-associated molecular pattern molecules, (DAMPS) or a DRS polypeptide to cell surface receptors, such as toll-like receptors. Activation of toll-like receptors and Ipaf-signaling pathways in response to PAMPs or other signals leads to the production of immunomodulatory molecules, such as cytokines and co-stimulatory molecules, which induce and/or enhance an immune response. Cells involved in the innate immune response include, for example, dendritic cells, macrophages, natural killer cells, and neutrophils, among others.

Certain embodiments relate to increasing an innate immune response. Other embodiments relate to decreasing an innate immune response. In certain aspects, an innate immune response is mediated by one or more toll-like receptors (TLRs), such as TLR2 and/or TLR4. Certain DRS polypeptides of the invention bind to TLRS such as TLR2 and/or TLR4. More generally, DRS polypeptides are capable of selectively modulating host immune responses via specific interactions with Toll like receptors, and may therefore be used to modulate host immune responses and thereby to manage diseases and conditions associated with the same, as described herein and known in the art. Exemplary uses for the DRS polypeptides of the invention therefore include both methods for the treatment and prevention of TLR associated diseases, as well as for use in the breakdown of immune tolerance, for example for the development of vaccines, and in the development of immune therapies.

Exemplary "TLR associated diseases" include for example, inflammatory conditions, and diseases and disorders associated with the dysfunction of the innate immune response, including for example, autoimmunity, cancer, allergy, autoimmunity, radiation induced toxicity, and the treatment and prevention of bacterial and viral infections. Accordingly in one embodiment the present invention includes a method for treating a TLR associated disease in a subject in need thereof, comprising administering to the subject a therapeutic dose of a DRS-Fc conjugate polypeptide described herein.

Exemplary uses associated with the breakdown of immune tolerance include for example the development of vaccines and adjutants comprising DRS polypeptides mixed with antigens, or comprising DRS fusion proteins with antigens, which exhibit enhanced immunogenicity. In some embodiments the antigen is a self-antigen. DRS polypeptide compositions that stimulate innate immunity (e.g., via TLR2 and/r TLR4) can be useful in the treatment of a wide variety of conditions, either alone or in combination with other therapies. Specific examples of such conditions include infectious diseases, such as bacterial, viral, and parasitic infectious diseases. DRS polypeptide compositions that stimulate innate immunity can also be useful as vaccine adjuvants, to enhance a subject's immune response to the primary antigen, whether in a live, attenuated, or other type of vaccine.

Examples of viral infectious diseases or agents (and their corresponding vaccines) include, but are not limited to, Hepatitis A, Hepatitis B, Hepatitis C, Hepatitis E, Caliciviruses associated diarrhoea, Rotavirus diarrhoea, *Haemophilus influenzae* B pneumonia and invasive disease, influenza, measles, mumps, rubella, Parainfluenza associated pneumonia, Respiratory syncytial virus (RSV) pneumonia, Severe Acute Respiratory Syndrome (SARS), Human papillomavirus, Herpes simplex type 2 genital ulcers, HIV/AIDS, Dengue Fever, Japanese encephalitis, Tick-borne encephalitis, West-Nile virus associated disease, Yellow Fever, Epstein-Barr virus, Lassa fever, Crimean-Congo haemorrhagic fever, Ebola haemorrhagic fever, Marburg haemorrhagic fever, Rabies, Rift Valley fever, Smallpox, leprosy, upper and lower respiratory infections, poliomyelitis, among others described elsewhere herein.

Examples of bacterial infections disease or agents include, but are not limited to, *Bacillus antracis, Borellia burgdorferi, Brucella abortus, Brucella canus, Brucella melitensis, Brucella suis, Campylobacter jejuni, Chlamydia pneumoniae, Chlamydia psitacci, Chlamydia trachomatis, Clostridium botulinum, C. difficile, C. perfringens, C. tetani, Corynebacterium diphtheriae* (i.e., diphtheria), *Enterococcus, Escherichia coli, Haemophilus influenza, Helicobacter pylori, Legionella pneumophila, Leptospira, Listeria monocytogenes, Mycobacterium leprae, M. tuberculosis, Mycoplasma pneumoniae, Neisseria gonorrhea, N. meningitidis, Pseudomonas aeruginosa, Rickettsia recketisii, Salmonella typhi, S. typhimurium, Shigella sonnei, Staphylococcus aureus, S. epidermidis, S. saprophytics, Streptococcus agalactiae, S. pneumoniae, S. pyogenes, Treponema pallidum, Vibrio cholera, Yersinia pestis, Bordatella pertussis,* and otitis media (e.g., often caused by *Streptococcus pneumoniae, Haemophilus influenzae,* or *Moraxella catarrhalis*), among others described elsewhere herein.

Examples of parasitic infectious diseases include, but are not limited to, Amoebiasis (e.g., *Entemoeba histolytica*), Hookworm Disease (e.g., nematode parasites such as *Necator americanus* and *Ancylostoma duodenale*), Leishmaniasis, Malaria (four species of the protozoan parasite *Plasmodium; P. falciparum, P. vivax, P. ovale,* and *P. malariae*), Schistosomiasis (parasitic *Schistosoma; S. mansoni, S. haematobium,* and *S. japonicum*), *Onchocerca volvulus* (River blindness), *Trypanosoma cruzi* (Chagas disease/American sleeping sickness), and *Dracunculus medinensis*, lymphatic filariasis. Certain DRS polypeptide compositions may be useful in the treatment or reduction of endotoxic shock, which often results from exposure to foreign antigens, such as lipopolysacchande (LPS). Because endotoxic shock can be mediated by TLR signaling, and naturally-occurring endogenous DRS polypeptide fragments may stimulate TLRs, certain of the binding agents, antisense agents, or RNAi agents provided herein may render a subject more resistant to endotoxic shock by antagonizing or otherwise reducing the endogenous DRS polypeptide fragment-mediated stimulation of TLR2 and/or TLR4.

Also included are methods of treating immune diseases. Illustrative immune system diseases, disorders or conditions that may be treated according to the present invention include, but are not limited to, primary immunodeficiencies, immune-mediated thrombocytopenia, Kawasaki syndrome, bone marrow transplant (for example, recent bone marrow transplant in adults or children), chronic B cell lymphocytic leukemia, HIV infection (for example, adult or pediatric HIV infection), chronic inflammatory demyelinating polyneuropathy, post-transfusion purpura, and the like.

Additionally, further diseases, disorders and conditions include Guillain-Barre syndrome, anemia (for example, anemia associated with parvovirus B19, patients with stable multiple myeloma who are at high risk for infection (for example, recurrent infection), autoimmune hemolytic anemia (for example, warm-type autoimmune hemolytic anemia), thrombocytopenia (for example, neonatal thrombocytopenia), and immune-mediated neutropenia), transplantation (for example, cytomegalovirus (CMV)-negative recipients of CMV-positive organs), hypogammaglobulinemia (for example, hypogammaglobulinemic neonates with risk factor for infection or morbidity), epilepsy (for example, intractable epilepsy), systemic vasculitic syndromes, myasthenia gravis (for example, decompensation in myasthenia gravis), dermatomyositis, and polymyositis.

Further autoimmune diseases, disorders and conditions include but are not limited to, autoimmune hemolytic anemia, autoimmune neonatal thrombocytopenia, idiopathic thrombocytopenia purpura, autoimmunocytopenia, hemolytic anemia, antiphospholipid syndrome, dermatitis, allergic encephalomyelitis, myocarditis, relapsing polychondritis, rheumatic heart disease, glomerulonephritis (for example, IgA nephropathy), multiple sclerosis, neuritis, uveitis ophthalmia, polyendochnopathies, purpura (for example, Henloch-Scoenlein purpura), Reiter's disease, stiff-man syndrome, autoimmune pulmonary inflammation, Guillain-Barre Syndrome, insulin dependent diabetes mellitus, and autoimmune inflammatory eye disease.

Additional autoimmune diseases, disorders or conditions include, but are not limited to, autoimmune thyroiditis; hypothyroidism, including Hashimoto's thyroiditis and thyroiditis characterized, for example, by cell-mediated and humoral thyroid cytotoxicity; SLE (which is often characterized, for example, by circulating and locally generated immune complexes); Goodpasture's syndrome (which is often characterized, for example, by anti-basement membrane antibodies); pemphigus (which is often characterized, for example, by epidermal acantholytic antibodies); receptor autoimmunities such as, for example, Graves' disease (which is often characterized, for example, by antibodies to a thyroid stimulating hormone receptor; myasthenia gravis, which is often characterized, for example, by acetylcholine receptor antibodies); insulin resistance (which is often characterized, for example, by insulin receptor antibodies); autoimmune hemolytic anemia (which is often characterized, for example, by phagocytosis of antibody-sensitized red blood cells); and autoimmune thrombocytopenic purpura (which is often characterized, for example, by phagocytosis of antibody-sensitized platelets).

Further autoimmune diseases, disorders or conditions include, but are not limited to, rheumatoid arthritis (which is often characterized, for example, by immune complexes in joints); scleroderma with anti-collagen antibodies (which is often characterized, for example, by nucleolar and other nuclear antibodies); mixed connective tissue disease, (which is often characterized, for example, by antibodies to extractable nuclear antigens, for example, ribonucleoprotein); polymyositis/dermatomyositis (which is often characterized, for example, by nonhistone anti-nuclear antibodies); pernicious anemia (which is often characterized, for example, by antiparietal cell, antimicrosome, and anti-intrinsic factor antibodies); idiopathic Addison's disease (which is often characterized, for example, by humoral and cell-mediated adrenal cytotoxicity); infertility (which is often characterized, for example, by antispennatozoal antibodies); glomerulonephritis (which is often characterized, for example, by glomerular basement membrane antibodies or immune complexes); by primary glomerulonephritis, by IgA nephropathy; bullous pemphigoid (which is often characterized, for example, by IgG and complement in the basement membrane); Sjogren's syndrome (which is often characterized, for example, by multiple tissue antibodies and/or the specific nonhistone antinuclear antibody (SS-B)); diabetes mellitus (which is often characterized, for example, by cell-mediated and humoral islet cell antibodies); and adrenergic drug resistance, including adrenergic drug resistance with asthma or cystic fibrosis (which is often characterized, for example, by beta-adrenergic receptor antibodies).

Still further autoimmune diseases, disorders or conditions include, but are not limited to chronic active hepatitis (which is often characterized, for example by smooth muscle antibodies); primary biliary cirrhosis (which is often characterized, for example, by anti-mitochondrial antibodies); other endocrine gland failure (which is characterized, for example, by specific tissue antibodies in some cases); vitiligo (which is often characterized, for example, by anti-melanocyte antibodies); vasculitis (which is often characterized, for example, by immunoglobulin and complement in vessel walls and/or low serum complement); post-myocardial infarction conditions (which are often characterized, for example, by anti-myocardial antibodies); cardiotomy syndrome (which is often characterized, for example, by anti-myocardial antibodies); urticaria (which is often characterized, for example, by IgG and IgM antibodies to IgE); atopic dermatitis (which is often characterized, for example, by IgG and IgM antibodies to IgE); asthma (which is often characterized, for example, by IgG and IgM antibodies to IgE); inflammatory myopathies; and other inflammatory, granulomatous, degenerative, and atrophic disorders.

Further embodiments the present invention include methods for killing cancer cells, comprising administering a vaccine or immunogenic composition comprising a DRS-Fc conjugate polypeptide of the invention fused to, or otherwise associated with an antigen, or vector comprising a nucleic acid encoding a DRS-Fc fusion polypeptide fused to an antigen, to a subject in need thereof. In some embodiments the antigen is a self-antigen, in some embodiments the antigen is a tumor derived antigen. In some embodiments, the antigen is a pathogen derived antigen. In some embodiments the pathogen derived antigen is derived from a virus, bacteria or prion. In some embodiments, the antigen is covalently attached to the DRS-Fc polypeptide through conjugation at Cys130, Cys 259, Cys334, and/or Cys349. In some embodiments the antigen and DRS polypeptide are mixed together.

In some embodiments the present invention includes a method for treating a subject with cancer, or preventing the development of cancer in a subject, comprising administering a vaccine or immunogenic composition comprising a DRS-Fc conjugate polypeptide of the invention fused or otherwise covalently attached to an antigen, or vector comprising a nucleic acid encoding a DRS-Fc fusion polypeptide fused to an antigen, wherein the vaccine elicits an immune response to the cancer. In some embodiments the antigen is a self-antigen, in some embodiments the antigen is a tumor derived antigen. In some embodiments, the antigen is a pathogen derived antigen. In some embodiments the pathogen derived antigen is derived from a virus, bacteria or prion. In some embodiments, the antigen is covalently attached to the DRS polypeptide through conjugation at Cys130, Cys 259, Cys334, and/or Cys349.

In some embodiments the present invention includes a method for overcoming tolerance of a subject to an antigen, comprising administering a vaccine or immunogenic composition comprising a DRS-Fc conjugated polypeptide of the invention fused or otherwise covalently attached to the antigen, or vector comprising a nucleic acid encoding a DRS-Fc fusion polypeptide fused to the antigen. In different embodiments, the antigen may be selected from self-antigens, tumor derived antigens, and pathogen derived antigens. In some embodiments the pathogen derived antigen is derived from a virus, bacteria or prion. In some embodiments, the antigen is covalently attached to the DRS polypeptide through conjugation at Cys130, Cys 259, Cys334, and/or Cys349.

Pharmaceutical Formulations, Administration, and Kits

Embodiments of the present invention include compositions comprising DRS-Fc conjugate polypeptides formulated in pharmaceutically-acceptable or physiologically-acceptable solutions for administration to a cell, subject, or an animal, either alone, or in combination with one or more other modalities of therapy. It will also be understood that, if desired, the compositions of the invention may be administered in combination with other agents as well, for example, other proteins or polypeptides or various pharmaceutically-active agents. There is virtually no limit to other components that may also be included in the compositions, provided that the additional agents do not adversely affect the modulatory or other effects desired to be achieved.

For pharmaceutical production, DRS polypeptide therapeutic compositions will typically be substantially endotoxin free. Endotoxins are toxins associated with certain bacteria, typically gram-negative bacteria, although endotoxins may be found in gram-positive bacteria, such as *Listeria monocytogenes*. The most prevalent endotoxins are lipopolysaccharides (LPS) or lipo-oligo-saccharides (LOS) found in the outer membrane of various Gram-negative bacteria, and which represent a central pathogenic feature in the ability of these bacteria to cause disease. Small amounts of endotoxin in humans may produce fever, a lowering of the blood pressure, and activation of inflammation and coagulation, among other adverse physiological effects.

Endotoxins can be detected using routine techniques known in the art. For example, the Limulus Amoebocyte Lysate assay, which utilizes blood from the horseshoe crab, is a very sensitive assay for detecting presence of endotoxin. In this test, very low levels of LPS can cause detectable coagulation of the limulus lysate due a powerful enzymatic cascade that amplifies this reaction. Endotoxins can also be quantitated by enzyme-linked immunosorbent assay (ELISA).

To be substantially endotoxin free, endotoxin levels may be less than about 0.001, 0.005, 0.01, 0.02, 0.03, 0.04, 0.05, 0.06, 0.08, 0.09, 0.1, 0.5, 1.0, 1.5, 2, 2.5, 3, 4, 5, 6, 7, 8, 9, or 10 EU/mg of protein. Typically, 1 ng lipopolysaccharide (LPS) corresponds to about 1-10 EU.

In certain embodiments, as noted herein, the DRS polypeptide compositions have an endotoxin content of less than about 10 EU/mg of DRS polypeptide, or less than about 5 EU/mg of DRS polypeptide, less than about 3 EU/mg of DRS polypeptide, or less than about 1 EU/mg of DRS polypeptide, or less than about 0.1 EU/mg of DRS polypeptide, or less than about 0.01 EU/mg of DRS polypeptide. In certain embodiments, as noted above, the DRS polypeptide pharmaceutical compositions are about 95% endotoxin free, preferably about 99% endotoxin free, and more preferably about 99.99% endotoxin free on wt/wt protein basis.

Pharmaceutical compositions comprising a therapeutic dose of a DRS-Fc conjugate polypeptide include all homologues, orthologs, and naturally-occurring isoforms of aspartyl-tRNA synthetase (e.g., any one or more of the proteins or nucleic acids listed in or derivable from Tables D1 to D9).

In some embodiments such pharmaceutical compositions may comprise an arginine buffer, which may be present in any of the pharmaceutical compositions within the range of about 1 mM to about 100 mM. In different embodiments, the arginine buffer may be present at a concentration of about 1 mM, about 5 mM, about 10 mM, about 15 mM, about 20 mM, about 40 mM, about 50 mM, about 60 mM, about 70 mM, about 80 mM, about 90 mM, or about 100 mM, including all ranges and integers in between.

In one aspect such compositions may comprises DRS-Fc conjugate polypeptides that are substantially monodisperse, meaning that the DRS polypeptide compositions exist primarily (i.e., at least about 90%, or greater) in one apparent molecular weight form when assessed for example, by size exclusion chromatography, dynamic light scattering, or analytical ultracentrifugation.

In another aspect, such compositions have a purity (on a protein basis) of at least about 90%, or in some aspects at least about 95% purity, or in some embodiments, at least 98% purity. Purity may be determined via any routine analytical method as known in the art.

In another aspect, such compositions have a high molecular weight aggregate content of less than about 10%, compared to the total amount of protein present, or in some embodiments such compositions have a high molecular weight aggregate content of less than about 5%, or in some aspects such compositions have a high molecular weight aggregate content of less than about 3%, or in some embodiments a high molecular weight aggregate content of less than about 1%. High molecular weight aggregate content may be determined via a variety of analytical techniques including for example, by size exclusion chromatography, dynamic light scattering, or analytical ultracentrifugation.

Pharmaceutical compositions may include pharmaceutically acceptable salts of a DRS-Fc conjugate polypeptide. For a review on suitable salts, see *Handbook of Pharmaceutical Salts: Properties, Selection, and Use* by Stahl and Wermuth (Wiley-VCH, 2002). Suitable base salts are formed from bases which form non-toxic salts. Representative examples include the aluminum, arginine, benzathine, calcium, choline, diethylamine, diolamine, glycine, lysine, magnesium, meglumine, olamine, potassium, sodium, tromethamine, and zinc salts. Hemisalts of acids and bases may also be formed, e.g., hemisulphate and hemicalcium salts. Compositions to be used in the invention suitable for parenteral administration may comprise sterile aqueous solutions and/or suspensions of the pharmaceutically active ingredients preferably made isotonic with the blood of the recipient, generally using sodium chloride, glycerin, glucose, mannitol, sorbitol, and the like. Organic acids suitable for forming pharmaceutically acceptable acid addition salts include, by way of example and not limitation, acetic acid, trifluoroacetic acid, propionic acid, hexanoic acid, cyclopentanepropionic acid, glycolic acid, oxalic acid, pyruvic acid, lactic acid, malonic acid, succinic acid, malic acid, maleic acid, fumaric acid, tartaric acid, citric acid, palmitic acid, benzoic acid, 3-(4-hydroxybenzoyl)benzoic acid, cinnamic acid, mandelic acid, alkylsulfonic acids (e.g., methanesulfonic acid, ethanesulfonic acid, 1,2-ethane-disulfonic acid, 2-hydroxyethanesulfonic acid), arylsulfonic acids (e.g., benzenesulfonic acid, 4-chlorobenzenesulfonic acid, 2-naphthalenesulfonic acid, 4-toluenesulfonic acid, camphorsulfonic acid), 4-methylbicyclo(2.2.2)-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like.

In particular embodiments, the carrier may include water. In some embodiments, the carrier may be an aqueous solution of saline, for example, water containing physiological concentrations of sodium, potassium, calcium, magnesium, and chloride at a physiological pH. In some embodiments, the carrier may be water and the formulation may further include NaCl. In some embodiments, the formulation may be isotonic. In some embodiments, the formulation may be hypotonic. In other embodiments, the formulation may be hypertonic. In some embodiments, the formulation may be isosmotic. In some embodiments, the formulation is substantially free of polymers (e.g., gel-forming polymers, polymeric viscosity-enhancing agents). In some embodiments, the formulation is substantially free of viscosity-increasing agents (e.g., carboxymethylcellulose, polyanionic polymers). In some embodiments, the formulation is substantially free of gel-forming polymers. In some embodiments, the viscosity of the formulation is about the same as the viscosity of a saline solution containing the same concentration of a DRS polypeptide (or a pharmaceutically acceptable salt thereof).

In the pharmaceutical compositions of the invention, formulation of pharmaceutically-acceptable excipients and carrier solutions is well-known to those of skill in the art, as is the development of suitable dosing and treatment regimens for using the particular compositions described herein in a variety of treatment regimens, including e.g., oral, parenteral, intravenous, intranasal, and intramuscular administration and formulation.

In certain embodiments, the DRS-Fc conjugate polypeptide have a solubility that is desirable for the particular mode of administration, such intravenous administration. Examples of desirable solubility's include at least about 1 mg/ml, at least about 10 mg/ml, at least about 25 mg/ml, and at least about 50 mg/ml.

In certain applications, the pharmaceutical compositions disclosed herein may be delivered via oral administration to a subject. As such, these compositions may be formulated with an inert diluent or with an edible carrier, or they may be enclosed in hard- or soft-shell gelatin capsule, or they may be compressed into tablets, or they may be incorporated directly with the food of the diet.

Pharmaceutical compositions suitable for the delivery of DRS polypeptides and methods for their preparation will be readily apparent to those skilled in the art. Such compositions and methods for their preparation may be found, for example, in *Remington's Pharmaceutical Sciences,* 19th Edition (Mack Publishing Company, 1995).

Administration of a therapeutic dose of a DRS polypeptide may be by any suitable method known in the medicinal arts, including for example, oral, intranasal, parenteral administration include intravitreal, subconjuctival, subtenon, retrobulbar, suprachoroidal intravenous, intra-arterial, intraperitoneal, intrathecal, intraventricular, intraurethral, intrasternal, intracranial, intramuscular, intrasynovial, intraocular, topical and subcutaneous. Suitable devices for parenteral administration include needle (including microneedle) injectors, needle-free injectors, and infusion techniques.

Parenteral formulations are typically aqueous solutions which may contain excipients such as salts, carbohydrates, and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water. The preparation of parenteral formulations under sterile conditions, for instance, by lyophilization, may readily be accomplished using standard pharmaceutical techniques well-known to those skilled in the art.

Formulations for parenteral administration may be formulated to be immediate and/or sustained release. Sustained release compositions include delayed, modified, pulsed, controlled, targeted and programmed release. Thus a DRS polypeptide may be formulated as a suspension or as a solid, semi-solid, or thixotropic liquid for administration as an implanted depot providing sustained release of DRS polypeptides. Examples of such formulations include without limitation, drug-coated stents and semi-solids and suspensions comprising drug-loaded poly(DL-lactic-co-glycolic) acid (PGLA), poly(DL-lactide-co-glycolide) (PLG) or poly (lactide) (PLA) lamellar vesicles or microparticles, hydrogels (Hoffman A S: *Ann. N.Y. Acad. Sci.* 944: 62-73 (2001)), poly-amino acid nanoparticles systems, such as the Medusa system developed by Flamel Technologies Inc., non aqueous gel systems such as Atrigel developed by Atrix, Inc., and SABER (Sucrose Acetate Isobutyrate Extended Release) developed by Durect Corporation, and lipid-based systems such as DepoFoam developed by SkyePharma.

Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions (U.S. Pat. No. 5,466,468, incorporated by reference in its entirety). In all cases the form should be sterile and should be fluid to the extent that easy syringability exists. It should be stable under the conditions of manufacture and storage and should be preserved against the contaminating action of microorganisms, such as bacteria and fungi. The carrier can be a solvent or dispersion medium containing, for example, water, ethanol, polyol (e.g., glycerol, propylene glycol, liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be facilitated by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, a sterile aqueous medium that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion (see, e.g., *Remington's Pharmaceutical Sciences,* 15th Edition, pp. 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, and the general safety and purity standards as required by FDA Office of Biologics standards.

Sterile injectable solutions can be prepared by incorporating the active compounds in the required amount in the appropriate solvent with the various other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The compositions disclosed herein may be formulated in a neutral or salt form. Pharmaceutically-acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug-release capsules, and the like.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The phrase "pharmaceutically-acceptable" refers to molecular entities and compositions that do not produce an allergic or similar untoward reaction when administered to a human. The preparation of an aqueous composition that contains a protein as an active ingredient is well understood in the art. Typically, such compositions are prepared as injectables, either as liquid solutions or suspensions; solid forms suitable for solution in, or suspension in, liquid prior to injection can also be prepared. The preparation can also be emulsified.

DRS-Fc conjugate polypeptides for use in the present invention may also be administered topically, (intra)dermally, or transdermally to the skin, mucosa, or surface of the eye, either alone or in combination with one or more antihistamines, one or more antibiotics, one or more antifungal agents, one or more beta blockers, one or more anti-inflammatory agents, one or more antineoplastic agents, one or more immunosuppressive agents, one or more antiviral agents, one or more antioxidant agents, or other active agents. Formulations for topical and ocular administration may be formulated to be immediate and/or modified release. Modified release formulations include delayed, sustained, pulsed, controlled, targeted and programmed release.

Typical formulations for this purpose include gels, hydrogels, lotions, solutions, eye drops, creams, ointments, dusting powders, dressings, foams, films, skin patches, wafers, implants, sponges, fibers, bandages, and microemulsions. Liposomes may also be used. Typical carriers include alcohol, water, mineral oil, liquid petrolatum, white petrolatum, glycerin, polyethylene glycol, and propylene glycol. Penetration enhancers may be incorporated—see, e.g., Finnin and Morgan: *J. Pharm. Sci.* 88(10): 955-958, (1999). Other means of topical administration include delivery by electroporation, iontophoresis, phonophoresis, sonophoresis, and microneedle or needle-free injection (e.g., the systems sold under the trademarks POWDERJECT™, BIOJECT™).

Examples of antihistamines include, but are not limited to, loradatine, hydroxyzine, diphenhydramine, chlorpheniramine, brompheniramine, cyproheptadine, terfenadine, clemastine, triprolidine, carbinoxamine, diphenylpyraline, phenindamine, azatadine, tripelennamine, dexchlorpheniramine, dexbrompheniramine, methdilazine, and trimprazine doxylamine, pheniramine, pyrilamine, chiorcyclizine, thonzylamine, and derivatives thereof.

Examples of antibiotics include, but are not limited to, aminoglycosides (e.g., amikacin, apramycin, arbekacin, bambermycins, butirosin, dibekacin, dihydrostreptomycin, fortimicin(s), gentamicin, isepamicin, kanamycin, micronomicin, neomycin, neomycin undecylenate, netilmicin, paromomycin, ribostamycin, sisomicin, spectinomycin, streptomycin, tobramycin, trospectomycin), amphenicols (e.g., azidamfenicol, chloramphenicol, florfenicol, thiamphenicol), ansamycins (e.g., rifamide, rifampin, rifamycin sv, rifapentine, rifaximin), lactams (e.g., carbacephems (e.g., loracarbef), carbapenems (e.g., biapenem, imipenem, meropenem, panipenem), cephalosporins (e.g., cefaclor, cefadroxil, cefamandole, cefatrizine, cefazedone, cefazolin, cefcapene pivoxil, cefclidin, cefdinir, cefditoren, cefepime, cefetamet, cefixime, cefinenoxime, cefodizime, cefonicid, cefoperazone, ceforanide, cefotaxime, cefotiam, cefozopran, cefpimizole, cefpiramide, cefpirome, cefpodoxime proxetil, cefprozil, cefroxadine, cefsulodin, ceftazidime, cefteram, ceftezole, ceftibuten, ceftizoxime, ceftriaxone, cefuroxime, cefuzonam, cephacetrile sodium, cephalexin, cephaloglycin, cephaloridine, cephalosporin, cephalothin, cephapirin sodium, cephradine, pivcefalexin), cephamycins (e.g., cefbuperazone, cefinetazole, cefminox, cefotetan, cefoxitin), monobactams (e.g., aztreonam, carumonam, tigemonam), oxacephems, flomoxef, moxalactam), penicillins (e.g., amdinocillin, amdinocillin pivoxil, amoxicillin, ampicillin, apalcillin, aspoxicillin, azidocillin, azlocillin, bacampicillin, benzylpenicillinic acid, benzylpenicillin sodium, carbenicillin, carindacillin, clometocillin, cloxacillin, cyclacillin, dicloxacillin, epicillin, fenbenicillin, floxacillin, hetacillin, lenampicillin, metampicillin, methicillin sodium, mezlocillin, nafcillin sodium, oxacillin, penamecillin, penethamate hydriodide, penicillin g benethamine, penicillin g benzathine, penicillin g benzhydrylamine, penicillin g calcium, penicillin g hydrabamine, penicillin g potassium, penicillin g procaine, penicillin n, penicillin o, penicillin v, penicillin v benzathine, penicillin v hydrabamine, penimepicycline, phenethicillin potassium, piperacillin, pivampicillin, propicillin, quinacillin, sulbenicillin, sultamicillin, talampicillin, temocillin, ticarcillin), other (e.g., ritipenem), lincosamides (e.g., clindamycin, lincomycin), macrolides (e.g., azithromycin, carbomycin, clarithromycin, dirithromycin, erythromycin, erythromycin acistrate, erythromycin estolate, erythromycin glucoheptonate, erythromycin lactobionate, erythromycin propionate, erythromycin stearate, josamycin, leucomycins, midecamycins, miokamycin, oleandomycin, primycin, rokitamycin, rosaramicin, roxithromycin, spiramycin, troleandomycin), polypeptides (e.g., amphomycin, bacitracin, capreomycin, colistin, enduracidin, enviomycin, fusafungine, gramicidin s, gramicidin(s), mikamycin, polymyxin, pristinamycin, ristocetin, teicoplanin, thiostrepton, tuberactinomycin, tyrocidine, tyrothricin, vancomycin, viomycin, virginiamycin, zinc bacitracin), tetracyclines (e.g., apicycline, chlortetracycline, clomocycline, demeclocycline, doxycycline, guamecycline, lymecycline, meclocycline, methacycline, minocycline, oxytetracycline, penimepicycline, pipacycline, rolitetracycline, sancycline, tetracycline), and others (e.g., cycloserine, mupirocin, tuberin). 2,4-Diaminopyrimidines (e.g., brodimoprim, tetroxoprim, trimethoprim), nitrofurans (e.g., furaltadone, furazolium chloride, nifuradene, nifuratel, nifurfoline, nifurpirinol, nifurprazine, nifurtoinol, nitrofurantoin), quinolones and analogs (e.g., cinoxacin, ciprofloxacin, clinafloxacin, difloxacin, enoxacin, fleroxacin, flumequine, grepafloxacin, lomefloxacin, miloxacin, nadifloxacin, nalidixic acid, norfloxacin, ofloxacin, oxolinic acid, pazufloxacin, pefloxacin, pipemidic acid, piromidic acid, rosoxacin, rufloxacin, sparfloxacin, temafloxacin, tosufloxacin, trovafloxacin), sulfonamides (e.g., acetyl sulfamethoxypyrazine, benzylsulfamide, chloramine-b, chloramine-t, dichloramine t, $n^2$-formylsulfisomidine, mafenide, 4'-(methylsulfamoyl)sulfanilanilide, noprylsulfamide, phthalylsulfacetamide, phthalylsulfathiazole, salazosulfadimidine, succinylsulfathiazole, sulfabenzamide, sulfacetamide, sulfachlorpyridazine, sulfachrysoidine, sulfacytine, sulfadiazine, sulfadicramide, sulfadimethoxine, sulfadoxine, sulfaethidole, sulfaguanidine, sulfaguanol, sulfalene, sulfaloxic acid, sulfamerazine, sulfameter, sulfamethazine, sulfamethizole, sulfamethomidine, sulfamethoxazole, sulfamethoxypyridazine, sulfametrole, sulfamidochrysoidine, sulfamoxole, sulfanilamide, 4-sulfanilamidosalicylic acid, $n^4$-sulfanilylsulfanilamide, sulfanilylurea, n-sulfanilyl-3,4-xylamide, sulfanitran, sulfaperine, sulfaphenazole, sulfaproxyline, sulfapyrazine, sulfapyridine, sulfasomizole, sulfasymazine, sulfathiazole, sulfathiourea, sulfatolamide, sulfisomidine, sulfisoxazole) sulfones (e.g., acedapsone, acediasulfone, acetosulfone sodium, dapsone, diathymosulfone, glucosulfone sodium, solasulfone, succisulfone, sulfanilic acid, p-sulfanilylbenzylamine, sulfoxone sodium, thiazolsulfone), and others (e.g., clofoctol, hexedine, methenamine, methenamine anhydromethylene-citrate, methenamine hippurate, methenamine mandelate, methenamine sulfosalicylate, nitroxoline, taurolidine, xibornol).

Examples of antifungal agents include, but are not limited to Polyenes (e.g., amphotericin b, candicidin, dermostatin, filipin, fungichromin, hachimycin, hamycin, lucensomycin, mepartricin, natamycin, nystatin, pecilocin, perimycin), others (e.g., azaserine, griseofulvin, oligomycins, neomycin undecylenate, pyrroInitrin, siccanin, tubercidin, viridin), Allylamines (e.g., butenafine, naftifine, terbinafine), imidazoles (e.g., bifonazole, butoconazole, chlordantoin, chlormidazole, cloconazole, clotrimazole, econazole, enilconazole, fenticonazole, flutrimazole, isoconazole, ketoconazole, lanoconazole, miconazole, omoconazole, oxiconazole nitrate, sertaconazole, sulconazole, tioconazole), thiocarbamates (e.g., tolciclate, tolindate, tolnaftate), triazoles (e.g., fluconazole, itraconazole, saperconazole, terconazole) others (e.g., acrisorcin, amorolfine, biphenamine, bromosalicylchloranilide, buclosamide, calcium propionate, chlorphenesin, ciclopirox, cloxyquin, coparaffinate, diamthazole dihydrochloride, exalamide, flucytosine, halethazole, hexetidine, loflucarban, nifuratel, potassium iodide, propionic acid, pyrithione, salicylanilide, sodium propionate, sulbentine, tenonitrozole, triacetin, ujothion, undecylenic acid, zinc propionate).

Examples of beta blockers include but are not limited to acebutolol, atenolol, labetalol, metoprolol, propranolol, timolol, and derivatives thereof.

Examples of antineoplastic agents include, but are not limited to antibiotics and analogs (e.g., aclacinomycins, actinomycin $f_1$, anthramycin, azaserine, bleomycins, cactinomycin, carubicin, carzinophilin, chromomycins, dactinomycin, daunorubicin, 6-diazo-5-oxo-L-norleucine, doxorubicin, epirubicin, idarubicin, menogaril, mitomycins, mycophenolic acid, nogalamycin, olivomycines, peplomycin, pirarubicin, plicamycin, porfiromycin, puromycin, streptonigrin, streptozocin, tubercidin, zinostatin, zorubicin), antimetabolites (e.g., folic acid analogs (e.g., denopterin, edatrexate, methotrexate, piritrexim, pteropterin, Tomudex®, trimetrexate), purine analogs (e.g., cladribine, fludarabine, 6-mercaptopurine, thiamiprine, thioguanine), pyrimidine analogs (e.g., ancitabine, azacitidine, 6-azauridine, carmofur, cytarabine, doxifluridine, emitefur, enocitabine, floxuridine, fluorouracil, gemcitabine, tagafur).

Examples of anti-inflammatory agents include but are not limited to steroidal anti-inflammatory agents and non-steroidal anti-inflammatory agents. Exemplary steroidal anti-inflammatory agents include acetoxypregnenolone, alclometasone, algestone, amcinonide, beclomethasone, betamethasone, budesonide, chloroprednisone, clobetasol, clobetasone, clocortolone, cloprednol, corticosterone, cortisone, cortivazol, deflazacort, desonide, desoximetasone, dexamethasone, diflorasone, diflucortolone, difluprednate, enoxolone, fluazacort, flucloronide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, halopredone acetate, hydrocortamate, hydrocortisone, loteprednol etabonate, mazipredone, medrysone, meprednisone, methylprednisolone, mometasone furoate, paramethasone, prednicarbate, prednisolone, prednisolone 25-diethylamino-acetate, prednisolone sodium phosphate, prednisone, prednival, prednylidene, rimexolone, tixocortol, triamcinolone, triamcinolone acetonide, triamcinolone benetonide, and triamcinolone hexacetonide.

Exemplary non-steroidal anti-inflammatory agents include aminoarylcarboxylic acid derivatives (e.g., enfenamic acid, etofenamate, flufenamic acid, isonixin, meclofenamic acid, mefenamic acid, niflumic acid, talniflumate, terofenamate, tolfenamic acid), arylacetic acid derivatives (e.g., aceclofenac, acemetacin, alclofenac, amfenac, amtolmetin guacil, bromfenac, bufexamac, cinmetacin, clopirac, diclofenac sodium, etodolac, felbinac, fenclozic acid, fentiazac, glucametacin, ibufenac, indomethacin, isofezolac, isoxepac, lonazolac, metiazinic acid, mofezolac, oxametacine, pirazolac, proglumetacin, sulindac, tiaramide, tolmetin, tropesin, zomepirac), arylbutyric acid derivatives (e.g., bumadizon, butibufen, fenbufen, xenbucin), arylcarboxylic acids (e.g., clidanac, ketorolac, tinoridine), arylpropionic acid derivatives (e.g., alminoprofen, benoxaprofen, bermoprofen, bucloxic acid, carprofen, fenoprofen, flunoxaprofen, flurbiprofen, ibuprofen, ibuproxam, indoprofen, ketoprofen, loxoprofen, naproxen, oxaprozin, piketoprolen, pirprofen, pranoprofen, protizinic acid, suprofen, tiaprofenic acid, ximoprofen, zaltoprofen), pyrazoles (e.g., difenamizole, epirizole), pyrazolones (e.g., apazone, benzpiperylon, feprazone, mofebutazone, morazone, oxyphenbutazone, phenylbutazone, pipebuzone, propyphenazone, ramifenazone, suxibuzone, thiazolinobutazone), salicylic acid derivatives (e.g., acetaminosalol, aspirin, benorylate, bromosaligenin, calcium acetylsalicylate, diflunisal, etersalate, fendosal, gentisic acid, glycol salicylate, imidazole salicylate, lysine acetylsalicylate, mesalamine, morpholine salicylate, 1-naphthyl salicylate, olsalazine, parsalmide, phenyl acetylsalicylate, phenyl salicylate, salacetamide, salicylamide o-acetic acid, salicylsulfuric acid, salsalate, sulfasalazine), thiazinecarboxamides (e.g., ampiroxicam, droxicam, isoxicam, lornoxicam, piroxicam, tenoxicam), ε-acetamidocaproic acid, s-adenosylmethionine, 3-amino-4-hydroxybutyric acid, amixetrine, bendazac, benzydamine-bucolome, difenpiramide, ditazol, emorfazone, fepradinol, guaiazulene, nabumetone, nimesulide, oxaceprol, paranyline, perisoxal, proquazone, superoxide dismutase, tenidap, and zileuton.

Examples of antiviral agents include interferon gamma, zidovudine, amantadine hydrochloride, ribavirin, acyclovir, valciclovir, dideoxycytidine, phosphonoformic acid, ganciclovir, and derivatives thereof.

Examples of antioxidant agents include ascorbate, alphatocopherol, mannitol, reduced glutathione, various carotenoids, cysteine, uric acid, taurine, tyrosine, superoxide dismutase, lutein, zeaxanthin, cryotpxanthin, astazanthin, lycopene, N-acetyl-cysteine, carnosine, gamma-glutamylcysteine, quercitin, lactoferrin, dihydrolipoic acid, citrate, *Ginkgo Biloba* extract, tea catechins, bilberry extract, vitamins E or esters of vitamin E, retinyl palmitate, and derivatives thereof. Other therapeutic agents include squalamine, carbonic anhydrase inhibitors, alpha-2 adrenergic receptor agonists, antiparasitics, antifungals, and derivatives thereof.

The exact dose of each component administered will, of course, differ depending on the specific components prescribed, on the subject being treated, on the severity of the disease, for example, severity of the inflammatory reaction, on the manner of administration and on the judgment of the prescribing physician. Thus, because of patient-to-patient variability, the dosages given above are a guideline and the physician may adjust doses of the compounds to achieve the treatment that the physician considers appropriate.

As will be understood by the skilled artisan, for DRS polypeptide (e.g., ocular) formulations where the carrier includes a gel-forming polymer, in certain formulations the inclusion of salt(s), in particular saline solution, is contraindicated as inclusion of salt may either cause the solution to gel prior to topical administration, as with certain in situ gel-forming polymers (e.g., gellan gel), or the inclusion of salts may inhibit the gelling properties of the gel-forming polymer. The skilled artisan will be able to select appropriate combinations based on the desired properties of the formulation and characteristics of gel-forming polymers known in the art.

Suitable aqueous saline solutions will be understood by those of skill in the art and may include, for example, solutions at a pH of from about pH 4.5 to about pH 8.0. In further variations of aqueous solutions (where water is included in the carrier), the pH of the formulation is between any of about 6 and about 8.0; between about 6 and about 7.5; between about 6 and about 7.0; between about 6.2 and about 8; between about 6.2 and about 7.5; between about 7 and about 8; between about 6.2 and about 7.2; between about 5.0 and about 8.0; between about 5 and about 7.5; between about 5.5 and about 8.0; between about 6.1 and about 7.7; between about 6.2 and about 7.6; between about 7.3 and about 7.4; about 6.0; about 7.1; about 6.2; about 7.3; about 6.4; about 6.5; about 6.6; about 6.7; about 6.8; about 6.9; about 7.0; about 7.1; about 7.2; about 7.3; about 7.4; about 7.5; about 7.6; or about 8.0. In some variations, the DRS polypeptide formulation has a pH of about 6.0 to about 7.0. In some variations, the formulation has a pH of about 7.4. In particular variations, the formulation has a pH of about 6.2 to about 7.5.

In certain embodiments the concentration of the salt (e.g., NaCl) will be, for example, from about 0% to about 0.9% (w/v). For example, the concentration of salt may be from about 0.01 to about 0.9%, from about 0.02% to about 0.9%, from about 0.03% to about 9%, from about 0.05% to about 0.9% from about 0.07% to about 0.9%, from about 0.09% to about 0.9%, from about 0.1% to about 0.9% from about 0.2% to about 0.9%, from about 0.3% to about 0.9%, from about 0.4% to about 0.9% from about 0.5% to about 0.9%, from about 0.6% to about 0.9%, from about 0.7% to about 0.9%, from about 0.8% to about 0.9%, about 0.9%, about 0%, about 0.05%, about 0.01%, about 0.09%, about 0.1%, about 0.2%, about 0.3%, about 0.4%, about 0.5%, about 0.6%, about 0.7%, or about 0.8%. In certain embodiments, the aqueous saline solution will be isotonic (e.g., NaCl concentration of about 0.9% NaCl (w/v)). In certain embodiments, the aqueous solution will contain a NaCl concentration of about 0.5%, about 0.7%, about 0.8%, about 0.85, or about 0.75%. As will be appreciated the skilled artisan, depending on the concentrations of other components, for example where the DRS polypeptides are present as salts of, the concentration of NaCl or other salt needed to achieve an formulation suitable for administration may vary.

In some embodiments, where the ocular formulation is substantially free of viscosity-increasing agents, the formulation may be substantially free of viscosity-increasing agents such as, but not limited to polyanionic polymers, water soluble cellulose derivatives (e.g., hypromellose (also known as HPMC, hydroxypropylmethyl cellulose, and hydroxypropylcellulose), hydroxyethylcellulose, carboxmethylcellulose, etc.), polyvinyl alcohol, polyvinyl pyrrolidone, chondroitin sulfate, hyaluronic acid, soluble starches, etc. In some variations, the formulation does not incorporate a hydrogel or other retention agent (e.g., such as those disclosed in U.S. Pat. Pub. No. 2005/0255144 (incorporated by reference herein in its entirety)), e.g., where the hydrogel may include hydrogels incorporating homopolymers; copolymers (e.g., tetrapolymers of hydroxymethylmethacrylate, ethylene glycol, dimethylmethacrylate, and methacrylic acid), copolymers of trimethylene carbonate and polyglycolicacid, polyglactin 910, glyconate, poly-p-dioxanone, polyglycolic acid, polyglycolic acid felt, poly-4-hydroxybutyrate, a combination of poly(L-lactide) and poly(L-lactide-co-glycolide), glycol methacrylate, poly-DL-lactide, or Primacryl); composites of oxidized regenerated cellulose, polypropylene, and polydioxanone or a composite of polypropylene and poligelcaprone; etc. In some variations, the formulations do not include one or more of polyvinyl alcohol, hydroxypropyl methylcellulose, polyethylene glycol 400 castor oil emulsion, carboxymethylcellulose sodium, propylene glycol, hydroxypropyl guar, carboxymethylcelluose sodium, white petrolatum, mineral oil, dextran 70, glycerin, hypromellose, flaxseed oil, fish oils, omega 3 and omega 6 fatty acids, lutein, or primrose oil. In some variations, the formulations do not include one or more of the carriers described in U.S. Pat. No. 4,888,354 (incorporated by reference herein in its entirety), e.g., such as one or more of oleic acid, ethanol, isopropanol, glycerol monooleate, glycerol diooleate, methyl laurate, propylene glycol, propanol or dimethyl sulfoxide. In some variations, the formulations are substantially free of glycerol diooleate and isopropanol.

In particular embodiments, the gel-forming polymer may be, for example, a polysaccharide. In certain embodiments, the polysaccharide is gellan gum. Gellan gum refers to a heteropolysaccharide elaborated by the bacterium *Pseudomonas elodea*, though the name "gellan gum" is more commonly used in the field. Gellan gum, in particular the formulation GELRITE® is described in detail in U.S. Pat. No. 4,861,760 (hereby incorporated by reference in its entirety), in particular in its use in formulation of timolol. GELRITE®, a low acetyl clarified grade of gellan gum, is commercially available from Merck & Co (Rahway, N.J.) and gellan gum can be commercially obtained from, among others CPKelco (Atlanta, Ga.). The preparation of polysaccharides such as gellan gum is described in, for example, U.S. Pat. Nos. 4,326,053 and 4,326,052, which are hereby incorporated by reference in their entirety.

In certain embodiments, the gel-forming polymer is present at a concentration of from about 0.03% to about 2% (w/v). In some embodiments, the gel-forming polymer is present at a concentration from about 0.03% to about 1.75%; from about 0.03% to about 1.5%, from about 0.03% to about 1.25%, from about 0.03% to about 1%, from about 0.03% to about 0.9%, from about 0.03% to about 0.8%, from about 0.03% to about 0.7%, from about 0.03% to about 0.6%, from about 0.03% to about 0.5%, from about 0.05% to about 2%, from about 0.05% to about 1.75%; from about 0.05% to about 1.5%, from about 0.05% to about 1.25%, from about 0.05% to about 1%, from about 0.05% to about 0.9%, from about 0.05% to about 0.8%, from about 0.05% to about 0.7%, from about 0.05% to about 0.6%, from about 0.05% to about 0.5%, from about 0.1% to about 2%, from about 0.1% to about 1.75%; from about 0.1% to about 1.5%, from about 0.1% to about 1.25%, from about 0.1% to about 1%, from about 0.1% to about 0.9%, from about 0.1% to about 0.8%, from about 0.1% to about 0.7%, from about 0.1% to about 0.6%, from about 0.1% to about 0.5%, from about 0.2% to about 2%, from about 0.2% to about 1.75%; from about 0.2% to about 1.5%, from about 0.2% to about 1.25%, from about 0.2% to about 1%, from about 0.2% to about 0.9%, from about 0.2% to about 0.8%, from about 0.2% to about 0.7%, from about 0.2% to, about 0.6%, from about 0.2% to about 0.5%, or from about 0.5% to about 1.5%. In some embodiments, the concentration of gel-forming polymer is about 0.1%, about 0.2%, about 0.4%, about 0.6%, about 0.8%, about 1%.

In particular embodiments, the gel-forming polymer is gellan gum at a concentration of from about 0.05% to about 2% (w/v), from about 0.1% to about 2% (w/v), from about 0.1% to about 1% (w/v), from about 0.05% to about 1% (w/v) or from about 0.1% to about 0.6% (w/v). In some embodiments, the concentration of gellan gum is about 0.1%, about 0.2%, about 0.4%, about 0.6%, about 0.8%, about 1%.

In some embodiments of the ocular formulations, the formulation may include additional components such as one or more preservatives, one or more surfactants, or one or more pharmaceutical agents. In particular embodiments, the formulation may include additional components such as one or more preservatives, one or more surfactants, one or more tonicity agents, one or more buffering agents, one or more chelating agents, one or more viscosity-increasing agents, one or more salts, or one or more pharmaceutical agents. In certain of these embodiments, the formulation may include (in addition to a DRS polypeptide (or a pharmaceutically acceptable salt thereof) and carrier): one or more preservatives, one or more buffering agents (e.g., one, two, three, etc.), one or more chelating agents, and one or more salts. In some embodiments, the formulation may include (in addition to a DRS polypeptide (or a pharmaceutically acceptable salt thereof) and carrier): one or more preservatives, one or more tonicity agents, one or more buffering agents, one or more chelating agents, and one or more viscosity-increasing agents.

In some embodiments, the viscosity of the formulation is about the same as the viscosity of a saline solution containing the same concentration of a DRS polypeptide (or a pharmaceutically acceptable salt thereof). In some embodiments, the formulation is substantially free of gel-forming polymers. In certain embodiments, where the carrier is water, the formulation may additionally include one or more chelating agents (e.g., EDTA disodium (EDTA), one or more preservatives (e.g., benzalkonium chloride, benzethonium chloride, chlorhexidine, chlorobutanol, methylparaben, phenylethyl alcohol, propylparaben, thimerosal, phenylmercuric nitrate, phenylmercuric borate, phenylmercuric acetate, or combinations of two or more of the foregoing), salt (e.g., NaCl) and one or more buffering agents (e.g., one or more phosphate buffers (e.g., dibasic sodium phosphate, monobasic sodium phosphate, combinations thereof, etc.), citrate buffers, maleate buffers, borate buffers, and combination of two or more of the foregoing.).

In particular embodiments, the chelating agent is EDTA disodium, the preservative is benzalkonium chloride, the salt is NaCl, and the buffering agents are dibasic sodium phosphate and monobasic sodium phosphate. In certain of these embodiments, the formulation is substantially free of polymer. In some embodiments, the formulation is substantially free of substantially viscosity-increasing agent(s) (e.g., carboxymethylcellulose, polyanionic polymers, etc.). In some embodiments, the viscosity of the formulation is about the same as the viscosity of a saline solution containing the same concentration of a DRS polypeptide (or a pharmaceutically acceptable salt thereof). In some of these embodiments, the concentration of a DRS polypeptide (or a pharmaceutically acceptable salt thereof) if from about 0.02% to about 3%, from about 0.02% to about 2%, from about 0.02% to about 1% (w/v). In certain embodiments, the concentration of a DRS polypeptide (or a pharmaceutically acceptable salt thereof), is about 0.01%, about 0.02%, about 0.03%, about 0.05%, about 0.07%, about 0.1%, about 0.3%, about 0.4%, about 0.5%, about 0.6%, about 0.8% or about 1% (w/v).

In certain embodiments, where the carrier includes water, a viscosity-increasing agent may also be included in the formulation. The skilled artisan will be familiar with viscosity-increasing agents that are suitable (e.g., water-soluble cellulose derivatives (e.g., hypromellose (also known as HPMC, hydroxypropylmethyl cellulose, and hydroxypropylcellulose), hydroxyethylcellulose, carboxmethylcellulose), polyvinyl alcohol, polyvinyl pyrrolidone, chondroitin sulfate, hyaluronic acid, and soluble starches. It is intended that when viscosity-increasing agents are used, they are not included in high enough concentrations such that the formulation would form a gel prior to or after administration (e.g., wherein the concentration of the viscosity-increasing agent is not sufficient to induce gel formation).

While exact concentrations of viscosity-increasing agents will depend upon the selection and concentration of other components in the formulation as well as the particular viscosity-increasing agent(s) selected, in general, viscosity-increasing agents may be present in a concentration such that the viscosity of the resulting solution is less than about 1000 centipoise. In certain embodiments, the viscosity of the formulation is less than about 900, less than about 800, less than about 700, less than about 600, less than about 500, less than about 400, less than about 300, less than about 200, less than about 150, less than about 100, less than about 50 centipoise. In some embodiments, the viscosity of the formulation is about 200, about 150, about 100, about 50 centipoise. In particular embodiments, the viscosity is less than about 200 centipoise. In others, less than about 120 centipoise or less than about 100 centipoise. In some embodiments, the viscosity is about 100 centipoise. In others about 50 centipoise. In still other embodiments the viscosity is about 200 centipoise. Methods for measuring viscosity are well known to the skilled artisan. For example, as described in United States Pharmacopoeia 29 (Chapter 911) Viscosity, page 2785 (which is herein incorporated by reference in its entirety). As is well known to the skilled artisan, formulations commonly considered "gels" will have viscosity significantly greater than 1000 centipoise, for example, greater than about 2000 centipoise, greater than about 5000 centipoise.

In some embodiments, including (but not limited to) where the use of salts is contraindicated as described above, the ocular formulation may further include one or more tonicity agents. As used herein, the term "tonicity agent" and its cognates refers to agents that adjust the tonicity of the formulation, but are not salts (e.g., not NaCl), which, as will be appreciated by the skill artisan in view of the teaching provided herein, are contraindicated for some formulations due to the presence of certain of the gel-forming polymers or viscosity-increasing agents. These agents may be used to prepare formulations that are isotonic or near isotonic (e.g., somewhat hyper- or hypo-isotonic; e.g., within about ±20%, about ±15%, about ±10%, about ±5% of being isotonic). Tonicity agent(s) may also be used in formulations where the use of salts is not contraindicated.

Tonicity agents that may be used to adjust the tonicity of formulation the formulations described herein and are known to the skilled artisan and can be selected based on the teaching provided herein. For example, tonicity agents include polyols (e.g., sugar alcohols (e.g., mannitol, etc.), trihydroxy alcohols (e.g., glycerin, etc.), propylene glycol or polyethylene glycol, etc.), or combinations of two or more polyols. Likewise, the concentration of the tonicity agent(s) will depend upon the identity and concentrations of the other components in the formulation and can be readily determined by the skilled artisan in view of the teaching provided herein.

In certain embodiments, the tonicity agent is glycerin or mannitol. In some embodiments, the tonicity agent is glycerin. In other embodiments it is, mannitol. In still others a combination of mannitol and glycerin may be used. Exemplary concentrations of tonicity agents include, for example from about 0.001 to about 3%. In some embodiments, the concentration of the tonicity agent (e.g., mannitol or glycerin) is, for example, about 0.001% to about 2.7%, about 0.001% to about 2.5%, about 0.001% to about 2%, about 0.001% to about 1.5%, about 0.001% to about 1%, about 0.01% to about 3%, about 0.01% to about 2.7%, about 0.01% to about 2.5%, about 0.01% to about 2%, about 0.01% to about 1.5%, about 0.01% to about 1%, about 0.1% to about 3%, about 0.1% to about 2.7%, about 0.1% to about 2.5%, about 0.1% to about 2%, about 0.1% to about 1.5%, about 0.1% to about 1%, about 0.01% about 1% to about 3%; about 1% to about 2.5%; about 1% to about 2%; about 1% to about 1.8%; about 1% to about 1.5%; or about 0.001%, about 0.01%, about 0.05%, about 0.08%, about 0.1%, about 0.2%, about 0.5%, about 0.8%, about 1%, about 1.5%, about 1.8%, about 2%, about 2.2%, about 2.5%, about 2.8%, or about 3% (w/v). In certain embodiments, the tonicity agent is mannitol. In some of these embodiments, the carrier includes a gel-forming agent (e.g., gellan gum).

In some embodiments, the tonicity agent is mannitol. In certain of these embodiments, the carrier includes a viscosity-increasing agent (e.g., water soluble cellulose derivatives (e.g., hypromellose), polyvinyl alcohol, polyvinyl pyrrolidone, chondroitin sulfate, hyaluronic acid, or soluble starches).

In some embodiments, the ocular formulation may additionally include a preservative (e.g., benzalkonium chloride, benzethonium chloride, chlorhexidine, chlorobutanol, methylparaben, Phenylethyl alcohol, propylparaben, thimerosal, phenylmercuric nitrate, phenylmercuric borate, or phenylmercuric acetate, peroxides), or a combination of two or more of the foregoing preservatives. In certain embodiments, the preservative is benzalkonium chloride.

As will be appreciated by the skilled artisan, preservatives may be present in concentrations of from about 0.001% to about 0.7% (w/v). In particular embodiments, the preservative(s) may be present in a concentration of from about 0.001% to about 0.5% (w/v); from about 0.001% to about 0.05% (w/v), from about 0.001% to about 0.02% (w/v), from about 0.001% to about 0.015% (w/v), from about 0.001% to about 0.005% (w/v), from about 0.01% to about 0.02%, from about 0.002% to about 0.01%, from about 0.015% to about 0.05%, less than about <0.5%, from about 0.005% to about 0.01%, from about 0.001% to about 0.15%, from about 0.002% to about 0.004%, from about 0.001% to about 0.002%. In some embodiments the concentration of the preservative may be, for example, about 0.001%, about 0.005%, about 0.01%, about 0.02%, about 0.03%, about 0.05%, about 0.1%, about 0.2%, about 0.5%, or about 0.7% (w/v). Typical concentrations (w/v) for various commonly used preservatives are listed in Table C below.

TABLE C

| Preservative | Approximate Concentration Range (w/v) |
|---|---|
| Benzalkonium chloride | 0.01-0.02% |
| Benzethonium chloride | 0.01-0.02% |
| Chlorhexidine | 0.002-0.01% |
| Chlorobutanol | <0.5% |
| Methylparaben | 0.015-0.05% |
| Phenylethyl alcohol | <0.5% |
| Propylparaben | 0.005-0.01% |
| Thimerosal | 0.001-0.15% |
| Phenylmercuric nitrate | 0.002-0.004% |
| Phenylmercuric borate | 0.002-0.004 |
| Phenylmercuric acetate | 0.001-0.002 |

In certain embodiments, the formulation may additionally include a surfactant, or combinations of two or more surfactants. In particular embodiments, the formulation is substantially free of surfactant. As used herein, the term "substantially free" is intended to refer to levels of a particular component that are undetectable using routine detection methods and protocols known to the skilled artisan. For example, HPLC (including chiral HPLC, chiral HPLC/MS, LC/MS/MS etc.), thin layer chromatography, mass spectrometry, polarimetry measurements, Gas-chromatography-mass spectrometry, or others.

In particular embodiments, the ocular formulation may further include a chelating agent (e.g., EDTA disodium (EDTA) (e.g., EDTA disodium (dihydrate), etc.) citrates, etc.). In some embodiments, a combination of chelating agents may be present. As will be appreciated by those of skill in the field, chelating agents can be used to hinder degradation of the formulation components and thereby increase the shelf life of ocular formulations. As will be appreciated by the skilled artisan, use of EDTA in combination with gellan gum formulation may be contraindicated as the EDTA can cause gel formation prior to administration of the gellan gum formulation.

Typical concentrations for chelating agents are from about 0.005% to 0.1% (w/v). For example, from about 0.005% to about 0.09%, from about 0.005% to about 0.08%, from about 0.005% to about 07%, from about 0.005%, to about 0.06%, from about 0.005% to about 0.05%, from about 0.005 to about 0.04%, from about 0.005% to about 0.03%, from about 0.01% to about 0.1%, from about 0.01% to about 0.09%, from about 0.01% to about 0.08%, from about 0.01% to about 0.07%, from about 0.01% to about 0.06%, from about 0.01% to about 0.05%, from about 0.01% to about 0.04%, etc. In certain embodiments, the concentration of chelating agent(s) is about 0.005%, about 0.01%, about 0.02%, about 0.03%, about 0.05%, about 0.06%, about 0.07%, about 0.08%, about 0.09%, or about 0.1%.

In particular embodiments, the chelating agent is EDTA disodium. In certain embodiments, the chelating agent is EDTA disodium (dihydrate). In some of these embodiments, the EDTA disodium dihydrate is present at a concentration of about 0.01% (w/v).

In some embodiments, the ocular formulation may additionally include one or more buffering agents (e.g., phosphate buffer(s) (e.g., sodium phosphate buffers (e.g., dibasic sodium phosphate, monobasic sodium phosphate, etc.), citrate buffers, maleate buffers, borate buffers, etc.). As will be appreciated by the skilled artisan, the one or more buffering agent(s) should be selected in combination with the other components of a given formulation to achieve a pH suitable for use (e.g., pH of about 4.5 to about 8).

In certain embodiments, the buffering agent is a phosphate buffer or combination of two or more phosphate buffers. In certain embodiments, the buffering agents are dibasic sodium phosphate and monobasic sodium phosphate.

Typical concentrations for buffering agent(s) for example, phosphate buffering agent(s) may be from about 0.005 molar to 0.1 molar. In some embodiments, the buffering agent(s) may be at a concentration of about 0.01 to about 0.1, from about 0.01 to about 0.08, from about 0.01 to about 0.05, from about 0.01 to about 0.04, from about 0.02 to about 0.1, from about 0.02 to about 0.08, from about 0.02 to about 0.06, from about 0.02 to about 0.05, from about 0.02 to about 0.04 molar, etc. In particular embodiments, there are two buffering agents. Exemplary buffering agents include a combination of dibasic sodium phosphate (e.g., dibasic sodium phosphate.7H$_2$O) and monobasic sodium phosphate (e.g., monobasic sodium phosphate anhydrous). In some embodiments, the concentration of the buffering agent(s) is about 0.005 molar, about 0.01 molar, about 0.02 molar, about 0.03 molar, about 0.04 molar, about 0.05 molar, about 0.06 molar, about 0.07 molar, or about 0.1 molar.

An additional aspect of the invention includes use of the formulations as described herein in the manufacture of a medicament. Particularly, the manufacture of a medicament for use in the treatment and/or prevention of conditions as described herein. Further, the formulations, variously described herein, are also intended for use in the manufacture of a medicament for use in treatment and/or prevention of the conditions and, in accordance with the methods, described herein, unless otherwise noted.

Methods of formulation are well known in the art and are disclosed, for example, in Remington: The Science and Practice of Pharmacy, Mack Publishing Company, Easton, Pa., 19th Edition (1995). The compositions and agents provided herein may be administered according to the methods of the present invention in any therapeutically effective dosing regime. The dosage amount and frequency are selected to create an effective level of the agent without harmful effects. The effective amount of a compound of the present invention will depend on the route of administration, the type of warm-blooded animal being treated, and the physical characteristics of the specific warm-blooded animal under consideration. These factors and their relationship to determining this amount are well known to skilled practitioners in the medical arts. This amount and the method of administration can be tailored to achieve optimal efficacy but will depend on such factors as weight, diet, concurrent medication and other factors which those skilled in the medical arts will recognize.

In certain embodiments, the pharmaceutical compositions may be delivered by intranasal sprays, inhalation, and/or other aerosol delivery vehicles. Methods for delivering genes, polynucleotides, and peptide compositions directly to the lungs via nasal aerosol sprays have been described e.g., in U.S. Pat. No. 5,756,353 and U.S. Pat. No. 5,804,212 (each specifically incorporated herein by reference in its entirety). Likewise, the delivery of drugs using intranasal microparticle resins (Takenaga et al., 1998) and lysophosphatidyl-glycerol compounds (U.S. Pat. No. 5,725,871, specifically incorporated herein by reference in its entirety) are also well-known in the pharmaceutical arts. Likewise, transmucosal drug delivery in the form of a polytetrafluoroetheylene support matrix is described in U.S. Pat. No. 5,780,045 (specifically incorporated herein by reference in its entirety).

In certain embodiments, the delivery may occur by use of liposomes, nanocapsules, microparticles, microspheres, lipid particles, vesicles, and the like, for the introduction of the compositions of the present invention into suitable host cells. In particular, the compositions of the present invention may be formulated for delivery either encapsulated in a lipid particle, a liposome, a vesicle, a nanosphere, a nanoparticle or the like. The formulation and use of such delivery vehicles can be carried out using known and conventional techniques.

In certain embodiments, the agents provided herein may be attached to a pharmaceutically acceptable solid substrate, including biocompatible and biodegradable substrates such as polymers and matrices. Examples of such solid substrates include, without limitation, polyesters, hydrogels (for example, poly(2-hydroxyethyl-methacrylate), or poly(vinyl-alcohol)), polylactides (U.S. Pat. No. 3,773,919), copolymers of L-glutamic acid and γ-ethyl-L-glutamate, non-degradable ethylene-vinyl acetate, degradable lactic acid-glycolic acid copolymers such as poly(lactic-co-glycolic acid) (PLGA) and the LUPRON DEPOT™ (injectable microspheres composed of lactic acid-glycolic acid copolymer and leuprolide acetate), poly-D-(–)-3-hydroxybutyric acid, collagen, metal, hydroxyapatite, bioglass, aluminate, bioceramic materials, and purified proteins.

In one particular embodiment, the solid substrate comprises Atrigel™ (QLT, Inc., Vancouver, B.C.). The Atrigel® drug delivery system consists of biodegradable polymers dissolved in biocompatible carriers. Pharmaceuticals may be blended into this liquid delivery system at the time of manufacturing or, depending upon the product, may be added later by the physician at the time of use. When the liquid product is injected into the subcutaneous space through a small gauge needle or placed into accessible tissue sites through a cannula, water in the tissue fluids causes the polymer to precipitate and trap the drug in a solid implant. The drug encapsulated within the implant is then released in a controlled manner as the polymer matrix biodegrades with time.

In particular embodiments, the amount of a DRS-Fc conjugate composition the agent administered will generally range from a dosage of from about 0.1 to about 100 mg/kg/day, and typically from about 0.1 to 10 mg/kg where administered orally or intravenously. In particular embodiments, a dosage is 5 mg/kg or 7.5 mg/kg. For humans, the daily dosage used may range from, about 0.1 mg/kg to 0.5 mg/kg, about 1 mg/kg to 5 mg/kg, about 5 mg/kg to 10 mg/kg, about 10 mg/kg to 20 mg/kg, about 20 mg/kg to 30 mg/kg, about 30 mg/kg to 50 mg/kg, and about 50 mg/kg to 100 mg/kg/24 hours.

In certain embodiments, a composition or agent is administered in a single dosage of 0.1 to 10 mg/kg or 0.5 to 5 mg/kg. In other embodiments, a composition or agent is administered in a dosage of 0.1 to 50 mg/kg/day, 0.5 to 20 mg/kg/day, or 5 to 20 mg/kg/day.

In various embodiments, the dosage is about 50-2500 mg per day, 100-2500 mg/day, 300-1800 mg/day, or 500-1800 mg/day. In one embodiment, the dosage is between about 100 to 600 mg/day. In another embodiment, the dosage is between about 300 and 1200 mg/day. In particular embodiments, the composition or agent is administered at a dosage of 100 mg/day, 240 mg/day 300 mg/day, 600 mg/day, 1000 mg/day, 1200 mg/day, or 1800 mg/day, in one or more doses per day (i.e., where the combined doses achieve the desired daily dosage). In related embodiments, a dosage is 100 mg bid, 150 mg bid, 240 mg bid, 300 mg bid, 500 mg bid, or 600 mg bid. In various embodiments, the composition or agent is administered in single or repeat dosing. The initial dosage and subsequent dosages may be the same or different.

In some embodiments, total daily dose may be about 0.001 mg, about 0.005 mg, about 0.01 mg, about 0.05 mg, about 0.1 mg, 0.5 mg, 1 mg, about 2 mg, about 3 mg, about 4 mg, about 5 mg, about 6 mg, about 7 mg, about 8 mg, about 9 mg, about 10 mg, about 20 mg, about 30 mg, about 40 mg, about 50 mg, about 60 mg, about 70 mg, about 80 mg, about 90 mg or about 100 mg/24 hours. For repeated administrations over several days or longer, depending on the condition, the treatment is sustained until a desired suppression of disease symptoms occurs. The progress of these and other therapies (e.g., ex vivo therapies) can be readily monitored by conventional methods and assays and based on criteria known to the physician or other persons of skill in the art.

It will be further appreciated that for sustained delivery devices and compositions the total dose of DRS contained in such delivery system will be correspondingly larger depending upon the release profile of the sustained release system. Thus, a sustained release composition or device that is intended to deliver DRS polypeptide over a period of 5 days will typically comprise at least about 5 to 10 times the daily dose of DRS polypeptide; a sustained release composition or device that is intended to deliver a DRS peptide over a period of 365 days will typically comprise at least about 400 to 800 times the daily dose of the DRS polypeptide (depending upon the stability and bioavailability of the DRS polypeptide when administered using the sustained release system).

In certain embodiments, a composition or agent is administered orally or intravenously, e.g., by infusion over a period of time of about, e.g., 10 minutes to 90 minutes. In other related embodiments, a composition or agent is administered by continuous infusion, e.g., at a dosage of between about 0.1 to about 10 mg/kg/hr over a time period. While the time period can vary, in certain embodiments the time period may be between about 10 minutes to about 24 hours or between about 10 minutes to about three days.

In particular embodiments, an effective amount or therapeutically effective amount is an amount sufficient to achieve a total concentration of the composition or agent in the blood plasma of a subject with a $C_{max}$ of between about 0.1 µg/ml and about 20 µg/ml or between about 0.3 µg/ml and about 20 Kg/ml. In certain embodiments, an oral dosage is an amount sufficient to achieve a blood plasma concentration ($C_{max}$) of between about 0.1 µg/ml to about 5 µg/ml or between about 0.3 µg/ml to about 3 µg/ml. In certain embodiments, an intravenous dosage is an amount sufficient to achieve a blood plasma concentration ($C_{max}$) of between about 1 µg/ml to about 10 µg/ml or between about 2 µg/ml and about 6 µg/ml. In a related embodiment, the total concentration of an agent in the blood plasma of the subject has a mean trough concentration of less than about 20 µg/ml and/or a steady state concentration of less than about 20 µg/ml. In a further embodiment, the total concentration of an agent in the blood plasma of the subject has a mean trough concentration of less than about 10 µg/ml and/or a steady state concentration of less than about 10 µg/ml.

In yet another embodiment, the total concentration of an agent in the blood plasma of the subject has a mean trough concentration of between about 1 ng/ml and about 10 µg/ml and/or a steady state concentration of between about 1 µg/ml and about 10 µg/ml. In one embodiment, the total concentration of an agent in the blood plasma of the subject has a mean trough concentration of between about 0.3 µg/ml and about 3 µg/ml and/or a steady state concentration of between about 0.3 µg/ml and about 3 µg/ml.

In particular embodiments, a composition or agent is administered in an amount sufficient to achieve in the mammal a blood plasma concentration having a mean trough concentration of between about 1 ng/ml and about 10 µg/ml and/or a steady state concentration of between about 1 ng/ml and about 10 µg/ml. In related embodiments, the total concentration of the agent in the blood plasma of the mammal has a mean trough concentration of between about 0.3 µg/ml and about 3 µg/ml and/or a steady state concentration of between about 0.3 µg/ml and about 3 µg/ml.

In particular embodiments of the present invention, the effective amount of a composition or agent, or the blood plasma concentration of composition or agent is achieved or maintained, e.g., for at least 15 minutes, at least 30 minutes, at least 45 minutes, at least 60 minutes, at least 90 minutes, at least 2 hours, at least 3 hours, at least 4 hours, at least 8 hours, at least 12 hours, at least 24 hours, at least 48 hours, at least 3 days, at least 4 days, at least 5 days, at least 6 days, at least one week, at least 2 weeks, at least one month, at least 2 months, at least 4 months, at least 6 months, at least one year, at least 2 years, or greater than 2 years.

In certain DRS polypeptide-based embodiments, the amount of polypeptide administered will typically be in the range of about 0.1 µg/kg to about 0.1 mg/kg to about 50 mg/kg of patient body weight. Depending on the type and severity of the disease, about 0.1 µg/kg to about 0.1 mg/kg to about 50 mg/kg body weight (e.g., about 0.1-15 mg/kg/ dose) of polypeptide can be an initial candidate dosage for administration to the patient, whether, for example, by one or more separate administrations, or by continuous infusion. For example, a dosing regimen may comprise administering an initial loading dose of about 4 mg/kg, followed by a weekly maintenance dose of about 2 mg/kg of the polypeptide, or about half of the loading dose. However, other dosage regimens may be useful. A typical daily dosage might range from about 0.1 µg/kg to about 1 µg/kg to 100 mg/kg or more, depending on the factors mentioned above. For repeated administrations over several days or longer, depending on the condition, the treatment is sustained until a desired suppression of disease symptoms occurs.

In particular embodiments, the effective dosage achieves the blood plasma levels or mean trough concentration of a composition or agent described herein. These may be readily determined using routine procedures.

Embodiments of the present invention, in other aspects, provide kits comprising one or more containers filled with one or more of the polypeptides, polynucleotides, antibodies, multiunit complexes, compositions thereof, etc., of the invention, as described herein. The kits can include written instructions on how to use such compositions (e.g., to modulate cellular signaling, angiogenesis, cancer, inflammatory conditions, diagnosis etc.).

The kits herein may also include a one or more additional therapeutic agents or other components suitable or desired for the indication being treated, or for the desired diagnostic application. An additional therapeutic agent may be contained in a second container, if desired. Examples of additional therapeutic agents include, but are not limited to, anti-neoplastic agents, anti-inflammatory agents, antibacterial agents, antiviral agents, angiogenic agents, etc.

The kits herein can also include one or more syringes or other components necessary or desired to facilitate an intended mode of delivery (e.g., stents, implantable depots, etc.).

Certain embodiments of the present invention now will be illustrated by the following Examples. The present invention may, however, be embodied in many different forms and should not be construed as limited to the embodiments set forth herein; rather, these embodiments are provided so that this disclosure will be thorough and complete, and will fully convey the scope of the invention to those skilled in the art.

EXAMPLES

Example 1

Production of DRS Polypeptides

Codon Optimization and Gene Synthesis:

An *E. coli* codon optimized nucleic acid sequence encoding the DRS polypeptide AspRS1$^{N1}$(C76S) (comprising amino acids 1-154, and a cysteine→serine mutation at position 76) was designed for optimal *E. coli* expression using the algorithm developed by DNA2.0 (Menlo Park, Calif.). The gene was synthesized with a C-terminal V5His tag and subcloned into pJExpress411 vector where the T7 promoter was used to drive the transcription and the kanamycin resistance was used for antibiotic selection.

The codon-optimized DNA sequence is as follows:

(SEQ ID NO: 28)
```
ATGCCGAGCGCGAGCGCCAGCCGTAAGAGCCAGGAAAAACCACGTGAGATTATGGATGCCG
CAGAGGACTATGCGAAAGAACGTTACGGTATTTCCAGCATGATCCAATCTCAGGAGAAACC
GGACCGCGTTCTGGTTCGTGTTCGCGATCTGACCATTCAGAAGGCGGACGAGGTGGTTTGGG
TGCGTGCGCGCGTGCACACCAGCCGTGCAAAAGGCAAACAGAGCTTTCTGGTCCTGCGTCAG
CAGCAATTCAACGTCCAGGCGCTGGTGGCAGTGGGTGACCACGCCAGCAAACAAATGGTGA
AGTTCGCTGCTAACATCAATAAAGAATCCATTGTTGATGTTGAAGGCGTCGTTCGCAAGGTC
AATCAAAAGATCGGCTCGTGTACGCAACAAGATGTCGAGCTGCATGTGCAGAAGATTTACG
TCATCAGCCTGGCGGAGCCGCGTTTGCCGCTGGGTAAGCCGATCCCTAACCCGCTGTTGGGT
CTGGACAGCACGCATCACCATCACCACCACTAA
```

The corresponding translated protein sequence is:

(SEQ ID NO: 29)
```
MPSASASRKSQEKPREIMDAAEDYAKERYGISSMIQSQEKPDRVLVRVRDLTIQKADEVV
WVRARVHTSRAKGKQSFLVLRQQQFNVQALVAVGDHASKQMVKFAANINKESIVDVEGVV
RKVNQKIGSCTQQDVELHVQKIYVISLAEPRLPLGKPIPNPLLGLDSTHHHHHH
```

As a control, the non-mutated AspRS1$^{N1}$ protein was also prepared, using wild type (human codon usage), and cloned into the identical expression cassette. The nucleic acid sequence of the native AspRS1$^{N1}$ is as follows:

(SEQ ID NO: 30)
```
ATGCCCAGCGCCAGCGCCAGCCGCAAGAGTCAGGAGAAGCCGCGGGAGATCATGGACGCG
GCGGAAGATTATGCTAAAGAGAGATATGGAATATCTTCAATGATACAATCACAAGAAAAAC
CAGATCGAGTTTTGGTTCGGGTTAGAGACTTGACAATACAAAAAGCTGATGAAGTTGTTTGG
GTACGTGCAAGAGTTCATACAAGCAGAGCTAAAGGGAAACAGTGCTTCTTAGTCCTACGTCA
GCAGCAGTTTAATGTCCAGGCTCTTGTGGCGGTGGGAGACCATGCAAGCAAGCAGATGGTT
AAATTTGCTGCCAACATCAACAAAGAGAGCATTGTGGATGTAGAAGGTGTTGTGAGAAAAG
TGAATCAGAAAATTGGAAGCTGTACACAGCAAGACGTTGAGTTACATGTTCAGAAGATTTAT
GTGATCAGTTTGGCTGAACCCCGTCTGCCCCTGGGTAAGCCTATCCCTAACCCTCTCCTCGGT
CTCGATTCTACGCACCACCACCACCACCACTGA
```

The encoding protein, containing the identical C-terminal tag, but the wild type Cys76 is shown below:

(SEQ ID NO: 31)
```
MPSASASRKSQEKPREIMDAAEDYAKERYGISSMIQSQEKPDRVLVRVRDLTIQKADEVV
WVRARVHTSRAKGKQCFLVLRQQQFNVQALVAVGDHASKQMVKFAANINKESIVDVEGVV
RKVNQKIGSCTQQDVELHVQKIYVISLAEPRLPLGKPIPNPLLGLDSTHHHHHH
```

Expression Strains:

BL21-CodonPlus (DE3)-RIPL competent cells (Agilent cat. no. 230280) were transformed with the non-mutated AspRS1$^{N1}$ expression construct. BL21(DE3) competent cells (Novagen, cat. no. 69450) were transformed with the AspRS1$^{N1}$(C76S) expression construct. Briefly, the plasmid (1 µL) was added into 50 µL of the competent cells. The reaction was mixed and incubated on ice for 30 minutes. The reaction was heat-shocked for at 42° C. for 30 sec followed by a cold-shock on ice for 2 minutes. Then the SOC medium (500 µL) was added and the tube was incubated at 37° C., 250 rpm for 1 hour. Finally, an aliquot of the culture (50 µL) was spread on the Kanamycin plate (Teknova 59641) and incubated at 37° C. overnight. Single colony was picked and used for expression scale-up.

Fed-Batch Fermentation Production of Proteins:

M9YE medium was prepared by mixing 200 mL sterile M9 minimal salt 5× (BD248510), 778 mL30 g/L yeast extract in sterile purified water (BD212750), 20 mL sterilized 20% glucose (Sigma G7021) and 2 mL sterile 1.0 M MgSO$_4$ (Sigma M7506). The feeding solution contains 5% yeast extract, 50% glucose, trace elements and 2 g/L magnesium sulfate. Kanamycin sulfate (Invitrogen 15160) was added to a final concentration of 100 µg/mL in both M9YE and feeding solution.

A 4 L fermentor (Sartorius Biostat B plus) with MFCS/DA software was used for the fed-batch fermentation of both proteins. The agitation was set at 1000 rpm. The pH value was controlled at 7.0 automatically by the addition of 30% ammonium hydroxide (Sigma 221228) and 30% phosphoric acid (Sigma P5811). The air was provided at a flow rate of 4 L/min with an oil-free diaphragm air compressor (Cole-Parmer). The air was passed through a 0.2 µm Midisart 2000 filter (Sartorius 17805). The pure oxygen (West Air) was supplied automatically to control the dissolved oxygen level at 70%. The temperature was controlled at 30° C. with a Neslab RTE7 circulator (Thermo Scientific). The foaming was controlled by addition of the antifoam 204 (Sigma A8311). The initial volume of M9YE medium in the fermentor was 3 L. The fermentor was inoculated with 150 mL of the seed culture grown overnight at 30° C. and 250 rpm. When the glucose was depleted in the vessel, the concentrated feeding solution was introduced into the vessel by a peristaltic pump set at 0.9 ml/min. When the optical density of the cells at 600 nm reached about 30, the culture was induced with 0.5 mM IPTG (Fisher Scientific BP1755). The culture was run overnight (about 18-hour fed-batch phase) and harvested by centrifugation at 6,000 g for 1 hour. The cell pellet was stored at −20° C. until purification. The expression of each protein was confirmed by SDS-PAGE analysis (data not shown).

Purification of Proteins:

Frozen cell pellets from each production run were resuspended in 4 volumes (i.e., 4 mL/g cell pellet) of Lysis Buffer (50 mM Tris, 300 mM NaCl, 25 mM Imidazole, 14 mM β-ME, pH 8.0). Complete EDTA-FREE protease inhibitor cocktail tablets (Roche Cat. #05 056 489 001) were added to the suspension at a ratio of 1 tablet/50 mL. The suspension was passed through a microfluidizer (Microfluidics) twice at 14,000 psi with cooling by ice. The lysate was centrifuged at 35,000×g for 45 min at 4° C. The supernatant was filtered through 0.45+0.22 µm Sartobran capsule filters (Sartorius).

The clarified lysate was bound to the Ni-NTA resin (Qiagen), pre-equilibrated with Ni-NTA Binding Buffer (50 mM Tris, 300 mM NaCl, 25 mM Imidazole, pH 8.0). The column was washed with 300 column volumes of Ni-NTA Binding Buffer+0.1% Triton X-114 followed by 33 column volumes of the Ni-NTA Binding Buffer. The bound protein, D1-C76S, was eluted with 5 column volumes of Ni-NTA Elution Buffer (50 mM Tris, 300 mM NaCl, 300 mM Imidazole, pH 8.0).

The purified proteins were dialyzed into a buffer containing 20 mM sodium phosphate, 200 mM Arginine, at pH 7.3. The dialyzed protein was passed through a Q membrane filter (Sartobind-Q from Sartorius or Mustang-Q from Pall) or a Q-Sepharose column (GE Healthcare) for further endotoxin removal, and then filtered through a 0.22 µm sterile filter.

Comparison of Production Yield, Purity and Endotoxin Content of AspRS1$^{N1}$ (C76S) with AspRS1$^{N1}$.

A direct comparison of the yields of soluble proteins from the AspRS1$^{N1}$ (C76S) and non-mutated AspRS1$^{N1}$ constructs, over several independent production runs, (Table E1) reveals that the AspRS1$^{N1}$ (C76S) variant has a consistently higher yield compared to the non-mutated parent protein. Table E1 lists the average purification yield of AspRS1$^{N1}$(C76S) and non-mutated AspRS1$^{N1}$.

TABLE E1

Production yields for different AspRS1$^{N1}$ variants

| DRS polypeptide form | Purified protein yield (mg/g cell pellet) |
|---|---|
| AspRS1$^{N1}$ (C76S) | 1.72 ± 0.25 (n = 8) |
| AspRS1$^{N1}$ | 1.38 ± 0.57 (n = 7) |

An analysis of representative proteins by SDS-gel is shown in FIG. 1. The gel demonstrates that the purified AspRS1$^{N1}$ (C76S) has less low molecular weight impurities, and contains less disulfide cross-linked dimer species, compared to comparable batches of AspRS1$^{N1}$ prepared under identical conditions.

Moreover an analysis of the proteins endotoxin content reveals that the AspRS1$^{N1}$(C76S) proteins exhibited a significantly reduced endotoxin content compared to the non-mutated AspRS1$^{N1}$ (Table E2).

TABLE E2

Endotoxin Content

| DRS polypeptide form | Average Endotoxin level in purified protein (EU/mg) |
|---|---|
| AspRS1$^{N1}$ (C76S) | 7.3 (n = 8) |
| AspRS1$^{N1}$ | 43.5 (n = 7) |

Accordingly it is concluded that the DRS polypeptides comprising a reduced a cysteine content, specifically AspRS1$^{N1}$ (C76S) exhibits improved manufacturability, improved production yields and significantly less endotoxin contamination compared to the corresponding non mutated protein.

Example 2

Production of DRS Polypeptides in Mammalian Cells

As an alternative production system, exemplary DRS polypeptides were prepared using a mammalian expression system. This approach has the potential advantage of eliminating any potential contamination of the DRS polypeptides with *E. coli* derived endotoxins.

Cloning:

The AspRS1$^{N1}$ fragment (amino acid 1-154 of human cytoplasmic Aspartyl-tRNA synthetase) was amplified by polymerase chain reaction (PCR) using the following primer pairs synthesized at Integrated DNA Technologies to create either cytoplasmic, or secreted versions of the AspRS1$^{N1}$.

```
Primer Pair 1
                                                          (SEQ ID NO: 140)
AGTCTTGCACTTGTCACGAATTCGATGCCCAGCGCCAGCGCCAGC (SEQ ID NO: 141)
CGGTGGGCATGTGTGAGTTTTGTCTCACTTGTCGTCATCGTCTTTGTAGTCCGTAGAATCGAGACCGAG

GAGAGG

Primer Pair 2
                                                          (SEQ ID NO: 142)
GATCACCGGCGAAGGAGGGCCACCATGCCCAGCGCCAGCGCCAGC (SEQ ID NO: 143)
CGGTGGGCATGTGTGAGTTTTGTCTCACTTGTCGTCATCGTCTTTGTAGTCCGTAGAATCGAGACCGAG

GAGAGG
```

The primers were mixed with the template (AspRS1$^{N1}$ nucleic acid fragment in the pET28 vector) (see above), Accuprime pfx supermix (Invitrogen cat. no. 12344-040) and denatured for 5 minutes at 95° C. The amplification was done in the Eppendorf thermal cycler for 35 cycles of 95° C. for 30 seconds, 52° C. for 30 seconds and 68° C. for 40 seconds. The amplified fragments were purified with QIAquick PCR Purification Kit (Qiagen cat. no. 28104). The fragment size, quantity and purity were confirmed on the 1% agarose gel in the TAE buffer (Invitrogen cat. no. 15558). The fragment was inserted into the pFUSE-hIgG1-Fc2 (Invivogen cat. no. pfuse-hg1fc2) by mutagenesis using the QuikChange Lightning Site-Directed Mutagenesis Kit (Agilent, cat. no. 210518). Eighteen thermal cycles were performed at 95° C. for 30 seconds, 52° C. for 30 seconds and 68° C. for 4 minutes. After mutagenesis, the sample was treated with Dpn I enzyme at 37° C. and transformed into XL10 gold competent cells. The heat shock was done at 42° C. for 30 seconds followed by 2 minutes on ice. The XL10 gold transformants were resuspended in SOC medium and incubated at 37° C. for 1 hour and then were spread onto zeocin agar and incubated at 37° C. overnight. Multiple colonies were grown in terrific broth overnight at 37° C. and the plasmids were purified with QIAprep Spin Miniprep Kit (Qiagen cat. no. 27106). The plasmids were sequenced to confirm the DNA identity. The correct clones were transformed into NovaBlue competent cells (Novagen cat. no. 70181) and grown in 250 ml M9YE medium at 37° C. overnight. The maxiprep was performed using the HiSpeed Plasmid Maxi Kit (Qiagen cat. no. 12663). The concentration and purity were determined by measuring A260, A280 and A230. The purified plasmids were stored at −20° C. before transfection.

The secretory AspRS1$^{N1}$ sequence is as follows:

```
                                                          (SEQ ID NO: 32)
ATGTACAGGATGCAACTCCTGTCTTGCATTGCACTAAGTCTTGCACTTGTCACGAATTCGATGCCCAGC

GCCAGCGCCAGCCGCAAGAGTCAGGAGAAGCCGCGGGAGATCATGGACGCGGCGGAAGATTATGCTA

AAGAGAGATATGGAATATCTTCAATGATACAATCACAAGAAAAACCAGATCGAGTTTTGGTTCGGGTT

AGAGACTTGACAATACAAAAAGCTGATGAAGTTGTTTGGGTACGTGCAAGAGTTCATACAAGCAGAG

CTAAAGGGAAACAGTGCTTCTTAGTCCTACGTCAGCAGCAGTTTAATGTCCAGGCTCTTGTGGCGGTG

GGAGACCATGCAAGCAAGCAGATGGTTAAATTTGCTGCCAACATCAACAAAGAGAGCATTGTGGATG

TAGAAGGTGTTGTGAGAAAAGTGAATCAGAAAATTGGAAGCTGTACACAGCAAGACGTTGAGTTACA

TGTTCAGAAGATTTATGTGATCAGTTTGGCTGAACCCCGTCTGCCCCTGGGTAAGCCTATCCCTAACCC

TCTCCTCGGTCTCGATTCTACGGACTACAAAGACGATGACGACAAGTGA
```

The intracellular AspRS1$^{N1}$ sequence is as follows:

```
                                                          (SEQ ID NO: 33)
ATGCCCAGCGCCAGCGCCAGCCGCAAGAGTCAGGAGAAGCCGCGGGAGATCATGGACGCGGCGGAA

GATTATGCTAAAGAGAGATATGGAATATCTTCAATGATACAATCACAAGAAAAACCAGATCGAGTTTT

GGTTCGGGTTAGAGACTTGACAATACAAAAAGCTGATGAAGTTGTTTGGGTACGTGCAAGAGTTCATA

CAAGCAGAGCTAAAGGGAAACAGTGCTTCTTAGTCCTACGTCAGCAGCAGTTTAATGTCCAGGCTCTT
```

-continued

```
GTGGCGGTGGGAGACCATGCAAGCAAGCAGATGGTTAAATTTGCTGCCAACATCAACAAAGAGAGCA

TTGTGGATGTAGAAGGTGTTGTGAGAAAAGTGAATCAGAAAATTGGAAGCTGTACACAGCAAGACGT

TGAGTTACATGTTCAGAAGATTTATGTGATCAGTTTGGCTGAACCCCGTCTGCCCCTGGGTAAGCCTAT

CCCTAACCCTCTCCTCGGTCTCGATTCTACGGACTACAAAGACGATGACGACAAGTGA
```

The hEF1-HTLV promoter comprising the Elongation Factor-1α (EF-1α) core promoter and the R segment and part of the U5 sequence of the Human T-Cell Leukemia Virus (HTLV) Type 1 Long Terminal Repeat was used to drive the transcription. The V5 (GKPIPNPLLGLDST) (SEQ ID NO:74) and Flag (DYKDDDDK) (SEQ ID NO:75) tags were added to the C-terminus of the D1 fragments for detection and purification purpose. The Sh ble gene from *Streptoalloteichus hindustanus* was used for antibiotic resistance. The Simian Virus 40 late polyadenylation signal enables the cleavage and polyadenylation resulting in stable mRNA.

Expression:

The FREESTYLE™ MAX CHO Expression System (Invitrogen cat. no. K9000-20) was used for expression of the secretory form of AspRS1$^{N1}$. The CHO-S cells were thawed from liquid nitrogen and grown in the serum-free medium (FREESTYLE™ CHO Expression Medium) supplemented with 8 mM L-Glutamine in a 37° C. incubator containing a humidified atmosphere of 8% $CO_2$ in air on an orbital shaker platform rotating at 125 rpm. The cells were diluted to 2-3×10$^5$ cells/ml when the density reached about 10$^6$ cells/ml and were repeated a few passages. The DNA was mixed 1:1 with the Freestyle Max reagent in the Optipro SFM and incubated 10 minutes at room temperature. The complex was added slowly into the cells at the density about 10$^6$ cells/ml. The cell density and viability were monitored daily until harvest.

The FREESTYLE™ 293 Expression (Invitrogen cat. no. K9000-01) was used for expression of the intracellular form of AspRS1$^{N1}$. The 293-F cells were thawed from liquid nitrogen and grown in the serum-free medium (FREESTYLE™ 293 Expression Medium) supplemented with Glutamax-I in a 37° C. incubator containing a humidified atmosphere of 8% $CO_2$ in air on an orbital shaker platform rotating at 125 rpm. The cells were diluted to 2-3×10$^5$ cells/ml when the density reached about 10$^6$ cells/ml and were repeated for a few passages. The DNA was mixed 1:2 with the 293 transfectin reagent in the Opti-MEM I and incubated 20-30 minutes at room temperature. The complex was added slowly into the cells at the density about 10$^6$ cells/ml. The cell density and viability were monitored daily until harvest.

Purification:

In the case of secretory form of AspRS1$^{N1}$, the supernatant of the cell culture was separated from the cells by centrifugation. The clarified sample was loaded onto M2 agarose (Sigma cat. no. A2220) in a gravity column. The resin was then washed with TBS (50 mM Tris HCl, with 150 mM NaCl, pH 7.4). The bound protein was eluted with 0.1 M glycine HCl, pH 3.0 and neutralized immediately with 1M Tris buffer at pH8.0.

In the case of intracellular form of AspRS1$^{N1}$, the cells were recovered by centrifugation. The cells were lysed using M-PER Mammalian Protein Extraction Reagent (Pierce cat. no. 78501) and then centrifuged to remove the insoluble debris. The clarified lysate was loaded onto M2 agarose (Sigma cat. no. A2220) in a gravity column. The resin was then washed with TBS (50 mM Tris HCl, with 150 mM NaCl, pH 7.4). The bound protein was eluted with 0.1 M glycine HCl, pH 3.0 and neutralized immediately with 1M Tris buffer at pH8.0. The purified protein was analyzed by SDS-PAGE and Western blot. Purified proteins may be evaluated for binding to TLRs as described in Example 3 below.

Example 3

Evaluation of Biological Activity

To evaluate the binding of the DRS polypeptides to human toll like receptors a series of studies were conducted with commercially available reporter HEK 293 and THP-1 cell lines over expressing the TLR 2 and TLR 4 receptors.

Genetically modified Human HEK293 cells sold under the trademark HEK-Blue™ TLR cells (Invivogen) selectively express the TLR2 or TLR4 receptors and include a secreted embryonic alkaline phosphatase (SEAP)reporter gene under the control of an IFN-beta minimal promoter which is fused to five NF-kB and AP-1 transcription factors binding sites. With the use of specific TLR 2 or 4 agonists (respectively), HEK-BLUE™ TLR2 and HEK-BLUE™ TLR4 cells activate NF-kB and/or AP-1 leading to the secretion of SEAP which is measurable when using SEAP detection reagent.

The HEK-BLUE™ TLR2 cells are co-transfected with the LPS co-receptor protein CD14 to enhance TLR2 responsiveness and improve signal quality. The parent cell expresses endogenous levels of TLR1, 3, 5, 6 and also NOD1. The THP-1 monocyte reporter cells (Invivogen THP1-XBlue™ cells). Stably express CD14, MD-2, & and also include a secreted embryonic alkaline phosphatase (SEAP) reporter gene under the control of NF-kB and AP-1 promoter elements as described above.

Figure 2:
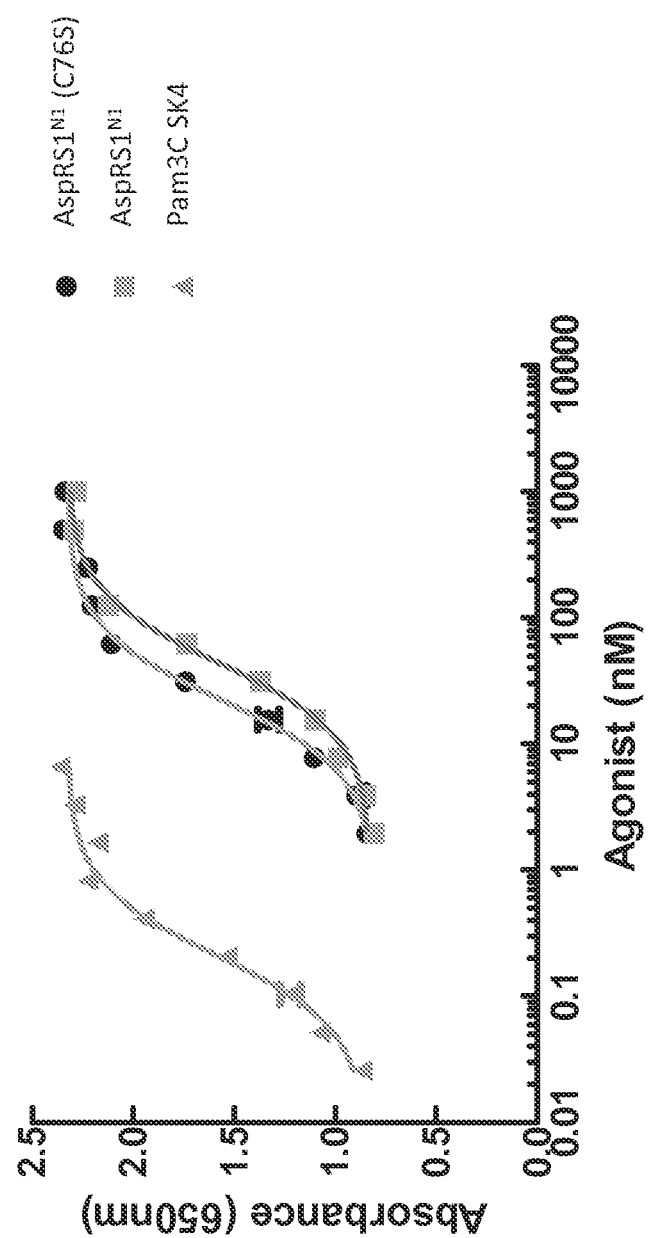
FIG. 2 shows a direct comparison of AspRS1$^{N1}$ (SEQ ID NO:31) (grey squares) and AspRS1$^{N1}$ (C76S) (SEQ ID NO:29) (black circles) on their ability to stimulate reporter gene activity mediated by the TLR2 receptor in HEK-Blue 2 cells. Grey triangles—Pam3C SK4.
Figure 3:
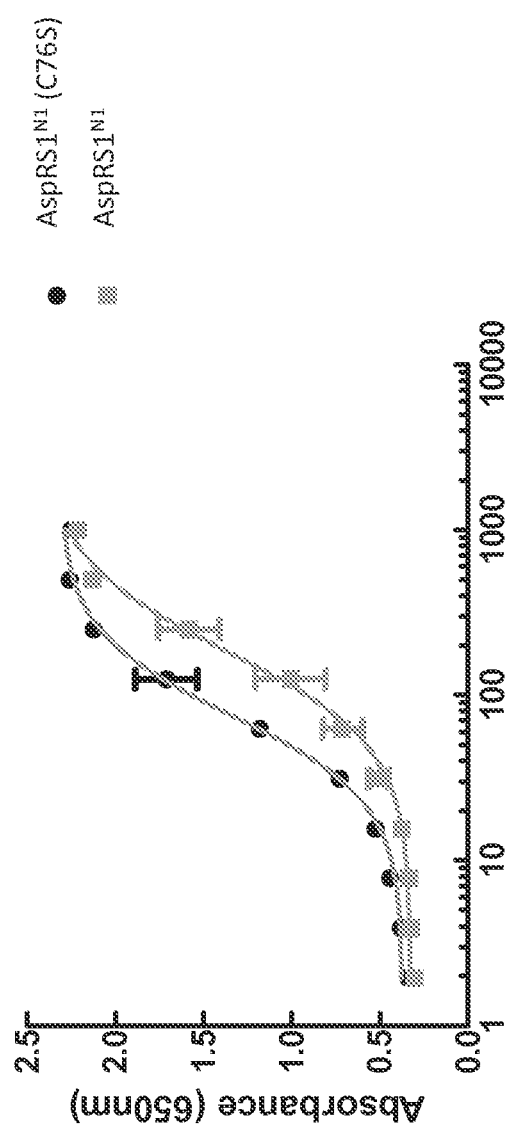
FIG. 3 shows a direct comparison of AspRS1$^{N1}$ (SEQ ID NO:31) (grey squares) and AspRS1$^{N1}$ (C76S) (SEQ ID NO:29) (Black circles) on their ability to stimulate reporter gene activity mediated by the TLR4 receptor in HEK-Blue 4 cells.

Methods:

HEK-BLUE™-TLR2 or HEK-BLUE™-TLR4 cells were washed twice with PBS, trypsinized and resuspended in fresh Growth Medium (Growth Medium: DMEM, 4.5 g/L glucose, 10% heat-inactivated fetal bovine serum (30 minutes at 56° C.), 100 mg/mL ZEOCIN™, 2 mM L-glutamine). Cells were plated at a concentration of 50,000 cells/well in a 96 well plate in a total volume of 100 μL, and DRS polypeptides, (AspRS1$^{N1}$ or AspRS1$^{N1}$(C76S)), were added to each well at the concentrations shown for 16 hours. On the next day, SEAP detection medium (QUANTI-BLUE™) (Invivogen Catalog code: rep-qbl) was prepared following the manufacturer's instructions and 120 μL was added per well to a clear flat-bottom 96-well plate, followed by (20 μL) of cell supernatant. Samples were incubated at 37° C. for 24 hours. SEAP levels were determined using a spectrophotometer and reading absorbance at 650 nM.
\Results: The results shown in FIGS. 2 and 3, demonstrate that the DRS polypeptide AspRS1$^{N1}$ (C76S) exhibited significantly more activity, and displayed an apparent $EC_{50}$ which was significantly higher compared to the non-mutated AspRS1$^{N1}$ parent molecule with respect to both TLR2 and TLR4 receptor binding (Table E3).

TABLE E3

Activity of AspRS1$^{N1}$ variant C76S on TLR2 and TLR4 receptors

| DRS polypeptide form | Fold increase in activity over AspRS1$^{N1}$ |
|---|---|
| TLR2 Activity | |
| AspRS1$^{N1}$ (C76S) | 3.2 ± 0.14 (n = 2) |
| TLR4 Activity | |
| AspRS1$^{N1}$ (C76S) | 3.6 ± 0.17 (n = 2) |

These results demonstrate the DRS polypeptides with altered cysteine content, and in particular DRS mutants comprising the mutation of cysteine 76 to another amino acid, result in the creation of new product forms which surprisingly exhibit enhanced activities, improved production yields and further surprisingly demonstrate reduced endotoxin content.

Example 4

Mutation of C76 and C130 to Other Amino Acids

To determine whether other favorable mutations in addition to Cys76→Ser could be identified, both cysteine residues (i.e., those at either Cys76 or Cys130) were mutated to all 19 alternative naturally occurring amino acid residues. To accomplish this in either the native human codon usage DRS polypeptides, or the E. coli optimized DRS polypeptides, the following primers were used:

TABLE E4

Mutagenesis Primer Sequences

| Name | Amino Acid Residue Range of SEQ ID NO: 1 | Nucleic acid sequence | SEQ ID NO: |
|---|---|---|---|
| Human C76X Primer | 211-247 | GCTAAAGGGAAACAGNNNTTCTTAGTCCTACGTCAGC (NNN = AGC) | 144 |
| Human C130X Primer | 367-403 | GTGAATCAGAAAATTGGAAGCNNNACACAGCAAGACG (NNN = AGC) | 145 |
| E.coli codon optimized C76X Primer | 208-247 | CGTGCAAAAGGCAAACAGNNNTTTCTGGTCCTGCGTCAGC (NNN = AGC) | 146 |
| E.coli codon optimized C130X Primer | 369-409 | CAATCAAAAGATCGGCTCGNNNACGCAACAAGATGTCGAGC (NNN = AGC) | 147 |

Mutations at either position were introduced by mutagenesis using the QuikChange Lightning Site-Directed Mutagenesis Kit (Agilent, cat. no. 210518) as described above. After mutagenesis, the sample is treated with Dpn I enzyme at 37° C. and transformed into XL10 gold competent cells as described. Multiple colonies are grown in terrific broth overnight at 37° C. and the resulting plasmids are purified with QIAprep Spin Miniprep Kit (Qiagen cat. no. 27106). The plasmids are sequenced to confirm the identity of the amino acid substitution of each clone. The representative clones are transformed into NovaBlue competent cells (Novagen cat. no. 70181) and grown in 250 ml M9YE medium at 37° C. overnight. A maxiprep is performed using the HiSpeed Plasmid Maxi Kit (Qiagen cat. no. 12663) to create a plasmid stock of mutant for further analysis. The concentration and purity are determined by measuring A260, A280 and A230. The purified plasmids are stored at −20° C. before transfection into E. coli or mammalian cells using the methods described above.

To assess the impact of the mutation of Cys76 or Cys130, representative clones were transformed into E. coli, or mammalian cells, and the production yields, endotoxin contents were compared. Also, the relative activity of the purified proteins are compared in the HEK293-TLR2 and HEK293-TLR4 expressing cell lines as described above. The optimal substitutions are identified based on the results obtained. Representative results are shown in Table E5.

TABLE E5

| Variant | Yield<br>+ <1.2 mg, ++ >1.2 mg,<br>+++ >1.4 mg,<br>++++ >2.0 mg | EU/mg<br>+ <1 EU/mg, ++ <5 EU/mg,<br>+++ <10 EU/mg, ++++ <20 EU/mg,<br>+++++ >20 EU/mg |
|---|---|---|
| C76A | ++++ | +++++ |
| C76I | +++ | +++ |
| C76L | + | +++ |
| C76T | ++ | +++ |
| C76V | + | + |
| C130F | ++ | + |
| C130L | +++ | ++++ |
| C130T | + | +++ |
| C130V | + | +++++ |

The results show that C76V, C76L, and C76T show enhanced yields and reduced endotoxin content. Additionally the results show that C130T and C130V demonstrate enhanced yields and reduced endotoxin content. All of the clones demonstrated TLR mod

Example 5

Preparation of DRS-Fc Polypeptides

N-terminal and C-terminal Fc-Aspartyl-tRNA synthetase (DRS-Fc) fusion proteins were prepared, purified, and analyzed as follows.

Plasmid Construction.

The human IgG1 Fc domain was amplified by polymerase chain reaction (PCR) before inserting into the C-term or N-term of the DRS polypeptide. The reaction mixture contains 47 ul of Accuprime pfx supermix (Invitrogen 12344), 1 ul template, and 1 ul forward/reverse primers. The following primers were used:

```
D1Fc_F:
                                          (SEQ ID NO: 148)
CTGAACCCCGTCTGCCCCTGGACAAAACTCACACATGCCCACCG

D1Fc_R:
                                          (SEQ ID NO: 149)
GCTTTGTTAGCAGCCGGATCTCATTTACCCGGAGACAGGGAGAGGCT

FcD1_F:
                                          (SEQ ID NO: 150)
TTTTGTTTAACTTTAAGAAGGAGATATACCATGGACAAAACTCACACATG
CCCACCG

FcD1_R:
                                          (SEQ ID NO: 151)
CTGGCGCTGGCGCTGGGTTTACCCGGAGACAGGGAGAGGCT
```

The PCR reaction was performed as follows: 30 seconds at 95° C., 30 seconds at 50° C. and 42 seconds at 68° C. for 35 cycles. The PCR-amplified fragments were verified on the agarose gel.

The fragments were inserted into C-term or N-term of the pET28 vector (Novagen 69864) carrying the DRS gene. The mutagenesis reaction mixture included 5 ul 10× buffer, 1 ul template, 5 ul PCR primers, 1 ul dNTP, 1.5 ul Quiksolution, 1 ul QCL enzyme and 35.5 ul deionized water. The thermal cycle was performed with 30 sec at 95 C, 30 sec at 50 C and 4 min at 68 C for 18 cycles. The reaction was treated with 2 ul DpnI for 5 minutes before transforming into the XL10-Gold competent cells (Agilent 200314). The transformed cells were spread onto agarose plates containing kanamycin and incubated at 37 C overnight. Several colonies were picked and the plasmid was isolated by QIAprep Spin Miniprep Kit (Qiagen 27106).

The sequence was confirmed by performing alignment with the theoretical sequence using EMBOSS Pairwise Alignment Algorithms. The cloned DNA sequences of DRS_Fc and Fc_DRS are shown below:

```
DNA sequence of DRS_Fc (C-terminal Fc fusion):
                                          (SEQ ID NO: 34)
ATGCCCAGCGCCAGCGCCAGCCGCAAGAGTCAGGAGAAGCCGCGGGAGATCATGGACGCGGCGGAA

GATTATGCTAAAGAGAGATATGGAATATCTTCAATGATACAATCACAAGAAAAACCAGATCGAGTTTT

GGTTCGGGTTAGAGACTTGACAATACAAAAAGCTGATGAAGTTGTTTGGGTACGTGCAAGAGTTCATA

CAAGCAGAGCTAAAGGGAAACAGTGCTTCTTAGTCCTACGTCAGCAGCAGTTTAATGTCCAGGCTCTT

GTGGCGGTGGGAGACCATGCAAGCAAGCAGATGGTTAAATTTGCTGCCAACATCAACAAAGAGAGCA

TTGTGGATGTAGAAGGTGTTGTGAGAAAAGTGAATCAGAAAATTGGAAGCTGTACACAGCAAGACGT

TGAGTTACATGTTCAGAAGATTTATGTGATCAGTTTGGCTGAACCCCGTCTGCCCCTGGACAAAACTCA

CACATGCCCACCGTGCCCAGCACCTGAACTCCTGGGGGACCGTCAGTCTTCCTCTTCCCCCCAAAACC

CAAGGACACCCTCATGATCTCCCGGACCCCTGAGGTCACATGCGTGGTGGTGGACGTGAGCCACGAAG

ACCCTGAGGTCAAGTTCAACTGGTACGTGGACGGCGTGGAGGTGCATAATGCCAAGACAAAGCCGCG

GGAGGAGCAGTACAACAGCACGTACCGTGTGGTCAGCGTCCTCACCGTCCTGCACCAGGACTGGCTGA

ATGGCAAGGAGTACAAGTGCAAGGTCTCCAACAAAGCCCTCCCAGCCCCCATCGAGAAAACCATCTCC

AAAGCCAAAGGGCAGCCCCGAGAACCACAGGTGTACACCCTGCCCCCATCCCGGGAGGAGATGACCA

AGAACCAGGTCAGCCTGACCTGCCTGGTCAAAGGCTTCTATCCCAGCGACATCGCCGTGGAGTGGGAG

AGCAATGGGCAGCCGGAGAACAACTACAAGACCACGCCTCCCGTGCTGGACTCCGACGGCTCCTTCTT

CCTCTACAGCAAGCTCACCGTGGACAAGAGCAGGTGGCAGCAGGGGAACGTCTTCTCATGCTCCGTGA

TGCACGAGGCTCTGCACAACCACTACACGCAGAAGAGCCTCTCCCTGTCTCCGGGTAAATGA

DNA sequence of Fc_DRS (N-terminal Fc fusion)
                                          (SEQ ID NO: 35)
ATGGACAAAACTCACACATGCCCACCGTGCCCAGCACCTGAACTCCTGGGGGGACCGTCAGTCTTCCT

CTTCCCCCCAAAACCCAAGGACACCCTCATGATCTCCCGGACCCCTGAGGTCACATGCGTGGTGGTGG

ACGTGAGCCACGAAGACCCTGAGGTCAAGTTCAACTGGTACGTGGACGGCGTGGAGGTGCATAATGC

CAAGACAAAGCCGCGGGAGGAGCAGTACAACAGCACGTACCGTGTGGTCAGCGTCCTCACCGTCCTG
```

-continued
```
CACCAGGACTGGCTGAATGGCAAGGAGTACAAGTGCAAGGTCTCCAACAAAGCCCTCCCAGCCCCCA

TCGAGAAAACCATCTCCAAAGCCAAAGGGCAGCCCCGAGAACCACAGGTGTACACCCTGCCCCCATC

CCGGGAGGAGATGACCAAGAACCAGGTCAGCCTGACCTGCCTGGTCAAAGGCTTCTATCCCAGCGAC

ATCGCCGTGGAGTGGGAGAGCAATGGGCAGCCGGAGAACAACTACAAGACCACGCCTCCCGTGCTGG

ACTCCGACGGCTCCTTCTTCCTCTACAGCAAGCTCACCGTGGACAAGAGCAGGTGGCAGCAGGGGAAC

GTCTTCTCATGCTCCGTGATGCACGAGGCTCTGCACAACCACTACACGCAGAAGAGCCTCTCCCTGTCT

CCGGGTAAACCCAGCGCCAGCGCCAGCCGCAAGAGTCAGGAGAAGCCGCGGGAGATCATGGACGCGG

CGGAAGATTATGCTAAAGAGAGATATGGAATATCTTCAATGATACAATCACAAGAAAAACCAGATCG

AGTTTTGGTTCGGGTTAGAGACTTGACAATACAAAAAGCTGATGAAGTTGTTTGGGTACGTGCAAGAG

TTCATACAAGCAGAGCTAAAGGGAAACAGTGCTTCTTAGTCCTACGTCAGCAGCAGTTTAATGTCCAG

GCTCTTGTGGCGGTGGGAGACCATGCAAGCAAGCAGATGGTTAAATTTGCTGCCAACATCAACAAAGA

GAGCATTGTGGATGTAGAAGGTGTTGTGAGAAAAGTGAATCAGAAAATTGGAAGCTGTACACAGCAA

GACGTTGAGTTACATGTTCAGAAGATTTATGTGATCAGTTTGGCTGAACCCCGTCTGCCCCTGTGA
```

The cloned protein sequences of DRS_Fc and Fc_DRS are shown below:

```
Protein sequence of DRS_Fc (C-terminal Fc fusion)
                                                   (SEQ ID NO: 36)
MPSASASRKSQEKPREIMDAAEDYAKERYGISSMIQSQEKPDRVLVRVRDLTIQKADEVVWVRARVHTSR

AKGKQCFLVLRQQQFNVQALVAVGDHASKQMVKFAANINKESIVDVEGVVRKVNQKIGSCTQQDVELHV

QKIYVISLAEPRLPLDKTHTCPPCPAPELLGGPSVFLFPPKPKDTLMISRTPEVTCVVVDVSHEDPEVKFNWY

VDGVEVHNAKTKPREEQYNSTYRVVSVLTVLHQDWLNGKEYKCKVSNKALPAPIEKTISKAKGQPREPQV

YTLPPSREEMTKNQVSLTCLVKGFYPSDIAVEWESNGQPENNYKTTPPVLDSDGSFFLYSKLTVDKSRWQQ

GNVFSCSVMHEALHNHYTQKSLSLSPGK

Protein sequence of Fc_DRS (N-terminal Fc fusion)
                                                   (SEQ ID NO: 37)
MDKTHTCPPCPAPELLGGPSVFLFPPKPKDTLMISRTPEVTCVVVDVSHEDPEVKFNWYVDGVEVHNAKT

KPREEQYNSTYRVVSVLTVLHQDWLNGKEYKCKVSNKALPAPIEKTISKAKGQPREPQVYTLPPSREEMTK

NQVSLTCLVKGFYPSDIAVEWESNGQPENNYKTTPPVLDSDGSFFLYSKLTVDKSRWQQGNVFSCSVMHE

ALHNHYTQKSLSLSPGKPSASASRKSQEKPREIMDAAEDYAKERYGISSMIQSQEKPDRVLVRVRDLTIQKA

DEVVWVRARVHTSRAKGKQCFLVLRQQQFNVQALVAVGDHASKQMVKFAANINKESIVDVEGVVRKVN

QKIGSCTQQDVELHVQKIYVISLAEPRLPL
```

E. coli Strain.

The E. coli BL21-CodonPlus® (DE3) RIPL Competent Cells (Agilent 230280) transformed with the expression construct was used for production of Fc fusion proteins.

Media.

M9YE medium was prepared by mixing sterile 5×M9 minimal salt (BD 248510), yeast extract solution in sterile purified water (BD 212750), sterilized 20% glucose (Sigma G7021), and sterile 1.0 M $MgSO_4$ (Sigma M7506). For the feeding solution, the yeast extract solution (5%), glucose solution (50%), and 10 ml concentrated trace element solution (containing $Fe^{3+}$, $Mn^{2+}$, boric acid, $Mo^{6+}$, $Co^{2+}$, $Cu^{2+}$, $Zn^{2+}$ and EDTA), as well 10 ml magnesium sulfate solution, were autoclaved separately. The components were mixed just prior to the fed-batch phase. Kanamycin sulfate was added to a final concentration of 100 µg/ml in the culture medium.

Fed-Batch Fermentation.

A 0.5 L Multifors fermentors (HT-Infors) with Iris software was used for the fed-batch fermentation process. The agitation was set at 1000 rpm. The pH value was controlled at 7.0 automatically by the addition of 30% ammonium hydroxide (Sigma 221228) and 30% phosphoric acid (Sigma P5811). Air was provided at a flow rate of 0.5 L/min with an oil-free diaphragm air compressor (Cole-Parmer) and passed through a 0.2 µm filter. The dissolved oxygen level was controlled at 70% by providing pure oxygen (West Air). The temperature was controlled at 30° C. with a Neslab RTE7 circulator (Thermo Scientific). Foaming was controlled by addition of the antifoam 204 (Sigma A8311).

The initial volume of M9YE medium in the fermentor was 0.3 L. The fermentor was inoculated with 15 ml of the seed culture grown overnight at 30° C. and 250 rpm. When the carbon source was depleted in the vessel, the concentrated feeding solution was introduced into the vessel by a peristaltic pump at 0.12 ml/min.

When the optical density of the cells at 600 nm reached exponential phase, the culture was induced with 0.5 mM IPTG (Fisher Scientific BP1755). The culture was grown overnight (about 17-hour induction) and the final $OD_{600}$ reached about 120. The cells were harvested by centrifugation at 8,000 g for 30 min. The supernatant was decanted and the pellet was stored at −20° C. until purification.

Purification of DRS-Fc.

Frozen cell pellets were resuspended in 4 volumes (i.e., 4 mL/g cell pellet) of Lysis Buffer (50 mM Tris, 500 mM NaCl, 14 mM β-ME, pH 7.5). Complete EDTA-FREE protease inhibitor tablets (Roche) were added to the suspension at a ratio of 1 tablet/50 mL. The suspension was passed through a microfluidizer (Microfluidics) twice at 14,000 psi with cooling by ice. The lysate was centrifuged at ≥10,000×g for 45 min at 4° C. The supernatant was filtered through 0.45+0.22 μm Sartobran capsule filters (Sartorius).

The clarified lysate was bound to the MabSelect resin (GE Healthcare), pre-equilibrated with Binding Buffer (50 mM Tris, 500 mM NaCl, pH 7.5). The column was washed with 500 column volumes of Binding Buffer+0.1% Triton X-114 followed by 100 column volumes of the Binding Buffer. The bound protein, DRS-Fc, was eluted with 4 column volumes of Elution Buffer (0.1 M glycine, 0.5 M Arginine, pH 3.0) to a collection tube containing ¼ volume of Neutralization Buffer (1 M Tris, pH 8.0).

The purified DRS-Fc was buffer exchanged into a buffer containing 20 mM sodium phosphate, 200 mM Arginine, at pH 7.3. The dialyzed protein was passed through a Q membrane filter (Sartobind-Q from Sartorius or Mustang-Q from Pall) or a Q-Sepharose column (GE Healthcare) for further endotoxin removal, and filtered through a 0.22 μm sterile filter. The fusion protein concentration was determined by Bradford protein assay (Thermo Scientific). The endotoxin level was below 15 EU/mg as determined by EndoSafe PTS LAL assay (Charles River).

The relative activity of the DRS-Fc proteins compared to untagged DRS(1-154) in the HEK293-TLR2 and HEK293-TLR4 expressing cell lines as described above, is shown in Table E6.

TABLE E6

Relative EC50 of DRS-Fc fusion protein compared to untagged DRS polypeptide in TLR2 assays

| DRS polypeptide form | Fold increase in potency (EC50) over AspRS1$^{N1}$ |
|---|---|
| | TLR2 Activity |
| DRS-Fc | 2.8 |

The results shown in Table E6 demonstrate that DRS-Fc demonstrates significantly enhanced biological potency relative to the unmodified core protein DRS(1-154).

To assess the pharmacokinetic characteristics of the DRS-Fc constructs, compared to the unmodified proteins, samples of proteins were injected into Spague Dawley catheterized rats (3 animals per group) via a single IV bolus at a concentration of 5 mg/kg. Test article concentrations were determined by ELISA, and kinetic parameters were determined using *Phoenix* non-compartmental analysis half-life determination. The results shown in Table E7, demonstrates that the DRS-Fc fusion construct ehibits improved recovery, AUC, and reduced clearance compared to the unmodified protein.

TABLE E7

Pharmacokinetic analysis of DRS-Fc fusion proteins

| Product Form | $C_0$ theor [ng/ml] | Recovery % | $AUC_{inf}$/dose [hr*kg*ng/mL/mg] | % $AUC_{inf}$ extrapolated | % $AUC_{inf}$ back extrapolated | $V_{ss}$ [mL/kg] | Clearance [mL/hr/kg] |
|---|---|---|---|---|---|---|---|
| DRS (1-154) | 83,333 | 15% | 1988 | 19% | 25% | 13862 | 503 |
| DRS(1-154)-Fc | 83,333 | 57% | 8169 | 0.01% | 25% | 109 | 122 |

In Table E7, $C_0$ theor = Theoretical concentration immediately after dose based on 250 g rat with 15 mL blood volume; Recovery = % of dose recovered calculated by (software estimate of $C_0$)/($C_0$ theor); $AUC_{inf}$ = AUC predicted from time of dose to infinity; % $AUC_{inf}$ extrapolated = % of $AUC_{inf}$ software extrapolated from last data point to infinity; % $AUC_{inf}$ back extrapolated = % of $AUC_{inf}$ extrapolated from first data point back to $C_0$; $V_{ss}$ = volume of distribution at steady state Analysis of DRS-Fc.

Figure 4:
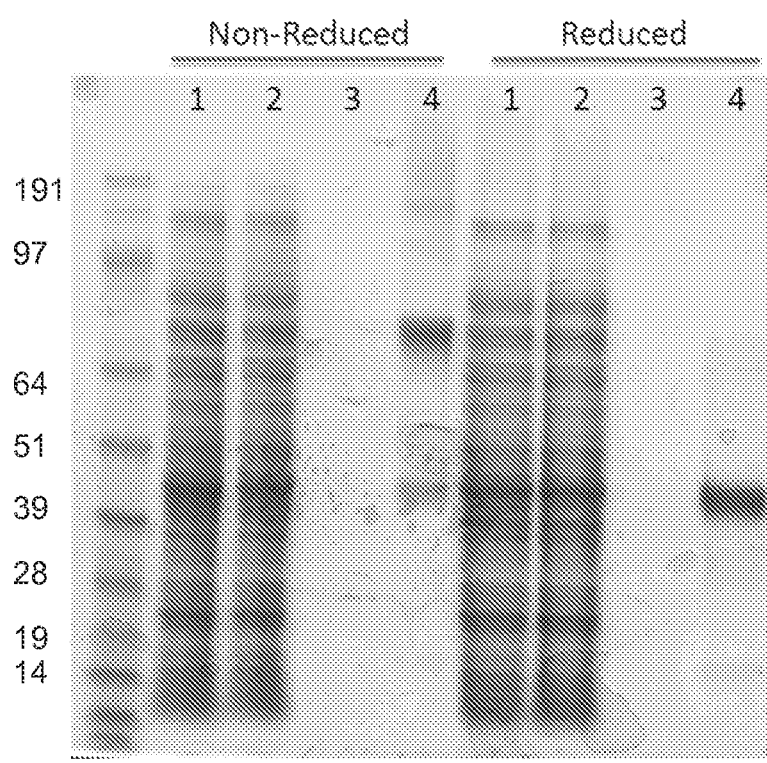
FIG. 4 shows SDS-PAGE analysis of a DRS-Fc (SEQ ID NO:37) purification. Lane 1, clarified lysate; lane 2, Mab-Select flow-through; lane 3, MabSelect wash; lane 4, purified DRS-Fc.

The DRS-Fc purification process was analyzed by SDS-PAGE as shown in FIG. 4.

Figure 5:
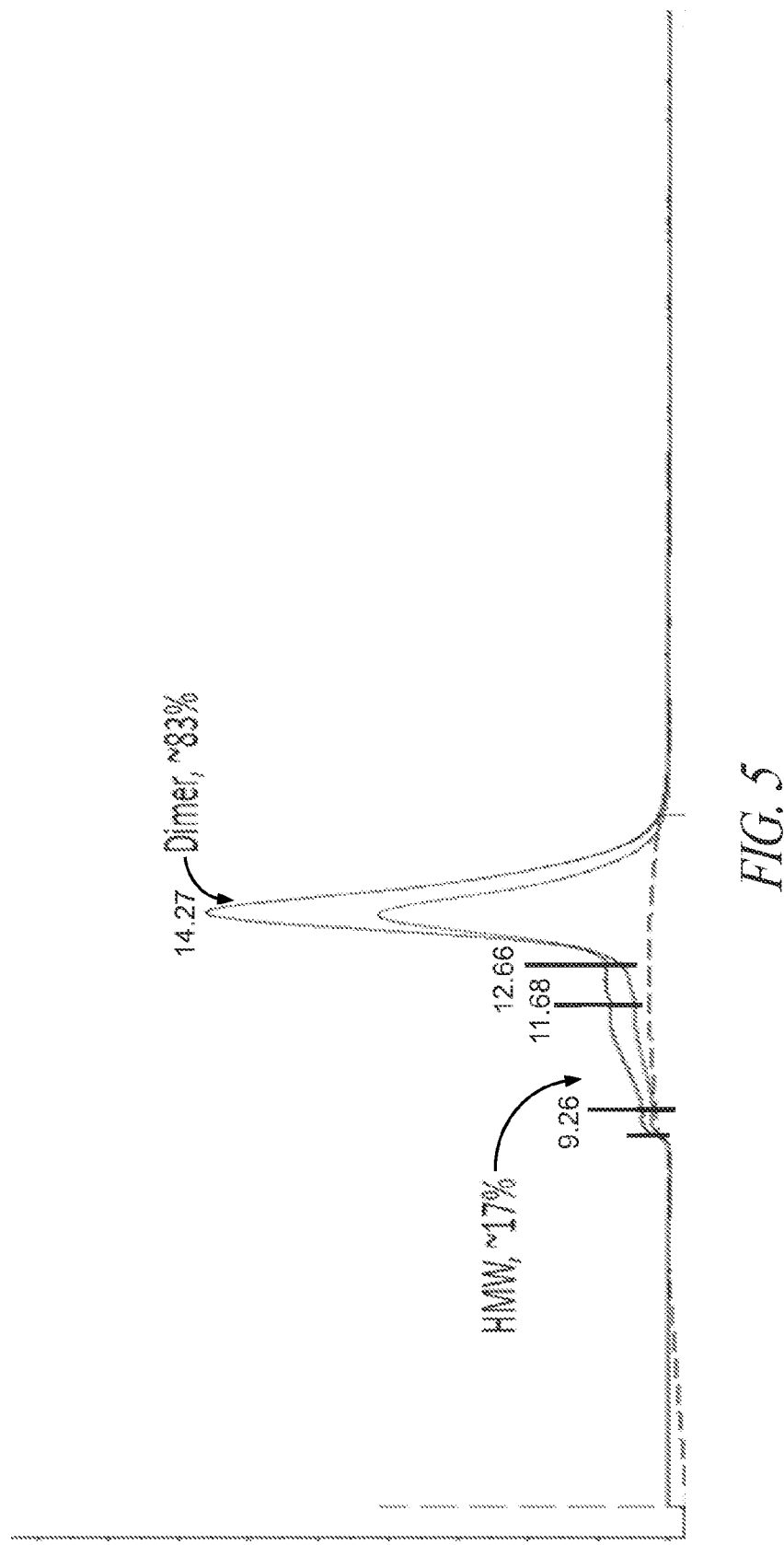
FIG. 5 shows an SEC analysis of a DRS-Fc fusion protein (SEQ ID NO:37). The upper trace is 280 nm absorbance, and the lower trace is 260 nm absorbance.

The purified DRS-Fc was also analyzed by a size-exclusion chromatography (SEC) method. The sample was loaded to a Superdex 200 10/300 HR column (GE Healthcare, cat. no. 17-5175-01) and the column run was controlled by the AKTA Explorer system with the Unicorn software (GE Healthcare). The column was pre-equilibrated with 1×PBS buffer. After sample loading, the column was run with 1.5 column volume of 1×PBS isocratic flow and the absorbance at 280 nm and 260 nm was monitored. The chromatogram is shown in FIG. 5.

Approximately 83% of the protein is in the desired dimer form. Most of the dimer protein contains the inter-chain disulfide bond in the Fc hinge region, while some non-covalent dimer also exists.

Example 6

Production of DRS Cysteine Mutants

Creation of DRS Cysteine Mutants:

To improve the stability of full length DRS and reduce the impact of non-specific disulfide bond mediated aggregation formation, potential problematic cysteines were identified based on the crystal structure (see, e.g., commonly owned U.S. application Ser. No. 12/751,358), and mutated into Ser or Ala or Val. In particular cysteines C334, C349, C203 and C259 in wild type DRS were initially targeted for mutagenesis. To systematically assess the impact of each cysteine in mediating protein aggregation, mini libraries were created in which each DRS cysteine mutant could contain either a mutation on one cysteine position or multiple positions. To make DRS mutants C334S, C349S, C334S/C349S, C334S/C349S/C259A/C203A, C334S/C349S/C259A/C203V, C334S/C349S/C203A, C334S/C349S/C203V, C203A and C203V, the following primers were used as listed in Table E8:

TABLE E8

| Mutation Oligo sequence | SEQ ID NO: |
|---|---|
| C334SCAGTTCCCATCTGAGCCATTC | 242 |
| C349SGACTAGAATATTCTGAAGCATTGGC | 243 |
| C203ACCAGTCTGGCATCGCCCATCTCTTCC | 244 |
| C203VCCAGTCTGGCATCGTCCATCTCTTCC | 245 |
| C259ACCACAGCTATATAAGCAAATGTGCATTGCGGCTGATTTTGAG | 246 |

Mutations at cysteine positions were introduced by mutagenesis using the QuickChange Lightning Site-Directed Mutagenesis Kit (Agilent, cat. no. 210518) following the manufacturer's instructions. After mutagenesis, the sample was treated with Dpn I enzyme at 37° C. and transformed into XL10 gold competent cells using routine procedures. Multiple colonies were grown in LB media overnight at 37° C. and the resulting plasmids are purified with QIAprep Spin Miniprep Kit (Qiagen cat. no. 27106). The plasmids were sequenced to confirm the identity of the amino acid substitution of each clone.

The DRS cysteine mutant DNA sequences are as follows:

1. DRS-C334S:

(SEQ ID NO: 198)

ATGCCCAGCGCCAGCGCCAGCCGCAAGAGTCAGGAGAAGCCGCGGGAGATCATGGACGCG

GCGGAAGATTATGCTAAAGAGAGATATGGAATATCTTCAATGATACAATCACAAGAAAAAC

CAGATCGAGTTTTGGTTCGGGTTAGAGACTTGACAATACAAAAAGCTGATGAAGTTGTTTGG

GTACGTGCAAGAGTTCATACAAGCAGAGCTAAAGGGAAACAGTGCTTCTTAGTCCTACGTCA

GCAGCAGTTTAATGTCCAGGCTCTTGTGGCGGTGGGAGACCATGCAAGCAAGCAGATGGTT

AAATTTGCTGCCAACATCAACAAAGAGAGCATTGTGGATGTAGAAGGTGTTGTGAGAAAAG

TGAATCAGAAAATTGGAAGCTGTACACAGCAAGACGTTGAGTTACATGTTCAGAAGATTTAT

GTGATCAGTTTGGCTGAACCCCGTCTGCCCCTGCAGCTGGATGATGCTGTTCGGCCTGAGGC

AGAAGGAGAAGAGGAAGGAAGAGCTACTGTTAACCAGGATACAAGATTAGACAACAGAGT

CATTGATCTTAGGACATCAACTAGTCAGGCAGTCTTCCGTCTCCAGTCTGGCATCTGCCATCT

CTTCCGAGAAACTTTAATTAACAAAGGTTTTGTGGAAATCCAAACTCCTAAAATTATTTCAG

CTGCCAGTGAAGGAGGAGCCAATGTTTTTACTGTGTCATATTTTAAAAATAATGCATACCTG

GCTCAGTCCCCACAGCTATATAAGCAAATGTGCATTTGTGCTGATTTTGAGAAGGTTTTCTCT

ATTGGACCAGTATTCAGAGCGGAAGACTCTAATACCCATAGACATCTAACTGAGTTTGTTGG

TTTGGACATTGAAATGGCTTTTAATTACCATTACCACGAAGTTATGGAAGAAATTGCTGACA

CCATGGTACAAATATTCAAAGGACTTCAAGAAAGGTTTCAGACTGAAATTCAAACAGTGAA

TAAACAGTTCCCATCTGAGCCATTCAAATTTTTGGAGCCAACTCTAAGACTAGAATATTGTG

AAGCATTGGCTATGCTTAGGGAAGCTGGAGTCGAAATGGGAGATGAAGACGATCTGAGCAC

ACCAAATGAAAAGCTGTTGGGTCATTTGGTAAAGGAAAAGTATGATACAGATTTTTATATTC

TTGATAAATATCCATTGGCTGTAAGACCTTTCTATACCATGCCTGACCCAAGAAATCCCAAA

CAGTCCAACTCTTACGATATGTTCATGAGAGGAGAAGAAATATTGTCAGGAGCTCAAAGAA

TACATGATCCTCAACTGCTAACAGAGAGAGCTTTACATCATGGAATTGATTTGGAGAAAATT

AAGGCTTACATTGATTCCTTCCGCTTTGGAGCCCCTCCTCATGCTGGTGGAGGCATTGGATTG

GAACGAGTTACTATGCTGTTTCTGGGATTGCATAATGTTCGTCAGACCTCCATGTTCCCTCGT

GATCCCAAACGACTCACTCCT

2. DRS-C349S:

(SEQ ID NO: 199)

ATGCCCAGCGCCAGCGCCAGCCGCAAGAGTCAGGAGAAGCCGCGGGAGATCATGGACGCG

GCGGAAGATTATGCTAAAGAGAGATATGGAATATCTTCAATGATACAATCACAAGAAAAAC

-continued

CAGATCGAGTTTTGGTTCGGGTTAGAGACTTGACAATACAAAAAGCTGATGAAGTTGTTTGG

GTACGTGCAAGAGTTCATACAAGCAGAGCTAAAGGGAAACAGTGCTTCTTAGTCCTACGTCA

GCAGCAGTTTAATGTCCAGGCTCTTGTGGCGGTGGGAGACCATGCAAGCAAGCAGATGGTT

AAATTTGCTGCCAACATCAACAAAGAGAGCATTGTGGATGTAGAAGGTGTTGTGAGAAAAG

TGAATCAGAAAATTGGAAGCTGTACACAGCAAGACGTTGAGTTACATGTTCAGAAGATTTAT

GTGATCAGTTTGGCTGAACCCCGTCTGCCCCTGCAGCTGGATGATGCTGTTCGGCCTGAGGC

AGAAGGAGAAGAGGAAGGAAGAGCTACTGTTAACCAGGATACAAGATTAGACAACAGAGT

CATTGATCTTAGGACATCAACTAGTCAGGCAGTCTTCCGTCTCCAGTCTGGCATCTGCCATCT

CTTCCGAGAAACTTTAATTAACAAAGGTTTTGTGGAAATCCAAACTCCTAAAATTATTTCAG

CTGCCAGTGAAGGAGGAGCCAATGTTTTTACTGTGTCATATTTTAAAAATAATGCATACCTG

GCTCAGTCCCCACAGCTATATAAGCAAATGTGCATTTGTGCTGATTTTGAGAAGGTTTTCTCT

ATTGGACCAGTATTCAGAGCGGAAGACTCTAATACCCATAGACATCTAACTGAGTTTGTTGG

TTTGGACATTGAAATGGCTTTTAATTACCATTACCACGAAGTTATGGAAGAAATTGCTGACA

CCATGGTACAAATATTCAAAGGACTTCAAGAAAGGTTTCAGACTGAAATTCAAACAGTGAA

TAAACAGTTCCCATGTGAGCCATTCAAATTTTTGGAGCCAACTCTAAGACTAGAATATTCTG

AAGCATTGGCTATGCTTAGGGAAGCTGGAGTCGAAATGGGAGATGAAGACGATCTGAGCAC

ACCAAATGAAAAGCTGTTGGGTCATTTGGTAAAGGAAAAGTATGATACAGATTTTTATATTC

TTGATAAATATCCATTGGCTGTAAGACCTTTCTATACCATGCCTGACCCAAGAAATCCCAAA

CAGTCCAACTCTTACGATATGTTCATGAGAGGAGAAGAAATATTGTCAGGAGCTCAAAGAA

TACATGATCCTCAACTGCTAACAGAGAGAGCTTTACATCATGGAATTGATTTGGAGAAAATT

AAGGCTTACATTGATTCCTTCCGCTTTGGAGCCCCTCCTCATGCTGGTGGAGGCATTGGATTG

GAACGAGTTACTATGCTGTTTCTGGGATTGCATAATGTTCGTCAGACCTCCATGTTCCCTCGT

GATCCCAAACGACTCACTCCT

3. DRS C334S/C349S:
(SEQ ID NO: 200)
ATGCCCAGCGCCAGCGCCAGCCGCAAGAGTCAGGAGAAGCCGCGGGAGATCATGGACGCG

GCGGAAGATTATGCTAAAGAGAGATATGGAATATCTTCAATGATACAATCACAAGAAAAAC

CAGATCGAGTTTTGGTTCGGGTTAGAGACTTGACAATACAAAAAGCTGATGAAGTTGTTTGG

GTACGTGCAAGAGTTCATACAAGCAGAGCTAAAGGGAAACAGTGCTTCTTAGTCCTACGTCA

GCAGCAGTTTAATGTCCAGGCTCTTGTGGCGGTGGGAGACCATGCAAGCAAGCAGATGGTT

AAATTTGCTGCCAACATCAACAAAGAGAGCATTGTGGATGTAGAAGGTGTTGTGAGAAAAG

TGAATCAGAAAATTGGAAGCTGTACACAGCAAGACGTTGAGTTACATGTTCAGAAGATTTAT

GTGATCAGTTTGGCTGAACCCCGTCTGCCCCTGCAGCTGGATGATGCTGTTCGGCCTGAGGC

AGAAGGAGAAGAGGAAGGAAGAGCTACTGTTAACCAGGATACAAGATTAGACAACAGAGT

CATTGATCTTAGGACATCAACTAGTCAGGCAGTCTTCCGTCTCCAGTCTGGCATCTGCCATCT

CTTCCGAGAAACTTTAATTAACAAAGGTTTTGTGGAAATCCAAACTCCTAAAATTATTTCAG

CTGCCAGTGAAGGAGGAGCCAATGTTTTTACTGTGTCATATTTTAAAAATAATGCATACCTG

GCTCAGTCCCCACAGCTATATAAGCAAATGTGCATTTGTGCTGATTTTGAGAAGGTTTTCTCT

ATTGGACCAGTATTCAGAGCGGAAGACTCTAATACCCATAGACATCTAACTGAGTTTGTTGG

TTTGGACATTGAAATGGCTTTTAATTACCATTACCACGAAGTTATGGAAGAAATTGCTGACA

CCATGGTACAAATATTCAAAGGACTTCAAGAAAGGTTTCAGACTGAAATTCAAACAGTGAA

TAAACAGTTCCCATCTGAGCCATTCAAATTTTTGGAGCCAACTCTAAGACTAGAATATTCTG

AAGCATTGGCTATGCTTAGGGAAGCTGGAGTCGAAATGGGAGATGAAGACGATCTGAGCAC

ACCAAATGAAAAGCTGTTGGGTCATTTGGTAAAGGAAAAGTATGATACAGATTTTTATATTC

TTGATAAATATCCATTGGCTGTAAGACCTTTCTATACCATGCCTGACCCAAGAAATCCCAAA

CAGTCCAACTCTTACGATATGTTCATGAGAGGAGAAGAAATATTGTCAGGAGCTCAAAGAA

TACATGATCCTCAACTGCTAACAGAGAGAGCTTTACATCATGGAATTGATTTGGAGAAAATT

AAGGCTTACATTGATTCCTTCCGCTTTGGAGCCCCTCCTCATGCTGGTGGAGGCATTGGATTG

GAACGAGTTACTATGCTGTTTCTGGGATTGCATAATGTTCGTCAGACCTCCATGTTCCCTCGT

GATCCCAAACGACTCACTCCT

4. DRS C203A:

(SEQ ID NO: 201)

ATGCCCAGCGCCAGCGCCAGCCGCAAGAGTCAGGAGAAGCCGCGGGAGATCATGGACGCG

GCGGAAGATTATGCTAAAGAGAGATATGGAATATCTTCAATGATACAATCACAAGAAAAAC

CAGATCGAGTTTTGGTTCGGGTTAGAGACTTGACAATACAAAAAGCTGATGAAGTTGTTTGG

GTACGTGCAAGAGTTCATACAAGCAGAGCTAAAGGGAAACAGTGCTTCTTAGTCCTACGTCA

GCAGCAGTTTAATGTCCAGGCTCTTGTGGCGGTGGGAGACCATGCAAGCAAGCAGATGGTT

AAATTTGCTGCCAACATCAACAAAGAGAGCATTGTGGATGTAGAAGGTGTTGTGAGAAAAG

TGAATCAGAAAATTGGAAGCTGTACACAGCAAGACGTTGAGTTACATGTTCAGAAGATTTAT

GTGATCAGTTTGGCTGAACCCCGTCTGCCCCTGCAGCTGGATGATGCTGTTCGGCCTGAGGC

AGAAGGAGAAGAGGAAGGAAGAGCTACTGTTAACCAGGATACAAGATTAGACAACAGAGT

CATTGATCTTAGGACATCAACTAGTCAGGCAGTCTTCCGTCTCCAGTCTGGCATCGCCCATCT

CTTCCGAGAAACTTTAATTAACAAAGGTTTTGTGGAAATCCAAACTCCTAAAATTATTTCAG

CTGCCAGTGAAGGAGGAGCCAATGTTTTTACTGTGTCATATTTTAAAAATAATGCATACCTG

GCTCAGTCCCCACAGCTATATAAGCAAATGTGCATTTGTGCTGATTTTGAGAAGGTTTTCTCT

ATTGGACCAGTATTCAGAGCGGAAGACTCTAATACCCATAGACATCTAACTGAGTTTGTTGG

TTTGGACATTGAAATGGCTTTTAATTACCATTACCACGAAGTTATGGAAGAAATTGCTGACA

CCATGGTACAAATATTCAAAGGACTTCAAGAAAGGTTTCAGACTGAAATTCAAACAGTGAA

TAAACAGTTCCCATGTGAGCCATTCAAATTTTTGGAGCCAACTCTAAGACTAGAATATTGTG

AAGCATTGGCTATGCTTAGGGAAGCTGGAGTCGAAATGGGAGATGAAGACGATCTGAGCAC

ACCAAATGAAAAGCTGTTGGGTCATTTGGTAAAGGAAAAGTATGATACAGATTTTTATATTC

TTGATAAATATCCATTGGCTGTAAGACCTTTCTATACCATGCCTGACCCAAGAAATCCCAAA

CAGTCCAACTCTTACGATATGTTCATGAGAGGAGAAGAAATATTGTCAGGAGCTCAAAGAA

TACATGATCCTCAACTGCTAACAGAGAGAGCTTTACATCATGGAATTGATTTGGAGAAAATT

AAGGCTTACATTGATTCCTTCCGCTTTGGAGCCCCTCCTCATGCTGGTGGAGGCATTGGATTG

GAACGAGTTACTATGCTGTTTCTGGGATTGCATAATGTTCGTCAGACCTCCATGTTCCCTCGT

GATCCCAAACGACTCACTCCT

5. DRS C203V:

(SEQ ID NO: 202)

ATGCCCAGCGCCAGCGCCAGCCGCAAGAGTCAGGAGAAGCCGCGGGAGATCATGGACGCG

GCGGAAGATTATGCTAAAGAGAGATATGGAATATCTTCAATGATACAATCACAAGAAAAAC

CAGATCGAGTTTTGGTTCGGGTTAGAGACTTGACAATACAAAAAGCTGATGAAGTTGTTTGG

GTACGTGCAAGAGTTCATACAAGCAGAGCTAAAGGGAAACAGTGCTTCTTAGTCCTACGTCA

GCAGCAGTTTAATGTCCAGGCTCTTGTGGCGGTGGGAGACCATGCAAGCAAGCAGATGGTT

-continued

AAATTTGCTGCCAACATCAACAAAGAGAGCATTGTGGATGTAGAAGGTGTTGTGAGAAAAG

TGAATCAGAAAATTGGAAGCTGTACACAGCAAGACGTTGAGTTACATGTTCAGAAGATTTAT

GTGATCAGTTTGGCTGAACCCCGTCTGCCCCTGCAGCTGGATGATGCTGTTCGGCCTGAGGC

AGAAGGAGAAGAGGAAGGAAGAGCTACTGTTAACCAGGATACAAGATTAGACAACAGAGT

CATTGATCTTAGGACATCAACTAGTCAGGCAGTCTTCCGTCTCCAGTCTGGCATCGTCCATCT

CTTCCGAGAAACTTTAATTAACAAAGGTTTTGTGGAAATCCAAACTCCTAAAATTATTTCAG

CTGCCAGTGAAGGAGGAGCCAATGTTTTTACTGTGTCATATTTTAAAAATAATGCATACCTG

GCTCAGTCCCCACAGCTATATAAGCAAATGTGCATTTGTGCTGATTTTGAGAAGGTTTTCTCT

ATTGGACCAGTATTCAGAGCGGAAGACTCTAATACCCATAGACATCTAACTGAGTTTGTTGG

TTTGGACATTGAAATGGCTTTTAATTACCATTACCACGAAGTTATGGAAGAAATTGCTGACA

CCATGGTACAAATATTCAAAGGACTTCAAGAAAGGTTTCAGACTGAAATTCAAACAGTGAA

TAAACAGTTCCCATGTGAGCCATTCAAATTTTTGGAGCCAACTCTAAGACTAGAATATTGTG

AAGCATTGGCTATGCTTAGGGAAGCTGGAGTCGAAATGGGAGATGAAGACGATCTGAGCAC

ACCAAATGAAAAGCTGTTGGGTCATTTGGTAAAGGAAAAGTATGATACAGATTTTTATATTC

TTGATAAATATCCATTGGCTGTAAGACCTTTCTATACCATGCCTGACCCAAGAAATCCCAAA

CAGTCCAACTCTTACGATATGTTCATGAGAGGAGAAGAAATATTGTCAGGAGCTCAAAGAA

TACATGATCCTCAACTGCTAACAGAGAGAGCTTTACATCATGGAATTGATTTGGAGAAAATT

AAGGCTTACATTGATTCCTTCCGCTTTGGAGCCCCTCCTCATGCTGGTGGAGGCATTGGATTG

GAACGAGTTACTATGCTGTTTCTGGGATTGCATAATGTTCGTCAGACCTCCATGTTCCCTCGT

GATCCCAAACGACTCACTCCT

6. DRS C334S/C349S/C203A:

(SEQ ID NO: 203)
ATGCCCAGCGCCAGCGCCAGCCGCAAGAGTCAGGAGAAGCCGCGGGAGATCATGGACGCG

GCGGAAGATTATGCTAAAGAGAGATATGGAATATCTTCAATGATACAATCACAAGAAAAAC

CAGATCGAGTTTTGGTTCGGGTTAGAGACTTGACAATACAAAAAGCTGATGAAGTTGTTTGG

GTACGTGCAAGAGTTCATACAAGCAGAGCTAAAGGGAAACAGTGCTTCTTAGTCCTACGTCA

GCAGCAGTTTAATGTCCAGGCTCTTGTGGCGGTGGGAGACCATGCAAGCAAGCAGATGGTT

AAATTTGCTGCCAACATCAACAAAGAGAGCATTGTGGATGTAGAAGGTGTTGTGAGAAAAG

TGAATCAGAAAATTGGAAGCTGTACACAGCAAGACGTTGAGTTACATGTTCAGAAGATTTAT

GTGATCAGTTTGGCTGAACCCCGTCTGCCCCTGCAGCTGGATGATGCTGTTCGGCCTGAGGC

AGAAGGAGAAGAGGAAGGAAGAGCTACTGTTAACCAGGATACAAGATTAGACAACAGAGT

CATTGATCTTAGGACATCAACTAGTCAGGCAGTCTTCCGTCTCCAGTCTGGCATCGCCCATCT

CTTCCGAGAAACTTTAATTAACAAAGGTTTTGTGGAAATCCAAACTCCTAAAATTATTTCAG

CTGCCAGTGAAGGAGGAGCCAATGTTTTTACTGTGTCATATTTTAAAAATAATGCATACCTG

GCTCAGTCCCCACAGCTATATAAGCAAATGTGCATTTGTGCTGATTTTGAGAAGGTTTTCTCT

ATTGGACCAGTATTCAGAGCGGAAGACTCTAATACCCATAGACATCTAACTGAGTTTGTTGG

TTTGGACATTGAAATGGCTTTTAATTACCATTACCACGAAGTTATGGAAGAAATTGCTGACA

CCATGGTACAAATATTCAAAGGACTTCAAGAAAGGTTTCAGACTGAAATTCAAACAGTGAA

TAAACAGTTCCCATCTGAGCCATTCAAATTTTTGGAGCCAACTCTAAGACTAGAATATTCTG

AAGCATTGGCTATGCTTAGGGAAGCTGGAGTCGAAATGGGAGATGAAGACGATCTGAGCAC

ACCAAATGAAAAGCTGTTGGGTCATTTGGTAAAGGAAAAGTATGATACAGATTTTTATATTC

TTGATAAATATCCATTGGCTGTAAGACCTTTCTATACCATGCCTGACCCAAGAAATCCCAAA

-continued

CAGTCCAACTCTTACGATATGTTCATGAGAGGAGAAGAAATATTGTCAGGAGCTCAAAGAA

TACATGATCCTCAACTGCTAACAGAGAGAGCTTTACATCATGGAATTGATTTGGAGAAAATT

AAGGCTTACATTGATTCCTTCCGCTTTGGAGCCCCTCCTCATGCTGGTGGAGGCATTGGATTG

GAACGAGTTACTATGCTGTTTCTGGGATTGCATAATGTTCGTCAGACCTCCATGTTCCCTCGT

GATCCCAAACGACTCACTCCT

7. DRS C334S/C349S/C203V:
(SEQ ID NO: 204)
ATGCCCAGCGCCAGCGCCAGCCGCAAGAGTCAGGAGAAGCCGCGGGAGATCATGGACGCG

GCGGAAGATTATGCTAAAGAGAGATATGGAATATCTTCAATGATACAATCACAAGAAAAAC

CAGATCGAGTTTTGGTTCGGGTTAGAGACTTGACAATACAAAAAGCTGATGAAGTTGTTTGG

GTACGTGCAAGAGTTCATACAAGCAGAGCTAAAGGGAAACAGTGCTTCTTAGTCCTACGTCA

GCAGCAGTTTAATGTCCAGGCTCTTGTGGCGGTGGGAGACCATGCAAGCAAGCAGATGGTT

AAATTTGCTGCCAACATCAACAAAGAGAGCATTGTGGATGTAGAAGGTGTTGTGAGAAAAG

TGAATCAGAAAATTGGAAGCTGTACACAGCAAGACGTTGAGTTACATGTTCAGAAGATTTAT

GTGATCAGTTTGGCTGAACCCCGTCTGCCCCTGCAGCTGGATGATGCTGTTCGGCCTGAGGC

AGAAGGAGAAGAGGAAGGAAGAGCTACTGTTAACCAGGATACAAGATTAGACAACAGAGT

CATTGATCTTAGGACATCAACTAGTCAGGCAGTCTTCCGTCTCCAGTCTGGCATCGTCCATCT

CTTCCGAGAAACTTTAATTAACAAAGGTTTTGTGGAAATCCAAACTCCTAAAATTATTTCAG

CTGCCAGTGAAGGAGGAGCCAATGTTTTTACTGTGTCATATTTTAAAAATAATGCATACCTG

GCTCAGTCCCCACAGCTATATAAGCAAATGTGCATTTGTGCTGATTTTGAGAAGGTTTTCTCT

ATTGGACCAGTATTCAGAGCGGAAGACTCTAATACCCATAGACATCTAACTGAGTTTGTTGG

TTTGGACATTGAAATGGCTTTTAATTACCATTACCACGAAGTTATGGAAGAAATTGCTGACA

CCATGGTACAAATATTCAAAGGACTTCAAGAAAGGTTTCAGACTGAAATTCAAACAGTGAA

TAAACAGTTCCCATCTGAGCCATTCAAATTTTTGGAGCCAACTCTAAGACTAGAATATTCTG

AAGCATTGGCTATGCTTAGGGAAGCTGGAGTCGAAATGGGAGATGAAGACGATCTGAGCAC

ACCAAATGAAAAGCTGTTGGGTCATTTGGTAAAGGAAAAGTATGATACAGATTTTTATATTC

TTGATAAATATCCATTGGCTGTAAGACCTTTCTATACCATGCCTGACCCAAGAAATCCCAAA

CAGTCCAACTCTTACGATATGTTCATGAGAGGAGAAGAAATATTGTCAGGAGCTCAAAGAA

TACATGATCCTCAACTGCTAACAGAGAGAGCTTTACATCATGGAATTGATTTGGAGAAAATT

AAGGCTTACATTGATTCCTTCCGCTTTGGAGCCCCTCCTCATGCTGGTGGAGGCATTGGATTG

GAACGAGTTACTATGCTGTTTCTGGGATTGCATAATGTTCGTCAGACCTCCATGTTCCCTCGT

GATCCCAAACGACTCACTCCT

8. DRS C334S/C349S/C259A/C203A:
(SEQ ID NO: 205)
ATGCCCAGCGCCAGCGCCAGCCGCAAGAGTCAGGAGAAGCCGCGGGAGATCATGGACGCG

GCGGAAGATTATGCTAAAGAGAGATATGGAATATCTTCAATGATACAATCACAAGAAAAAC

CAGATCGAGTTTTGGTTCGGGTTAGAGACTTGACAATACAAAAAGCTGATGAAGTTGTTTGG

GTACGTGCAAGAGTTCATACAAGCAGAGCTAAAGGGAAACAGTGCTTCTTAGTCCTACGTCA

GCAGCAGTTTAATGTCCAGGCTCTTGTGGCGGTGGGAGACCATGCAAGCAAGCAGATGGTT

AAATTTGCTGCCAACATCAACAAAGAGAGCATTGTGGATGTAGAAGGTGTTGTGAGAAAAG

TGAATCAGAAAATTGGAAGCTGTACACAGCAAGACGTTGAGTTACATGTTCAGAAGATTTAT

GTGATCAGTTTGGCTGAACCCCGTCTGCCCCTGCAGCTGGATGATGCTGTTCGGCCTGAGGC

-continued

AGAAGGAGAAGAGGAAGGAAGAGCTACTGTTAACCAGGATACAAGATTAGACAACAGAGT

CATTGATCTTAGGACATCAACTAGTCAGGCAGTCTTCCGTCTCCAGTCTGGCATCGCCCATCT

CTTCCGAGAAACTTTAATTAACAAAGGTTTTGTGGAAATCCAAACTCCTAAAATTATTTCAG

CTGCCAGTGAAGGAGGAGCCAATGTTTTTACTGTGTCATATTTTAAAAATAATGCATACCTG

GCTCAGTCCCCACAGCTATATAAGCAAATGTGCATTGCGGCTGATTTTGAGAAGGTTTTCTCT

ATTGGACCAGTATTCAGAGCGGAAGACTCTAATACCCATAGACATCTAACTGAGTTTGTTGG

TTTGGACATTGAAATGGCTTTTAATTACCATTACCACGAAGTTATGGAAGAAATTGCTGACA

CCATGGTACAAATATTCAAAGGACTTCAAGAAAGGTTTCAGACTGAAATTCAAACAGTGAA

TAAACAGTTCCCATCTGAGCCATTCAAATTTTTGGAGCCAACTCTAAGACTAGAATATTCTG

AAGCATTGGCTATGCTTAGGGAAGCTGGAGTCGAAATGGGAGATGAAGACGATCTGAGCAC

ACCAAATGAAAAGCTGTTGGGTCATTTGGTAAAGGAAAAGTATGATACAGATTTTTATATTC

TTGATAAATATCCATTGGCTGTAAGACCTTTCTATACCATGCCTGACCCAAGAAATCCCAAA

CAGTCCAACTCTTACGATATGTTCATGAGAGGAGAAGAAATATTGTCAGGAGCTCAAAGAA

TACATGATCCTCAACTGCTAACAGAGAGAGCTTTACATCATGGAATTGATTTGGAGAAAATT

AAGGCTTACATTGATTCCTTCCGCTTTGGAGCCCCTCCTCATGCTGGTGGAGGCATTGGATTG

GAACGAGTTACTATGCTGTTTCTGGGATTGCATAATGTTCGTCAGACCTCCATGTTCCCTCGT

GATCCCAAACGACTCACTCCT

9. DRS C334S/C349S/C259A/C203V:

(SEQ ID NO: 206)
ATGCCCAGCGCCAGCGCCAGCCGCAAGAGTCAGGAGAAGCCGCGGGAGATCATGGACGCG

GCGGAAGATTATGCTAAAGAGAGATATGGAATATCTTCAATGATACAATCACAAGAAAAAC

CAGATCGAGTTTTGGTTCGGGTTAGAGACTTGACAATACAAAAAGCTGATGAAGTTGTTTGG

GTACGTGCAAGAGTTCATACAAGCAGAGCTAAAGGGAAACAGTGCTTCTTAGTCCTACGTCA

GCAGCAGTTTAATGTCCAGGCTCTTGTGGCGGTGGGAGACCATGCAAGCAAGCAGATGGTT

AAATTTGCTGCCAACATCAACAAAGAGAGCATTGTGGATGTAGAAGGTGTTGTGAGAAAAG

TGAATCAGAAAATTGGAAGCTGTACACAGCAAGACGTTGAGTTACATGTTCAGAAGATTTAT

GTGATCAGTTTGGCTGAACCCCGTCTGCCCCTGCAGCTGGATGATGCTGTTCGGCCTGAGGC

AGAAGGAGAAGAGGAAGGAAGAGCTACTGTTAACCAGGATACAAGATTAGACAACAGAGT

CATTGATCTTAGGACATCAACTAGTCAGGCAGTCTTCCGTCTCCAGTCTGGCATCGTCCATCT

CTTCCGAGAAACTTTAATTAACAAAGGTTTTGTGGAAATCCAAACTCCTAAAATTATTTCAG

CTGCCAGTGAAGGAGGAGCCAATGTTTTTACTGTGTCATATTTTAAAAATAATGCATACCTG

GCTCAGTCCCCACAGCTATATAAGCAAATGTGCATTGCGGCTGATTTTGAGAAGGTTTTCTCT

ATTGGACCAGTATTCAGAGCGGAAGACTCTAATACCCATAGACATCTAACTGAGTTTGTTGG

TTTGGACATTGAAATGGCTTTTAATTACCATTACCACGAAGTTATGGAAGAAATTGCTGACA

CCATGGTACAAATATTCAAAGGACTTCAAGAAAGGTTTCAGACTGAAATTCAAACAGTGAA

TAAACAGTTCCCATCTGAGCCATTCAAATTTTTGGAGCCAACTCTAAGACTAGAATATTCTG

AAGCATTGGCTATGCTTAGGGAAGCTGGAGTCGAAATGGGAGATGAAGACGATCTGAGCAC

ACCAAATGAAAAGCTGTTGGGTCATTTGGTAAAGGAAAAGTATGATACAGATTTTTATATTC

TTGATAAATATCCATTGGCTGTAAGACCTTTCTATACCATGCCTGACCCAAGAAATCCCAAA

CAGTCCAACTCTTACGATATGTTCATGAGAGGAGAAGAAATATTGTCAGGAGCTCAAAGAA

TACATGATCCTCAACTGCTAACAGAGAGAGCTTTACATCATGGAATTGATTTGGAGAAAATT

AAGGCTTACATTGATTCCTTCCGCTTTGGAGCCCCTCCTCATGCTGGTGGAGGCATTGGATTG

-continued

```
GAACGAGTTACTATGCTGTTTCTGGGATTGCATAATGTTCGTCAGACCTCCATGTTCCCTCGT

GATCCCAAACGACTCACTCCT
```

The corresponding translated protein sequences are:

1. DRS C334S:

(SEQ ID NO: 189)

```
MPSASASRKSQEKPREIMDAAEDYAKERYGISSMIQSQEKPDRVLVRVRDLTIQKADEVVWVRA

RVHTSRAKGKQCFLVLRQQQFNVQALVAVGDHASKQMVKFAANINKESIVDVEGVVRKVNQK

IGSCTQQDVELHVQKIYVISLAEPRLPLQLDDAVRPEAEGEEEGRATVNQDTRLDNRVIDLRTSTS

QAVFRLQSGICHLFRETLINKGFVEIQTPKIISAASEGGANVFTVSYFKNNAYLAQSPQLYKQMCI

CADFEKVFSIGPVFRAEDSNTHRHLTEFVGLDIEMAFNYHYHEVMEEIADTMVQIFKGLQERFQT

EIQTVNKQFPSEPFKFLEPTLRLEYCEALAMLREAGVEMGDEDDLSTPNEKLLGHLVKEKYDTDF

YILDKYPLAVRPFYTMPDPRNPKQSNSYDMFMRGEEILSGAQRIHDPQLLTERALHHGIDLEKIK

AYIDSFRFGAPPHAGGGIGLERVTMLFLGLHNVRQTSMFPRDPKRLTP
```

2. DRS C349S:

(SEQ ID NO: 190)

```
MPSASASRKSQEKPREIMDAAEDYAKERYGISSMIQSQEKPDRVLVRVRDLTIQKADEVVWVRA

RVHTSRAKGKQCFLVLRQQQFNVQALVAVGDHASKQMVKFAANINKESIVDVEGVVRKVNQK

IGSCTQQDVELHVQKIYVISLAEPRLPLQLDDAVRPEAEGEEEGRATVNQDTRLDNRVIDLRTSTS

QAVFRLQSGICHLFRETLINKGFVEIQTPKIISAASEGGANVFTVSYFKNNAYLAQSPQLYKQMCI

CADFEKVFSIGPVFRAEDSNTHRHLTEFVGLDIEMAFNYHYHEVMEEIADTMVQIFKGLQERFQT

EIQTVNKQFPCEPFKFLEPTLRLEYSEALAMLREAGVEMGDEDDLSTPNEKLLGHLVKEKYDTDF

YILDKYPLAVRPFYTMPDPRNPKQSNSYDMFMRGEEILSGAQRIHDPQLLTERALHHGIDLEKIK

AYIDSFRFGAPPHAGGGIGLERVTMLFLGLHNVRQTSMFPRDPKRLTP
```

3. DRS C334S/C349S:

(SEQ ID NO: 191)

```
MPSASASRKSQEKPREIMDAAEDYAKERYGISSMIQSQEKPDRVLVRVRDLTIQKADEVVWVRA

RVHTSRAKGKQCFLVLRQQQFNVQALVAVGDHASKQMVKFAANINKESIVDVEGVVRKVNQK

IGSCTQQDVELHVQKIYVISLAEPRLPLQLDDAVRPEAEGEEEGRATVNQDTRLDNRVIDLRTSTS

QAVFRLQSGICHLFRETLINKGFVEIQTPKIISAASEGGANVFTVSYFKNNAYLAQSPQLYKQMCI

CADFEKVFSIGPVFRAEDSNTHRHLTEFVGLDIEMAFNYHYHEVMEEIADTMVQIFKGLQERFQT

EIQTVNKQFPSEPFKFLEPTLRLEYSEALAMLREAGVEMGDEDDLSTPNEKLLGHLVKEKYDTDF

YILDKYPLAVRPFYTMPDPRNPKQSNSYDMFMRGEEILSGAQRIHDPQLLTERALHHGIDLEKIK

AYIDSFRFGAPPHAGGGIGLERVTMLFLGLHNVRQTSMFPRDPKRLTP
```

4. DRS C203A:

(SEQ ID NO: 192)

```
MPSASASRKSQEKPREIMDAAEDYAKERYGISSMIQSQEKPDRVLVRVRDLTIQKADEVVWVRA

RVHTSRAKGKQCFLVLRQQQFNVQALVAVGDHASKQMVKFAANINKESIVDVEGVVRKVNQK

IGSCTQQDVELHVQKIYVISLAEPRLPLQLDDAVRPEAEGEEEGRATVNQDTRLDNRVIDLRTSTS

QAVFRLQSGIAHLFRETLINKGFVEIQTPKIISAASEGGANVFTVSYFKNNAYLAQSPQLYKQMCI

CADFEKVFSIGPVFRAEDSNTHRHLTEFVGLDIEMAFNYHYHEVMEEIADTMVQIFKGLQERFQT

EIQTVNKQFPCEPFKFLEPTLRLEYCEALAMLREAGVEMGDEDDLSTPNEKLLGHLVKEKYDTD

FYILDKYPLAVRPFYTMPDPRNPKQSNSYDMFMRGEEILSGAQRIHDPQLLTERALHHGIDLEKIK

AYIDSFRFGAPPHAGGGIGLERVTMLFLGLHNVRQTSMFPRDPKRLTP
```

-continued

5. DRS C203V:
(SEQ ID NO: 193)
MPSASASRKSQEKPREIMDAAEDYAKERYGISSMIQSQEKPDRVLVRVRDLTIQKADEVVWVRA

RVHTSRAKGKQCFLVLRQQQFNVQALVAVGDHASKQMVKFAANINKESIVDVEGVVRKVNQK

IGSCTQQDVELHVQKIYVISLAEPRLPLQLDDAVRPEAEGEEEGRATVNQDTRLDNRVIDLRTSTS

QAVFRLQSGIVHLFRETLINKGFVEIQTPKIISAASEGGANVFTVSYFKNNAYLAQSPQLYKQMCI

CADFEKVFSIGPVFRAEDSNTHRHLTEFVGLDIEMAFNYHYHEVMEEIADTMVQIFKGLQERFQT

EIQTVNKQFPCEPFKFLEPTLRLEYCEALAMLREAGVEMGDEDDLSTPNEKLLGHLVKEKYDTD

FYILDKYPLAVRPFYTMPDPRNPKQSNSYDMFMRGEEILSGAQRIHDPQLLTERALHHGIDLEKIK

AYIDSFRFGAPPHAGGGIGLERVTMLFLGLHNVRQTSMFPRDPKRLTP

6. DRS C334S/C349S/C203A:
(SEQ ID NO: 194)
MPSASASRKSQEKPREIMDAAEDYAKERYGISSMIQSQEKPDRVLVRVRDLTIQKADEVVWVRA

RVHTSRAKGKQCFLVLRQQQFNVQALVAVGDHASKQMVKFAANINKESIVDVEGVVRKVNQK

IGSCTQQDVELHVQKIYVISLAEPRLPLQLDDAVRPEAEGEEEGRATVNQDTRLDNRVIDLRTSTS

QAVFRLQSGIAHLFRETLINKGFVEIQTPKIISAASEGGANVFTVSYFKNNAYLAQSPQLYKQMCI

CADFEKVFSIGPVFRAEDSNTHRHLTEFVGLDIEMAFNYHYHEVMEEIADTMVQIFKGLQERFQT

EIQTVNKQFPSEPFKFLEPTLRLEYSEALAMLREAGVEMGDEDDLSTPNEKLLGHLVKEKYDTDF

YILDKYPLAVRPFYTMPDPRNPKQSNSYDMFMRGEEILSGAQRIHDPQLLTERALHHGIDLEKIK

AYIDSFRFGAPPHAGGGIGLERVTMLFLGLHNVRQTSMFPRDPKRLTP

7. DRS C334S/C349S/C203V
(SEQ ID NO: 195)
MPSASASRKSQEKPREIMDAAEDYAKERYGISSMIQSQEKPDRVLVRVRDLTIQKADEVVWVRA

RVHTSRAKGKQCFLVLRQQQFNVQALVAVGDHASKQMVKFAANINKESIVDVEGVVRKVNQK

IGSCTQQDVELHVQKIYVISLAEPRLPLQLDDAVRPEAEGEEEGRATVNQDTRLDNRVIDLRTSTS

QAVFRLQSGIVHLFRETLINKGFVEIQTPKIISAASEGGANVFTVSYFKNNAYLAQSPQLYKQMCI

AADFEKVFSIGPVFRAEDSNTHRHLTEFVGLDIEMAFNYHYHEVMEEIADTMVQIFKGLQERFQT

EIQTVNKQFPSEPFKFLEPTLRLEYSEALAMLREAGVEMGDEDDLSTPNEKLLGHLVKEKYDTDF

YILDKYPLAVRPFYTMPDPRNPKQSNSYDMFMRGEEILSGAQRIHDPQLLTERALHHGIDLEKIK

AYIDSFRFGAPPHAGGGIGLERVTMLFLGLHNVRQTSMFPRDPKRLTP

8. DRS C334S/C349S/C259A/C203A:
(SEQ ID NO: 196)
MPSASASRKSQEKPREIMDAAEDYAKERYGISSMIQSQEKPDRVLVRVRDLTIQKADEVVWVRA

RVHTSRAKGKQCFLVLRQQQFNVQALVAVGDHASKQMVKFAANINKESIVDVEGVVRKVNQK

IGSCTQQDVELHVQKIYVISLAEPRLPLQLDDAVRPEAEGEEEGRATVNQDTRLDNRVIDLRTSTS

QAVFRLQSGIAHLFRETLINKGFVEIQTPKIISAASEGGANVFTVSYFKNNAYLAQSPQLYKQMCI

AADFEKVFSIGPVFRAEDSNTHRHLTEFVGLDIEMAFNYHYHEVMEEIADTMVQIFKGLQERFQT

EIQTVNKQFPSEPFKFLEPTLRLEYSEALAMLREAGVEMGDEDDLSTPNEKLLGHLVKEKYDTDF

YILDKYPLAVRPFYTMPDPRNPKQSNSYDMFMRGEEILSGAQRIHDPQLLTERALHHGIDLEKIK

AYIDSFRFGAPPHAGGGIGLERVTMLFLGLHNVRQTSMFPRDPKRLTP

9. DRS C334S/C349S/C259A/C203V:
(SEQ ID NO: 197)
MPSASASRKSQEKPREIMDAAEDYAKERYGISSMIQSQEKPDRVLVRVRDLTIQKADEVVWVRA

RVHTSRAKGKQCFLVLRQQQFNVQALVAVGDHASKQMVKFAANINKESIVDVEGVVRKVNQK

IGSCTQQDVELHVQKIYVISLAEPRLPLQLDDAVRPEAEGEEEGRATVNQDTRLDNRVIDLRTSTS

QAVFRLQSGIVHLFRETLINKGFVEIQTPKIISAASEGGANVFTVSYFKNNAYLAQSPQLYKQMCI

-continued

AADFEKVFSIGPVFRAEDSNTHRHLTEFVGLDIEMAFNYHYHEVMEEIADTMVQIFKGLQERFQT

EIQTVNKQFPSEPFKFLEPTLRLEYSEALAMLREAGVEMGDEDDLSTPNEKLLGHLVKEKYDTDF

YILDKYPLAVRPFYTMPDPRNPKQSNSYDMFMRGEEILSGAQRIHDPQLLTERALHHGIDLEKIK

AYIDSFRFGAPPHAGGGIGLERVTMLFLGLHNVRQTSMFPRDPKRLTP

Expression of DRS Cysteine Mutants:

DRS cysteine mutant constructs were transformed into BL21 (DE3) competent cells (Novagen, cat. N. 69450-4) and expressed in LB media in flask at 30° C. for 16 hrs.

Purification of DRS Cysteine Mutants:

Frozen cell pellets were resuspended in lysis buffer (50 mM Tris, 300 mM NaCl, 25 mM Imidazole, 5 mM DTT, pH 8.0 with complete EDTA-FREE protease inhibitor cocktail tablets (Roche cat. no: 05 056 489 001) and the then rotated for 30 mins at 4° C. with 300 mg chicken egg lysozyme. The suspension was sonicated for two cycles 50% and 75% for 60 seconds each with 10 second on and 5 second off. The lysate was centrifuged at 35,000×g for 45 min at 4° C. The supernatant was filtered through 0.22 μm Sartobran capsule filters (Sartorius). The clarified lysate was bound to the Ni-NTA resin (Qiagen), pre-equilibrated with Ni-NTA Binding Buffer (50 mM Tris, 300 mM NaCl, 25 mM Imidazole, 5 mM DTT, pH 8.0). The column was washed with 1000 column volumes of Ni-NTA Binding Buffer plus 0.1% Triton X-114 and 5 mM DTT followed by 50 column volumes of the Ni-NTA Binding Buffer. The bound protein was eluted with 5 column volumes of Ni-NTA Elution Buffer (50 mM Tris, 300 mM NaCl, 300 mM Imidazole, 1 mM DTT pH 8.0).

The purified proteins were dialyzed into a PBS. The dialyzed protein was passed through a Q membrane filter (Sartobind-Q from Sartorius or Mustang-Q from Pall) or a Q-Sepharose column (GE Healthcare) for further endotoxin removal when endotoxin level is detectable using Charles River endotoxin detection kit (product code: PTS20), and then filtered through a 0.22 μm sterile filter.

Testing of the relative activity of the purified proteins compared in the HEK293-TLR2 and HEK293-TLR4 expressing cell lines as described above confirmed that the proteins were active (data not shown).

Comparison of Production Yield and Stability of Purified DRS Cysteine Mutants:

Purification yield of each DRS cysteine mutant is summarized in Table E9. Tm of these mutants is measured by DSF (differential scanning fluorimetry) using Protein Thermo Shift Dye Kit from Life Technologies (cat. no. 4461146) following the manufacturer's instructions. Stability was assessed by incubating 50 μl of each of thr DRS cysteine mutants in PBS at 1 mg/ml at 37° C. for 1 hr, and then by running an analytical SEC column (YMC America, Inc, cat. no. YMC-Pack Diol-300) using 200 mM phosphate, 100 mM NaCl pH7.0 as running buffer to compare monomer loss with samples before incubation.

TABLE E9

| Variant | Yield (mg/L) | Tm (° C., in PBS) | % monomer loss* |
|---|---|---|---|
| wild type | 6.8 | 47.7 | + |
| C334S | 6.5 | 53.2 | +++++ |
| C349S | 16.9 | 53.8 | ++ |
| C334S/C349S | 11.9 | 53.8 | +++ |

TABLE E9-continued

| Variant | Yield (mg/L) | Tm (° C., in PBS) | % monomer loss* |
|---|---|---|---|
| C203A | 9.3 | 53.1 | NA |
| C203V | 10.2 | 53.5 | NA |
| C334S/C349S/C203A | 12.7 | 53.8 | + |
| C3334S/C349S/C203V | 13.9 | 53.4 | + |
| C334S/C3349S/C259A/C203A | 16.8 | 50.8 | + |
| C334S/C349S/C259A/C203V | 11.1 | 51 | + |

*monomer loss after 1 hr incubation at 37° C.

+: >5%;

++: >50%;

+++: 75%;

+++++: >90%;

NA: no loss

The results demonstrate that the cysteine mutants at position 203 display enhanced stability, and reduced tendency for aggregation formation. Surprisingly the C203 mutants also enhanced stability in the context of mutations at position C334, C349 and C259, even if these mutations alone did not themselves confer significantly enhanced stability alone. The results thus demonstrate that C203 represents a key residue in the non specific cysteine dependent aggregation of DRS.

Example 7

Construction and Production of Truncated Homeokine (DRS) Mutants

To systematically evaluate the minimal active, and most stable N-terminal DRS polypeptide fragment, a series of N-terminal, C-terminal and double truncated Homeokine (DRS 1-154) variants were made using the primers listed in Table E10. The corresponding DNA and protein sequences for the constructs are listed below. Briefly, the N-terminal truncated form variants of Homeokine (DRS) were designed by truncating two amino acids at a time from the N- or C terminus of the Homeokine (DRS 1-154) sequence. Additionally a series of C-terminal extension variants was created to extend the C-terminal of the Homeokine sequence from amino acid 154 to 182 by 2 amino acid additions. Double truncated Homeokine variants were designed based on the DRS structure in order to define a minimally active core domain of Homeokine.

TABLE E10

| HK variants | Primers | SEQ ID NO |
|---|---|---|
| C-terminal truncation variant | Reverse primers | |
| 1-148 | 5'- GGG TTA GGG ATA GGC TTA CCA GCC AAA CTG ATC ACA TAA ATC -3' | 247 |
| 1-150 | 5'- GGG TTA GGG ATA GGC TTA CCG GGT TCA GCC AAA CTG ATC AC -3' | 248 |
| 1-152 | 5'- GGG TTA GGG ATA GGC TTA CCC AGA CGG GGT TCA GCC AAA C -3' | 249 |
| 1-156 | 5'- GGG TTA GGG ATA GGC TTA CCC AGC TGC AGG GGC AGA CGG GG -3' | 250 |
| 1-158 | 5'- GGG TTA GGG ATA GGC TTA CCA TCA TCC AGC TGC AGG GGC AG -3' | 251 |
| 1-160 | 5'- GGG TTA GGG ATA GGC TTA CCA ACA GCA TCA TCC AGC TGC AGG -3' | 252 |
| 1-162 | 5'- GGG TTA GGG ATA GGC TTA CCA GGC CGA ACA GCA TCA TCC AG -3' | 253 |
| 1-164 | 5'- GGG TTA GGG ATA GGC TTA CCT GCC TCA GGC CGA ACA GCA TC -3' | 254 |
| 1-166 | 5'- GGG TTA GGG ATA GGC TTA CCT CCT TCT GCC TCA GGC CGA AC -3' | 255 |
| 1-168 | 5'- GGG TTA GGG ATA GGC TTA CCC TCT TCT CCT TCT GCC TCA GG -3' | 256 |
| 1-170 | 5'- GGG TTA GGG ATA GGC TTA CCT CCT TCC TCT TCT CCT TCT GC -3' | 257 |
| 1-172 | 5'- GGG TTA GGG ATA GGC TTA CCA GCT CTT CCT TCC TCT TCT CC -3' | 258 |
| 1-176 | 5'- GGG TTA GGG ATA GGC TTA CCC TGG TTA ACA GTA GCT CTT CC -3' | 259 |
| 1-178 | 5'- GGG TTA GGG ATA GGC TTA CCT GTA TCC TGG TTA ACA GTA GC -3' | 260 |
| 1-180 | 5'- GGG TTA GGG ATA GGC TTA CCT AAT CTT GTA TCC TGG TTA AC -3' | 261 |
| 1-182 | 5'-GGG TTA GGG ATA GGC TTA CCG TTG TCT AAT CTT GTA TCC TGG-3' | 262 |
| N-terminal truncation variant | Forward primers | |
| 3-154 | 5'- GAA GGA GAT ATA CCATGA GCG CCA GCG CCA GCC G -3' | 263 |
| 5-154 | 5'- GAA GGA GAT ATA CCATGA GCG CCA GCC GCA AGA G -3' | 264 |
| 7-154 | 5'- GAA GGA GAT ATA CCATGA GCC GCA AGA GTC AGG AG-3' | 265 |
| 9-154 | 5'- GAA GGA GAT ATA CCATGA AGA GTC AGG AGA AGC C -3' | 266 |
| 11-154 | 5'-GAAGGAGATATCATATGCAGGAGAAGCCGCGGGAG-3' | 267 |
| 13-154 | 5'-GAAGGAGATATCATATGAAGCCGCGGGAGATCATG-3' | 268 |
| 15-154 | 5'-GAAGGAGATATCATATGCGGGAGATCATGGACGCGG-3' | 269 |
| 17-154 | 5'-GAAGGAGATATCATATGATCATGGACGCGGCGG-3' | 270 |
| 21-154 | 5'-GAAGGAGATATCATATGGCGGAAGATTATGCTAAAG-3' | 271 |
| 23-154 | 5'-GAAGGAGATATCATATGGATTATGCTAAAG-3' | 272 |
| double truncated HK variant | Forward primers | |
| 11-146-F | 5'-ACC GAT CAC ATA TGC AGG AGA AGC CGC GGG AGA TCA TGG A-3' | 273 |
| 13-146-F | 5'-AAG CTT ACG CAT ATG AAG CCG CGG GAG ATC ATG GAC GCG-3' | 274 |
| 17-146-F | 5'-AAC TGT TAC CAT ATG ATC ATG GAC GCG GCG GAA GAT TAT G-3' | 275 |
| 21-146-F | 5'-AAC TGT CAT CAT ATG GCG GAA GAT TAT GCT AAA GAG AGA TAT-3' | 276 |

TABLE E10-continued

| HK variants | Primers | SEQ ID NO |
|---|---|---|
| | Reverse primer | |
| X-146-R | 5'-TGA CGG CTC GAG ACT GAT CAC ATA AAT CTT CTG-3' | 277 |
| | Forward primers | |
| A106C-F | 5'-GCA GAT GGT TAA ATT TGC TTG CAA CAT CAA CAA AGA GAG CAT TGT GG-3' | 278 |

The truncated Homeokine (DRS) DNA sequences are as follows

DRS 1-182

(SEQ ID NO: 207)
ATGCCCAGCGCCAGCGCCAGCCGCAAGAGTCAGGAGAAGCCGCGGGAGATCATGGACGCG

GCGGAAGATTATGCTAAAGAGAGATATGGAATATCTTCAATGATACAATCACAAGAAAAAC

CAGATCGAGTTTTGGTTCGGGTTAGAGACTTGACAATACAAAAAGCTGATGAAGTTGTTTGG

GTACGTGCAAGAGTTCATACAAGCAGAGCTAAAGGGAAACAGTGCTTCTTAGTCCTACGTCA

GCAGCAGTTTAATGTCCAGGCTCTTGTGGCGGTGGGAGACCATGCAAGCAAGCAGATGGTT

AAATTTGCTGCCAACATCAACAAAGAGAGCATTGTGGATGTAGAAGGTGTTGTGAGAAAAG

TGAATCAGAAAATTGGAAGCTGTACACAGCAAGACGTTGAGTTACATGTTCAGAAGATTTAT

GTGATCAGTTTGGCTGAACCCCGTCTGCCCCTGCAGCTGGATGATGCTGTTCGGCCTGAGGC

AGAAGGAGAAGAGGAAGGAAGAGCTACTGTTAACCAGGATACAAGATTAGACAAC

DRS 1-180

(SEQ ID NO: 208)
ATGCCCAGCGCCAGCGCCAGCCGCAAGAGTCAGGAGAAGCCGCGGGAGATCATGGACGCG

GCGGAAGATTATGCTAAAGAGAGATATGGAATATCTTCAATGATACAATCACAAGAAAAAC

CAGATCGAGTTTTGGTTCGGGTTAGAGACTTGACAATACAAAAAGCTGATGAAGTTGTTTGG

GTACGTGCAAGAGTTCATACAAGCAGAGCTAAAGGGAAACAGTGCTTCTTAGTCCTACGTCA

GCAGCAGTTTAATGTCCAGGCTCTTGTGGCGGTGGGAGACCATGCAAGCAAGCAGATGGTT

AAATTTGCTGCCAACATCAACAAAGAGAGCATTGTGGATGTAGAAGGTGTTGTGAGAAAAG

TGAATCAGAAAATTGGAAGCTGTACACAGCAAGACGTTGAGTTACATGTTCAGAAGATTTAT

GTGATCAGTTTGGCTGAACCCCGTCTGCCCCTGCAGCTGGATGATGCTGTTCGGCCTGAGGC

AGAAGGAGAAGAGGAAGGAAGAGCTACTGTTAACCAGGATACAAGATTA

DRS 1-178

(SEQ ID NO: 209)
ATGCCCAGCGCCAGCGCCAGCCGCAAGAGTCAGGAGAAGCCGCGGGAGATCATGGACGCG

GCGGAAGATTATGCTAAAGAGAGATATGGAATATCTTCAATGATACAATCACAAGAAAAAC

CAGATCGAGTTTTGGTTCGGGTTAGAGACTTGACAATACAAAAAGCTGATGAAGTTGTTTGG

GTACGTGCAAGAGTTCATACAAGCAGAGCTAAAGGGAAACAGTGCTTCTTAGTCCTACGTCA

GCAGCAGTTTAATGTCCAGGCTCTTGTGGCGGTGGGAGACCATGCAAGCAAGCAGATGGTT

AAATTTGCTGCCAACATCAACAAAGAGAGCATTGTGGATGTAGAAGGTGTTGTGAGAAAAG

TGAATCAGAAAATTGGAAGCTGTACACAGCAAGACGTTGAGTTACATGTTCAGAAGATTTAT

GTGATCAGTTTGGCTGAACCCCGTCTGCCCCTGCAGCTGGATGATGCTGTTCGGCCTGAGGC

AGAAGGAGAAGAGGAAGGAAGAGCTACTGTTAACCAGGATACA

-continued

DRS 1-176
(SEQ ID NO: 210)
ATGCCCAGCGCCAGCGCCAGCCGCAAGAGTCAGGAGAAGCCGCGGGAGATCATGGACGCG

GCGGAAGATTATGCTAAAGAGAGATATGGAATATCTTCAATGATACAATCACAAGAAAAAC

CAGATCGAGTTTTGGTTCGGGTTAGAGACTTGACAATACAAAAAGCTGATGAAGTTGTTTGG

GTACGTGCAAGAGTTCATACAAGCAGAGCTAAAGGGAAACAGTGCTTCTTAGTCCTACGTCA

GCAGCAGTTTAATGTCCAGGCTCTTGTGGCGGTGGGAGACCATGCAAGCAAGCAGATGGTT

AAATTTGCTGCCAACATCAACAAAGAGAGCATTGTGGATGTAGAAGGTGTTGTGAGAAAAG

TGAATCAGAAAATTGGAAGCTGTACACAGCAAGACGTTGAGTTACATGTTCAGAAGATTTAT

GTGATCAGTTTGGCTGAACCCCGTCTGCCCCTGCAGCTGGATGATGCTGTTCGGCCTGAGGC

AGAAGGAGAAGAGGAAGGAAGAGCTACTGTTAACCAG

DRS 1-174
(SEQ ID NO: 211)
ATGCCCAGCGCCAGCGCCAGCCGCAAGAGTCAGGAGAAGCCGCGGGAGATCATGGACGCG

GCGGAAGATTATGCTAAAGAGAGATATGGAATATCTTCAATGATACAATCACAAGAAAAAC

CAGATCGAGTTTTGGTTCGGGTTAGAGACTTGACAATACAAAAAGCTGATGAAGTTGTTTGG

GTACGTGCAAGAGTTCATACAAGCAGAGCTAAAGGGAAACAGTGCTTCTTAGTCCTACGTCA

GCAGCAGTTTAATGTCCAGGCTCTTGTGGCGGTGGGAGACCATGCAAGCAAGCAGATGGTT

AAATTTGCTGCCAACATCAACAAAGAGAGCATTGTGGATGTAGAAGGTGTTGTGAGAAAAG

TGAATCAGAAAATTGGAAGCTGTACACAGCAAGACGTTGAGTTACATGTTCAGAAGATTTAT

GTGATCAGTTTGGCTGAACCCCGTCTGCCCCTGCAGCTGGATGATGCTGTTCGGCCTGAGGC

AGAAGGAGAAGAGGAAGGAAGAGCTACTGTT

DRS 1-172
(SEQ ID NO: 212)
ATGCCCAGCGCCAGCGCCAGCCGCAAGAGTCAGGAGAAGCCGCGGGAGATCATGGACGCG

GCGGAAGATTATGCTAAAGAGAGATATGGAATATCTTCAATGATACAATCACAAGAAAAAC

CAGATCGAGTTTTGGTTCGGGTTAGAGACTTGACAATACAAAAAGCTGATGAAGTTGTTTGG

GTACGTGCAAGAGTTCATACAAGCAGAGCTAAAGGGAAACAGTGCTTCTTAGTCCTACGTCA

GCAGCAGTTTAATGTCCAGGCTCTTGTGGCGGTGGGAGACCATGCAAGCAAGCAGATGGTT

AAATTTGCTGCCAACATCAACAAAGAGAGCATTGTGGATGTAGAAGGTGTTGTGAGAAAAG

TGAATCAGAAAATTGGAAGCTGTACACAGCAAGACGTTGAGTTACATGTTCAGAAGATTTAT

GTGATCAGTTTGGCTGAACCCCGTCTGCCCCTGCAGCTGGATGATGCTGTTCGGCCTGAGGC

AGAAGGAGAAGAGGAAGGAAGAGCT

DRS 1-170
(SEQ ID NO: 213)
ATGCCCAGCGCCAGCGCCAGCCGCAAGAGTCAGGAGAAGCCGCGGGAGATCATGGACGCG

GCGGAAGATTATGCTAAAGAGAGATATGGAATATCTTCAATGATACAATCACAAGAAAAAC

CAGATCGAGTTTTGGTTCGGGTTAGAGACTTGACAATACAAAAAGCTGATGAAGTTGTTTGG

GTACGTGCAAGAGTTCATACAAGCAGAGCTAAAGGGAAACAGTGCTTCTTAGTCCTACGTCA

GCAGCAGTTTAATGTCCAGGCTCTTGTGGCGGTGGGAGACCATGCAAGCAAGCAGATGGTT

AAATTTGCTGCCAACATCAACAAAGAGAGCATTGTGGATGTAGAAGGTGTTGTGAGAAAAG

TGAATCAGAAAATTGGAAGCTGTACACAGCAAGACGTTGAGTTACATGTTCAGAAGATTTAT

GTGATCAGTTTGGCTGAACCCCGTCTGCCCCTGCAGCTGGATGATGCTGTTCGGCCTGAGGC

AGAAGGAGAAGAGGAAGGA

-continued

DRS 1-168
(SEQ ID NO: 214)
ATGCCCAGCGCCAGCGCCAGCCGCAAGAGTCAGGAGAAGCCGCGGGAGATCATGGACGCG

GCGGAAGATTATGCTAAAGAGAGATATGGAATATCTTCAATGATACAATCACAAGAAAAAC

CAGATCGAGTTTTGGTTCGGGTTAGAGACTTGACAATACAAAAAGCTGATGAAGTTGTTTGG

GTACGTGCAAGAGTTCATACAAGCAGAGCTAAAGGGAAACAGTGCTTCTTAGTCCTACGTCA

GCAGCAGTTTAATGTCCAGGCTCTTGTGGCGGTGGGAGACCATGCAAGCAAGCAGATGGTT

AAATTTGCTGCCAACATCAACAAAGAGAGCATTGTGGATGTAGAAGGTGTTGTGAGAAAAG

TGAATCAGAAAATTGGAAGCTGTACACAGCAAGACGTTGAGTTACATGTTCAGAAGATTTAT

GTGATCAGTTTGGCTGAACCCCGTCTGCCCCTGCAGCTGGATGATGCTGTTCGGCCTGAGGC

AGAAGGAGAAGAG

DRS 1-166
(SEQ ID NO: 215)
ATGCCCAGCGCCAGCGCCAGCCGCAAGAGTCAGGAGAAGCCGCGGGAGATCATGGACGCG

GCGGAAGATTATGCTAAAGAGAGATATGGAATATCTTCAATGATACAATCACAAGAAAAAC

CAGATCGAGTTTTGGTTCGGGTTAGAGACTTGACAATACAAAAAGCTGATGAAGTTGTTTGG

GTACGTGCAAGAGTTCATACAAGCAGAGCTAAAGGGAAACAGTGCTTCTTAGTCCTACGTCA

GCAGCAGTTTAATGTCCAGGCTCTTGTGGCGGTGGGAGACCATGCAAGCAAGCAGATGGTT

AAATTTGCTGCCAACATCAACAAAGAGAGCATTGTGGATGTAGAAGGTGTTGTGAGAAAAG

TGAATCAGAAAATTGGAAGCTGTACACAGCAAGACGTTGAGTTACATGTTCAGAAGATTTAT

GTGATCAGTTTGGCTGAACCCCGTCTGCCCCTGCAGCTGGATGATGCTGTTCGGCCTGAGGC

AGAAGGA

DRS 1-164
(SEQ ID NO: 216)
ATGCCCAGCGCCAGCGCCAGCCGCAAGAGTCAGGAGAAGCCGCGGGAGATCATGGACGCG

GCGGAAGATTATGCTAAAGAGAGATATGGAATATCTTCAATGATACAATCACAAGAAAAAC

CAGATCGAGTTTTGGTTCGGGTTAGAGACTTGACAATACAAAAAGCTGATGAAGTTGTTTGG

GTACGTGCAAGAGTTCATACAAGCAGAGCTAAAGGGAAACAGTGCTTCTTAGTCCTACGTCA

GCAGCAGTTTAATGTCCAGGCTCTTGTGGCGGTGGGAGACCATGCAAGCAAGCAGATGGTT

AAATTTGCTGCCAACATCAACAAAGAGAGCATTGTGGATGTAGAAGGTGTTGTGAGAAAAG

TGAATCAGAAAATTGGAAGCTGTACACAGCAAGACGTTGAGTTACATGTTCAGAAGATTTAT

GTGATCAGTTTGGCTGAACCCCGTCTGCCCCTGCAGCTGGATGATGCTGTTCGGCCTGAGGC

A

DRS 1-162
(SEQ ID NO: 217)
ATGCCCAGCGCCAGCGCCAGCCGCAAGAGTCAGGAGAAGCCGCGGGAGATCATGGACGCG

GCGGAAGATTATGCTAAAGAGAGATATGGAATATCTTCAATGATACAATCACAAGAAAAAC

CAGATCGAGTTTTGGTTCGGGTTAGAGACTTGACAATACAAAAAGCTGATGAAGTTGTTTGG

GTACGTGCAAGAGTTCATACAAGCAGAGCTAAAGGGAAACAGTGCTTCTTAGTCCTACGTCA

GCAGCAGTTTAATGTCCAGGCTCTTGTGGCGGTGGGAGACCATGCAAGCAAGCAGATGGTT

AAATTTGCTGCCAACATCAACAAAGAGAGCATTGTGGATGTAGAAGGTGTTGTGAGAAAAG

TGAATCAGAAAATTGGAAGCTGTACACAGCAAGACGTTGAGTTACATGTTCAGAAGATTTAT

GTGATCAGTTTGGCTGAACCCCGTCTGCCCCTGCAGCTGGATGATGCTGTTCGGCCT

-continued

DRS 1-160
(SEQ ID NO: 218)
ATGCCCAGCGCCAGCGCCAGCCGCAAGAGTCAGGAGAAGCCGCGGGAGATCATGGACGCG

GCGGAAGATTATGCTAAAGAGAGATATGGAATATCTTCAATGATACAATCACAAGAAAAAC

CAGATCGAGTTTTGGTTCGGGTTAGAGACTTGACAATACAAAAAGCTGATGAAGTTGTTTGG

GTACGTGCAAGAGTTCATACAAGCAGAGCTAAAGGGAAACAGTGCTTCTTAGTCCTACGTCA

GCAGCAGTTTAATGTCCAGGCTCTTGTGGCGGTGGGAGACCATGCAAGCAAGCAGATGGTT

AAATTTGCTGCCAACATCAACAAAGAGAGCATTGTGGATGTAGAAGGTGTTGTGAGAAAAG

TGAATCAGAAAATTGGAAGCTGTACACAGCAAGACGTTGAGTTACATGTTCAGAAGATTTAT

GTGATCAGTTTGGCTGAACCCCGTCTGCCCCTGCAGCTGGATGATGCTGTT

DRS 1-158
(SEQ ID NO: 219)
ATGCCCAGCGCCAGCGCCAGCCGCAAGAGTCAGGAGAAGCCGCGGGAGATCATGGACGCG

GCGGAAGATTATGCTAAAGAGAGATATGGAATATCTTCAATGATACAATCACAAGAAAAAC

CAGATCGAGTTTTGGTTCGGGTTAGAGACTTGACAATACAAAAAGCTGATGAAGTTGTTTGG

GTACGTGCAAGAGTTCATACAAGCAGAGCTAAAGGGAAACAGTGCTTCTTAGTCCTACGTCA

GCAGCAGTTTAATGTCCAGGCTCTTGTGGCGGTGGGAGACCATGCAAGCAAGCAGATGGTT

AAATTTGCTGCCAACATCAACAAAGAGAGCATTGTGGATGTAGAAGGTGTTGTGAGAAAAG

TGAATCAGAAAATTGGAAGCTGTACACAGCAAGACGTTGAGTTACATGTTCAGAAGATTTAT

GTGATCAGTTTGGCTGAACCCCGTCTGCCCCTGCAGCTGGATGAT

DRS 1-156
(SEQ ID NO: 220)
ATGCCCAGCGCCAGCGCCAGCCGCAAGAGTCAGGAGAAGCCGCGGGAGATCATGGACGCG

GCGGAAGATTATGCTAAAGAGAGATATGGAATATCTTCAATGATACAATCACAAGAAAAAC

CAGATCGAGTTTTGGTTCGGGTTAGAGACTTGACAATACAAAAAGCTGATGAAGTTGTTTGG

GTACGTGCAAGAGTTCATACAAGCAGAGCTAAAGGGAAACAGTGCTTCTTAGTCCTACGTCA

GCAGCAGTTTAATGTCCAGGCTCTTGTGGCGGTGGGAGACCATGCAAGCAAGCAGATGGTT

AAATTTGCTGCCAACATCAACAAAGAGAGCATTGTGGATGTAGAAGGTGTTGTGAGAAAAG

TGAATCAGAAAATTGGAAGCTGTACACAGCAAGACGTTGAGTTACATGTTCAGAAGATTTAT

GTGATCAGTTTGGCTGAACCCCGTCTGCCCCTGCAGCTG

DRS 1-154
(SEQ ID NO: 221)
ATGCCCAGCGCCAGCGCCAGCCGCAAGAGTCAGGAGAAGCCGCGGGAGATCATGGACGCG

GCGGAAGATTATGCTAAAGAGAGATATGGAATATCTTCAATGATACAATCACAAGAAAAAC

CAGATCGAGTTTTGGTTCGGGTTAGAGACTTGACAATACAAAAAGCTGATGAAGTTGTTTGG

GTACGTGCAAGAGTTCATACAAGCAGAGCTAAAGGGAAACAGTGCTTCTTAGTCCTACGTCA

GCAGCAGTTTAATGTCCAGGCTCTTGTGGCGGTGGGAGACCATGCAAGCAAGCAGATGGTT

AAATTTGCTGCCAACATCAACAAAGAGAGCATTGTGGATGTAGAAGGTGTTGTGAGAAAAG

TGAATCAGAAAATTGGAAGCTGTACACAGCAAGACGTTGAGTTACATGTTCAGAAGATTTAT

GTGATCAGTTTGGCTGAACCCCGTCTGCCCCTG

DRS 1-152
(SEQ ID NO: 222)
ATGCCCAGCGCCAGCGCCAGCCGCAAGAGTCAGGAGAAGCCGCGGGAGATCATGGACGCG

GCGGAAGATTATGCTAAAGAGAGATATGGAATATCTTCAATGATACAATCACAAGAAAAAC

CAGATCGAGTTTTGGTTCGGGTTAGAGACTTGACAATACAAAAAGCTGATGAAGTTGTTTGG

-continued

GTACGTGCAAGAGTTCATACAAGCAGAGCTAAAGGGAAACAGTGCTTCTTAGTCCTACGTCA

GCAGCAGTTTAATGTCCAGGCTCTTGTGGCGGTGGGAGACCATGCAAGCAAGCAGATGGTT

AAATTTGCTGCCAACATCAACAAAGAGAGCATTGTGGATGTAGAAGGTGTTGTGAGAAAAG

TGAATCAGAAAATTGGAAGCTGTACACAGCAAGACGTTGAGTTACATGTTCAGAAGATTTAT

GTGATCAGTTTGGCTGAACCCCGTCTG

DRS 1-150
(SEQ ID NO: 223)
ATGCCCAGCGCCAGCGCCAGCCGCAAGAGTCAGGAGAAGCCGCGGGAGATCATGGACGCG

GCGGAAGATTATGCTAAAGAGAGATATGGAATATCTTCAATGATACAATCACAAGAAAAAC

CAGATCGAGTTTTGGTTCGGGTTAGAGACTTGACAATACAAAAAGCTGATGAAGTTGTTTGG

GTACGTGCAAGAGTTCATACAAGCAGAGCTAAAGGGAAACAGTGCTTCTTAGTCCTACGTCA

GCAGCAGTTTAATGTCCAGGCTCTTGTGGCGGTGGGAGACCATGCAAGCAAGCAGATGGTT

AAATTTGCTGCCAACATCAACAAAGAGAGCATTGTGGATGTAGAAGGTGTTGTGAGAAAAG

TGAATCAGAAAATTGGAAGCTGTACACAGCAAGACGTTGAGTTACATGTTCAGAAGATTTAT

GTGATCAGTTTGGCTGAACCC

DRS 1-148
(SEQ ID NO: 224)
ATGCCCAGCGCCAGCGCCAGCCGCAAGAGTCAGGAGAAGCCGCGGGAGATCATGGACGCG

GCGGAAGATTATGCTAAAGAGAGATATGGAATATCTTCAATGATACAATCACAAGAAAAAC

CAGATCGAGTTTTGGTTCGGGTTAGAGACTTGACAATACAAAAAGCTGATGAAGTTGTTTGG

GTACGTGCAAGAGTTCATACAAGCAGAGCTAAAGGGAAACAGTGCTTCTTAGTCCTACGTCA

GCAGCAGTTTAATGTCCAGGCTCTTGTGGCGGTGGGAGACCATGCAAGCAAGCAGATGGTT

AAATTTGCTGCCAACATCAACAAAGAGAGCATTGTGGATGTAGAAGGTGTTGTGAGAAAAG

TGAATCAGAAAATTGGAAGCTGTACACAGCAAGACGTTGAGTTACATGTTCAGAAGATTTAT

GTGATCAGTTTGGCT

DRS 1-146
(SEQ ID NO: 225)
ATGCCCAGCGCCAGCGCCAGCCGCAAGAGTCAGGAGAAGCCGCGGGAGATCATGGACGCG

GCGGAAGATTATGCTAAAGAGAGATATGGAATATCTTCAATGATACAATCACAAGAAAAAC

CAGATCGAGTTTTGGTTCGGGTTAGAGACTTGACAATACAAAAAGCTGATGAAGTTGTTTGG

GTACGTGCAAGAGTTCATACAAGCAGAGCTAAAGGGAAACAGTGCTTCTTAGTCCTACGTCA

GCAGCAGTTTAATGTCCAGGCTCTTGTGGCGGTGGGAGACCATGCAAGCAAGCAGATGGTT

AAATTTGCTGCCAACATCAACAAAGAGAGCATTGTGGATGTAGAAGGTGTTGTGAGAAAAG

TGAATCAGAAAATTGGAAGCTGTACACAGCAAGACGTTGAGTTACATGTTCAGAAGATTTAT

GTGATCAGT

DRS 3-154
(SEQ ID NO: 226)
GCCAGCGCCAGCCGCAAGAGTCAGGAGAAGCCGCGGGAGATCATGGACGCGGCGGAAGAT

TATGCTAAAGAGAGATATGGAATATCTTCAATGATACAATCACAAGAAAAACCAGATCGAG

TTTTGGTTCGGGTTAGAGACTTGACAATACAAAAAGCTGATGAAGTTGTTTGGGTACGTGCA

AGAGTTCATACAAGCAGAGCTAAAGGGAAACAGTGCTTCTTAGTCCTACGTCAGCAGCAGTT

TAATGTCCAGGCTCTTGTGGCGGTGGGAGACCATGCAAGCAAGCAGATGGTTAAATTTGCTG

CCAACATCAACAAAGAGAGCATTGTGGATGTAGAAGGTGTTGTGAGAAAAGTGAATCAGAA

AATTGGAAGCTGTACACAGCAAGACGTTGAGTTACATGTTCAGAAGATTTATGTGATCAGTT

TGGCTGAACCCCGTCTGCCCCTG

-continued

DRS 5-154

(SEQ ID NO: 227)

GCCAGCCGCAAGAGTCAGGAGAAGCCGCGGGAGATCATGGACGCGGCGGAAGATTATGCTA

AAGAGAGATATGGAATATCTTCAATGATACAATCACAAGAAAAACCAGATCGAGTTTTGGT

TCGGGTTAGAGACTTGACAATACAAAAAGCTGATGAAGTTGTTTGGGTACGTGCAAGAGTTC

ATACAAGCAGAGCTAAAGGGAAACAGTGCTTCTTAGTCCTACGTCAGCAGCAGTTTAATGTC

CAGGCTCTTGTGGCGGTGGGAGACCATGCAAGCAAGCAGATGGTTAAATTTGCTGCCAACAT

CAACAAAGAGAGCATTGTGGATGTAGAAGGTGTTGTGAGAAAAGTGAATCAGAAAATTGGA

AGCTGTACACAGCAAGACGTTGAGTTACATGTTCAGAAGATTTATGTGATCAGTTTGGCTGA

ACCCCGTCTGCCCCTG

DRS 7-154

(SEQ ID NO: 228)

CGCAAGAGTCAGGAGAAGCCGCGGGAGATCATGGACGCGGCGGAAGATTATGCTAAAGAG

AGATATGGAATATCTTCAATGATACAATCACAAGAAAAACCAGATCGAGTTTTGGTTCGGGT

TAGAGACTTGACAATACAAAAAGCTGATGAAGTTGTTTGGGTACGTGCAAGAGTTCATACA

AGCAGAGCTAAAGGGAAACAGTGCTTCTTAGTCCTACGTCAGCAGCAGTTTAATGTCCAGGC

TCTTGTGGCGGTGGGAGACCATGCAAGCAAGCAGATGGTTAAATTTGCTGCCAACATCAACA

AAGAGAGCATTGTGGATGTAGAAGGTGTTGTGAGAAAAGTGAATCAGAAAATTGGAAGCTG

TACACAGCAAGACGTTGAGTTACATGTTCAGAAGATTTATGTGATCAGTTTGGCTGAACCCC

GTCTGCCCCTG

DRS 9-154

(SEQ ID NO: 229)

AGTCAGGAGAAGCCGCGGGAGATCATGGACGCGGCGGAAGATTATGCTAAAGAGAGATAT

GGAATATCTTCAATGATACAATCACAAGAAAAACCAGATCGAGTTTTGGTTCGGGTTAGAGA

CTTGACAATACAAAAAGCTGATGAAGTTGTTTGGGTACGTGCAAGAGTTCATACAAGCAGA

GCTAAAGGGAAACAGTGCTTCTTAGTCCTACGTCAGCAGCAGTTTAATGTCCAGGCTCTTGT

GGCGGTGGGAGACCATGCAAGCAAGCAGATGGTTAAATTTGCTGCCAACATCAACAAAGAG

AGCATTGTGGATGTAGAAGGTGTTGTGAGAAAAGTGAATCAGAAAATTGGAAGCTGTACAC

AGCAAGACGTTGAGTTACATGTTCAGAAGATTTATGTGATCAGTTTGGCTGAACCCCGTCTG

CCCCTG

DRS 11-154

(SEQ ID NO: 230)

GAGAAGCCGCGGGAGATCATGGACGCGGCGGAAGATTATGCTAAAGAGAGATATGGAATAT

CTTCAATGATACAATCACAAGAAAAACCAGATCGAGTTTTGGTTCGGGTTAGAGACTTGACA

ATACAAAAAGCTGATGAAGTTGTTTGGGTACGTGCAAGAGTTCATACAAGCAGAGCTAAAG

GGAAACAGTGCTTCTTAGTCCTACGTCAGCAGCAGTTTAATGTCCAGGCTCTTGTGGCGGTG

GGAGACCATGCAAGCAAGCAGATGGTTAAATTTGCTGCCAACATCAACAAAGAGAGCATTG

TGGATGTAGAAGGTGTTGTGAGAAAAGTGAATCAGAAAATTGGAAGCTGTACACAGCAAGA

CGTTGAGTTACATGTTCAGAAGATTTATGTGATCAGTTTGGCTGAACCCCGTCTGCCCCTG

DRS 13-154

(SEQ ID NO: 231)

CCGCGGGAGATCATGGACGCGGCGGAAGATTATGCTAAAGAGAGATATGGAATATCTTCAA

TGATACAATCACAAGAAAAACCAGATCGAGTTTTGGTTCGGGTTAGAGACTTGACAATACA

AAAAGCTGATGAAGTTGTTTGGGTACGTGCAAGAGTTCATACAAGCAGAGCTAAAGGGAAA

CAGTGCTTCTTAGTCCTACGTCAGCAGCAGTTTAATGTCCAGGCTCTTGTGGCGGTGGGAGA

-continued

CCATGCAAGCAAGCAGATGGTTAAATTTGCTGCCAACATCAACAAAGAGAGCATTGTGGAT

GTAGAAGGTGTTGTGAGAAAAGTGAATCAGAAAATTGGAAGCTGTACACAGCAAGACGTTG

AGTTACATGTTCAGAAGATTTATGTGATCAGTTTGGCTGAACCCCGTCTGCCCCTG

DRS 15-154
(SEQ ID NO: 232)
GAGATCATGGACGCGGCGGAAGATTATGCTAAAGAGAGATATGGAATATCTTCAATGATAC

AATCACAAGAAAAACCAGATCGAGTTTTGGTTCGGGTTAGAGACTTGACAATACAAAAAGC

TGATGAAGTTGTTTGGGTACGTGCAAGAGTTCATACAAGCAGAGCTAAAGGGAAACAGTGC

TTCTTAGTCCTACGTCAGCAGCAGTTTAATGTCCAGGCTCTTGTGGCGGTGGGAGACCATGC

AAGCAAGCAGATGGTTAAATTTGCTGCCAACATCAACAAAGAGAGCATTGTGGATGTAGAA

GGTGTTGTGAGAAAAGTGAATCAGAAAATTGGAAGCTGTACACAGCAAGACGTTGAGTTAC

ATGTTCAGAAGATTTATGTGATCAGTTTGGCTGAACCCCGTCTGCCCCTG

DRS 17-154
(SEQ ID NO: 233)
ATGGACGCGGCGGAAGATTATGCTAAAGAGAGATATGGAATATCTTCAATGATACAATCAC

AAGAAAAACCAGATCGAGTTTTGGTTCGGGTTAGAGACTTGACAATACAAAAAGCTGATGA

AGTTGTTTGGGTACGTGCAAGAGTTCATACAAGCAGAGCTAAAGGGAAACAGTGCTTCTTAG

TCCTACGTCAGCAGCAGTTTAATGTCCAGGCTCTTGTGGCGGTGGGAGACCATGCAAGCAAG

CAGATGGTTAAATTTGCTGCCAACATCAACAAAGAGAGCATTGTGGATGTAGAAGGTGTTGT

GAGAAAAGTGAATCAGAAAATTGGAAGCTGTACACAGCAAGACGTTGAGTTACATGTTCAG

AAGATTTATGTGATCAGTTTGGCTGAACCCCGTCTGCCCCTG

DRS 19-154
(SEQ ID NO: 234)
GCGGCGGAAGATTATGCTAAAGAGAGATATGGAATATCTTCAATGATACAATCACAAGAAA

AACCAGATCGAGTTTTGGTTCGGGTTAGAGACTTGACAATACAAAAAGCTGATGAAGTTGTT

TGGGTACGTGCAAGAGTTCATACAAGCAGAGCTAAAGGGAAACAGTGCTTCTTAGTCCTAC

GTCAGCAGCAGTTTAATGTCCAGGCTCTTGTGGCGGTGGGAGACCATGCAAGCAAGCAGAT

GGTTAAATTTGCTGCCAACATCAACAAAGAGAGCATTGTGGATGTAGAAGGTGTTGTGAGA

AAAGTGAATCAGAAAATTGGAAGCTGTACACAGCAAGACGTTGAGTTACATGTTCAGAAGA

TTTATGTGATCAGTTTGGCTGAACCCCGTCTGCCCCTG

DRS 21-154
(SEQ ID NO: 235)
GCGGCGGAAGATTATGCTAAAGAGAGATATGGAATATCTTCAATGATACAATCACAAGAAA

AACCAGATCGAGTTTTGGTTCGGGTTAGAGACTTGACAATACAAAAAGCTGATGAAGTTGTT

TGGGTACGTGCAAGAGTTCATACAAGCAGAGCTAAAGGGAAACAGTGCTTCTTAGTCCTAC

GTCAGCAGCAGTTTAATGTCCAGGCTCTTGTGGCGGTGGGAGACCATGCAAGCAAGCAGAT

GGTTAAATTTGCTGCCAACATCAACAAAGAGAGCATTGTGGATGTAGAAGGTGTTGTGAGA

AAAGTGAATCAGAAAATTGGAAGCTGTACACAGCAAGACGTTGAGTTACATGTTCAGAAGA

TTTATGTGATCAGTTTGGCTGAACCCCGTCTG

DRS 23-154
(SEQ ID NO: 236)
GCGGCGGAAGATTATGCTAAAGAGAGATATGGAATATCTTCAATGATACAATCACAAGAAA

AACCAGATCGAGTTTTGGTTCGGGTTAGAGACTTGACAATACAAAAAGCTGATGAAGTTGTT

TGGGTACGTGCAAGAGTTCATACAAGCAGAGCTAAAGGGAAACAGTGCTTCTTAGTCCTAC

GTCAGCAGCAGTTTAATGTCCAGGCTCTTGTGGCGGTGGGAGACCATGCAAGCAAGCAGAT

GGTTAAATTTGCTGCCAACATCAACAAAGAGAGCATTGTGGATGTAGAAGGTGTTGTGAGA

-continued

```
AAAGTGAATCAGAAAATTGGAAGCTGTACACAGCAAGACGTTGAGTTACATGTTCAGAAGA

TTTATGTGATCAGTTTGGCTGAACCC
```

Double truncated coding sequences are as follows:

DRS 11-146:
(SEQ ID NO: 237)
```
ATGCAGGAGAAGCCGCGGGAGATCATGGACGCGGCGGAAGATTATGCTAAAGAGAGATAT

GGAATATCTTCAATGATACAATCACAAGAAAAACCAGATCGAGTTTTGGTTCGGGTTAGAGA

CTTGACAATACAAAAAGCTGATGAAGTTGTTTGGGTACGTGCAAGAGTTCATACAAGCAGA

GCTAAAGGGAAACAGTGCTTCTTAGTCCTACGTCAGCAGCAGTTTAATGTCCAGGCTCTTGT

GGCGGTGGGAGACCATGCAAGCAAGCAGATGGTTAAATTTGCTTGCAACATCAACAAAGAG

AGCATTGTGGATGTAGAAGGTGTTGTGAGAAAAGTGAATCAGAAAATTGGAAGCTGTACAC

AGCAAGACGTTGAGTTACATGTTCAGAAGATTTATGTGATCAGT
```

DRS 13-146:
(SEQ ID NO: 238)
```
ATGAAGCCGCGGGAGATCATGGACGCGGCGGAAGATTATGCTAAAGAGAGATATGGAATAT

CTTCAATGATACAATCACAAGAAAAACCAGATCGAGTTTTGGTTCGGGTTAGAGACTTGACA

ATACAAAAAGCTGATGAAGTTGTTTGGGTACGTGCAAGAGTTCATACAAGCAGAGCTAAAG

GGAAACAGTGCTTCTTAGTCCTACGTCAGCAGCAGTTTAATGTCCAGGCTCTTGTGGCGGTG

GGAGACCATGCAAGCAAGCAGATGGTTAAATTTGCTTGCAACATCAACAAAGAGAGCATTG

TGGATGTAGAAGGTGTTGTGAGAAAAGTGAATCAGAAAATTGGAAGCTGTACACAGCAAGA

CGTTGAGTTACATGTTCAGAAGATTTATGTGATCAGT
```

DRS 13-146/A106C:
(SEQ ID NO: 239)
```
ATGAAGCCGCGGGAGATCATGGACGCGGCGGAAGATTATGCTAAAGAGAGATATGGAATAT

CTTCAATGATACAATCACAAGAAAAACCAGATCGAGTTTTGGTTCGGGTTAGAGACTTGACA

ATACAAAAAGCTGATGAAGTTGTTTGGGTACGTGCAAGAGTTCATACAAGCAGAGCTAAAG

GGAAACAGTGCTTCTTAGTCCTACGTCAGCAGCAGTTTAATGTCCAGGCTCTTGTGGCGGTG

GGAGACCATGCAAGCAAGCAGATGGTTAAATTTGCTTGCAACATCAACAAAGAGAGCATTG

TGGATGTAGAAGGTGTTGTGAGAAAAGTGAATCAGAAAATTGGAAGCTGTACACAGCAAGA

CGTTGAGTTACATGTTCAGAAGATTTATGTGATCAGT
```

DRS 17-146:
(SEQ ID NO: 240)
```
ATGATCATGGACGCGGCGGAAGATTATGCTAAAGAGAGATATGGAATATCTTCAATGATAC

AATCACAAGAAAAACCAGATCGAGTTTTGGTTCGGGTTAGAGACTTGACAATACAAAAAGC

TGATGAAGTTGTTTGGGTACGTGCAAGAGTTCATACAAGCAGAGCTAAAGGGAAACAGTGC

TTCTTAGTCCTACGTCAGCAGCAGTTTAATGTCCAGGCTCTTGTGGCGGTGGGAGACCATGC

AAGCAAGCAGATGGTTAAATTTGCTTGCAACATCAACAAAGAGAGCATTGTGGATGTAGAA

GGTGTTGTGAGAAAAGTGAATCAGAAAATTGGAAGCTGTACACAGCAAGACGTTGAGTTAC

ATGTTCAGAAGATTTATGTGATCAGT
```

DRS 21-146:
(SEQ ID NO: 241)
```
ATGGCGGAAGATTATGCTAAAGAGAGATATGGAATATCTTCAATGATACAATCACAAGAAA

AACCAGATCGAGTTTTGGTTCGGGTTAGAGACTTGACAATACAAAAAGCTGATGAAGTTGTT

TGGGTACGTGCAAGAGTTCATACAAGCAGAGCTAAAGGGAAACAGTGCTTCTTAGTCCTAC
```

```
-continued
GTCAGCAGCAGTTTAATGTCCAGGCTCTTGTGGCGGTGGGAGACCATGCAAGCAAGCAGAT

GGTTAAATTTGCTTGCAACATCAACAAAGAGAGCATTGTGGATGTAGAAGGTGTTGTGAGA

AAAGTGAATCAGAAAATTGGAAGCTGTACACAGCAAGACGTTGAGTTACATGTTCAGAAGA

TTTATGTGATCAGT
```

The corresponding protein sequences of the DRS truncations are as follows:

```
DRS 1-182
                                                       (SEQ ID NO: 154)
MPSASASRKSQEKPREIMDAAEDYAKERYGISSMIQSQEKPDRVLVRVRDLTIQKADEVVWVRA

RVHTSRAKGKQCFLVLRQQQFNVQALVAVGDHASKQMVKFAANINKESIVDVEGVVRKVNQK

IGSCTQQDVELHVQKIYVISLAEPRLPLQLDDAVRPEAEGEEEGRATVNQDTRLDN

DRS 1-180
                                                       (SEQ ID NO: 155)
MPSASASRKSQEKPREIMDAAEDYAKERYGISSMIQSQEKPDRVLVRVRDLTIQKADEVVWVRA

RVHTSRAKGKQCFLVLRQQQFNVQALVAVGDHASKQMVKFAANINKESIVDVEGVVRKVNQK

IGSCTQQDVELHVQKIYVISLAEPRLPLQLDDAVRPEAEGEEEGRATVNQDTRL

DRS 1-178
                                                       (SEQ ID NO: 156)
MPSASASRKSQEKPREIMDAAEDYAKERYGISSMIQSQEKPDRVLVRVRDLTIQKADEVVWVRA

RVHTSRAKGKQCFLVLRQQQFNVQALVAVGDHASKQMVKFAANINKESIVDVEGVVRKVNQK

IGSCTQQDVELHVQKIYVISLAEPRLPLQLDDAVRPEAEGEEEGRATVNQDT

DRS 1-176
                                                       (SEQ ID NO: 157)
MPSASASRKSQEKPREIMDAAEDYAKERYGISSMIQSQEKPDRVLVRVRDLTIQKADEVVWVRA

RVHTSRAKGKQCFLVLRQQQFNVQALVAVGDHASKQMVKFAANINKESIVDVEGVVRKVNQK

IGSCTQQDVELHVQKIYVISLAEPRLPLQLDDAVRPEAEGEEEGRATVNQ

DRS 1-174
                                                       (SEQ ID NO: 158)
MPSASASRKSQEKPREIMDAAEDYAKERYGISSMIQSQEKPDRVLVRVRDLTIQKADEVVWVRA

RVHTSRAKGKQCFLVLRQQQFNVQALVAVGDHASKQMVKFAANINKESIVDVEGVVRKVNQK

IGSCTQQDVELHVQKIYVISLAEPRLPLQLDDAVRPEAEGEEEGRATV

DRS 1-172
                                                       (SEQ ID NO: 159)
MPSASASRKSQEKPREIMDAAEDYAKERYGISSMIQSQEKPDRVLVRVRDLTIQKADEVVWVRA

RVHTSRAKGKQCFLVLRQQQFNVQALVAVGDHASKQMVKFAANINKESIVDVEGVVRKVNQK

IGSCTQQDVELHVQKIYVISLAEPRLPLQLDDAVRPEAEGEEEGRA

DRS 1-170
                                                       (SEQ ID NO: 160)
MPSASASRKSQEKPREIMDAAEDYAKERYGISSMIQSQEKPDRVLVRVRDLTIQKADEVVWVRA

RVHTSRAKGKQCFLVLRQQQFNVQALVAVGDHASKQMVKFAANINKESIVDVEGVVRKVNQK

IGSCTQQDVELHVQKIYVISLAEPRLPLQLDDAVRPEAEGEEEG

DRS 1-168
                                                       (SEQ ID NO: 161)
MPSASASRKSQEKPREIMDAAEDYAKERYGISSMIQSQEKPDRVLVRVRDLTIQKADEVVWVRA

RVHTSRAKGKQCFLVLRQQQFNVQALVAVGDHASKQMVKFAANINKESIVDVEGVVRKVNQK

IGSCTQQDVELHVQKIYVISLAEPRLPLQLDDAVRPEAEGEE
```

```
DRS 1-166
                                                     (SEQ ID NO: 162)
MPSASASRKSQEKPREIMDAAEDYAKERYGISSMIQSQEKPDRVLVRVRDLTIQKADEVVWVRA

RVHTSRAKGKQCFLVLRQQQFNVQALVAVGDHASKQMVKFAANINKESIVDVEGVVRKVNQK

IGSCTQQDVELHVQKIYVISLAEPRLPLQLDDAVRPEAEG

DRS 1-164
                                                     (SEQ ID NO: 163)
MPSASASRKSQEKPREIMDAAEDYAKERYGISSMIQSQEKPDRVLVRVRDLTIQKADEVVWVRA

RVHTSRAKGKQCFLVLRQQQFNVQALVAVGDHASKQMVKFAANINKESIVDVEGVVRKVNQK

IGSCTQQDVELHVQKIYVISLAEPRLPLQLDDAVRPEA

DRS 1-162
                                                     (SEQ ID NO: 164)
MPSASASRKSQEKPREIMDAAEDYAKERYGISSMIQSQEKPDRVLVRVRDLTIQKADEVVWVRA

RVHTSRAKGKQCFLVLRQQQFNVQALVAVGDHASKQMVKFAANINKESIVDVEGVVRKVNQK

IGSCTQQDVELHVQKIYVISLAEPRLPLQLDDAVRP

DRS 1-160
                                                     (SEQ ID NO: 165)
MPSASASRKSQEKPREIMDAAEDYAKERYGISSMIQSQEKPDRVLVRVRDLTIQKADEVVWVRA

RVHTSRAKGKQCFLVLRQQQFNVQALVAVGDHASKQMVKFAANINKESIVDVEGVVRKVNQK

IGSCTQQDVELHVQKIYVISLAEPRLPLQLDDAV

DRS 1-158
                                                     (SEQ ID NO: 166)
MPSASASRKSQEKPREIMDAAEDYAKERYGISSMIQSQEKPDRVLVRVRDLTIQKADEVVWVRA

RVHTSRAKGKQCFLVLRQQQFNVQALVAVGDHASKQMVKFAANINKESIVDVEGVVRKVNQK

IGSCTQQDVELHVQKIYVISLAEPRLPLQLDD

DRS 1-156
                                                     (SEQ ID NO: 167)
MPSASASRKSQEKPREIMDAAEDYAKERYGISSMIQSQEKPDRVLVRVRDLTIQKADEVVWVRA

RVHTSRAKGKQCFLVLRQQQFNVQALVAVGDHASKQMVKFAANINKESIVDVEGVVRKVNQK

IGSCTQQDVELHVQKIYVISLAEPRLPLQL

DRS 1-154
                                                     (SEQ ID NO: 168)
MPSASASRKSQEKPREIMDAAEDYAKERYGISSMIQSQEKPDRVLVRVRDLTIQKADEVVWVRA

RVHTSRAKGKQCFLVLRQQQFNVQALVAVGDHASKQMVKFAANINKESIVDVEGVVRKVNQK

IGSCTQQDVELHVQKIYVISLAEPRLPL

DRS 1-152
                                                     (SEQ ID NO: 169)
MPSASASRKSQEKPREIMDAAEDYAKERYGISSMIQSQEKPDRVLVRVRDLTIQKADEVVWVRA

RVHTSRAKGKQCFLVLRQQQFNVQALVAVGDHASKQMVKFAANINKESIVDVEGVVRKVNQK

IGSCTQQDVELHVQKIYVISLAEPRL

DRS 1-150
                                                     (SEQ ID NO: 170)
MPSASASRKSQEKPREIMDAAEDYAKERYGISSMIQSQEKPDRVLVRVRDLTIQKADEVVWVRA

RVHTSRAKGKQCFLVLRQQQFNVQALVAVGDHASKQMVKFAANINKESIVDVEGVVRKVNQK

IGSCTQQDVELHVQKIYVISLAEP

DRS 1-148
                                                     (SEQ ID NO: 171)
MPSASASRKSQEKPREIMDAAEDYAKERYGISSMIQSQEKPDRVLVRVRDLTIQKADEVVWVRA

RVHTSRAKGKQCFLVLRQQQFNVQALVAVGDHASKQMVKFAANINKESIVDVEGVVRKVNQK

IGSCTQQDVELHVQKIYVISLA
```

-continued

DRS 1-146
(SEQ ID NO: 172)
MPSASASRKSQEKPREIMDAAEDYAKERYGISSMIQSQEKPDRVLVRVRDLTIQKADEVVWVRA

RVHTSRAKGKQCFLVLRQQQFNVQALVAVGDHASKQMVKFAANINKESIVDVEGVVRKVNQK

IGSCTQQDVELHVQKIYVIS

DRS 3-154
(SEQ ID NO: 173)
ASASRKSQEKPREIMDAAEDYAKERYGISSMIQSQEKPDRVLVRVRDLTIQKADEVVWVRARVH

TSRAKGKQCFLVLRQQQFNVQALVAVGDHASKQMVKFAANINKESIVDVEGVVRKVNQKIGSC

TQQDVELHVQKIYVISLAEPRLPL

DRS 5-154
(SEQ ID NO: 174)
ASRKSQEKPREIMDAAEDYAKERYGISSMIQSQEKPDRVLVRVRDLTIQKADEVVWVRARVHTS

RAKGKQCFLVLRQQQFNVQALVAVGDHASKQMVKFAANINKESIVDVEGVVRKVNQKIGSCT

QQDVELHVQKIYVISLAEPRLPL

DRS 7-154
(SEQ ID NO: 175)
RKSQEKPREIMDAAEDYAKERYGISSMIQSQEKPDRVLVRVRDLTIQKADEVVWVRARVHTSRA

KGKQCFLVLRQQQFNVQALVAVGDHASKQMVKFAANINKESIVDVEGVVRKVNQKIGSCTQQ

DVELHVQKIYVISLAEPRLPL

DRS 9-154
(SEQ ID NO: 176)
SQEKPREIMDAAEDYAKERYGISSMIQSQEKPDRVLVRVRDLTIQKADEVVWVRARVHTSRAKG

KQCFLVLRQQQFNVQALVAVGDHASKQMVKFAANINKESIVDVEGVVRKVNQKIGSCTQQDVE

LHVQKIYVISLAEPRLPL

DRS 11-154
(SEQ ID NO: 177)
EKPREIMDAAEDYAKERYGISSMIQSQEKPDRVLVRVRDLTIQKADEVVWVRARVHTSRAKGK

QCFLVLRQQQFNVQALVAVGDHASKQMVKFAANINKESIVDVEGVVRKVNQKIGSCTQQDVEL

HVQKIYVISLAEPRLPL

DRS 13-154
(SEQ ID NO: 178)
PREIMDAAEDYAKERYGISSMIQSQEKPDRVLVRVRDLTIQKADEVVWVRARVHTSRAKGKQC

FLVLRQQQFNVALVAVGDHASKQMVKFAANINKESIVDVEGVVRKVNQKIGSCTQQDVELHV

QKIYVISLAEPRLPL

DRS 15-154
(SEQ ID NO: 179)
EIMDAAEDYAKERYGISSMIQSQEKPDRVLVRVRDLTIQKADEVVWVRARVHTSRAKGKQCFL

VLRQQQFNVQALVAVGDHASKQMVKFAANINKESIVDVEGVVRKVNQKIGSCTQQDVELHVQ

KIYVISLAEPRLPL

DRS 17-154
(SEQ ID NO: 180)
MDAAEDYAKRRYGISSMIQSQEKPDRVLVRVRDLTIQKADEVVWVRARVHTSRAKGKQCFLVL

RQQQFNVQALVAVGDHASKQMVKFAANINKESIVDVEGVVRKVNQKIGSCTQQDVELHVQKIY

VISLAEPRLPL

DRS 19-154
(SEQ ID NO: 181)
MDAAEDYAKERYGISSMIQSQEKPDRVLVRVRDLTIQKADEVVWVRARVHTSRAKGKQCFLVL

RQQQFNVQALVAVGDHASKQMVKFAANINKESIVDVEGVVRKVNQKIGSCTQQDVELHVQKIY

VISLAEPRL

-continued

DRS 21-154
(SEQ ID NO: 182)
MDAAEDYAKERYGISSMIQSQEKPDRVLVRVRDLTIQKADEVVWVRARVHTSRAKGKQCFLVL

RQQQFNVQALVAVGDHASKQMVKFAANINKESIVDVEGVVRKVNQKIGSCTQQDVELHVQKIY

VISLAEPRL

DRS 23-154
(SEQ ID NO: 183)
AAEDYAKERYGISSMIQSQEKPDRVLVRVRDLTIQKADEVVWVRARVHTSRAKGKQCFLVLRQ

QQFNVQALVAVGDHASKQMVKFAANINKESIVDVEGVVRKVNQKIGSCTQQDVELHVQKIYVI

SLAEPRL

DRS 11-146:
(SEQ ID NO: 184)
MQEKPREIMDAAEDYAKERYGISSMIQSQEKPDRVLVRVRDLTIQKADEVVWVRARVHTSRAK

GKQCFLVLRQQQFNVQALVAVGDHASKQMVKFACNINKESIVDVEGVVRKVNQKIGSCTQQD

VELHVQKIYVIS

DRS 13-146:
(SEQ ID NO: 185)
MKPREIMDAAEDYAKERYGISSMIQSQEKPDRVLVRVRDLTIQKADEVVWVRARVHTSRAKGK

QCFLVLRQQQFNVQALVAVGDHASKQMVKFACNINKESIVDVEGVVRKVNQKIGSCTQQDVEL

HVQKIYVIS

DRS 13-146/A106C:
(SEQ ID NO: 186)
MKPREIMDAAEDYAKERYGISSMIQSQEKPDRVLVRVRDLTIQKADEVVWVRARVHTSRAKGK

QCFLVLRQQQFNVQALVAVGDHASKQMVKFACNINKESIVDVEGVVRKVNQKIGSCTQQDVEL

HVQKIYVIS

DRS 17-146:
(SEQ ID NO: 187)
MIMDAAEDYAKERYGISSMIQSQEKPDRVLVRVRDLTIQKADEVVWVRARVHTSRAKGKQCFL

VLRQQQFNVQALVAVGDHASKQMVKFACNINKESIVDVEGVVRKVNQKIGSCTQQDVELHVQ

KIYVIS

DRS 21-146:
(SEQ ID NO: 188)
MAEDYAKERYGISSMIQSQEKPDRVLVRVRDLTIQKADEVVWVRARVHTSRAKGKQCFLVLRQ

QQFNVQALVAVGDHASKQMVKFACNINKESIVDVEGVVRKVNQKIGSCTQQDVELHVQKIYVI

S

N-terminal truncated Homeokine variants 3-154, 5-154, 7-154 and 9-154 were made by QuickChange Lightning Site-Directed Mutagenesis Kit (Agilent, cat. no. 210518) following the manufacturer's instructions using construct plasmid pET28a-C-V5/His-DRS aa1-154 as template. Homeokine variants 13-146/A106C were also made by direct mutagenesis approach using the truncated form DRS 13-146 as template.

C-terminal Homeokine variants 1-148, 1-150, 1-152, 1-156, 1-158, 1-160, 1-162, 1-164, 1-166, 1-168, 1-170, 1-172, 1-174, 1-176, 1-178 and 1-180 were made by via Kunkle mutagenesis approach using pET28a C-V5/His DRS as template. The whole process can be divided into two steps, ssDNA preparation and Kunkle mutagenesis. To prepare ssDNA, the dsDNA vector was transformed into CJ236 bacterial cells (NEB, cat no E4141S) and plated on ampicillin (100 ug/mL) and chloramphenicol (30 ug/mL) containing LB-Agar plates. Plates were incubated overnight at 37° C. A colony was used to inoculate LB medium containing ampicillin and chloramphenicol and incubated overnight at 225 rpm and 37° C. 20 mL of LB containing ampicillin and chloramphenicol was inoculated with 200 uL of the overnight culture and grown for 2 hr at 225 rpm and 37° C. The culture was infected with 5e9 pfu of M13KO7 Helper Phage (NEB, cat no N0315S). After 1 hr, kanamycin was added to the culture at a final concentration of 50 ug/mL and incubated overnight at 225 rpm and 37° C. Bacteria were separated and discarded from culture by two centrifugations at 1900×g. ssDNA was precipitated by incubation at 4° C. with final concentrations of 4% PEG-8000 and 500 mM Sodium Acetate for 2 hr. ssDNA was centrifuged at 12000×g and resuspended in 1.4 mL LB medium. Cell debris was eliminated by subsequent centrifugation at 14500×g. ssDNA was purified from the supernatant using Qiagen QIAprep M13 kit (Qiagen, cat no 27704). Kunkel mutagenesis was performed by first diluting primers to 100 ng/uL. 100 ng of the oligo was then incubated with 5U PNK kinase (Roche, cat no 10633542001) in the presence of 1×PNK kinase buffer and 0.5 mM ATP. This reaction was incubated at 37° C. for 1 hr. 100 ng of ssDNA vector was incubated with 6.9 ng of kinased oligo in annealing buffer (20 mM Tris, pH7.4, 2 mM MgCl2, 50 mM NaCl, final concentrations) for 5 min in a heat block at 75° C. Reactions were allowed to cool to room temperature while contained in the heat block. For elongation of the plasmid, 1U of T4 DNA Polymerase (Roche, cat no 11004786001) and 1 U T4 DNA Ligase (Roche, cat no 10481220001) was added to the reaction. Additionally, synthesis buffer was added to a final concentration of 0.45 mM dNTPs, 0.91 mM ATP, 9.1 mM Tris, pH7.4, 4.5 mM MgCl2, and 1.8 mM DTT. This reaction was incubated on ice for 5 min and then at 37° C. for 90 min. 5 uL of the elongation reaction was transformed into 200 uL DH5a cells. Transformations were plated on Ampicillin plates and incubated overnight at 37° C. Individual colonies were used to inoculate 6 mL LB medium containing ampicillin. Cultures were grown overnight at 37° C. DNA plasmids were prepared using Qiagen Spin Miniprep kit (Qiagen, cat no 27106) and sequence verified.

Double truncated Homeokine variants 11-146, 13-146, 17-146 and 21-146 were made by traditional cloning method using construct pet28a+_CtermV5His_DRSNdeI-XhoI_revcomp as template. Briefly, the desired fragment was amplified by PCR (Invitrogen, cat no 12344-040) and double digested by NdeI (NEB, cat. no R0111S) and XhoI (NEB, cat no. R0146S) restriction enzymes. Purified double digested fragment was ligated with NdeI/XhoI double vector pet28a+_CtermV5His_DRS_NdeI-XhoI_revcomp by T4 DNA Ligase (Roche, cat no 10481220001) and transformed into DH5α competent cells (Invitrogen, cat. no 18263-012) and plated on LB-agar plates containing ampicillin (100 ug/mL). Colonies were grown individually in LB/Amp media and sequenced to confirm sequence.

Expression of Truncated Homeokine Variant:

Homeokine truncated variant constructs with correct sequences are transformed into BL21 (DE3) competent cells (Novagen, cat. no. 69450-4) and expressed at 30° C. for 16 hrs in LB media with 100 ug/ml ampicillin as described above.

Purification of truncated Homeokine variants were prepared as described, except for the final lysis step. In which for these constructs frozen cell pellets were resuspended in lysis buffer (50 mM Tris, 300 mM NaCl, 25 mM Imidazole, 5 mM DTT, pH 8.0 with complete EDTA-FREE protease inhibitor cocktail tablets (Roche cat. no: 05 056 489 001) and the then rotated for 30 mins at 4° C. with 300 mg chicken egg lysozyme. The suspension was then sonicated for two cycles 50% and 75% for 60 seconds each with 10 second on and 5 second off. The lysate was centrifuged at 35,000×g for 45 min at 4° C., and the supernatant then filtered through 0.22 µm Sartobran capsule filters (Sartorius). The clarified lysate was bound to the Ni-NTA resin (Qiagen), pre-equilibrated with Ni-NTA Binding Buffer (50 mM Tris, 300 mM NaCl, 25 mM Imidazole, 5 mM DTT, pH 8.0). The column was washed with 1000 column volumes of Ni-NTA Binding Buffer plus 0.1% Triton X-114 and 5 mM DTT followed by 50 column volumes of the Ni-NTA Binding Buffer. The bound protein was eluted with 5 column volumes of Ni-NTA Elution Buffer (50 mM Tris, 300 mM NaCl, 300 mM Imidazole, 1 mM DTT pH 8.0).

The purified proteins were dialyzed into 20 mM sodium phosphate, 200 mM Arginine, at pH7.3. The dialyzed protein was passed through a Q membrane filter (Sartobind-Q from Sartorius or Mustang-Q from Pall) or a Q-Sepharose column (GE Healthcare) for further endotoxin removal when endotoxin level is detectable using Charles River endotoxin detection kit (product code: PTS20), and then filtered through a 0.22 µm sterile filter.

Testing of the relative activity of the purified proteins compared in the HEK293-TLR2 and HEK293-TLR4 expressing cell lines as described above confirmed that the majority of proteins were active (data not shown).

Example 8

Comparison of Stability of Purified Truncated Homeokine (DRS) Mutants

Stability was assessed by incubating 50 µl of each of the deletion mutants in PBS at 1 mg/ml at 37° C. for 1 hr, and then by running an analytical SEC column (YMC America, Inc, cat. no. YMC-Pack Diol-300) using 200 mM phosphate, 100 mM NaCl pH7.0 as running buffer to compare the % High molecular weight (HMW) component after incubation at 37 C, and via determining turbidity as assessed via absorption at A340 nM. Results are summarized in Table E11.

TABLE E11

| Variant | % Change A340 nm after incubation after 5 hr at 37 C. +: <50%; ++: >50%; +++: >100%; ++++: >500%; | % HMW determined via SEC (Time zero) +: <7%; ++: >7%; +++: >10%; ++++: >15%; | % HMW determined via SEC after incubation after 5 hr at 37 C. +: <7%; ++: >7%; +++: >10%; ++++: >15%; |
|---|---|---|---|
| 1-148 | + | + | + |
| 1-150 | ++ | + | + |
| 1-152 | +++ | + | + |
| 1-154 | ++ | + | + |
| 1-156 | ++ | + | + |
| 1-158 | ++ | + | + |
| 1-160 | +++ | ++ | ++ |
| 1-162 | + | + | ++ |
| 1-164 | + | + | ++ |
| 1-166 | ++++ | ++++ | + |
| 1-168 | + | ++ | ++++ |
| 1-170 | + | + | +++ |
| 1-172 | + | + | ++++ |
| 1-174 | + | + | ++++ |
| 1-176 | +++ | ++++ | ++ |
| 1-178 | + | ++ | ++++ |
| 1-180 | + | + | +++ |
| 1-182 | + | ++ | ++++ |

TABLE E11-continued

N-terminal mutations

| | | | |
|---|---|---|---|
| 3-154 | ++++ | ++++ | ++ |
| 5-154 | ++++ | ++++ | ++ |
| 7-154 | ++++ | ++++ | ++ |
| 9-154 | ++++ | ++++ | ++ |
| 11-154 | + | + | + |
| 13-154 | + | + | + |
| 17-154 | + | + | + |
| 21-154 | ++ | + | + |
| 23-154 | ++ | + | + |

| Double truncations | | | % HMW determined via SEC after incubation after 24 hr at 37 C. |
|---|---|---|---|
| 11-146 | Not determined | + | Not determined |
| 13-146 | Not determined | + | +++ |
| 17-146 | Not determined | + | Not determined |
| 21-146 | Not determined | + | Not determined |
| 13-146/A106C | Not determined | + | ++ |

These results demonstrate that C-terminal deletions from about 1-158 to about 1-146 of DRS display enhanced stability and reduced tendency for aggregation. With respect to N-terminal deletions, deletions in the range of 11-154 to 17-154 of DRS results in constructs with improved stability profiles. Additionally all of the doubly deleted constructs, including 11-146, 13-146, 17-146 and 21-146 of DRS all exhibited extremely low tendency for aggregation and enhanced stability.

Example 9

Testing of Reduced Cysteine Variants In Vivo in a Partial Body Irradiation Survival Model Methods.

Adult (10-12 week) C57BL/6 male mice were divided into 10 groups of 26. Mice were irradiated at 15:00 hours+/−1 hour with 14 Gy (five groups) or 14.5 Gy (five groups) irradiation. Irradiation was performed using a Pantak HF320 X-ray operated at 300 kV, 10 mA. The X-ray tube had additional filtration to give a radiation quality of 2.3 mm Cu half-value layer (HVL). Mice were anaesthetized and restrained in a jig and irradiation was delivered at a dose rate of 70.0 cGy/min. (Epistem, UK). Animals received partial body irradiation to the abdomen only—the head, thorax and forelimbs were lead shielded. This equates to approximately 40% bone marrow shielding. 24 hours post irradiation each group of mice was dosed i.v. (5 ml/kg) with a test item via the tail vein. The test item groups tested at each radiation dose using a PBS diluent. Mice were then dosed every 24 hours for a total of 7 days with DRS(1-154) C76S or with PBS as a control.

Mice were weighed daily and signs of diarrhea noted twice daily from day 4-10 post irradiation. Moribund mice from day 10 onwards were anaesthetized and subjected to terminal cardiac puncture to obtain a cardiac bleed. An aliquot of blood was used to perform a complete blood count, with the remainder used to isolate serum, which was then snap frozen. The small and large intestine were removed and fixed. The spleen, femur, Iliac bones and vertebrae, heart, lung and kidneys were also collected from selected mice on day 15 following 14 Gy and fixed in formalin.

Results.

Figure 8:
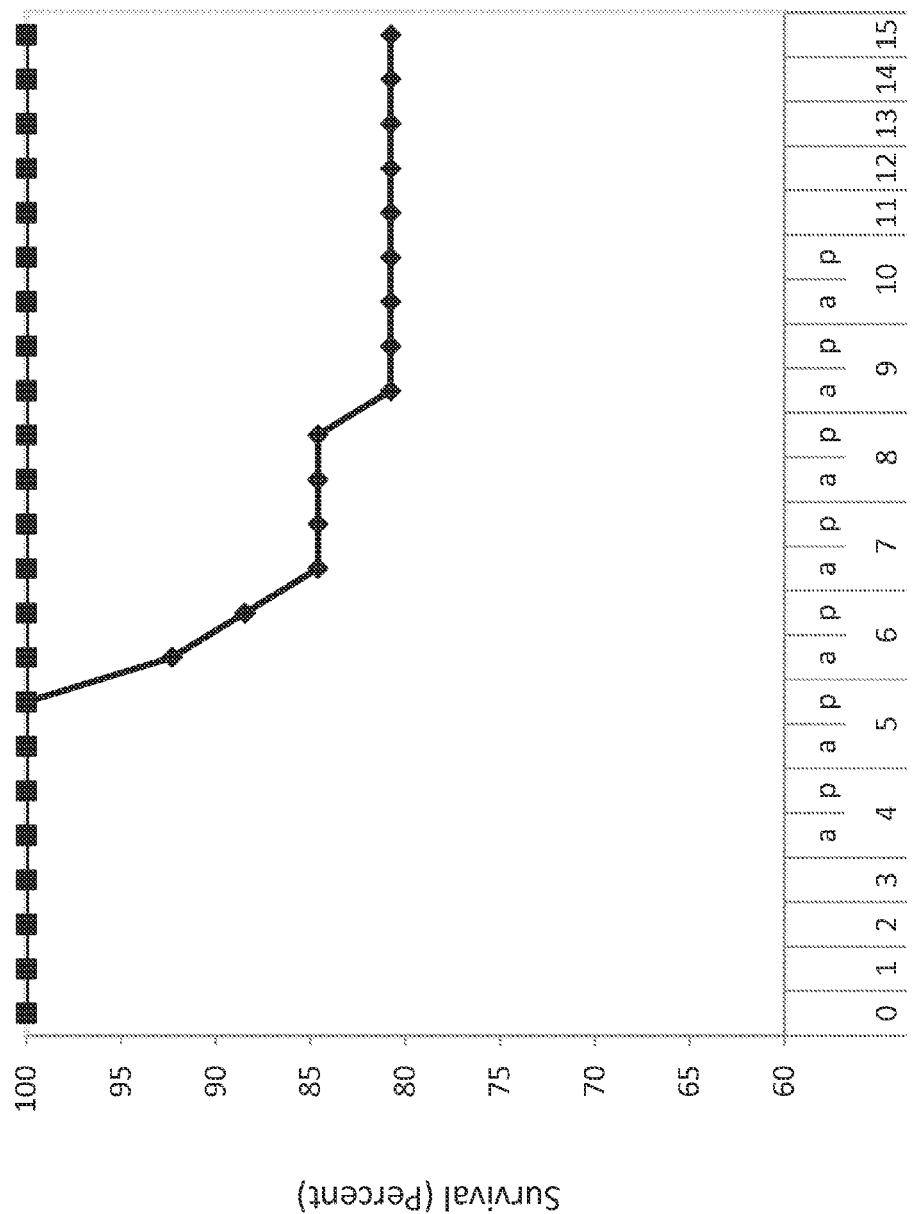
FIG. 8 shows the results of the administration of AspRS1$^{N1}$(C76S) in a partial body irradiation survival model; AspRS1$^{N1}$(C76S) shown in squares and the PBS control shown as diamonds.

The survival data obtained with 14 Gy is shown in FIG. 8, and demonstrates that the cysteine variant DRS1-154 C76S displays improved survival in a radiation survival model.

Example 10

Testing of Reduced Cysteine Variants In Vivo in a MSU Induced Gout Model

Methods.

Gout like inflammation was induced in groups of 5 female C57BL/6 mice by single administration of MSU crystals into the left tarsal joint (Performed by Comparative Biosciences Inc., Sunnyvale, Calif.). One hour before the injection of the MSU crystals, mice were dosed prophylactically once by single injection of vehicle, DRS1-154(C76S) (5 mg/kg, IV) or dexamethasone. Clinical measurements of joint inflammation severity (joint thickness, erythema and lameness) were assessed three times during the study. Mice were sacrificed one day after dosing; blood for serum was collected and the hind limbs were collected for histopathological evaluation. Throughout the study, general clinical observations were recorded daily; body weights were recorded prior to dosing and at necropsy.

Results.

Figure 9A:
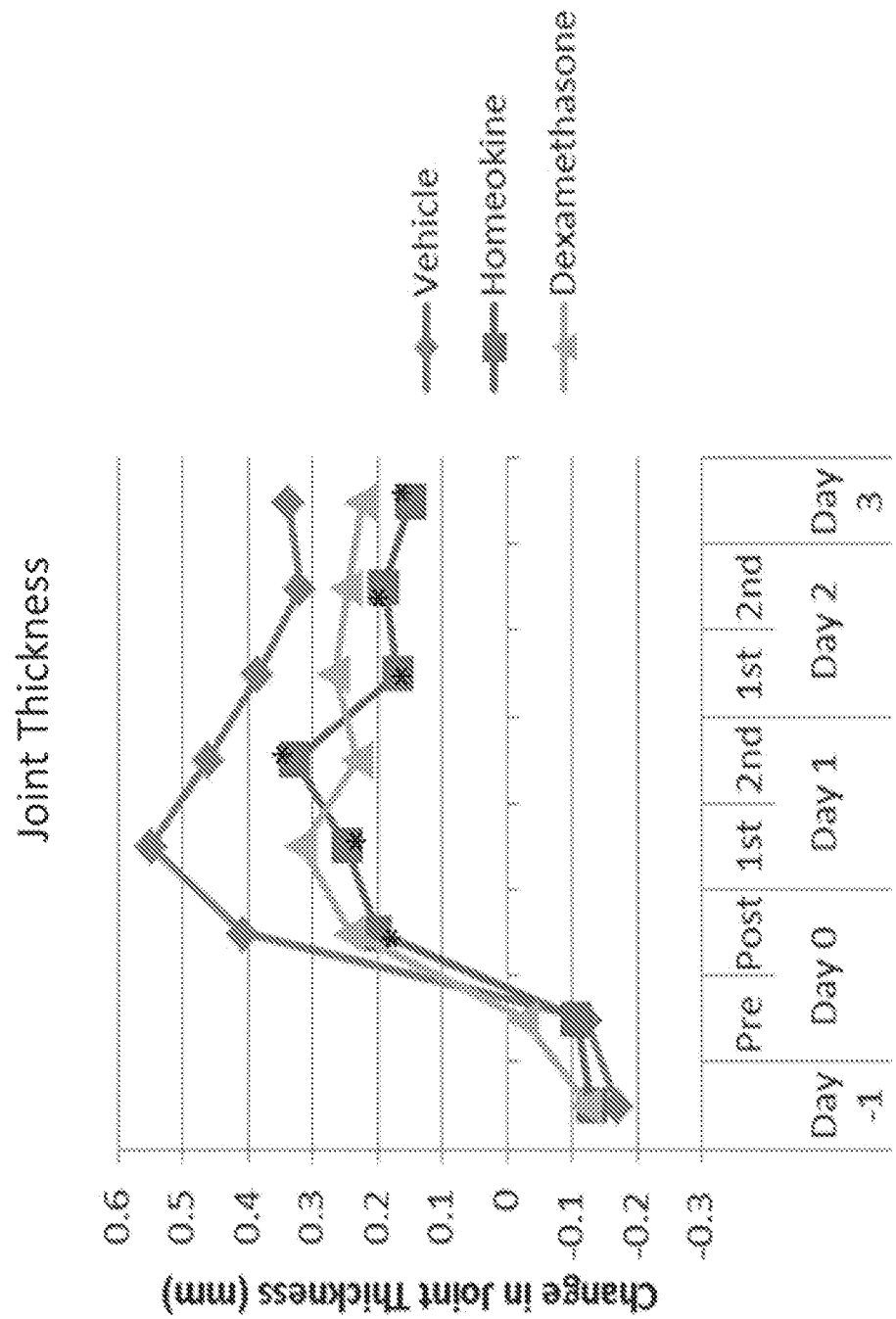
FIGS. 9A and 9B show the results of the administration of AspRS1$^{N1}$(C76S) in an MSU induced model of gout inflammation (squares), compared to vehicle control (PBS) diamonds, and a positive control (dexamethasone (triangles) The insert shows the statistical significance for AspRS1$^{N1}$(C76S) ("Homeokine") compared to the vehicle control.
Figure 9B:
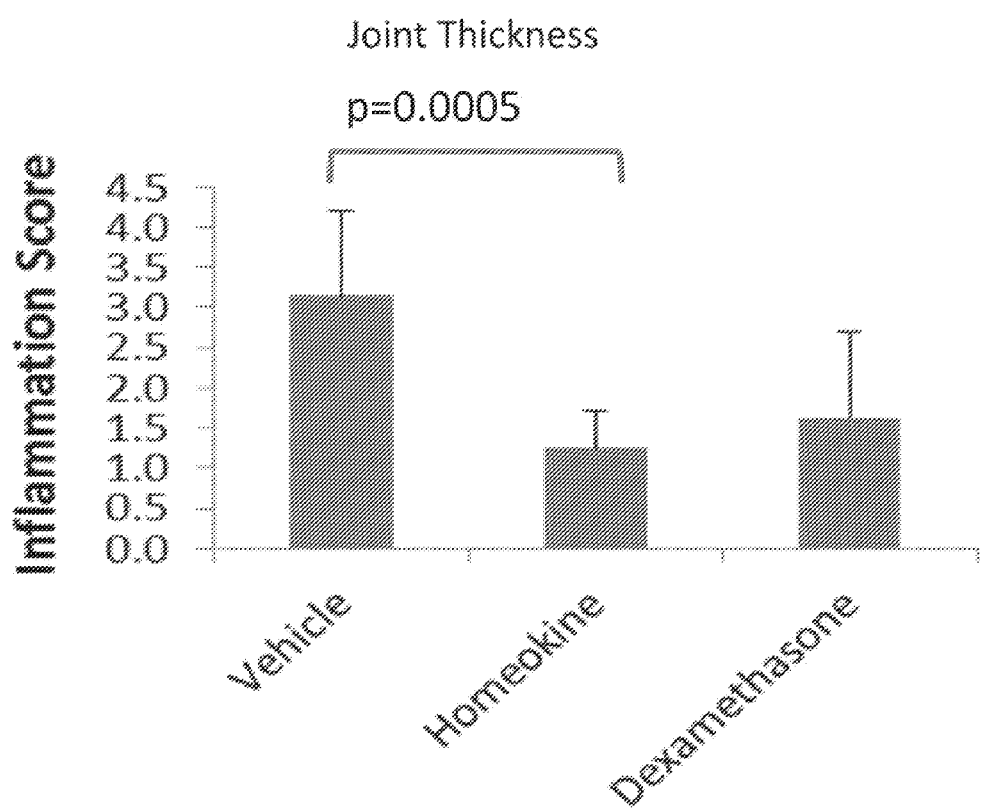

Administration of MSU induced an appropriate brisk inflammatory response characterized by joint swelling and erythema which corresponded clinically to the acute inflammation as seen by histopathology examination. Clinically, dexamethasone administration was associated with reduced swelling (attenuated severity score and mean joint diameter) compared to those treated with saline. Histopathologic examination (FIGS. 9A and 9B) of the MSU injected left tarsal joint showed that dexamethasone and DRS1-154 (C76S) induced a significant reduction in inflammation.

These results demonstrate that DRS1-154 comprising the C76S mutation exhibits enhanced anti-inflammatory activity in the MSU induced model of gout and gout flares.

Example 11

Activity of DRS(1-154) C76S in the TNBS Mouse Model

The DRS(1-154) C76S polypeptide was tested in the TNBS mouse model of colitis. In this model, colonic irritation is induced by intracolonic administration of TNBS in ethanol. This provokes an acute colitis that has a TH1-type cytokine profile, which is characterized by the expression of genes coding for TNF-α, IFN-γ and IL-12 amongst others (see Fichtner-Feigl et al., *J. Clin. Invest.* 115:3057-3071, 2005). The colitis can be severe and localized to the area of the colon into which the TNBS is introduced. The inflammatory response results in localized swelling, inflammatory cell infiltration, and epithelial loss.

Methods.

A total of 62 male BDF-1 mice were used in this study. The mice were randomized into four treatment groups of 12 mice each, one treatment group of eight mice and one group of six mice each. All mice in the five largest treatment groups received 3 mg TNBS in 50% ethanol/saline by colonic instillation on study day 0, in order to induce colitis. Test items (DRS(1-154) C76S)) were first administered three hours prior to the instillation of TNBS, by i.v. injection, at a dose of 5 mg/Kg, and subsequently on study days 1-3 inclusive. Budesonide was employed as a reference test item and was dosed daily, by oral gavage, at 5 mg/kg, with the first dose being given 3 hours prior to the instillation of TNBS. Weight, faecal consistency and presence of overt blood, in faeces and around the anus, were assessed daily. All mice were euthanized on study day 4, and the large bowel taken for assessment of intestinal morphology, a small sample was also snap-frozen.

Harvesting and Preparation of Tissue for Histological Examination.

Mice were sacrificed at 09:00 by cervical dislocation on study day 4, 24 hours after receiving the last dose of test item. Blood was collected, post-sacrifice, by cardiac puncture, into EDTA-treated tubes, and immediately placed on ice. Plasma was prepared by centrifugation of blood samples at 3000 g for 10 minutes, and stored at −80° C. The large intestine was removed and flushed with PBS and its length and wet weight were recorded, prior to cutting into caecum, mid-colon and rectum and fixation in Carnoy's solution. A small sample of mid-colon was also snap-frozen in liquid nitrogen. Fixed tissue was dehydrated through a series of alcohols and xylene and embedded in paraffin, using a Leica TP1020 tissue processor and an EG1140H work station. Sections (3 μm thick) were cut using a Leica RM2125RTF microtome, and air-dried on to microscope slides, overnight at 37° C. Subsequently, slides were dewaxed in xylene and rehydrated through graded alcohols to PBS. All sections were then stained with haematoxylin and eosin (H&E), and mounted. The results are shown in Table E12 below.

TABLE E12

| | % of surviving animals | | | |
|---|---|---|---|---|
| Study Day | untreated | TNBS alone | TNBS + budesonide | TNBS + DRS (1-154)C76S |
| 0 | 100 | 100 | 100 | 100 |
| 1 | 100 | 90 | 100 | 100 |
| 2 | 100 | 90 | 100 | 100 |
| 3 | 100 | 75 | 75 | 100 |
| 4 | 100 | 45 | 75 | 75 |
| 5 | 100 | 45 | 70 | 75 |

These results demonstrate that the DRS polypeptide DRS (1-154) C76S exhibits anti-inflammatory activity in the TNBS model of inflammatory bowel disease.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. An aspartyl-tRNA synthetase (DRS) fusion polypeptide, which comprises an amino acid sequence at least 95% identical to SEQ ID NO:36.

2. The DRS fusion polypeptide of claim 1, which comprises an amino acid sequence at least 97% identical to SEQ ID NO:36.

3. The DRS fusion polypeptide of claim 1, which comprises an amino acid sequence at least 98% identical to SEQ ID NO:36.

4. The DRS fusion polypeptide of claim 1, which comprises an amino acid sequence at least 99% identical to SEQ ID NO:36.

5. The DRS fusion polypeptide of claim 1, where the Fc region comprises one or more of a hinge, CH2, CH3, and/or CH4 domain from a mammalian IgA1, IgA2, IgD, IgE, IgG1, IgG2, IgG3, IgG4, and/or IgM.

6. The DRS fusion polypeptide of claim 1, which has altered pharmacokinetics, immune effector activity, binding to one or more Fc receptors, and/or solubility, relative to a corresponding DRS polypeptide.

7. The DRS fusion polypeptide of claim 6, where said altered pharmacokinetics are increased serum half-life, increased bioavailability, and/or decreased clearance.

8. The DRS fusion polypeptide of claim 6, where said immune effector activity is one or more of complement activation, complement-dependent cytotoxicity (CDC), antibody-dependent cell-mediated cytotoxicity (ADCC), or antibody-dependent cell-mediated phagocytosis (ADCP).

9. The DRS fusion polypeptide of claim 1, where the Fc region comprises a variant Fc region, relative to a wild-type Fc region.

10. The DRS fusion polypeptide of claim 9, where the variant Fc region comprises a hybrid of one or more Fc regions from different species, different Ig classes, or different Ig subclasses.

11. The DRS fusion polypeptide of claim 9, where the variant Fc region comprises a hybrid of one or more hinge, CH2, CH3, and/or CH4 domains of Fc regions from different species, different Ig classes, and/or different Ig subclasses.

12. The DRS fusion polypeptide of claim 1, which is substantially in dimeric form in a physiological solution.

13. The DRS fusion polypeptide of claim 1, which has substantially the same secondary structure a corresponding unmodified DRS polypeptide, as determined via UV circular dichroism analysis.

14. The DRS fusion polypeptide of claim 1, which has a plasma or sera pharmacokinetic AUC profile at least 5-fold greater than a corresponding, unmodified DRS polypeptide when administered to a mammal.

15. A pharmaceutical composition comprising a DRS fusion polypeptide of claim 1, and a pharmaceutically acceptable carrier or excipient.

16. The pharmaceutical composition of claim 15, wherein the composition comprises between about 10 nM and about 100 nM arginine.

* * * * *